US009803002B2

(12) United States Patent
Brown et al.

(10) Patent No.: US 9,803,002 B2
(45) Date of Patent: *Oct. 31, 2017

(54) ANTI-WALL TEICHOIC ANTIBODIES AND CONJUGATES

(71) Applicant: Genentech, Inc., South San Francisco, CA (US)

(72) Inventors: Eric J. Brown, San Francisco, CA (US); Martine Darwish, San Francisco, CA (US); John Flygare, Burlingame, CA (US); Wouter Hazenbos, San Francisco, CA (US); Byoung Chul Lee, Palo Alto, CA (US); Sophie M. Lehar, Montara, CA (US); Sanjeev Mariathasan, Millbrae, CA (US); John Hiroshi Morisaki, San Francisco, CA (US); Thomas H. Pillow, San Francisco, CA (US); Leanna Staben, San Francisco, CA (US); Richard Vandlen, Hillsborough, CA (US); Klaus Koefoed, Lyngby (DK); Magnus Strandh, Lyngby (DK); Peter S. Andersen, Vanløse (DK)

(73) Assignee: Genentench, Inc., South San Francisco, CA (US)

( * ) Notice: Subject to any disclaimer, the term of this patent is extended or adjusted under 35 U.S.C. 154(b) by 302 days.

This patent is subject to a terminal disclaimer.

(21) Appl. No.: 14/292,289

(22) Filed: May 30, 2014

(65) Prior Publication Data

US 2014/0356376 A1 Dec. 4, 2014

Related U.S. Application Data

(63) Continuation-in-part of application No. 14/284,609, filed on May 22, 2014, now abandoned.

(60) Provisional application No. 61/829,461, filed on May 31, 2013.

(51) Int. Cl.
| | |
|---|---|
| *A61K 39/40* | (2006.01) |
| *C07K 16/12* | (2006.01) |
| *A61K 31/5386* | (2006.01) |
| *A61K 45/06* | (2006.01) |
| *A61K 31/4025* | (2006.01) |
| *A61K 47/68* | (2017.01) |

(52) U.S. Cl.
CPC ...... *C07K 16/1271* (2013.01); *A61K 31/4025* (2013.01); *A61K 31/5386* (2013.01); *A61K 39/40* (2013.01); *A61K 45/06* (2013.01); *A61K 47/6809* (2017.08); *A61K 47/6835* (2017.08); *C07K 2317/21* (2013.01); *C07K 2317/522* (2013.01); *C07K 2317/55* (2013.01); *C07K 2317/565* (2013.01); *C07K 2317/567* (2013.01); *C07K 2317/624* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,150,046 A | 9/1964 | Sensi et al. |
| 4,859,661 A | 8/1989 | Kano et al. |
| 4,867,973 A * | 9/1989 | Goers ............... A61K 41/0042 424/179.1 |
| 4,983,602 A | 1/1991 | Yamane et al. |
| 5,545,721 A | 8/1996 | Carroll |
| 5,786,349 A | 7/1998 | Yamashita |
| 5,981,522 A | 11/1999 | Yamashita et al. |
| 6,322,788 B1 | 11/2001 | Kim |
| 6,660,267 B1 | 12/2003 | Carroll |
| 7,271,165 B2 | 9/2007 | Van Duzer et al. |
| 7,342,011 B2 | 3/2008 | Van Duzer et al. |
| 7,498,298 B2 | 3/2009 | Doronina et al. |
| 7,521,541 B2 | 4/2009 | Eigenbrot |
| 7,547,692 B2 | 6/2009 | Van Duzer et al. |
| 7,569,677 B2 | 8/2009 | Kim |
| 7,723,485 B2 | 5/2010 | Junutula et al. |
| 8,283,294 B2 | 10/2012 | Kastrup |
| 8,617,556 B2 | 12/2013 | Beaumont et al. |
| 2005/0238649 A1 | 10/2005 | Doronina et al. |
| 2011/0059085 A1 | 3/2011 | Kim |
| 2011/0178001 A1 | 7/2011 | Dietrich et al. |
| 2011/0262477 A1 | 10/2011 | Cheng et al. |
| 2011/0301334 A1 | 12/2011 | Bhakta et al. |
| 2015/0147328 A1 | 5/2015 | Lee et al. |
| 2016/0024190 A1 | 1/2016 | Ohsawa et al. |

FOREIGN PATENT DOCUMENTS

| | | |
|---|---|---|
| WO | 00/71585 | 11/2000 |
| WO | 00/71585 A1 | 11/2000 |
| WO | 2004/050846 A2 | 6/2004 |
| WO | 2005/081711 A2 | 9/2005 |
| WO | 2009/052249 A1 | 4/2009 |
| WO | 2011/008092 A2 | 1/2011 |
| WO | 2012/113847 | 8/2012 |

OTHER PUBLICATIONS (Paul, Fundamental Immunology, 3rd Edition, 1993, pp. 292-295, under the heading "Fv Structure and Diversity in Three Dimensions").*

(Continued)

*Primary Examiner* — Patricia Duffy
(74) *Attorney, Agent, or Firm* — Viksnins Harris Padys Malen LLP

(57) ABSTRACT

The invention provides anti-wall teichoic acid antibodies and antibiotic conjugates thereof, and methods of using the same.

58 Claims, 57 Drawing Sheets

(56) References Cited

OTHER PUBLICATIONS

Rudikoff et al (PNAS, USA, Mar. 1982, 79/6:1979-1983).*
Colman P.M. (Research in Immunology, 145:33-36, 1994).*
Padlan et al (PNAS, USA 1989, 86:5938-5942).*
Bendig (Methods: A Companion to Methods in Enzymology 1995; 8: 83-93).*
MacCallum et al. (J. Mol. Biol., 262, 732-745, 1996).*
Casset et al. (Biochemical and Biophysical Research Communications, 307:198-205, 2003).*
Bamberger et al (American Family Physician 72(12):2474-2481, 2005).*
Dubowchik et al., "Doxorubicin Immunoconjugates Containing Bivalent, Lysosmally-Cleavable Dipeptide Linkages" Bioorg. & Med. Chem. Letters 12:1529-1532 ( 2002).
Kaliska et al., "Substrate specificity of *Staphylococcus aureus* cysteine proteases—Staphopains A, B and C" Biochimie 94:318-327 (Jul. 13, 2011).
Kim et al., "Glycopeptide Antibiotics Inhibit Cell-Wall Teichoic Acid Biosynthesis in *Staphylococcus aureus*" Abstracts of the Interscience Conference of Antimicrobial Agents and Chemotherapy 50 ( 2010).
King et al., "Monoclonal Antibody Conjugates of Doxorubicin Prepared with Branched Linkers: A Novel Method for Increasing the Potency of Doxorubicin Immunoconjugates" Bioconjugate Chemistry 10(2):279-288 (Mar. 1, 1999).
Suzuki et al., "In Vitro Antimicrobial Activity of Wall Teichoic Acid Biosynthesis Inhibitors against *Staphylococcus aureus* Isolates" Antimicrobial Agents and Chemotherapy 55(2):767-774 (Feb. 1, 2011).
Brown et al., "Methicillin resistance in *Staphylococcus aureus* requires glycosylated wall teichoic acids" Proc Natl Acad Sci U S A. 109(46):18909-14 ( 2012).
Dornan et al., "Therapeutic potential of an anti-CD79b antibody-drug conjugate, anti-CD79b-vc-MMAE, for the treatment of non-Hodgkin lymphoma" Blood 114(13):2721-9 (2009).
Doronina et al., "Development of potent monoclonal antibody auristatin conjugates for cancer therapy" Nat Biotechnol 21(7):778-784 (Jul. 2003).
Doronina et al., "Novel peptide linkers for highly potent antibody-auristatin conjugate" Bioconjug Chem. 19(10):1960-3 ( 2008).
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity" Bioconjugate Chem 13:855-869 ( 2002).
Flygare et al., "Antibody-drug conjugates for the treatment of cancer" Chem Biol Drug Des. 81(1):113-21 ( 2013).
Fujii et al., "In vitro and in vivo antibacterial activities of KRM-1648 and KRM-1657, new rifamycin derivatives" Antimicrob Agents Chemother. 38(5):1118-22 ( 1994).
Garzoni et al., "*Staphylococcus aureus*: new evidence for intracellular persistence" Trends Microbiol. 17(2):59-65 ( 2009).
Hamann, "Monoclonal antibody—drug conjugates" Expert Opin Ther Patents 15(39):1087-1103 ( 2005).

Harriman et al., "Antibody discovery via multiplexed single cell characterization" J Immunol Methos. 341(1-2):135-45 ( 2009).
Hartung et al., "Stereochemical assignment of intermediates in the rifamycin biosynthetic pathway by precursor-directed biosynthesis" J Am Chem Soc. 127(32):11202-3 ( 2005).
Hazenbos et al., "Novel staphylococcal glycosyltransferases SdgA and SdgB mediate immunogenicity and protection of virulence-associated cell wall proteins" PLoS Pathog. 9(10):e1003653 ( 2013).
Junutula et al., "Rapid identification of reactive cysteine residues for site-specific labeling of antibody-Fabs" J Immunol Methods 332:41-52 ( 2008).
Junutula et al., "Site-specific conjugation of a cytotoxic drug to an antibody improves the therapeutic index" Nat Biotechnol 26(8):925-32 (Aug. 2008).
Klussman et al., "Secondary mAb-vcMMAE conjugates are highly sensitive reporters of antibody internalization via the lysosome pathway" Bioconjugate Chem 15:765-773 ( 2004).
Lantto et al., "Capturing the natural diversity of the human antibody response against vaccinia virus" J Virol. 85(4):1820-33 ( 2011).
Lehar et al., "Novel antibody-antibiotic conjugate eliminates intracellular *S. aureus*" Nature 527(7578)::323-8 ( 2015).
Lyon et al., "Conjugation of anticancer drugs through endogenous monoclonal antibody cysteine residues" Methods Enzymol 502:123-138 ( 2012).
Meijer et al., "Human antibody repertoires" Methods Mol Biol. 525:261-77 ( 2009).
Meijer et al., "Isolation of human antibody repertoires with preservation of the natural heavy and light chain pairing" J Mol Biol. 358(3):764-72 ( 2006).
Rothstein et al., "Development potential of rifalazil" Expert Opin Investig Drugs 12(2):255-71 ( 2003).
Shen et al., "Conjugation site modulates the in vivo stability and therapeutic activity of antibody-drug conjugates" Nature Biotechnology 30(2):184-190 (Feb. 2012).
Staben et al., "Targeted drug delivery through the traceless release of tertiary and heteroaryl amines from antibody-drug conjugates" Nat Chem. 8(12):1112-1119.
Xia et al., "The wall teichoic acid and lipoteichoic acid polymers of *Staphylococcus aureus*" Int J Med Microbiol. 300:148-54 ( 2010).
Yamane et al., "Synthesis and biological activity of 3'-hydroxy-5'-aminobenzoxazinorifamycin derivatives" Chem Pharm Bull 41(1):148-55 ( 1993).
Zhou et al., "Pharmacokinetics and pharmacodynamics of DSTA4637A: A novel THIOMAB™ antibody antibiotic conjugate against *Staphylococcus aureus* in mice" MAbs 8(8):1612-1619 (.
Brown et al.; "Methicillin resistance in *Staphylococcus aureus* requires glycosylated wall teichoic acids" Proc Natl Acad Sci U S A. 109(46):18909-14 ( 2012).
Dornan et al., "Therapeutic potential of an anti-CD79b antibody-drug conjugate, anti-CD79b-vc-MMAE, for the treatment of non-Hodgkin lymphoma" Blood 114(13):2721-9 ( 2009).
Hamann, "Monoclonal antibody—drug conjugates" Expert Opin Ther Patents 15(9):1087-1103 ( 2005).
Harriman et al., "Antibody discovery via multiplexed single cell characterization" J Immunol Methos. 341(1-2):135-45 ( 2009).

* cited by examiner

FIG. 6

| FIG. 6A |
| FIG. 6B |

FIG. 6A

| Antibody | Antigen | GlcNAc | KD(nM) | Antigen Density Ave.Sites Bacterium | Donor | Source Cells | Binding to Coating(s) in Primary Screening Ag (ELISA) |
|---|---|---|---|---|---|---|---|
| 4497 | WTA | beta | 2.5 | 50 | 327 | PB/PC | WTA; PGN; CW USA300 stat (iron depl:TSB in 96:4 ratio) |
| 4462 | WTA | beta | 3.1 | 43 | 326 | sMBC | WTA; PGN; CW USA300 stat (iron depl:TSB in 96:4 ratio) |
| 4450 | WTA | beta | | | 326 | sMBC | WTA; PGN; CW USA300 stat (iron depl:TSB in 96:4 ratio) |
| 4487 | WTA | beta | | | 327 | PB/PC | WTA; PGN; CW USA300 stat (iron depl:TSB in 96:4 ratio) |
| 6078 | WTA | beta | 1.4 | 22,000 | 349 | sMBC | PGN+WTA (1:1); CW USA300 stat (iron depl:TSB in 96:4 ratio) |
| 6263 | WTA | beta | 1.1 | 21,000 | 350 | PB/PC | PGN+WTA (1:1); CW USA300 stat (iron depl:TSB in 96:4 ratio) |
| 6297 | WTA | beta | | | 350 | PB/PC | PGN+WTA (1:1); CW USA300 stat (iron depl:TSB in 96:4 ratio) |
| 6239 | WTA | beta | | | 350 | PB/PC | PGN+WTA (1:1); CW USA300 stat (iron depl:TSB in 96:4 ratio) |
| 6292 | WTA | beta | | | 350 | PB/PC | PGN+WTA (1:1); CW USA300 stat (iron depl:TSB in 96:4 ratio) |
| 6232 | WTA | beta | | | 350 | PB/PC | PGN+WTA (1:1); CW USA300 stat (iron depl:TSB in 96:4 ratio) |
| 6259 | WTA | beta | | | 350 | PB/PC | CW USA300 stat (iron depl:TSB in 96:4 ratio) |
| 6253 | WTA | beta | | | 350 | PB/PC | PGN+WTA (1:1); CW USA300 stat (iron depl:TSB in 96:4 ratio) |
| 6265 | WTA | beta | | | 350 | PB/PC | PGN+WTA (1:1); CW USA300 stat (iron depl:TSB in 96:4 ratio) |

| | | | | | | |
|---|---|---|---|---|---|---|
| 4461(7574) | WTA | alpha | | | sMBC | CW USA300 stat (iron depl:TSB in 96:4 ratio) |
| 4624(7578) | WTA | alpha | 0.4 | 16 | sMBC | CW USA300 stat (iron depl:TSB in 96:4 ratio) |
| 4399 | WTA | alpha | | | sMBC | CW USA300 stat (iron depl:TSB in 96:4 ratio) |
| 6267 | WTA | alpha | | | PB/PC | CW USA300 stat (iron depl:TSB in 96:4 ratio) |
| rF1 | SDR-proteins | ? | 0.3 | 1600 | | |
| 4516(7577) | SDR-proteins | ? | | | PB/PC | WTA; PGN; CW USA300 stat (iron depl:TSB in 96:4 ratio) |
| 6234 | SDR-proteins | ? | | | PB/PC | PGN+WTA (1:1); CW USA300 stat (iron depl:TSB in 96:4 ratio) |
| 6060 | SDR-proteins | ? | | | sMBC | PGN+WTA (1:1); CW USA300 stat (iron depl:TSB in 96:4 ratio) |
| 4569 | LTA | ? | | | PB/PC | CW Wood46 stat TSB |
| 4479 | PGN | | | | PB/PC | WTA; PGN; CW USA300 stat (iron depl:TSB in 96:4 ratio) |

*FIG. 6B*

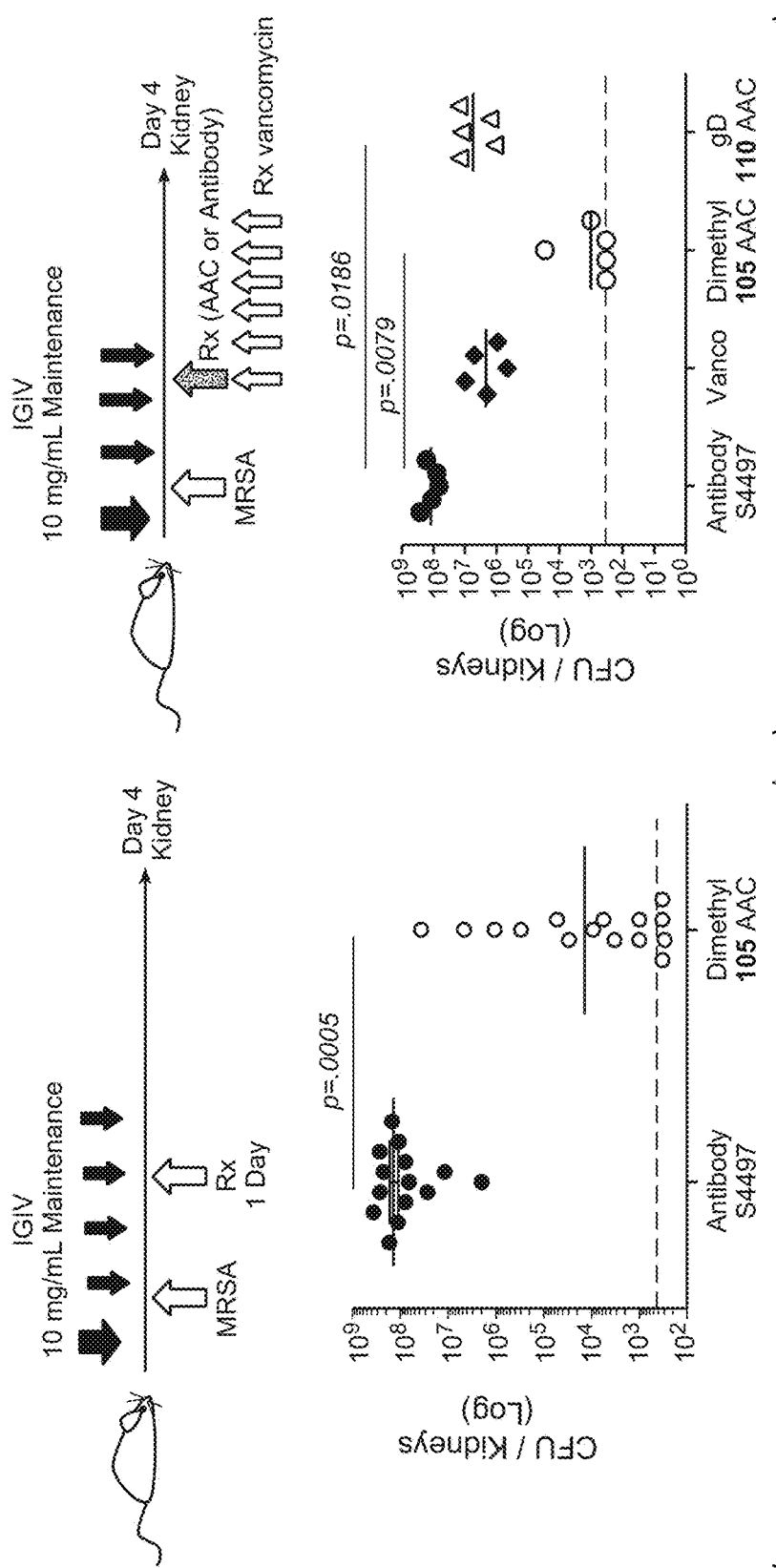

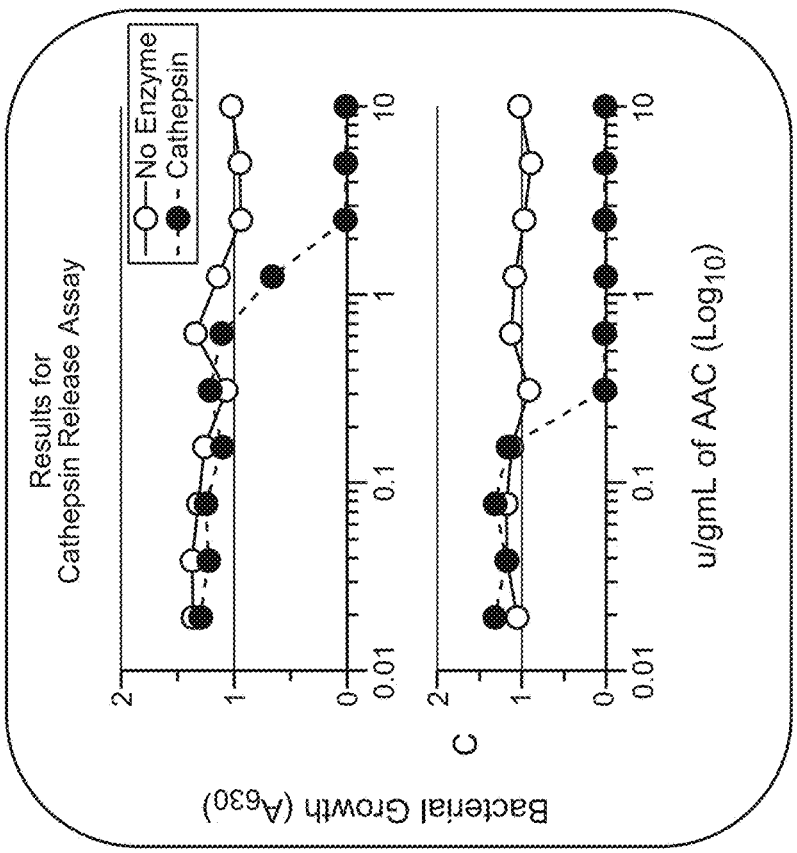
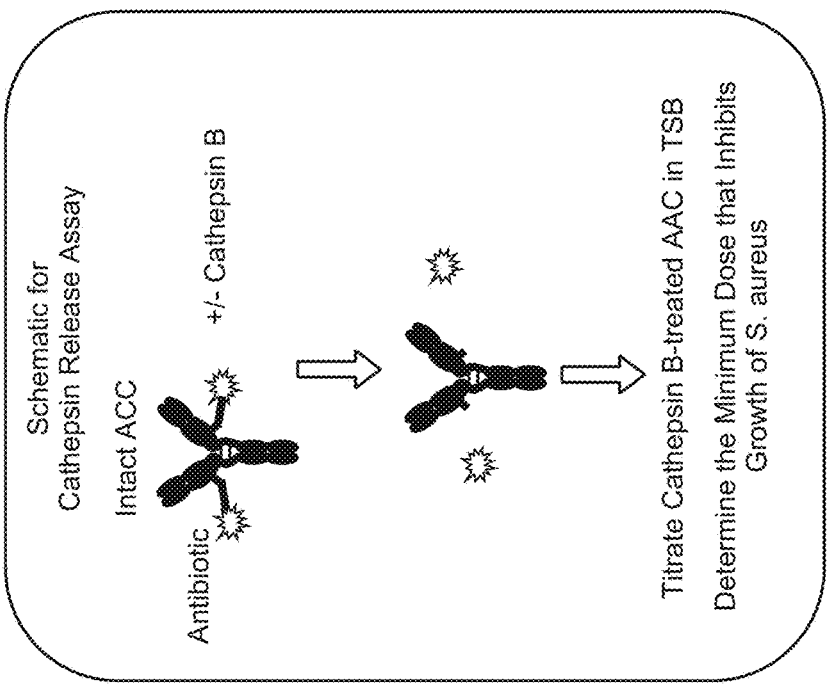
FIG. 12

CDR Sequences According to Kabat Definition are Underlined
Light Chain Variable Region

|  |  |  |  |  |  |  |  |  |  |  |  |  |  |  |  |  |  |  |  |  |  |  | CDR L1 - Chothia | | | | | | | | CDR L1 - Contact | | | |
| --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
|  |  |  |  |  |  |  |  |  |  |  |  |  |  |  |  |  |  |  |  |  |  |  |  | CDR L1 - Kabat | | | | | | | | | | | |
| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 27e | 27f | 28 | 29 | 30 | 31 | 32 | 33 | 34 | 35 | 36 |
| 4461 | D | I | Q | M | T | Q | S | P | D | S | L | A | V | S | L | G | E | R | A | T | I | N | C | K | S | S | Q | S | V | L | – | – | – | N | N | Y | V | A | W | Y |
| 4624 | D | I | Q | M | T | Q | S | P | D | S | L | A | V | S | L | G | E | R | A | T | I | N | C | R | S | S | Q | N | L | L | – | – | – | R | N | Y | Y | L | A | W | Y |
| 4399 | E | I | V | L | T | Q | S | P | A | T | L | S | L | S | P | G | E | R | A | T | I | T | C | K | S | N | Q | N | V | L | L | A | S | S | N | D | K | N | Y | L | A | W | Y |
| 6267 | D | I | Q | L | T | Q | S | P | D | S | L | A | V | S | L | G | E | R | A | T | I | N | C | K | S | S | Q | S | V | L | Y | S | S | N | N | K | N | Y | L | A | W | Y |

|  |  |  |  |  |  |  |  |  |  |  | CDR L2 - Contact | | | | | | | | |  |  |  |  |  |  |  |  |  |  |  |  |  |
| --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
|  |  |  |  |  |  |  |  |  |  |  |  |  | CDR L2 - Chothia | | | | | | |  |  |  |  |  |  |  |  |  |  |  |  |  |  |
|  |  |  |  |  |  |  |  |  |  |  |  |  |  | CDR L2 - Kabat | | | | | |  |  |  |  |  |  |  |  |  |  |  |  |  |  |
| Kabat Number | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
| 4461 | Q | H | K | P | G | Q | P | P | K | L | L | I | Y | W | A | S | T | R | E | F | G | V | P | D | R | F | S | G | S | G | S | G | T | D | F | T | L | T | I | S | S | L |
| 4624 | Q | Q | K | P | G | Q | P | P | K | L | L | I | Y | W | A | S | T | R | E | S | G | V | P | D | R | F | S | G | S | G | S | G | T | D | F | T | L | T | I | S | S | L |
| 4399 | Q | H | R | P | G | Q | P | P | R | L | L | I | Y | W | A | S | T | R | E | S | G | V | P | A | R | F | S | G | S | G | S | G | T | D | F | T | L | T | I | S | S | L |
| 6267 | Q | Q | K | P | G | Q | P | P | K | L | L | I | Y | W | A | S | T | R | E | S | G | V | P | D | R | F | S | G | S | G | S | G | T | D | F | T | L | T | I | S | S | L |

|  |  |  |  |  |  |  |  |  |  | CDR L3 - Contact | | | | | | | | |  |  |  |  |  |  |  |  |  |  |
| --- | --- | --- | --- | --- | --- | --- | --- | --- | --- | --- | --- | --- | --- | --- | --- | --- | --- | --- | --- | --- | --- | --- | --- | --- | --- | --- | --- | --- |
|  |  |  |  |  |  |  |  |  |  |  | CDR L3 - Chothia | | | | | | |  |  |  |  |  |  |  |  |  |  |  |
|  |  |  |  |  |  |  |  |  |  |  | CDR L3 - Kabat | | | | | | |  |  |  |  |  |  |  |  |  |  |  |
| Kabat Number | 79 | 80 | 81 | 82 | 83 | 84 | 85 | 86 | 87 | 88 | 89 | 90 | 91 | 92 | 93 | 94 | 95 | 95a | 96 | 97 | 98 | 99 | 100 | 101 | 102 | 103 | 104 | 105 | 106 | 107 |
| 4461 | Q | A | E | D | V | A | V | Y | Y | C | Q | Q | Y | Y | T | S | R | . | . | R | T | F | G | Q | G | T | K | V | E | I | K |
| 4624 | Q | A | E | D | V | A | V | Y | Y | C | Q | Q | Y | Y | A | N | P | . | . | R | T | F | G | Q | G | T | K | V | E | I | K |
| 4399 | R | A | E | D | V | A | V | Y | Y | C | Q | Q | Y | T | N | P | . | . | P | P | Y | T | F | G | Q | G | T | K | L | E | F | N | I |
| 6267 | Q | A | E | D | V | A | V | Y | Y | C | Q | Q | Y | Y | T | S | P | P | Y | T | F | G | G | G | T | K | L | E | I | E |

FIG. 13A

CDR Sequences According to Kabat Definition are Underlined
Heavy Chain Variable Region

```
                                                                    CDR H1 - Contact
                                                            CDR H1 - Chothia
                                                                   CDR H1 - Kabat
Kabat Number  1  2  3  4  5  6  7  8  9  10 11 12 13 14 15 16 17 18 19 20 21 22 23 24 25 26 27 28 29 30 31 32 33 34 35 36 37 38 39 40 41 42
4461          Q  V  Q  L  V  Q  S  G  A  E  V  R  K  P  G  A  S  V  K  V  S  C  K  A  S  G  Y  S  F  T  D  Y  Y  M  H  W  V  R  Q  A  P  G
4624          Q  V  Q  L  V  Q  S  G  R  V  E  V  K  K  P  G  T  S  V  K  V  S  C  K  K  T  S  G  Y  T  F  S  D  Y  Y  I  H  W  V  R  L  A  P  G
4399          E  V  Q  L  V  Q  S  G  A  E  V  K  K  P  G  E  S  L  K  I  S  C  K  G  S  G  Y  T  F  T  D  Y  Y  I  H  W  V  R  Q  M  P  G
6267          E  V  Q  L  V  Q  S  G  A  E  V  K  K  P  G  E  S  L  K  I  S  C  K  G  S  G  Y  S  F  T  S  Y  W  I  G  W  V  R  Q  M  P  G CDR H2 - Contact
                                                 CDR H2 - Chothia
                                                    CDR H2 - Kabat
Kabat Number  43 44 45 46 47 48 49 50 51 52 52a 53 54 55 56 57 58 59 60 61 62 63 64 65 66 67 68 69 70 71 72 73 74 75 76 77 78 79 80 81 82 82a
4461          Q  G  L  E  W  M  G  W  I  N  P   K  S  G  G  T  N  Y  A  Q  K  F  Q  G  R  V  T  M  T  G  D  T  S  I  S  A  A  Y  M  D  L  A
4624          Q  G  L  E  W  I  G  W  I  N  P   N  T  G  G  T  N  Y  A  Q  K  F  Q  G  R  V  T  F  T  M  T  R  D  T  S  I  A  T  A  Y  M  E  M  S
4399          Q  G  L  E  W  M  G  W  I  T  H   P  G  D  S  K  T  R  Y  S  P  S  F  Q  G  Q  V  T  I  S  A  D  K  S  I  S  T  A  Y  L  Q
6267          K  G  L  E  W  M  G  I  I   H  P  S  D  S  D  T  R  Y  S  P  S  F  Q  G  Q  V  T  I  S  A  D  K  S  I  S  T  A  Y  L  Q  W  N CDR H3 - Contact
                                                                                         CDR H3 - Chothia
                                                                                            CDR H3 - Kabat
Kabat Number  82b 82c 83 84 85 86 87 88 89 90 91 92 93 94 95 96 97 98 99 100 100a 100b 100c 100d 100e 100f 100g 100h 100i 100j 100k 100l 100m 100n 100o 100p 100q 100r 100s 100t 100u 101
4461          S   L   T  S  D  D  T  A  V  Y  Y  C  V  K  D  C  G  G  I  R   .    .    .    .    .    S    R    A    F    S    .    L    G    A    G    G    Y    Y    Y    .    G    M    G
4624          S   L   T  S  E  D  T  A  M  Y  Y  C  C  A  K  D  C  G  G  L  R   .    .    .    .    .    S    D    R    .    .    .    .    .    .    .    C    Y    S    .    .    G    M    G
4399          S   L   K  A  S  D  T  A  M  Y  Y  C  A  R  H  Y  C  S  G  G   .    .    .    .    .    .    .    .    .    .    .    .    .    .    .    .    .    .    .    .    .    Y    G   
6267          S   L   Q  F  S  S  V  T  A  A  D  T  A  V  Y  Y  C  A  R  H  Y  C  S  S  S  C  Y  .  .  S  D  R  A  F  S  L  G  A  G  G  Y  Y  Y  Y  Y  G  M  G Kabat Number  102 103 104 105 106 107 108 109 110 111 112 113
4461          F   W   G   Q   G   T   T   V   T   V   S   S
4624          Q   G   T   L   V   T   V   S   S
4399          Y   W   G   Q   G   T   L   V   T   V   S   S
6267          V   W   G   Q   G   T   T   V   T   V   S   S
```

FIG. 13B

| Antibody | CDR L1 | CDR L2 | CDR L3 | CDR H1 | CDR H2 | CDR H3 |
|---|---|---|---|---|---|---|
| 6078 | RASQTISGWLA (SEQ ID NO:33) | KASTLES (SEQ ID NO:34) | QQYKSYSFN (SEQ ID NO:35) | SYDIN (SEQ ID NO:36) | WMNANSGNTGYAQKFQG (SEQ ID NO:37) | SSILVRGALGRYFDL (SEQ ID NO:38) |
| 6263 | RASQTISGWLA (SEQ ID NO:39) | KASTLES (SEQ ID NO:40) | QQYKSYSFN (SEQ ID NO:41) | SYDIN (SEQ ID NO:42) | WMNANSGNTGYAQKFQG (SEQ ID NO:43) | SSILVRGALGRYFDL (SEQ ID NO:44) |
| 4450 | RASQFVSRTSLA (SEQ ID NO:45) | ETSSRAT (SEQ ID NO:46) | HKYGSGPRT (SEQ ID NO:47) | NYDFI (SEQ ID NO:48) | WMNPSYNTGYGQKFQG (SEQ ID NO:49) | AVRGQLLSEY (SEQ ID NO:50) |
| 6297 | RASQSVSSSYLA (SEQ ID NO:51) | DASSRAT (SEQ ID NO:52) | QKYGSTPRP (SEQ ID NO:53) | SYDIN (SEQ ID NO:54) | WMNPNSGNTNYAQRFQG (SEQ ID NO:55) | ERWSKDTGHYYYYGMDV (SEQ ID NO:56) |
| 6239 | RASLDITNHLA (SEQ ID NO:57) | EASILQS (SEQ ID NO:58) | EKCNSTPRT (SEQ ID NO:59) | NYDIN (SEQ ID NO:60) | WMNPSSGRTGYAPKFRG (SEQ ID NO:61) | GGGYYDSSGNYHISGLDV (SEQ ID NO:62) |
| 6232 | RASQSVGAIYLA (SEQ ID NO:63) | GVSNRAT (SEQ ID NO:64) | QLYTSSRALT (SEQ ID NO:65) | AYAMN (SEQ ID NO:66) | SITKNSDSLYYADSVKG (SEQ ID NO:67) | LAARIMATDY (SEQ ID NO:68) |
| 6259 | RASQGIRNGLG (SEQ ID NO:69) | PASTLES (SEQ ID NO:70) | LQDHNYPPT (SEQ ID NO:71) | YYSMI (SEQ ID NO:72) | SIDSSSRYLYYADSVKG (SEQ ID NO:73) | DGDDILSVYRGSGRPFDY (SEQ ID NO:74) |
| 6292 | RASQGIRNGLG (SEQ ID NO:75) | PASTLES (SEQ ID NO:76) | LQDHNYPPS (SEQ ID NO:77) | YYSMI (SEQ ID NO:78) | SIDSSSRYRYYTDSVKG (SEQ ID NO:79) | DGDDILSVYQGSGRPFDY (SEQ ID NO:80) |
| 4462 | RASQSVRTNVA (SEQ ID NO:81) | GASTRAS (SEQ ID NO:82) | LQYNTWPRT (SEQ ID NO:83) | TNDMS (SEQ ID NO:84) | TIIGIDDTTHYADSVRG (SEQ ID NO:85) | NSGIYSF (SEQ ID NO:86) |
| 6265 | RASQDIGSSLA (SEQ ID NO:87) | ATSTLQS (SEQ ID NO:88) | QQLNNYVHS (SEQ ID NO:89) | DYAMG (SEQ ID NO:90) | VVTGHSYRTHYADSVKG (SEQ ID NO:91) | RIWSYGDDSFDV (SEQ ID NO:92) |
| 6253 | RASQSIGDRLA (SEQ ID NO:93) | WASNLEG (SEQ ID NO:94) | QQYKSQWS (SEQ ID NO:95) | SYAMN (SEQ ID NO:96) | YISSIETIYYADSVKG (SEQ ID NO:97) | DRLVDVPLSSPNS (SEQ ID NO:98) |
| 4497 | KSSQSIFRTSRNKNLLN (SEQ ID NO:99) | WASTRKS (SEQ ID NO:100) | QQYFSPPYT (SEQ ID NO:101) | SFWMH (SEQ ID NO:102) | FTNNEGTTTAYADSVRG (SEQ ID NO:103) | GDGGLDD (SEQ ID NO:104) |
| 4487 | RASQFTNHYLN (SEQ ID NO:105) | VASNLQS (SEQ ID NO:106) | QQSYRTPYT (SEQ ID NO:107) | SGYYN (SEQ ID NO:108) | YILSGAHTDIKASLGS (SEQ ID NO:109) | SGVYSKYSLDV (SEQ ID NO:110) |

6263 has same CDR sequences as 6078.

Heavy Chain

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 6078 | Q | V | Q | L | V | Q | S | G | A | E | V | K | K | P | G | A | S | V | K | V | S | C | E | A | S | G | Y | T | F | T | S | Y | D | I | N | W | V | R | Q | A | T | G |
| 6078.v2HC-Cys | E | T | Q | L | V | Q | S | G | A | E | V | K | K | P | G | A | S | V | K | V | S | C | E | A | S | G | Y | T | F | T | S | Y | D | I | N | W | V | R | Q | A | T | G |
| 6078.v2LC-Cys | E | T | Q | L | V | Q | S | G | A | E | V | K | K | P | G | A | S | V | K | V | S | C | E | A | S | G | Y | T | F | T | S | Y | D | I | N | W | V | R | Q | A | T | G |
| 6078.v3HC-Cys | E | T | Q | L | V | Q | S | G | A | E | V | K | K | P | G | A | S | V | K | V | S | C | E | A | S | G | Y | T | F | T | S | Y | D | I | N | W | V | R | Q | A | T | G |
| 6078.v3LC-Cys | E | V | Q | L | V | Q | S | G | A | E | V | K | K | P | G | A | S | V | K | V | S | C | E | A | S | G | Y | T | F | T | S | Y | D | I | N | W | V | R | Q | A | T | G |
| 6078.v4HC-Cys | E | V | Q | L | V | Q | S | G | A | E | V | K | K | P | G | A | S | V | K | V | S | C | E | A | S | G | Y | T | F | T | S | Y | D | I | N | W | V | R | Q | A | T | G |
| 6078.v4LC-Cys | E | V | Q | L | V | Q | S | G | A | E | V | K | K | P | G | A | S | V | K | V | S | C | E | A | S | G | Y | T | F | T | S | Y | D | I | N | W | V | R | Q | A | T | G |
| 6078.v4HCLC-Cys | E | V | Q | L | V | Q | S | G | A | E | V | K | K | P | G | A | S | V | K | V | S | C | E | A | S | G | Y | T | F | T | S | Y | D | I | N | W | V | R | Q | A | T | G |

CDR H1 - Contact: positions 30-35
CDR H1 - Chothia: positions 26-32
CDR H1 - Kabat: positions 31-35

| Kabat Number | 43 | 44 | 45 | 46 | 47 | 48 | 49 | 50 | 51 | 52 | 52a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82a |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 6078 | Q | G | L | E | W | M | G | W | M | N | A | N | S | G | N | T | G | Y | A | Q | K | F | Q | G | R | V | T | L | T | T | D | T | S | T | S | T | A | Y | M | E | L | S |
| 6078.v2HC-Cys | Q | G | L | E | W | M | G | W | M | N | A | N | S | G | N | T | G | Y | A | Q | K | F | Q | G | R | V | T | L | T | T | D | T | S | T | S | T | A | Y | M | E | L | S |
| 6078.v2LC-Cys | Q | G | L | E | W | M | G | W | M | N | A | N | S | G | N | T | G | Y | A | Q | K | F | Q | G | R | V | T | L | T | T | D | T | S | T | S | T | A | Y | M | E | L | S |
| 6078.v3HC-Cys | Q | G | L | E | W | M | G | W | M | N | A | N | S | G | N | T | G | Y | A | Q | K | F | Q | G | R | V | T | L | T | T | D | T | S | T | S | T | A | Y | M | E | L | S |
| 6078.v3LC-Cys | Q | G | L | E | W | M | G | W | M | N | A | N | S | G | N | T | G | Y | A | Q | K | F | Q | G | R | V | T | L | T | T | D | T | S | T | S | T | A | Y | M | E | L | S |
| 6078.v4HC-Cys | Q | G | L | E | W | M | G | W | M | N | A | N | S | G | N | T | G | Y | A | Q | K | F | Q | G | R | V | T | L | T | T | D | T | S | T | S | T | A | Y | M | E | L | S |
| 6078.v4LC-Cys | Q | G | L | E | W | M | G | W | M | N | A | N | S | G | N | T | G | Y | A | Q | K | F | Q | G | R | V | T | L | T | T | D | T | S | T | S | T | A | Y | M | E | L | S |
| 6078.v4HCLC-Cys | Q | G | L | E | W | M | G | W | M | N | A | N | S | G | N | T | G | Y | A | Q | K | F | Q | G | R | V | T | L | T | T | D | T | S | T | S | T | A | Y | M | E | L | S |

CDR H2 - Contact: positions 50-58
CDR H2 - Chothia: positions 52-56
CDR H2 - Kabat: positions 50-65

CDR Sequences According to Kabat Definition are Underlined
Light Chain

| Kabat Number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 27e | 27f | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 4497 | D | I | Q | L | T | Q | S | P | S | S | L | A | V | S | L | G | E | R | A | T | I | N | C | K | S | S | Q | S | I | F | R | T | S | R | N | K | L | L | N | W | Y |
| 4497.v8-HC-Cys | D | I | Q | L | T | Q | S | P | S | S | L | A | V | S | L | G | E | R | A | T | I | N | C | K | S | S | Q | S | I | F | R | T | S | R | N | K | L | L | N | W | Y |
| 4497.v8-LC-Cys | D | I | Q | L | T | Q | S | P | S | S | L | A | V | S | L | G | E | R | A | T | I | N | C | K | S | S | Q | S | I | F | R | T | S | R | N | K | L | L | N | W | Y |
| 4497.v8-HCLC-Cys | D | I | Q | L | T | Q | S | P | S | S | L | A | V | S | L | G | E | R | A | T | I | N | C | K | S | S | Q | S | I | F | R | T | S | R | N | K | L | L | N | W | Y |

CDR L1 – Chothia: positions 24–34; CDR L1 – Kabat: positions 24–36; CDR H1 – Contact

| Kabat Number | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 4497 | Q | Q | K | P | G | Q | P | P | R | L | L | I | H | W | A | S | T | R | K | S | G | V | P | D | R | F | S | G | S | G | F | G | T | D | F | T | L | T | I | S | S | L |
| 4497.v8-HC-Cys | Q | Q | K | P | G | Q | P | P | R | L | L | I | H | W | A | S | T | R | K | S | G | V | P | D | R | F | S | G | S | G | F | G | T | D | F | T | L | T | I | S | S | L |
| 4497.v8-LC-Cys | Q | Q | K | P | G | Q | P | P | R | L | L | I | H | W | A | S | T | R | K | S | G | V | P | D | R | F | S | G | S | G | F | G | T | D | F | T | L | T | I | S | S | L |
| 4497.v8-HCLC-Cys | Q | Q | K | P | G | Q | P | P | R | L | L | I | H | W | A | S | T | R | K | S | G | V | P | D | R | F | S | G | S | G | F | G | T | D | F | T | L | T | I | S | S | L |

CDR L2 – Contact; CDR L2 – Chothia; CDR L2 – Kabat

| Kabat Number | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 | 116 | 117 | 118 | 119 | 120 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 4497 | Q | A | E | D | V | A | I | Y | Y | C | Q | Q | Y | F | S | P | P | Y | T | F | G | Q | G | T | K | L | E | I | K | R | T | V | A | A | P | S | V | F | I | F | P | P |
| 4497.v8-HC-Cys | Q | A | E | D | V | A | I | Y | Y | C | Q | Q | Y | F | S | P | P | Y | T | F | G | Q | G | T | K | L | E | I | K | R | T | V | A | A | P | S | V | F | I | F | P | P |
| 4497.v8-LC-Cys | Q | A | E | D | V | A | I | Y | Y | C | Q | Q | Y | F | S | P | P | Y | T | F | G | Q | G | T | K | L | E | I | K | R | T | V | A | A | P | S | V | F | I | F | P | P |
| 4497.v8-HCLC-Cys | Q | A | E | D | V | A | I | Y | Y | C | Q | Q | Y | F | S | P | P | Y | T | F | G | Q | G | T | K | L | E | I | K | R | T | V | A | A | P | S | V | F | I | F | P | P |

CDR L3 – Contact; CDR L3 – Chothia; CDR L3 – Kabat; Constant Region, Eu Number

| Eu Number | 380 | 381 | 382 | 383 | 384 | 385 | 386 | 387 | 388 | 389 | 390 | 391 | 392 | 393 | 394 | 395 | 396 | 397 | 398 | 399 | 400 | 401 | 402 | 403 | 404 | 405 | 406 | 407 | 408 | 409 | 410 | 411 | 412 | 413 | 414 | 415 | 416 | 417 | 418 | 419 | 420 | 421 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 4497 | E | W | E | S | N | G | Q | P | E | N | N | Y | K | T | T | P | P | V | L | D | S | D | G | S | F | F | L | Y | S | K | L | T | V | D | K | S | R | W | Q | Q | G | N |
| 4497.v8-HC-Cys | E | W | E | S | N | G | Q | P | E | N | N | Y | K | T | T | P | P | V | L | D | S | D | G | S | F | F | L | Y | S | K | L | T | V | D | K | S | R | W | Q | Q | G | N |
| 4497.v8-LC-Cys | E | W | E | S | N | G | Q | P | E | N | N | Y | K | T | T | P | P | V | L | D | S | D | G | S | F | F | L | Y | S | K | L | T | V | D | K | S | R | W | Q | Q | G | N |
| 4497.v8-HCLC-Cys | E | W | E | S | N | G | Q | P | E | N | N | Y | K | T | T | P | P | V | L | D | S | D | G | S | F | F | L | Y | S | K | L | T | V | D | K | S | R | W | Q | Q | G | N |

| Eu Number | 422 | 423 | 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 |
|---|---|---|---|---|---|---|---|---|---|---|---|---|---|---|---|---|---|---|---|---|---|---|---|---|---|
| 4497 | V | F | S | C | S | V | M | H | E | A | L | H | N | H | Y | T | Q | K | S | L | S | L | S | P | G |
| 4497.v8-HC-Cys | V | F | S | C | S | V | M | H | E | A | L | H | N | H | Y | T | Q | K | S | L | S | L | S | P | G |
| 4497.v8-LC-Cys | V | F | S | C | S | V | M | H | E | A | L | H | N | H | Y | T | Q | K | S | L | S | L | S | P | G |
| 4497.v8-HCLC-Cys | V | F | S | C | S | V | M | H | E | A | L | H | N | H | Y | T | Q | K | S | L | S | L | S | P | G |

| Eu Number | 411 | 412 | 413 | 414 | 415 | 416 | 417 | 418 | 419 | 420 | 421 | 422 | 423 | 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 |
|---|---|---|---|---|---|---|---|---|---|---|---|---|---|---|---|---|---|---|---|---|---|---|---|---|---|---|---|---|---|---|---|---|---|---|---|---|
| 6078 | T | V | D | K | S | R | W | Q | Q | G | N | V | F | S | C | S | V | M | H | E | A | L | H | N | H | Y | T | Q | K | S | L | S | L | S | P | G |
| 6263 | T | V | D | K | S | R | W | Q | Q | G | N | V | F | S | C | S | V | M | H | E | A | L | H | N | H | Y | T | Q | K | S | L | S | L | S | P | G |
| 4450 | T | V | D | K | S | R | W | Q | Q | G | N | V | F | S | C | S | V | M | H | E | A | L | H | N | H | Y | T | Q | K | S | L | S | L | S | P | G |
| 6297 | T | V | D | K | S | R | W | Q | Q | G | N | V | F | S | C | S | V | M | H | E | A | L | H | N | H | Y | T | Q | K | S | L | S | L | S | P | G |
| 6239 | T | V | D | K | S | R | W | Q | Q | G | N | V | F | S | C | S | V | M | H | E | A | L | H | N | H | Y | T | Q | K | S | L | S | L | S | P | G |
| 6232 | T | V | D | K | S | R | W | Q | Q | G | N | V | F | S | C | S | V | M | H | E | A | L | H | N | H | Y | T | Q | K | S | L | S | L | S | P | G |
| 6259 | T | V | D | K | S | R | W | Q | Q | G | N | V | F | S | C | S | V | M | H | E | A | L | H | N | H | Y | T | Q | K | S | L | S | L | S | P | G |
| 6292 | T | V | D | K | S | R | W | Q | Q | G | N | V | F | S | C | S | V | M | H | E | A | L | H | N | H | Y | T | Q | K | S | L | S | L | S | P | G |
| 4462 | T | V | D | K | S | R | W | Q | Q | G | N | V | F | S | C | S | V | M | H | E | A | L | H | N | H | Y | T | Q | K | S | L | S | L | S | P | G |
| 6265 | T | V | D | K | S | R | W | Q | Q | G | N | V | F | S | C | S | V | M | H | E | A | L | H | N | H | Y | T | Q | K | S | L | S | L | S | P | G |
| 6253 | T | V | D | K | S | R | W | Q | Q | G | N | V | F | S | C | S | V | M | H | E | A | L | H | N | H | Y | T | Q | K | S | L | S | L | S | P | G |
| 4497 | T | V | D | K | S | R | W | Q | Q | G | N | V | F | S | C | S | V | M | H | E | A | L | H | N | H | Y | T | Q | K | S | L | S | L | S | P | G |
| 4487 | T | V | D | K | S | R | W | Q | Q | G | N | V | F | S | C | S | V | M | H | E | A | L | H | N | H | Y | T | Q | K | S | L | S | L | S | P | G |

FIG. 17B-6

| FIG. 25A | FIG. 25B |

ANTI-WALL TEICHOIC ANTIBODIES AND CONJUGATES

CROSS REFERENCE TO RELATED APPLICATIONS

This application is a continuation-in-part application of U.S. application Ser. No. 14/284,609, filed on May 22, 2014, which is non-provisional application filed under 37 CFR §1.53(b), claims the benefit under 35 USC §119(e) of U.S. Provisional Application Ser. No. 61/829,461 filed on 31 May 2013, which are incorporated by reference in entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: P4960R2_US_Sequence_Listing.txt, date recorded: May 30, 2014, size: 195,241 bytes).

FIELD OF THE INVENTION

The invention relates to anti-wall teichoic acid ("anti-WTA") antibodies conjugated to rifamycin-type antibiotics and to use of the resultant antibody-antibiotic conjugates in the treatment of infectious diseases.

BACKGROUND OF THE INVENTION

Pathogenic bacteria are a substantial cause of sickness and death in both humans and animals. Prominent among these is *Staphylococcus aureus* (*S. aureus*; SA) which is the leading cause of bacterial infections in humans worldwide. *S. aureus* can cause a range of illnesses, from minor skin infections to life-threatening diseases such as pneumonia, meningitis, osteomyelitis, endocarditis, toxic shock syndrome (TSS), bacteremia, and sepsis. Its incidence ranges from skin, soft tissue, respiratory, bone, joint, endovascular to wound infections. It is still one of the five most common causes of nosocomial infections and is often the cause of postsurgical wound infections. Each year, some 500,000 patients in American hospitals contract a staphylococcal infection.

Over the last several decades infection with *S. aureus* is becoming increasingly difficult to treat largely due to the emergence of methicillin-resistant *S. aureus* (MRSA) that is resistant to all known beta-lactam antibiotics (Boucher, H. W. et al. Bad bugs, no drugs: no ESKAPE! An update from the Infectious Diseases Society of America. *Clinical infectious diseases: an official publication of the Infectious Diseases Society of America* 48, 1-12 (2009)). The circumstances are so acute, that by 2005, infection with MRSA was reported to be the leading cause of death due to a single infectious agent—responsible for over 15,000 deaths in the United States (DeLeo, F. R. & Chambers, H. F. Reemergence of antibiotic-resistant *Staphylococcus aureus* in the genomics era. *The Journal of Clinical Investigation* 119: 2464-2474 (2009)). Vancomycin, linezolid and daptomycin have become the antibiotics of choice for treating invasive MRSA infections (Boucher, H., Miller, L. G. & Razonable, R. R. Serious infections caused by methicillin-resistant *Staphylococcus aureus*. *Clinical infectious diseases: an official publication of the Infectious Diseases Society of America* 51 Suppl 2, S183-197 (2010)). However, reduced susceptibility to vancomycin and cross-resistance to linezolid and daptomycin have also been reported in MRSA clinical strains (Nannini, E., Murray, B. E. & Arias, C. A. Resistance or decreased susceptibility to glycopeptides, daptomycin, and linezolid in methicillin-resistant *Staphylococcus aureus*. *Current opinion in pharmacology* 10, 516-521 (2010)). Over time, the vancomycin dose necessary to overcome resistance has crept upward to levels where nephrotoxicity occurs. Thus, mortality and morbidity from invasive MRSA infections remains high despite these antibiotics.

Although SA is generally thought to be an extracellular pathogen, investigations going back at least 50 years have revealed its ability to infect and survive in various types of host cells, both professional phagocytes and non-phagocytic cells (Gresham, H. D. et al. Survival of *Staphylococcus aureus* inside neutrophils contributes to infection. *J Immunol* 164, 3713-3722 (2000); Anwar, S., Prince, L. R., Foster, S. J., Whyte, M. K. & Sabroe, I. The rise and rise of *Staphylococcus aureus*: laughing in the face of granulocytes. *Clinical and Experimental Immunology* 157, 216-224 (2009); Fraunholz, M. & Sinha, B. Intracellular *staphylococcus aureus*: Live-in and let die. *Frontiers in cellular and infection microbiology* 2, 43 (2012); Garzoni, C. & Kelley, W. L. Return of the Trojan horse: intracellular phenotype switching and immune evasion by *Staphylococcus aureus*. *EMBO molecular medicine* 3:115-117 (2011)). This facultative intracellular persistence enables host immune evasion, long-term colonization of the host, maintenance of a chronically infected state, and is likely a cause for clinical failures of, and relapses after, conventional antibiotic therapy. Furthermore, exposure of intracellular bacteria to suboptimal antibiotic concentrations may encourage the emergence of antibiotic resistant strains, thus making this clinical problem more acute. Consistent with these observations, treatment of patients with invasive MRSA infections such as bacteremia or endocarditis with vancomycin or daptomycin was associated with failure rates greater than 50% (Kullar, R., Davis, S. L., Levine, D. P. & Rybak, M. J. Impact of vancomycin exposure on outcomes in patients with methicillin-resistant *Staphylococcus aureus* bacteremia: support for consensus guidelines suggested targets. *Clinical infectious diseases: an official publication of the Infectious Diseases Society of America* 52, 975-981 (2011); Fowler, V. G., Jr. et al. Daptomycin versus standard therapy for bacteremia and endocarditis caused by *Staphylococcus aureus*. The New England journal of medicine 355, 653-665 (2006); Yoon, Y. K., Kim, J. Y., Park, D. W., Sohn, J. W. & Kim, M. J. Predictors of persistent methicillin-resistant *Staphylococcus aureus* bacteraemia in patients treated with vancomycin. *The Journal of antimicrobial chemotherapy* 65:1015-1018 (2010)). Therefore, a more successful anti-staphylococcal therapy should include the elimination of intracellular bacteria.

Most of today's antibacterials chemically are semisynthetic modifications of various natural compounds. These include, for example, the beta-lactam antibacterials, which include the penicillins (produced by fungi in the genus *Penicillium*), the cephalosporins, and the carbapenems. Antimicrobial compounds that are still isolated from living organisms include the aminoglycosides, whereas other antibacterials—for example, the sulfonamides, the quinolones, and the oxazolidinones, are produced solely by chemical synthesis. In accordance with this, many antibacterial compounds are classified on the basis of chemical/biosynthetic origin into natural, semisynthetic, and synthetic. Another classification system is based on biological activity; in this classification, antibacterials are divided into two broad groups according to their biological effect on microorganisms: bactericidal agents kill bacteria, and bacteriostatic agents slow down or stall bacterial growth.

Ansamycins are a class of antibiotics, including rifamycin, rifampin, rifamypicin, rifabutin, rifapentine, rifalazil, ABI-1657, and analogs thereof, that inhibit bacterial RNA polymerase and have exceptional potency against gram-positive and selective gram-negative bacteria (Rothstein, D. M., et al (2003) Expert Opin. Invest. Drugs 12 (2):255-271; U.S. Pat. No. 7,342,011; U.S. Pat. No. 7,271,165).

Immunotherapies have been reported for preventing and treating *S. aureus* (including MRSA) infections. US2011/0262477 concerns uses of bacterial adhesion proteins Eap, Emp and AdsA as vaccines to stimulate immune response against MRSA. WO2000071585 describes isolated monoclonal antibodies reactive to specific *S. aureus* strain isolates. US20110059085A1 suggests an Ab-based strategy utilizing IgM Abs specific for one or more SA capsular antigens, although no actual antibodies were described.

Teichoic acids (TA) are bacterial polysaccharides found within the cell wall of Gram-positive bacteria including SA. Wall teichoic acids (WTA) are those covalently linked to the peptidoglycan (PDG) layer of the cell wall; whereas lipoteichoic acids (LTA) are those covalently linked to the lipids of the cytoplasmic membrane. Xia et al. (2010) *Intl. J. Med. Microbiol.* 300:148-54. These glycopolymers play crucial roles in bacterial survival under disadvantageous conditions and in other basic cellular processes. The known WTA structures vary widely between bacterial species. *S. aureus* TAs are composed of repetitive polyol phosphate subunits such as ribitol phosphate or glycerol phosphate. Given their structural diversity and variability, WTAs are considered attractive targets for antibodies and as vaccines, ibid.

Antibody-drug conjugates (ADC), also known as immunoconjugates, are targeted chemotherapeutic molecules which combine ideal properties of both antibodies and cytotoxic drugs by targeting potent cytotoxic drugs to antigen-expressing tumor cells (Teicher, B. A. (2009) *Curr. Cancer Drug Targets* 9:982-1004), thereby enhancing the therapeutic index by maximizing efficacy and minimizing off-target toxicity (Carter, P. J. and Senter P. D. (2008) *The Cancer J.* 14 (3):154-169; Chari, R. V. (2008) *Acc. Chem. Res.* 41:98-107. ADC comprise a targeting antibody covalently attached through a linker unit to a cytotoxic drug moiety. Immunoconjugates allow for the targeted delivery of a drug moiety to a tumor, and intracellular accumulation therein, where systemic administration of unconjugated drugs may result in unacceptable levels of toxicity to normal cells as well as the tumor cells sought to be eliminated (Polakis P. (2005) *Curr. Opin. Pharmacol.* 5:382-387). Effective ADC development for a given target antigen depends on optimization of parameters such as target antigen expression levels, tumor accessibility (Kovtun, Y. V. and Goldmacher V. S. (2007) Cancer Lett. 255:232-240), antibody selection (U.S. Pat. No. 7,964,566), linker stability (Erickson et al (2006) Cancer Res. 66 (8):4426-4433; Doronina et al (2006) Bioconjugate Chem. 17:114-124; Alley et al (2008) Bioconjugate Chem. 19:759-765), cytotoxic drug mechanism of action and potency, drug loading (Hamblett et al (2004) Clin. Cancer Res. 10:7063-7070) and mode of linker-drug conjugation to the antibody (Lyon, R. et al (2012) Methods in Enzym. 502:123-138; Xie et al (2006) Expert. Opin. Biol. Ther. 6 (3):281-291; Kovtun et al (2006) Cancer Res. 66 (6):3214-3121; Law et al (2006) Cancer Res. 66 (4):2328-2337; Wu et al (2005) Nature Biotech. 23 (9):1137-1145; Lambert J. (2005) Current Opin. in Pharmacol. 5:543-549; Hamann P. (2005) Expert Opin. Ther. Patents 15 (9):1087-1103; Payne, G. (2003) Cancer Cell 3:207-212; Trail et al (2003) Cancer Immunol. Immunother. 52:328-337; Syrigos and Epenetos (1999) Anticancer Res. 19:605-614).

The concept of ADC in cancer therapy has also been expanded into antibacterial therapy, in this case the drug portion is an antibiotic, resulting in antibody-antibiotic conjugate (AAC). U.S. Pat. No. 5,545,721 and U.S. Pat. No. 6,660,267 describe synthesis of a non-specific immuno-globulin-antibiotic conjugate that binds to the surface of target bacteria via the antibiotic, and uses thereof for treating sepsis. U.S. Pat. No. 7,569,677 and related patents suggest prophetically antibiotic-conjugated antibodies that have an antigen-binding portion specific for a bacterial antigen (such as SA capsular polysaccharide), but lack a constant region that reacts with a bacterial Fc-binding protein (e.g., staphylococcal protein A).

SUMMARY OF THE INVENTION

The invention provides compositions referred to as "antibody-antibiotic conjugates," or "AAC") comprising an antibody conjugated by a covalent attachment to one or more rifamycin-type antibiotic moieties.

One aspect of the invention is an isolated anti-WTA monoclonal antibody, comprising a light chain and a H chain, the L chain comprising CDR L1, CDR L2, and CDR L3 and the H chain comprising CDR H1, CDR H2 and CDR H3, wherein the CDR L1, CDR L2, and CDR L3 and CDR H1, CDR H2 and CDR H3 comprise the amino acid sequences of the CDRs of each of Abs 4461 (SEQ ID NO. 1-6), 4624 (SEQ ID NO. 7-12), 4399 (SEQ ID NO. 13-18), and 6267 (SEQ ID NO. 19-24) respectively, as shown in Tables 6A and 6B.

In one embodiment, the isolated anti-WTA monoclonal antibody comprises a heavy chain variable region comprising a heavy chain variable region (VH), wherein the VH comprises at least 95% sequence identity over the length of the VH region selected from the VH sequence of SEQ ID NO. 26, SEQ ID NO. 28, SEQ ID NO. 30, SEQ ID NO. 32 of antibodies 4461, 4624, 4399, and 6267, respectively. In one embodiment this antibody further comprises a L chain variable region (VL) wherein the VL comprises at least 95% sequence identity over the length of the VL region selected from the VL sequence of SEQ ID NO: 25, SEQ ID NO. 27, SEQ ID NO. 29, SEQ ID NO. 31 of antibodies 4461, 4624, 4399, and 6267, respectively. In another embodiment, the isolated anti-WTA monoclonal antibody comprises a L chain variable region (VL) wherein the VL comprises at least 95% sequence identity over the length of the VL region selected from the VL sequence of SEQ ID NO. 25, SEQ ID NO. 27, SEQ ID NO. 29, SEQ ID NO. 31 of antibodies 4461, 4624, 4399, and 6267, respectively. In any of the preceding embodiments, the sequence identity may be 96%, 97%, 98%, 99% or 100%.

In more specific embodiments, the antibody comprises:
  (i) VL of SEQ ID NO. 25 and VH of SEQ ID NO. 26;
  (ii) VL of SEQ ID NO. 27 and VH of SEQ ID NO. 28;
  (iii) VL of SEQ ID NO. 29 and VH of SEQ ID NO. 30; or
  (iv) VL of SEQ ID NO. 31 and VH of SEQ ID NO. 32.

In some embodiments, the isolated anti-WTA (wall teichoic acid) monoclonal antibody comprising a light (L) chain and a heavy (H) chain, wherein:
  (a) the L chain comprising CDR L1 comprising the sequence of KSSQSVLSRANNNYYVA (SEQ ID NO: 1), CDR L2 comprising the sequence of WASTREF (SEQ ID NO: 2), and CDR L3 comprising the sequence of QQYYTSRRT (SEQ ID NO: 3); and the H chain comprising CDR H1 comprising the sequence of DYYMH (SEQ ID NO: 4), CDR H2 comprising the sequence of WINPKSGGTNYAQRFQG (SEQ ID NO: 5), and CDR H3 comprising the sequence of DCGSGGLRDF (SEQ ID NO: 6);

(b) the L chain comprising CDR L1 comprising the sequence of RSNQNLLSSSNNNYLA (SEQ ID NO: 7), CDR L2 comprising the sequence of WASTRES (SEQ ID NO: 8), and CDR L3 comprising the sequence of QQYYANPRT (SEQ ID NO: 9); and the H chain comprising CDR H1 comprising the sequence of DYYIH (SEQ ID NO: 10), CDR H2 comprising the sequence of WINPNTGGTYYAQKFRD (SEQ ID NO: 11), and CDR H3 comprising the sequence of DCGRG-GLRDI (SEQ ID NO: 12);

(c) the L chain comprising CDR L1 comprising the sequence of KSNQNVLASSNDKNYLA (SEQ ID NO: 13), CDR L2 comprising the sequence of WASIRES (SEQ ID NO: 14), and CDR L3 comprising the sequence of QQYYTNPRT (SEQ ID NO: 15); and the H chain comprising CDR H1 comprising the sequence of DYYIH (SEQ ID NO: 16), CDR H2 comprising the sequence of WINPNTGGTNYAQKFQG (SEQ ID NO: 17), and CDR H3 comprising the sequence of DCG-NAGLRDI (SEQ ID NO: 18); or (d) the L chain comprising CDR L1 comprising the sequence of KSSQNVLYSSNNKNYLA (SEQ ID NO: 19), CDR L2 comprising the sequence of WASTRES (SEQ ID NO: 20), and CDR L3 comprising the sequence of QQYYTSPPYT (SEQ ID NO: 21); and the H chain comprising CDR H1 comprising the sequence of SYWIG (SEQ ID NO: 22), CDR H2 comprising the sequence of IIHPGDSKTRYSPSFQG (SEQ ID NO: 23), and CDR H3 comprising the sequence of LYC-SGGSCYSDRAFSSLGAGGYYYYGMGV (SEQ ID NO: 24).

In any one of the preceding embodiments, the antibody may be an antigen-binding fragment lacking a Fc region. In some embodiments, the antibody is a F(ab) or F(ab')$_2$. In some embodiments, the antibody further comprises a heavy chain constant region and/or a light chain constant region, wherein the heavy chain constant region and/or the light chain constant region comprise one or more amino acids that are substituted with cysteine residues. In some embodiments, the heavy chain constant region comprises amino acid substitution A118C and/or S400C, and/or the light chain constant region comprises amino acid substitution V205C, wherein the numbering is according to the EU numbering. In some embodiments, the heavy chain constant region comprises the amino acid sequence of SEQ ID NO: 149 and/or the light chain constant region comprises the amino acid sequence of SEQ ID NO: 151. In some embodiments, the heavy chain constant region comprises the amino acid sequence of SEQ ID NO: 149 and the light chain constant region comprises the amino acid sequence of SEQ ID NO: 150. In some embodiments, the heavy chain constant region comprises the amino acid sequence of SEQ ID NO: 148 and the light chain constant region comprises the amino acid sequence of SEQ ID NO: 151.

In one aspect, the Ab of any one of the preceding embodiments binds WTA alpha.

In another aspect, the invention provides an isolated anti-WTA monoclonal antibody comprising a light chain and a H chain, the L chain comprising CDR L1, CDR L2, and CDR L3 and/or the H chain comprising CDR H1, CDR H2 and CDR H3, wherein the CDR L1, CDR L2, and CDR L3 and CDR H1, CDR H2 and CDR H3 comprise the amino acid sequences of the corresponding CDRs of each of Abs shown in FIG. 14 (SEQ ID NO. 33-110). In another aspect, the invention provides an isolated anti-WTA monoclonal antibody comprising a light chain and a H chain, the L chain comprising CDR L1, CDR L2, and CDR L3 and/or the H chain comprising CDR H1, CDR H2 and CDR H3, wherein the CDR L1, CDR L2, and CDR L3 and CDR H1, CDR H2 and CDR H3 comprise the amino acid sequences of the corresponding CDRs of each of Abs shown in FIGS. 15A, 15B, 16A and 16B (antibodies 6078, 6078.v2HC-Cys, 6078.v2LC-Cys, 6078.v3HC-Cys, 6078.v3LC-Cys, 6078.v4HC-Cys, 6078.v4LC-Cys, 6078.v4HCLC-Cys, 4497, 4497.v8HC-Cys, 4497.v8LC-Cys, and 4497.v8HCLC-Cys). In a specific embodiment these Abs bind WTA beta.

In another aspect, the invention provides an isolated anti-WTA monoclonal antibody, specifically anti-WTA beta monoclonal antibody which comprises a L chain variable region (VL) wherein the VL comprises at least 95% sequence identity over the length of the VL region selected from the VL sequence corresponding to each of the antibodies 6078, 6263, 4450, 6297, 6239, 6232, 6259, 6292, 4462, 6265, 6253, 4497, and 4487 respectively, as shown in FIGS. 17A-1 to 17A-2 at Kabat positions 1-107. In further embodiments, the antibody further comprises a heavy chain variable region comprising a heavy chain variable region (VH), wherein the VH comprises at least 95% sequence identity over the length of the VH region selected from the VH sequences corresponding to each of the antibodies 6078, 6263, 4450, 6297, 6239, 6232, 6259, 6292, 4462, 6265, 6253, 4497, and 4487 respectively, as shown in FIGS. 17B-1 to 17B-2 at Kabat positions 1-113. In any of the preceding embodiments, the sequence identity may be 96%, 97%, 98%, 99% or 100%. In a more specific embodiment of the antibody, the VH comprises the sequence of SEQ ID NO. 112 and the VL comprises the SEQ ID NO. 111.

In another aspect, the invention provides an isolated anti-WTA monoclonal antibody, specifically anti-WTA beta monoclonal antibody which comprises a L chain variable region (VL) wherein the VL comprises at least 95% sequence identity over the length of the VL region selected from the VL sequence corresponding to each of the antibodies as shown in FIG. 15A or 16A (antibodies 6078, 6078.v2HC-Cys, 6078.v2LC-Cys, 6078.v3HC-Cys, 6078.v3LC-Cys, 6078.v4HC-Cys, 6078.v4LC-Cys, 6078.v4HCLC-Cys, 4497, 4497.v8HC-Cys, 4497.v8LC-Cys, and 4497.v8HCLC-Cys) at Kabat positions 1-107. In further embodiments, the antibody further comprises a heavy chain variable region comprising a heavy chain variable region (VH), wherein the VH comprises at least 95% sequence identity over the length of the VH region selected from the VH sequences corresponding to each of the antibodies as shown in FIGS. 15B and 16B (antibodies 6078, 6078.v2HC-Cys, 6078.v2LC-Cys, 6078.v3HC-Cys, 6078.v3LC-Cys, 6078.v4HC-Cys, 6078.v4LC-Cys, 6078.v4HCLC-Cys, 4497, 4497.v8HC-Cys, 4497.v8LC-Cys, and 4497.v8HCLC-Cys) at Kabat positions 1-113. In any of the preceding embodiments, the sequence identity may be 96%, 97%, 98%, 99% or 100%.

In a certain embodiment, the isolated anti-WTA beta antibody is one wherein the light chain comprises the sequence of SEQ ID NO. 115 and the H chain having an engineered cysteine comprises the sequence of SEQ ID NO. 116. In another embodiment, the antibody is one wherein the light chain comprises the sequence of SEQ ID NO. 115 and the H chain having an engineered cysteine comprises the sequence of SEQ ID NO. 117, wherein X is M, I or V. In a different embodiment the L chain comprising the sequence of SEQ ID NO. 113) is paired with a Cys-engineered H chain variant of SEQ ID NO. 117; the variant is one wherein X is M, I or V.

Another isolated anti-WTA beta antibody provided by the invention comprises a heavy chain and a light, wherein the heavy chain comprises a VH having at least 95% sequence identity to SEQ ID NO. 120. In an additional embodiment, this antibody further comprises a VL having at least 95% sequence identity to SEQ ID NO. 119. In a specific embodiment, the anti-WTA beta antibody comprises a light chain and a heavy chain, wherein the L chain comprises a VL sequence of SEQ ID NO. 119 and the H chain comprises a VH sequence of SEQ ID NO. 120. In a yet more specific embodiment, the isolated antibody that binds WTA beta comprises a L chain of SEQ ID NO. 121 and a H chain of SEQ ID NO. 122.

The anti-WTA beta Cys-engineered H and L chain variants can be paired in any of the following combinations to form full Abs for conjugating to linker-Abx intermediates to generate anti-WTA AACs of the invention. In one embodiment, the L chain comprises the sequence of SEQ ID NO. 121 and the H chain comprises the sequence of SEQ ID NO. 124. In another embodiment, the isolated antibody comprises a L chain of SEQ ID NO. 123 and a H chain comprising a sequence of SEQ ID NO. 124 or SEQ ID NO. 157. In a particular embodiment, the anti-WTA beta antibody as well as the anti-WTA beta AAC of the invention comprises a L chain of SEQ ID NO. 123.

Yet another embodiment is an antibody that binds to the same epitope as each of the anti-WTA alpha Abs of FIG. 13A and FIG. 13B. Also provided is an antibody that binds to the same epitope as each of the anti-WTA beta Abs of FIG. 14, FIGS. 15A and 15B, FIGS. 16A and 16B, and FIGS. 17A and 17B.

In a further embodiment, the anti-WTA beta and anti-WTA alpha antibodies of the present invention are antigen-binding fragments lacking the Fc region, preferably F(ab')$_2$ or F(ab). Thus, the present invention provides antibody-antibiotic conjugates wherein the WTA antibody is a F(ab')$_2$ or F(ab).

In another aspect, the invention provides an anti-WTA monoclonal antibody that binds to WTA beta.

In some embodiments, the isolated anti-WTA (wall teichoic acid) monoclonal antibody comprising a light (L) chain and a heavy (H) chain, wherein:

(a) the L chain comprising CDR L1 comprising the sequence of RASQTISGWLA (SEQ ID NO: 33), CDR L2 comprising the sequence of KASTLES (SEQ ID NO: 34), and CDR L3 comprising the sequence of QQYKSYSFN (SEQ ID NO: 35); and the H chain comprising CDR H1 comprising the sequence of SYDIN (SEQ ID NO: 36), CDR H2 comprising the sequence of WMNANSGNTGYAQKFQG (SEQ ID NO: 37), and CDR H3 comprising the sequence of SSILVRGALGRYFDL (SEQ ID NO: 38);

(b) the L chain comprising CDR L1 comprising the sequence of RASQTISGWLA (SEQ ID NO: 39), CDR L2 comprising the sequence of KASTLES (SEQ ID NO: 40), and CDR L3 comprising the sequence of QQYKSYSFN (SEQ ID NO: 41); and the H chain comprising CDR H1 comprising the sequence of SYDIN (SEQ ID NO: 42), CDR H2 comprising the sequence of WMNANSGNTGYAQKFQG (SEQ ID NO: 43), and CDR H3 comprising the sequence of SSILVRGALGRYFDL (SEQ ID NO: 44);

(c) the L chain comprising CDR L1 comprising the sequence of RASQFVSRTSLA (SEQ ID NO: 45), CDR L2 comprising the sequence of ETSSRAT (SEQ ID NO: 46), and CDR L3 comprising the sequence of HKYGSGPRT (SEQ ID NO: 47); and the H chain comprising CDR H1 comprising the sequence of NYDFI (SEQ ID NO: 48), CDR H2 comprising the sequence of WMNPNSYNTGYGQKFQG (SEQ ID NO: 49), and CDR H3 comprising the sequence of AVRGQLLSEY (SEQ ID NO: 50);

(d) the L chain comprising CDR L1 comprising the sequence of RASQSVSSSYLA (SEQ ID NO: 51), CDR L2 comprising the sequence of DASSRAT (SEQ ID NO: 52), and CDR L3 comprising the sequence of QKYGSTPRP (SEQ ID NO: 53); and the H chain comprising CDR H1 comprising the sequence of SYDIN (SEQ ID NO: 54), CDR H2 comprising the sequence of WMNPNSGNTNYAQRFQG (SEQ ID NO: 55), and CDR H3 comprising the sequence of ERSKDTGHYYYYGMDV (SEQ ID NO: 56);

(e) the L chain comprising CDR L1 comprising the sequence of RASLDITNHLA (SEQ ID NO: 57), CDR L2 comprising the sequence of EASILQS (SEQ ID NO: 58), and CDR L3 comprising the sequence of EKCNSTPRT (SEQ ID NO: 59); and the H chain comprising CDR H1 comprising the sequence of NYDIN (SEQ ID NO: 60), CDR H2 comprising the sequence of WMNPSSGRTGYAPKFRG (SEQ ID NO: 61), and CDR H3 comprising the sequence of GGGYYDSSGNYHISGLDV (SEQ ID NO: 62);

(f) the L chain comprising CDR L1 comprising the sequence of RASQSVGAIYLA (SEQ ID NO: 63), CDR L2 comprising the sequence of GVSNRAT (SEQ ID NO: 64), and CDR L3 comprising the sequence of QLYTSSRALT (SEQ ID NO: 65); and the H chain comprising CDR H1 comprising the sequence of AYAMN (SEQ ID NO: 66), CDR H2 comprising the sequence of SITKNSDSLYYADSVKG (SEQ ID NO: 67), and CDR H3 comprising the sequence of LAARIMATDY (SEQ ID NO: 68); (g) the L chain comprising CDR L1 comprising the sequence of RASQGIRNGLG (SEQ ID NO: 69), CDR L2 comprising the sequence of PASTLES (SEQ ID NO: 70), and CDR L3 comprising the sequence of LQDHNYPPT (SEQ ID NO: 71); and the H chain comprising CDR H1 comprising the sequence of YYSMI (SEQ ID NO: 72), CDR H2 comprising the sequence of SIDSSSRYLYYADSVKG (SEQ ID NO: 73), and CDR H3 comprising the sequence of DGDDILSVYRGSGRPFDY (SEQ ID NO: 74);

(h) the L chain comprising CDR L1 comprising the sequence of RASQGIRNGLG (SEQ ID NO: 75), CDR L2 comprising the sequence of PASTLES (SEQ ID NO: 76), and CDR L3 comprising the sequence of LQDHNYPPS (SEQ ID NO: 77); and the H chain comprising CDR H1 comprising the sequence of YYSMI (SEQ ID NO: 78), CDR H2 comprising the sequence of SIDSSSRYRYYTDSVKG (SEQ ID NO: 79), and CDR H3 comprising the sequence of DGDDILSVYQGSGRPFDY (SEQ ID NO: 80);

(i) the L chain comprising CDR L1 comprising the sequence of RASQSVRTNVA (SEQ ID NO: 81), CDR L2 comprising the sequence of GASTRAS (SEQ ID NO: 82), and CDR L3 comprising the sequence of LQYNTWPRT (SEQ ID NO: 83); and the H chain comprising CDR H1 comprising the sequence of TNDMS (SEQ ID NO: 84), CDR H2 comprising the sequence of TIIGIDDTTHYADSVRG (SEQ ID NO: 85), and CDR H3 comprising the sequence of NSGI-YSF (SEQ ID NO: 86);

(j) the L chain comprising CDR L1 comprising the sequence of RASQDIGSSLA (SEQ ID NO: 87), CDR L2 comprising the sequence of ATSTLQS (SEQ ID NO: 88), and CDR L3 comprising the sequence of QQLNNYVHS (SEQ ID NO: 89); and the H chain comprising CDR H1 comprising the sequence of DYAMG (SEQ ID NO: 90), CDR H2 comprising the sequence of VVTGHSYRTHYADSVKG (SEQ ID NO: 91), and CDR H3 comprising the sequence of RIWSYGDDSFDV (SEQ ID NO: 92);

(k) the L chain comprising CDR L1 comprising the sequence of RASQSIGDRLA (SEQ ID NO: 93), CDR L2 comprising the sequence of WASNLEG (SEQ ID NO: 94), and CDR L3 comprising the sequence of QQYKSQWS (SEQ ID NO: 95); and the H chain comprising CDR H1 comprising the sequence of SYAMN (SEQ ID NO: 96), CDR H2 comprising the sequence of YISSIETIYYADSVKG (SEQ ID NO: 97), and CDR H3 comprising the sequence of DRLVDV-PLSSPNS (SEQ ID NO: 98);

(l) the L chain comprising CDR L1 comprising the sequence of KSSQSIFRTSRNKNLLN (SEQ ID NO: 99), CDR L2 comprising the sequence of WASTRKS (SEQ ID NO: 100), and CDR L3 comprising the sequence of QQYFSPPYT (SEQ ID NO: 101); and the H chain comprising CDR H1 comprising the sequence of SFWMH (SEQ ID NO: 102), CDR H2 comprising the sequence of FTNNEGTTTAYADSVRG (SEQ ID NO: 103), and CDR H3 comprising the sequence of GDGGLDD (SEQ ID NO: 104);

(m) the L chain comprising CDR L1 comprising the sequence of RASQFTNHYLN (SEQ ID NO: 105), CDR L2 comprising the sequence of VASNLQS (SEQ ID NO: 106), and CDR L3 comprising the sequence of QQSYRTPYT (SEQ ID NO: 107); and the H chain comprising CDR H1 comprising the sequence of SGYYN (SEQ ID NO: 108), CDR H2 comprising the sequence of YILSGAHTDIKASLGS (SEQ ID NO: 109), and CDR H3 comprising the sequence of SGVYSKYSLDV (SEQ ID NO: 110); or (n) the L chain comprising CDR L1 comprising the sequence of KSSQSIFRTSRNKNLLN (SEQ ID NO: 99), CDR L2 comprising the sequence of WASTRKS (SEQ ID NO: 100), and CDR L3 comprising the sequence of QQYFSPPYT (SEQ ID NO: 101); and the H chain comprising CDR H1 comprising the sequence of SFWMH (SEQ ID NO: 102), CDR H2 comprising the sequence of FTNNEGTTTAYADSVRG (SEQ ID NO: 103), and CDR H3 comprising the sequence of GEGGLDD (SEQ ID NO: 118).

In some embodiments, the isolated anti-WTA monoclonal antibody comprises a heavy chain variable region (VH), wherein the VH comprises an amino acid sequence having at least 95% sequence identity over the length of the VH sequence of SEQ ID NO. 112, wherein amino acid Xaa at position 1 of SEQ ID NO. 112 is Q or E, and amino acid Xaa at position 2 of SEQ ID NO. 112 is M, I or V. In some embodiments, the antibody further comprises a light chain variable region (VL), wherein the VL comprises an amino acid sequence having at least 95% sequence identity over the length of the VL sequence of SEQ ID NO. 111. In some embodiments, the isolated anti-WTA monoclonal antibody comprises a light chain variable region (VL), wherein the VL comprises an amino acid sequence having at least 95% sequence identity over the length of the VL sequence of SEQ ID NO. 111. In any of the preceding embodiments, the sequence identity may be 96%, 97%, 98%, 99%, or 100%. In some embodiments, the VH of the antibody comprises the sequence of SEQ ID NO. 112 and the VL of the antibody comprises the sequence of SEQ ID NO. 111.

In some embodiments, the isolated anti-WTA monoclonal antibody comprises a heavy chain variable region (VH), wherein the VH comprises an amino acid sequence having at least 95% sequence identity over the length of the VH sequence SEQ ID NO. 120 or SEQ ID NO: 156. In some embodiments, the antibody further comprises a light chain variable region (VL), wherein the VL comprises an amino acid sequence having at least 95% sequence identity over the length of the VL sequence SEQ ID NO. 119. In some embodiments, the isolated anti-WTA monoclonal antibody comprising a light chain variable region (VL), wherein the VL comprises an amino acid sequence having at least 95% sequence identity over the length of the VL sequence SEQ ID NO. 119. In any of the preceding embodiments, the sequence identity may be 96%, 97%, 98%, 99%, or 100%. In some embodiments, the isolated anti-WTA monoclonal antibody comprising a light chain variable region (VL) and a heavy chain variable region (VH), wherein the VL comprises the sequence of SEQ ID NO. 119 and the VH comprises the sequence SEQ ID NO. 120 or SEQ ID NO: 156.

In some embodiments, the isolated anti-WTA monoclonal antibody comprising a light chain variable region (VL), wherein the VL comprises a sequence having at least 95% sequence identity over the length of the VL sequence selected from the VL sequence of SEQ ID NO: 158, SEQ ID NO. 159, SEQ ID NO. 160, SEQ ID NO. 161, SEQ ID NO. 162, SEQ ID NO: 163, SEQ ID NO. 164, SEQ ID NO. 165, SEQ ID NO. 166, SEQ ID NO. 167, and SEQ ID NO: 168. In some embodiments, the isolated anti-WTA monoclonal antibody comprising a heavy chain variable region (VH) comprising an amino acid sequence having at least 95% sequence identity over the length of the VH sequence elected from the VH sequence of SEQ ID NO. 127, SEQ ID NO. 133, SEQ ID NO. 134, SEQ ID NO. 169, SEQ ID NO. 170, SEQ ID NO: 171, SEQ ID NO. 172, SEQ ID NO. 173, SEQ ID NO. 174, SEQ ID NO. 175, and SEQ ID NO: 176. In any of the preceding embodiments, the sequence identity may be 96%, 97%, 98%, 99%, or 100%. In some embodiments, the isolated anti-WTA monoclonal antibody comprising a light chain variable region (VL) and a heavy chain variable region (VH), wherein:

(a) the VL of the antibody comprises an amino acid sequence having at least 95% sequence identity over the length of the VL sequence of SEQ ID NO. 158, and the VH of the antibody comprises an amino acid sequence having at least 95% sequence identity over the length of the VH sequence of SEQ ID NO. 169;

(b) the VL of the antibody comprises an amino acid sequence having at least 95% sequence identity over the length of the VL sequence of SEQ ID NO. 159, and the VH of the antibody comprises an amino acid sequence having at least 95% sequence identity over the length of the VH sequence of SEQ ID NO. 170;

(c) the VL of the antibody comprises an amino acid sequence having at least 95% sequence identity over the length of the VL sequence of SEQ ID NO. 160, and the VH of the antibody comprises an amino acid sequence having at least 95% sequence identity over the length of the VH sequence of SEQ ID NO. 171;

(d) the VL of the antibody comprises an amino acid sequence having at least 95% sequence identity over the length of the VL sequence of SEQ ID NO. 161, and the VH of the antibody comprises an amino acid sequence having at least 95% sequence identity over the length of the VH sequence of SEQ ID NO. 172;
(e) the VL of the antibody comprises an amino acid sequence having at least 95% sequence identity over the length of the VL sequence of SEQ ID NO. 162, and the VH of the antibody comprises an amino acid sequence having at least 95% sequence identity over the length of the VH sequence of SEQ ID NO. 173;
(f) the VL of the antibody comprises an amino acid sequence having at least 95% sequence identity over the length of the VL sequence of SEQ ID NO. 163, and the VH of the antibody comprises an amino acid sequence having at least 95% sequence identity over the length of the VH sequence of SEQ ID NO. 174;
(g) the VL of the antibody comprises an amino acid sequence having at least 95% sequence identity over the length of the VL sequence of SEQ ID NO. 164, and the VH of the antibody comprises an amino acid sequence having at least 95% sequence identity over the length of the VH sequence of SEQ ID NO. 175;
(h) the VL of the antibody comprises an amino acid sequence having at least 95% sequence identity over the length of the VL sequence of SEQ ID NO. 165, and the VH of the antibody comprises an amino acid sequence having at least 95% sequence identity over the length of the VH sequence of SEQ ID NO. 176;
(i) the VL of the antibody comprises an amino acid sequence having at least 95% sequence identity over the length of the VL sequence of SEQ ID NO. 166, and the VH of the antibody comprises an amino acid sequence having at least 95% sequence identity over the length of the VH sequence of SEQ ID NO. 133;
(j) the VL of the antibody comprises an amino acid sequence having at least 95% sequence identity over the length of the VL sequence of SEQ ID NO. 167, and the VH of the antibody comprises an amino acid sequence having at least 95% sequence identity over the length of the VH sequence of SEQ ID NO. 134; or
(k) the VL of the antibody comprises an amino acid sequence having at least 95% sequence identity over the length of the VL sequence of SEQ ID NO. 168, and the VH of the antibody comprises an amino acid sequence having at least 95% sequence identity over the length of the VH sequence of SEQ ID NO. 127.

In some embodiments, the isolated anti-WTA monoclonal antibody comprising a light chain variable region (VL) and a heavy chain variable region (VH), wherein:
(a) the VL of the antibody comprises the VL sequence of SEQ ID NO. 158, and the VH of the antibody comprises the VH sequence of SEQ ID NO. 169;
(b) the VL of the antibody comprises the VL sequence of SEQ ID NO. 159, and the VH of the antibody comprises the VH sequence of SEQ ID NO. 170;
(c) the VL of the antibody comprises the VL sequence of SEQ ID NO. 160, and the VH of the antibody comprises the VH sequence of SEQ ID NO. 171;
(d) the VL of the antibody comprises the VL sequence of SEQ ID NO. 161, and the VH of the antibody comprises the VH sequence of SEQ ID NO. 172;
(e) the VL of the antibody comprises the VL sequence of SEQ ID NO. 162, and the VH of the antibody comprises the VH sequence of SEQ ID NO. 173;
(f) the VL of the antibody comprises the VL sequence of SEQ ID NO. 163, and the VH of the antibody comprises the VH sequence of SEQ ID NO. 174;
(g) the VL of the antibody comprises the VL sequence of SEQ ID NO. 164, and the VH of the antibody comprises the VH sequence of SEQ ID NO. 175;
(h) the VL of the antibody comprises the VL sequence of SEQ ID NO. 165, and the VH of the antibody comprises the VH sequence of SEQ ID NO. 176;
(i) the VL of the antibody comprises the VL sequence of SEQ ID NO. 166, and the VH of the antibody comprises the VH sequence of SEQ ID NO. 133;
(j) the VL of the antibody comprises the VL sequence of SEQ ID NO. 167, and the VH comprises the VH sequence of SEQ ID NO. 134;
(k) the VL of the antibody comprises the VL sequence of SEQ ID NO. 168, and the VH comprises the VH sequence of SEQ ID NO. 127;
(l) the VL of the antibody comprises the VL sequence of SEQ ID NO. 113, and the VH comprises the VH sequence of SEQ ID NO. 114; or
(m) the VL of the antibody comprises the VL sequence of SEQ ID NO. 121, and the VH comprises the VH sequence of SEQ ID NO. 138.

In some embodiments of the antibodies described above, the antibody is an antigen-binding fragment lacking a Fc region. In some embodiments, the antibody is a F(ab) or F(ab')$_2$. In some embodiments, the antibody further comprises a heavy chain constant region and/or a light chain constant region, wherein the heavy chain constant region and/or the light chain constant region comprise one or more amino acids that are substituted with cysteine residues. In some embodiments, the heavy chain constant region comprises amino acid substitution A118C or S400C, and/or the light chain constant region comprises amino acid substitution V205C, wherein the numbering is according to the EU numbering. In some embodiments, the heavy chain constant region comprises the amino acid sequence of SEQ ID NO: 149 and/or the light chain constant region comprises the amino acid sequence of SEQ ID NO: 151. In some embodiments, the heavy chain constant region comprises the amino acid sequence of SEQ ID NO: 149 and the light chain constant region comprises the amino acid sequence of SEQ ID NO: 150. In some embodiments, the heavy chain constant region comprises the amino acid sequence of SEQ ID NO: 148 and the light chain constant region comprises the amino acid sequence of SEQ ID NO: 151.

In some embodiments, the isolated anti-WTA monoclonal antibody comprising a light chain and a heavy chain, wherein the heavy chain of the antibody comprises the sequence of SEQ ID NO. 114, SEQ ID NO. 116, or SEQ ID NO. 117, and the light chain of the antibody comprises the sequence of SEQ ID NO. 113; wherein amino acid Xaa at position 2 of SEQ ID NO: 116 or SEQ ID NO. 117 is M, I or V. In some embodiments, isolated anti-WTA monoclonal antibody comprising a light chain and a heavy chain, wherein the heavy chain of the antibody comprises the sequence of SEQ ID NO. 114, SEQ ID NO. 116, or SEQ ID NO: 117, and the light chain of the antibody comprises the sequence of SEQ ID NO. 115; wherein amino acid Xaa at position 2 of SEQ ID NO: 116 or SEQ ID NO. 117 is M, I or V. In some embodiments, the isolated anti-WTA monoclonal antibody comprising a light chain and a heavy chain, wherein the heavy chain of the antibody comprises the sequence selected from the group consisting of SEQ ID NO. 139, SEQ ID NO. 140, SEQ ID NO. 141, SEQ ID NO: 142, SEQ ID NO. 143, and SEQ ID NO. 144; and the light chain of the antibody comprises the sequence of SEQ ID NO. 113. In some embodiments, the isolated anti-WTA monoclonal antibody comprising a light chain and a heavy chain, wherein the heavy chain of the antibody comprises the sequence selected from the group consisting of SEQ ID NO. 139, SEQ ID NO. 140, SEQ ID NO. 141, SEQ ID NO. 142, SEQ ID NO. 143, and SEQ ID NO. 144; and the light chain of the antibody comprises the sequence of SEQ ID NO. 115.

In some embodiments, the isolated anti-WTA monoclonal antibody comprising a heavy chain and a light chain, wherein the heavy chain comprises the sequence of SEQ ID NO: 146, SEQ ID NO. 147, SEQ ID NO. 157 or SEQ ID NO. 124, and the light chain comprises the sequence of SEQ ID NO. 121. In some embodiments, the isolated anti-WTA monoclonal antibody comprising a heavy chain and a light chain, wherein the heavy chain comprises the sequence of SEQ ID NO: 146, SEQ ID NO. 147, SEQ ID NO. 157 or SEQ ID NO: 124, and the light chain comprises the sequence of SEQ ID NO. 123. In some embodiments, the isolated anti-WTA monoclonal antibody comprising a heavy chain and a light chain, wherein the heavy chain comprises the sequence of SEQ ID NO: 146, SEQ ID NO: 147, SEQ ID NO. 157 or SEQ ID NO. 124, and the light chain comprises the sequence of SEQ ID NO. 145.

In some embodiments of any of the antibodies described above, the antibody is not an IgM isotype. In some embodiments of any of the antibodies described above, the antibody is an IgG (e.g., IgG1, IgG2, IgG3, IgG4), IgE, IgD, or IgA (e.g., IgA1 or IgA2) isotype. In some embodiments of any of the antibodies described above, the antibody is produced by a host cell in cell culture. In some embodiments, the host cell is a non-human cell. In some embodiments, the host cell is prokaryotic or eukaryotic. In some embodiments, the host cell is a mammalian cell (e.g., a human or non-human mammalian cell). In some embodiments, the host cell is a CHO cell.

Another aspect, the invention provides a pharmaceutical composition comprising any of the antibodies disclosed herein, and a pharmaceutically acceptable carrier.

In yet another aspect, the invention also provides an isolated nucleic acid encoding any of the antibodies disclosed herein. In still another aspect, the invention provides a vector comprising a nucleic acid encoding any of the antibodies disclosed herein. In a further embodiment, the vector is an expression vector.

The invention also provides a host cell comprising a nucleic acid encoding any of the antibodies disclosed herein. In a further embodiment, the host cell is prokaryotic or eukaryotic. In some embodiments, the host cell is a mammalian cell (e.g., a human or non-human mammalian cell). In some embodiments, the host cell is a CHO cell.

The invention further provides a method of producing an antibody comprising culturing a host cell comprising a nucleic acid encoding any of the antibodies disclosed herein under conditions suitable for expression of the nucleic acid; and recovering the antibody produced by the cell. In some embodiments, the method further comprises purifying the antibody.

Another aspect of the invention is an antibody-antibiotic conjugate (AAC) compound comprising an anti-wall teichoic acid (WTA) antibody of the invention, covalently attached by a peptide linker to a rifamycin-type antibiotic. In some embodiments of the antibody—antibiotic conjugates disclosed herein, the anti-wall teichoic acid (WTA) antibody binds to *Staphylococcus aureus*. In some embodiments, the anti-wall teichoic acid antibody binds to methicillin-resistant *Staphylococcus aureus* (MRSA).

In some embodiments of the antibody-antibiotic conjugates disclosed herein, the antibody comprises: i) L chain and H chain CDRs of SEQ ID NOs 99-104 or the L chain and H chain CDRs of SEQ ID NOs. 33-38; or ii) the VL of SEQ ID NO. 119 or SEQ ID NO. 123 paired with the VH of SEQ ID NO. 120 or SEQ ID NO. 156; or iii) the VL of SEQ ID NO: 111 paired with the VH of SEQ ID NO. 112.

In some embodiments, the rifamycin-type antibiotic is a rifalazil-type antibiotic. In some embodiments, the rifamycin-type antibiotic comprises a quaternary amine attached to the peptide linker. In some embodiments, the antibiotic is attached to the antibody via a peptide linker which is attached to an engineered cysteine of the anti-WTA antibody. The engineered cysteine may be in the L or H chain of the modified antibody. In some embodiments, the cysteine residue is in the L chain. In some embodiments, the cysteine residue is in the H chain.

The antibody-antibiotic conjugate compounds of the invention can comprise a peptide linker which is a *S. aureus* cysteine protease cleavable linker; such linkers include a staphopain B or a staphopain A cleavable linker. In one embodiment, the *S. aureus* protease is an endopeptidase. In another embodiment the linker is a host protease cleavable linker preferably a human protease cathepsin B cleavable linker (e.g., a val-cit dipeptide linker).

An exemplary embodiment of an antibody-antibiotic conjugate compound has the formula:

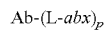

wherein:
Ab is the anti-wall teichoic acid antibody;
L is the peptide linker having the formula:

where Str is a stretcher unit; Pep is a peptide of two to twelve amino acid residues, and Y is a spacer unit;
abx is the rifamycin-type antibiotic; and
p is an integer from 1 to 8.

In one embodiment, the antibody-antibiotic conjugate compounds of any of the preceding comprise a antibiotic antibody ratio (AAR) of 2 or 4.

In some embodiments, the antibody-antibiotic conjugate compound is of the formula I:

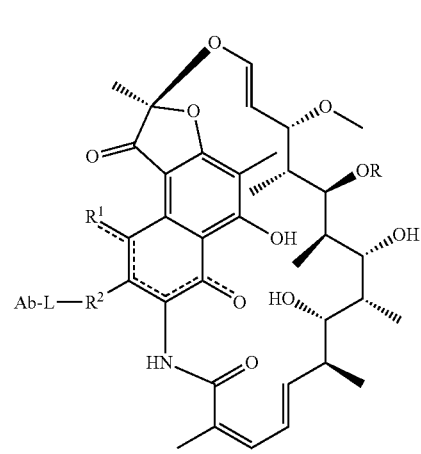

wherein:
the dashed lines indicate an optional bond;
R is H, $C_1$-$C_{12}$ alkyl, or $C(O)CH_3$;
$R^1$ is OH;

R² is CH=N-(heterocyclyl), wherein the heterocyclyl is optionally substituted with one or more groups independently selected from C(O)CH₃, $C_1$-$C_{12}$ alkyl, $C_1$-$C_{12}$ heteroaryl, $C_2$-$C_{20}$ heterocyclyl, $C_6$-$C_{20}$ aryl, and $C_3$-$C_{12}$ carbocyclyl;

or R¹ and R² form a five- or six-membered fused heteroaryl or heterocyclyl, and optionally forming a spiro or fused six-membered heteroaryl, heterocyclyl, aryl, or carbocyclyl ring, wherein the spiro or fused six-membered heteroaryl, heterocyclyl, aryl, or carbocyclyl ring is optionally substituted H, F, Cl, Br, I, $C_1$-$C_{12}$ alkyl, or OH;

L is the peptide linker attached to R² or the fused heteroaryl or heterocyclyl formed by R¹ and R²; and Ab is the anti-wall teichoic acid (WTA) antibody.

In some of these embodiments, the antibody-antibiotic conjugate compound of formula I is of the formula:

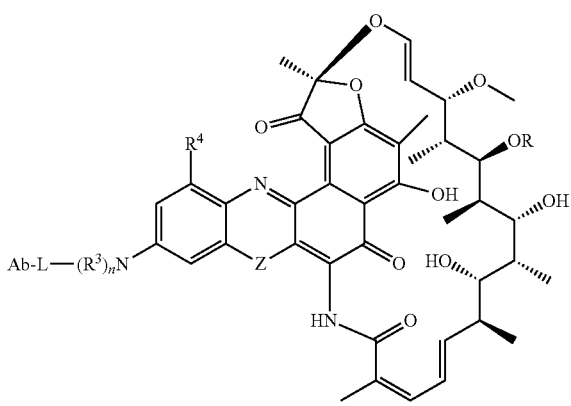

wherein

R³ is independently selected from H and $C_1$-$C_{12}$ alkyl;

n is 1 or 2;

R⁴ is selected from H, F, Cl, Br, I, $C_1$-$C_{12}$ alkyl, and OH; and

Z is selected from NH, N($C_1$-$C_{12}$ alkyl), O and S.

In some of these embodiments, the antibody-antibiotic conjugate compound of formula I is of the formula:

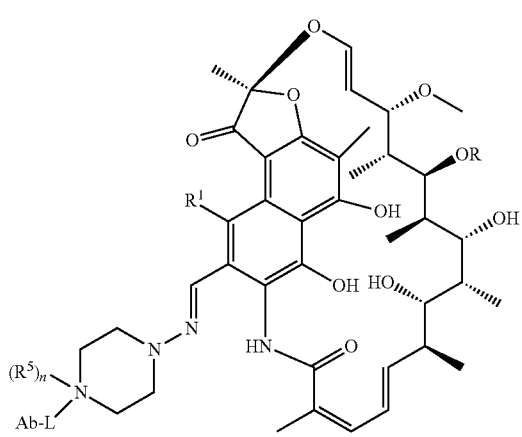

wherein R⁵ is selected from H and $C_1$-$C_{12}$ alkyl; and n is 0 or 1.

In some of these embodiments, the antibody-antibiotic conjugate compound of formula I is of the formula:

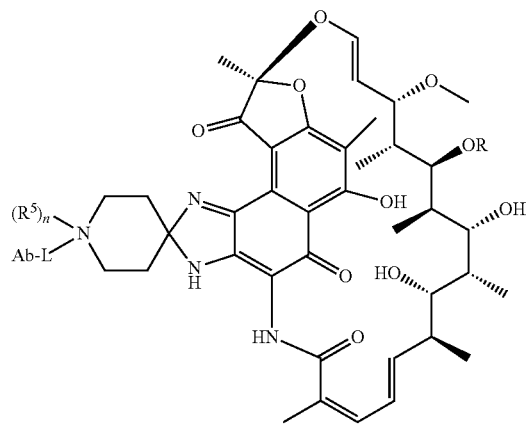

wherein R⁵ is selected from H and $C_1$-$C_{12}$ alkyl; and n is 0 or 1.

In some of these embodiments, the antibody-antibiotic conjugate compound of formula I is of the formula:

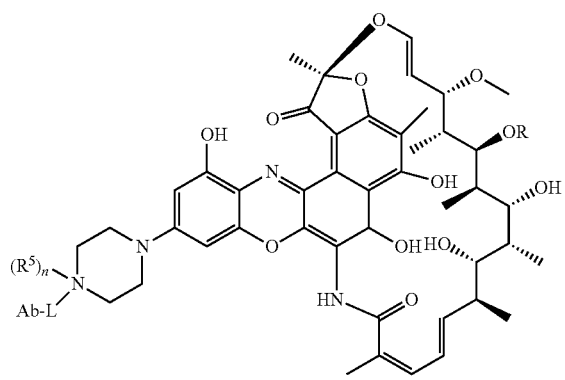

wherein R⁵ is independently selected from H and $C_1$-$C_{12}$ alkyl; and n is 0 or 1.

In some of these embodiments, the antibody-antibiotic conjugate compound of formula I is of the formula:

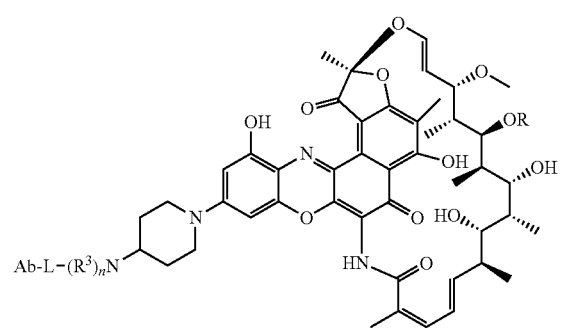

wherein R³ is independently selected from H and $C_1$-$C_{12}$ alkyl; and n is 1 or 2.

In some particular embodiments, the antibody-antibiotic conjugate compound of formula I is of the formula:

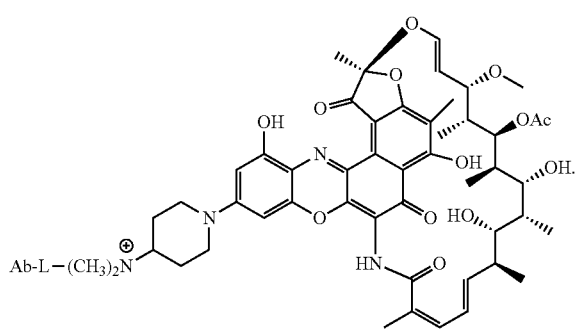

In some embodiments, provided is an antibody-antibiotic conjugate (AAC) compound comprising an anti-wall teichoic acid (WTA) antibody of the invention, covalently attached by a peptide linker to a rifamycin-type antibiotic, where the peptide linker has the formula:

-Str-Pep-Y- where Str is a stretcher unit covalently attached to the anti-wall teichoic acid (WTA) antibody; Pep is a peptide of two to twelve amino acid residues, and Y is a spacer unit covalently attached to the rifamycin-type antibiotic. In some of these embodiments, Str has the formula:

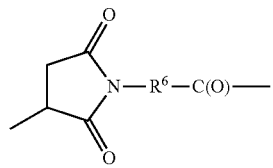

wherein $R^6$ is selected from the group consisting of $C_1$-$C_{10}$ alkylene-, —$C_3$-$C_8$ carbocyclo, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O)_r$—, and —($CH_2CH_2O)_r$—$CH_2$—; and r is an integer ranging from 1 to 10. In one variation, $R^6$ is —$(CH_2)_5$—. In some of these embodiments, Pep comprises two to twelve amino acid residues independently selected from glycine, alanine, phenylalanine, lysine, arginine, valine, and citrulline. In one variation, Pep is selected from valine-citrulline (val-cit, vc); phenylalanine-lysine (fk); GGAFAGGG (SEQ ID NO: 126); tpm-cit; GPImeLFF (SEQ ID NO: 129); valine-citrulline-phenylalanine (val-cit-phe); GGAFA (SEQ ID NO: 131); and LAFG (SEQ ID NO: 128). In some of these embodiments, Y comprises para-aminobenzyl or para-aminobenzyloxycarbonyl.

In some embodiments, the antibody-antibiotic conjugate compound is of the formula:

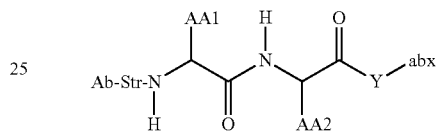

where Ab, Str, Y and abx are as defined herein, and AA1 and AA2 are independently selected from an amino acid side chain. In some of these embodiments, the amino acid side chain is independently selected from H, —$CH_3$, —$CH_2$($C_6H_5$), —$CH_2CH_2CH_2CH_2NH_2$, —$CH_2CH_2CH_2NHC$(NH)$NH_2$, —$CHCH(CH_3)CH_3$, and —$CH_2CH_2CH_2NHC$(O)$NH_2$. In some of these embodiments, the antibody-antibiotic conjugate compound is of the formula:

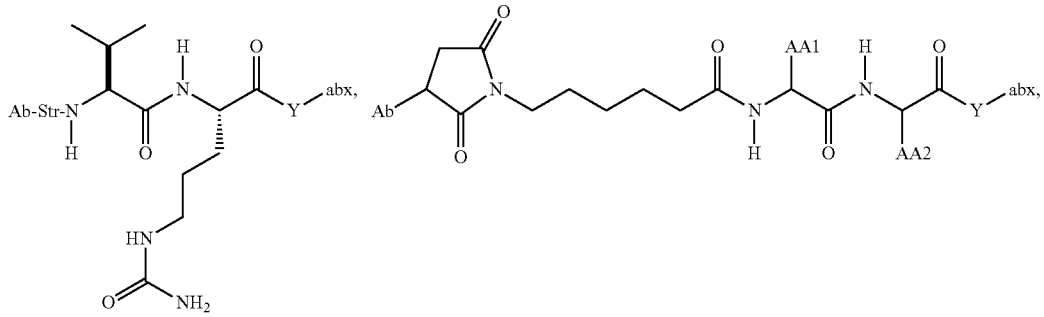

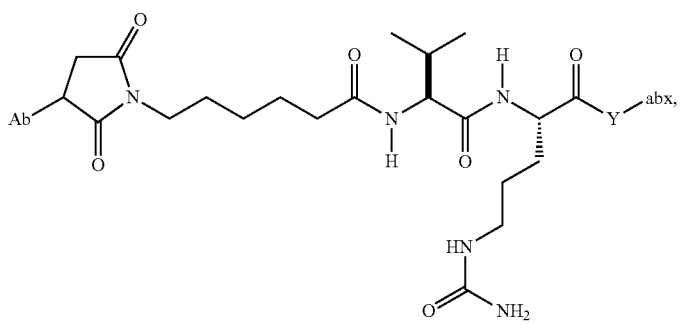

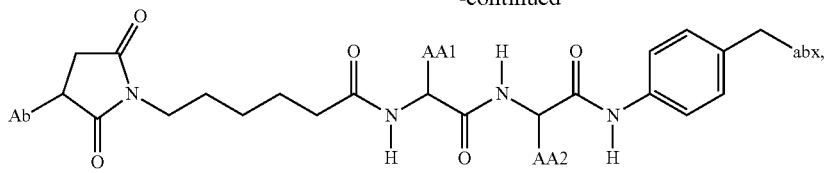
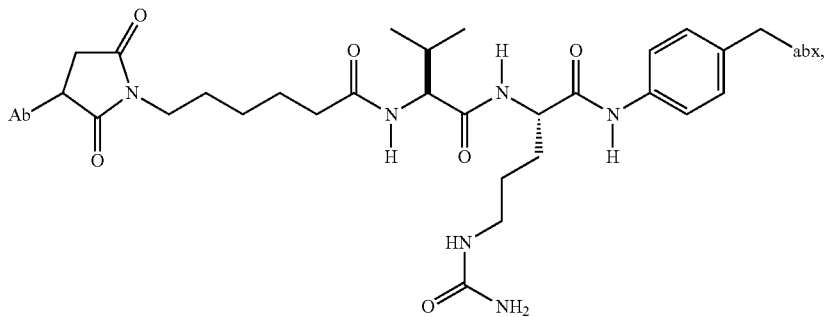
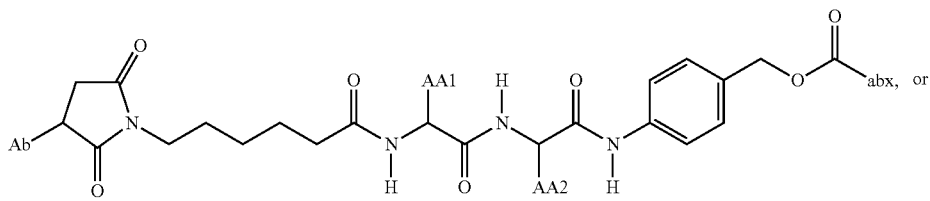
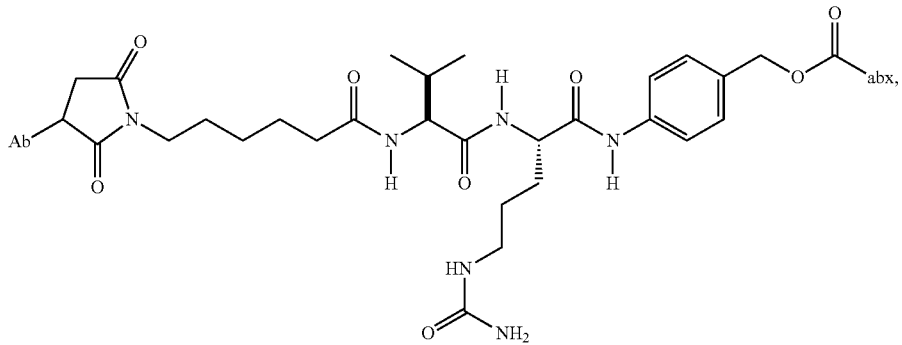
In some of these embodiments, the antibody-antibiotic conjugate compound is of the formula:
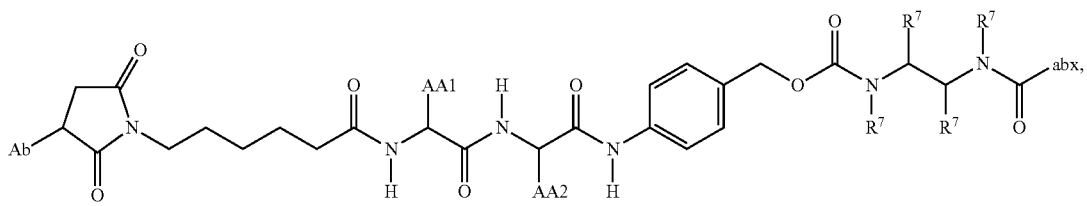

where $R^7$ is independently selected from H and $C_1$-$C_{12}$ alkyl. In some of these embodiments, the antibody-antibiotic conjugate compound is of the formula:
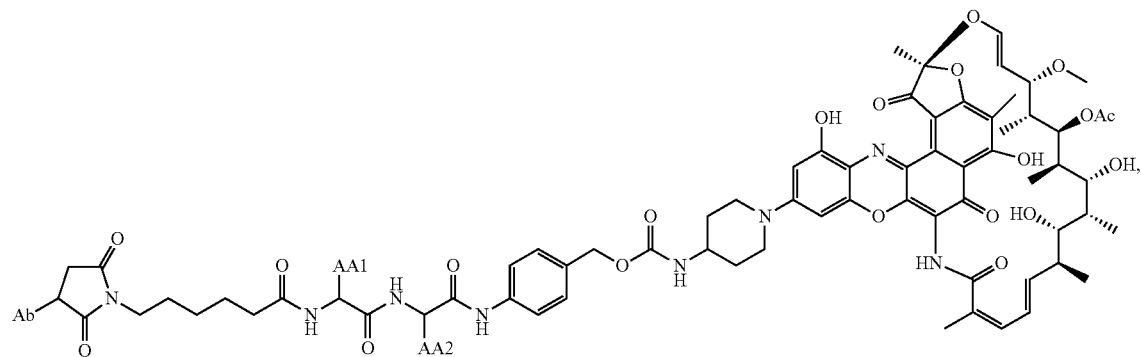
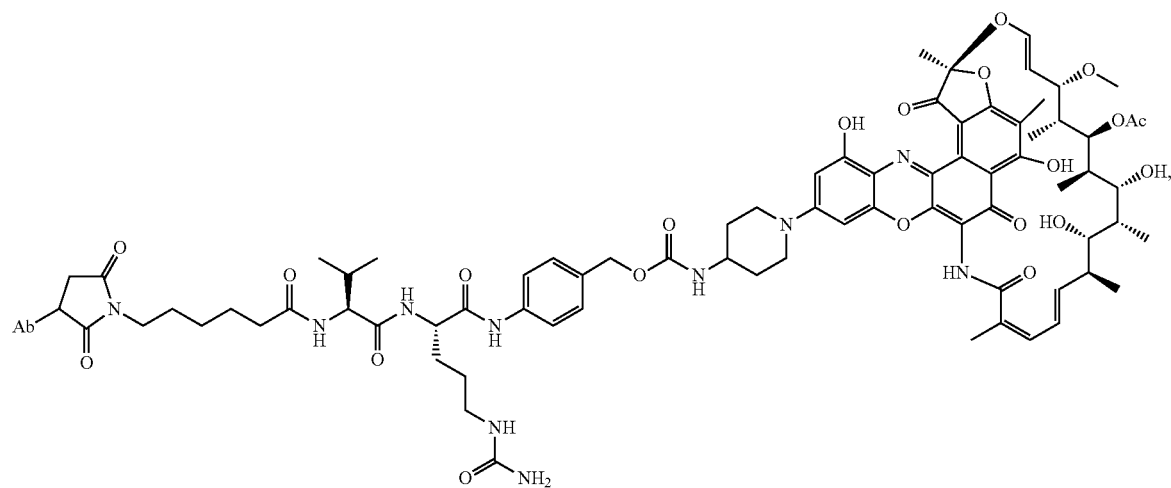
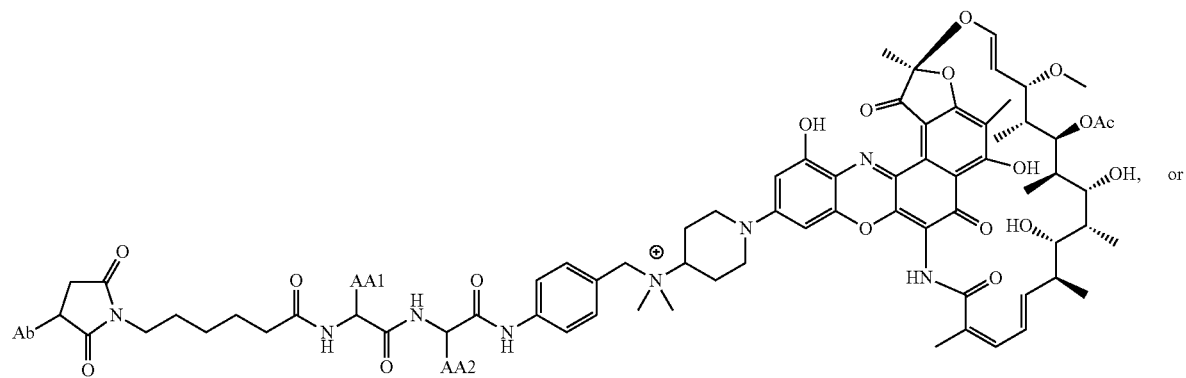
or -continued

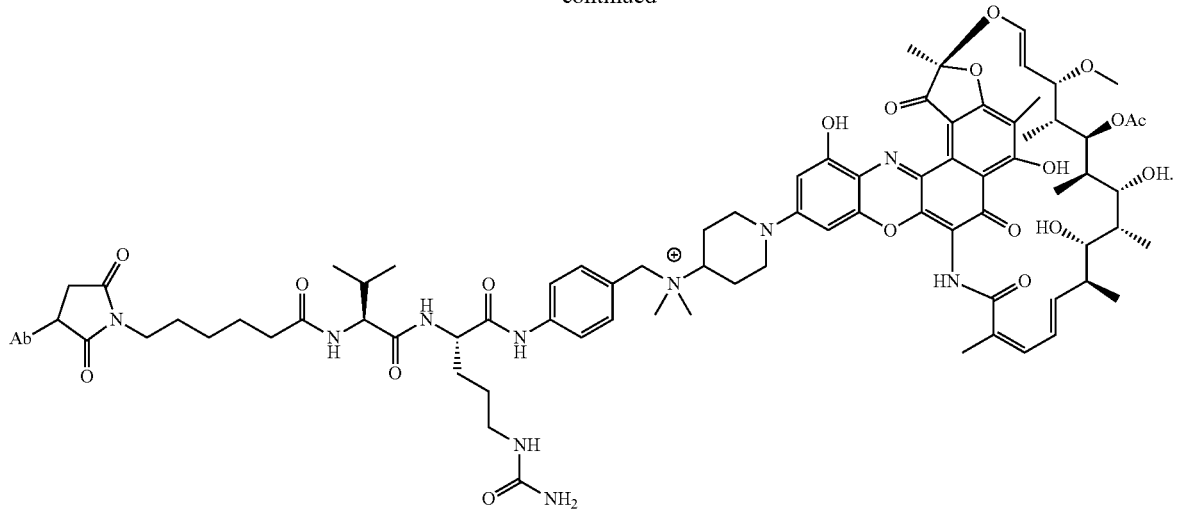

Another aspect of the invention is a pharmaceutical composition comprising an antibody-antibiotic conjugate compound of the invention.

Another aspect of the invention is a method of treating a bacterial infection by administering to a patient a therapeutically-effective amount of an antibody-antibiotic conjugate compound of any of the above embodiments. In one embodiment, the patient is a human. In one embodiment the bacterial infection is a *Staphylococcus aureus* infection. In some embodiments, the patient has been diagnosed with a *Staph aureus* infection. In some embodiments, treating the bacterial infection comprises reducing bacterial load.

The invention further provides a method of killing intracellular *Staph aureus* in the host cells of a *staph aureus* infected patient without killing the host cells by administering an anti-WTA-antibiotic conjugate compound of any of the above embodiments. Another method is provided for killing persister bacterial cells (e.g, *staph* A) in vivo by contacting the persister bacteria with an AAC of any of the preceding embodiments.

In another embodiment, the method of treatment further comprises administering a second therapeutic agent. In a further embodiment, the second therapeutic agent is an antibiotic including an antibiotic against *Staph aureus* in general or MRSA in particular.

In one embodiment, the second antibiotic administered in combination with the antibody-antibiotic conjugate compound of the invention is selected from the structural classes: (i) aminoglycosides; (ii) beta-lactams; (iii) macrolides/cyclic peptides; (iv) tetracyclines; (v) fluoroquinolines/fluoroquinolones; (vi) and oxazolidinones.

In one embodiment, the second antibiotic administered in combination with the antibody-antibiotic conjugate compound of the invention is selected from clindamycin, novobiocin, retapamulin, daptomycin, GSK-2140944, CG-400549, sitafloxacin, teicoplanin, triclosan, napthyridone, radezolid, doxorubicin, ampicillin, vancomycin, imipenem, doripenem, gemcitabine, dalbavancin, and azithromycin.

In some embodiments herein, the bacterial load in the subject has been reduced to an undetectable level after the treatment. In one embodiment, the patient's blood culture is negative after treatment as compared to a positive blood culture before treatment. In some embodiments herein, the bacterial resistance in the subject is undetectable or low. In some embodiments herein, the subject is not responsive to treatment with methicillin or vancomycin.

Another aspect of the invention is a process for making an antibody or an antibody-antibiotic conjugate compound of the invention comprising conjugating a rifamycin-type antibiotic to an anti-wall teichoic acid (WTA) antibody.

Another aspect of the invention is a kit for treating a bacterial infection comprising a pharmaceutical composition of the invention and instructions for use.

Another aspect of the invention is a linker-antibiotic intermediate having Formula II:

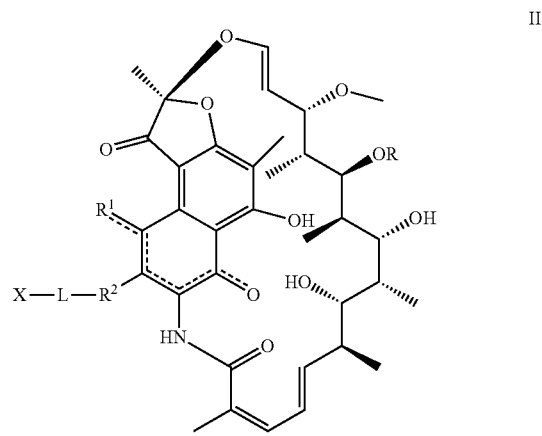

II wherein:
the dashed lines indicate an optional bond;
R is H, $C_1$-$C_{12}$ alkyl, or $C(O)CH_3$;
$R^1$ is OH;
$R^2$ is CH=N-(heterocyclyl), wherein the heterocyclyl is optionally substituted with one or more groups independently selected from $C(O)CH_3$, $C_1$-$C_{12}$ alkyl, $C_1$-$C_{12}$ heteroaryl, $C_2$-$C_{20}$ heterocyclyl, $C_6$-$C_{20}$ aryl, and $C_3$-$C_{12}$ carbocyclyl;
or $R^1$ and $R^2$ form a five- or six-membered fused heteroaryl or heterocyclyl, and optionally forming a spiro or fused six-membered heteroaryl, heterocyclyl, aryl, or carbocyclyl ring, wherein the spiro or fused six-membered heteroaryl, heterocyclyl, aryl, or carbocyclyl ring is optionally substituted H, F, Cl, Br, I, $C_1$-$C_{12}$ alkyl, or OH;

L is a peptide linker attached to $R^2$ or the fused heteroaryl or heterocyclyl formed by $R^1$ and $R^2$; and having the formula:

-Str-Pep-Y- where Str is a stretcher unit; Pep is a peptide of two to twelve amino acid residues, and Y is a spacer unit; and X is a reactive functional group selected from maleimide, thiol, amino, bromide, bromoacetamido, iodoacetamido, p-toluenesulfonate, iodide, hydroxyl, carboxyl, pyridyl disulfide, and N-hydroxysuccinimide.

In some embodiments of the linker-antibiotic intermediate of Formula II, X is

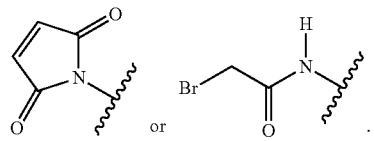 [SMILES: *N1C(=O)C=CC1=O ; *NC(=O)CBr]

In some embodiments, the linker-antibiotic intermediate of Formula II has the formula:

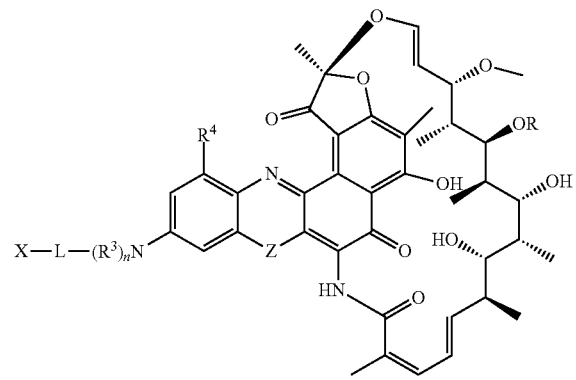

wherein $R^3$ is independently selected from H and $C_1$-$C_{12}$ alkyl;

n is 1 or 2;

$R^4$ is selected from H, F, Cl, Br, I, $C_1$-$C_{12}$ alkyl, and OH; and

Z is selected from NH, $N(C_1$-$C_{12}$ alkyl), O and S.

In some of these embodiments, the linker-antibiotic intermediate of Formula II has the formula:

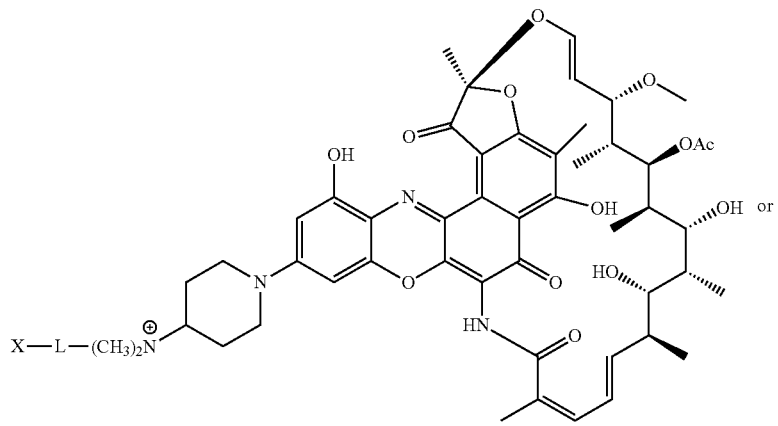

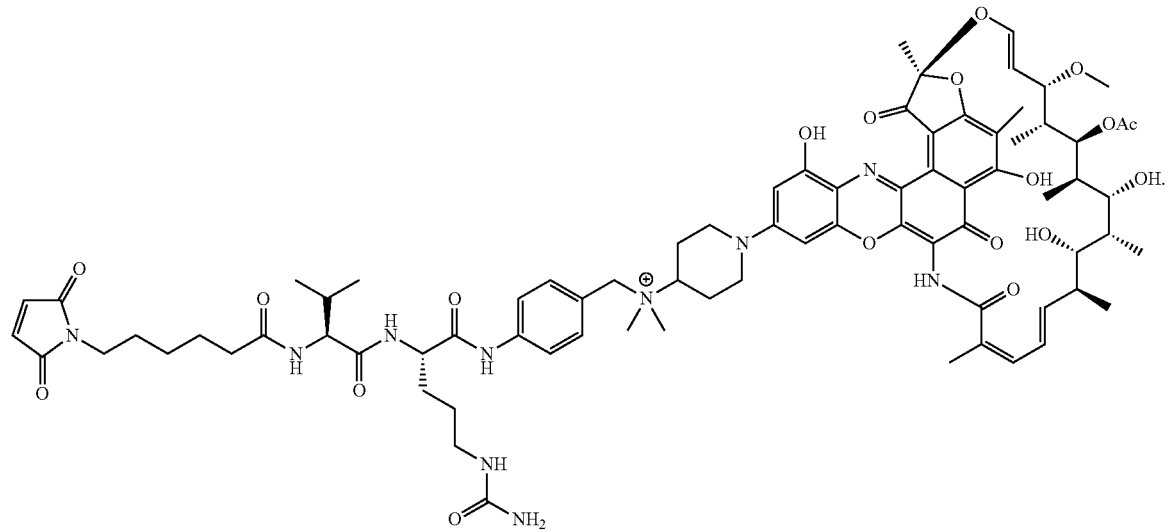

Also provided is a method of killing intracellular *Staph aureus* in the host cells of a *Staph aureus* infected patient without killing the host cells comprising administering an anti-WTA-antibiotic conjugate detailed herein.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

FIGS. 6A and 6B summarize the characteristics of the Abs from the primary screening of a library of mAbs showing positive ELISA binding to cell wall preparations from USA300 or Wood46 strain *S. aureus* strains, as described in Example 21. Of the Abs that bind to WTA, 4 are specific to WTA alpha and 13 bind specifically to WTA beta.

FIG. 10C shows an in vivo infection model demonstrating that AAC is efficacious in the presence of physiological levels of human IgG. The combined data are from 3 independent experiments using two separate preparations of thio-S4497-HC-A118C-MC-vc-PAB-dimethylpipBOR 105 or 112 AAC. Mice treated with the AAC had a greater than 4-log reduction in bacterial loads (Students t-test p=0.0005).

FIG. 11A shows in vivo infection model demonstrating that AAC are more efficacious than the current standard of care (SOC) antibiotic vancomycin in mice that are reconstituted with normal levels of human IgG. Mice were treated with S4497 antibody (50 mg/Kg), vancomycin (100 mg/Kg), thio-S4497-HC-A118C-MC-vc-PAB-dimethylpipBOR 105 AAC (50 mg/Kg), or an AAC made with an isotype control antibody that does not recognize MRSA, thio-hu-anti gD 5B5-HC-A118C-MC-vc-PAB-dimethylpipBOR 110 AAC (50 mg/Kg).

FIG. 12 shows a growth inhibition assay demonstrating that AAC are not toxic to *S. aureus* unless the linker is cleaved by cathepsin B. A schematic cathepsin release assay (Example 20) is shown on the left. AAC is treated with cathepsin B to release free antibiotic. The total amount of antibiotic activity in the intact vs. the cathepsin B treated AAC is determined by preparing serial dilutions of the resulting reaction and determining the minimum dose of AAC that is able to inhibit the growth of *S. aureus*. The upper right plot shows the cathepsin release assay for thio-S4497-HC-A118C-MC-vc-PAB-pipBOR 102 and the lower right plot shows the cathepsin release assay for thio-S4497-HC-A118C-MC-vc-PAB-dimethylpipBOR 105.

FIG. 13A shows an amino acid sequence alignment of the light chain variable regions (VL) of four human anti-WTA alpha antibodies (SEQ ID NOS 25, 27, 29 and 31, respectively, in order of appearance). The CDR sequences CDRL1, L2 and L3 according to Kabat numbering are underlined.

FIG. 13B shows an amino acid sequence alignment of the heavy chain variable regions (VH) of the four human anti-WTA alpha antibodies of FIG. 13A. The CDR sequences CDR H1, H2 and H3 according to Kabat numbering are underlined (SEQ ID NOS 26, 28, 30 and 32, respectively, in order of appearance).

FIG. 14 shows the CDR sequences of the L and H chains of 13 human anti-WTA beta antibodies (SEQ ID NOS 33-110).

FIGS. 15A-1 and 15A-2 show an alignment of the full length L chain (light chain) of anti-WTA beta Ab 6078 (unmodified) and its variants, v2, v3, v4 (SEQ ID NOS 113, 113, 115, 113, 115, 113, 115 and 115, respectively, in order of appearance). The CDR sequences CDRL1, L2 and L3 according to Kabat numbering are underlined. Boxes show the contact residues and CDR residues according to Kabat and Chothia. L chain variants that contain an engineered Cys are indicated by the C in the black box the end of the constant region (at EU residue no. 205 in this case). The variant designation, e.g., v2LC-Cys means variant 2 containing a Cys engineered into the L chain. HCLC-Cys means each of the H and L chains contain an engineered Cys. Variants 2, 3 and 4 have changes in the beginning of the H chain as shown in FIG. 15B.

FIGS. 15B-1, 15B-2, 15B-3, 15B-4 show an alignment of the full length H chain (heavy chain) of anti-WTA beta Ab 6078 (unmodified) and its variants, v2, v3, v4 (SEQ ID NOS 114, 139-144 and 143, respectively, in order of appearance) which have changes in the beginning of the H chain. H chain variants that contain an engineered Cys are indicated by the C in the black box the end of the constant region (at EU residue no. 118 in this case).

FIGS. 16A-1 and 16A-2 show an alignment of the full length L chain of anti-WTA beta Ab 4497 (unmodified) and Cys engineered L chains (SEQ ID NOS 121, 123, 145 and 145, respectively, in order of appearance). The CDR sequences CDRL1, L2 and L3 according to Kabat numbering are underlined. Boxes show the contact residues and CDR residues according to Kabat and Chothia. L chain variants that contain an engineered Cys are indicated by the C in the dotted box near the end of the constant region (at EU residue no. 205 in this case).

FIGS. 16B-1, 16B-2, 16B-3 show an alignment of the full length H chain of anti-WTA beta Ab 4497 (unmodified) and its v8 variant with D altered to E in CDR H3 position 96, with or without the engineered Cys (SEQ ID NOS 146-147, 157 and 147, respectively, in order of appearance). H chain variants that contain an engineered Cys are indicated by the C in the black box the end of the constant region (at EU residue no. 118 in this case).

Figure 17A-1:
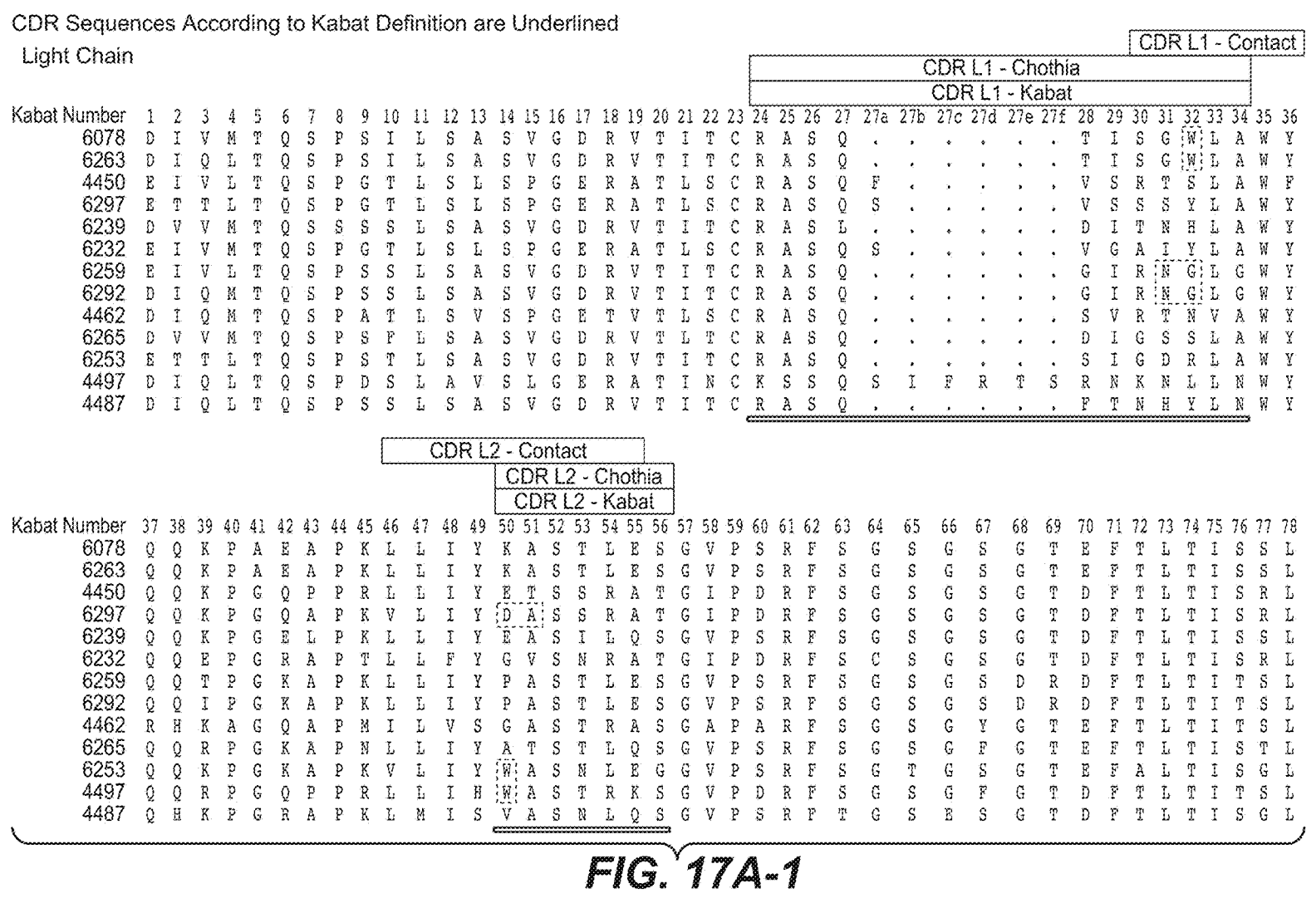
Figure 17A-2:
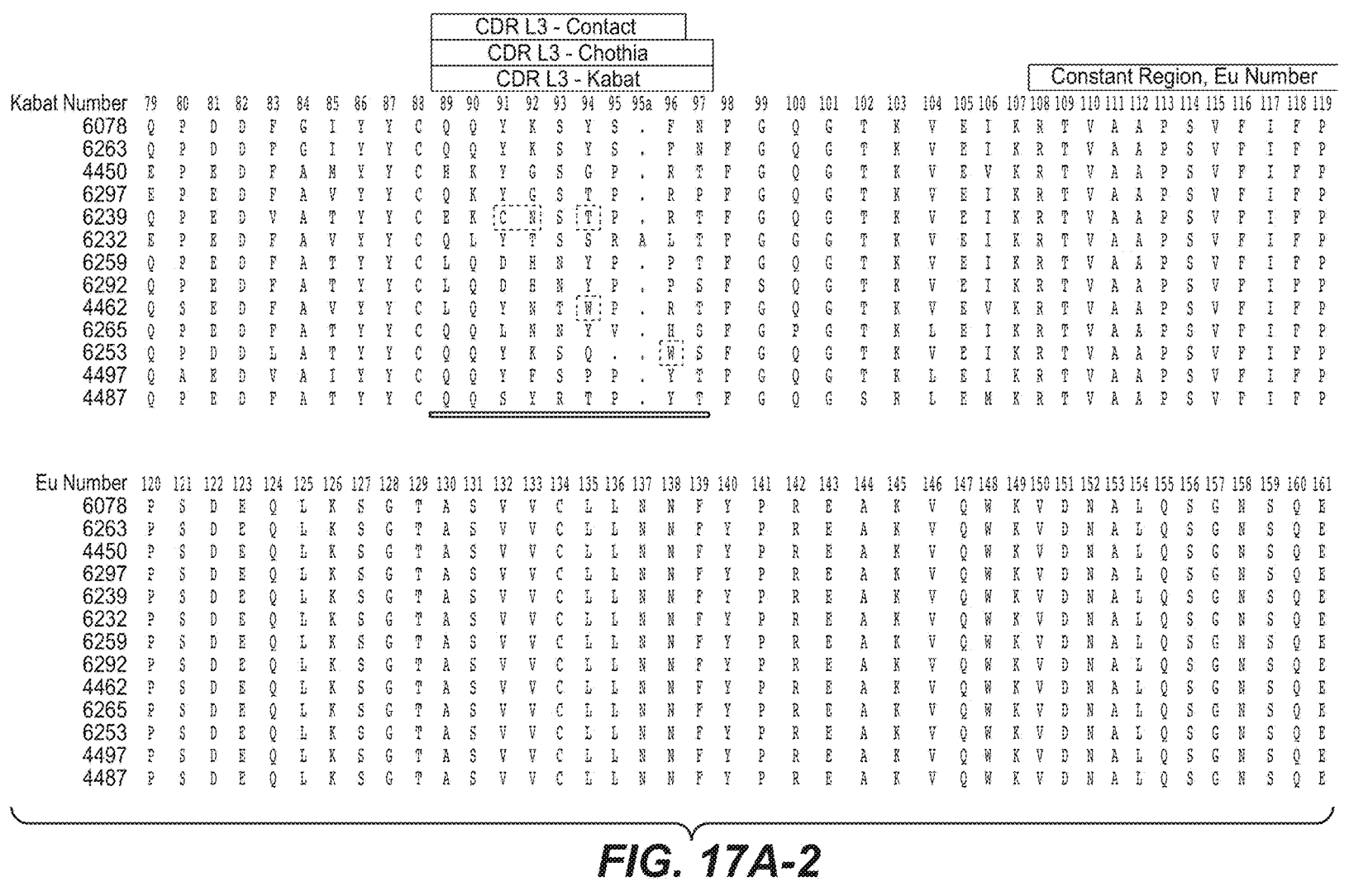
Figure 17A-3:
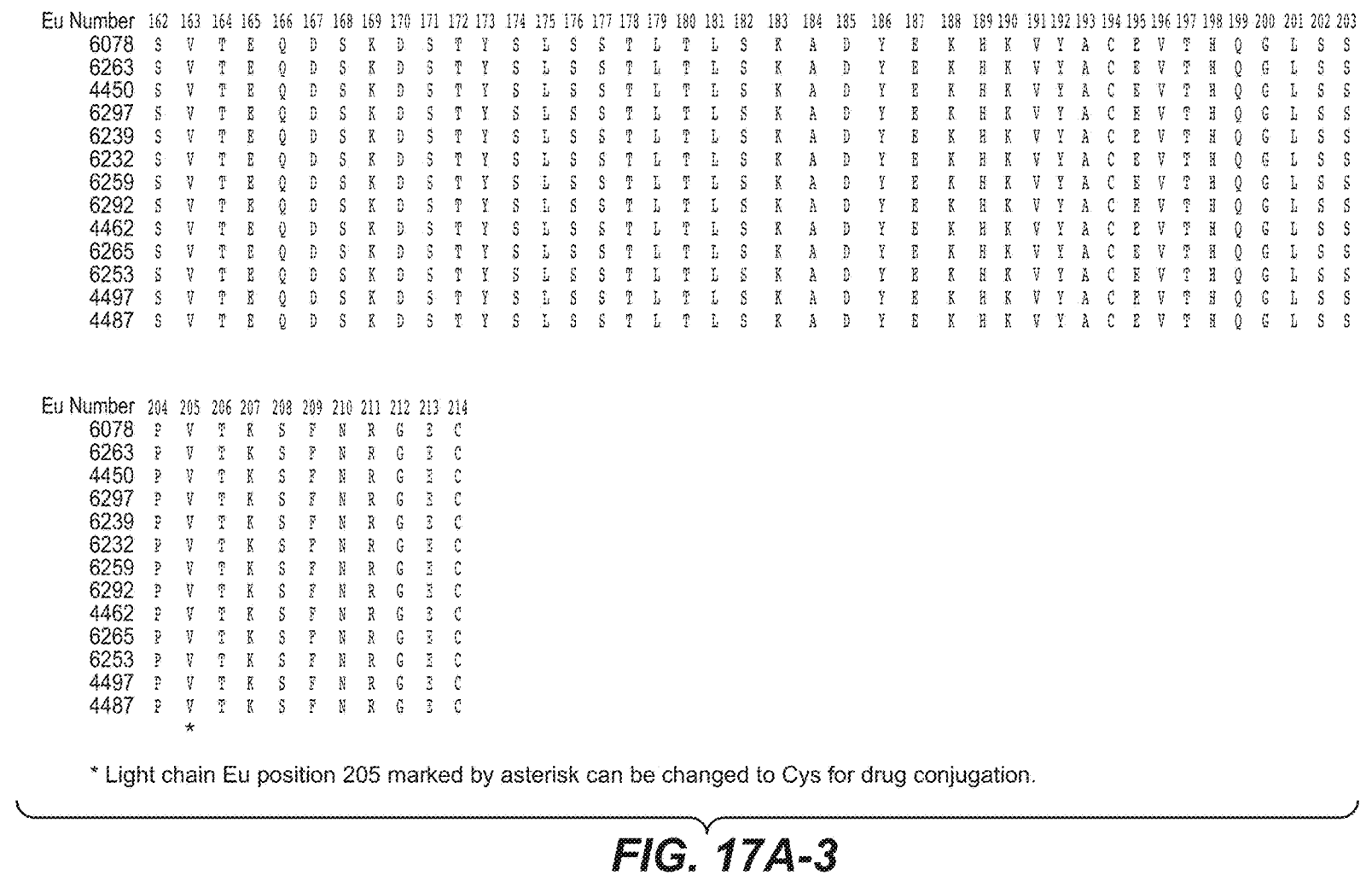
Figure 17B-1:
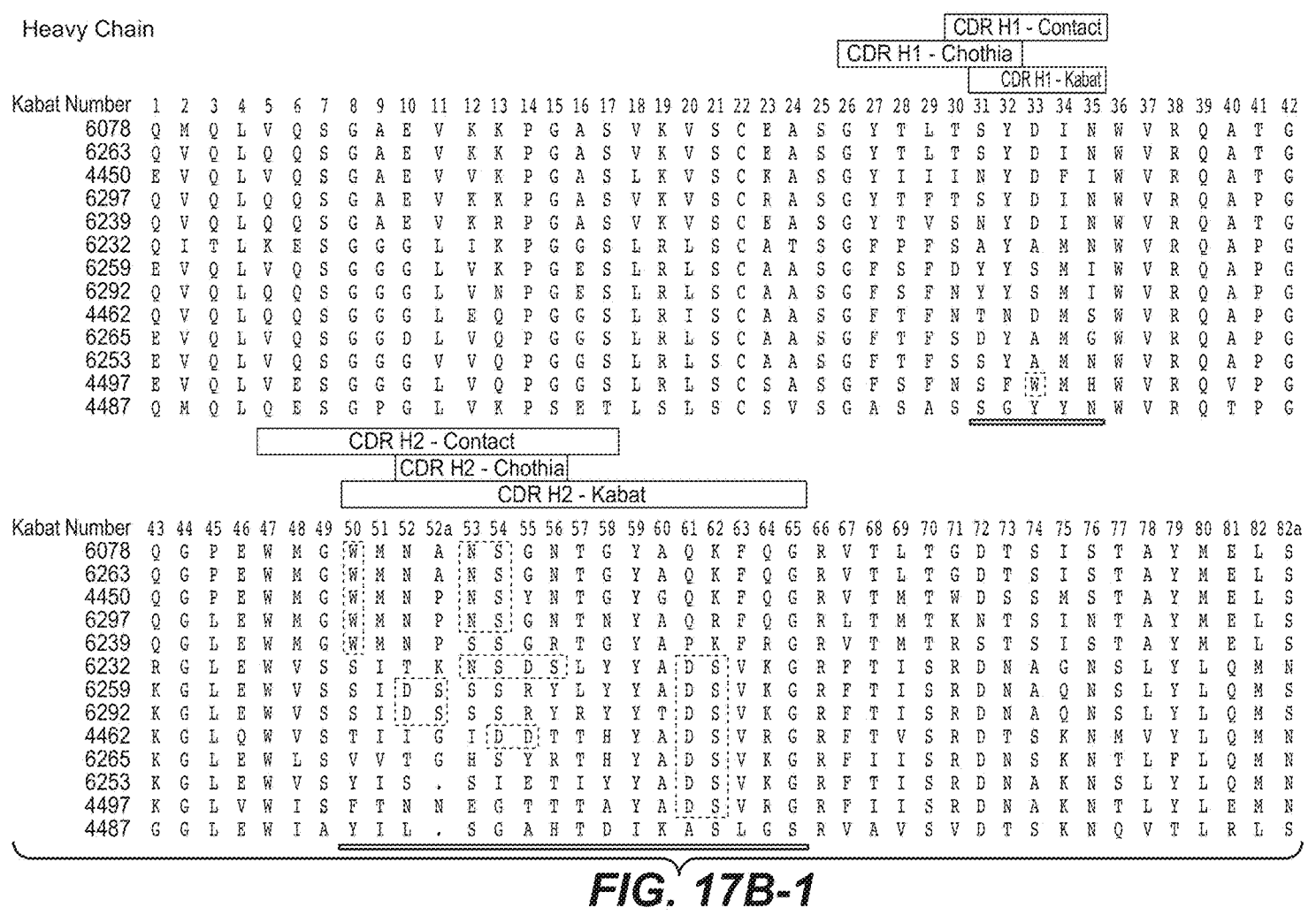
Figure 17B-2:
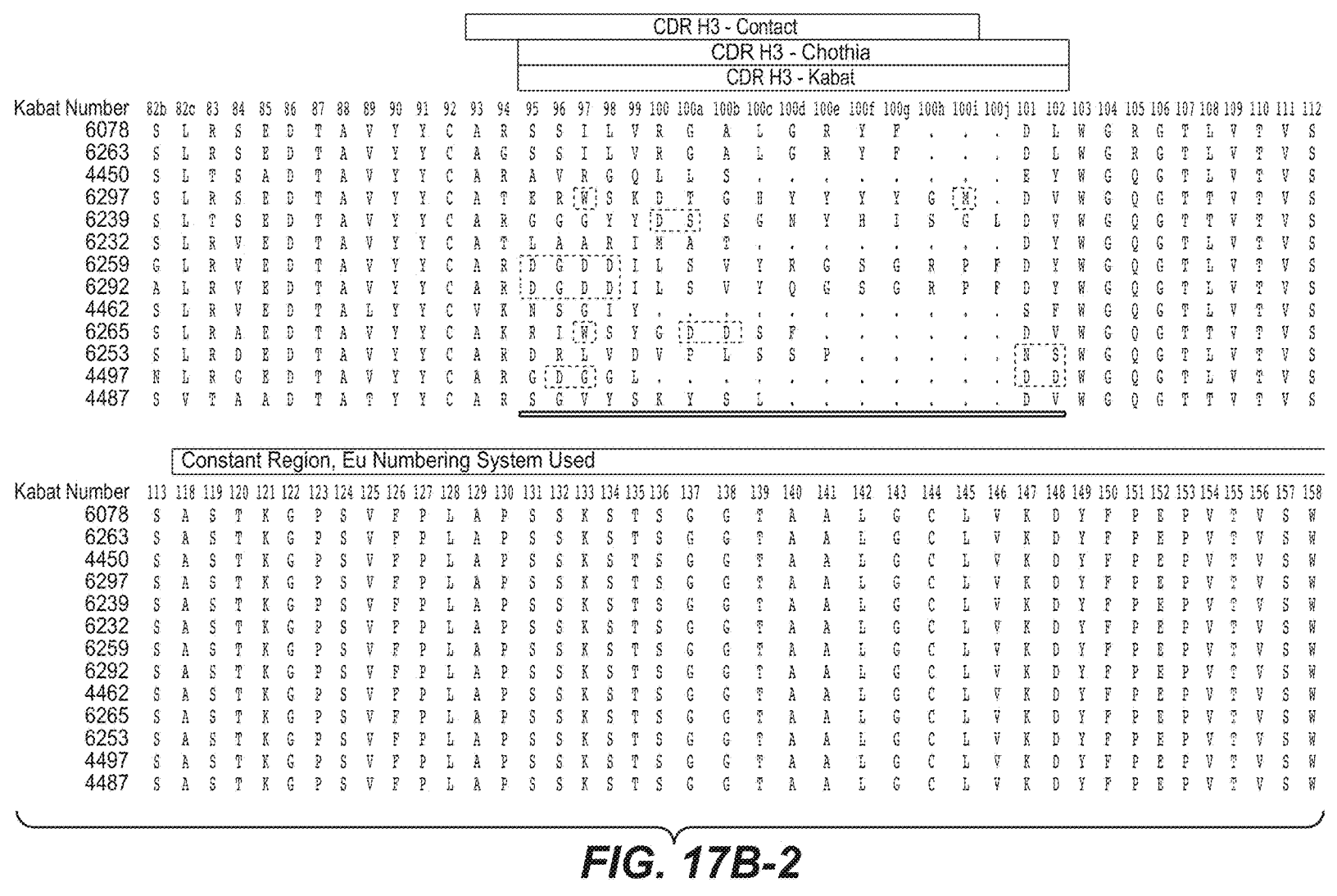
Figure 17B-3:
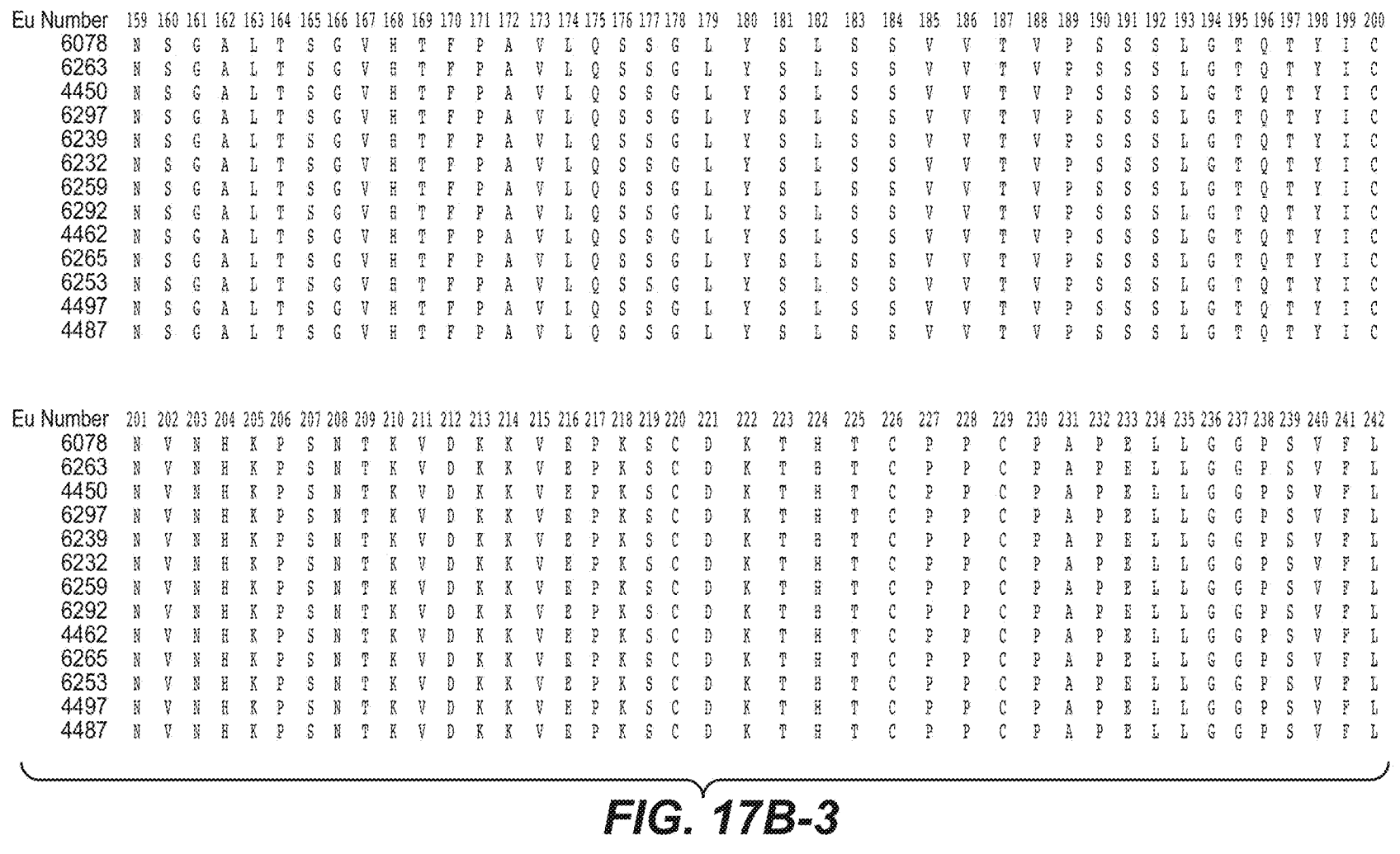
Figure 17B-4:
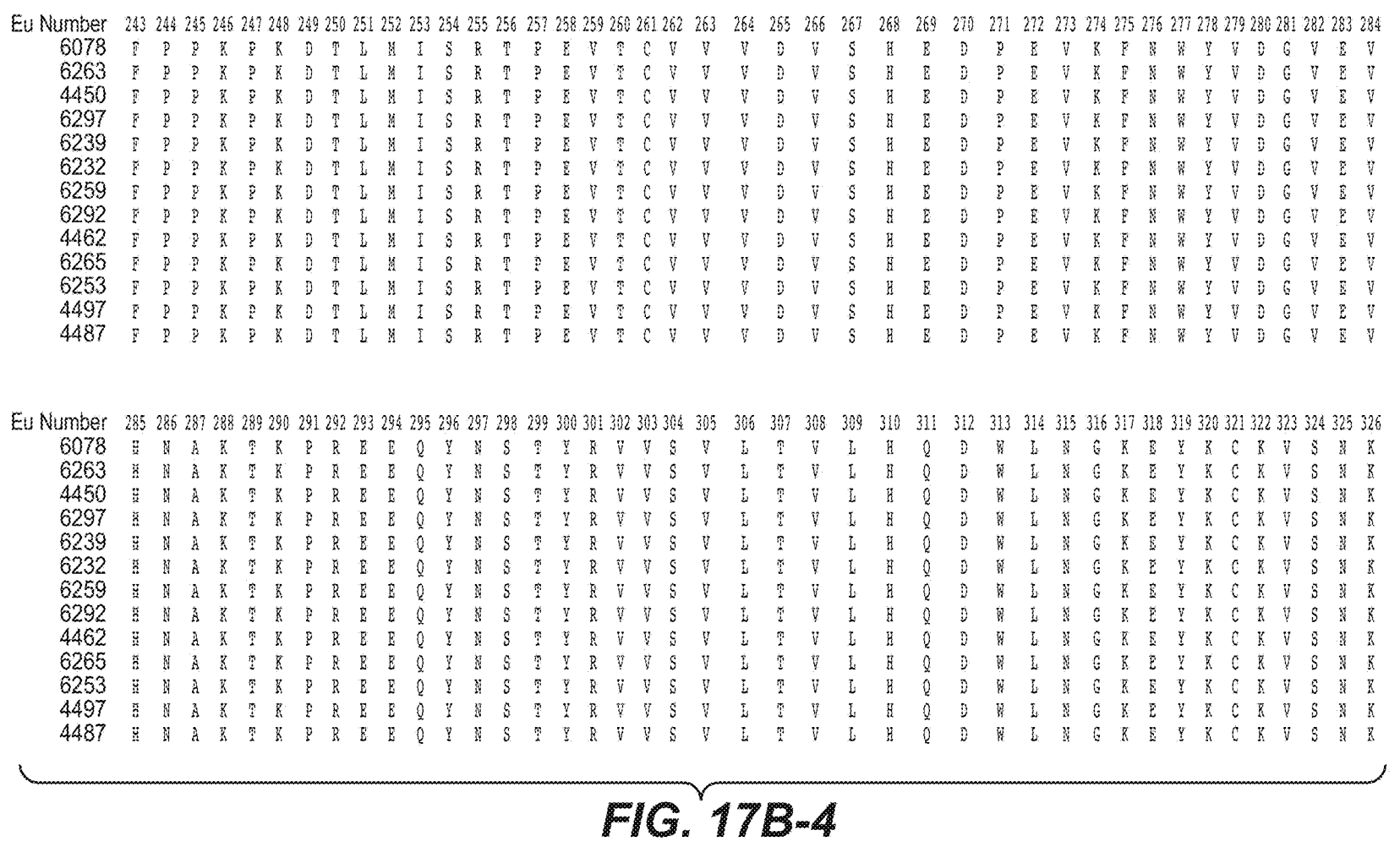
Figure 17B-5:
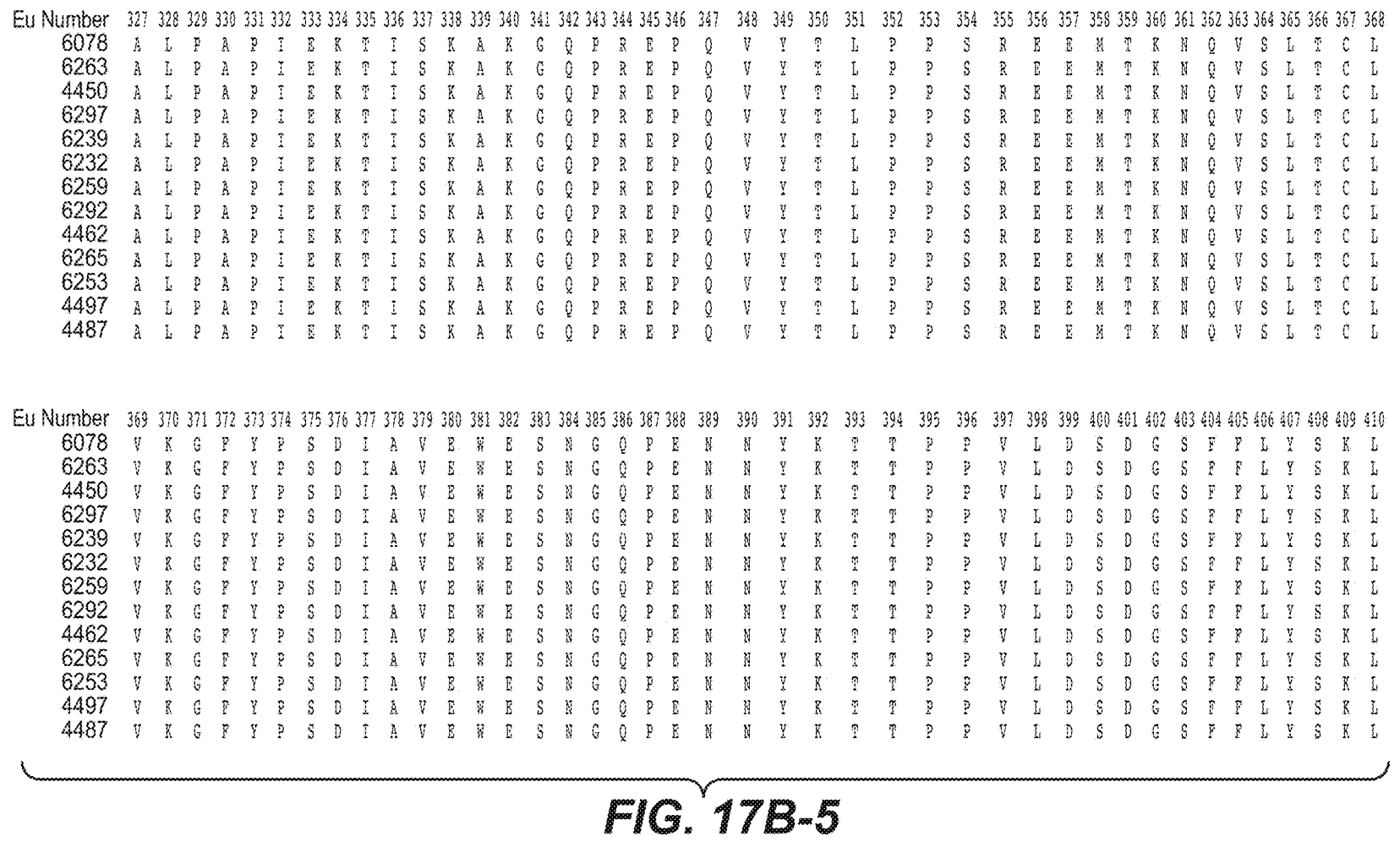

FIGS. 17A-1, 17A-2, 17A-3 show an amino acid sequence alignment of the full length light chain of the thirteen human anti-WTA beta antibodies (SEQ ID NOS 113, 158-167, 121 and 168, respectively, in order of appearance). The variable region (VL) spans Kabat amino acid positions 1 to 107. The CDR sequences CDRL1, L2 and L3 according to Kabat numbering are underlined.

FIGS. 17B-1 to 17B-6 show an amino acid sequence alignment of the full length heavy chain of the thirteen human anti-WTA beta antibodies of FIGS. 17A-1, 17A-2, 17A-3 (SEQ ID NOS 114, 169-176, 133-134, 138 and 127, respectively, in order of appearance). The variable region (VH) spans Kabat amino acid positions 1-113. The CDR sequences CDR H1, H2 and H3 according to Kabat numbering are underlined. H chain Eu position 118 marked by an asterisk can be changed to Cys for drug conjugation. Residues highlighted in black can be replaced with other residues that do not affect antigen binding to avoid deamidation, aspartic acid isomerization, oxidation or N-linked glycosylation.

In FIG. 35, thio-S6078.v4.HC-WT, LC-Cys-MC-vc-PAB-(dimethylpip- BOR) AAC was effective at killing intracellular bacteria at doses at or above 0.5 µg/mL with an antibiotic loading of 2.0 (AAC-173) or 3.9 (AAC-171) dimethylpipBOR antibiotics (LA-54) per thio-S6078 antibody. In FIG. 36, thio-S6078.v4.HC-WT, LC-Cys-MC-vc-PAB-(piperazBOR) was effective at killing intracellular bacteria at doses at or above 0.5 µg/mL with an antibiotic loading of 1.8 (AAC-174) or 3.9 (AAC-172) piperazBOR antibiotics (LA-65) per thio-S6078 antibody.

DETAILED DESCRIPTION OF EMBODIMENTS OF THE INVENTION

Figure 1:
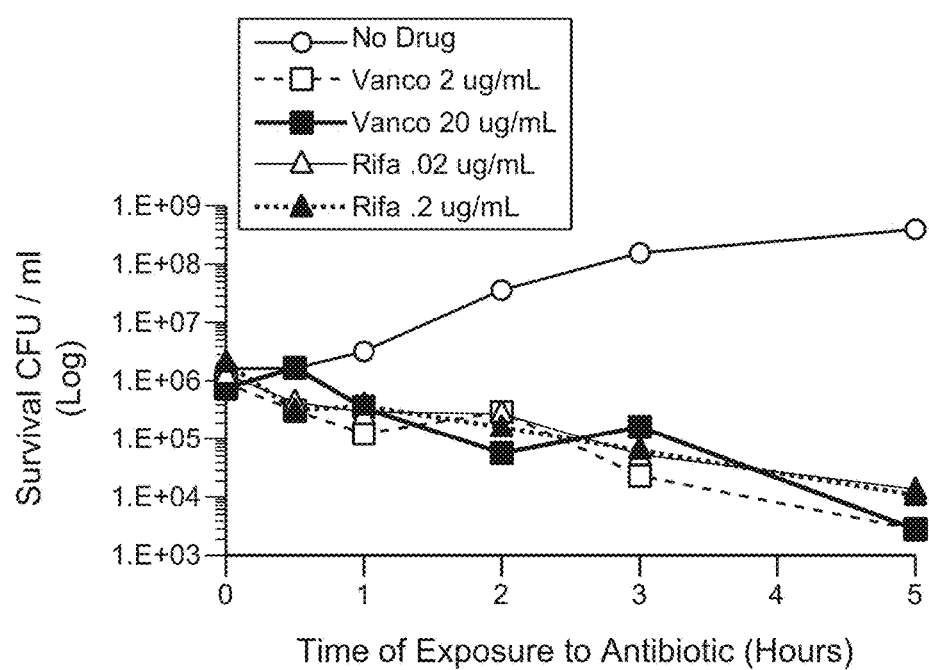
FIG. 1 shows that exposure to vancomycin or rifampicin kills MRSA gradually. Vancomycin was tested at 2 μg/mL (open square) and 20 μg/mL (closed square). Rifampicin was tested at 0.02 μg/mL (open triangle) and 0.2 μg/mL (closed triangle).

Reference will now be made in detail to certain embodiments of the invention, examples of which are illustrated in the accompanying structures and formulas. While the invention will be described in conjunction with the enumerated embodiments, including methods, materials and examples, such description is non-limiting and the invention is intended to cover all alternatives, modifications, and equivalents, whether they are generally known, or incorporated herein. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. One skilled in the art will recognize many methods and materials similar or equivalent to those described herein, which could be used in the practice of the present invention. The present invention is in no way limited to the methods and materials described.

All publications, patent applications, patents, and other references mentioned herein are incorporated by reference in their entirety.

I. General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

The nomenclature used in this application is based on IUPAC systematic nomenclature, unless indicated otherwise. Unless defined otherwise, technical and scientific terms used herein have the same meaning as commonly understood by one of ordinary skill in the art to which this invention belongs, and are consistent with: Singleton et al (1994) *Dictionary of Microbiology and Molecular Biology*, 2nd Ed., J. Wiley & Sons, New York, N.Y.; and Janeway, C., Travers, P., Walport, M., Shlomchik (2001) *Immunobiology*, 5th Ed., Garland Publishing, New York.

II. Definitions

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "wall teichoic acid" (WTA) means anionic glycopolymers that are covalently attached to peptidoglycan via phosphodiester linkage to the C6 hydroxyl of the N-acetyl muramic acid sugars. While the precise chemical structure can vary among organisms, in one embodiment, WTA is a ribitol teichoic acid with repeating units of 1,5-phosphodiester linkages of D-ribitol and D-alanyl ester on position 2 and glycosyl substituents on position 4. The glycosyl groups may be N-acetylglucosaminyl α (alpha) or β (beta) as present in S. Aureus. The hydroxyls on the alditol/sugar alcohol phosphate repeats are substituted with cationic D-alanine esters and monosaccharides, such as N-acetylglucosamine. In one aspect, the hydroxyl substituents include D-alanyl and alpha (α) or beta (β) GlcNHAc. In one specific aspect, WTA comprises a compound of the formula:

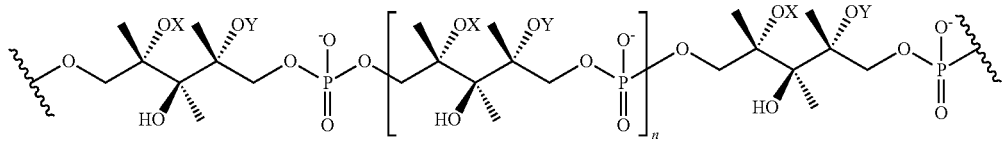

where the wavy lines indicate repeating linkage units or the attachment sites of Polyalditol-P or the peptidoglycan, where X is D-alanyl or —H; and Y is α (alpha)-GlcNHAc or β (beta)-GlcNHAc.

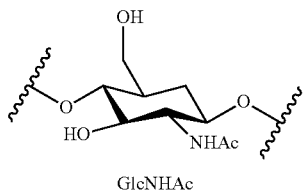

GlcNHAc

In S. aureus, WTA is covalently linked to the 6-OH of N-acetyl muramic acid (MurNAc) via a disaccharide composed of N-acetylglucosamine (GlcNAc)-1-P and N-acetylmannoseamine (ManNAc), which is followed by two or three units of glycerol-phosphates. The actual WTA polymer is then composed of 11-40 ribitol-phosphate (Rbo-P) repeating units. The step-wise synthesis of WTA is first initiated by the enzyme called TagO, and S. aureus strains lacking the TagO gene (by artificial deletion of the gene) do not make any WTA. The repeating units can be further tailored with D-alanine (D-Ala) at C2-OH and/or with N-acetylglucosamine (GlcNAc) at the C4-OH position via α-(alpha) or β-(beta) glycosidic linkages. Depending of the S. aureus strain, or the growth phase of the bacteria the glycosidic linkages could be α-, β-, or a mixture of the two anomers.

The term "antibiotic" (abx or Abx) includes any molecule that specifically inhibits the growth of or kill micro-organisms, such as bacteria, but is non-lethal to the host at the concentration and dosing interval administered. In a specific aspect, an antibiotic is non-toxic to the host at the administered concentration and dosing intervals. Antibiotics effective against bacteria can be broadly classified as either bactericidal (i.e., directly kills) or bacteriostatic (i.e., prevents division). Anti-bactericidal antibiotics can be further subclassified as narrow-spectrum or broad-spectrum. A broad-spectrum antibiotic is one effective against a broad range of bacteria including both Gram-positive and Gram-negative bacteria, in contrast to a narrow-spectrum antibiotic, which is effective against a smaller range or specific families of bacteria. Examples of antibiotics include: (i) aminoglycosides, e.g., amikacin, gentamicin, kanamycin, neomycin, netilmicin, streptomycin, tobramycin, paromycin, (ii) ansamycins, e.g., geldanamycin, herbimycin, (iii) carbacephems, e.g., loracarbef, (iv), carbapenems, e.g., ertapenem, doripenem, imipenem/cilastatin, meropenem, (v) cephalosporins (first generation), e.g., cefadroxil, cefazolin, cefalotin, cefalexin, (vi) cephalosporins (second generation), e.g., ceflaclor, cefamandole, cefoxitin, cefprozil, cefuroxime, (vi) cephalosporins (third generation), e.g., cefixime, cefdinir, cefditoren, cefoperazone, cefotaxime, cefpodoxime, ceftazidime, ceftibuten, ceftizoxime, ceftriaxone, (vii) cephalosporins (fourth generation), e.g., cefepime, (viii), cephalosporins (fifth generation), e.g., ceftobiprole, (ix) glycopeptides, e.g., teicoplanin, vancomycin, (x) macrolides, e.g., axithromycin, clarithromycin, dirithromycine, erythromycin, roxithromycin, troleandomycin, telithromycin, spectinomycin, (xi) monobactams, e.g., axtreonam, (xii) penicilins, e.g., amoxicillin, ampicillin, axlocillin, carbenicillin, cloxacillin, dicloxacillin, flucloxacillin, mezlocillin, meticillin, nafcilin, oxacillin, penicillin, peperacillin, ticarcillin, (xiii) antibiotic polypeptides, e.g., bacitracin, colistin, polymyxin B, (xiv) quinolones, e.g., ciprofloxacin, enoxacin, gatifloxacin, levofloxacin, lemefloxacin, moxifloxacin, norfloxacin, orfloxacin, trovafloxacin, (xv) sulfonamides, e.g., mafenide, prontosil, sulfacetamide, sulfamethizole, sulfanilamide, sulfasalazine, sulfisoxazole, trimethoprim, trimethoprim-sulfamethoxazole (TMP-SMX), (xvi) tetracyclines, e.g., demeclocycline, doxycycline, minocycline, oxytetracycline, tetracycline and (xvii) others such as arspenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin or timidazole.

As used herein, the term "WTA antibody" refers to any antibody that binds WTA whether WTA alpha or WTA beta. The terms "anti-wall teichoic acid alpha antibody" or "anti-WTA alpha antibody" or "anti-αWTA" or "anti-αGlcNac WTA antibody" are used interchangeably to refer to an antibody that specifically binds wall teichoic acid (WTA) alpha. Similarly, the terms "anti-wall teichoic acid beta antibody" or "anti-WTA beta antibody" or "anti-βWTA" or "anti-βGlcNac WTA antibody" are used interchangeably to refer to an antibody that specifically binds wall teichoic acid (WTA) beta. The terms "anti-Staph antibody" and "an antibody that binds to Staph" refer to an antibody that is capable of binding an antigen on Staphylococcus aureus ("Staph" or "S. aureus") with sufficient affinity such that the antibody is useful as a diagnostic and/or therapeutic agent in targeting Staph. In one embodiment, the extent of binding of an anti-Staph antibody to an unrelated, non-Staph protein is less than about 10% of the binding of the antibody to MRSA as measured, e.g., by a radioimmunoassay (RIA). In certain embodiments, an antibody that binds to Staph has a dissociation constant (Kd) of ≤1 µM, ≤100 nM, ≤10 nM, ≤5 Nm, ≤4 nM, ≤3 nM, ≤2 nM, ≤1 nM, ≤0.1 nM, ≤0.01 nM, or ≤0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-Staph antibody binds to an epitope of *Staph* that is conserved among *Staph* from different species.

The term "methicillin-resistant *Staphylococcus aureus*" (MRSA), alternatively known as multidrug resistant *Staphylococcus aureus* or oxacillin-resistant *Staphylococcus aureus* (ORSA), refers to any strain of *Staphylococcus aureus* that is resistant to beta-lactam antibiotics, which in include the penicillins (e.g., methicillin, dicloxacillin, nafcillin, oxacillin, etc.) and the cephalosporins. "Methicillin-sensitive *Staphylococcus aureus*" (MSSA) refers to any strain of *Staphylococcus aureus* that is sensitive to beta-lactam antibiotics.

The term "minimum inhibitory concentration" ("MIC") refers to the lowest concentration of an antimicrobial that will inhibit the visible growth of a microorganism after overnight incubation. Assay for determining MIC are known. One method is as described in Example 18 below.

The term "antibody" herein is used in the broadest sense and specifically covers monoclonal antibodies, polyclonal antibodies, dimers, multimers, multispecific antibodies (e.g., bispecific antibodies), and antigen binding antibody fragments thereof, (Miller et al (2003) J. of Immunology 170: 4854-4861). Antibodies may be murine, human, humanized, chimeric, or derived from other species. An antibody is a protein generated by the immune system that is capable of recognizing and binding to a specific antigen (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may be recognized and bound by more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease, an infected cell or a microorganism such as a bacterium. The immunoglobulin (Ig) disclosed herein can be of any isotype except IgM (e.g., IgG, IgE, IgD, and IgA) and subclass (e.g., IgG1, IgG2, IgG3, IgG4, IgA1 and IgA2. The immunoglobulins can be derived from any species. In one aspect, the Ig is of human, murine, or rabbit origin. In a specific embodiment, the Ig is of human origin.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The terms "full length antibody," "intact antibody," and "whole antibody" are used herein interchangeably to refer to an antibody having a structure substantially similar to a native antibody structure or having heavy chains that contain an Fc region as defined herein.

An "antigen-binding fragment" of an antibody refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation (e.g., natural variation in glycosylation), such variants generally being present in minor amounts. One such possible variant for IgG1 antibodies is the cleavage of the C-terminal lysine (K) of the heavy chain constant region. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In addition to their specificity, the monoclonal antibodies are advantageous in that they may be synthesized uncontaminated by other antibodies.

The term "chimeric antibody" refers to an antibody in which a portion of the heavy and/or light chain is derived from a particular source or species, while the remainder of the heavy and/or light chain is derived from a different source or species.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized antibody" refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "hypervariable region," "HVR," or "HV," when used herein refers to the regions of an antibody variable domain which are hypervariable in sequence ("complementarity determining regions" or "CDRs") and/or form structurally defined loops and/or contain the antigen-contacting residues ("antigen contacts"). Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain (Hamers-Casterman et al., (1993) Nature 363:446-448; Sheriff et al., (1996) Nature Struct. Biol. 3:733-736).

A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk, (1987) J. Mol. Biol. 196: 901-917). For antigen contacts, refer to MacCallum et al. J. Mol. Biol. 262: 732-745 (1996). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| | | (Kabat numbering) | | |
| H1 | H31-H35B | H26-H35B | H26-H32 | H30-H35B |
| | | (Chothia numbering) | | |
| H1 | H31-H35 | H26-H35 | H26-H32 | H30-H35 |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. Unless otherwise indicated, HVR residues, CDR residues and other residues in the variable domain (e.g., FR residues) are numbered herein according to Kabat et al., supra.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

"Affinity" refers to the strength of the sum total of noncovalent interactions between a single binding site of a molecule (e.g., an antibody) and its binding partner (e.g., antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "epitope" refers to the particular site on an antigen molecule to which an antibody binds.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

A "naked antibody" refers to an antibody that is not conjugated to a heterologous moiety (e.g., a cytotoxic moiety) or radiolabel. The naked antibody may be present in a pharmaceutical formulation.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express Fcγ(gamma)RIII only, whereas monocytes express Fcγ(gamma)RI, Fcγ(gamma)RII and Fcγ(gamma)RIII. Fc expression on hematopoietic cells is summarized in Table 3 on page 464 of Ravetch and Kinet, Annu. Rev. Immunol. 9: 457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., PNAS USA 95:652-656 (1998).

"Phagocytosis" refers to a process by which a pathogen is engulfed or internalized by a host cell (e.g., macrophage or neutrophil). Phagocytes mediate phagocytosis by three pathways: (i) direct cell surface receptors (for example, lectins, integrins and scavenger receptors) (ii) complement enhanced—using complement receptors (including CRI, receptor for C3b, CR3 and CR4) to bind and ingest complement opsonized pathogens, and (iii) antibody enhanced—using Fc Receptors (including FcγgammaRI, FcγgammaRIIA and FcγgammaRIIIA) to bind antibody opsonized particles which then become internalized and fuse with lysosomes to become phagolysosomes. In the present invention, it is believed that pathway (iii) plays a significant role in the delivery of the anti-MRSA AAC therapeutics to infected leukocytes, e.g., neutrophils and macrophages (Phagocytosis of Microbes: complexity in Action by D. Underhill and A Ozinsky. (2002) Annual Review of Immunology, Vol 20:825).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202: 163 (1996), may be performed.

The term "Fc region" herein is used to define a C-terminal region of an immunoglobulin heavy chain. The term includes native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system—also called the EU index, as described in Kabat et al., Sequences of Proteins of Immunological Interest, 5th Ed. Public Health Service, National Institutes of Health, Bethesda, Md., 1991) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. The term "Fc receptor" or "FcR" also includes the neonatal receptor, FcRn, which is responsible for the transfer of maternal IgGs to the fetus. Guyer et al., J. Immunol. 117: 587 (1976) and Kim et al., J. Immunol. 24: 249 (1994). Methods of measuring binding to FcRn are known (see, e.g., Ghetie and Ward, Immunol. Today 18: (12): 592-8 (1997); Ghetie et al., Nature Biotechnology 15 (7): 637-40 (1997); Hinton et al., J. Biol. Chem. 279(8): 6213-6 (2004); WO 2004/92219 (Hinton et al.). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., J. Biol. Chem. 9 (2): 6591-6604 (2001).

The carbohydrate attached to the Fc region may be altered. Native antibodies produced by mammalian cells typically comprise a branched, biantennary oligosaccharide that is generally attached by an N-linkage to Asn297 of the CH2 domain of the Fc region. See, e.g., Wright et al. (1997) TIBTECH 15:26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an IgG may be made in order to create IgGs with certain additionally improved properties. For example, antibody modifications are provided having a carbohydrate structure that lacks fucose attached (directly or indirectly) to an Fc region. Such modifications may have improved ADCC function. See, e.g. US 2003/0157108 (Presta, L.); US 2004/0093621 (Kyowa Hakko Kogyo Co., Ltd). Examples of publications related to "defucosylated" or "fucose-deficient" antibody modifications include: US 2003/

0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al., J. Mol. Biol. 336: 1239-1249 (2004); Yamane-Ohnuki et al. Biotech. Bioeng. 87: 614 (2004). Examples of cell lines capable of producing defucosylated antibodies include Lee 13 CHO cells deficient in protein fucosylation (Ripka et al. Arch. Biochem. Biophys. 249: 533-545 (1986); US Pat. Appl. Pub. No. 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al., Biotech. Bioeng. 87: 614 (2004); Kanda, Y. et al, Biotechnol. Bioeng., 94 (4):680-688 (2006); and WO2003/085107).

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-WTA beta antibody" refers to one or more nucleic acid molecules encoding antibody heavy and light chains, including such nucleic acid molecule(s) in a single vector or separate vectors, and such nucleic acid molecule(s) present at one or more locations in a host cell.

As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to a target unrelated to WTA-beta is less than about 10% of the binding of the antibody to the target as measured, e.g., by a radioimmunoassay (RIA). In certain embodiments, an antibody that specifically binds to WTA beta has a dissociation constant (Kd) of ≤1 µM, ≤100 nM, ≤10 nM, ≤1 nM, or ≤0.1 nM. In certain embodiments, an antibody specifically binds to an epitope on that is conserved from different species. In another embodiment, specific binding can include, but does not require exclusive binding.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

In one embodiment, the "Kd" or "Kd value" according to this invention is measured by a radiolabeled antigen-binding assay (RIA) performed with the Fab version of an antibody of interest and its antigen as described by the following assay. Solution-binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., (1999) J. Mol. Biol. 293:865-881). To establish conditions for the assay, microtiter plates (DYNEX Technologies, Inc.) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% TWEEN-20™ surfactant in PBS. When the plates have dried, 150l/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, the Kd is measured by using surface-plasmon resonance assays using a BIA-CORE®-2000 or a BIACORE®-3000 instrument (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN 20™ surfactant (PBST) at 25° C. at a flow rate of approximately 25 µl/min. Association rates ($k_{on}$) and dissociation rates ($k_{off}$) are calculated using a simple one-to-one Langmuir binding model (BIAcore® Evaluation Software version 3.2) by simultaneously fitting the association and dissociation sensorgrams. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ $M^{-1}$ $s^{-1}$ by the surface-plasmon resonance assay above, then the on-rate can be determined by using a fluorescent quenching technique that measures the increase or decrease in fluorescence-emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow-equipped spectrophotometer (Aviv Instruments) or a 8000-series SLM-AMINCO™ spectrophotometer (ThermoSpectronic) with a stirred cuvette.

An "on-rate," "rate of association," "association rate," or "$k_{on}$" according to this invention can also be determined as described above using a BIACORE®-2000 or a BIACORE®-3000 system (BIAcore, Inc., Piscataway, N.J.).

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described.

The term "rifamycin-type antibiotic" means the class or group of antibiotics having the structure of, or similar structure to, rifamycin.

The term "rifalazil-type antibiotic" means the class or group of antibiotics having the structure of, or similar structure to, rifalazil.

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenylene radical may be optionally substituted independently with one or more substituents described herein, and includes radicals having "cis" and "trans" orientations, or alternatively, "E" and "Z" orientations. Examples include, but are not limited to, ethylenylene or vinylene (—CH=CH—), allyl (—$CH_2$CH=CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo [2.2.2]octane and bicyclo[3.2.2]nonane. Spiro moieties are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a] pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I compound of this invention with a mammal for a period of time sufficient to yield a metabolic product thereof.

The term "pharmaceutical formulation" refers to a preparation which is in such form as to permit the biological activity of an active ingredient contained therein to be effective, and which contains no additional components which are unacceptably toxic to a subject to which the formulation would be administered.

A "sterile" formulation is aseptic or free from all living microorganisms and their spores.

A "stable" formulation is one in which the protein therein essentially retains its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month and/or stable at 2-8° C. for at least 2 years. Where the formulation is to be stored at 30° C., generally the formulation should be stable for at least 2 years at 30° C. and/or stable at 40° C. for at least 6 months. For example, the extent of aggregation during storage can be used as an indicator of protein stability. Thus, a "stable" formulation may be one wherein less than about 10% and preferably less than about 5% of the protein are present as an aggregate in the formulation. In other embodiments, any increase in aggregate formation during storage of the formulation can be determined.

An "isotonic" formulation is one which has essentially the same osmotic pressure as human blood. Isotonic formulations will generally have an osmotic pressure from about 250 to 350 mOsm. The term "hypotonic" describes a formulation with an osmotic pressure below that of human blood. Correspondingly, the term "hypertonic" is used to describe a formulation with an osmotic pressure above that of human blood. Isotonicity can be measured using a vapor pressure or ice-freezing type osmometer, for example. The formulations of the present invention are hypertonic as a result of the addition of salt and/or buffer.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS™.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. A "pharmaceutically acceptable acid" includes inorganic and organic acids which are nontoxic at the concentration and manner in which they are formulated. For example, suitable inorganic acids include hydrochloric, perchloric, hydrobromic, hydroiodic, nitric, sulfuric, sulfonic, sulfinic, sulfanilic, phosphoric, carbonic, etc. Suitable organic acids include straight and branched-chain alkyl, aromatic, cyclic, cycloaliphatic, arylaliphatic, heterocyclic, saturated, unsaturated, mono, di- and tri-carboxylic, including for example, formic, acetic, 2-hydroxyacetic, trifluoroacetic, phenylacetic, trimethylacetic, t-butyl acetic, anthranilic, propanoic, 2-hydroxypropanoic, 2-oxopropanoic, propandioic, cyclopentanepropionic, cyclopentane propionic, 3-phenylpropionic, butanoic, butandioic, benzoic, 3-(4-hydroxybenzoyl)benzoic, 2-acetoxy-benzoic, ascorbic, cinnamic, lauryl sulfuric, stearic, muconic, mandelic, succinic, embonic, fumaric, malic, maleic, hydroxymaleic, malonic, lactic, citric, tartaric, glycolic, glyconic, gluconic, pyruvic, glyoxalic, oxalic, mesylic, succinic, salicylic, phthalic, palmoic, palmeic, thiocyanic, methanesulphonic, ethanesulphonic, 1,2-ethanedisulfonic, 2-hydroxyethanesulfonic, benzenesulphonic, 4-chorobenzenesulfonic, napthalene-2-sulphonic, p-toluenesulphonic, camphorsulphonic, 4-methylbicyclo[2.2.2]-oct-2-ene-1-carboxylic, glucoheptonic, 4,4'-methylenebis-3-(hydroxy-2-ene-1-carboxylic acid), hydroxynapthoic.

"Pharmaceutically-acceptable bases" include inorganic and organic bases which are non-toxic at the concentration and manner in which they are formulated. For example, suitable bases include those formed from inorganic base forming metals such as lithium, sodium, potassium, magnesium, calcium, ammonium, iron, zinc, copper, manganese, aluminum, N-methylglucamine, morpholine, piperidine and organic nontoxic bases including, primary, secondary and tertiary amines, substituted amines, cyclic amines and basic ion exchange resins, [e.g., $N(R')_4^+$ (where R' is independently H or $C_{1-4}$ alkyl, e.g., ammonium, Tris)], for example, isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

Additional pharmaceutically acceptable acids and bases useable with the present invention include those which are derived from the amino acids, for example, histidine, glycine, phenylalanine, aspartic acid, glutamic acid, lysine and asparagine.

"Pharmaceutically acceptable" buffers and salts include those derived from both acid and base addition salts of the above indicated acids and bases. Specific buffers and/or salts include histidine, succinate and acetate.

A "pharmaceutically acceptable sugar" is a molecule which, when combined with a protein of interest, significantly prevents or reduces chemical and/or physical instability of the protein upon storage. When the formulation is intended to be lyophilized and then reconstituted, "pharmaceutically acceptable sugars" may also be known as a "lyoprotectant". Exemplary sugars and their corresponding sugar alcohols include: an amino acid such as monosodium glutamate or histidine; a methylamine such as betaine; a lyotropic salt such as magnesium sulfate; a polyol such as trihydric or higher molecular weight sugar alcohols, e.g. glycerin, dextran, erythritol, glycerol, arabitol, xylitol, sorbitol, and mannitol; propylene glycol; polyethylene glycol; PLURONICS®; and combinations thereof. Additional exemplary lyoprotectants include glycerin and gelatin, and the sugars mellibiose, melezitose, raffinose, mannotriose and stachyose. Examples of reducing sugars include glucose, maltose, lactose, maltulose, iso-maltulose and lactulose. Examples of non-reducing sugars include non-reducing glycosides of polyhydroxy compounds selected from sugar alcohols and other straight chain polyalcohols. Preferred sugar alcohols are monoglycosides, especially those compounds obtained by reduction of disaccharides such as lactose, maltose, lactulose and maltulose. The glycosidic side group can be either glucosidic or galactosidic. Additional examples of sugar alcohols are glucitol, maltitol, lactitol and iso-maltulose. The preferred pharmaceutically-acceptable sugars are the non-reducing sugars trehalose or sucrose. Pharmaceutically acceptable sugars are added to the formulation in a "protecting amount" (e.g. pre-lyophilization) which means that the protein essentially retains its physical and chemical stability and integrity during storage (e.g., after reconstitution and storage).

The "diluent" of interest herein is one which is pharmaceutically acceptable (safe and non-toxic for administration to a human) and is useful for the preparation of a liquid formulation, such as a formulation reconstituted after lyophilization. Exemplary diluents include sterile water, bacteriostatic water for injection (BWFI), a pH buffered solution (e.g. phosphate-buffered saline), sterile saline solution, Ringer's solution or dextrose solution. In an alternative embodiment, diluents can include aqueous solutions of salts and/or buffers.

A "preservative" is a compound which can be added to the formulations herein to reduce bacterial activity. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

An "individual" or "subject" or "patient" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" (and grammatical variations thereof such as "treat" or "treating") refers to clinical intervention designed to alter the natural course of the individual, tissue or cell being treated during the course of clinical pathology. Desirable effects of treatment include, but are not limited to, decreasing the rate of disease progression, ameliorating or palliating the disease state, and remission or improved prognosis, all measurable by one of skill in the art such as a physician. In one embodiment, treatment can mean alleviation of symptoms, diminishment of any direct or indirect pathological consequences of the disease, decreasing the rate of infectious disease progression, amelioration or palliation of the disease state, and remission or improved prognosis. In some embodiments, antibodies of the invention are used to delay development of a disease or to slow the progression of an infectious disease.

As used herein, "in conjunction with" refers to administration of one treatment modality in addition to another treatment modality. As such, "in conjunction with" refers to administration of one treatment modality before, during or after administration of the other treatment modality to the individual.

The term "phagosome" refers to an internalized membrane-enclosed endocytic vessel of a phagocytic cell. It can be initiated by direct-, antibody- or complement-enhanced phagocytosis. The term "phagolysosome" refers to an internalized cellular vessel that has fused with one or more lyzosomes.

Bacteria are traditionally divided into two main groups, Gram-positive (Gm+) and Gram-negative (Gm−), based upon their Gram-stain retention. Gram-positive bacteria are bounded by a single unit lipid membrane, and they generally contain a thick layer (20-80 nm) of peptidoglycan responsible for retaining the Gram-stain. Gram-positive bacteria are those that are stained dark blue or violet by Gram staining. In contrast, Gram-negative bacteria cannot retain the crystal violet stain, instead taking up the counterstain (safranin or fuchsine) and appearing red or pink. Gram-positive cell walls typically lack the outer membrane found in Gram-negative bacteria.

The term "bacteremia" refers to the presence of bacteria in the bloodstream which is most commonly detected through a blood culture. Bacteria can enter the bloodstream as a severe complication of infections (like pneumonia or meningitis), during surgery (especially when involving mucous membranes such as the gastrointestinal tract), or due to catheters and other foreign bodies entering the arteries or veins. Bacteremia can have several consequences. The immune response to the bacteria can cause sepsis and septic shock, which has a relatively high mortality rate. Bacteria can also use the blood to spread to other parts of the body, causing infections away from the original site of infection. Examples include endocarditis or osteomyelitis.

A "therapeutically effective amount" is the minimum concentration required to effect a measurable improvement of a particular disorder. A therapeutically effective amount herein may vary according to factors such as the disease state, age, sex, and weight of the patient, and the ability of the antibody to elicit a desired response in the individual. A therapeutically effective amount is also one in which any toxic or detrimental effects of the antibody are outweighed by the therapeutically beneficial effects. In one embodiment, a therapeutically effective amount is an amount effective to reduce bacteremia in an in vivo infection. In one aspect, a "therapeutically effective amount" is at least the amount effective to reduce the bacterial load or colony forming units (CFU) isolated from a patient sample such as blood by at least one log relative to prior to drug administration. In a more specific aspect, the reduction is at least 2 logs. In another aspect, the reduction is 3, 4, 5 logs. In yet another aspect, the reduction is to below detectable levels. In another embodiment, a therapeutically effective amount is the amount of an AAC in one or more doses given over the course of the treatment period, that achieves a negative blood culture (i.e., does not grow out the bacteria that is the target of the AAC) as compared to the positive blood culture before or at the start of treatment of the infected patient.

A "prophylactically effective amount" refers to an amount effective, at the dosages and for periods of time necessary, to achieve the desired prophylactic result. Typically but not necessarily, since a prophylactic dose is used in subjects prior to, at the earlier stage of disease, or even prior to exposure to conditions where the risk of infection is elevated, the prophylactically effective amount can be less than the therapeutically effective amount. In one embodiment, a prophylactically effective amount is at least an amount effective to reduce, prevent the occurrence of or spread of infection from one cell to another.

"Chronic" administration refers to administration of the medicament(s) in a continuous as opposed to acute mode, so as to maintain the initial therapeutic effect (activity) for an extended period of time. "Intermittent" administration is treatment that is not consecutively done without interruption, but rather is cyclic in nature.

The term "package insert" is used to refer to instructions customarily included in commercial packages of therapeutic products, that contain information about the indications, usage, dosage, administration, combination therapy, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "protecting group" refers to a substituent that is commonly employed to block or protect a particular functionality while other functional groups react on the compound. For example, an "amino-protecting group" is a substituent attached to an amino group that blocks or protects the amino functionality in the compound. Suitable amino-protecting groups include, but are not limited to, acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see T. W. Greene, Protective Groups in Organic Synthesis, John Wiley & Sons, New York, 1991, or a later edition.

The term "about" as used herein refers to the usual error range for the respective value readily known to the skilled person in this technical field. Reference to "about" a value or parameter herein includes (ad describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

III. Compositions and Methods

Antibody-Antibiotic Conjugates (AAC)

The AAC compounds of the invention include those with antibacterial activity, effective against a number of human and veterinary Gram positive, Gram negative pathogens, including the Staphylococci. In an exemplary embodiment, the AAC compounds include a cysteine-engineered antibody conjugated, i.e. covalently attached by a linker, to a rifamycin-type antibiotic moiety. The biological activity of the rifamycin-type antibiotic moiety is modulated by conjugation to an antibody. The antibody-antibiotic conjugates (AAC) of the invention selectively deliver an effective dose of an antibacterial to an infection site whereby greater selectivity, i.e. a lower efficacious dose, may be achieved while increasing the therapeutic index ("therapeutic window").

The invention provides novel antibacterial therapy that aims to prevent antibiotic escape by targeting populations of bacteria that evade conventional antibiotic therapy. The novel antibacterial therapy is achieved with an Antibody Antibiotic Conjugate (AAC) in which an antibody specific for cell wall components found on S. aureus (including MRSA) is chemically linked to a potent antibiotic (a derivative of rifamycin). The antibiotic is joined to the antibody via a protease cleavable, peptide linker that is designed to be cleaved by cathepsin B, a lysosomal protease found in most mammalian cell types (Dubowchik et al (2002) Bioconj. Chem. 13:855-869). The AAC acts as a pro-drug in that the antibiotic is inactive (due to the large size of the antibody) until the linker is cleaved. Since a significant proportion of S. aureus found in a natural infection is taken up by host cells, primarily neutrophils and macrophages, at some point during the course of infection in the host, and that the time spent inside host cells provides a significant opportunity for the bacterium to evade antibiotic activity. The AACs of the invention are designed to bind to S. aureus and release the antibiotic inside the phagolysosome after bacteria are taken up by host cells. By this mechanism, AAC are able to concentrate the active antibiotic specifically in a location where S. aureus is poorly treated by conventional antibiotics. While the invention is not limited or defined by an particular mechanism of action, the AAC improve antibiotic activity via three potential mechanisms: (1) The AAC delivers antibiotic inside mammalian cells that take up the bacteria, thereby increasing the potency of antibiotics that diffuse poorly into the phagolysosomes where bacteria are sequestered. (2) AAC opsonize bacteria—thereby increasing uptake of free bacteria by phagocytic cells—and release the antibiotic locally to kill the bacteria while they are sequestered in the phagolysosome. (3) AAC improve the half-life of antibiotics in vivo (improved pharmacokinetics) by linking the antibiotic to an antibody. Improved pharmacokinetics of AAC enable delivery of sufficient antibiotic in regions where S. aureus is concentrated while limiting the overall dose of antibiotic that needs to be administered systemically. This property should permit long-term therapy with AAC to target persistent infection with minimal antibiotic side effects.

The present application describes the generation of novel conjugated anti-WTA antibody therapeutic agents and their use in the treatment of infections with Gram positive (Gm+) bacteria including S. aureus infections. These antibodies are capable of targeting populations of Gm+ bacteria that evade convention antibiotic therapy.

An antibody-antibiotic conjugate compound of the invention comprises an anti-wall teichoic acid beta (WTA beta) antibody covalently attached by a peptide linker to a rifamycin-type antibiotic.

In one embodiment, the antibody-antibiotic conjugate has the formula:

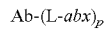

wherein:
Ab is the anti-wall teichoic acid antibody;
L is the peptide linker having the formula:

where Str is a stretcher unit; Pep is a peptide of two to twelve amino acid residues, and Y is a spacer unit;
abx is the rifamycin-type antibiotic; and
p is an integer from 1 to 8.

The number of antibiotic moieties which may be conjugated via a reactive linker moiety to an antibody molecule may be limited by the number of free cysteine residues, which are introduced by the methods described herein. Exemplary AAC of Formula I therefore comprise antibodies which have 1, 2, 3, or 4 engineered cysteine amino acids (Lyon, R. et al (2012) Methods in Enzym. 502:123-138).

Anti-Wall Teichoic (WTA) Antibodies

Disclosed herein are certain anti-WTA Abs and conjugated anti-WTA antibodies that bind to WTA expressed on a number of Gm+ bacteria including Staphylococcus aureus. Anti-WTA antibodies may be selected and produced by the methods taught in U.S. Pat. No. 8,283,294; Meijer P J et al (2006) J Mol. Biol. 358 (3):764-72; Lantto J, et al (2011) J. Virol. 85 (4):1820-33, and in Example 21 below. The invention provides compositions of these anti-WTA Abs.

Figure 3:
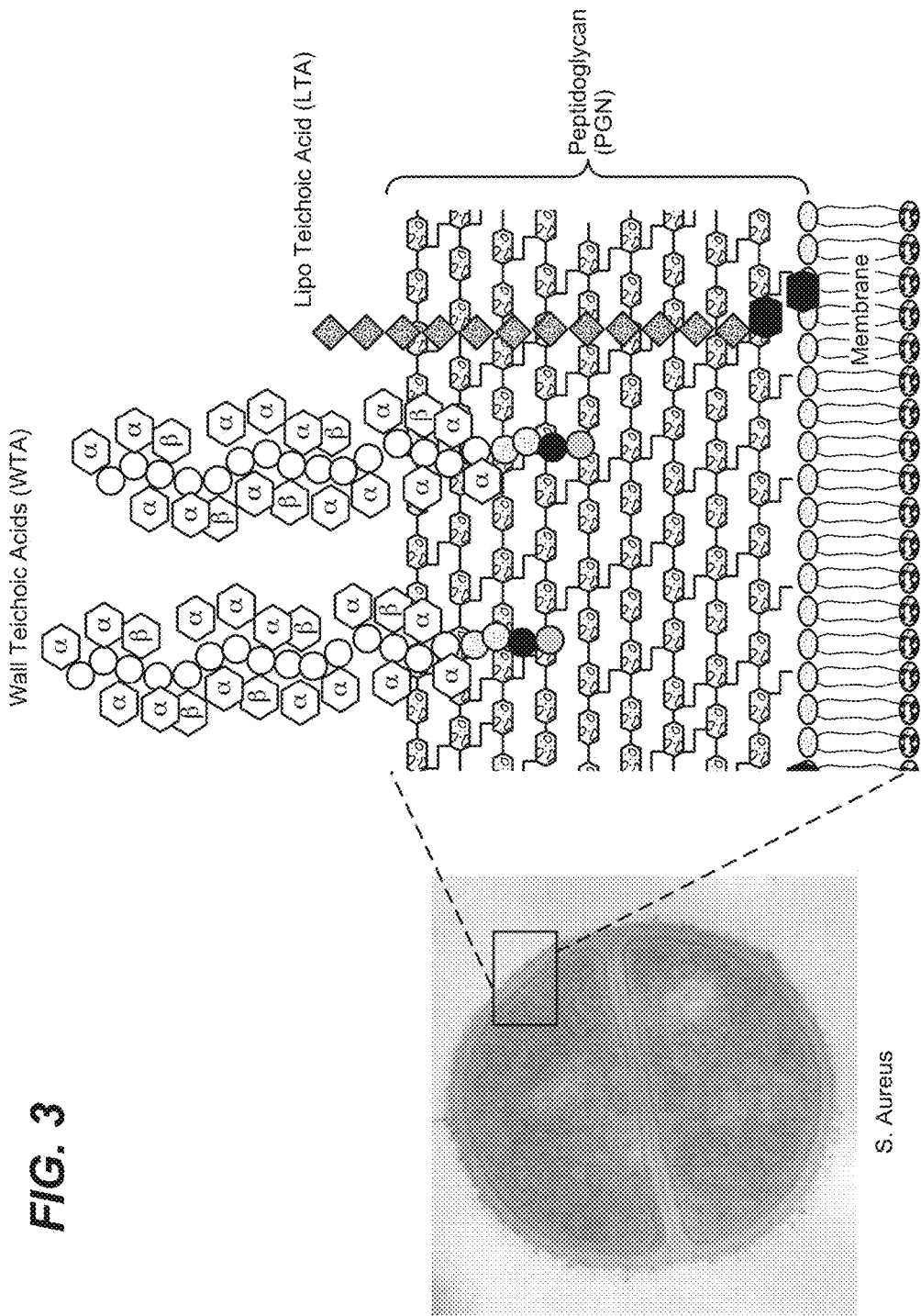
FIG. 3 shows the cell wall of Gram-positive bacteria, such as *S. aureus* with a cartoon representation of wall teichoic acids (WTA), Lipo teichoic acid (LTA) and the Peptidoglycan (PGN) sheaths that stabilize the cell membrane and provide attachment sites.

The cell wall of Gram-positive bacteria is comprised of thick layer of multiple peptidoglycan (PGN) sheaths that not only stabilize the cell membrane but also provide many sites to which other molecules could be attached (FIG. 3). A major class of these cell surface glycoproteins are teichoic acids ("TA"), which are phosphate-rich molecules found on many glycan-binding proteins (GPB). TA come in two types: (1) lipo teichoic acid ("LTA"), which are anchored to the plasma membrane and extend from the cell surface into the peptidoglycan layer; and (2) wall TA (WTA), which are covalently attached to peptidoglycan and extend through and beyond the cell wall (FIG. 3). WTA can account for as much as 60% of the total cell wall mass in GPB. As a result, it presents a highly expressed cell surface antigen.

The chemical structures of WTAs vary among organisms. In S. aureus, WTA is covalently linked to the 6-OH of N-acetyl muramic acid (MurNAc) via a disaccharide composed of N-acetylglycosamine (GlcNAc)-1-P and N-acetylmannoseamine (ManNAc), which is followed by about two or three units of glycerol-phosphates (FIG. 4) The actual WTA polymer is then composed of about 11-40 ribitol-phosphate (Rbo-P) repeating units. The step-wise synthesis of WTA is first initiated by the enzyme called TagO, and S. aureus strains lacking the TagO gene (by deletion of the gene) do not make any WTA. The repeating units can be further tailored with D-alanine (D-Ala) at C2-OH and/or with N-acetylglucosamine (GlcNAc) at the C4-OH position via α-(alpha) or β-(beta) glycosidic linkages. Depending of the *S. aureus* strain, or the growth phase of the bacteria the glycosidic linkages could be α-, β-, or a mixture of the two anomers. These GlcNAc sugar modifications are tailored by two specific *S. aureus*-derived glycosyltransferases (Gtfs): TarM Gtf mediates α-glycosidic linkages, whereas TarS Gtfs mediates β-(beta)glycosidic linkages.

Given significant evidence that intracellular stores of MRSA are protected from antibiotics, the novel therapeutic compositions of the invention were developed to prevent this method of antibiotic evasion by using a *S. aureus* specific antibody to tether an antibiotic onto the bacteria such that when the bacteria is engulfed or otherwise internalized by a host cell in vivo, it brings the antibiotic along into the host cell.

In one aspect, the invention provides anti-WTA antibodies which are anti-WTAα or anti-WTAβ. In another aspect, the invention provides anti-*Staph aureus* Abs. The exemplary Abs were cloned from B cells from *S. aureus* infected patients (as taught in Example 21). In one embodiment the anti-WTA and anti-*Staph aureus* Abs are human monoclonal antibodies. The invention encompasses chimeric Abs and humanized Abs comprising the CDRs of the present WTA Abs.

For therapeutic use, the WTA Abs of the invention for conjugation to antibiotics to generate AACs, can be of any isotype except IgM. In one embodiment, the WTA Abs are of the human IgG isotype. In more specific embodiments, the WTA Abs are human IgG1.

FIGS. 6A and 6B lists the Abs that are anti-WTAα or anti-WTA β. Throughout the specification and figures, the Abs designated by a 4-digit number (e.g., 4497) may also be referred to with a preceding "S", e.g., S4497; both names refer to the same antibody which is the wild type (WT) unmodified sequence of the antibody. Variants of the antibody are indicated by a "v" following the antibody no., e.g., 4497.v8. Unless specified (e.g. as by a variant number), the amino acid sequences shown are the original, unmodified/unaltered sequences. These Abs can be altered at one or more residues, for example to improve the pK, stability, expression, manufacturability (e.g., as described in the Examples below), while maintaining substantially about the same or improved binding affinity to the antigen as compared to the wild type, unmodified antibody. Variants of the present WTA antibodies having conservative amino acid substitutions are encompassed by the invention. Below, unless specified otherwise, the CDR numbering is according to Kabat and the Constant domain numbering is according to EU numbering.

FIG. 13A and FIG. 13B provide the amino acid sequence alignment of the Light chain Variable regions (VL) and the Heavy chain Variable region (VH), respectively of four human anti-WTA alpha antibodies. The CDR sequences CDR L1, L2, L3 and CDR H1, H2, H3 according to Kabat numbering are underlined.

TABLES 6A

Light chain CDR sequences of the anti-WTAα.

| Antibody | CDR L1 | CDR L2 | CDR L3 |
|---|---|---|---|
| 4461 | KSSQSVLSRANNNYYVA (SEQ ID NO. 1) | WASTREF (SEQ ID NO. 2) | QQYYTSRRT (SEQ ID NO. 3) |
| 4624 | RSNQNLLSSSNNNYLA (SEQ ID NO. 7) | WASTRES (SEQ ID NO. 8) | QQYYANPRT (SEQ ID NO. 9) |

TABLES 6A-continued

Light chain CDR sequences of the anti-WTAα.

| Antibody | CDR L1 | CDR L2 | CDR L3 |
|---|---|---|---|
| 4399 | KSNQNVLASSNDKNYLA (SEQ ID NO. 13) | WASIRES (SEQ ID NO. 14) | QQYYTNPRT (SEQ ID NO. 15) |
| 6267 | KSSQNVLYSSNNKNYLA (SEQ ID NO. 19) | WASTRES (SEQ ID NO. 20) | QQYYTSPPYT (SEQ ID NO. 21) |

TABLES 6B

Heavy chain CDR sequences of the anti-WTAα.

| Antibody | CDR H1 | CDR H2 | CDR H3 |
|---|---|---|---|
| 4461 | DYYMH (SEQ ID NO. 4) | WINPKSGGTNYAQRFQG (SEQ ID NO. 5) | DCGSGGLRDF (SEQ ID NO. 6) |
| 4624 | DYYIH (SEQ ID NO. 10) | WINPNTGGTYYAQKFRD (SEQ ID NO. 11) | DCGRGGLRDI (SEQ ID NO. 12) |
| 4399 | DYYIH (SEQ ID NO. 16) | WINPNTGGTNYAQKFQG (SEQ ID NO. 17) | DCGNAGLRDI (SEQ ID NO. 18) |
| 6267 | SYWIG (SEQ ID NO. 22) | IIHPGDSKTRYSPSFQG (SEQ ID NO. 23) | LYCSGGSCYSDRAFSSLGAGGYYYYGMGV (SEQ ID NO. 24) |

The sequences of the each pair of VL and VH are as follows:

4461 Light Chain Variable Region
(SEQ. ID NO. 25)
DIQMTQSPDSLAVSLGERATINCKSSQSVLSRANNNYYVAWYQHKPG

QPPKLLIYWASTREFGVPDRFSGSGSGTDFTLTINSLQAEDVAVYYC

QQYYTSRRTFGQGTKVEIK

4461 Heavy Chain Variable Region
(SEQ. ID NO. 26)
QVQLVQSGAEVRKPGASVKVSCKASGYSFTDYYMHWVRQAPGQGLEW

MGWINPKSGGTNYAQRFQGRVTMTGDTSISAAYMDLASLTSDDTAVY

YCVKDCGSGGLRDFWGQGTTVTVSS

4624 Light Chain Variable Region
(SEQ. ID NO. 27)
DIQMTQSPDSLSVSLGERATINCRSNQNLLSSSNNNYLAWYQQKPGQ

PLKLLIYWASTRESGVPDRFSGSGSGTDFTLTISSLQAEDVAVYYC

QQYYANPRTFGQGTKVEIK

4624 Heavy Chain Variable Region
(SEQ. ID NO. 28)
QVQLQQSRVEVKRPGTSVKVSCKTSGYTFSDYYIHWVRLAPGQGLEL

MGWINPNTGGTYYAQKFRDRVTMTRDTSIATAYLEMSSLTSDDTAVY

YCAKDCGRGGLRDIWGPGTMVTVSS

-continued

4399 Light Chain Variable Region
(SEQ. ID NO. 29)
EIVLTQSPDSLAVSLGERATINCKSNQNVLASSNDKNYLAWFQHKPG

QPLKLLIYWASIRESGVPDRFSGSGSGTDFTLTISSLRAEDVAVYYC

QQYYTNPRTFGQGTKVEFN

4399 Heavy Chain Variable Region
(SEQ. ID NO. 30)
EVQLVQSGAEVKKPGTSVKVSCKASGYTFTDYYIHWVRLAPGQGLEL

MGWINPNTGGTNYAQKFQGRVTMTRDTSIATAYMELSSLTSDDTAVY

YCAKDCGNAGLRDIWGQGTTVTVSS

6267 Light Chain Variable Region
(SEQ. ID NO. 31)
DIQLTQSPDSLAVSLGERATINCKSSQNVLYSSNNKNYLAWYQQKP

GQPPKLLIYWASTRESGVPDRFSGSGSGTDFTLTISSLQAEDVAVY

YCQQYYTSPPYTFGQGTKLEIE

6267 Heavy Chain Variable Region
(SEQ. ID NO. 32)
EVQLVQSGAEVKKPGESLKISCKGSGYSFTSYWIGWVRQMPGKGLE

WMGIIHPGDSKTRYSPSFQGQVTISADKSISTAYLQWNSLKASDTA

MYYCARLYCSGGSCYSDRAFSSLGAGGYYYYGMGVWGQGTTVTVSS

The invention provides an isolated monoclonal antibody that binds wall teichoic acid (WTA) comprising a light chain and a H chain, the L chain comprising CDR L1, L2, L3 and the H chain comprising CDR H1, H2, H3 wherein the CDR L1, L2, L3 and H1, H2, H3 comprise the amino acid sequences of the CDRs of each of Abs 4461 (SEQ ID NO. 1-6), 4624 (SEQ ID NO. 7-12), 4399 (SEQ ID NO. 13-18), and 6267 (SEQ ID NO. 19-24) respectively, as shown in Table 6A and 6B.

In another embodiment, the isolated monoclonal Ab that binds WTA comprises a H chain variable region (VH) and a L chain variable region (VL), wherein the VH comprises at least 95% sequence identity over the length of the VH region sequence of the each of antibodies 4461, 4624, 4399, and 6267, respectively. In yet another specific aspect, the sequence identity is 96%, 97%, 98%, 99% or 100%.

The present invention also provides anti-WTA beta Abs comprising the L and H chain CDR sequences as shown in FIG. 14. In one embodiment, the isolated anti-WTA beta monoclonal Abs comprise the CDR L1, L2, L3 and H1, H2, H3 selected from the group consisting of the CDRs of each of the 13 Abs in FIG. 14. In another embodiment, the invention provides an isolated anti-WTA beta Abs comprising at least 95% sequence identity over the length of the V region domains of each of 13 antibodies. In yet another specific aspect, the sequence identity is 96%, 97%, 98%, 99% or 100%.

Of the 13 anti-WTA beta Abs, 6078 and 4497 were modified to create variants i) having an engineered Cys in one or both L and H chains for conjugation to linker-antibiotic intermediates; and ii) wherein the first residue in the H chain Q is altered to E (v2) or the first two residues QM were changed to EI or EV (v3 and v4).

Figure 2:
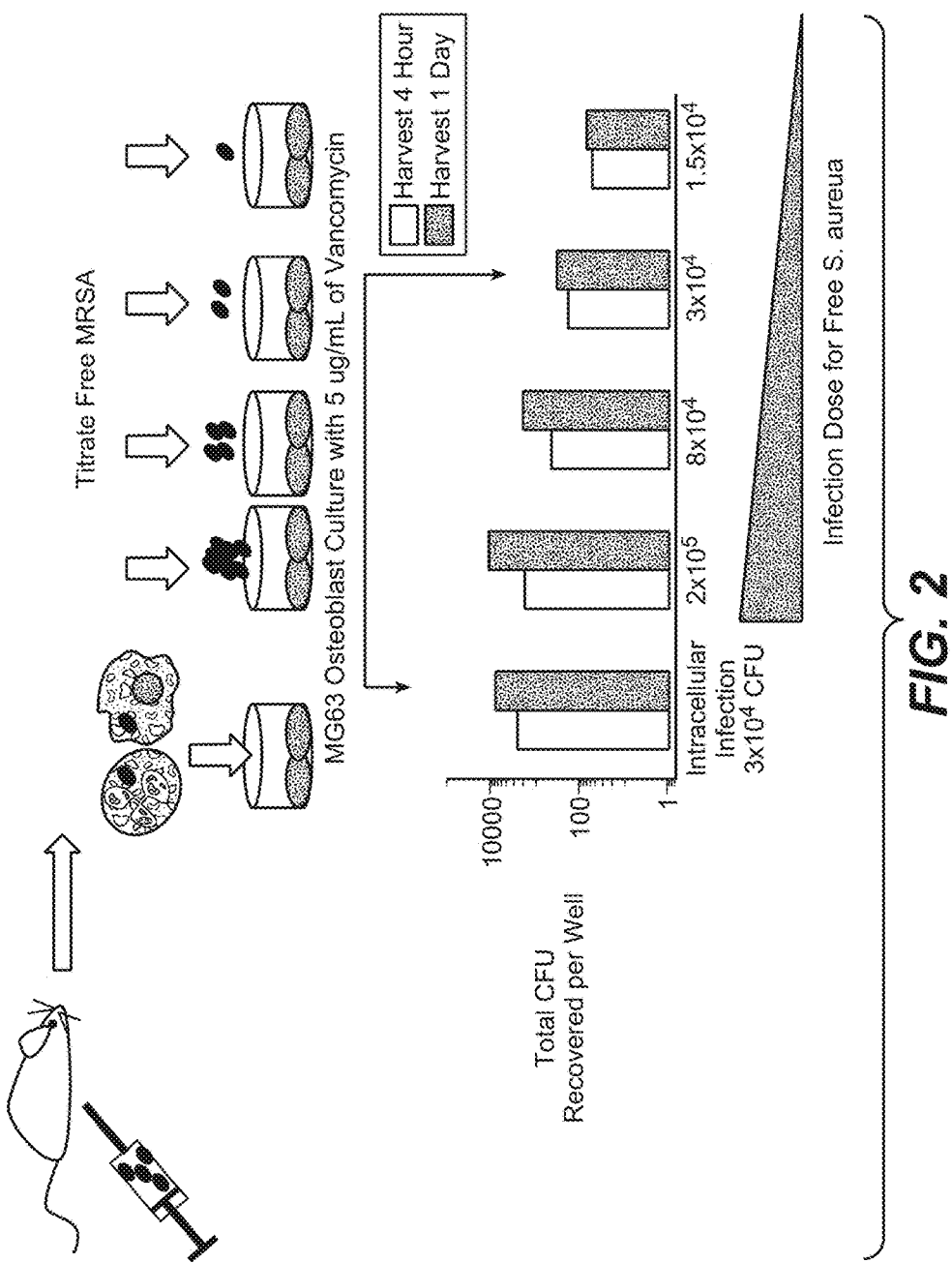
FIG. 2 shows infected peritoneal cells were able to transfer infection to osteoblasts in the presence of vancomycin.
Figure 4:
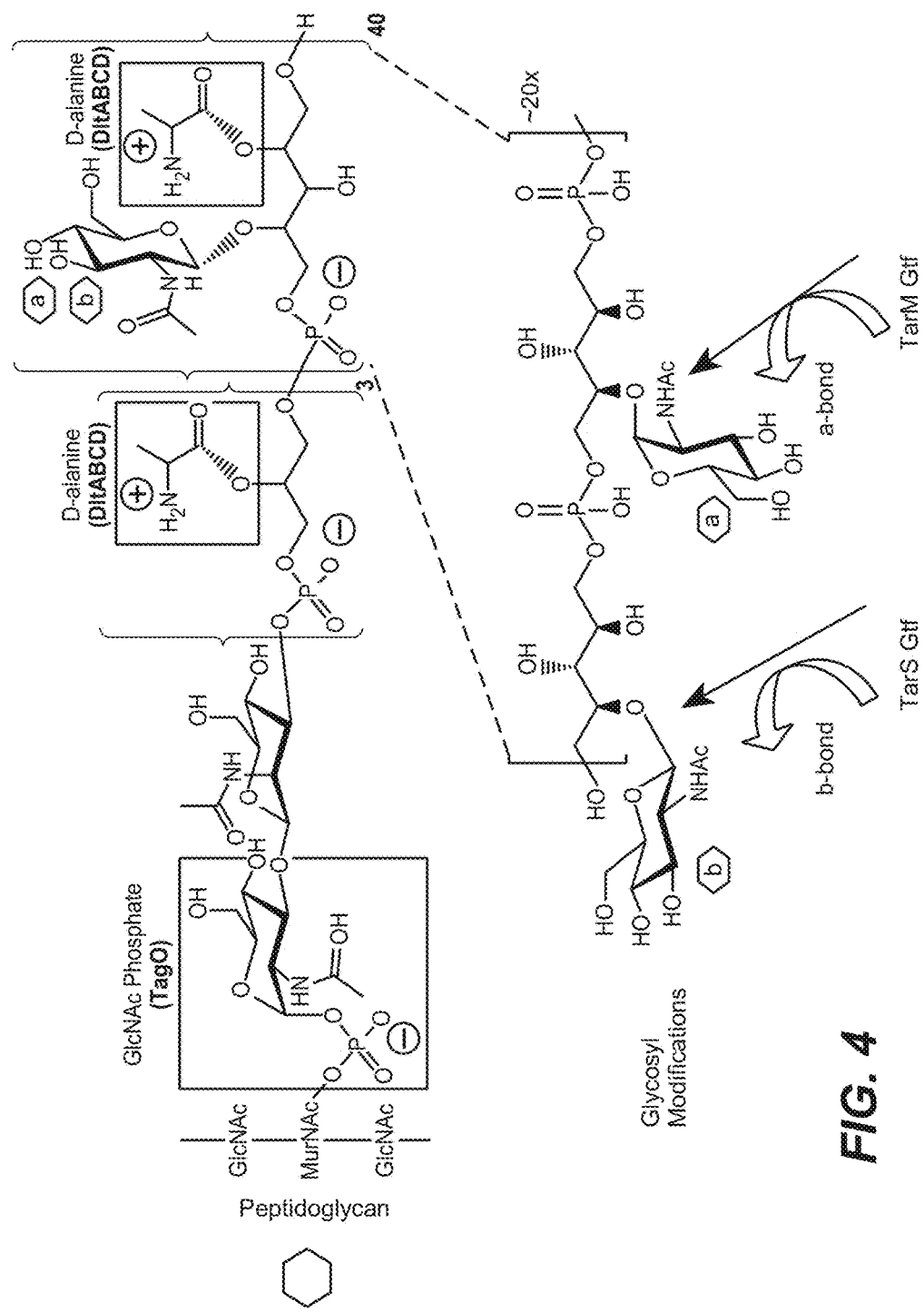
FIG. 4 shows the chemical structure and glycosyl modifications of Wall Teichoic Acid (WTA), described in detail under Definitions.
Figure 15A-1:
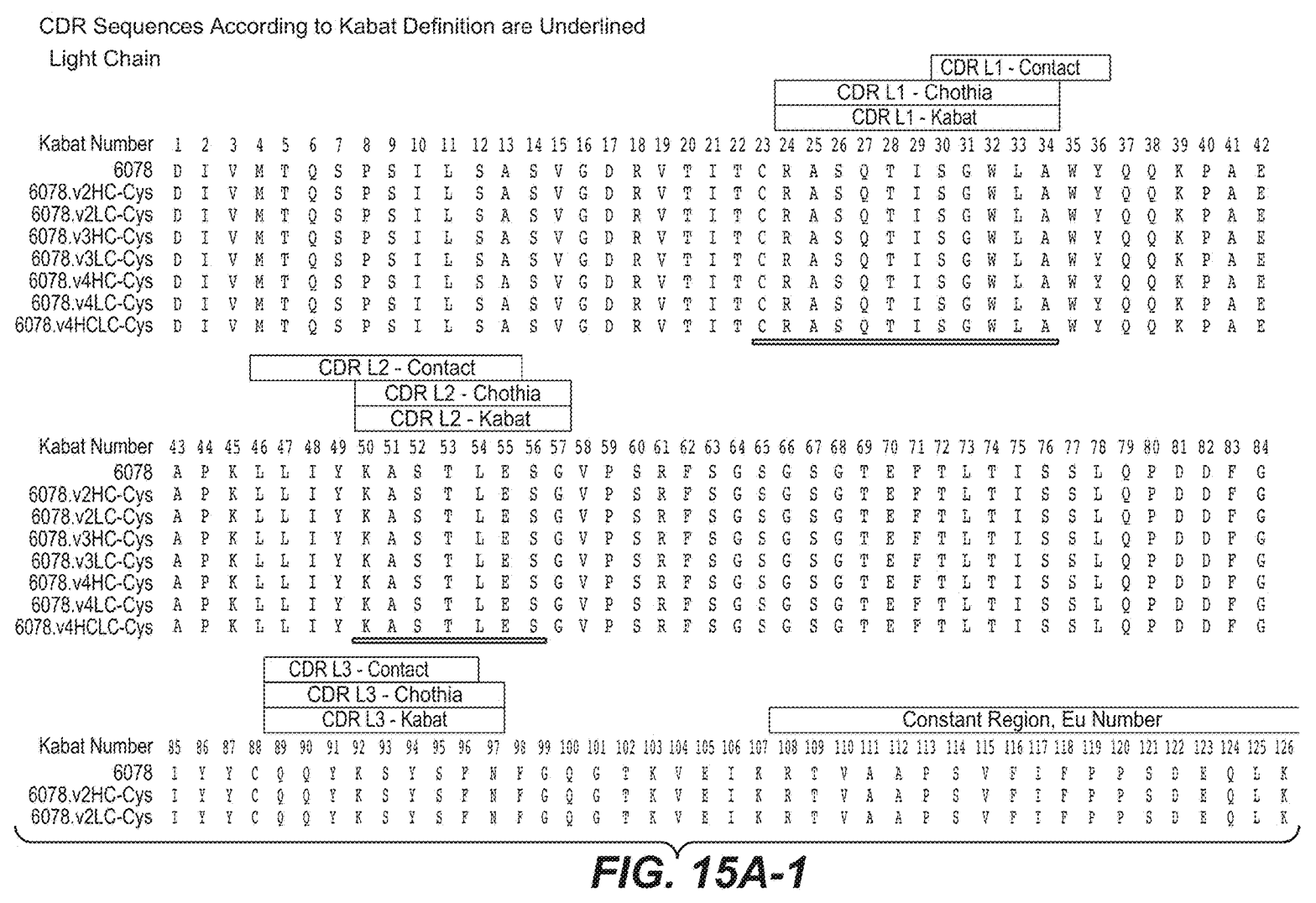
Figure 15A-2:
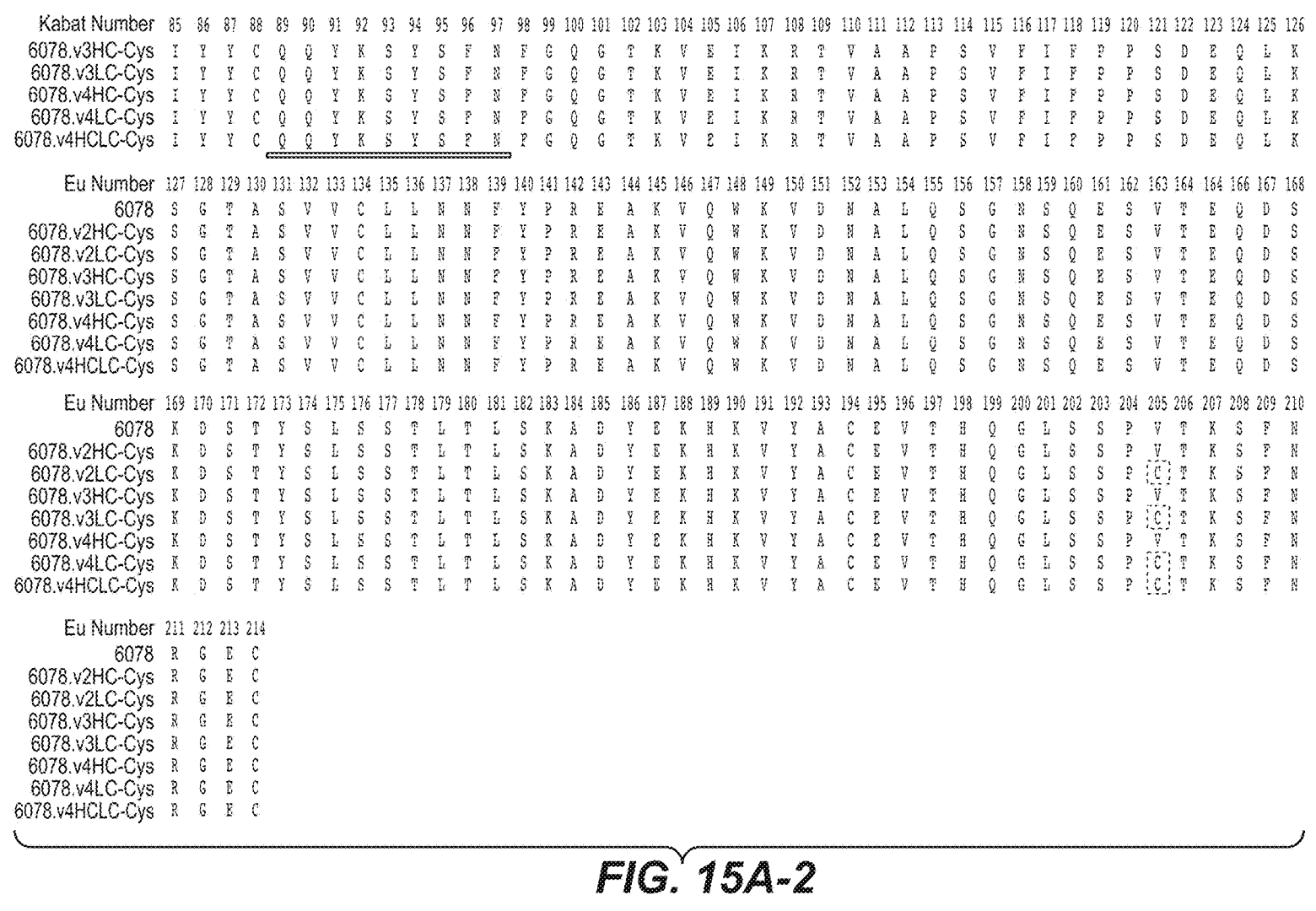
Figure 15B-2:
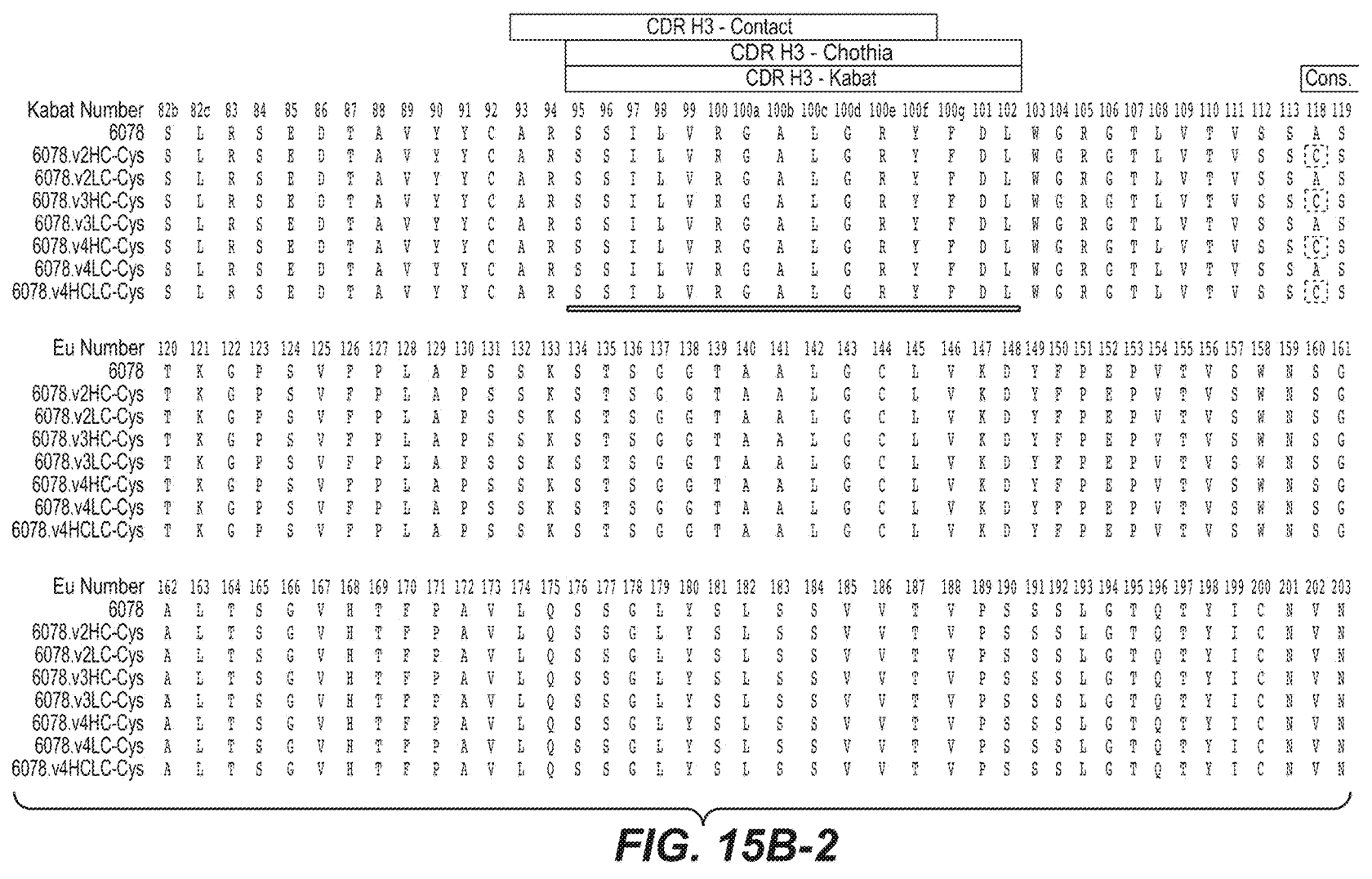
Figure 15B-3:
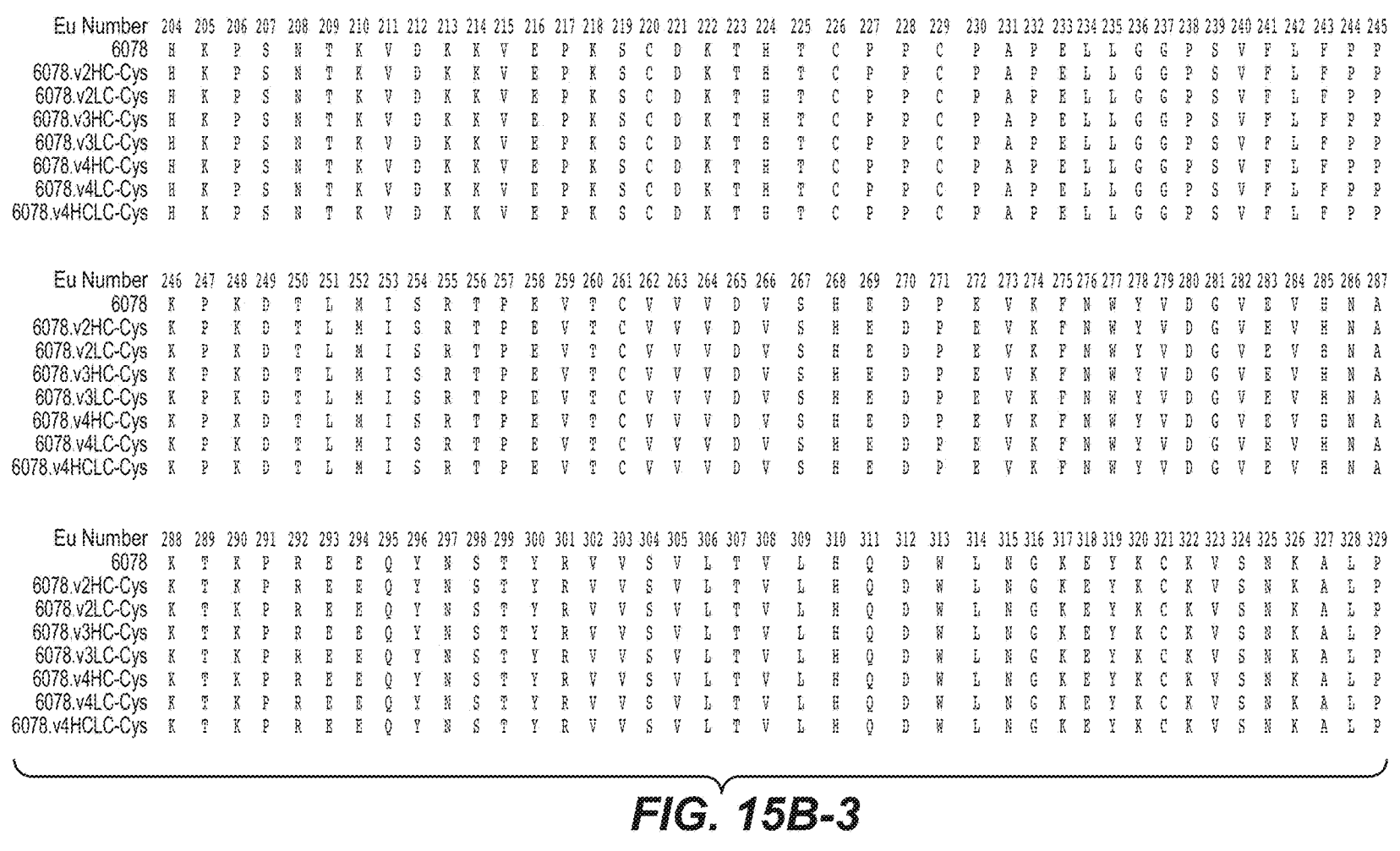
Figure 15B-4:
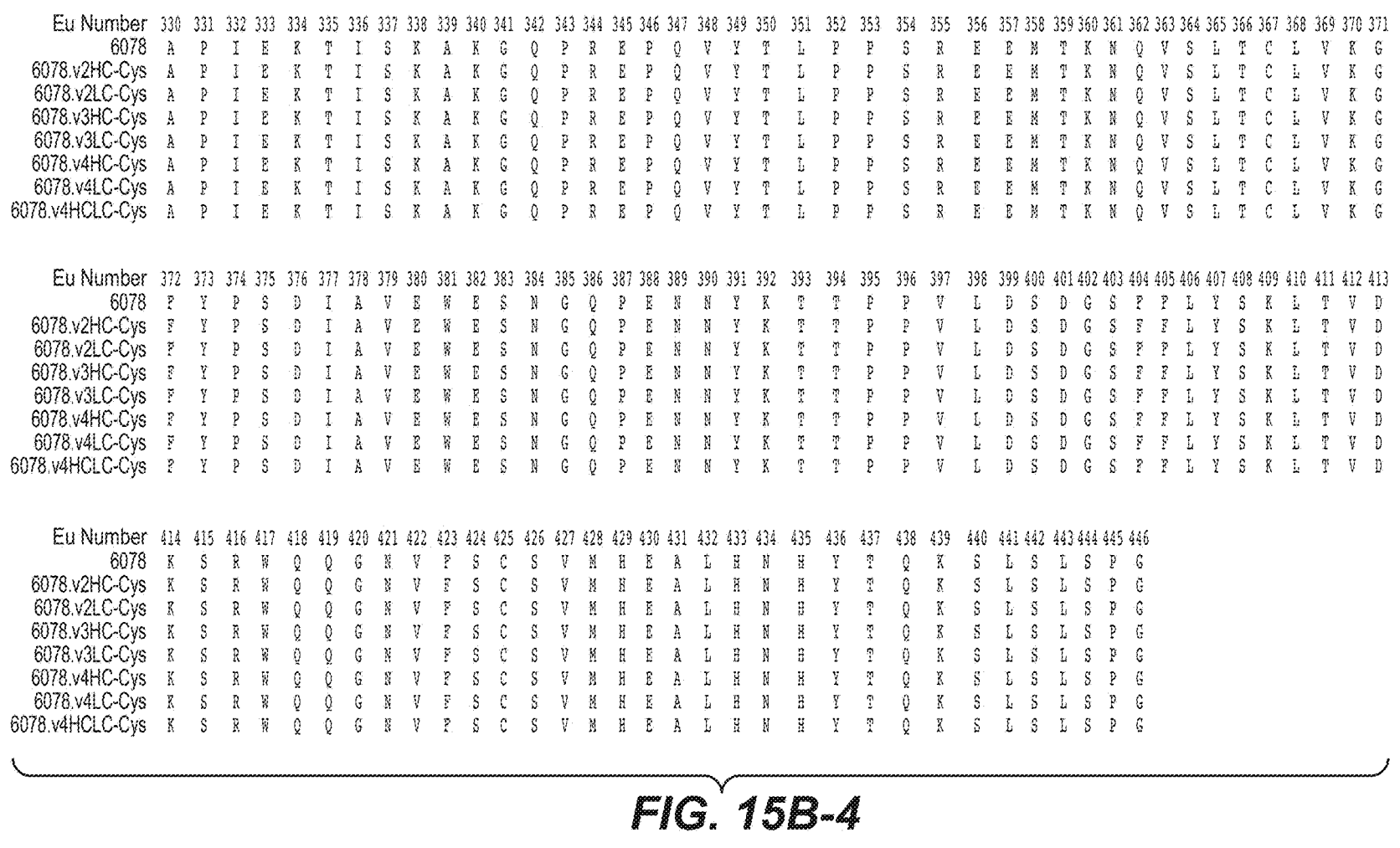

FIGS. 15A-1 and 15A-2 provide the amino acid sequence of the full length L chain of anti-WTA beta Ab 6078 (unmodified) and its variants, v2, v3, v4. L chain variants that contain an engineered Cys are indicated by the C in the black box the end of the constant region (at EU residue no. 205 in this case). The variant designation, e.g., v2LC-Cys means variant 2 containing a Cys engineered into the L chain. HCLC-Cys means both the H and L chains of the antibody contain an engineered Cys. FIGS. 15B-1 to 15B-4 show an alignment of the full length H chain of anti-WTA beta Ab 6078 (unmodified) and its variants, v2, v3, v4 which have changes in the first or first 2 residues of the H chain. H chain variants that contain an engineered Cys are indicated by the C in the black box the end of the constant region (at EU residue no. 118).

6078 Light Chain Variable Region (VL)
(SEQ ID NO. 111)
DIVMTQSPSILSASVGDRVTITCRASQTISGWLAWYQQKPAEAPKLL

IYKASTLESGVPSRFSGSGSGTEFTLTISSLQPDDFGIYYCQQYKSY

SFNFGQGTKVEIK

6078 Heavy Chain Variable Region (VH)
(SEQ ID NO. 112)
XX₁QLVQSGAEVKKPGASVKVSCEASGYTLTSYDINWVRQATGQGPEW

MGWMNANSGNTGYAQKFQGRVTLTGDTSISTAYMELSSLRSEDTAVYY

CARSSILVRGALGRYFDLWGRGTLVTVSS wherein X is Q or E; and X₁ is M, I or V.

6078 Light Chain
(SEQ. ID NO. 113)
DIVMTQSPSILSASVGDRVTITCRASQTISGWLAWYQQKPAEAPKLL

IYKASTLESGVPSRFSGSGSGTEFTLTISSLQPDDFGIYYCQQYKSY

SFNFGQGTKVEIKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGEC

6078 Cysteine-engineered Light Chain
(SEQ. ID NO. 115)
DIVMTQSPSILSASVGDRVTITCRASQTISGWLAWYQQKPAEAPKLLIYK

ASTLESGVPSRFSGSGSGTEFTLTISSLQPDDFGIYYCQQYKSYSFNFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPCTKSFNRGEC

6078 WT full length Heavy Chain
(SEQ. ID NO. 114)
QMQLVQSGAEVKKPGASVKVSCEASGYTLTSYDINWVRQATGQGPEWMGW

MNANSGNTGYAQKFQGRVTLTGDTSISTAYMELSSLRSEDTAVYYCARSS

ILVRGALGRYFDLWGRGTLVTVSSASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQP

REPQVYTLPPSREEMTKNQVSLTCLVKGFYPSDIAVEWESNGQPENNYKT

TPPVLDSDGSFFLYSKLTVDKSRWQQGNVFSCSVMHEALHNHYTQKSLSL
SPG 6078 variant (v2, v3, or v4) full
length Heavy Chain
(SEQ. ID NO. 116)
EXQLVQSGAEVKKPGASVKVSCEASGYTLTSYDINWVRQATGQGPEWMG

WMNANSGNTGYAQKFQGRVTLTGDTSISTAYMELSSLRSEDTAVYYCAR

-continued

SSILVRGALGRYFDLWGRGTLVTVSSASTKGPSVFPLAPSSKSTSGGTA

ALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGP

SVFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKT

ISKAKGQPREPQVYTLPPSREEMTKNQVSLTCLVKGFYPSDIAVEWES

NGQPENNYKTTPPVLDSDGSFFLYSKLTVDKSRWQQGNVFSCSVMHEA

LHNHYTQKSLSLSPG
wherein X can be M, I or V.

6078 variant (v2, v3 or v4),
Cys-engineered Heavy Chain
(SEQ. ID NO. 117)
EXQLVQSGAEVKKPGASVKVSCEASGYTLTSYDINWVRQATGQGPEWMG

WMNANSGNTGYAQKFQGRVTLTGDTSISTAYMELSSLRSEDTAVYYCAR

SSILVRGALGRYFDLWGRGTLVTVSSCSTKGPSVFPLAPSSKSTSGGTA

ALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGP

SVFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESNG

QPENNYKTTPPVLDSDGSFFLYSKLTVDKSRWQQGNVFSCSVMHEALHN

HYTQKSLSLSPG
wherein X is M, I or V.

In one embodiment, the invention provides an isolated anti-WTA beta antibody comprising a heavy chain and a light, wherein the heavy chain comprises a VH having at least 95% sequence identity to SEQ ID NO. 112. In an additional embodiment, this antibody further comprises a VL having at least 95% sequence identity to SEQ ID NO. 111. In a specific embodiment, the anti-WTA beta antibody comprises a light chain and a heavy chain, wherein the L chain comprises a VL of SEQ ID NO. 111 and the H chain comprises a VH of SEQ ID NO. 112. In a yet more specific embodiment, the isolated anti-WTA beta antibody comprises a L chain of SEQ ID NO. 113 and a H chain of SEQ ID NO. 114.

The 6078 Cys-engineered H and L chain variants can be paired in any of the following combinations to form full Abs for conjugating to linker-Abx intermediates to generate anti-WTA AACs of the invention. The unmodified L chain (SEQ ID NO. 113) can be paired with a Cys-engineered H chain variant of SEQ ID NO. 117; the variant can be one wherein X is M, I or V. The Cys-engineered L chain of SEQ ID NO. 115 can be paired with: the H chain of SEQ ID NO. 114; a H chain variant of SEQ ID NO. 116; or a Cys-engineered H chain variant of SEQ ID NO. 117 (in this version, both H and L chains are Cys engineered).

Figure 16A-2:
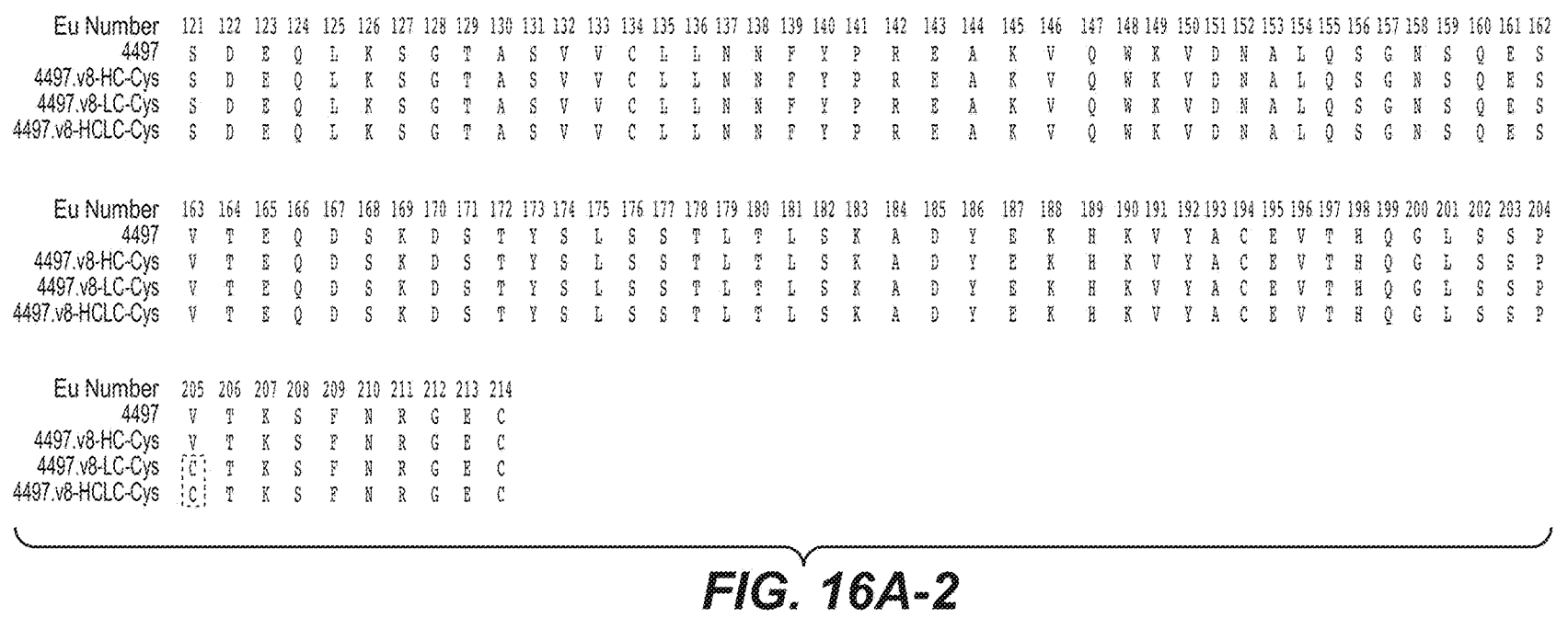
Figure 16B-1:
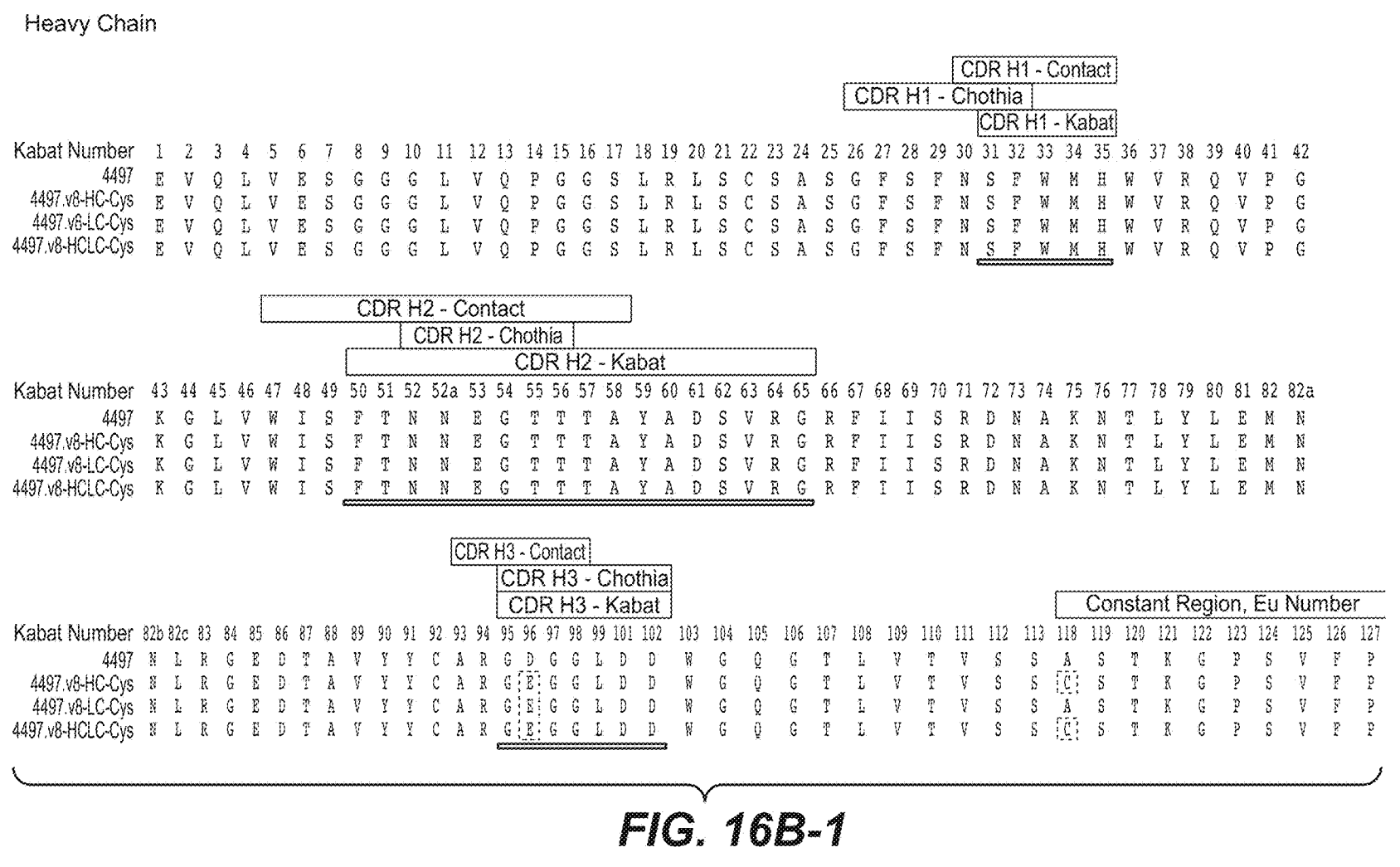
Figure 16B-2:
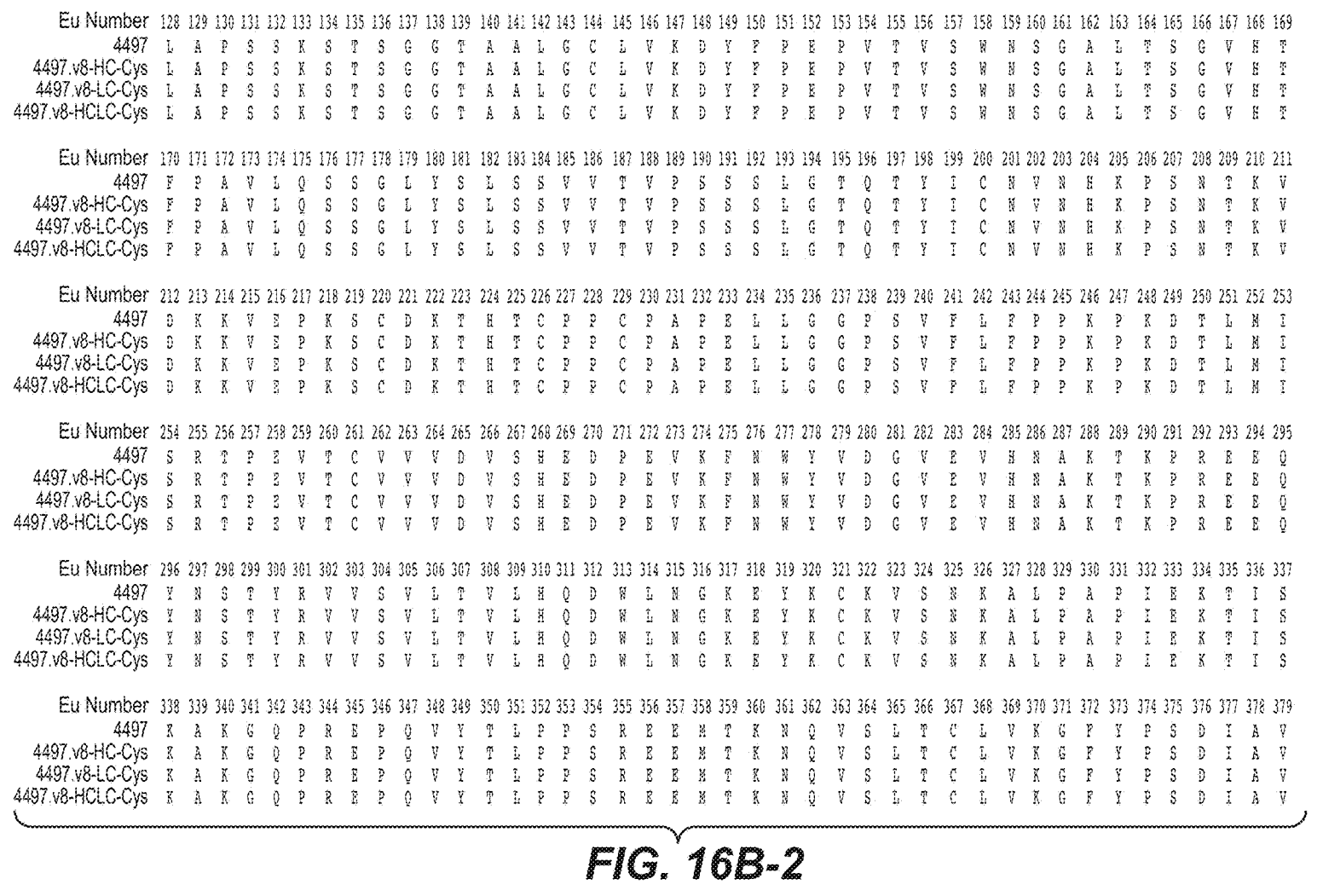

In a particular embodiment, the anti-WTA beta antibody and the anti-WTA beta AAC of the invention comprises a L chain of SEQ ID NO. 115 and H chain of SEQ ID NO. 116. FIGS. 16A-1 and 16A-2 provide the full length L chain of anti-WTA beta Ab 4497 (unmodified) and its v8 variants. L chain variants that contain an engineered Cys are indicated by the C in the black box the end of the constant region (at EU residue no. 205). FIGS. 16B-1, 16B-2, 16B-3 show an alignment of the full length H chain of anti-WTA beta Ab 4497 (unmodified) and its v8 variant with D altered to E in CDR H3 position 96, with or without the engineered Cys. H chain variants that contain an engineered Cys are indicated by the C in the black box the end of the constant region (at EU residue no. 118 in this case). Unmodified CDR H3 is GDGGLDD (SEQ ID NO. 104); 4497v8 CDR H3 is GEGGLDD (SEQ ID NO. 118).

4497 Light Chain Variable Region
(SEQ. ID NO. 119)
DIQLTQSPDSLAVSLGERATINCKSSQSIFRTSRNKNLLNWYQQRPG

QPPRLLIHWASTRKSGVPDRFSGSGFGTDFTLTITSLQAEDVAIYYC

QQYFSPPYTFGQGTKLEIK

4497 Heavy Chain Variable Region
(SEQ. ID NO. 120)
EVQLVESGGGLVQPGGSLRLSCSASGFSFNSFWMHWVRQVPGKGLV

WISFTNNEGTTTAYADSVRGRFIISRDNAKNTLYLEMNNLRGEDTA

VYYCARGDGGLDDWGQGTLVTVSS 4497.v8 Heavy Chain Variable Region
(SEQ. ID NO. 156)
EVQLVESGGGLVQPGGSLRLSCSASGFSFNSFWMHWVRQVPGKGLVWI

SFTNNEGTTTAYADSVRGRFIISRDNAKNTLYLEMNNLRGEDTAVYYC

ARGEGGLDDWGQGTLVTVSS

4497 Light Chain
(SEQ. ID NO. 121)
DIQLTQSPDSLAVSLGERATINCKSSQSIFRTSRNKNLLNWYQQRPGQP

PRLLIHWASTRKSGVPDRFSGSGFGTDFTLTITSLQAEDVAIYYCQQYF

SPPYTFGQGTKLEIKRTVAAPSVFIFPPSDEQLKSGTASVVCLLNNFYP

REAKVQWKVDNALQSGNSQESVTEQDSKDSTYSLSSTLTLSKADYEKHK

VYACEVTHQGLSSPVTKSFNRGEC 4497 v.8 Heavy Chain
(SEQ. ID NO. 122)
EVQLVESGGGLVQPGGSLRLSCSASGFSFNSFWMHWVRQVPGKGLVWI

SFTNNEGTTTAYADSVRGRFIISRDNAKNTLYLEMNNLRGEDTAVYYC

ARGEGGLDDWGQGTLVTVSSASTKGPSVFPLAPSSKSTSGGTAALGCL

VKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTIS

KAKGQPREPQVYTLPPSREEMTKNQVSLTCLVKGFYPSDIAVEWESNG

QPENNYKTTPPVLDSDGSFFLYSKLTVDKSRWQQGNVFSCSVMHEALH

NHYTQKSLSLSPG

4497-Cys Light Chain
(SEQ. ID NO. 123)
DIQLTQSPDSLAVSLGERATINCKSSQSIFRTSRNKNLLNWYQQRPGQ

PPRLLIHWASTRKSGVPDRFSGSGFGTDFTLTITSLQAEDVAIYYCQQ

YFSPPYTFGQGTKLEIKRTVAAPSVFIFPPSDEQLKSGTASVVCLLNN

FYPREAKVQWKVDNALQSGNSQESVTEQDSKDSTYSLSSTLTLSKADY

EKHKVYACEVTHQGLSSPVTKSFNRGEC

-continued 4497.v8-Heavy Chain
(SEQ. ID NO. 157; the same as SEQ ID NO.122)
EVQLVESGGGLVQPGGSLRLSCSASGFSFNSFWMHWVRQVPGKGLVW

ISFTNNEGTTTAYADSVRGRFIISRDNAKNTLYLEMNNLRGEDTAVY

YCARGEGGLDDWGQGTLVTVSSASTKGPSVFPLAPSSKSTSGGTAAL

GCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLG

GPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPA

PIEKTISKAKGQPREPQVYTLPPSREEMTKNQVSLTCLVKGFYPSDI

AVEWESNGQPENNYKTTPPVLDSDGSFFLYSKLTVDKSRWQQGNVFS

CSVMHEALHNHYTQKSLSLSPG.

4497.v8-Cys Heavy Chain
(SEQ. ID NO. 124)
EVQLVESGGGLVQPGGSLRLSCSASGFSFNSFWMHWVRQVPGKGLVWI

SFTNNEGTTTAYADSVRGRFIISRDNAKNTLYLEMNNLRGEDTAVYYC

ARGEGGLDDWGQGTLVTVSSCSTKGPSVFPLAPSSKSTSGGTAALGCL

VKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKT

KPREEQYNSTYRVVSVLTVLHQDWLGKEYKCKVSNKALPAPIEKTISK

AKGQPREPQVYTLPPSREEMTKNQVSLTCLVKGFYPSDIAVEWESNGQ

PENNYKTTPPVLDSDGSFFLYSKLTVDKSRWQQGNVFSCSVMHEALHN

HYTQKSLSLSPG

Another isolated anti-WTA beta antibody provided by the invention comprises a heavy chain and a light, wherein the heavy chain comprises a VH having at least 95% sequence identity to SEQ ID NO. 120. In an additional embodiment, this antibody further comprises a VL having at least 95% sequence identity to SEQ ID NO. 119. In a specific embodiment, the anti-WTA beta antibody comprises a light chain and a heavy chain, wherein the L chain comprises a VL of SEQ ID NO. 119 and the H chain comprises a VH of SEQ ID NO. 120. In a yet more specific embodiment, the isolated anti-WTA beta antibody comprises a L chain of SEQ ID NO. 121 and a H chain of SEQ ID NO. 122.

The 4497 Cys-engineered H and L chain variants can be paired in any of the following combinations to form full Abs for conjugating to linker-Abx intermediates to generate anti-WTA AACs of the invention. The unmodified L chain (SEQ ID NO. 121) can be paired with a Cys-engineered H chain variant of SEQ ID NO. 124. The Cys-engineered L chain of SEQ ID NO. 123 can be paired with: the H chain variant of SEQ ID NO. 157; or a Cys-engineered H chain variant of SEQ ID NO. 124 (in this version, both H and L chains are Cys engineered). In a particular embodiment, the anti-WTA beta antibody and the anti-WTA beta AAC of the invention comprises a L chain of SEQ ID NO. 123.

Yet another embodiment is an antibody that binds to the same epitope as each of the anti-WTA alpha Abs of FIG. 13A and FIG. 13B. Also provided is an antibody that binds to the same epitope as each of the anti-WTA beta Abs of FIG. 14, FIGS. 15A and 15B, and FIGS. 16A and 16B.

Binding of anti-WTA antibodies to WTA is influenced by the anomeric orientation of GlcNAc-sugar modifications on WTA. WTA are modified by N-acetylglucosamine (GlcNAc) sugar modifications at the C4-OH position via α- or β-glycosidic linkages, by TarM glycosyltransferase or TarS glycosyltransferase, respectively. Accordingly, cell wall preparations from glycosyltransferase mutant strains lacking TarM(ΔTarM), TarS (ΔTarS), or both TarM and TarS (ΔTarM/ΔTarS) were subjected to immunoblotting analysis with antibodies against WTA. WTA antibody (S7574) specific to α-GlcNAc modifications on WTA does not bind to cell wall preparation from ΔTarM strain. Vice versa, a WTA antibody (S4462) specific to β-GlcNAc modifications on WTA does not bind to cell wall preparation from ΔTarS strain. As expected, both these antibodies do not bind to cell wall preparations from a deletion strain lacking both glycosyltransferases (ΔTarM/ΔTarS) and also the strain lacking any WTA (ΔTagO). According to such analysis, antibodies have been characterized as anti-α-GlcNAc WTA mAbs, or as anti-β-GlcNAc WTA mAbs as listed in the Table in FIGS. 6A and 6B.

Cysteine amino acids may be engineered at reactive sites in an antibody and which do not form intrachain or intermolecular disulfide linkages (Junutula, et al., 2008b Nature Biotech., 26 (8):925-932; Dornan et al (2009) Blood 114 (13):2721-2729; U.S. Pat. No. 7,521,541; U.S. Pat. No. 7,723,485; WO2009/052249, Shen et al (2012) Nature Biotech., 30 (2):184-191; Junutula et al (2008) Jour of Immun. Methods 332:41-52). The engineered cysteine thiols may react with linker reagents or the linker-antibiotic intermediates of the present invention which have thiol-reactive, electrophilic groups such as maleimide or alpha-halo amides to form AAC with cysteine engineered antibodies (thioMabs) and the antibiotic (abx) moieties. The location of the antibiotic moiety can thus be designed, controlled, and known. The antibiotic loading can be controlled since the engineered cysteine thiol groups typically react with thiol-reactive linker reagents or linker-antibiotic intermediates in high yield. Engineering an anti-WTA antibody to introduce a cysteine amino acid by substitution at a single site on the heavy or light chain gives two new cysteines on the symmetrical tetramer antibody. An antibiotic loading near 2 can be achieved and near homogeneity of the conjugation product AAC.

In certain embodiments, it may be desirable to create cysteine engineered anti-WTA antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as antibiotic moieties or linker-antibiotic moieties, to create an immunoconjugate, as described further herein. In certain embodiments, any one or more of the following residues may be substituted with cysteine, including V205 (Kabat numbering) of the light chain; A118 (EU numbering) of the heavy chain; and S400 (EU numbering) of the heavy chain Fc region. Nonlimiting exemplary cysteine engineered heavy chain A118C (SEQ ID NO: 149) and light chain V205C (SEQ ID NO: 151) mutants of an anti-WTA antibody are shown. Cysteine engineered anti-WTA antibodies may be generated as described (Junutula, et al., 2008b Nature Biotech., 26 (8):925-932; U.S. Pat. No. 7,521,541; US-2011/0301334.

In another embodiment, the invention relates to an isolated anti-WTA antibody comprising a heavy chain and a light, wherein the heavy chain comprises a wild-type heavy chain constant region sequence or cysteine-engineered mutant (ThioMab) and the light chain comprises a wild-type light chain constant region sequence or cysteine-engineered mutant (ThioMab). In one aspect, the heavy chain has at least 95% sequence identity to:

```
Heavy chain (IgG1) constant region, wild-type
                                         (SEQ ID NO: 148)
ASTKGPSVFPLAPSSKSTSGGTAALGCLVKDYFPEPVTVSWNSGALT

SGVHTFPAVLQSSGLYSLSSVVTVPSSSLGTQTYICNVNHKPSNTKV

DKKVEPKSCDKTHTCPPCPAPELLGGPSVFLFPPKPKDTLMISRTPE

VTCVVVDVSHEDPEVKFNWYVDGVEVHNAKTKPREEQYNSTYRVVSV

LTVLHQDWLNGKEYKCKVSNKALPAPIEKTISKAKGQPREPQVYTLP

PSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK

Heavy chain (IgG1) constant region,
A118C "ThioMab"
                                         (SEQ ID NO: 149)
CSTKGPSVFPLAPSSKSTSGGTAALGCLVKDYFPEPVTVSWNSGA

LTSGVHTFPAVLQSSGLYSLSSVVTVPSSSLGTQTYICNVNHKPS

NTKVDKKVEPKSCDKTHTCPPCPAPELLGGPSVFLFPPKPKDTLM

ISRTPEVTCVVVDVSHEDPEVKFNWYVDGVEVHNAKTKPREEQYN

STYRVVSVLTVLHQDWLNGKEYKCKVSNKALPAPIEKTISKAKGQ

PREPQVYTLPPSREEMTKNQVSLTCLVKGFYPSDIAVEWESNGQP

ENNYKTTPPVLDSDGSFFLYSKLTVDKSRWQQGNVFSCSVMHEAL

HNHYTQKSLSLSPGK
``` and the light chain has at least 95% sequence identity to:

```
Light chain (kappa) constant region, wild-type
                                         (SEQ ID NO: 150)
RTVAAPSVFIFPPSDEQLKSGTASVVCLLNNFYPREAKVQWK

VDNALQSGNSQESVTEQDSKDSTYSLSSTLTLSKADYEKHKV

YACEVTHQGLSSPVTKSFNRGEC

Light chain (kappa) constant region,
V205C "ThioMab"
                                         (SEQ ID NO: 151)
RTVAAPSVFIFPPSDEQLKSGTASVVCLLNNFYPREAKV

QWKVDNALQSGNSQESVTEQDSKDSTYSLSSTLTLSKAD

YEKHKVYACEVTHQGLSSPCTKSFNRGEC
```

The AAC of the invention include cysteine engineered anti-WTA antibodies where one or more amino acids of a wild-type or parent anti-WTA antibody are replaced with a cysteine amino acid. Any form of antibody may be so engineered, i.e. mutated. For example, a parent Fab antibody fragment may be engineered to form a cysteine engineered Fab, referred to herein as "ThioFab." Similarly, a parent monoclonal antibody may be engineered to form a "ThioMab." It should be noted that a single site mutation yields a single engineered cysteine residue in a ThioFab, while a single site mutation yields two engineered cysteine residues in a thioMab, due to the dimeric nature of the IgG antibody. Mutants with replaced ("engineered") cysteine (Cys) residues are evaluated for the reactivity of the newly introduced, engineered cysteine thiol groups.

The antibodies described herein may be produced using host cells in culture. Host cells may be transformed with vectors (expression or cloning vectors) comprising one or more nucleic acids encoding the antibodies described herein. The cells may be cultured under conditions suitable for producing the antibodies, and antibodies produced by the cell may be further purified. Suitable cells for producing antibodies may include prokaryotic, yeast, or higher eukaryotic (e.g., mammalian) cells. In some embodiments, a mammalian cell (a human or a non-human mammalian cell) is used. In some embodiments, a Chinese Hamster Ovary (CHO) cell is used.

Mammalian cells may be cultured, and propagation of mammalian cells in culture (tissue culture) has become a routine procedure. Examples of mammalian host cell lines may include, without limitation, monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2). Other useful mammalian host cell lines include myeloma cell lines such as NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J., 2003), pp. 255-268.

Plant cell cultures of cotton, corn, potato, soybean, petunia, tomato, duckweed (Leninaceae), alfalfa (*M. truncatula*), and tobacco can also be utilized as hosts.

Suitable prokaryotic cells for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Rifamycin-Type Antibiotic Moieties

The antibiotic moiety (abx) of the antibody-antibiotic conjugates (AAC) of the invention is a rifamycin-type antibiotic or group that has a cytotoxic or cytostatic effect. The rifamycins are a group of antibiotics that are obtained either naturally by the bacterium, *Nocardia mediterranei, Amycolatopsis mediterranei* or artificially. They are a subclass of the larger Ansamycin family which inhibit bacterial RNA polymerase (Fujii et al (1995) Antimicrob. Agents Chemother. 39:1489-1492; Feklistov, et al (2008) Proc Natl Acad Sci USA, 105 (39): 14820-5) and have potency against gram-positive and selective gram-negative bacteria. Rifamycins are particularly effective against mycobacteria, and are therefore used to treat tuberculosis, leprosy, and *mycobacterium avium* complex (MAC) infections. The rifamycin-type group includes the "classic" rifamycin drugs as well as the rifamycin derivatives rifampicin (rifampin, CA Reg. No. 13292-46-1), rifabutin (CA Reg. No. 72559-06-9; US 2011/0178001), rifapentine and rifalazil (CA Reg. No. 129791-92-0, Rothstein et al (2003) Expert Opin. Investig. Drugs 12(2):255-271; Fujii et al (1994) Antimicrob. Agents Chemother. 38:1118-1122. Many rifamycin-type antibiotics share the detrimental property of resistance development (Wichelhaus et al (2001) J. Antimicrob. Chemother. 47:153-156). Rifamycins were first isolated in 1957 from a fermentation culture of *Streptomyces mediterranei*. About seven rifamycins were discovered, named Rifamycin A, B, C, D, E, S, and SV (U.S. Pat. No. 3,150,046). Rifamycin B was the first introduced commercially and was useful in treating drug-resistant tuberculosis in the 1960s. Rifamycins have been used for the treatment of many diseases, the most important one being HIV-related Tuberculosis. Due to the large number of available analogues and derivatives, rifamycins have been widely utilized in the elimination of pathogenic bacteria that have become resistant to commonly used antibiotics. For instance, Rifampicin is known for its potent effect and ability to prevent drug resistance. It rapidly kills fast-dividing bacilli strains as well as "persisters" cells, which remain biologically inactive for long periods of time that allow them to evade antibiotic activity. In addition, rifabutin and rifapentine have both been used against tuberculosis acquired in HIV-positive patients.

Antibiotic moieties (abx) of the Formula I antibody-antibiotic conjugates are rifamycin-type moieties having the structure:

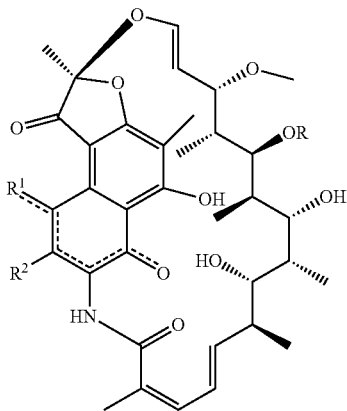

wherein:
the dashed lines indicate an optional bond;
R is H, $C_1$-$C_{12}$ alkyl, or $C(O)CH_3$;

$R^1$ is OH;

$R^2$ is CH=N-(heterocyclyl), wherein the heterocyclyl is optionally substituted with one or more groups independently selected from $C(O)CH_3$, $C_1$-$C_{12}$ alkyl, $C_1$-$C_{12}$ heteroaryl, $C_2$-$C_{20}$ heterocyclyl, $C_6$-$C_{20}$ aryl, and $C_3$-$C_{12}$ carbocyclyl;

or $R^1$ and $R^2$ form a five- or six-membered fused heteroaryl or heterocyclyl, and optionally forming a spiro or fused six-membered heteroaryl, heterocyclyl, aryl, or carbocyclyl ring, wherein the spiro or fused six-membered heteroaryl, heterocyclyl, aryl, or carbocyclyl ring is optionally substituted H, F, Cl, Br, I, $C_1$-$C_{12}$ alkyl, or OH; and where the peptide linker L is covalently attached to $R^2$.

An embodiment of a rifamycin-type moiety is:

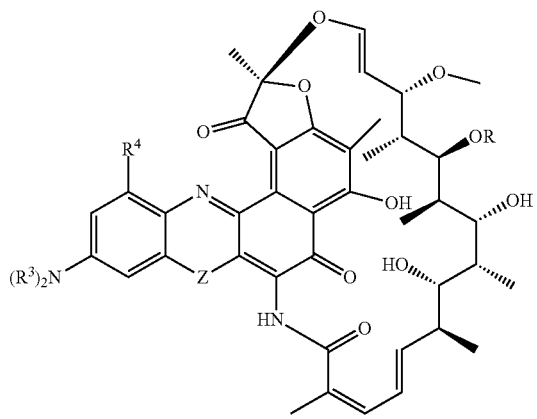

wherein $R^3$ is independently selected from H and $C_1$-$C_{12}$ alkyl; $R^4$ is selected from H, F, Cl, Br, I, $C_1$-$C_{12}$ alkyl, and OH; and Z is selected from NH, N($C_1$-$C_{12}$ alkyl), O and S; and where the peptide linker L is covalently attached to the nitrogen atom of $N(R^3)_2$.

An embodiment of a rifampicin-type moiety is:

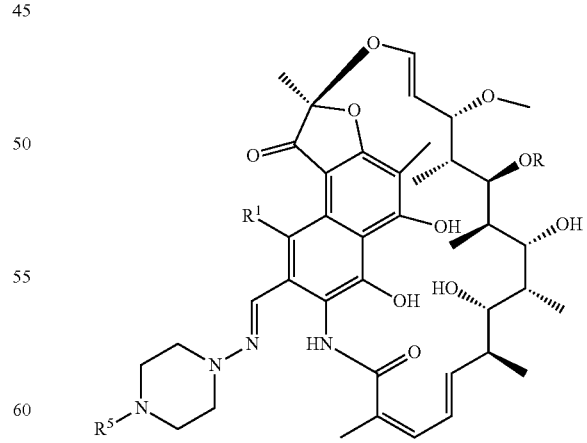

wherein $R^5$ is selected from H and $C_1$-$C_{12}$ alkyl; and where the peptide linker L is covalently attached to the nitrogen atom of $NR^5$.

An embodiment of a rifabutin-type moiety is:

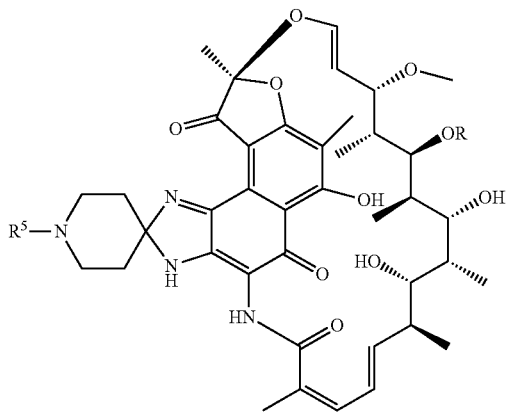

wherein $R^5$ is selected from H and $C_1$-$C_{12}$ alkyl; and where the peptide linker L is covalently attached to the nitrogen atom of $NR^5$.

An embodiment of a benzoxazinorifamycin-type moiety is:

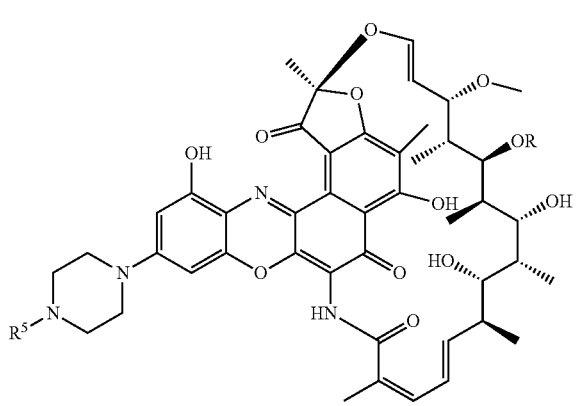

wherein $R^5$ is selected from H and $C_1$-$C_{12}$ alkyl; and where the peptide linker L is covalently attached to the nitrogen atom of $NR^5$.

An embodiment of a benzoxazinorifamycin-type moiety, referred to herein as pipBOR, is:

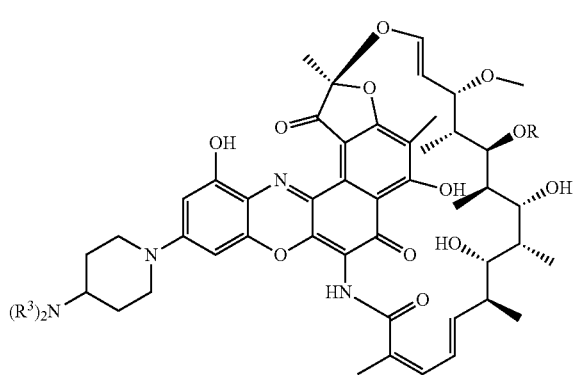

wherein $R^3$ is independently selected from H and $C_1$-$C_{12}$ alkyl; and where the peptide linker L is covalently attached to the nitrogen atom of $N(R^3)_2$.

An embodiment of a benzoxazinorifamycin-type moiety, referred to herein as dimethyl pipBOR, is:

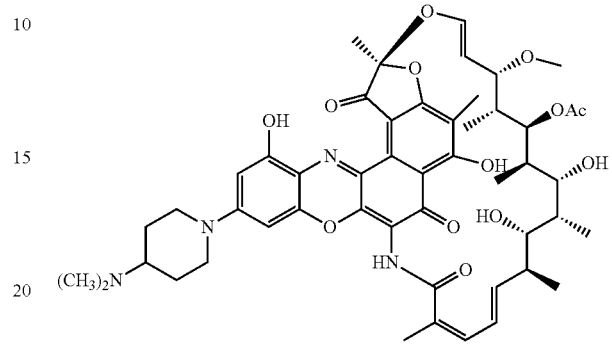

where the peptide linker L is covalently attached to the nitrogen atom of $N(CH_3)_2$.

The semi-synthetic derivative rifamycin S, or the reduced, sodium salt form rifamycin SV, can be converted to Rifalazil-type antibiotics in several steps, where R is H, or Ac, $R^3$ is independently selected from H and $C_1$-$C_{12}$ alkyl; $R^4$ is selected from H, F, Cl, Br, I, $C_1$-$C_{12}$ alkyl, and OH; and Z is selected from NH, $N(C_1$-$C_{12}$ alkyl), O and S, as exemplified in FIGS. 9-11. Benzoxazino (Z=O), benzthiazino (Z=S), benzdiazino (Z=NH, $N(C_1$-$C_{12}$ alkyl)rifamycins may be prepared (U.S. Pat. No. 7,271,165). Benzoxazinorifamycin (BOR), benzthiazinorifamycin (BTR), and benzdiazinorifamycin (BDR) analogs that contain substituents are numbered according to the numbering scheme provided in formula A at column 28 in U.S. Pat. No. 7,271,165, which is incorporated by reference for this purpose. By "25-O-deacetyl" rifamycin is meant a rifamycin analog in which the acetyl group at the 25-position has been removed. Analogs in which this position is further derivatized are referred to as a "25-O-deacetyl-25-(substituent)rifamycin", in which the nomenclature for the derivatizing group replaces "substituent" in the complete compound name.

Rifamycin-type antibiotic moieties can be synthesized by methods analogous to those disclosed in U.S. Pat. No. 4,610,919; U.S. Pat. No. 4,983,602; U.S. Pat. No. 5,786,349; U.S. Pat. No. 5,981,522; U.S. Pat. No. 4,859,661; U.S. Pat. No. 7,271,165; US 2011/0178001; Seligson, et al., (2001) Anti-Cancer Drugs 12:305-13; Chem. Pharm. Bull., (1993) 41:148, each of which is hereby incorporated by reference). Rifamycin-type antibiotic moieties can be screened for antimicrobial activity by measuring their minimum inhibitory concentration (MIC), using standard MIC in vitro assays (Tomioka et al., (1993) Antimicrob. Agents Chemother. 37:67).

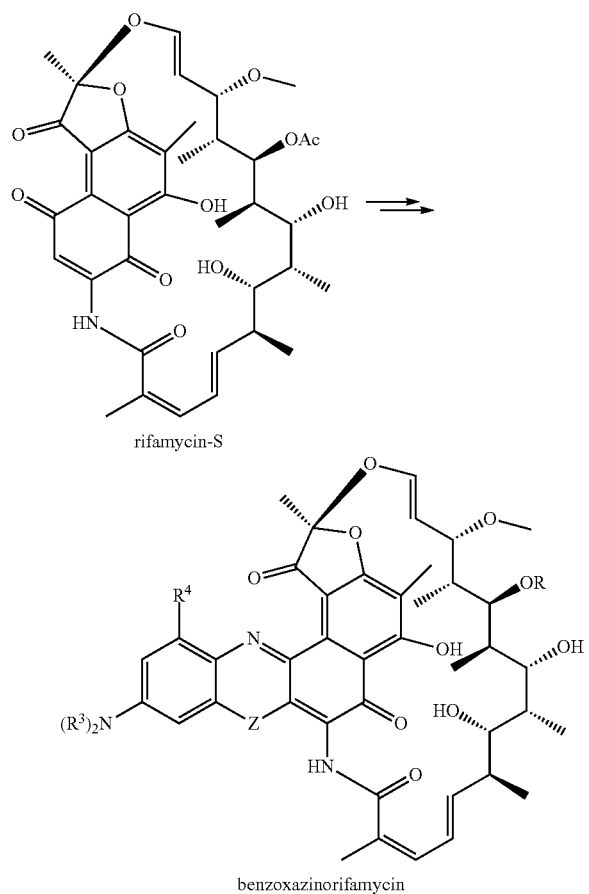

rifamycin-S benzoxazinorifamycin

Peptide Linkers

A "peptide linker" (L) is a bifunctional or multifunctional moiety which is covalently attached to one or more antibiotic moieties (abx) and an antibody unit (Ab) to form antibody-antibiotic conjugates (AAC) of Formula I. Peptide linkers in AAC are substrates for cleavage by intracellular proteases, including lysosomal conditions. Proteases includes various cathepsins and caspases. Cleavage of the peptide linker of an AAC inside a cell may release the rifamycin-type antibiotic with anti-bacterial effects.

The amount of active antibiotic released from cleavage of AAC can be measured by the Caspase release assay of Example 20.

Antibody-antibiotic conjugates (AAC) can be conveniently prepared using a linker reagent or linker-antibiotic intermediate having reactive functionality for binding to the antibiotic (abx) and to the antibody (Ab). In one exemplary embodiment, a cysteine thiol of a cysteine engineered antibody (Ab) can form a bond with a functional group of a linker reagent, an antibiotic moiety or antibiotic-linker intermediate.

The peptide linker moiety of an AAC In one aspect, a linker reagent or linker-antibiotic intermediate has a reactive site which has an electrophilic group that is reactive to a nucleophilic cysteine present on an antibody. The cysteine thiol of the antibody is reactive with an electrophilic group on a linker reagent or linker-antibiotic, forming a covalent bond. Useful electrophilic groups include, but are not limited to, maleimide and haloacetamide groups.

Cysteine engineered antibodies react with linker reagents or linker-antibiotic intermediates, with electrophilic functional groups such as maleimide or α-halo carbonyl, according to the conjugation method at page 766 of Klussman, et al (2004), Bioconjugate Chemistry 15 (4):765-773, and according to the protocol of Example 19.

In another embodiment, the reactive group of a linker reagent or linker-antibiotic intermediate contains a thiol-reactive functional group that can form a bond with a free cysteine thiol of an antibody. Examples of thiol-reaction functional groups include, but are not limited to, maleimide, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates.

In another embodiment, a linker reagent or antibiotic-linker intermediate has a reactive functional group which has a nucleophilic group that is reactive to an electrophilic group present on an antibody. Useful electrophilic groups on an antibody include, but are not limited to, pyridyl disulfide, aldehyde and ketone carbonyl groups. The heteroatom of a nucleophilic group of a linker reagent or antibiotic-linker intermediate can react with an electrophilic group on an antibody and form a covalent bond to an antibody unit. Useful nucleophilic groups on a linker reagent or antibiotic-linker intermediate include, but are not limited to, hydrazide, oxime, amino, thiol, hydrazine, thiosemicarbazone, hydrazine carboxylate, and arylhydrazide. The electrophilic group on an antibody provides a convenient site for attachment to a linker reagent or antibiotic-linker intermediate.

A peptide linker may comprise one or more linker components. Exemplary linker components include a peptide unit, 6-maleimidocaproyl ("MC"), maleimidopropanoyl ("MP"), valine-citrulline ("val-cit" or "vc"), alanine-phenyl-alanine ("ala-phe"), and p-aminobenzyloxycarbonyl ("PAB"), N-succinimidyl 4-(2-pyridylthio) pentanoate ("SPP"), and 4-(N-maleimidomethyl)cyclohexane-1 carboxylate ("MCC"). Various linker components are known in the art, some of which are described below.

In another embodiment, the linker may be substituted with groups that modulate solubility or reactivity. For example, a charged substituent such as sulfonate ($-SO_3^-$) or ammonium, may increase water solubility of the reagent and facilitate the coupling reaction of the linker reagent with the antibody or the antibiotic moiety, or facilitate the coupling reaction of Ab-L (antibody-linker intermediate) with abx, or abx-L (antibiotic-linker intermediate) with Ab, depending on the synthetic route employed to prepare the AAC.

The AAC of the invention expressly contemplate, but are not limited to, those prepared with linker reagents: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, SVSB (succinimidyl-(4-vinylsulfone) benzoate), and bis-maleimide reagents such as DTME, BMB, BMDB, BMH, BMOE, BM(PEG)$_2$, and BM(PEG)$_3$. Bis-maleimide reagents allow the attachment of the thiol group of a cysteine engineered antibody to a thiol-containing antibiotic moiety, label, or linker intermediate, in a sequential or convergent fashion. Other functional groups besides maleimide, which are reactive with a thiol group of a cysteine engineered antibody, antibiotic moiety, or linker-antibiotic intermediate include iodoacetamide, bromoacetamide, vinyl pyridine, disulfide, pyridyl disulfide, isocyanate, and isothiocyanate.

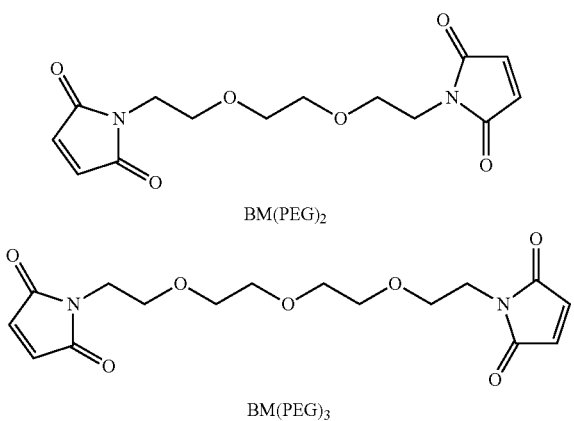

BM(PEG)₂

BM(PEG)₃

Useful linker reagents can also be obtained via other commercial sources, such as Molecular Biosciences Inc. (Boulder, Colo.), or synthesized in accordance with procedures described in Toki et al (2002) J. Org. Chem. 67:1866-1872; Dubowchik, et al. (1997) Tetrahedron Letters, 38:5257-60; Walker, M. A. (1995) J. Org. Chem. 60:5352-5355; Frisch et al (1996) Bioconjugate Chem. 7:180-186; U.S. Pat. No. 6,214,345; WO 02/088172; US 2003130189; US2003096743; WO 03/026577; WO 03/043583; and WO 04/032828.

In another embodiment, the peptide linker moiety of an AAC comprises a dendritic type linker for covalent attachment of more than one antibiotic moiety through a branching, multifunctional linker moiety to an antibody (Sun et al (2002) *Bioorganic & Medicinal Chemistry Letters* 12:2213-2215; Sun et al (2003) *Bioorganic & Medicinal Chemistry* 11:1761-1768). Dendritic linkers can increase the molar ratio of antibiotic to antibody, i.e. loading, which is related to the potency of the AAC. Thus, where a cysteine engineered antibody bears only one reactive cysteine thiol group, a multitude of antibiotic moieties may be attached through a dendritic linker.

In certain embodiments of Formula I AAC, the peptide linker has the formula:

-Str-Pep-Y- where Str is a stretcher unit covalently attached to the anti-wall teichoic acid (WTA) antibody; Pep is a peptide of two to twelve amino acid residues, and Y is a spacer unit covalently attached to the rifamycin-type antibiotic. Exemplary embodiments of such linkers are described in U.S. Pat. No. 7,498,298, expressly incorporated herein by reference.

In one embodiment, a stretcher unit "Str" has the formula:

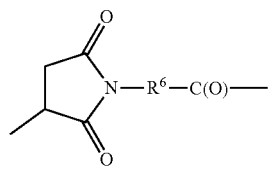

wherein $R^6$ is selected from the group consisting of $C_1$-$C_{10}$ alkylene-, —$C_3$-$C_8$ carbocyclo, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —(CH$_2$CH$_2$O)$_r$—, and —(CH$_2$CH$_2$O)$_r$—CH$_2$—; and r is an integer ranging from 1 to 10.

Exemplary stretcher units are shown below (wherein the wavy line indicates sites of covalent attachment to an antibody):

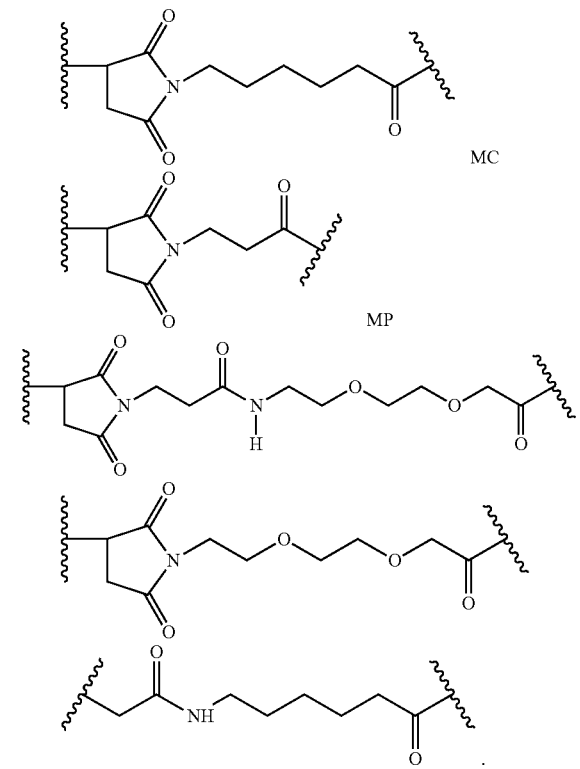

MC

MP

A peptide unit "Pep" comprises two or more amino acid residues that occur naturally, including the twenty major amino acids as well as minor amino acids such as citrulline, which are well known in the field of biochemistry. Amino acids are distinguished by their side chain. The peptide unit thus comprises two or more amino acid side chains, including but not limited to, —CH$_3$ (alanine), —CH$_2$CH$_2$CH$_2$NHC(NH)NH$_2$ (arginine), —CH$_2$C(O)NH$_2$ (asparagine), —CH$_2$CO$_2$H (aspartic acid), —CH$_2$CH$_2$CH$_2$NHC(O)NH$_2$ (citrulline), —CH$_2$SH (cysteine), —CH$_2$CH$_2$CO$_2$H (glutamic acid), —CH$_2$CH$_2$C(O)NH$_2$ (glutamine), —H (glycine), —CH$_2$(imidazolyl) (histidine), —CH(CH$_3$)CH$_2$CH$_3$ (isoleucine), —CH$_2$CH(CH$_3$)CH$_3$ (leucine), —CH$_2$CH$_2$CH$_2$CH$_2$NH$_2$ (lysine), —CH$_2$CH$_2$SCH$_3$ (methionine), —CH$_2$(C$_6$H$_5$) (phenylalanine), —CH$_2$CH$_2$CH$_2$— (proline), —CH$_2$OH (serine), —CH(OH)CH$_3$ (threonine), —CH$_2$(indole) (tryptophan), —CH$_2$(p-C$_6$H$_4$OH) (tyrosine), —CHCH(CH$_3$)CH$_3$ (valine). See page 1076-1077, "Organic Chemistry" 5th Ed. John McMurry, Brooks/Cole pub. (2000). The amino acid residues of the peptide unit include all stereoisomers, and may be in the D or L configurations. In one embodiment, Pep comprises two to twelve amino acid residues independently selected from glycine, alanine, phenylalanine, lysine, arginine, valine, and citrulline. In one such embodiment, the amino acid unit allows for cleavage of the linker by a protease, thereby facilitating release of the antibiotic from the AAC upon exposure to intracellular proteases, such as lysosomal enzymes (Doronina et al. (2003) *Nat. Biotechnol.* 21:778-784). Exemplary amino acid units include, but are not limited to, a dipeptide, a tripeptide, a tetrapeptide, a pentapeptide, and a hexapeptide. Exemplary dipeptides include: valine-citrulline (vc or val-cit), alanine-phenylalanine (af or ala-phe); phenylalanine-lysine (fk or phe-lys); or N-methyl-valine-citrulline (Me-val-cit). Exemplary tripeptides include: glycine-valine-citrulline (gly-val-cit), valine-citrulline-phenylalanine (val-cit-phe), and glycine-glycine-glycine (gly-gly-gly). Additional peptide linkers include GGAFAGGG (SEQ ID NO: 126); tpm-cit; GPImeLFF (SEQ ID NO: 129); and LAFG (SEQ ID NO: 128). Peptide linkers can be prepared by forming a peptide bond between two or more amino acids and/or peptide fragments. Such peptide bonds can be prepared, for example, according to the liquid phase synthesis method (E. Schröder and K. Lübke (1965) "The Peptides", volume 1, pp 76-136, Academic Press) which is well known in the field of peptide chemistry. Amino acid units can be designed and optimized in their selectivity for enzymatic cleavage by a particular enzyme, for example, a tumor-associated protease, cathepsin B, C and D, or a plasmin protease.

In one embodiment, spacer unit Y comprises para-aminobenzyl or para-aminobenzyloxycarbonyl. A "non-self-immolative" spacer unit is one in which part or all of the spacer unit remains bound to the antibiotic moiety upon enzymatic (e.g., proteolytic) cleavage of the AAC. Examples of non-self-immolative spacer units include, but are not limited to, a glycine spacer unit and a glycine-glycine spacer unit. Other combinations of peptidic spacers susceptible to sequence-specific enzymatic cleavage are also contemplated. For example, enzymatic cleavage of an AAC containing a glycine-glycine spacer unit by a tumor-cell associated protease would result in release of a glycine-glycine-antibiotic moiety from the remainder of the AAC. In one such embodiment, the glycine-glycine-antibiotic moiety is then subjected to a separate hydrolysis step in the tumor cell, thus cleaving the glycine-glycine spacer unit from the antibiotic moiety.

A spacer unit allows for release of the antibiotic moiety without a separate hydrolysis step. A spacer unit may be "self-immolative" or a "non-self-immolative." In certain embodiments, a spacer unit of a linker comprises a p-aminobenzyl unit (PAB). In one such embodiment, a p-aminobenzyl alcohol is attached to an amino acid unit via an amide bond, a carbamate, methylcarbamate, or carbonate between the p-aminobenzyl group and the antibiotic moiety (Hamann et al. (2005) *Expert Opin. Ther. Patents* (2005) 15:1087-1103). In one embodiment, the spacer unit is p-aminobenzyloxycarbonyl (PAB).

In one embodiment, the antibiotic forms a quaternary amine, such as the dimethylaminopiperidyl group, when attached to the PAB spacer unit of the peptide linker. Examples of such quaternary amines are linker-antibiotic intermediates (LA) are 54, 61, 66, 67, 73, 74, 76, 78, 79, 83, 84 from Table 2. The quaternary amine group may modulate cleavage of the antibiotic moiety to optimize the antibacterial effects of the AAC. In another embodiment, the antibiotic is linked to the PABC spacer unit of the peptide linker, forming a carbamate functional group in the AAC. Such carbamate functional group may also optimize the antibacterial effects of the AAC. Examples of PABC carbamate linker-antibiotic intermediates (LA) are 51, 52, 53, 55, 56, 57, 58, 62, 63, 64, 65, 72, 75, 80, 81, 87 from Table 2. Other linker-antibiotic intermediates (LA) employ amide (59, 69, 70, 71, 77, 82, 85) or phenolic (60, 68, 86) groups.

Other examples of self-immolative spacers include, but are not limited to, aromatic compounds that are electronically similar to the PAB group such as 2-aminoimidazol-5-methanol derivatives (U.S. Pat. No. 7,375,078; Hay et al. (1999) *Bioorg. Med. Chem. Lett.* 9:2237) and ortho- or para-aminobenzylacetals. Spacers can be used that undergo cyclization upon amide bond hydrolysis, such as substituted and unsubstituted 4-aminobutyric acid amides (Rodrigues et al (1995) *Chemistry Biology* 2:223), appropriately substituted bicyclo[2.2.1] and bicyclo[2.2.2] ring systems (Storm et al (1972) *J. Amer. Chem. Soc.* 94:5815) and 2-aminophenylpropionic acid amides (Amsberry, et al (1990) *J. Org. Chem.* 55:5867). Elimination of amine-containing drugs that are substituted at glycine (Kingsbury et al (1984) *J. Med. Chem.* 27:1447) is also exemplary of self-immolative spacers useful in AAC.

Linker-Antibiotic Intermediates Useful for AAC

Figures 23, 23A, 23B:
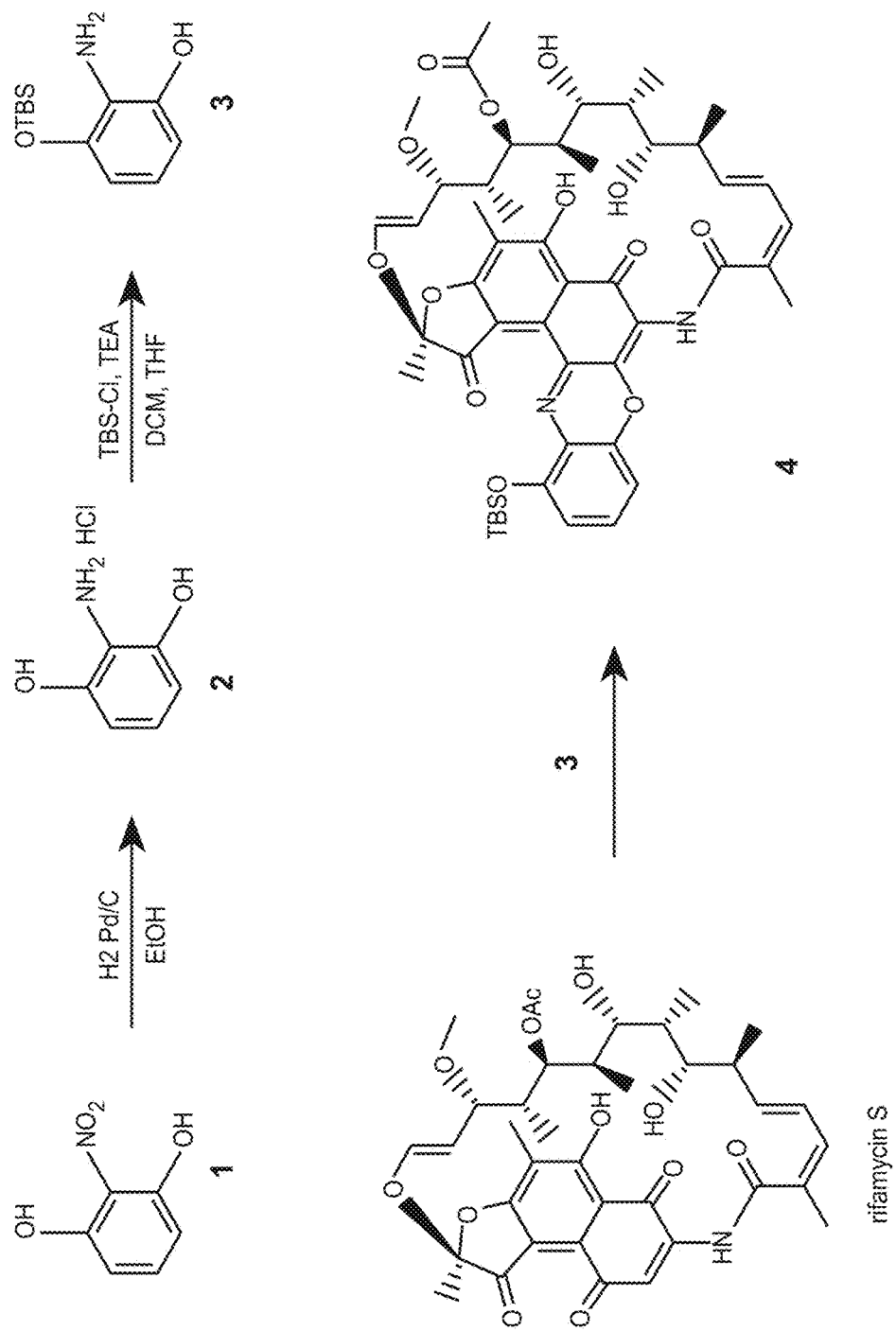
FIG. 23A and FIG. 23B show the synthesis of linker-antibiotic intermediate 51 from 2-nitrobenzene-1,3-diol 1.
Figure 23B:
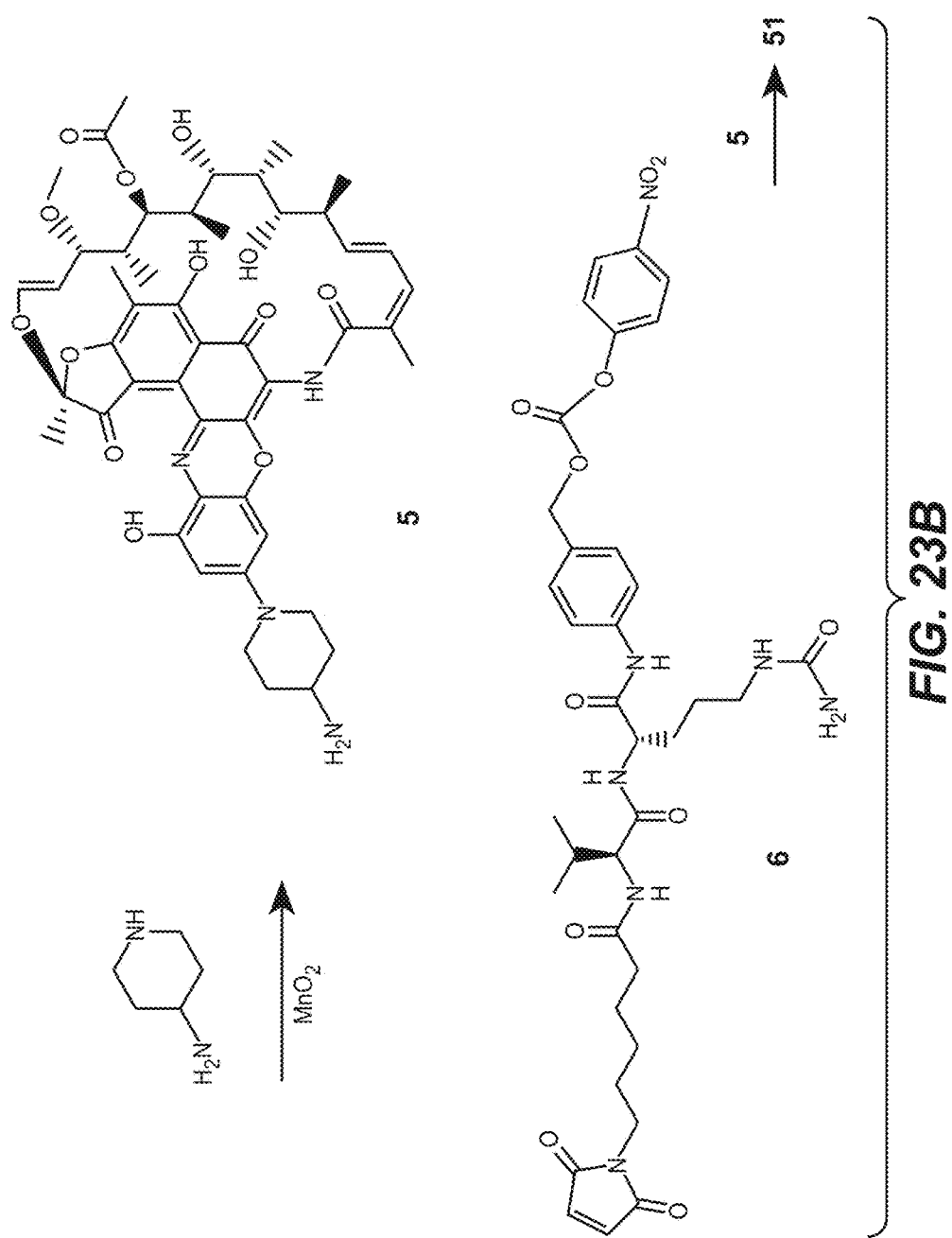
Figure 24:
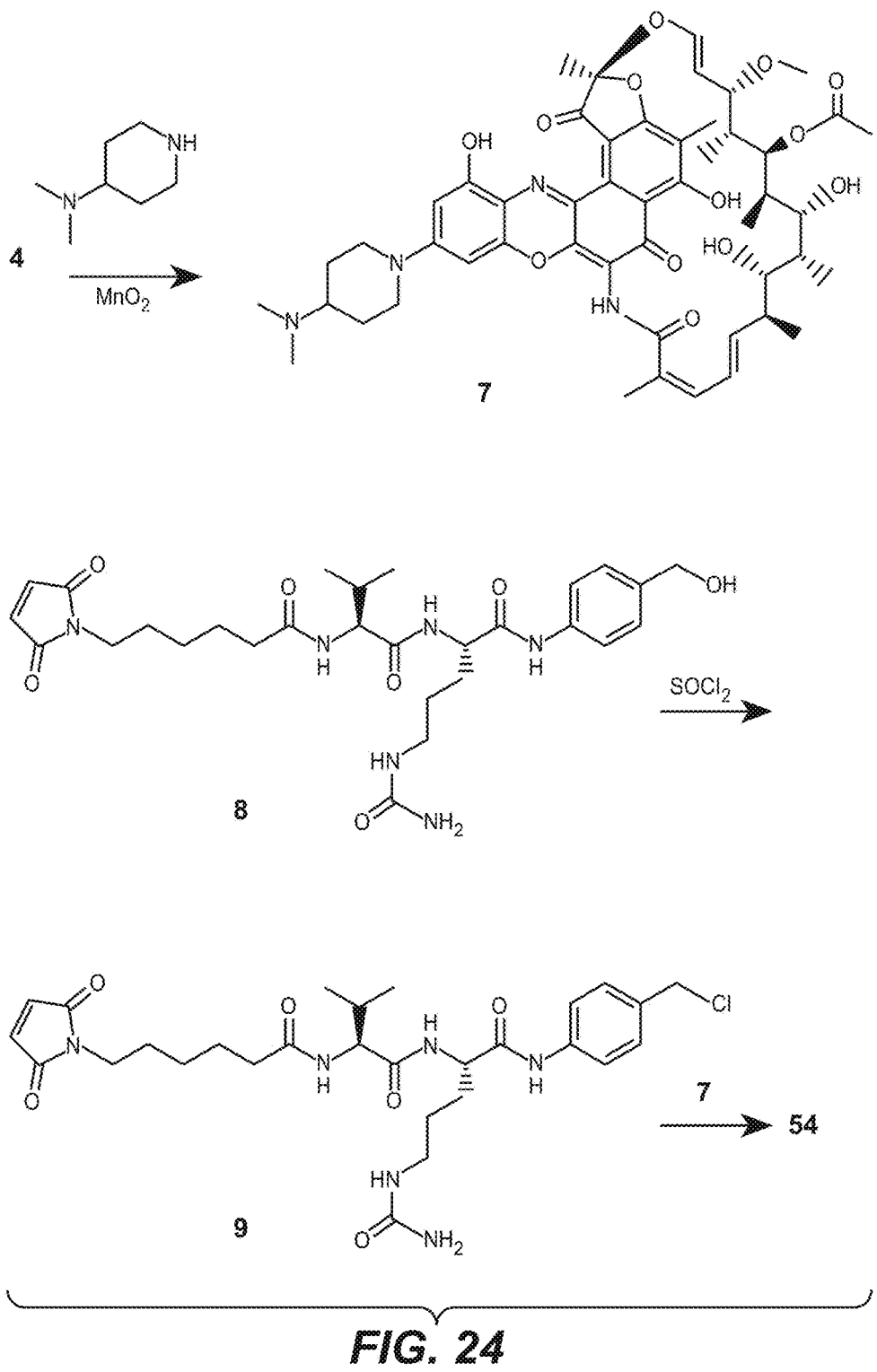
FIG. 24 shows the synthesis of linker-antibiotic intermediate, MC-vc-PAB-dimethylpipBOR 54 from TBS-protected benzoxazino rifamycin 4.
Figures 25, 25A:
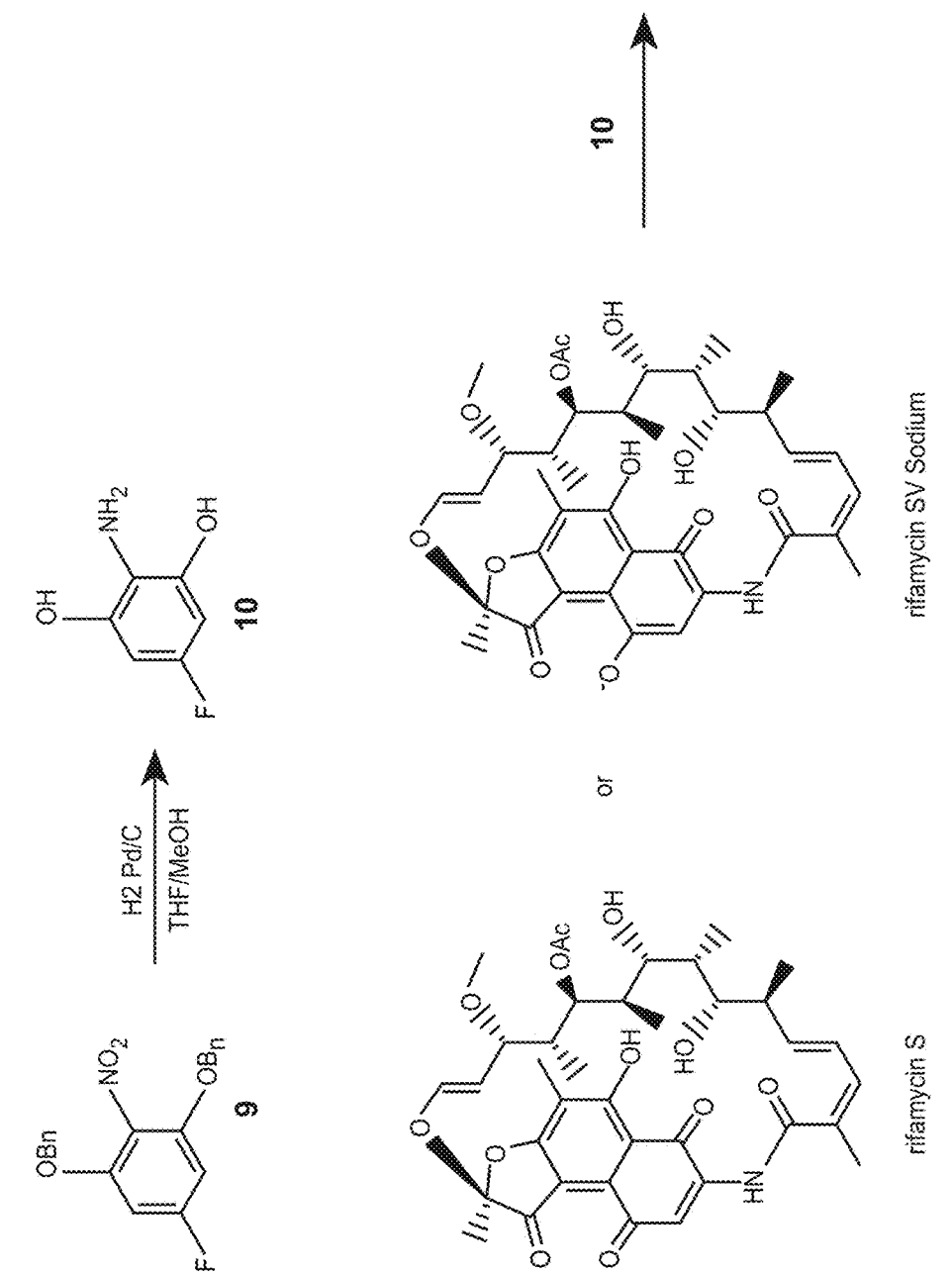
FIG. 25A and FIG. 25B show the synthesis of dimethyl pipBOR 7 from (5-fluoro-2-nitro-1,3-phenylene)bis(oxy)bis (methylene)dibenzene 9.

Linker-antibiotic intermediates (LA) of Formula II and Table 2 were prepared by coupling a rifamycin-type antibiotic moiety with a peptide-linker reagent, as exemplified in FIGS. 23-25 and Examples 1-17. Linker reagents were prepared by methods described in WO 2012/113847; U.S. Pat. No. 7,659,241; U.S. Pat. No. 7,498,298; US 20090111756; US 2009/0018086; U.S. Pat. No. 6,214,345; Dubowchik et al (2002) *Bioconjugate Chem.* 13 (4):855-869, including:

4-((S)-2-((S)-2-(6-(2,5-dioxo-2,5-dihydro-1H-pyrrol-1-yl)hexanamido)-3-methylbutanamido)-5-ureidopentanamido)benzyl 4-nitrophenyl carbonate 6

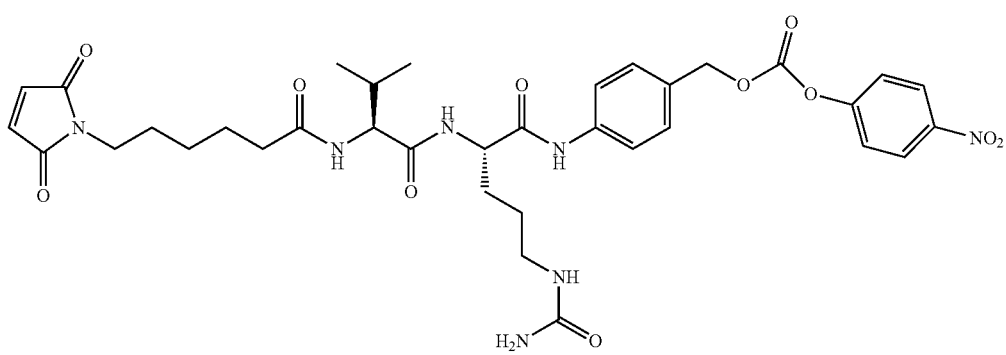

77
6-(2,5-dioxo-2,5-dihydro-1H-pyrrol-1-yl)-N—((S)-1-((S)-1-(4-(hydroxymethyl)phenylamino)-1-oxo-5-ureidopentan-2-ylamino)-3-methyl-1-oxobutan-2-yl) hexanamide 8
78
N—((S)-1-((S)-1-(4-(chloromethyl)phenylamino)-1-oxo-5-ureidopentan-2-ylamino)-3-methyl-1-oxobutan-2-yl)-6-(2,5-dioxo-2,5-dihydro-1H-pyrrol-1-yl) hexanamide 9
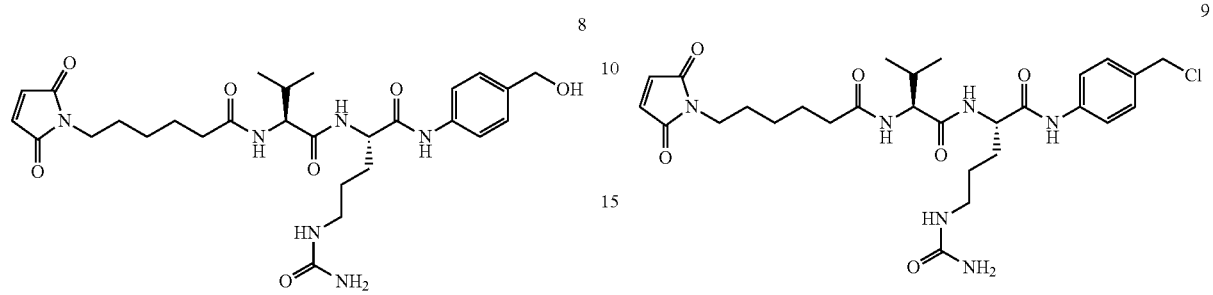

TABLE 2

Linker-antibiotic intermediates (LA)

| LA No. | Structure |
|---|---|
| LA-51 | 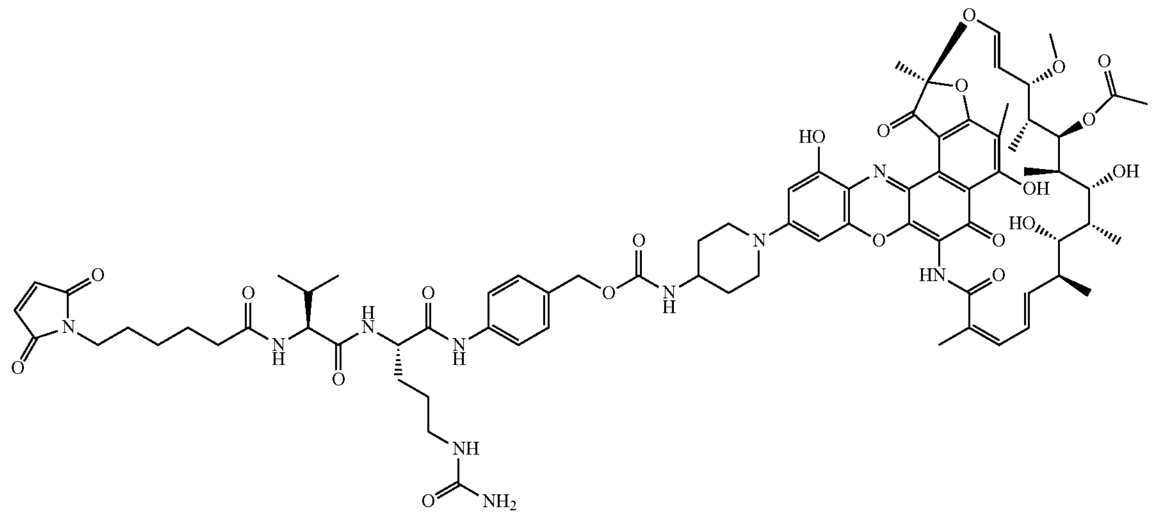 [SMILES: CO[C@H]1/C=C/O[C@@]2(C)Oc3c(C)c(O)c4c(=O)c(c5oc6cc(N7CCC(NC(=O)OCc8ccc(NC(=O)[C@H](CCCNC(N)=O)NC(=O)[C@@H](NC(=O)CCCCCN9C(=O)C=CC9=O)C(C)C)cc8)CC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] |

TABLE 2-continued
Linker-antibiotic intermediates (LA)
| LA No. | Structure |
|---|---|
| LA-52 | 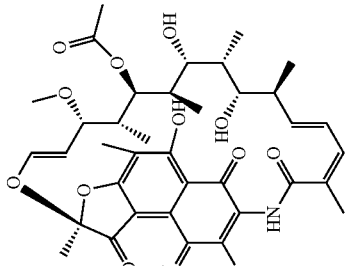 |
| LA-53 | 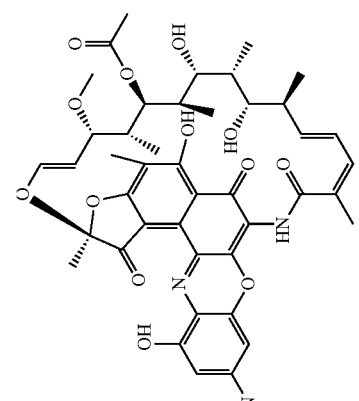 |

TABLE 2-continued
Linker-antibiotic intermediates (LA)
| LA No. | Structure |
|---|---|
| LA-54 | 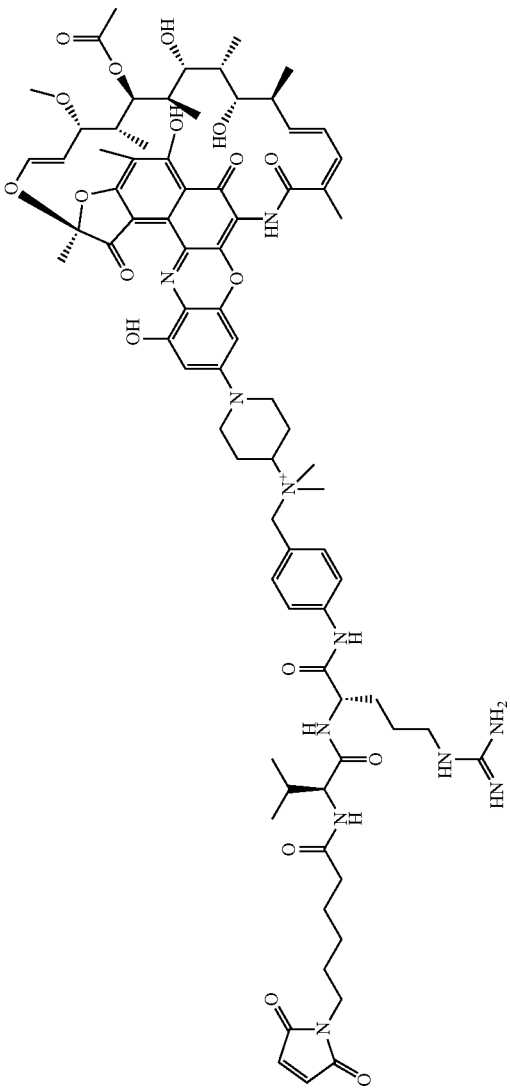 |

TABLE 2-continued

Linker-antibiotic intermediates (LA)

| LA No. | Structure |
|---|---|
| LA-55 | 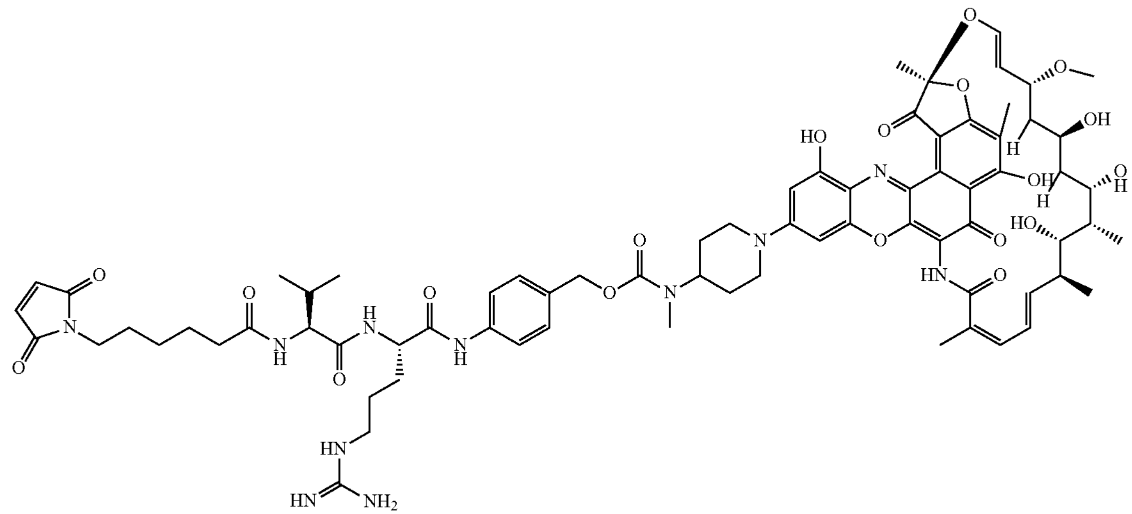 [SMILES: CO[C@H]1/C=C/O[C@@]2(C)Oc3c(C)c(O)c4c(=O)c(c5oc6cc(N7CCC(N(C)C(=O)OCc8ccc(NC(=O)[C@H](CCCNC(=N)N)NC(=O)[C@@H](NC(=O)CCCCCN9C(=O)C=CC9=O)C(C)C)cc8)CC7)cc(O)c6nc-5c4c3C2=O)NC(=O)/C(C)=C\C=C\[C@H](C)[C@H](O)[C@@H](C)[C@@H](O)C[C@H](O)C1] |
| LA-56 | 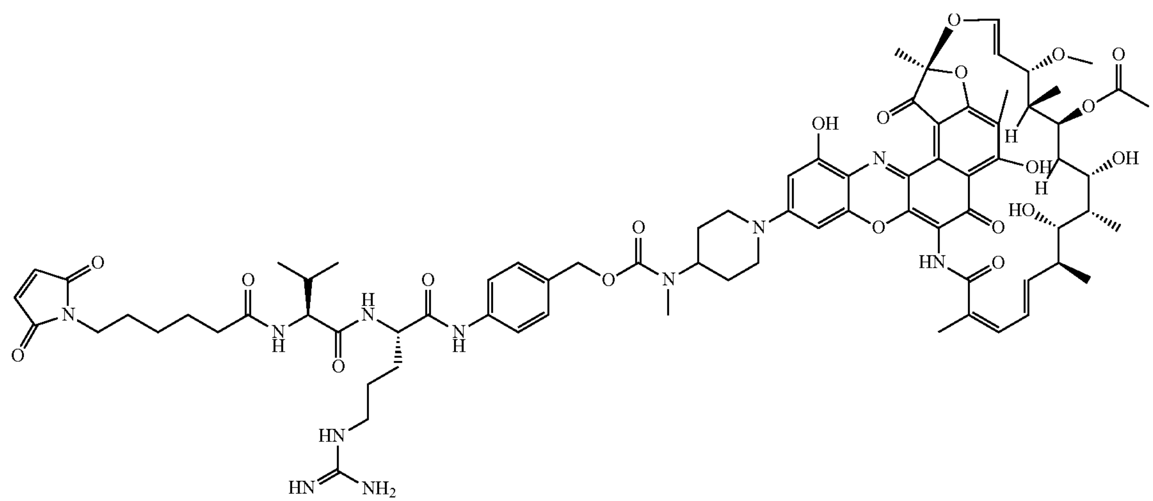 [SMILES: CO[C@H]1/C=C/O[C@@]2(C)Oc3c(C)c(O)c4c(=O)c(c5oc6cc(N7CCC(N(C)C(=O)OCc8ccc(NC(=O)[C@H](CCCNC(=N)N)NC(=O)[C@@H](NC(=O)CCCCCN9C(=O)C=CC9=O)C(C)C)cc8)CC7)cc(O)c6nc-5c4c3C2=O)NC(=O)/C(C)=C\C=C\[C@H](C)[C@H](O)[C@@H](C)[C@@H](O)C[C@H](OC(C)=O)[C@H]1C] |

TABLE 2-continued

Linker-antibiotic intermediates (LA)

| LA No. | Structure |
|---|---|
| LA-57 | 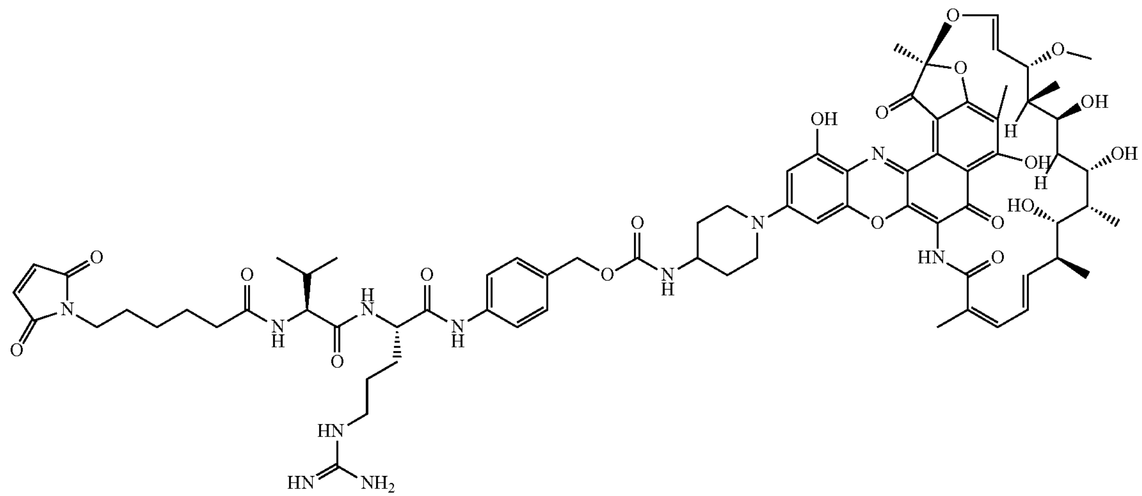 [SMILES: CO[C@H]1/C=C/O[C@@]2(C)Oc3c(C)c(O)c4c(=O)c(c5oc6cc(N7CCC(NC(=O)OCc8ccc(NC(=O)[C@H](CCCNC(=N)N)NC(=O)[C@@H](NC(=O)CCCCCN9C(=O)C=CC9=O)C(C)C)cc8)CC7)cc(O)c6nc-5c4c3C2=O)NC(=O)/C(C)=C\C=C\[C@H](C)[C@H](O)[C@@H](C)[C@@H](O)C[C@H](O)[C@H]1C] |
| LA-58 | 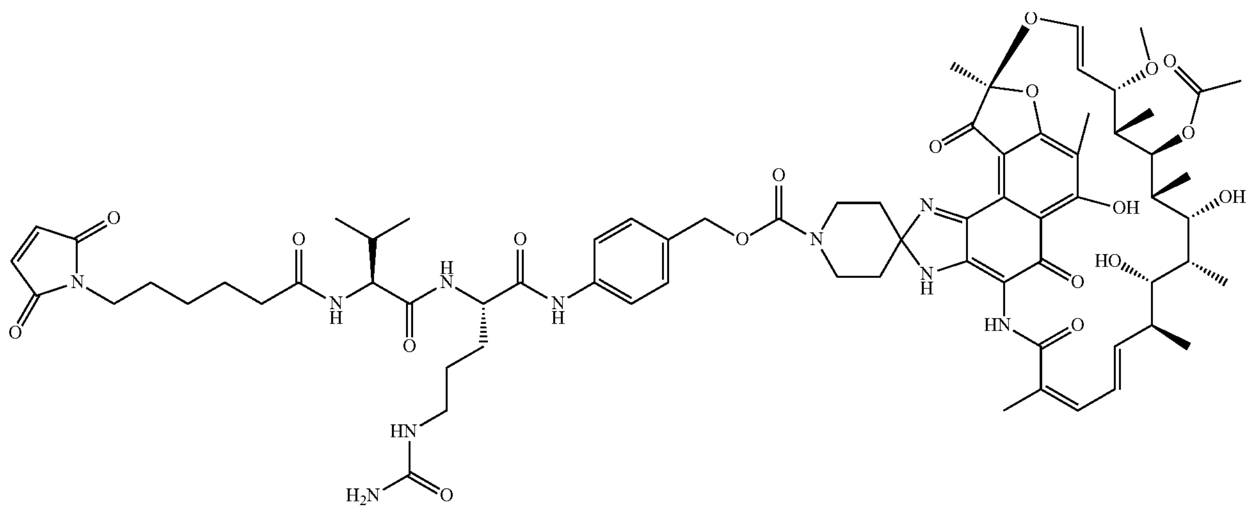 [SMILES: CO[C@H]1/C=C/O[C@@]2(C)Oc3c(C)c(O)c4c(c3C2=O)C2=NC3(CCN(C(=O)OCc5ccc(NC(=O)[C@H](CCCNC(N)=O)NC(=O)[C@@H](NC(=O)CCCCCN6C(=O)C=CC6=O)C(C)C)cc5)CC3)NC2=C(NC(=O)/C(C)=C\C=C\[C@H](C)[C@H](O)[C@@H](C)[C@@H](O)[C@@H](C)[C@H](OC(C)=O)[C@H]1C)C4=O] |

TABLE 2-continued
Linker-antibiotic intermediates (LA)
| LA No. | Structure |
|---|---|
| LA-59 | 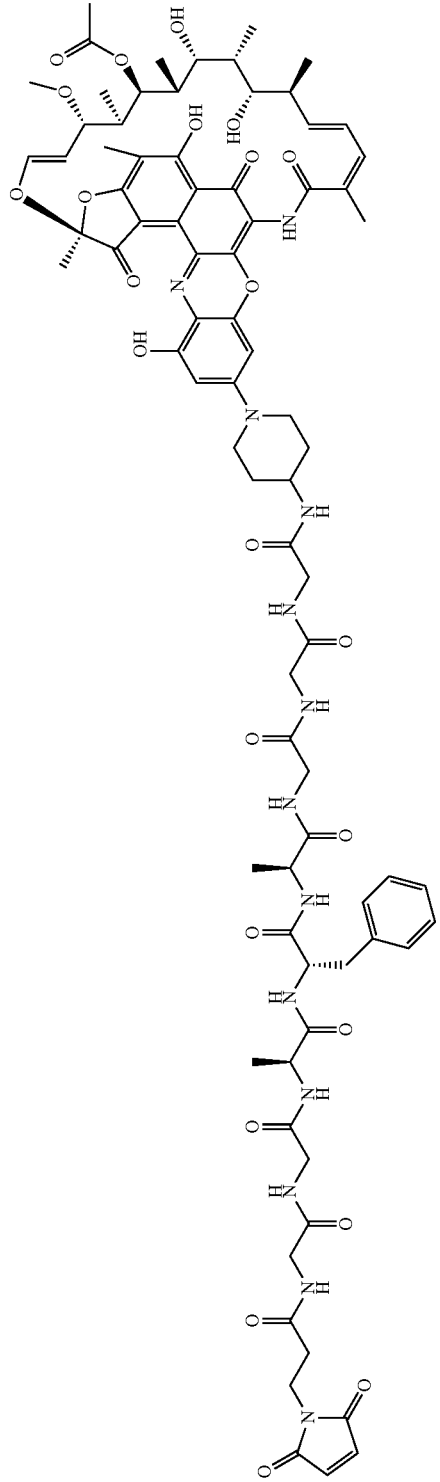 |
| LA-60 | 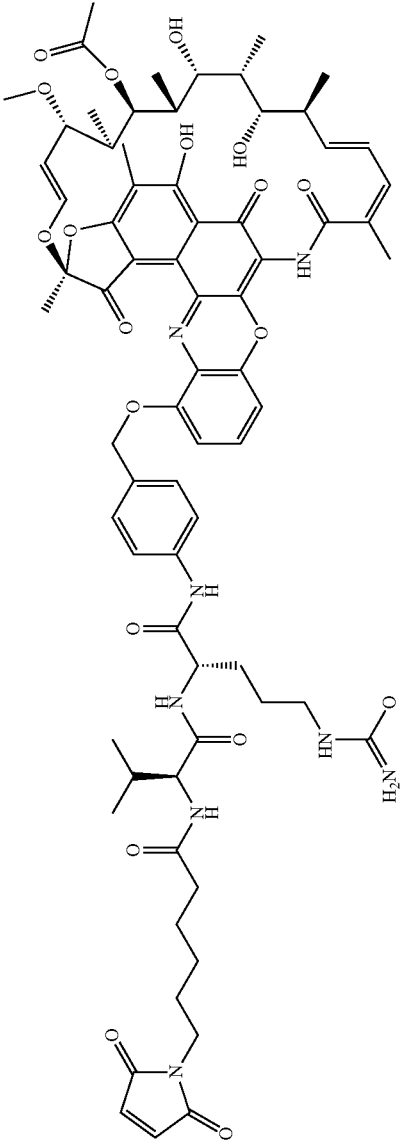 |

TABLE 2-continued
Linker-antibiotic intermediates (LA)
| LA No. | Structure |
|---|---|
| LA-61 | 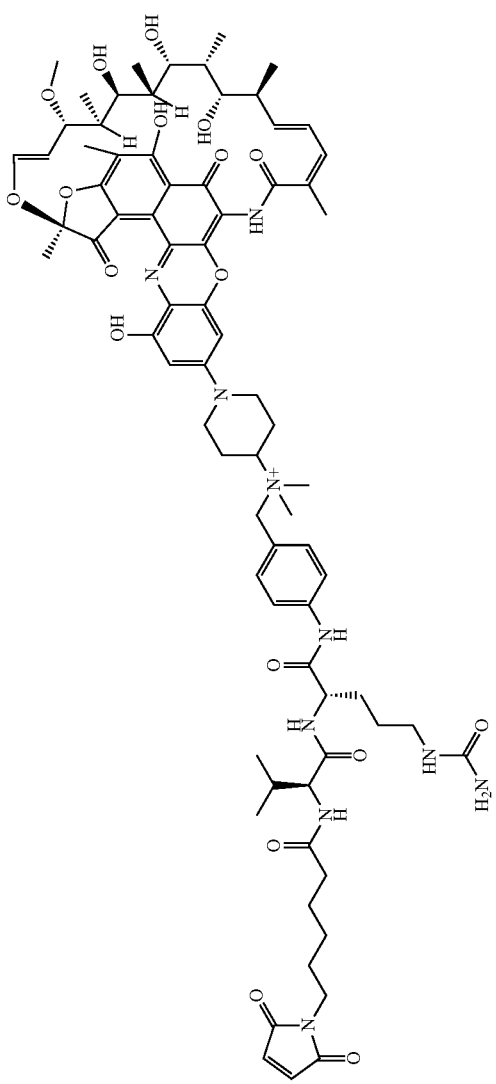 |
| LA-62 | 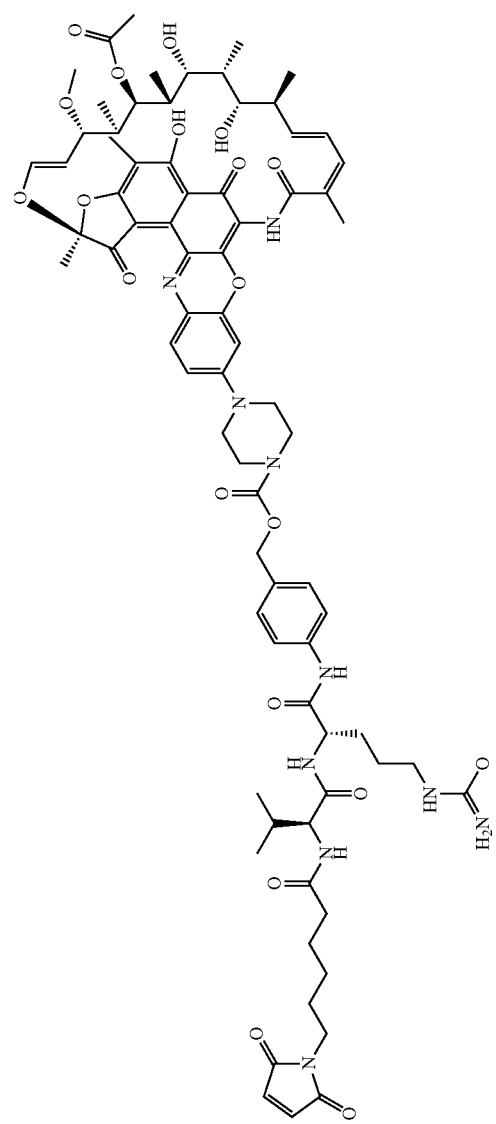 |

TABLE 2-continued
Linker-antibiotic intermediates (LA)
| LA No. | Structure |
|---|---|
| LA-63 | 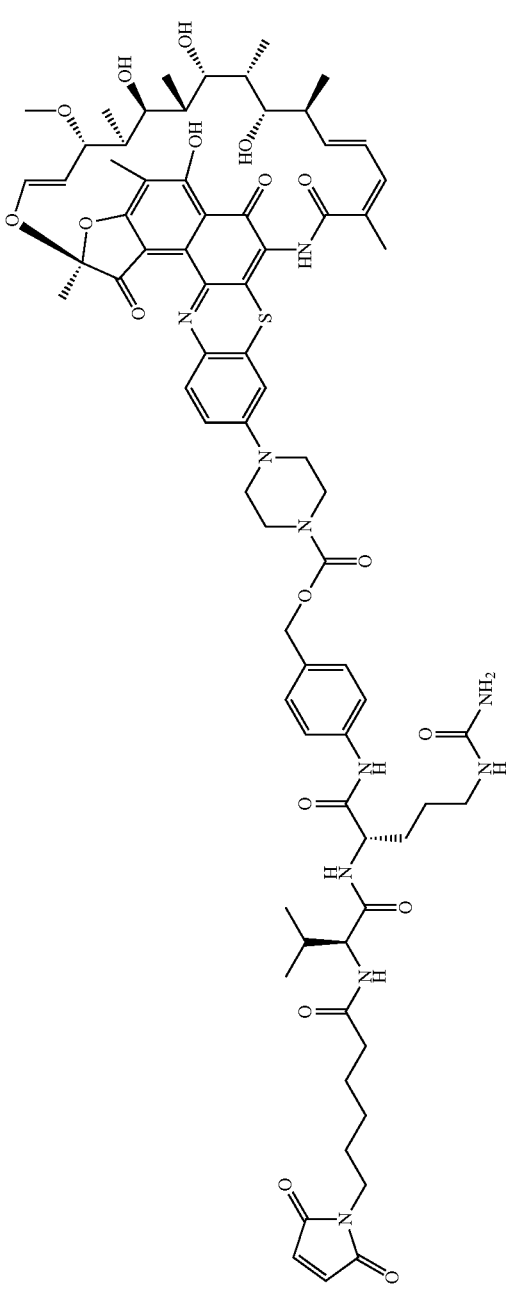 |
| LA-64 | 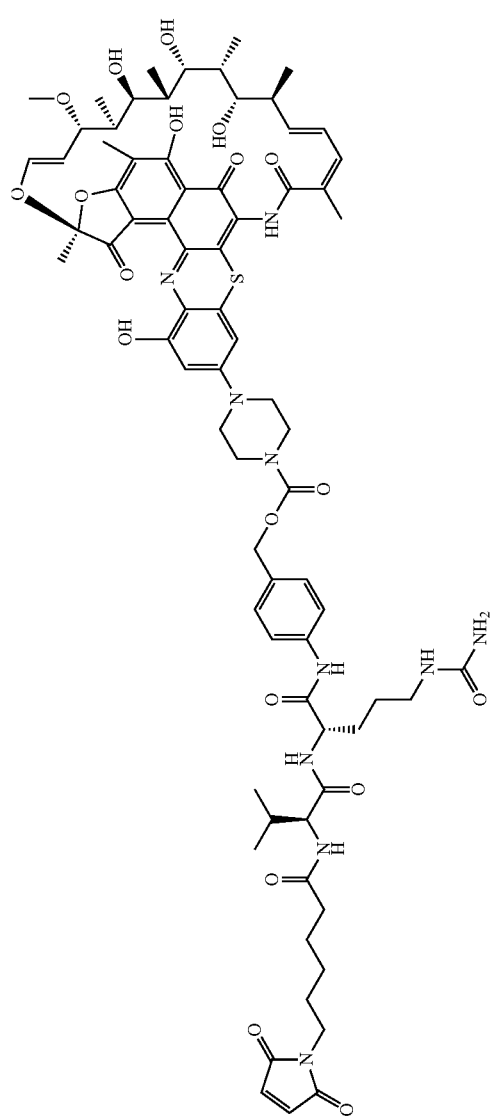 |

TABLE 2-continued

Linker-antibiotic intermediates (LA)

| LA No. | Structure |
|---|---|
| LA-65 | 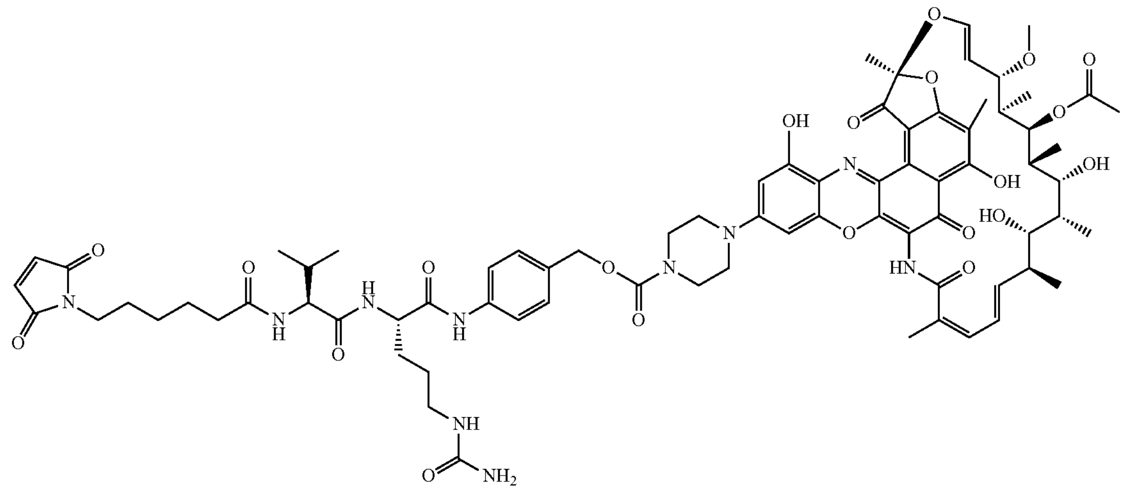 [SMILES: CO[C@H]1/C=C/O[C@@]2(C)Oc3c(C)c(O)c4c(=O)c(c5oc6cc(N7CCN(C(=O)OCc8ccc(NC(=O)[C@H](CCCNC(N)=O)NC(=O)[C@@H](NC(=O)CCCCCN9C(=O)C=CC9=O)C(C)C)cc8)CC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] |
| LA-66 | 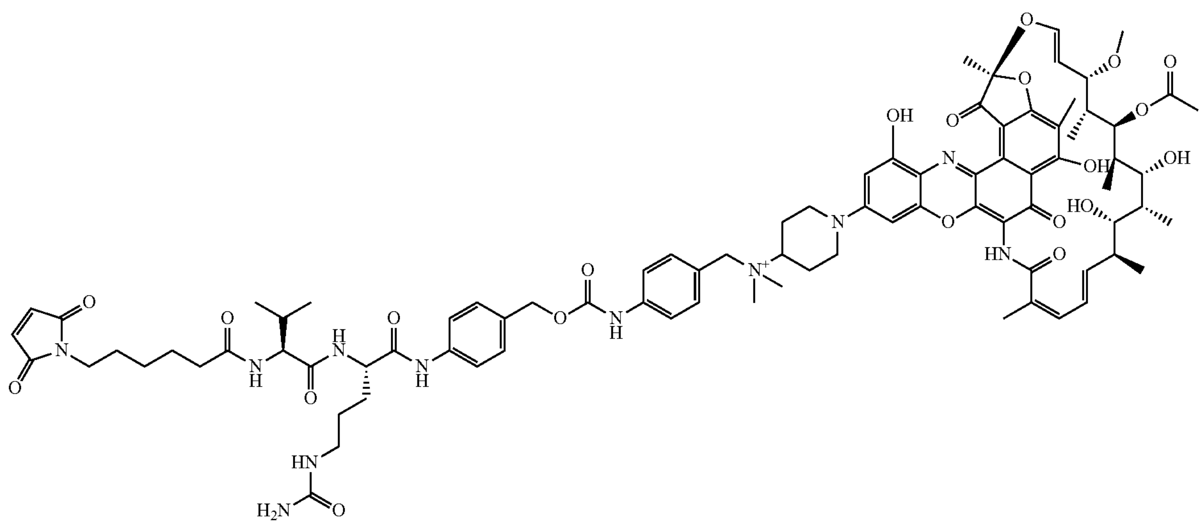 [SMILES: CO[C@H]1/C=C/O[C@@]2(C)Oc3c(C)c(O)c4c(=O)c(c5oc6cc(N7CCC([N+](C)(C)Cc8ccc(NC(=O)OCc9ccc(NC(=O)[C@H](CCCNC(N)=O)NC(=O)[C@@H](NC(=O)CCCCCN%10C(=O)C=CC%10=O)C(C)C)cc9)cc8)CC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] |

TABLE 2-continued
Linker-antibiotic intermediates (LA)
| LA No. | Structure |
|---|---|
| LA-67 | 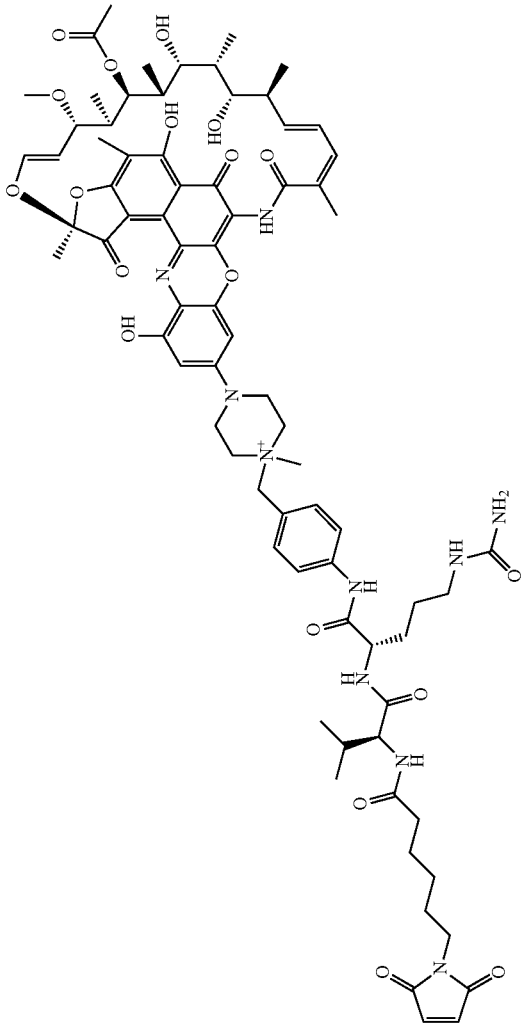 |
| LA-68 | 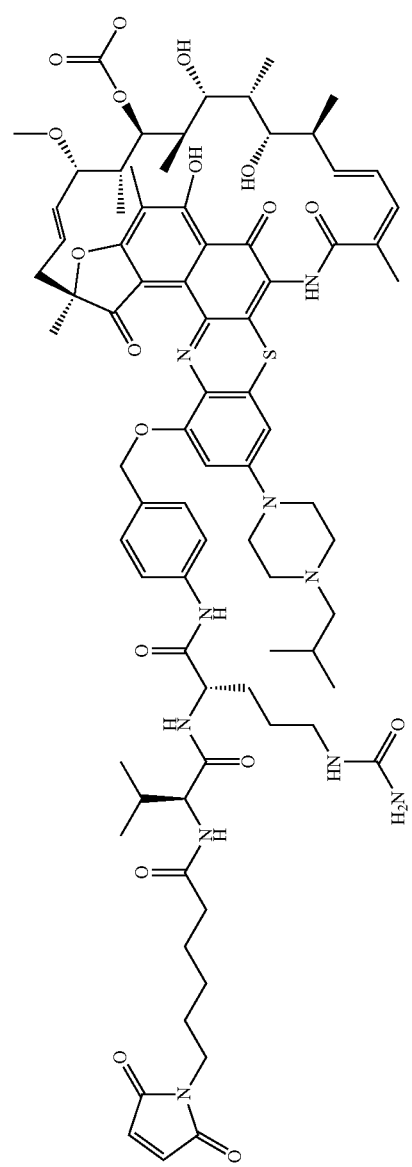 |

TABLE 2-continued

Linker-antibiotic intermediates (LA)

| LA No. | Structure |
|---|---|
| LA-69 | 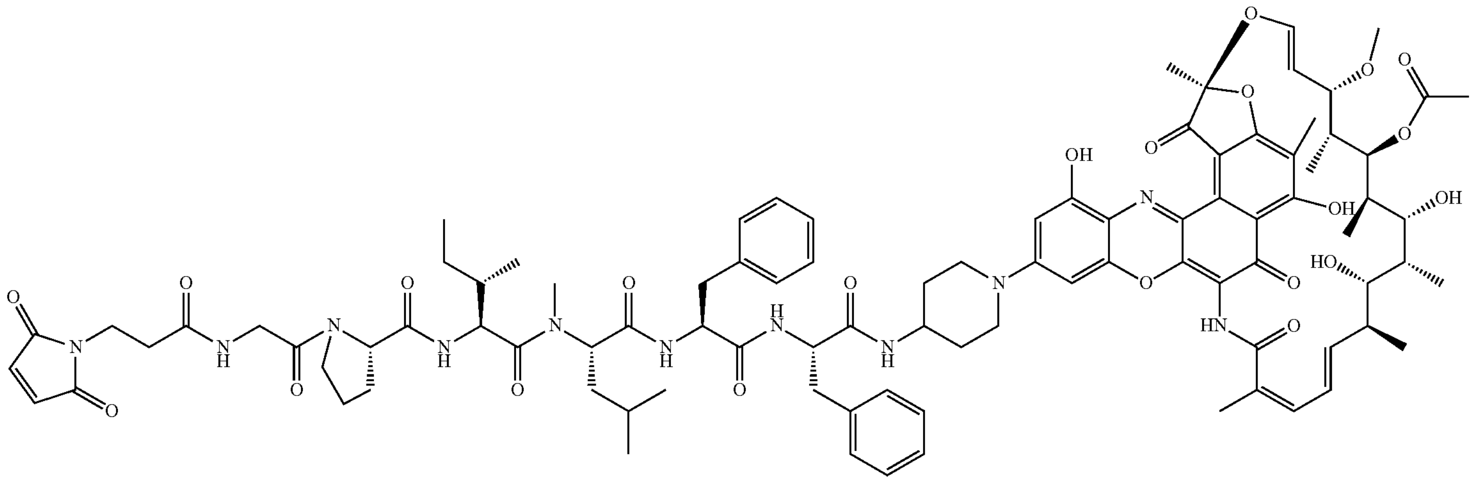 [SMILES: CC[C@H](C)[C@H](NC(=O)[C@@H]1CCCN1C(=O)CNC(=O)CCN1C(=O)C=CC1=O)C(=O)N(C)[C@@H](CC(C)C)C(=O)N[C@@H](Cc1ccccc1)C(=O)N[C@@H](Cc1ccccc1)C(=O)NC1CCN(c2cc(O)c3nc4c5c6c7c(C)c(O)c5c(=O)c(c-4oc3c2)NC(=O)/C(C)=C\C=C\[C@H](C)[C@H](O)[C@@H](C)[C@@H](O)[C@@H](C)[C@H](OC(C)=O)[C@H](C)[C@@H](OC)/C=C/O[C@@](C)(O7)C6=O)CC1] |
| LA-70 | 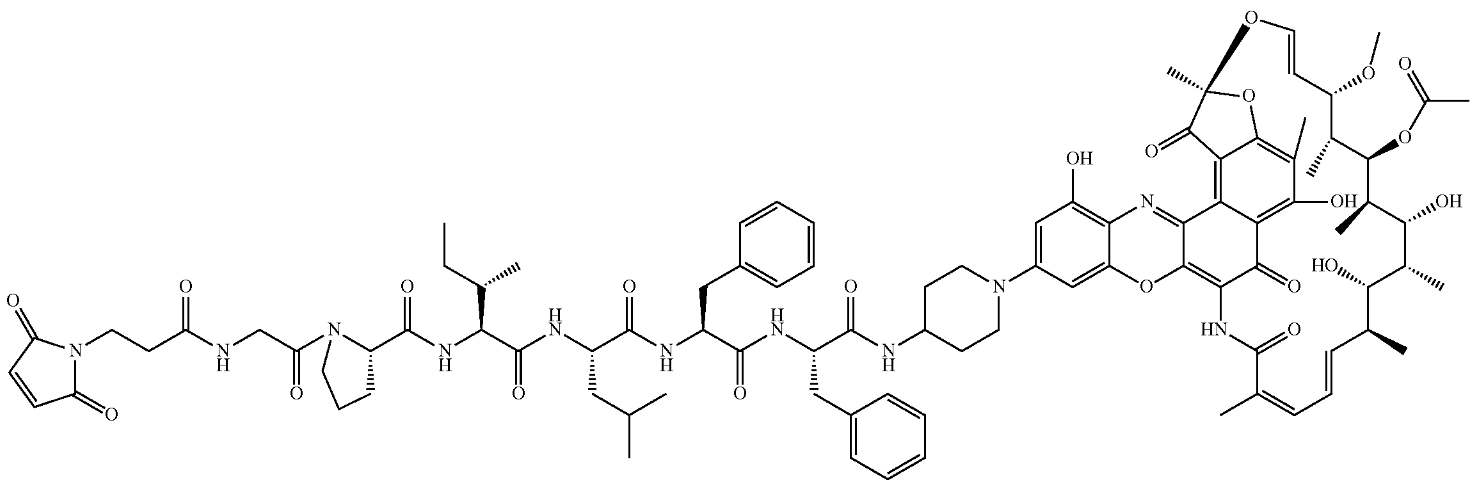 [SMILES: CC[C@H](C)[C@H](NC(=O)[C@@H]1CCCN1C(=O)CNC(=O)CCN1C(=O)C=CC1=O)C(=O)N[C@@H](CC(C)C)C(=O)N[C@@H](Cc1ccccc1)C(=O)N[C@@H](Cc1ccccc1)C(=O)NC1CCN(c2cc(O)c3nc4c5c6c7c(C)c(O)c5c(=O)c(c-4oc3c2)NC(=O)/C(C)=C\C=C\[C@H](C)[C@H](O)[C@@H](C)[C@@H](O)[C@@H](C)[C@H](OC(C)=O)[C@H](C)[C@@H](OC)/C=C/O[C@@](C)(O7)C6=O)CC1] |

TABLE 2-continued

Linker-antibiotic intermediates (LA)

| LA No. | Structure |
|---|---|
| LA-71 | 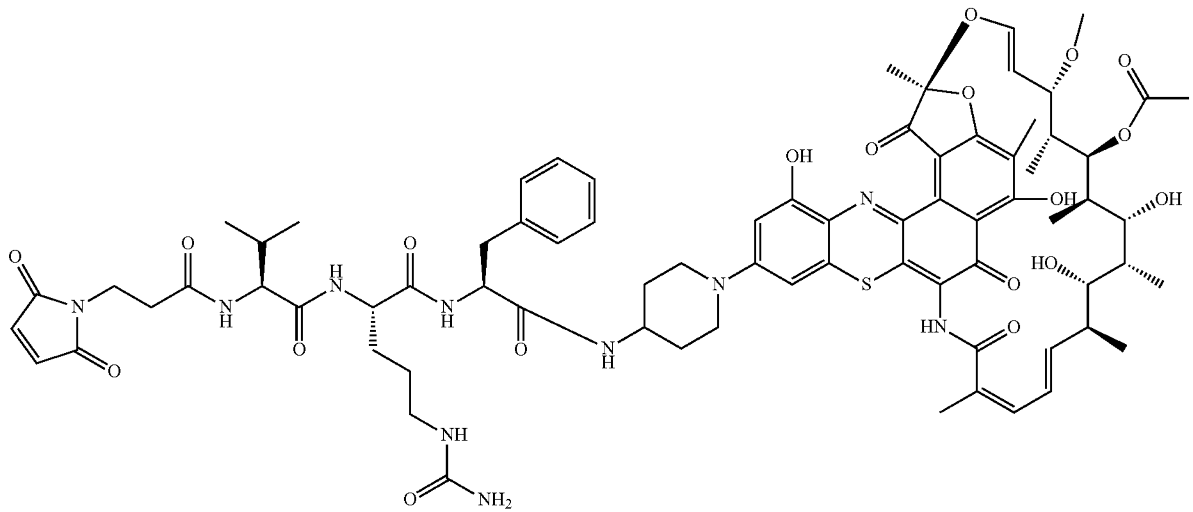 [SMILES: CO[C@H]1/C=C/O[C@@]2(C)Oc3c(C)c(O)c4c(=O)c(c5sc6cc(N7CCC(NC(=O)[C@H](Cc8ccccc8)NC(=O)[C@H](CCCNC(N)=O)NC(=O)[C@@H](NC(=O)CCN8C(=O)C=CC8=O)C(C)C)CC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] |
| LA-72 | 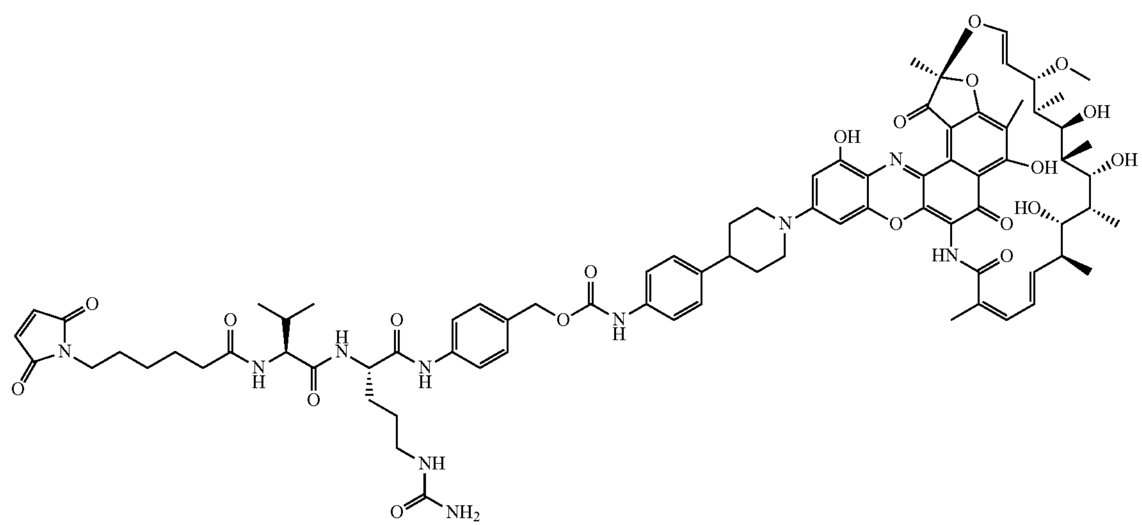 [SMILES: CO[C@H]1/C=C/O[C@@]2(C)Oc3c(C)c(O)c4c(=O)c(c5oc6cc(N7CCC(c8ccc(NC(=O)OCc9ccc(NC(=O)[C@H](CCCNC(N)=O)NC(=O)[C@@H](NC(=O)CCCCCN%10C(=O)C=CC%10=O)C(C)C)cc9)cc8)CC7)cc(O)c6nc-5c4c3C2=O)NC(=O)/C(C)=C\C=C\[C@H](C)[C@H](O)[C@@H](C)[C@@H](O)[C@@H](C)[C@H](O)[C@@H]1C] |

TABLE 2-continued
Linker-antibiotic intermediates (LA)
| LA No. | Structure |
|---|---|
| LA-73 | 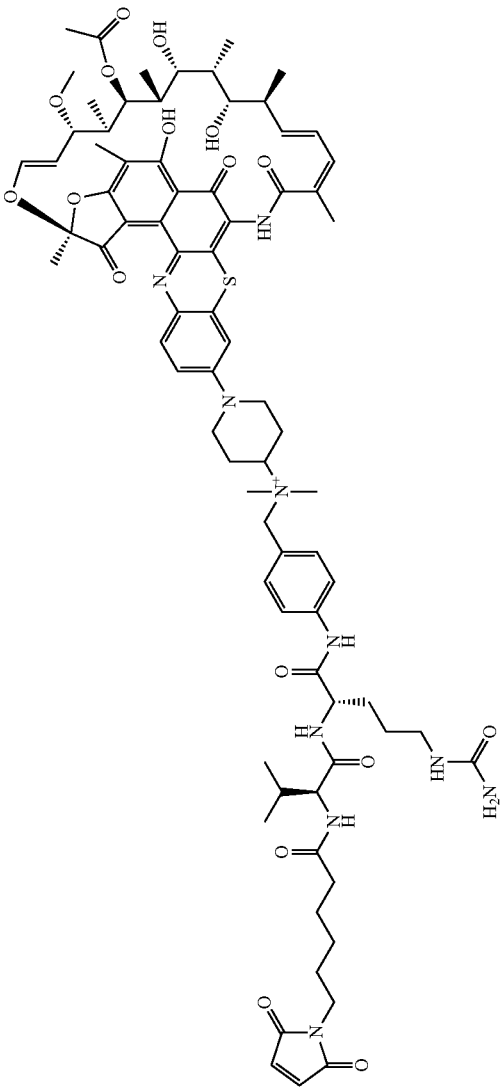 |
| LA-74 | 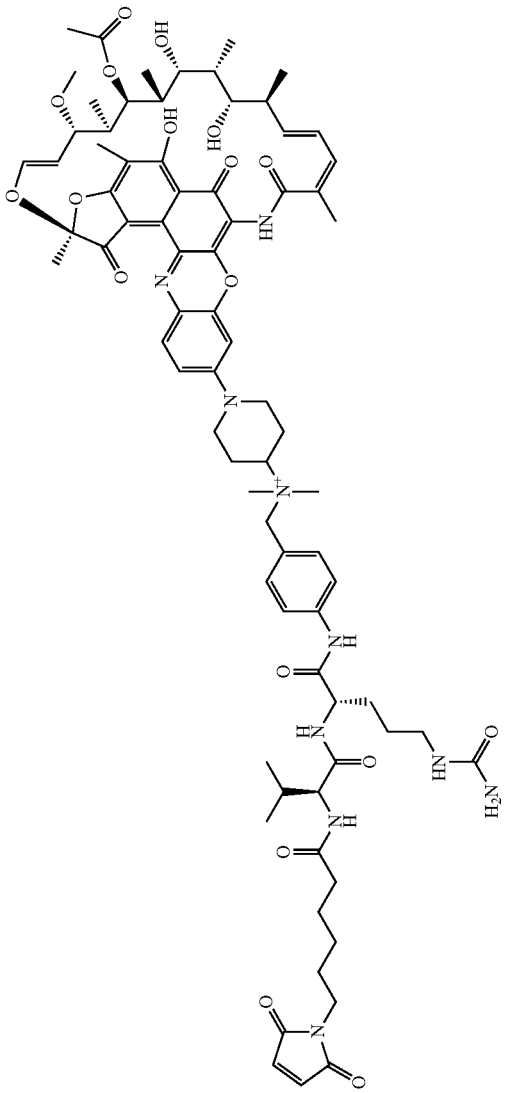 |

TABLE 2-continued

Linker-antibiotic intermediates (LA)

| LA No. | Structure |
|---|---|
| LA-75 | 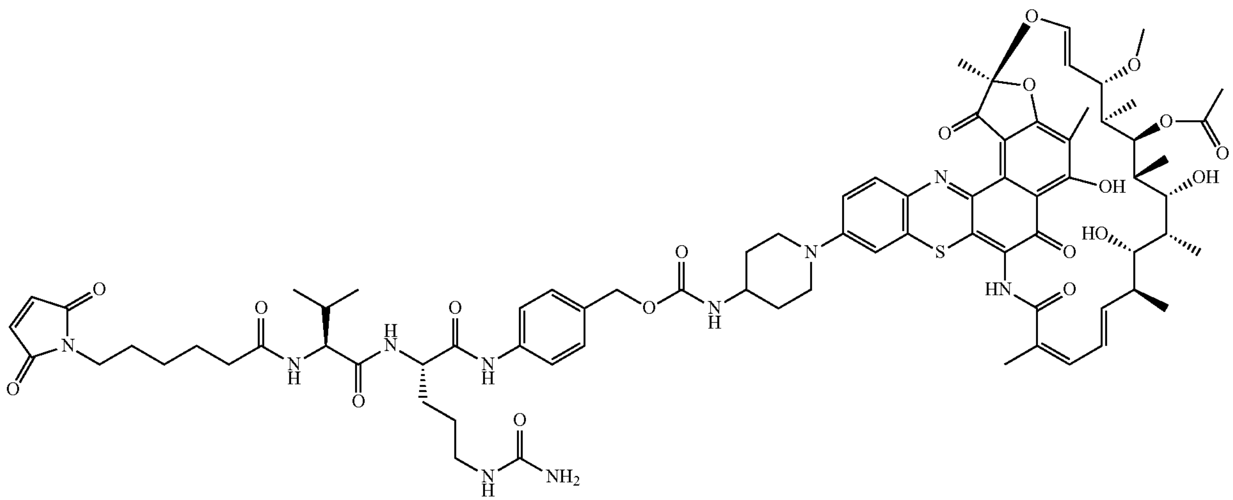 [SMILES: CO[C@H]1/C=C/O[C@@]2(C)Oc3c(C)c(O)c4c(=O)c(c5sc6cc(N7CCC(NC(=O)OCc8ccc(NC(=O)[C@H](CCCNC(N)=O)NC(=O)[C@@H](NC(=O)CCCCCN9C(=O)C=CC9=O)C(C)C)cc8)CC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] |
| LA-76 | 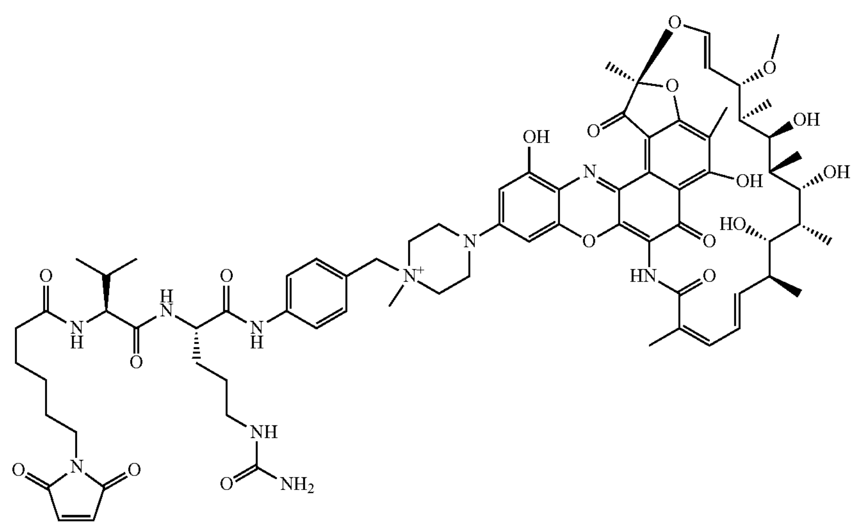 [SMILES: CO[C@H]1/C=C/O[C@@]2(C)Oc3c(C)c(O)c4c(=O)c(c5oc6cc(N7CC[N+](C)(Cc8ccc(NC(=O)[C@H](CCCNC(N)=O)NC(=O)[C@@H](NC(=O)CCCCCN9C(=O)C=CC9=O)C(C)C)cc8)CC7)cc(O)c6nc-5c4c3C2=O)NC(=O)/C(C)=C\C=C\[C@H](C)[C@H](O)[C@@H](C)[C@@H](O)[C@@H](C)[C@H](O)[C@@H]1C] |

TABLE 2-continued
Linker-antibiotic intermediates (LA)
| LA No. | Structure |
|---|---|
| LA-77 | 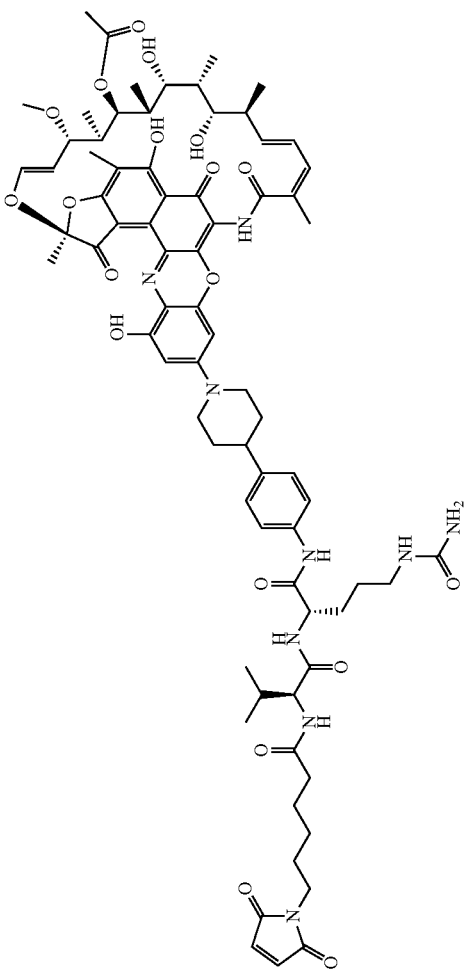 |
| LA-78 | 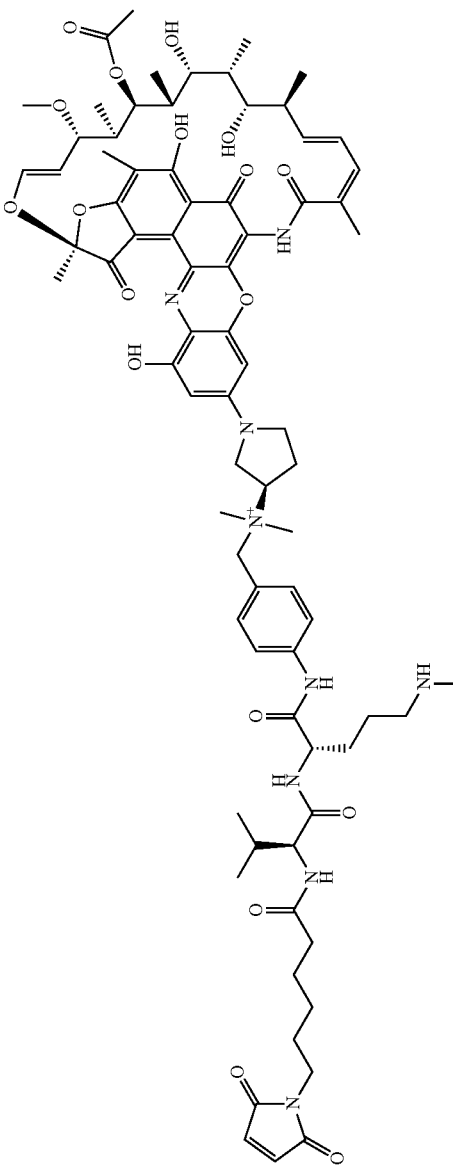 |

TABLE 2-continued

Linker-antibiotic intermediates (LA)

| LA No. | Structure |
|---|---|
| LA-79 | 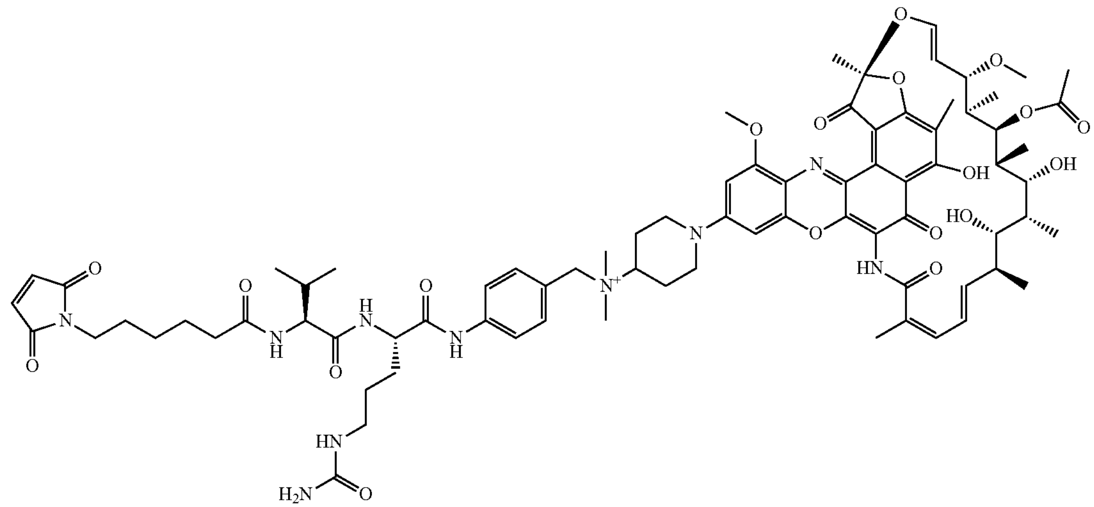 [SMILES: COc1cc(N2CCC([N+](C)(C)Cc3ccc(NC(=O)[C@H](CCCNC(N)=O)NC(=O)[C@@H](NC(=O)CCCCCN4C(=O)C=CC4=O)C(C)C)cc3)CC2)cc2oc3c4c(=O)c5c(O)c(C)c6c(c5c-3nc12)C(=O)[C@@](C)(O/C=C/[C@H](OC)[C@@H](C)[C@@H](OC(C)=O)[C@H](C)[C@H](O)[C@H](C)[C@@H](O)[C@@H](C)/C=C/C=C(/C)C(=O)N4)O6] |
| LA-80 | 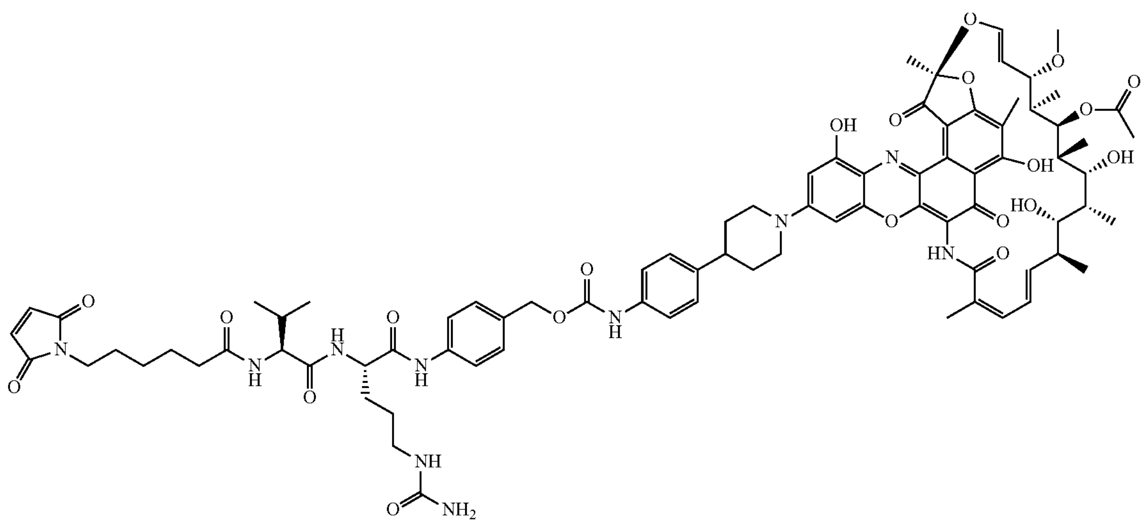 [SMILES: CO[C@H]1/C=C/O[C@@]2(C)Oc3c(C)c(O)c4c(=O)c(c5oc6cc(N7CCC(c8ccc(NC(=O)OCc9ccc(NC(=O)[C@H](CCCNC(N)=O)NC(=O)[C@@H](NC(=O)CCCCCN%10C(=O)C=CC%10=O)C(C)C)cc9)cc8)CC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] |

TABLE 2-continued
Linker-antibiotic intermediates (LA)
| LA No. | Structure |
|---|---|
| LA-81 | 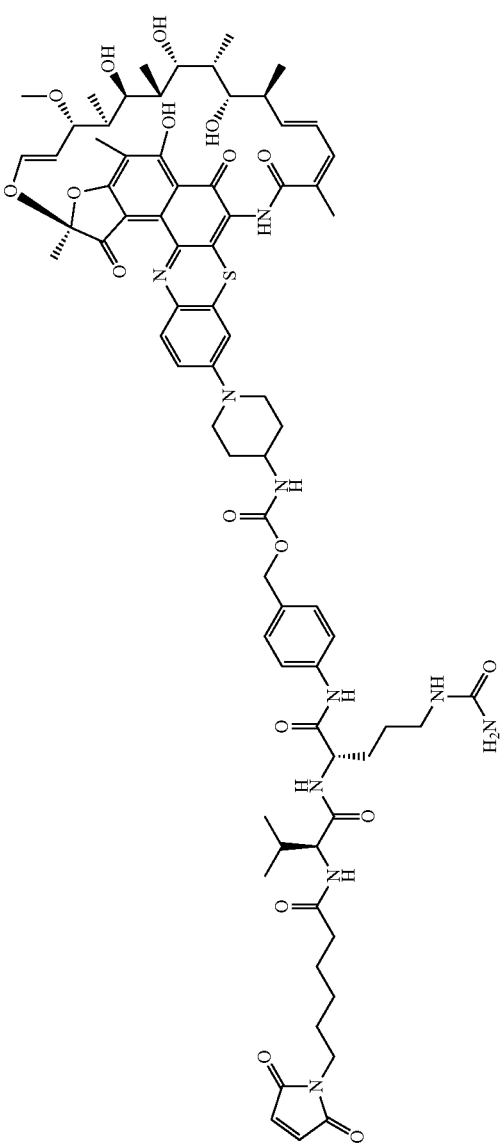 |
| LA-82 | 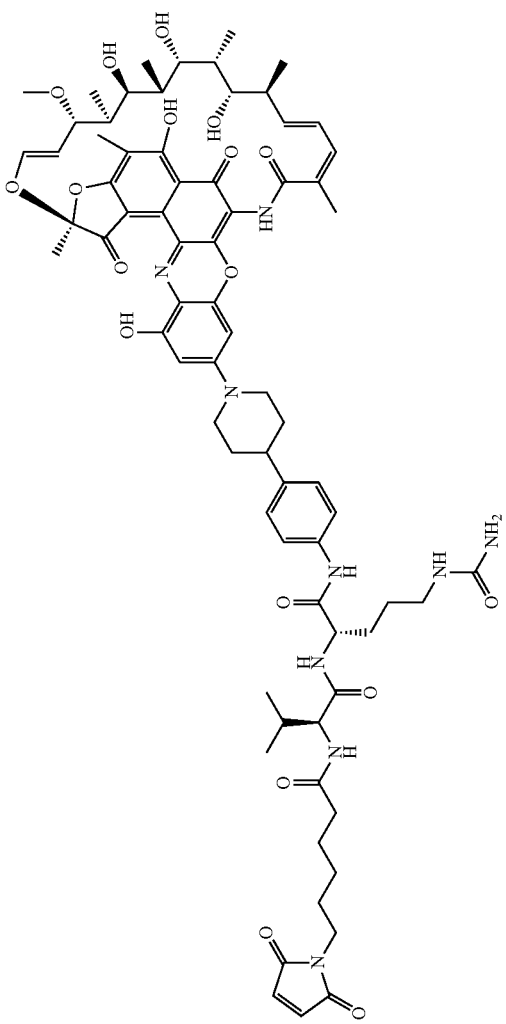 |

TABLE 2-continued
Linker-antibiotic intermediates (LA)
| LA No. | Structure |
|---|---|
| LA-83 | 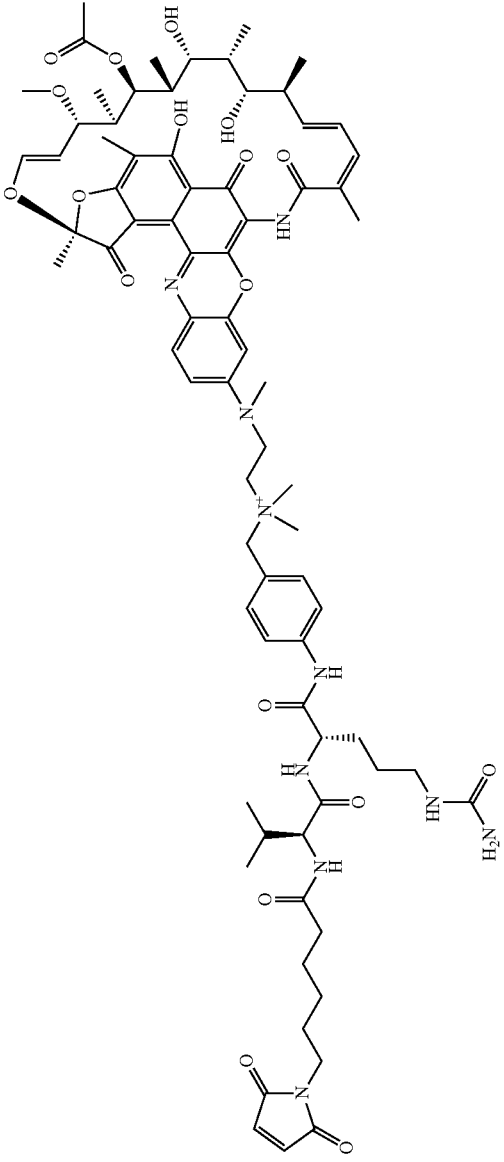 |
| LA-84 | 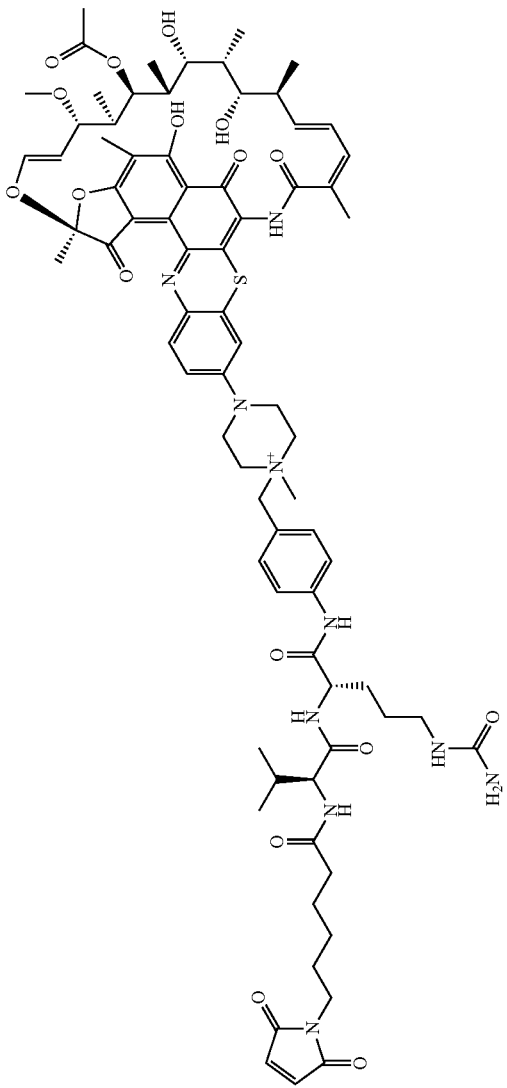 |

TABLE 2-continued
Linker-antibiotic intermediates (LA)
| LA No. | Structure |
|---|---|
| LA-85 | 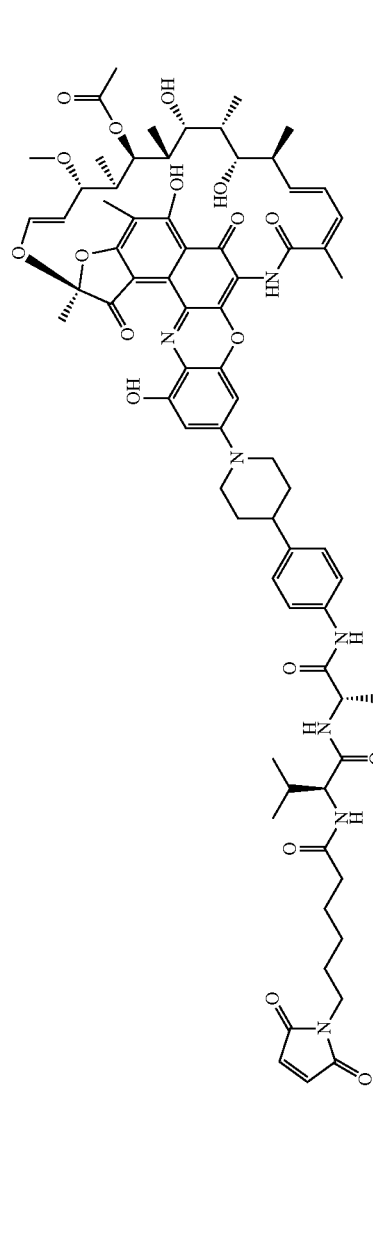 |
| LA-86 | 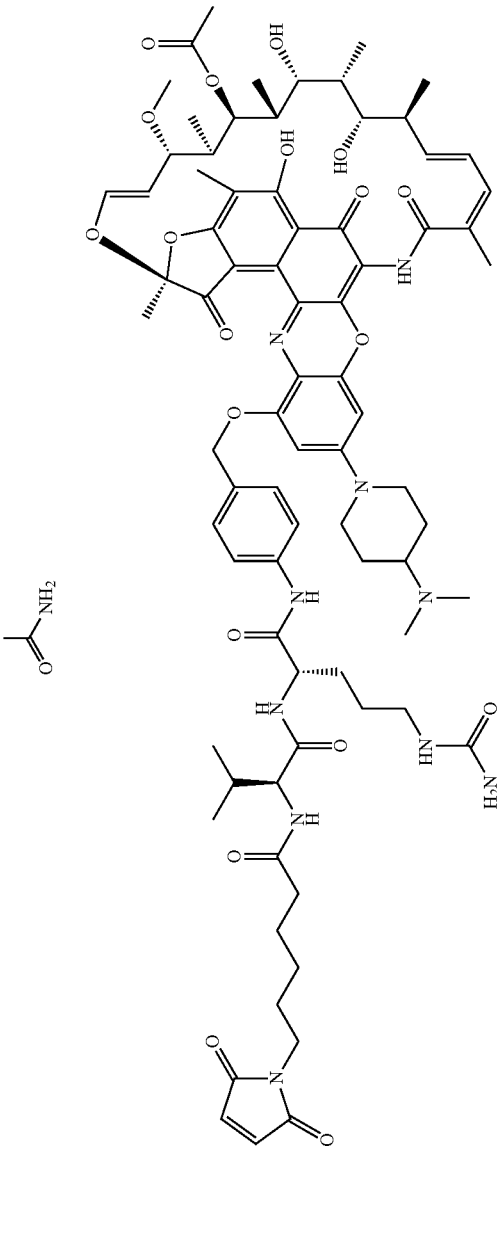 |

TABLE 2-continued

Linker-antibiotic intermediates (LA)

| LA No. | Structure |
|---|---|
| LA-87 | 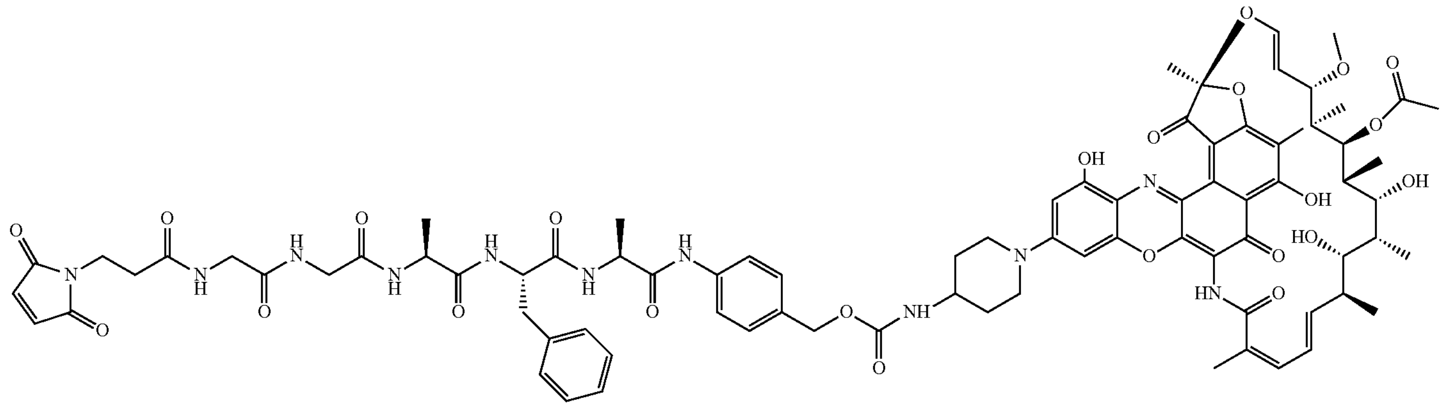 [SMILES: CO[C@H]1/C=C/O[C@@]2(C)Oc3c(C)c(O)c4c(=O)c(c5oc6cc(N7CCC(NC(=O)OCc8ccc(NC(=O)[C@H](C)NC(=O)[C@H](Cc9ccccc9)NC(=O)[C@H](C)NC(=O)CNC(=O)CNC(=O)CCN9C(=O)C=CC9=O)cc8)CC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] |
| LA-88 | 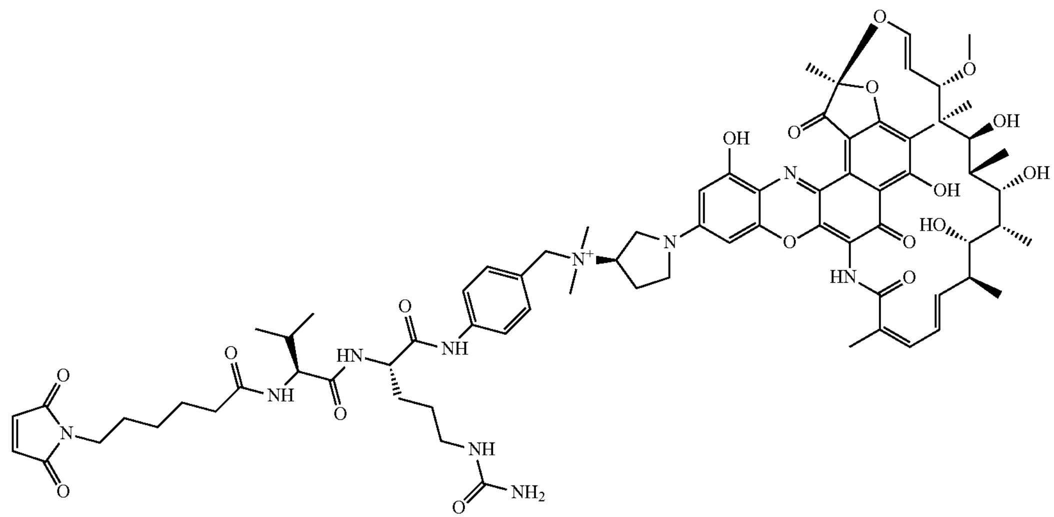 [SMILES: CO[C@H]1/C=C/O[C@@]2(C)Oc3c(C)c(O)c4c(=O)c(c5oc6cc(N7CC[C@@H]([N+](C)(C)Cc8ccc(NC(=O)[C@H](CCCNC(N)=O)NC(=O)[C@@H](NC(=O)CCCCCN9C(=O)C=CC9=O)C(C)C)cc8)C7)cc(O)c6nc-5c4c3C2=O)NC(=O)/C(C)=C\C=C\[C@H](C)[C@H](O)[C@@H](C)[C@@H](O)[C@@H](C)[C@H](O)[C@@H]1C] |

TABLE 2-continued
Linker-antibiotic intermediates (LA)
| LA No. | Structure |
|---|---|
| LA-89 | 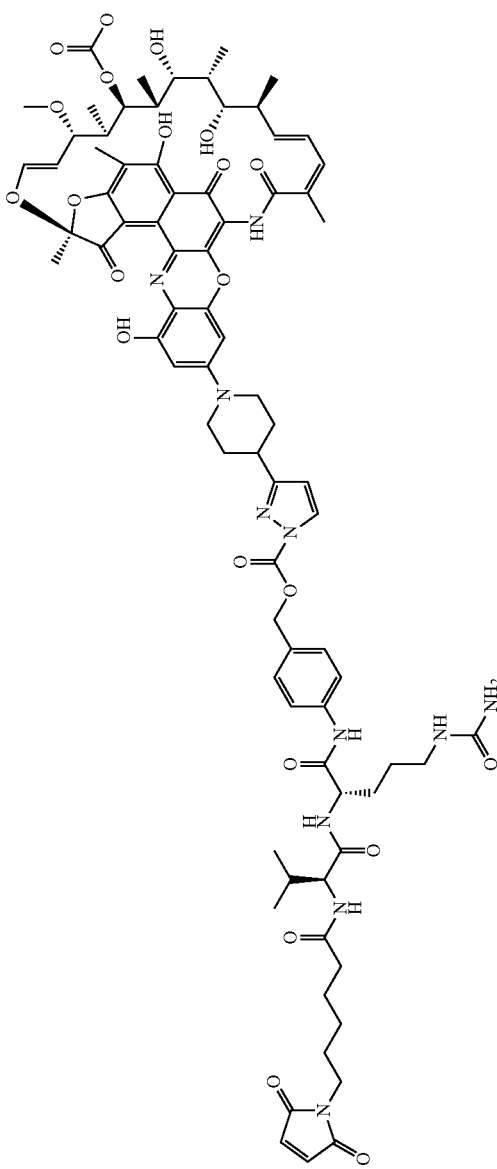 |
| LA-90 | 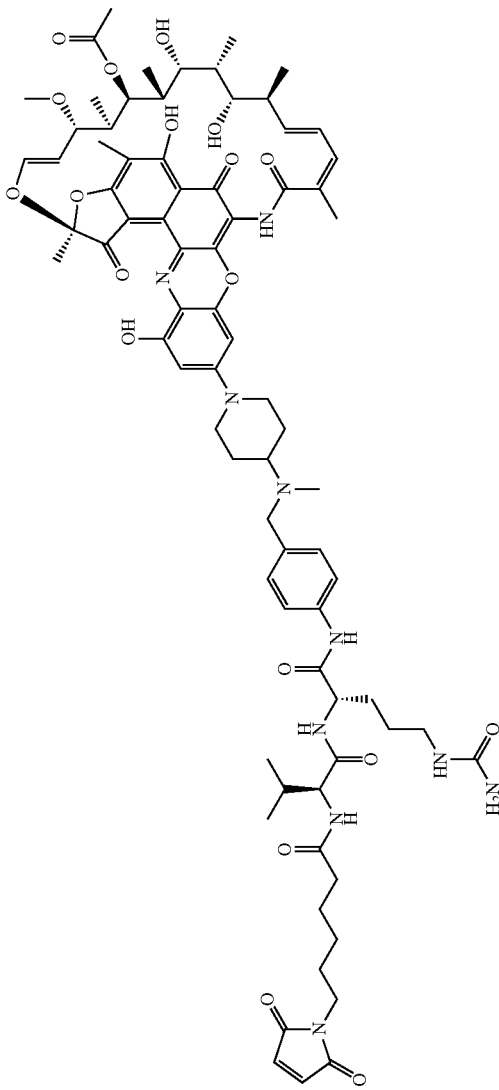 |

TABLE 2-continued
Linker-antibiotic intermediates (LA)
| LA No. | Structure |
|---|---|
| LA-91 | 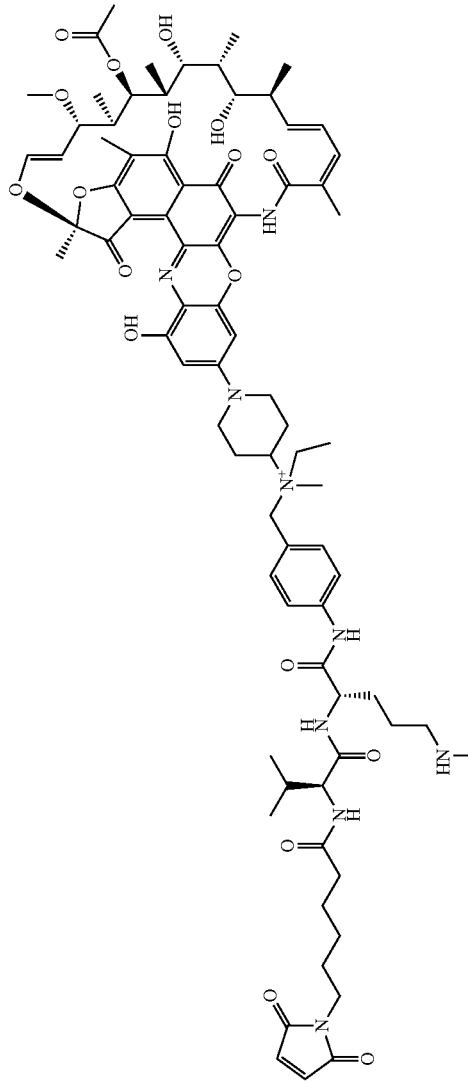 |
| LA-92 | 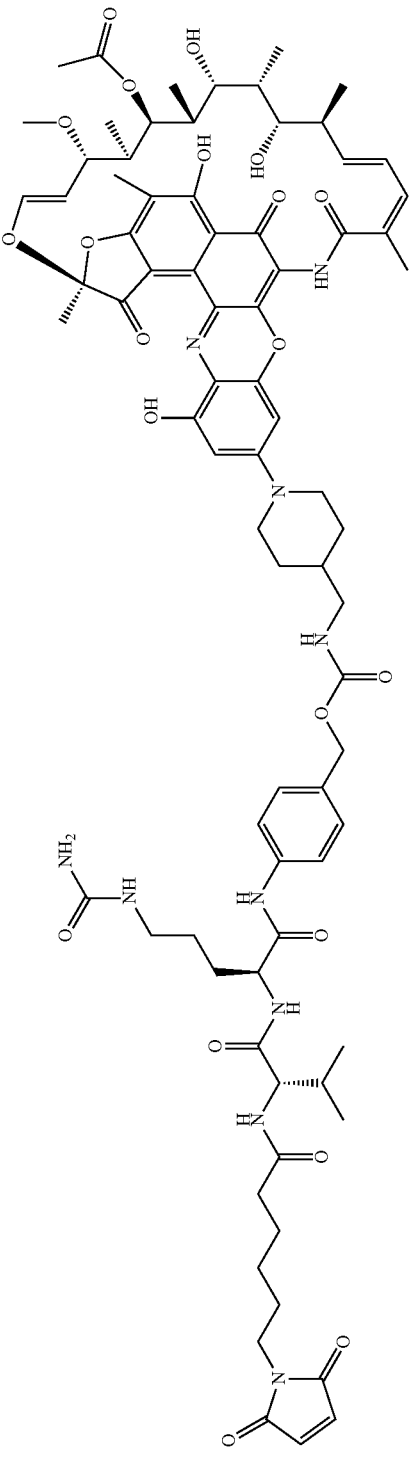 |

TABLE 2-continued
Linker-antibiotic intermediates (LA)
| LA No. | Structure |
|---|---|
| LA-93 | 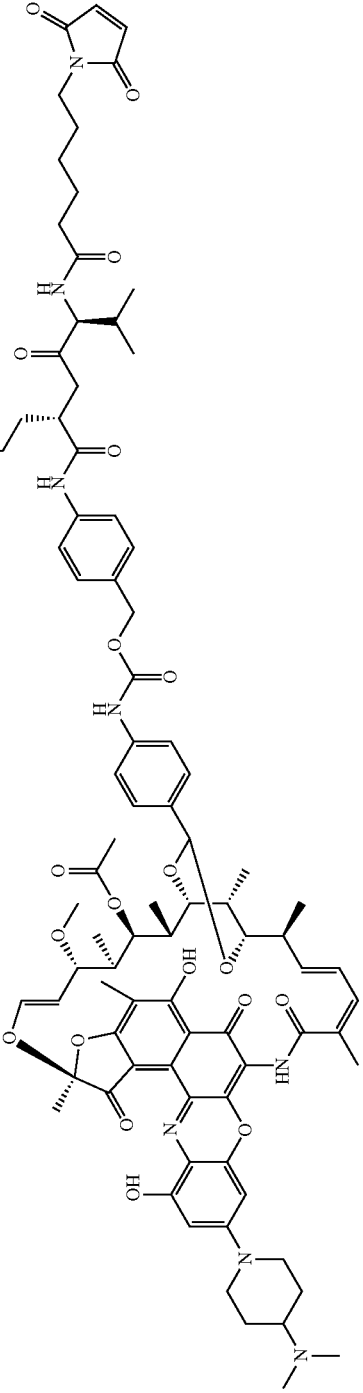 |
| LA-94 | 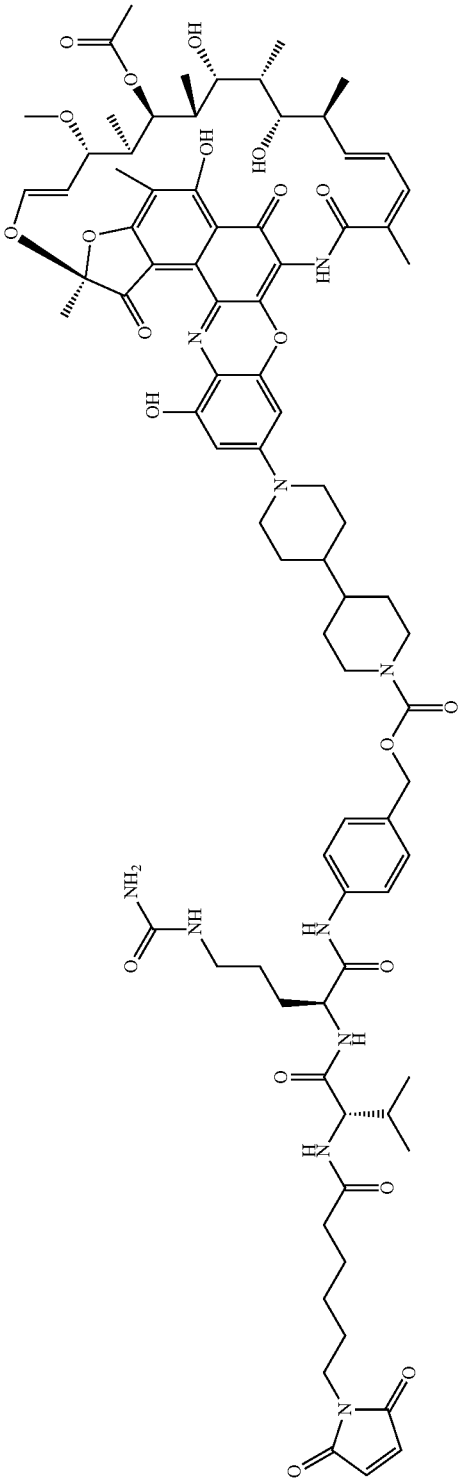 |

TABLE 2-continued
Linker-antibiotic intermediates (LA)
| LA No. | Structure |
|---|---|
| LA-95 | 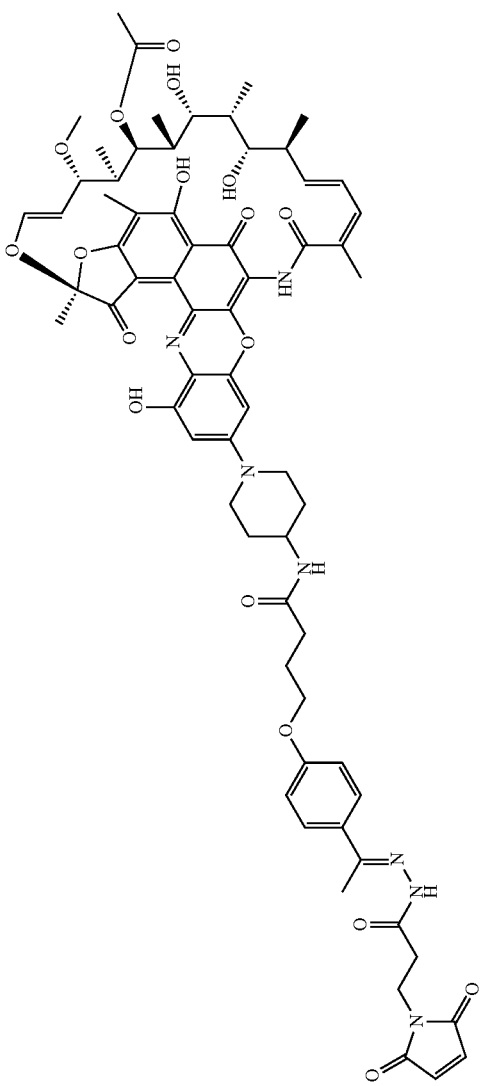 |
| LA-96 | 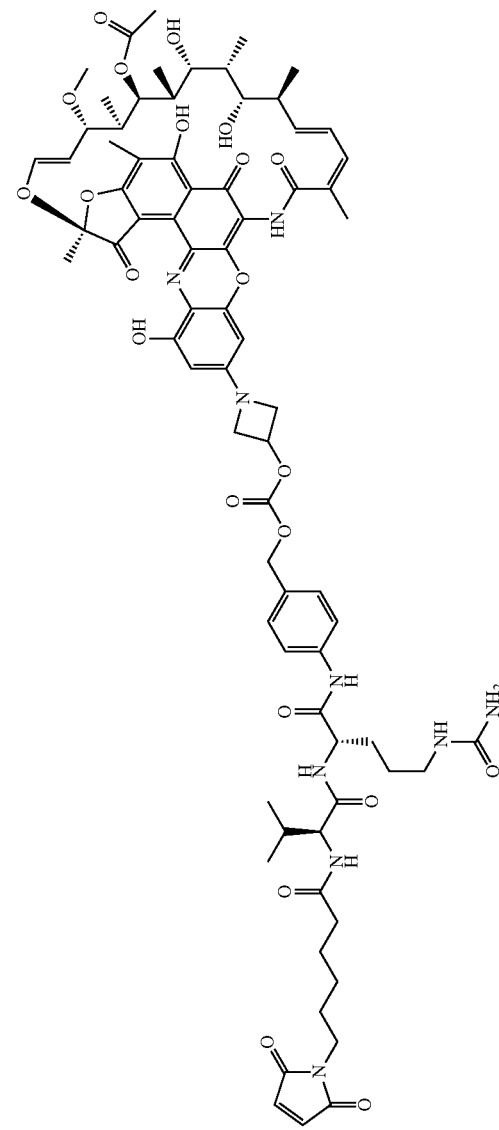 |

TABLE 2-continued
Linker-antibiotic intermediates (LA)
| LA No. | Structure |
|---|---|
| LA-97 | 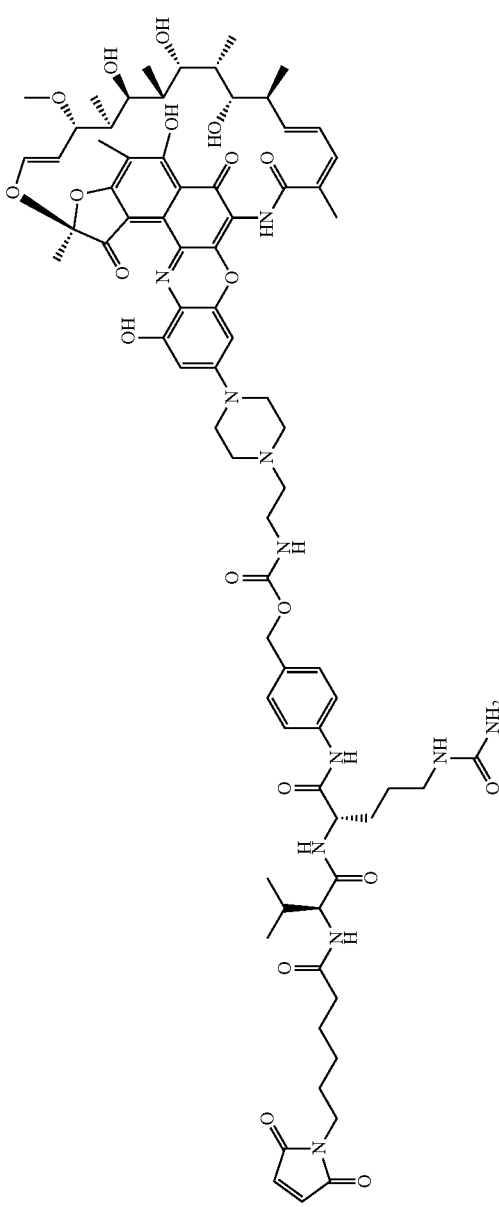 |
| LA-98 | 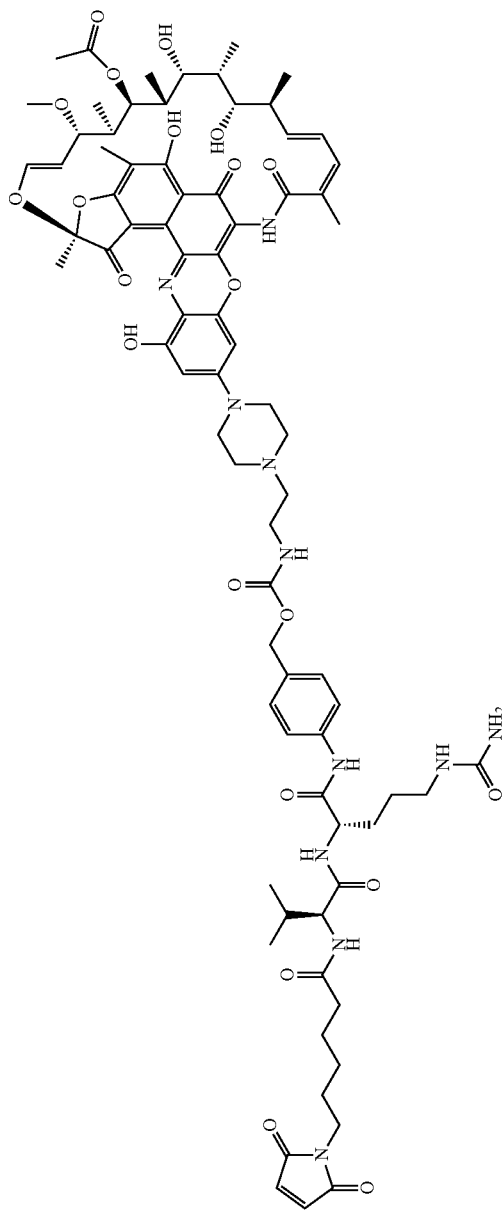 |

TABLE 2-continued
Linker-antibiotic intermediates (LA)
| LA No. | Structure |
|---|---|
| LA-99 | 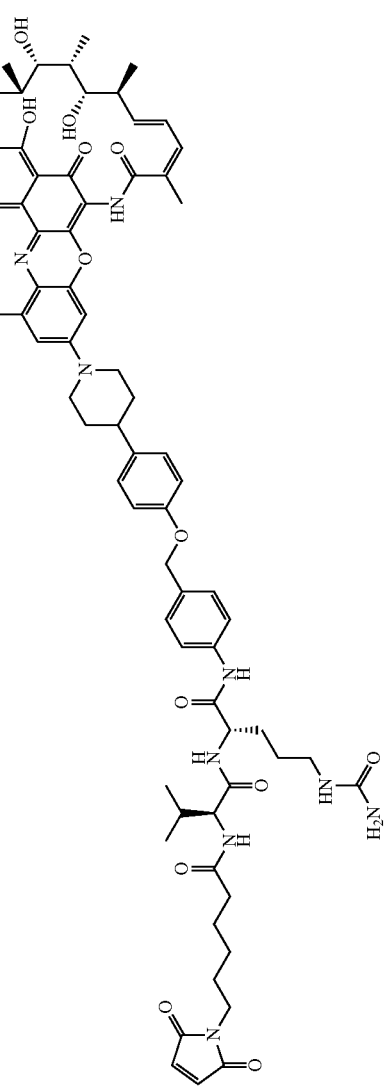 |

TABLE 2-continued
Linker-antibiotic intermediates (LA)
| LA No. | Structure |
|---|---|
| LA-100 | 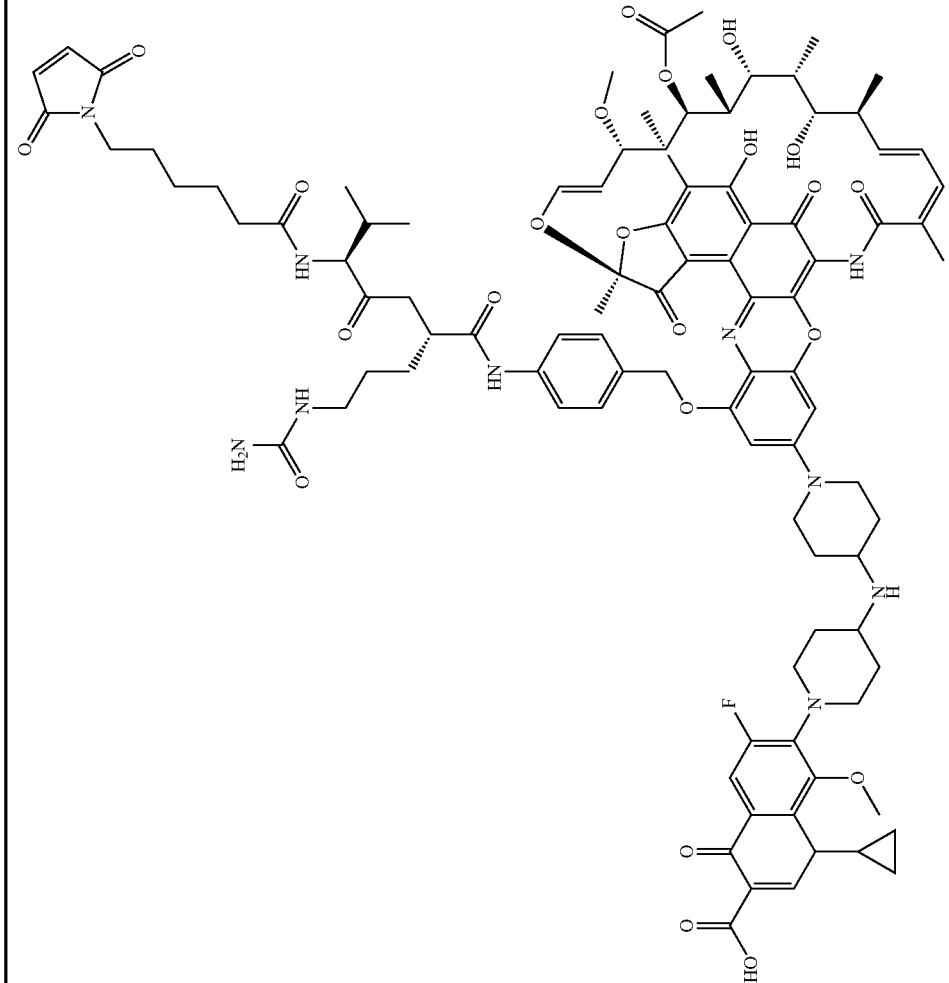 |

TABLE 2-continued
Linker-antibiotic intermediates (LA)
| LA No. | Structure |
|---|---|
| LA-101 | 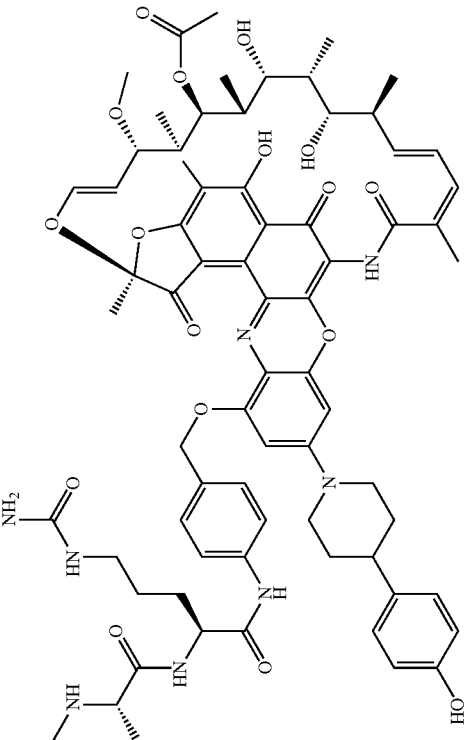 |

TABLE 2-continued
Linker-antibiotic intermediates (LA)
| LA No. | Structure |
|---|---|
| LA-102 | 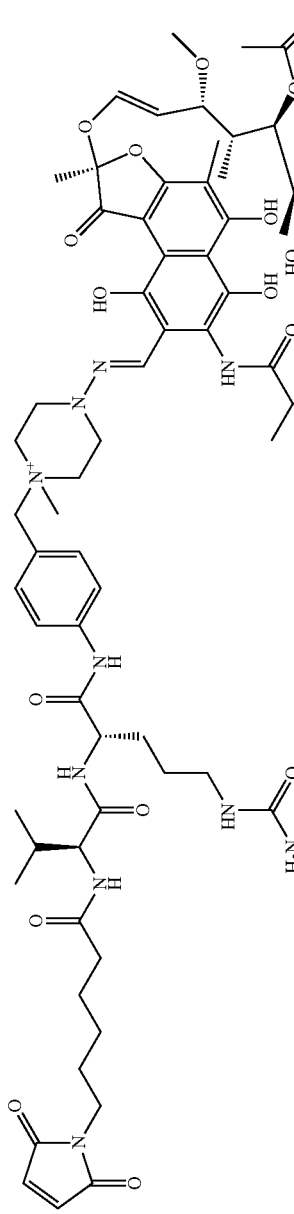 |
| LA-103 | 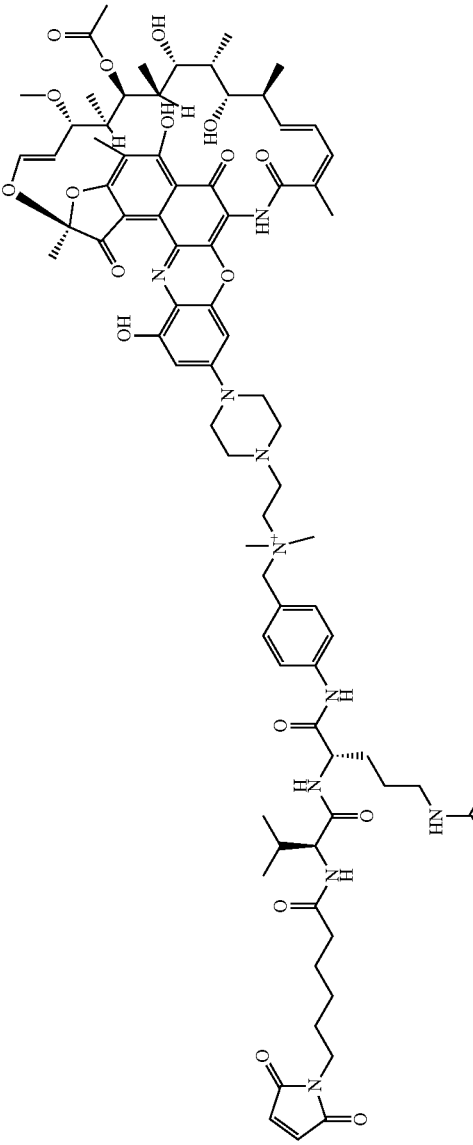 |

TABLE 2-continued
Linker-antibiotic intermediates (LA)
| LA No. | Structure |
|---|---|
| LA-104 | 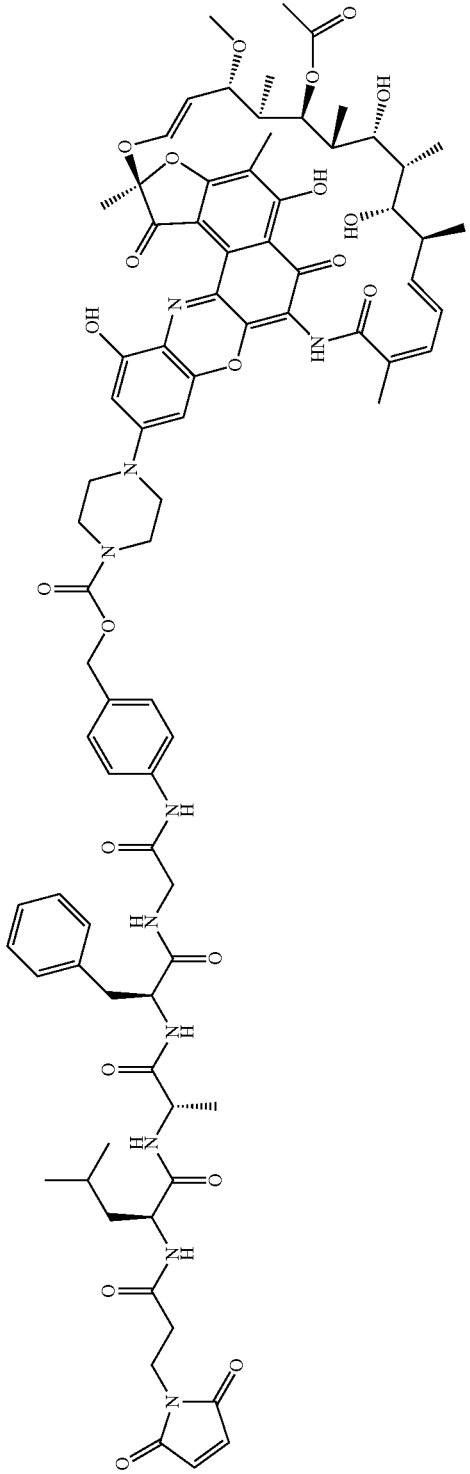 |
| LA-105 | 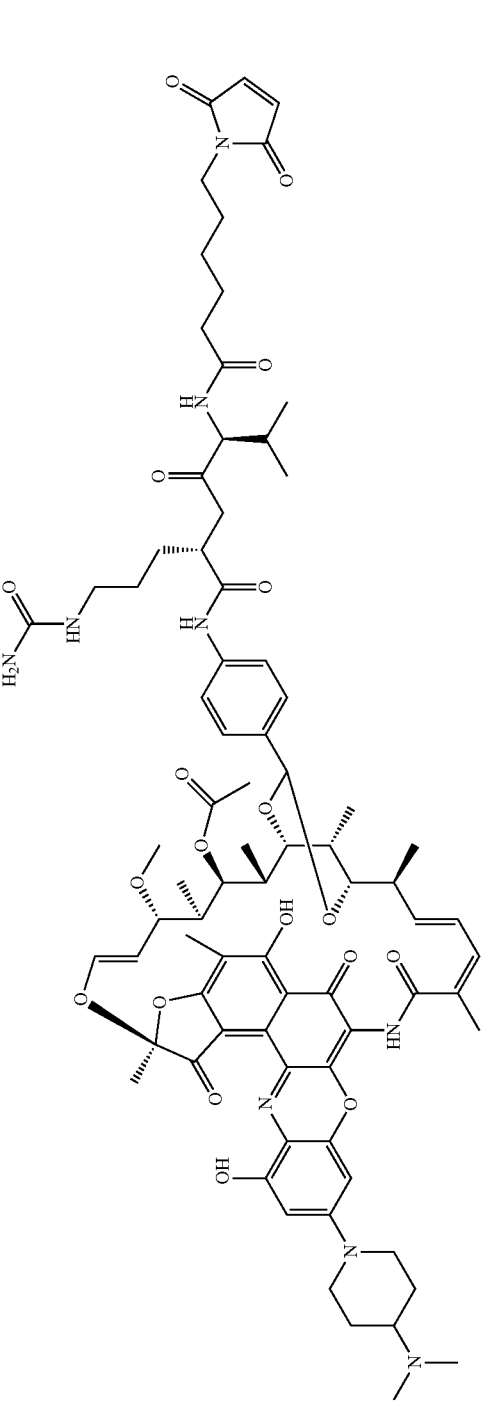 |

TABLE 2-continued
Linker-antibiotic intermediates (LA)
| LA No. | Structure |
|---|---|
| LA-106 | 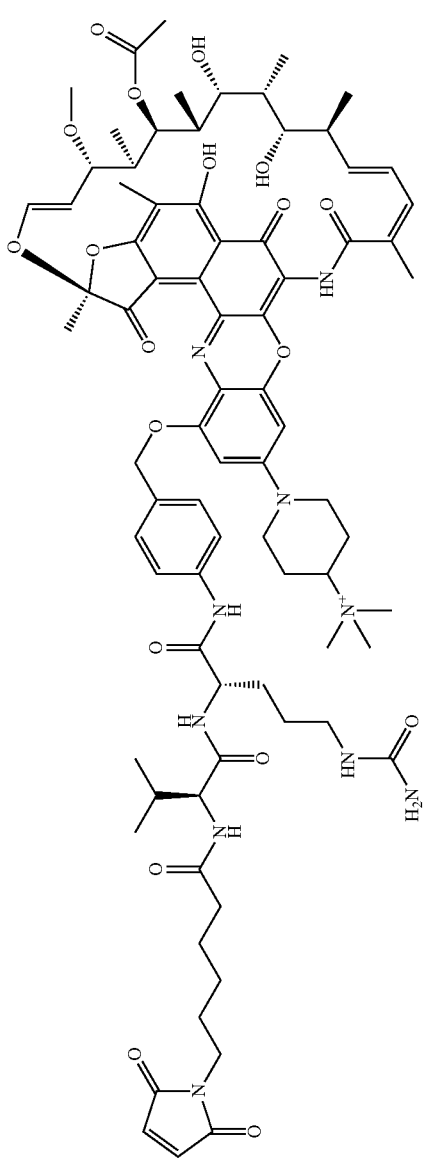 |
| LA-107 | 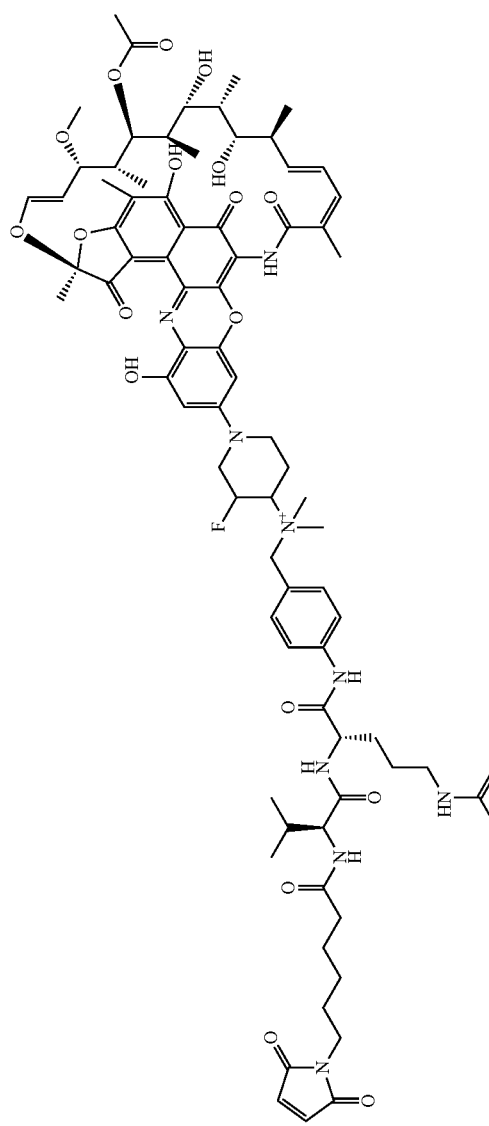 |

TABLE 2-continued
Linker-antibiotic intermediates (LA)
| LA No. | Structure |
|---|---|
| LA-108 | 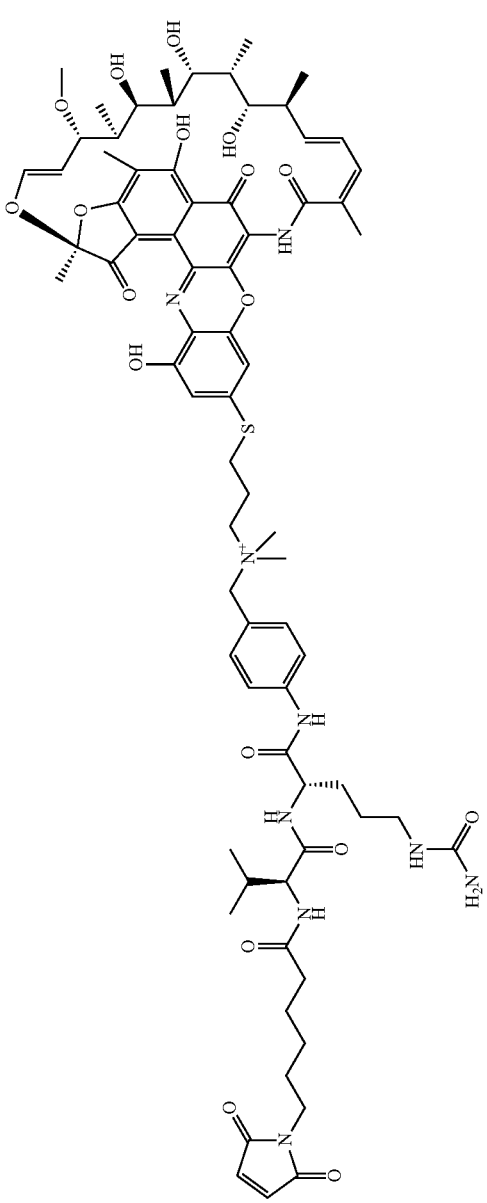 |
| LA-109 | 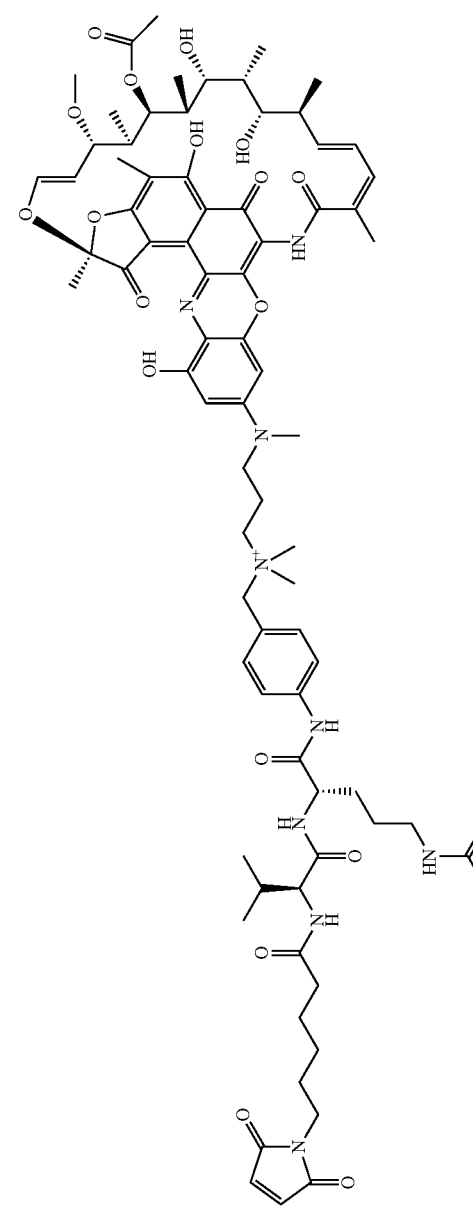 |

TABLE 2-continued
Linker-antibiotic intermediates (LA)
| LA No. | Structure |
|---|---|
| LA-110 | 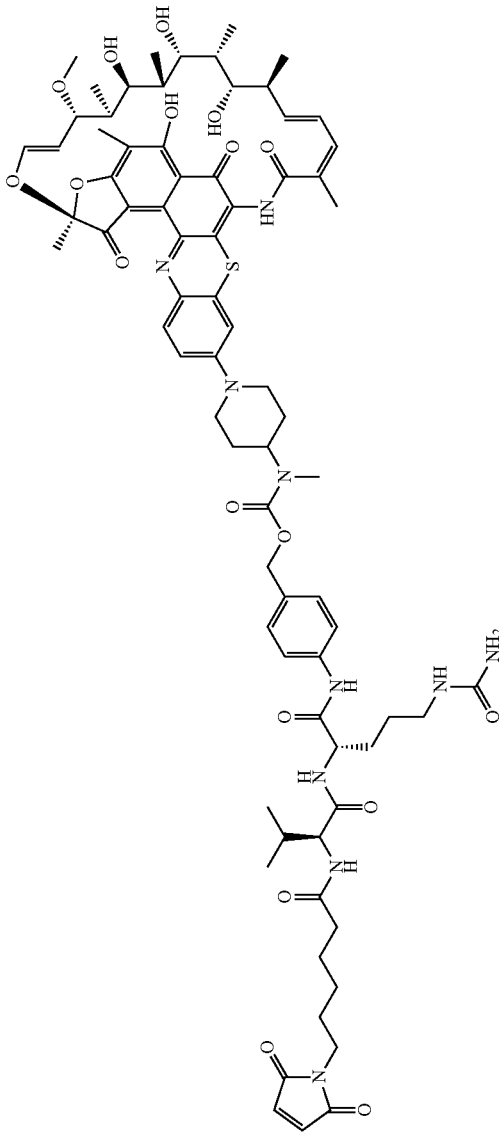 |
| LA-111 | 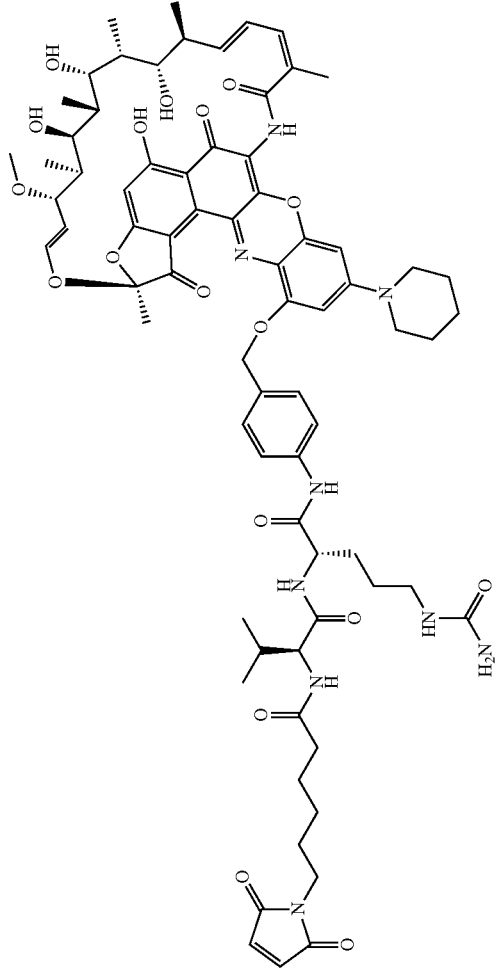 |

TABLE 2-continued
Linker-antibiotic intermediates (LA)
| LA No. | Structure |
|---|---|
| LA-112 | 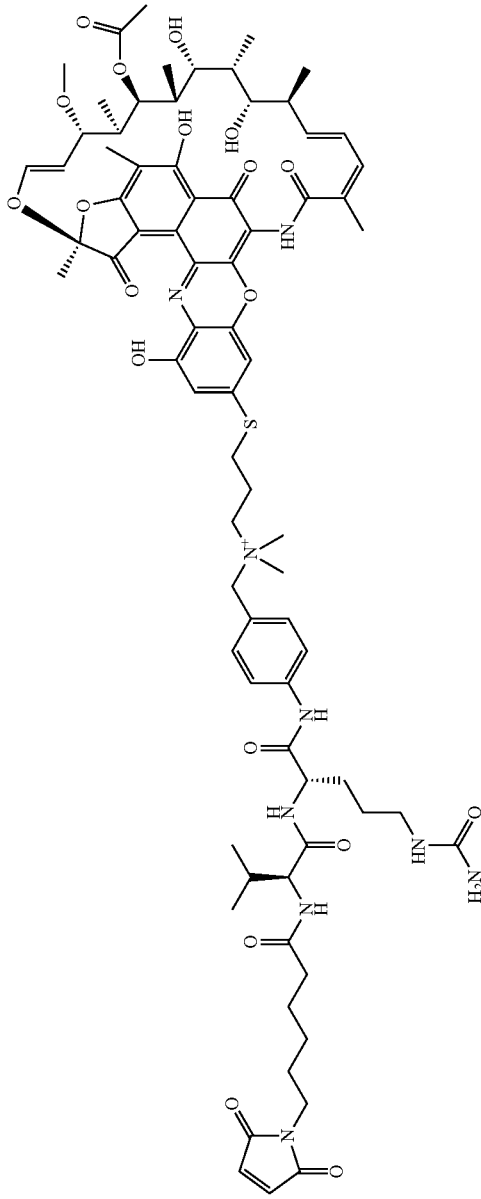 |
| LA-113 | 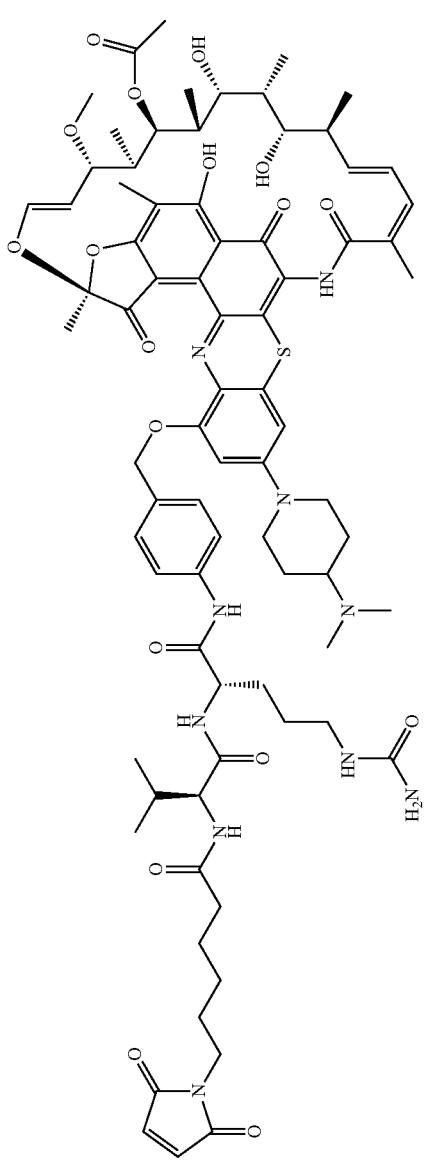 |

TABLE 2-continued

Linker-antibiotic intermediates (LA)

| LA No. | Structure |
|---|---|
| LA-114 | 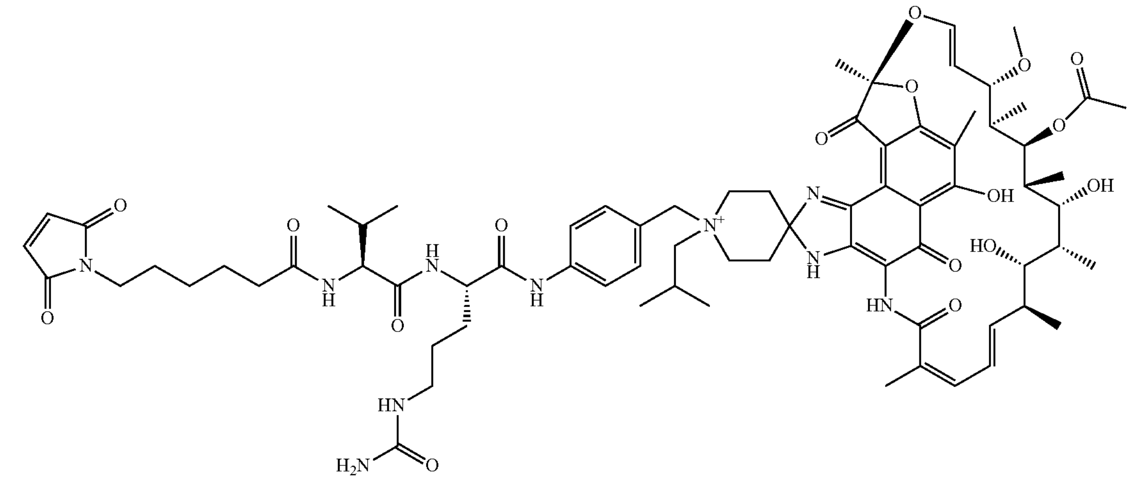 [SMILES: CO[C@H]1/C=C/O[C@@]2(C)Oc3c(C)c(O)c4c(c3C2=O)C2=NC3(CC[N+](Cc5ccc(NC(=O)[C@H](CCCNC(N)=O)NC(=O)[C@@H](NC(=O)CCCCCN6C(=O)C=CC6=O)C(C)C)cc5)(CC(C)C)CC3)NC2=C(NC(=O)/C(C)=C\C=C\[C@H](C)[C@H](O)[C@@H](C)[C@@H](O)[C@@H](C)[C@H](OC(C)=O)[C@@H]1C)C4=O] |
| LA-115 | 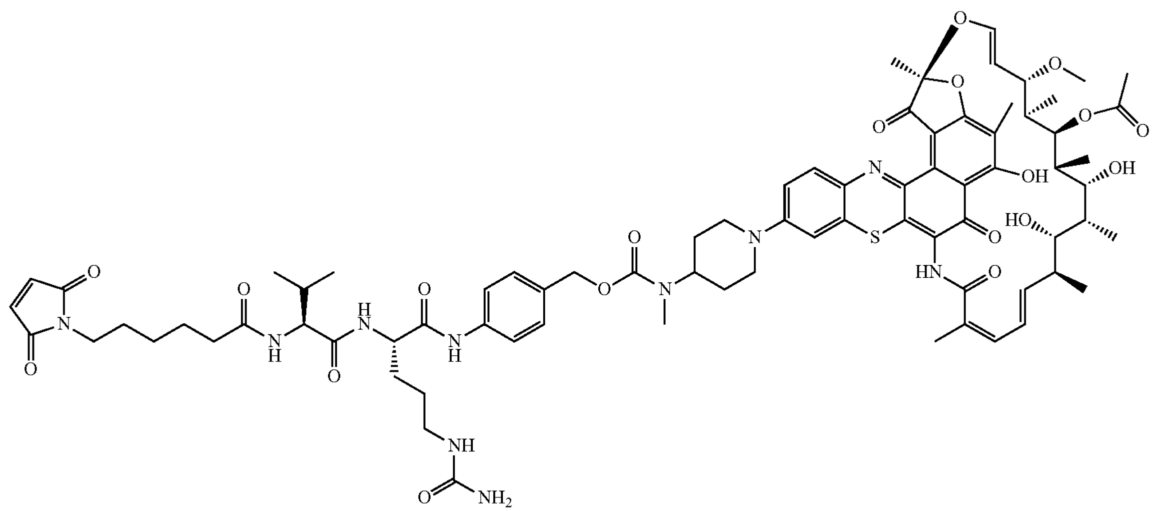 [SMILES: CO[C@H]1/C=C/O[C@@]2(C)Oc3c(C)c(O)c4c(=O)c(c5sc6cc(N7CCC(N(C)C(=O)OCc8ccc(NC(=O)[C@H](CCCNC(N)=O)NC(=O)[C@@H](NC(=O)CCCCCN9C(=O)C=CC9=O)C(C)C)cc8)CC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] |

TABLE 2-continued
Linker-antibiotic intermediates (LA)
| LA No. | Structure |
|---|---|
| LA-116 | 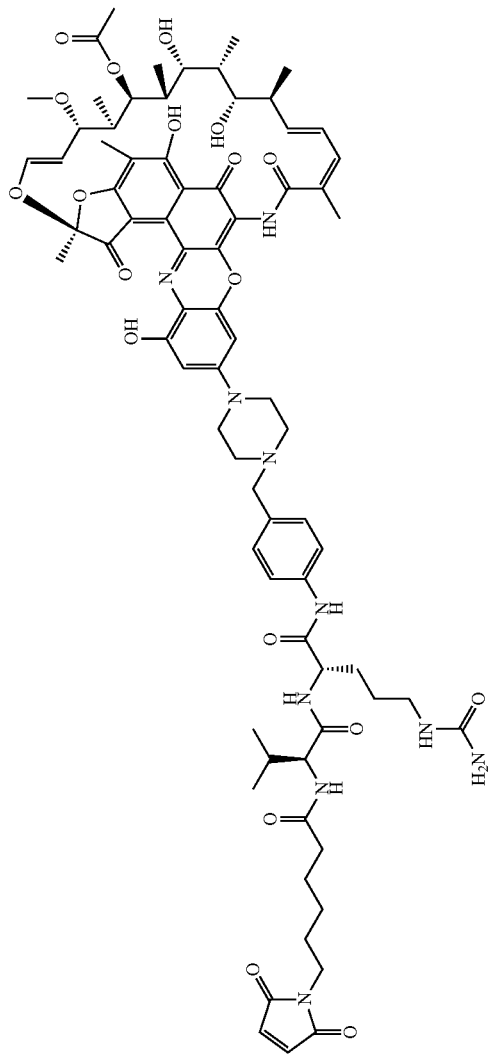 |

TABLE 2-continued
Linker-antibiotic intermediates (LA)
| LA No. | Structure |
|---|---|
| LA-117 | 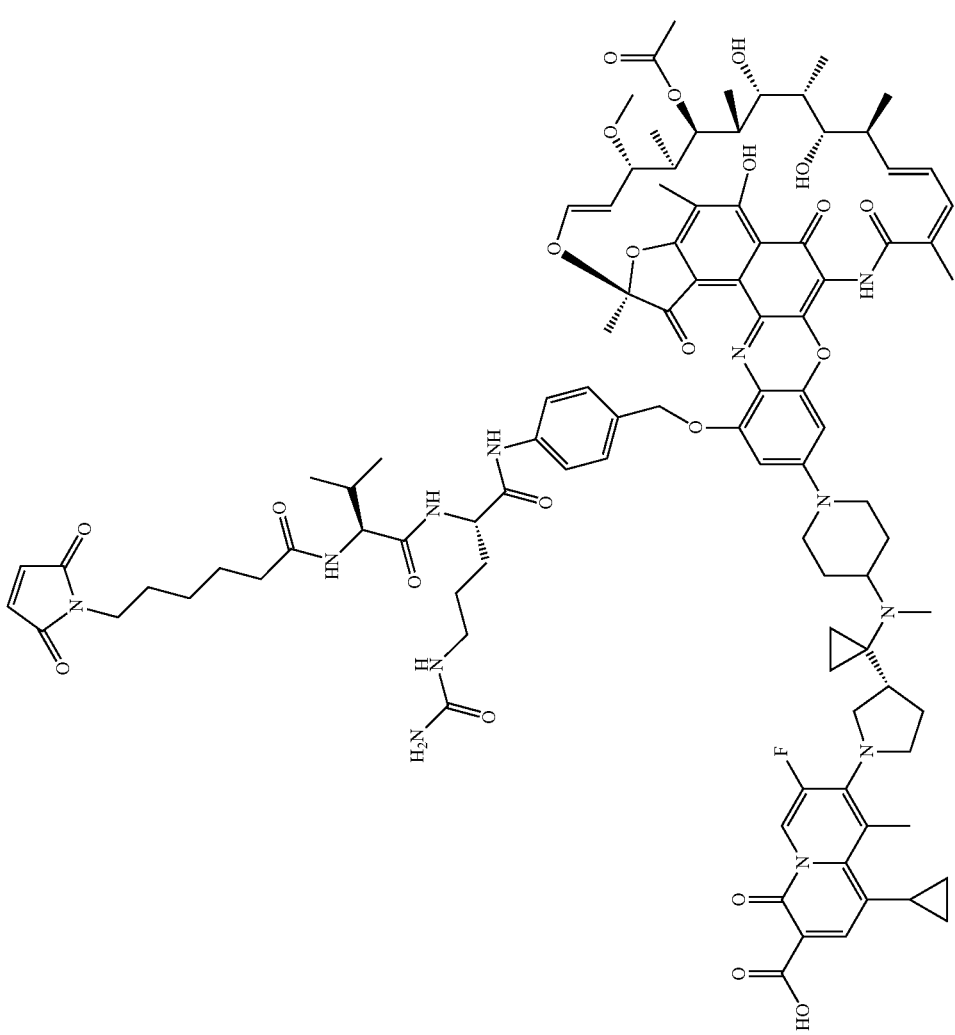 |

TABLE 2-continued
Linker-antibiotic intermediates (LA)
| LA No. | Structure |
|---|---|
| LA-118 | 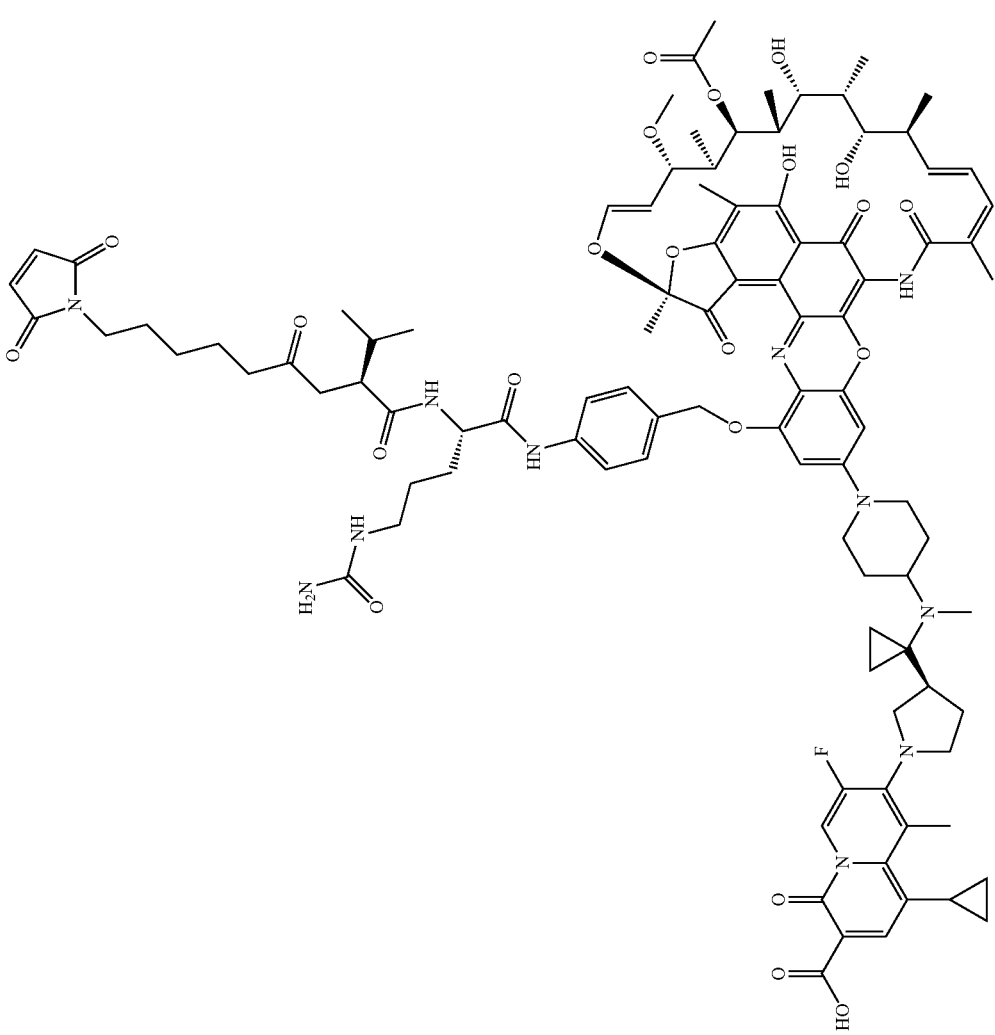 |

Embodiments of Antibody-Antibiotic Conjugates

The S4497 antibody was linked to derivatives of rifamycin in Table 3 termed pipBOR and others via a protease cleavable, peptide linker. The linker is designed to be cleaved by lysosomal proteases including cathepsins B, D and others, which recognize peptide units, including the Valine-Citrulline (val-cit, vc) dipeptide (Dubowchik et al (2002) Bioconj. Chem. 13:855-869). Generation of the linker-antibiotic intermediate consisting of the antibiotic and the MC-vc-PAB linker and others, is described in detail in Examples 1-17. The linker is designed such that cleavage of the amide bond at the PAB moiety separates the antibody from the antibiotic in an active state.

The AAC termed S4497-dimethyl-pipBOR is identical to the S4497-pipBOR AAC except for the dimethylated amino on the antibiotic and the oxycarbonyl group on the linker.

Figure 5:
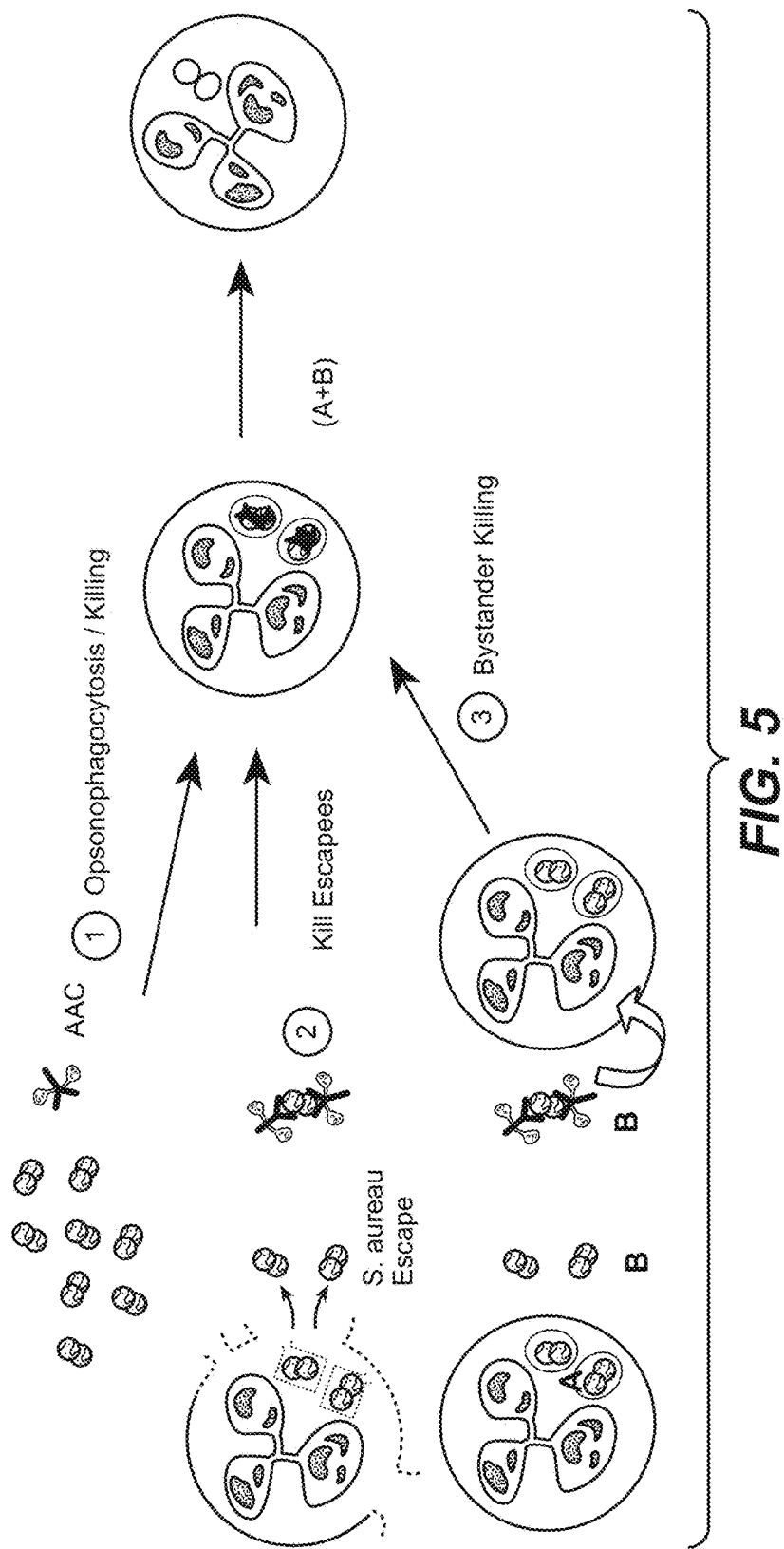
FIG. 5 shows a possible mechanism of drug activation for antibody-antibiotic conjugates (AAC). Active antibiotic (Abx) is released after internalization of the AAC inside mammalian cells.

FIG. 5 shows a possible mechanism of drug activation for antibody-antibiotic conjugates (AAC). Active antibiotic (Ab) is only released after internalization of the AAC inside mammalian cells. The Fab portion of the antibody in AAC binds S. aureus whereas the Fc portion of the AAC enhances uptake of the bacteria by Fc-receptor mediated binding to phagocytic cells including neutrophils and macrophages. After internalization into the phagolysosome, the Val-Cit linker is cleaved by lysosomal proteases releasing the active antibiotic inside the phagolysosome.

An embodiment of the antibody-antibiotic conjugate (AAC) compounds of the invention includes the following:

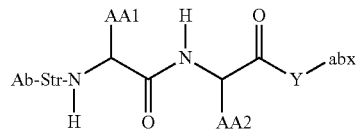

where AA1 and AA2 are independently selected from an amino acid side chain, including H, —CH$_3$, —CH$_2$(C$_6$H$_5$), —CH$_2$CH$_2$CH$_2$CH$_2$NH$_2$, —CH$_2$CH$_2$CH$_2$NHC(NH)NH$_2$, —CHCH(CH$_3$)CH$_3$, and —CH$_2$CH$_2$CH$_2$NHC(O)NH$_2$; and including the formulas:

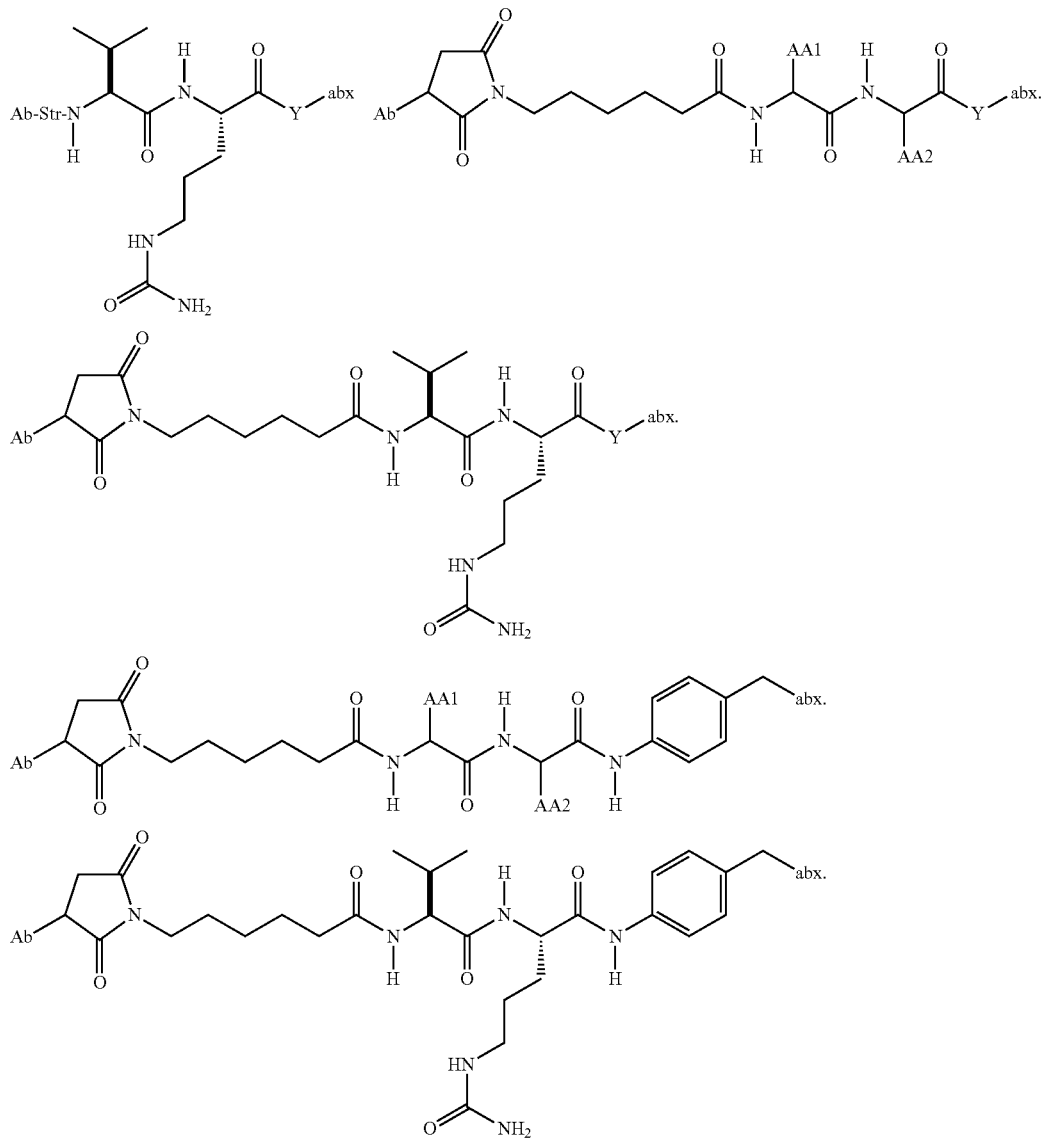

-continued

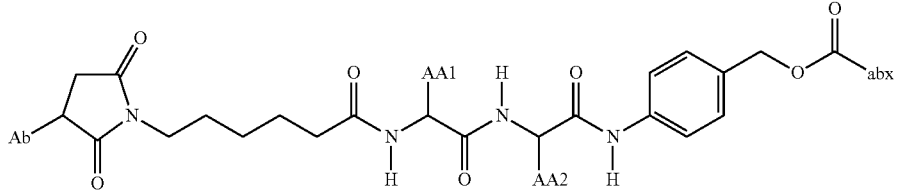

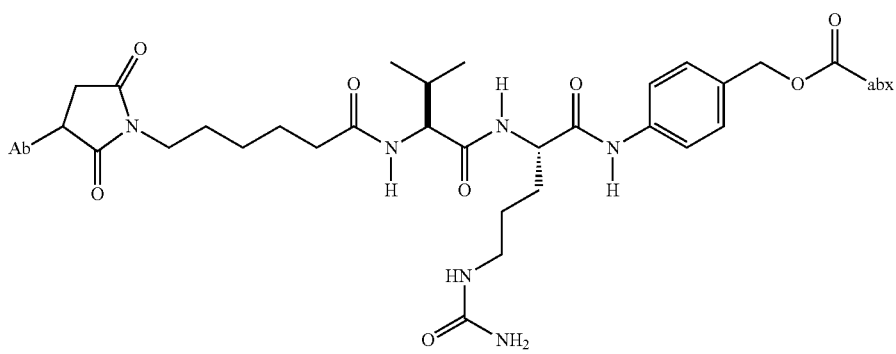

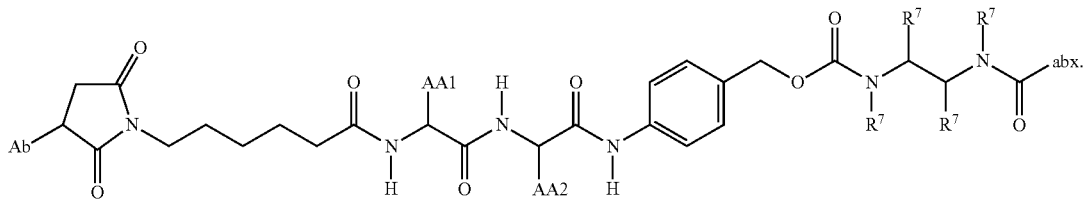

An embodiment of the antibody-antibiotic conjugate compounds of the invention includes the following:

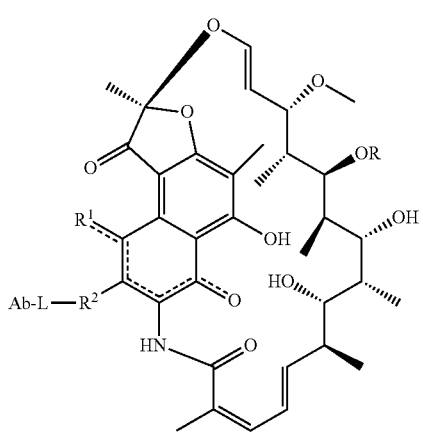

wherein:

the dashed lines indicate an optional bond;

R is H, $C_1$-$C_{12}$ alkyl, or $C(O)CH_3$;

$R^1$ is OH;

$R^2$ is CH=N-(heterocyclyl), wherein the heterocyclyl is optionally substituted with one or more groups independently selected from $C(O)CH_3$, $C_1$-$C_{12}$ alkyl, $C_1$-$C_{12}$ heteroaryl, $C_2$-$C_{20}$ heterocyclyl, $C_6$-$C_{20}$ aryl, and $C_3$-$C_{12}$ carbocyclyl;

or $R^1$ and $R^2$ form a five- or six-membered fused heteroaryl or heterocyclyl, and optionally forming a spiro or fused six-membered heteroaryl, heterocyclyl, aryl, or carbocyclyl ring, wherein the spiro or fused six-membered heteroaryl, heterocyclyl, aryl, or carbocyclyl ring is optionally substituted H, F, Cl, Br, I, $C_1$-$C_{12}$ alkyl, or OH;

L is the peptide linker attached to $R^2$ or the fused heteroaryl or heterocyclyl formed by $R^1$ and $R^2$; and Ab is the anti-wall teichoic acid (WTA) antibody.

An embodiment of the antibody-antibiotic conjugate compounds of the invention includes the following:

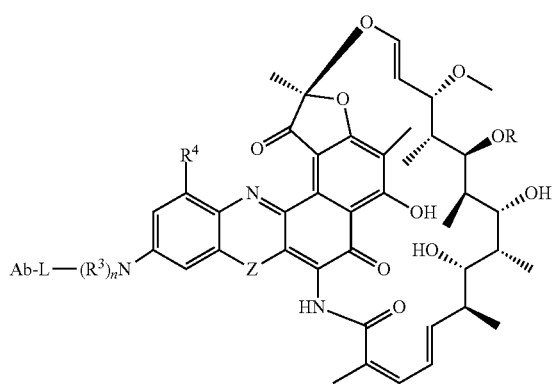

wherein $R^3$ is independently selected from H and $C_1$-$C_{12}$ alkyl; n is 1 or 2; $R^4$ is selected from H, F, Cl, Br, I, $C_1$-$C_{12}$ alkyl, and OH; and Z is selected from NH, N($C_1$-$C_{12}$ alkyl), O and S.

An embodiment of the antibody-antibiotic conjugate compounds of the invention includes the following rifampin-type antibiotic moiety:

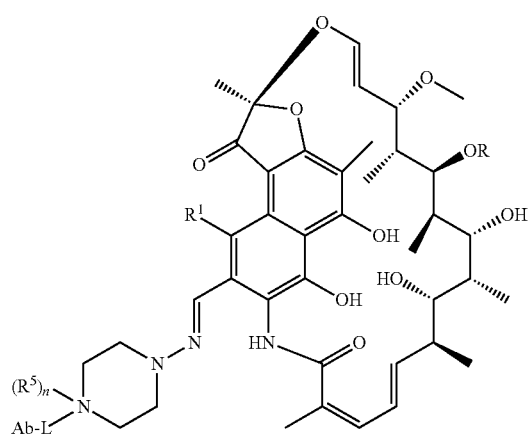

wherein $R^5$ is selected from H and $C_1$-$C_{12}$ alkyl; and n is 0 or 1.

An embodiment of the antibody-antibiotic conjugate compounds of the invention includes the following rifabutin-type antibiotic moiety:

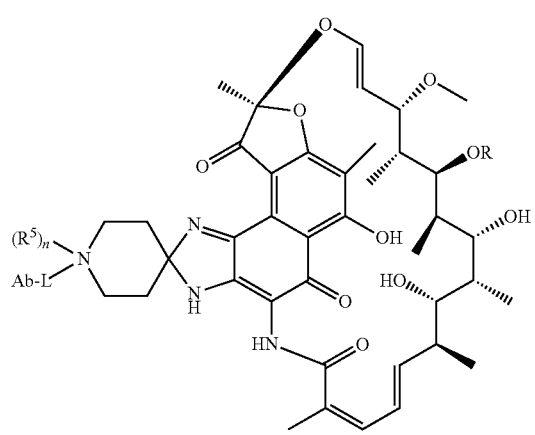

wherein $R^5$ is selected from H and $C_1$-$C_{12}$ alkyl; and n is 0 or 1.

An embodiment of the antibody-antibiotic conjugate compounds of the invention includes the following rifalazil-type antibiotic moiety:

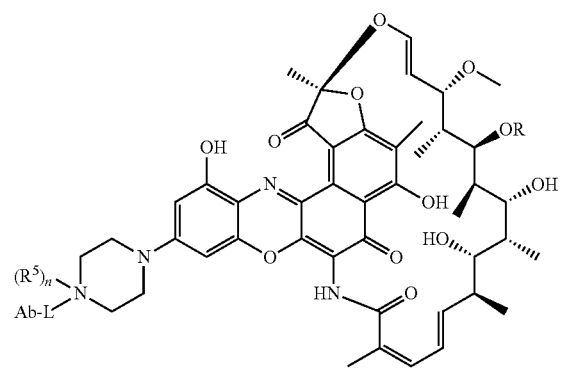

wherein $R^5$ is independently selected from H and $C_1$-$C_{12}$ alkyl; and n is 0 or 1.

An embodiment of the antibody-antibiotic conjugate compounds of the invention includes the following pipBOR-type antibiotic moiety:

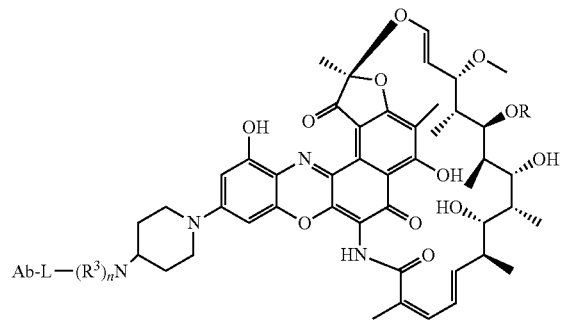

wherein $R^3$ is independently selected from H and $C_1$-$C_{12}$ alkyl; and n is 1 or 2.

An embodiment of the antibody-antibiotic conjugate compounds of the invention includes the following:

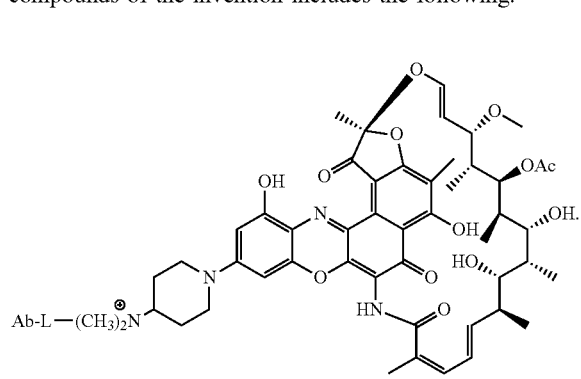

Further embodiments of the antibody-antibiotic conjugate compounds of the invention include the following:

161
162
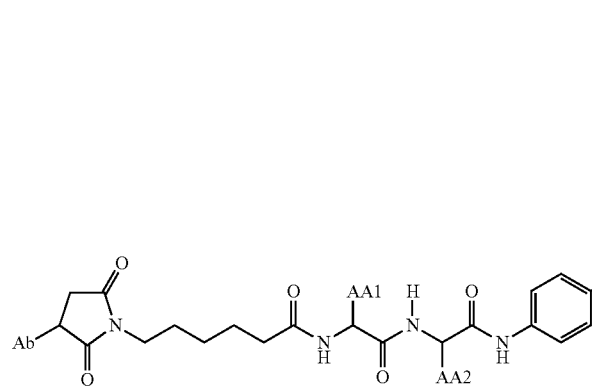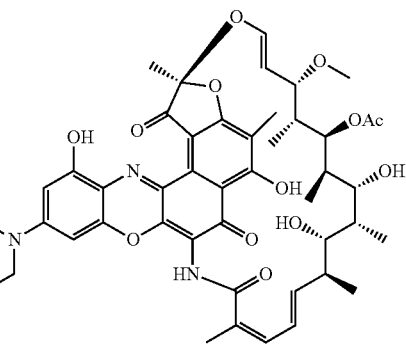
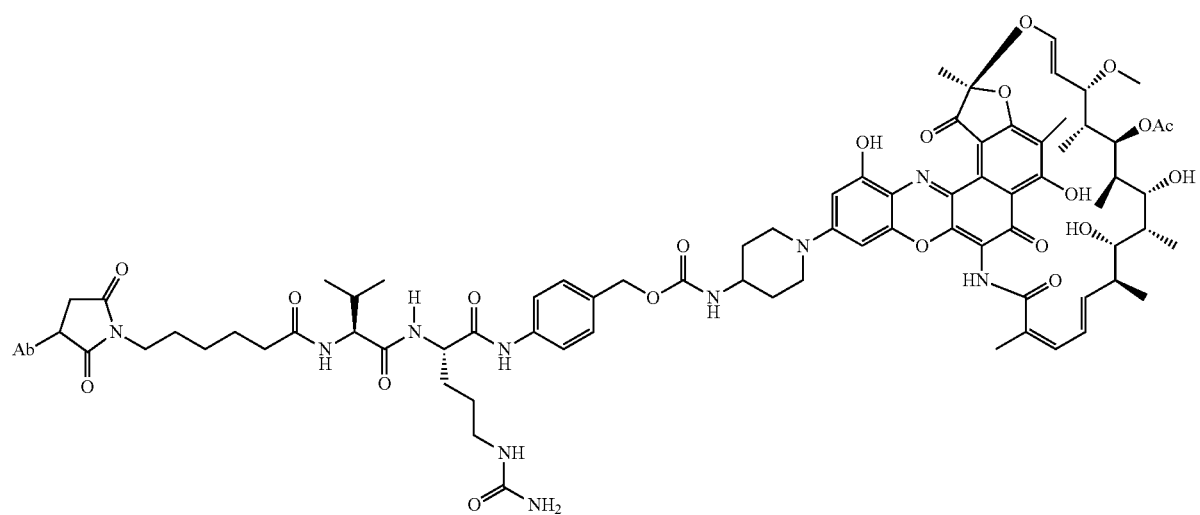
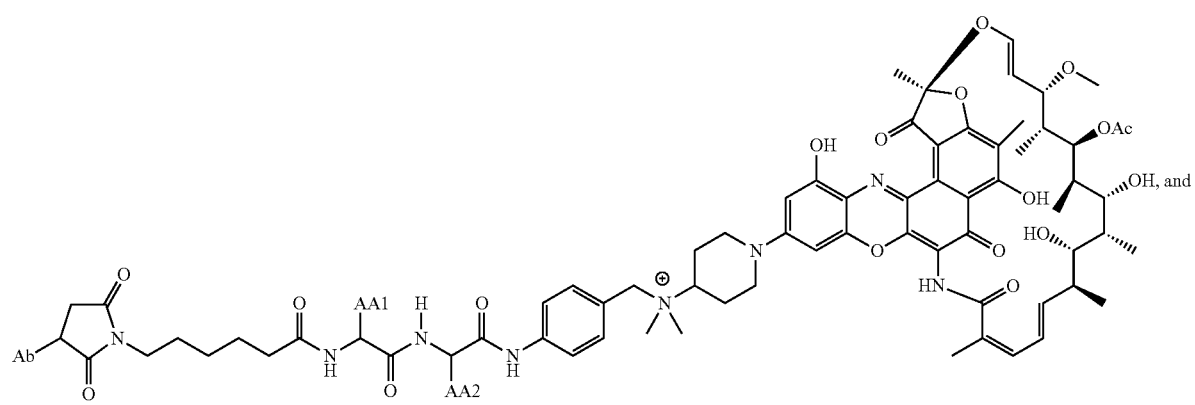

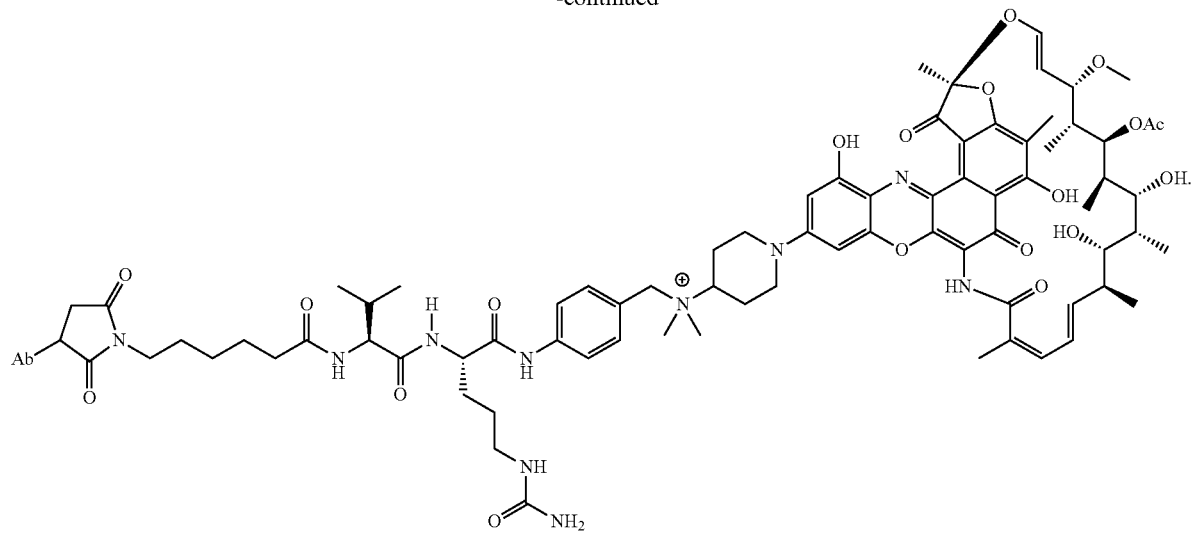

Antibiotic Loading of AAC

Antibiotic loading is represented by p, the average number of antibiotic (abx) moieties per antibody in a molecule of Formula I. Antibiotic loading may range from 1 to 20 antibiotic moieties (D) per antibody. The AAC of Formula I include collections or a pool of antibodies conjugated with a range of antibiotic moieties, from 1 to 20. The average number of antibiotic moieties per antibody in preparations of AAC from conjugation reactions may be characterized by conventional means such as mass spectroscopy, ELISA assay, and HPLC. The quantitative distribution of AAC in terms of p may also be determined. In some instances, separation, purification, and characterization of homogeneous AAC where p is a certain value from AAC with other antibiotic loadings may be achieved by means such as reverse phase HPLC or electrophoresis.

For some antibody-antibiotic conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher antibiotic loading, e.g. p>5, may cause aggregation, insolubility, toxicity, or loss of cellular permeability of certain antibody-antibiotic conjugates. In certain embodiments, the antibiotic loading for an AAC of the invention ranges from 1 to about 8; from about 2 to about 6; from about 2 to about 4; or from about 3 to about 5; about 4; or about 2.

In certain embodiments, fewer than the theoretical maximum of antibiotic moieties are conjugated to an antibody during a conjugation reaction. An antibody may contain, for example, lysine residues that do not react with the antibiotic-linker intermediate or linker reagent, as discussed below. Generally, antibodies do not contain many free and reactive cysteine thiol groups which may be linked to an antibiotic moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (antibiotic/antibody ratio, "AAR") of an AAC may be controlled in different ways, e.g., by: (i) limiting the molar excess of antibiotic-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with an antibiotic-linker intermediate or linker reagent followed by antibiotic moiety reagent, then the resulting product is a mixture of AAC compounds with a distribution of one or more antibiotic moieties attached to an antibody. The average number of antibiotics per antibody may be calculated from the mixture by a dual ELISA antibody assay, which is specific for antibody and specific for the antibiotic. Individual AAC molecules may be identified in the mixture by mass spectroscopy and separated by HPLC, e.g. hydrophobic interaction chromatography (see, e.g., McDonagh et al (2006) Prot. Engr. Design & Selection 19 (7):299-307; Hamblett et al (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous AAC with a single loading value may be isolated from the conjugation mixture by electrophoresis or chromatography. Cysteine-engineered antibodies of the invention enable more homogeneous preparations since the reactive site on the antibody is primarily limited to the engineered cysteine thiol. In one embodiment, the average number of antibiotic moieties per antibody is in the range of about 1 to about 20. In some embodiments the range is selected and controlled from about 1 to 4.

Methods of Preparing Antibody-Antibiotic Conjugates

An AAC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with an antibiotic moiety (abx); and (2) reaction of a nucleophilic group of an antibiotic moiety with a bivalent linker reagent, to form L-abx, via a covalent bond, followed by reaction with a nucleophilic group of an antibody. Exemplary methods for preparing an AAC of Formula I via the latter route are described in U.S. Pat. No. 7,498,298, which is expressly incorporated herein by reference.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may be introduced into an antibody by introducing one, two, three, four, or more cysteine residues (e.g., by preparing variant antibodies comprising one or more non-native cysteine amino acid residues).

Antibody-antibiotic conjugates of the invention may also be produced by reaction between an electrophilic group on an antibody, such as an aldehyde or ketone carbonyl group, with a nucleophilic group on a linker reagent or antibiotic. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or antibiotic. In another embodiment, the sugars of glycosylated antibodies may be oxidized, e.g. with periodate oxidizing reagents, to form aldehyde or ketone groups which may react with the amine group of linker reagents or antibiotic moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the antibiotic (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such an aldehyde can be reacted with an antibiotic moiety or linker nucleophile.

Nucleophilic groups on an antibiotic moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

The antibody-antibiotic conjugates (AAC) in Table 3 were prepared by conjugation of the described anti-WTA antibodies and linker-antibiotic intermediates of Table 2, and according to the described methods in Example 24. AAC were tested for efficacy by in vitro macrophage assay (Example 18) and in vivo mouse kidney model (Example 19).

TABLE 3

Antibody-antibiotic conjugates (AAC)

| AAC No. | AAC formula | linker-abx LA No. (Table 2) | AAR * |
|---|---|---|---|
| AAC-101 | thio-trastuzumab HC A118C-MC-vc-PAB-(dimethyl-pipBOR) | LA-54 | 1.8 |
| AAC-102 | thio-S4497-HC-A118C-MC-vc-PABC-(pipBOR) | LA-51 | 1.9 |
| AAC-103 | thio-S4497-HC-A114C-MC-fk-PABC-(pipBOR) | LA-52 | 1.0 |
| AAC-104 | thio-S4497-HC-A114C-MP-vc-PABC-(pipBOR) | LA-53 | 1.8 |
| AAC-105 | thio-S4497-HC-A118C-MC-vc-PAB-(dimethylpipBOR) | LA-54 | 1.73 1.9 |
| AAC-106 | thio-S4462-HC-A118C-MC-vc-PAB-(dimethylpipBOR) | LA-54 | |
| AAC-107 | thio-S4497-HC-A118C-MC-vc-PABC-(monomethylpip, desacetylBOR) | LA-55 | 1.75 |
| AAC-108 | thio-S4497-HC-A118C-MC-vc-PABC-(monomethylpipBOR) | LA-56 | 1.5 |
| AAC-109 | thio-S4497-HC-A118C-MC-vc-PABC-(pip, desacetylBOR) | LA-57 | 1.9 |
| AAC-110 | thio-hu-anti gD 5B5-HC-A118C-MC-vc-PAB-(dimethylpipBOR) | LA-54 | 1.94 |
| AAC-111 | thio-S4497-HC-A118C-MC-vc-PABC-(rifabutin) | LA-58 | 1.6 |
| AAC-112 | thio-S4497-HC-A118C-MC-vc-PAB-(dimethyl-pipBOR) | LA-54 | 1.65 |

TABLE 3-continued

| Antibody-antibiotic conjugates (AAC) | | | |
|---|---|---|---|
| AAC No. | AAC formula | linker-abx LA No. (Table 2) | AAR * |
| AAC-113 | thio-S4497 HC-MC-GGAFAGGG-(pipBOR) ("core peptide" disclosed as SEQ ID NO: 126) | LA-59 | 1.6 |
| AAC-114 | thio-S4462 HC-MC-GGAFAGGG-(pipBOR) ("core peptide" disclosed as SEQ ID NO: 126) | LA-59 | 1.8 |
| AAC-115 | thio-Tmab LC-MC-GGAFAGGG-(pipBOR) ("core peptide" disclosed as SEQ ID NO: 126) | LA-59 | 1.7 |
| AAC-116 | thio-S7578-MC-vc-PAB-(dimethyl-pipBOR) | LA-54 | tbd |
| AAC-117 | thio-S4497-HC-A118C-MC-vc-PABC-(pipBOR) | LA-51 | tbd |
| AAC-118 | thio-S4497-HC-A118C-MC-vc-PAB-(oxyBOR) | LA-60 | 1.8 |
| AAC-119 | thio-S4497-HC-A118C-MC-vc-PAB-(dimethylpip, desacetylBOR) | LA-61 | 1.7 |
| AAC-120 | thio-S4497-HC-A118C-MC-vc-PABC-(piperazBTR) | LA-62 | 1.8 |
| AAC-121 | thio-S4497-HC-A118C-MC-vc-PABC-(piperaz, desacetylBTR) | LA-63 | 1.8 |
| AAC-122 | thio-S4497-HC-A118C-MC-vc-PAB-(dimethylpipBOR) | LA-54 | 1.9 |
| AAC-123 | thio-S4497-HC-A118C-MC-vc-PAB-(dimethylpipBOR) | LA-54 | 1.9 |
| AAC-124 | thio-S4497-HC-A118C- MC-vc-PABC-(piperazBTR) | LA-62 | 1.8 |
| AAC-125 | thio-S4497-HC-A118C-MC-vc-PABC-(piperaz, desacetylBOR) | LA-64 | 0.9 |
| AAC-126 | thio-S4497-HC-A118C-MC-vc-PABC-(piperazBOR) | LA-65 | 1.7 |
| AAC-127 | thio-S4497-HC-A118C-MC-vc-PABC-PAB-(dimethylpipBOR) | LA-66 | 1.7 |
| AAC-128 | thio-S4497-HC-A118C-MC-vc-PAB-(methylpiperaz BOR) | LA-67 | 1.9 |
| AAC-129 | thio-S6078-HC A114C-LCWT-MC-vc-PAB-(dimethylpipBOR) | LA-54 | 1.6 |
| AAC-130 | thio-S4497-HC-A118C-MC-vc-PAB-(oxy, isopropylpipBOR) | LA-68 | 1.8 |
| AAC-131 | thio-S4497-HC-A118C-MC-tpm-cit-PAB-(dimethylpipBOR) | LA-69 | 1.8 |
| AAC-132 | thio-S4497 HC MC-GPImeLFF-(pipBOR) ("core peptide" disclosed as SEQ ID NO: 129) | LA-69 | 1.3 |
| AAC-133 | thio-S4497 HC MC-GPILFF-(pipBOR) ("core peptide" disclosed as SEQ ID NO: 130) | LA-70 | 1.2 |
| AAC-134 | thio-S4497 HC MC-val-cit-phe-(pipBOR) | LA-71 | 1.7 |
| AAC-135 | thio-S4497-HC-A118C-MC-vc-PAB-(dimethylpipBOR) | LA-54 | 1.9 |
| AAC-136 | thio-S4497.v1 HC WT, LC V205C- MC-vc-PAB-(dimethylpipBOR) | LA-54 | 2 |
| AAC-137 | thio-S4497.v1 HC WT, LC V205C-MC-vc-PAB-(piperazBOR) | LA-65 | tbd |
| AAC-138 | thio-S4497 HC WT v8, LC V205C- MC-vc-PAB-(dimethylpipBOR) | LA-54 | 1.9 |
| AAC-139 | thio-S4497-HC-A118C- MC-vc-PAB-(dimethylpipBOR) | LA-54 | 1.8 |
| AAC-140 | thio-S4497 HC WT (v8), LC V205C-MC-vc-PAB-(piperazBOR) | LA-65 | 1.6 |
| AAC-141 | thio-S6078-HCA114C-LCWT-MC-vc-PAB-(dimethylpipBOR) | LA-54 | 1.6 |
| AAC-142 | thio-S4497 HC WT (v8), LC V205C-MC-vc-PAB-(dimethylpipBOR) | LA-54 | 1.7 |
| AAC-143 | thio-S4497 HC-MP-GGAFA-PAB-(pipBOR) ("core peptide" disclosed as SEQ ID NO: 131) | LA-87 | 1.55 |
| AAC-144 | thio-S4497 v1HC-MC-vc-PAB-(phenylpipBOR) | LA-72 | 1.7 |
| AAC-145 | thio-S4497 v1HC-MC-vc-PAB-(dimethylBTR) | LA-73 | 1.7 |
| AAC-146 | thio-Tmab HC A118C-MP-GGAFA-PABC-(pipBOR) ("core peptide" disclosed as SEQ ID NO: 131) | LA-87 | 1.3 |
| AAC-147 | thio-S4497 v1HC-MC-vc-PAB-(dimethylpipBOR) | LA-74 | 1.9 |
| AAC-148 | thio-S4497v1 HC-MC-vc-PABC-(pipBTR) | LA-75 | 1.9 |
| AAC-149 | thio-S4497v1 HC-MC-vc-PAB-(methylpiperaz, desacetylBOR) | LA-76 | 2 |
| AAC-150 | thio-S4497v1 HC-MC-vc-(phenylpipBOR) | LA-77 | 1.8 |
| AAC-151 | thio-S4497-HC-A118C-MC-vc-PAB-(3-dimethylaminopyrrolBOR) | LA-78 | tbd |
| AAC-152 | thio-S4497-HC-A118C-MC-vc-PAB-(O-methyl, dimethylpipBOR) | LA-79 | 1.7 |

TABLE 3-continued

Antibody-antibiotic conjugates (AAC)

| AAC No. | AAC formula | linker-abx LA No. (Table 2) | AAR * |
|---|---|---|---|
| AAC-153 | thio-S4497-HC-A118C-MC-vc-PABC-(phenylpipBOR) | LA-80 | tbd |
| AAC-154 | thio-S4497v1 HC WT, LC V205C-MC-vc-PAB-(dimethylpipBOR) | LA-54 | 1.8 |
| AAC-155 | thio-S7578-HC WT-LC V205C-MC-vc-PAB-(dimethylpipBOR) | LA-54 | 1.9 |
| AAC-156 | thio-S4497v8-LC-MC-vc-PAB-(3-dimethylaminopyrrolBOR) | LA-78 | tbd |
| AAC-157 | thio-S4497v8-LC-MC-vc-PABC-(desacetyl, pipBTR) | LA-81 | 2.2 |
| AAC-158 | thio-S4497v8-LC-MC-vc-(desacetyl, phenylpipBOR) | LA-82 | — |
| AAC-159 | thio-S4497v8-LC-MC-vc-PAB-(dimethylamino, methylaminoethylBTR) | LA-83 | 2.2 |
| AAC-160 | thio-S4497v8-LC-MC-vc-PAB-(methylpiperazBTR) | LA-84 | tbd |
| AAC-161 | thio-S4497v8-LC-MC-vc-(phenylpipBOR) | LA-85 | tbd |
| AAC-162 | thio-S4497v8-LC-MC-vc-PAB-(oxy, dimethylaminopipBOR) | LA-86 | tbd |
| AAC-163 | thio-S4497-v8-LCV205C-MC-LAFG-PAB-(dimethylamino-3-pyrroloBOR) ("core peptide" disclosed as SEQ ID NO: 128) | LA-88 | 2.2 |
| AAC-164 | thio-S4497-v8-LCV205C-MC-vc-PABpyrazolo(pipBOR) | LA-89 | tbd |
| AAC-165 | thio-S4497-v8-LCV205C-MC-vc-PAB-(monomethylaminopipBOR) | LA-90 | 1.3 |
| AAC-166 | thio-S4497 HC WT (v8), LC V205C-MC-vc-PAB-(dimethylpipBOR) | LA-54 | 1.8 |
| AAC-167 | thio-S4497 HC WT (v8), LC V205C-MC-vc-PAB-(methyl, ethylaminopipBOR) | LA-91 | 2.0 |
| AAC-168 | thio-S4497 HC WT (v8), LC V205C-MC-vc-PABC-(aminomethylpipBOR) | LA-92 | 1.6 |
| AAC-169 | thio-S4497 WT (V8), LC V205C-MC-vc-PABC-C21,C23-phenylacetal-(dimethylaminopipBOR) | LA-93 | 1.6 |
| AAC-170 | thio-S4497 WT (V8), LC V205C-MC-vc-PABCpip-(pipBOR) | LA-94 | 1.4 |
| AAC-171 | thio-S6078 v4 HC-Cys LC-Cys-MC-vc-PAB-(dimethylpipBOR) | LA-54 | 3.9 |
| AAC-172 | thio-S6078 v4 HC-CYS, LC-CYS-MC-vc-PAB-(piperazBOR) | LA-65 | 3.9 |
| AAC-173 | thio-S6078 v4 HC-WT, LC-Cys-MC-vc-PAB-(dimethylpipBOR) | LA-54 | 2.0 |
| AAC-174 | thio-S6078.v4.HC-WT, LC-CYS-MC-vc-PAB-(piperazBOR) | LA-65 | 1.8 |
| AAC-175 | thio-S4497 HC WT (v8), LC V205C-MP-hydrazidePP-(pipBor) | LA-95 | 2.0 |
| AAC-176 | thio-S4497 HC WT (v8), LC V205C-MC-vc-PABC-(azetidinylBOR) | LA-96 | tbd |
| AAC-177 | thio-S4497-v8-LCV205C-MC-vc-PABC-(ethylpiperazino, desacetylBOR) | LA-97 | 1.6 |
| AAC-178 | thio-S4497-v8-LCV205C-MC-vc-PABC-(ethylaminopiperazinoBOR) | LA-98 | 1.7 |
| AAC-179 | thio-S4497-v8-LCV205C-MC-vc-PABphenyl-(pipBOR) | LA-99 | 1.9 |
| AAC-180 | thio-S4497-v8-LCV205C-MC-vc-PAB-(fluoroquinolone, oxyBOR) | LA-100 | 1.9 |
| AAC-181 | thio-S4497-v8-LCV205C-MC-vc-PAB-(phenoxypip, oxyBOR) | LA-101 | 1.6 |
| AAC-182 | thio-S6078 v4 HC-CYS, LC-CYS-MC-vc-PAB-(oxy, dimethylaminopipBOR) | LA-86 | 4.0 |
| AAC-183 | thio-S6078 v4 HC-CYS, LC-CYS-MC-vc-PABC-(desacetyl, pipBTR) | LA-81 | 3.8 |
| AAC-184 | thio-S6078 v4 HC-CYS, LC-CYS-MC-vc-PAB-(oxy, isopropylpipBOR) | LA-68 | tbd |
| AAC-185 | thio-S6078 v4 HC-CYS, LC-CYS-MC-vc-PAB-(methylrifampicin) | LA-102 | tbd |
| AAC-186 | thio-S4497 HC WT (v8), LC V205C-MC-vc-PAB-(dimethylpipBOR) | LA-54 | 1.9 |
| AAC-187 | thio-S6078 v4 HC-CYS, LC-CYS-MC-vc-PAB-(dimethylpipBOR) | LA-54 | 3.8 |
| AAC-188 | thio-S6078 v4 HC-WT, LCCYS-MC-vc-PAB-(oxy, isopropylpipBOR) | LA-68 | 1.6 |
| AAC-189 | thio-S6078 v4 HC-WT, LC-CYS-MC-vc-PAB-(methylrifampicin) | LA-102 | 1.8 |

TABLE 3-continued

| Antibody-antibiotic conjugates (AAC) | | | |
|---|---|---|---|
| AAC No. | AAC formula | linker-abx LA No. (Table 2) | AAR * |
| AAC-190 | thio-S7578-HC-WT-LC-Cys-MC-vc-PAB-(dimethylpipBOR) | LA-54 | 1.9 |
| AAC-191 | thio-S4497-v8-LC-V205C-MC-vc-PAB-(dimethylaminoethylpiperazinoBOR) | LA-103 | 1.7 |
| AAC-192 | thio-S4497 HC WT (v8), LC V205C-MC-vc-PAB-(dimethylpipBOR) | LA-54 | 1.9 |
| AAC-193 | thio-S4497 HC v1-MP-LAFG-PABC-(piperazinoBOR) ("core peptide" disclosed as SEQ ID NO: 128) | LA-104 | 1.8 |
| AAC-194 | thio-S6078 v4 HC-WT, LC-CYS-MC-vc-PAB-(piperazBOR) | LA-65 | 1.8 |
| AAC-195 | thio-S4497-v8-LC V205C-MC-vc-C21,C23-anilinoacetal-(dimethylaminopipBOR) | LA-105 | 2.0 |
| AAC-196 | thio-S4497-v8-LC V205C-MC-vc-anilino-(trimethylammonium-pip, oxyBOR) | LA-106 | 2.1 |
| AAC-197 | thio-S4497-v8-LC V205C-MC-vc-PAB-(dimethylammonium, fluoropipBOR) | LA-107 | 2.0 |
| AAC-198 | thio-S4497-v8-LC V205C-MC-vc-PAB-(dimethylammonium, thiopropyl, desacetyl BOR) | LA-108 | 1.9 |
| AAC-199 | thio-S4497-v8-LC V205C-MC-vc-PAB-(dimethylammonium, methylaminopropylBOR) | LA-109 | 1.8 |
| AAC-200 | thio-S4497-v8-LC V205C-MC-vc-PAB-(dimethylpipBOR) | LA-54 | 1.0 |
| AAC-201 | thio-S4497-v8-LC V205C-MC-vc-PABC-(methylaminopip, desacetyl BOR) | LA-110 | 1.9 |
| AAC-202 | thio-S4497-v8-LC V205C-MC-vc-PAB-(oxy, pip, desacetyl BOR) | LA-111 | 1.9 |
| AAC-203 | thio-S4497-v8-LC V205C-MC-vc-PAB-(methylrifampicin) | LA-102 | 1.8 |
| AAC-204 | thio-S4497-v8-LC-cys-MC-vc-PAB-(dimethylammonium, thiopropyl BOR) | LA-112 | 2.0 |
| AAC-205 | thio-S4497-v8-LC V205C-MC-vc-PAB-(oxy, dimethylaminopipBOR) | LA-113 | 1.8 |
| AAC-206 | thio-S4497-v8-LC V205C-MC-vc-PAB-(N-isobutylrifabutin) | LA-114 | 1.9 |
| AAC-207 | thio-S4497-v8-LC V205C-MC-vc-PAB-(methylrifampicin) | LA-102 | 1.8 |
| AAC-208 | thio-S4497-v8-LC V205C-MC-vc-PAB-(dimethylammonium, fluoropipBOR) | LA-107 | 1.8 |
| AAC-209 | thio-S4497-v8-LC cys-D10-MC-vc-PAB-(dimethylpipBOR) | LA-54 | 1.9 |
| AAC-210 | thio-S4497-v8-LC cys-MC-vc-PABC-(monomethylpipBTR) | LA-115 | 1.5 |
| AAC-211 | thio-S4497-v8-LC cys-MC-vc-PAB-(piperazinoBOR) | LA-116 | tbd |
| AAC-212 | thio-S4497-v8-LC cys-MC-vc-PAB-(R-fluoroquinolone, oxyBOR | LA-117 | tbd |
| AAC-213 | thio-S4497-v8-LC cys-MC-vc-PAB-(S-fluoroquinolone, oxyBOR | LA-118 | tbd |
| AAC-214 | thio-S4497-v8-LC-cys-MC-vc-PAB-(dimethylpip, desacetylBOR) | LA-61 | 2.0 |
| AAC-215 | thio-S4497 LC v8-MP-LAFG-PABC-(piperazinoBOR) ("core peptide" disclosed as SEQ ID NO: 128) | LA-104 | 1.6 |
| AAC-216 | thio-S4497 HC WT (v8), LC V205C-MC-vc-PAB-(piperazBOR) | LA-65 | 1.9 |
| AAC-217 | thio-S4497-v8-LCV205C-MC-vc-PAB-(monomethylaminopipBOR) | LA-90 | 1.8 |
| AAC-218 | thio-S4497 HC WT (v8), LC V205C-MC-vc-PAB-(dimethylpipBOR) | LA-54 | 1.9 |
| AAC-219 | thio-S4497 HC WT (v8), LC V205C-MC-vc-PABC-(piperazBOR) | LA-65 | 1.9 |
| AAC-220 | thio-S4497-v8-LCV205C-MC-vc-PAB-(piperazinoBOR) | LA-116 | tbd |
| AAC-221 | thio-S4497-v8-LCV205C-MC-vc-PAB-(methylpiperaz BOR) | LA-67 | tbd |

TABLE 3-continued

Antibody-antibiotic conjugates (AAC)

| AAC No. | AAC formula | linker-abx LA No. (Table 2) | AAR * |
|---|---|---|---|
| AAC-222 | thio-S4497 LC v8 -MP-LAFG-PABC-(piperazinoBOR) ("core peptide" disclosed as SEQ ID NO: 128) | LA-104 | tbd |

* AAR = antibiotic/antibody ratio average
Wild-type ("WT"), cysteine engineered mutant antibody ("thio"), light chain ("LC"), heavy chain ("HC"), 6-maleimidocaproyl ("MC"), maleimidopropanoyl ("MP"), valine-citrulline ("val-cit" or "vc"), alanine-phenylalanine ("ala-phe"), p-aminobenzyl ("PAB"), and p-aminobenzyloxycarbonyl ("PABC")
tbd = to be determined
HC-A114C (Kabat) = HC-A118C (EU)

In Vitro Analysis Demonstrating that AAC Kill Intracellular MRSA

In vitro experiments confirm that the AAC release active antibiotic only after the linker between the antibody and the antibiotic is cleaved by an appropriate enzyme such as cathepsin B. MRSA was cultured overnight in normal bacterial growth media and up to 10 µg/mL of AAC. Incubation of MRSA with the S4497-pipBOR or S4497-dimethyl-pipBOR AACs did not result in inhibition of bacterial growth unless the AACs were pre-treated with cathepsin B to release the active antibiotic. An in vitro assay utilizing murine peritoneal macrophages confirmed that AAC release active antibiotic and kill MRSA inside phagocytic cells (Example 18). An AAC comprising antibody rF1, which binds to a family of cell wall associated proteins was conjugated to a rifamycin derivative. S. aureus (Newman strain) was treated with various doses of the rF1-AAC or with equivalent doses of either antibody alone, rifampicin alone or a mixture of antibody and free rifampicin to permit antibody binding to the bacteria (opsonization) and after 1 hour incubation the opsonized bacteria were fed to macrophages (FIG. 7A).

Figure 7A:
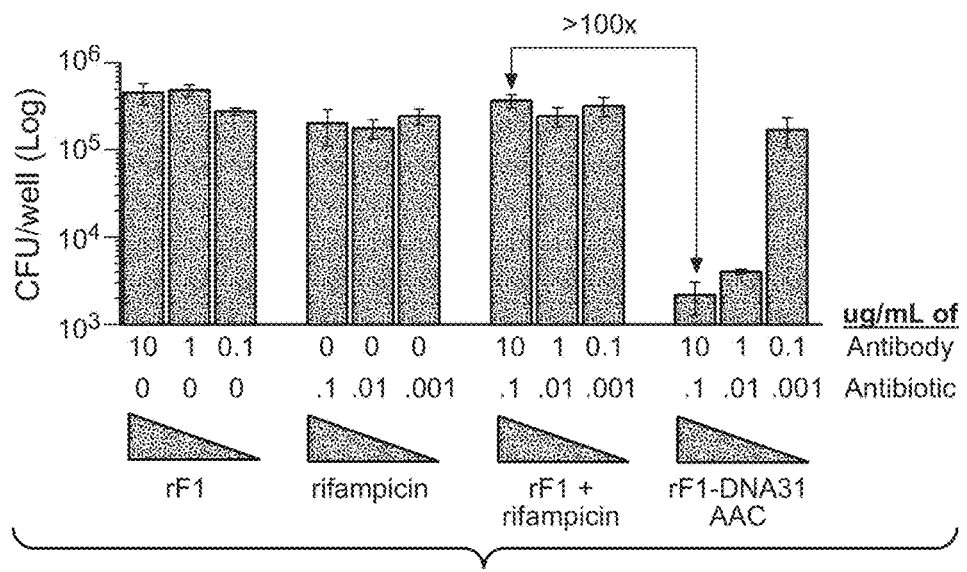
FIG. 7A shows an in vitro macrophage assay demonstrating that AAC kill intracellular MRSA.

FIG. 7A shows an in vitro macrophage assay demonstrating that AAC kill intracellular MRSA. S. aureus (Newman) was incubated with rF1 antibody alone, free rifampicin alone, a simple mixture of the rF1 antibody plus free rifampicin combined at the same ratio of antibody to antibiotic found in the AAC, or the rF1-AAC for 1 hour and added to murine macrophages. Macrophages were incubated at 37° C. for 2 hours to permit phagocytosis. After phagocytosis was complete, the infection mix was replaced with normal growth media supplemented with 50 µg/mL of gentamycin to inhibit the growth of extracellular bacteria and the total number of surviving intracellular bacteria was determined 2 days after infection by plating.

The macrophages were infected for 2 hours and the infection was removed and replaced with media containing gentamycin to kill any remaining extracellular bacteria that were not taken up by the macrophages. After 2 days, macrophages were lysed and the total number of surviving intracellular bacteria was determined by plating on agar plates. Analysis revealed that treatment with the AAC resulted in more than 100 fold reduction in the number of intracellular bacteria compared to treatment with a simple mixture of the rF1 antibody plus free rifampicin combined at the same antibody to antibiotic ratio found in the AAC (FIG. 7A).

Figure 7B:
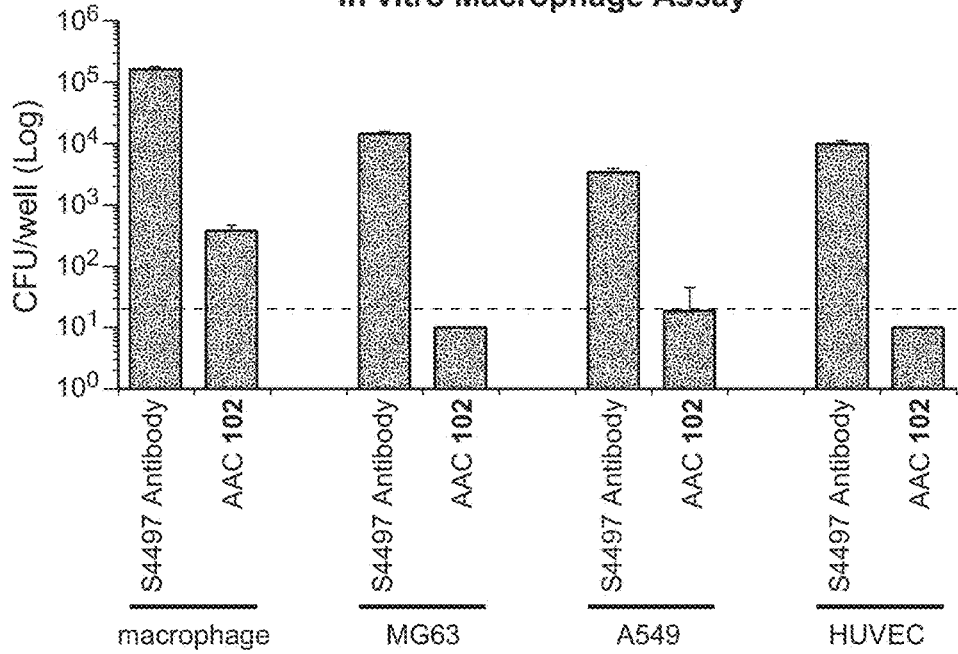
FIG. 7B shows intracellular killing of MRSA (USA300 strain) with 50 μg/mL of the thio-S4497-HC-A118C-pipBOR 102 in macrophages, osteoblasts (MG63), Airway epithelial cells (A549), and human umbilical vein endothelial cells (HUVEC) compared to naked, unconjugated anti-WTA antibody S4497. The dashed line indicates the limit of detection for the assay.

MRSA is able to invade a number of non-phagocytic cell types including osteoblasts and various epithelial and endothelial cell types (Garzoni and Kelly, (2008) Trends in Microbiology). MRSA is able to infect an osteoblast cell line (MG63), an airway epithelial cell line (A549) and primary cultures of human umbilical vein endothelial cells (HUVEC). FIG. 7B shows intracellular killing of MRSA (USA300 strain) with 50 µg/mL of S4497-pipBOR AAC 102 in macrophages, osteoblasts (MG63), Airway epithelial cells (A549), and human umbilical vein endothelial cells (HUVEC) where naked, unconjugated antibody S4497 does not. These cell types likely express lower overall levels of cathepsin B than professional phagocytic cells such as macrophages, however MRSA treated with 50 µg/mL the was effectively killed after internalization into all three of these cell lines. The dashed line indicates the limit of detection for the assay.

Figure 7C:
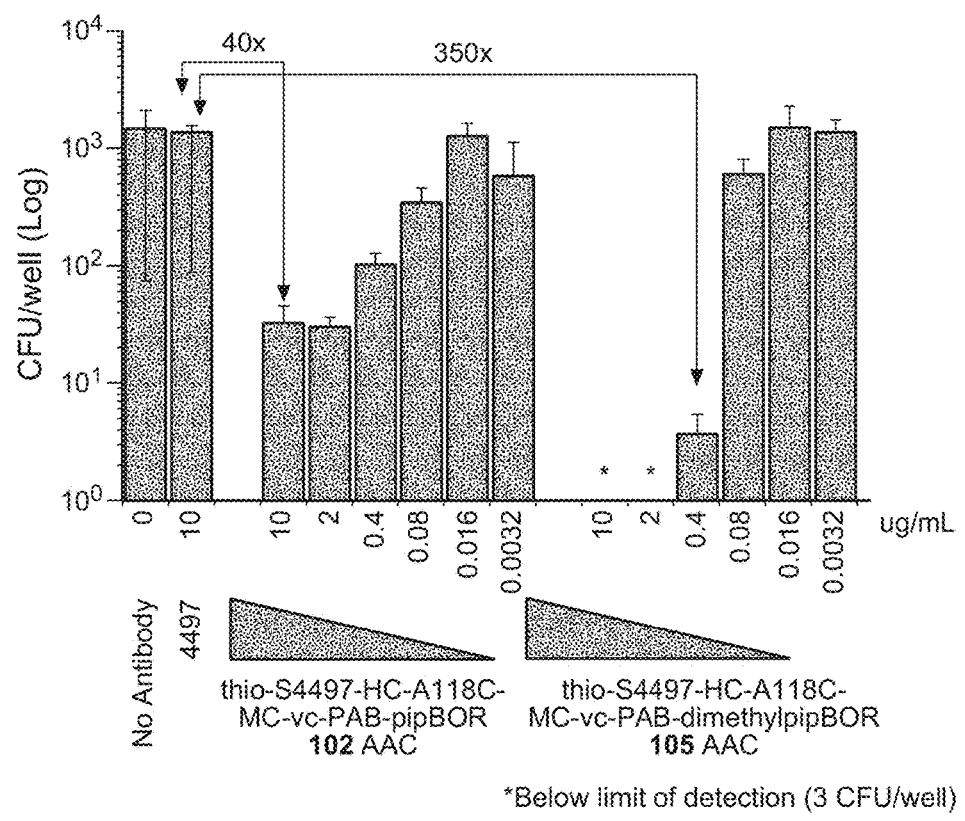
FIG. 7C shows comparison of AAC made with linker-antibiotic intermediates LA-51 and LA-54 (Table 2). MRSA was opsonized with S4497 antibody alone or with AAC: AAC-102 or AAC-105 (Table 3) at various concentrations ranging from 10 μg/mL to 0.003 μg/mL.

In vitro analysis was performed to compare the activity of AAC made with variations in the linker that joins the antibody to the antibiotic. The S4497-dimethyl-pipBOR AAC is more potent than the S4497-pipBOR AAC in the macrophage intracellular killing assay. The S4497-pipBOR AAC and the S4497-dimethyl-pipBOR AAC were titrated to determine the minimum effective dose in our macrophage intracellular killing assay (FIG. 7C). Treatment with at least 2 µg/mL of AAC may be necessary to achieve optimal clearance of intracellular bacteria.

FIG. 7C shows comparison of AAC made with pipBOR 51 vs. dimethyl-pipBOR (diMe-pipBOR) 54. MRSA was opsonized with S4497 antibody alone or with AACs: S4497-pipBOR 102 or S4497-diMethyl-pipBOR 105 at various concentrations ranging from 10 µg/mL to 0.003 µg/mL. These data revealed that for both AAC, optimal killing occurred when AAC were tested at more than 2 µg/mL, with a dose dependent loss in activity that became evident at 0.4 µg/mL. The overall level of killing was significantly superior with the S4497 dimethyl-pipBOR AAC 105. Treatment with higher doses of the S4497-dimethyl-pipBOR AAC 105 eliminated the intracellular bacteria to below the limit of detection and over 300 fold killing using a suboptimal dose of 0.4 µg/mL of AAC was observed.

Figure 7D:
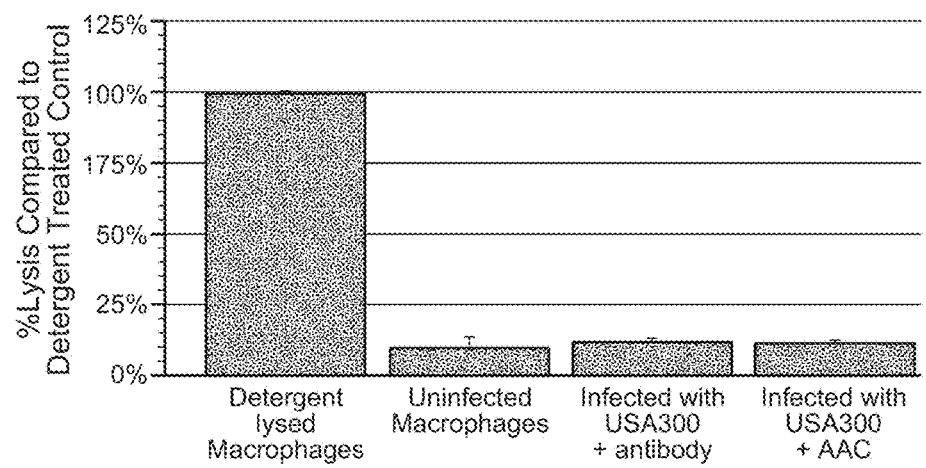
FIG. 7D shows AAC kills intracellular bacteria without harming the macrophages.

FIG. 7D shows AAC kills intracellular bacteria without harming the macrophages. The USA300 strain of S. aureus was pre-incubated with 50 µg/mL of the S4497 anti-S. aureus antibody (antibody) or with 50 µg/mL of thio-S4497-HC-A118C-MC-vc-PAB-dimethylpipBOR 105 AAC, for 1 hour to permit binding of antibody to the bacteria. Opsonized bacteria were added to murine peritoneal macrophages at a multiplicity of infection of 10-20 bacteria per macrophage and incubated at 37° C. for 2 hours to permit phagocytosis. After phagocytosis was complete, free bacteria were removed and the macrophages were cultured for 2 days in normal growth media supplemented with 50 µg/mL of gentamycin to kill non-internalized bacteria. At the end of the culture period, survival of macrophages was assessed by detecting release of cytoplasmic lactate dehydrogenase (LDH) into the culture supernatant. The total amount of LDH released from each well was compared to control wells containing macrophages that were lysed by addition of detergent to the wells. The extent of macrophage cell lysis in wells treated with detergent, uninfected macrophages, macrophages infected with USA300 pre-opsonized with S4497 antibody or macrophages infected with USA300 pre-opsonized with thio-S4497-HC-A118C-MC-vc-PAB-dimethylpipBOR 105 AAC was measured.

Figure 7E:
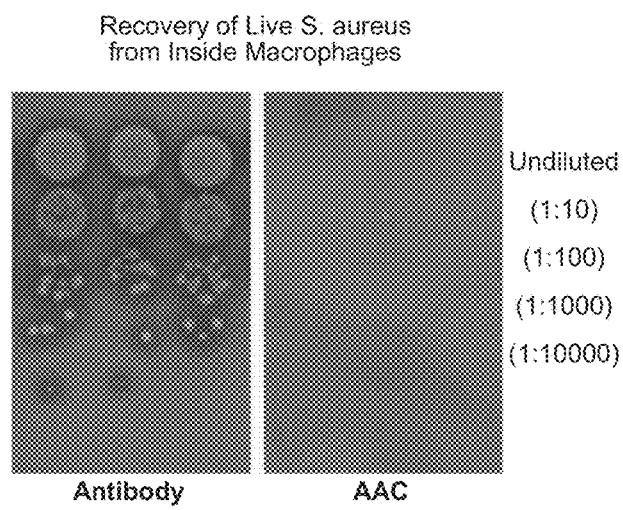
FIG. 7E shows recovery of live USA300 from inside macrophages from the macrophage cell lysis above. Few (10,000 fold fewer) live *S. aureus* were recovered from macrophages infected with S-4497-AAC opsonized bacteria compared to naked antibody treated controls.

FIG. 7E shows recovery of live USA300 from inside macrophages from the macrophage cell lysis above. Macrophages were lysed and serial dilutions of the cell lysate were plated to enumerate the number of surviving intracellular bacteria.

FIG. 9 shows a growth inhibition assay demonstrating that AAC are not toxic to *S. aureus* unless the linker is cleaved by cathepsin B. A schematic cathepsin release assay (Example 20) is shown on the left. AAC is treated with cathepsin B to release free antibiotic. The total amount of antibiotic activity in the intact vs. the cathepsin B treated AAC is determined by preparing serial dilutions of the resulting reaction and determining the minimum dose of AAC that is able to inhibit the growth of *S. aureus*. The upper right plot shows the cathepsin release assay for thio-S4497-HC-A118C-MC-vc-PAB-pipBOR 102 and the lower right plot shows the cathepsin release assay for thio-S4497-HC-A118C-MC-vc-PAB-dimethylpipBOR 105.

In Vivo Efficacy of Antibody Antibiotic Conjugates:

An in vivo peritonitis model in mice was established to test the efficacy of AAC. In this model, mice are infected by intraperitoneal injection (I.P.) of MRSA and the bacterial load is monitored 2 days after infection in the peritoneal fluid and kidney. Bacteria harvested from the peritoneum could be found either as free floating extracellular bacteria or internalized inside peritoneal cells—primarily neutrophils and macrophages—that are recruited to the site of the infection. Although extracellular bacteria identified in this model appeared to be sensitive to antibiotic treatment, the intracellular bacteria were shown to be unresponsive to treatment with a number of clinically relevant antibiotics including rifampin (Sandberg et al (2009) Antimicrobial Agents Chemother) and therefore appeared to be an excellent target to test efficacy of our AAC.

Figure 8B:
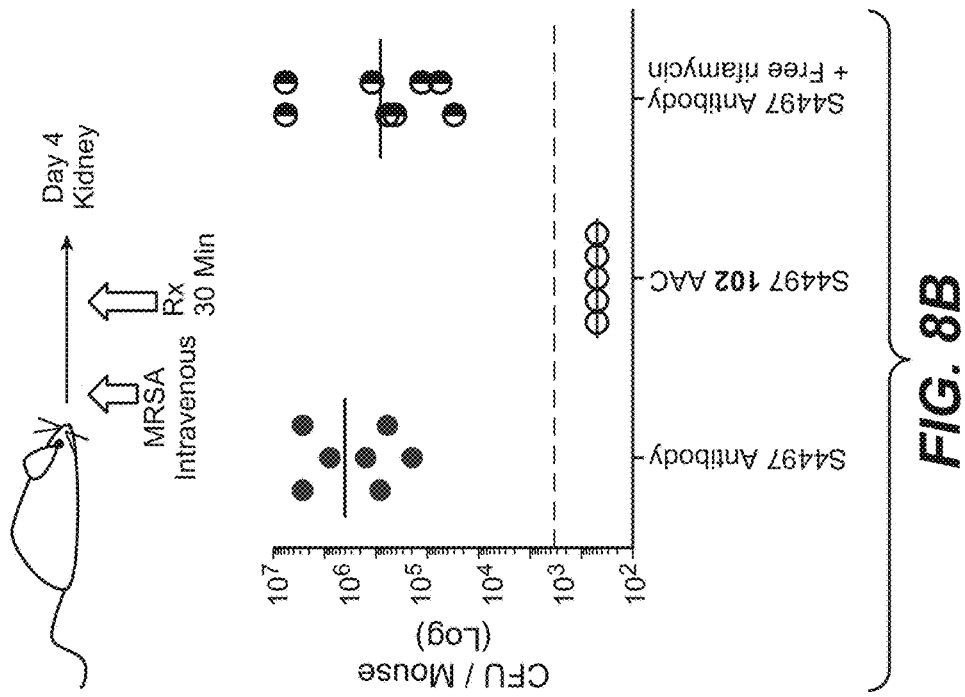
FIG. 8B shows intravenous, in vivo, infection model in A/J mice. Mice were infected with MRSA by intravenous injection and treated with 50 mg/Kg of S4497 antibody, 50 mg/Kg of thio-S4497-HC-A118C-MC-vc-PAB-pipBOR 102 AAC or a simple mixture of 50 mg/Kg of S4497 antibody+0.5 mg/Kg of free rifamycin. The grey dashed line indicates the limit of detection for each organ.
Figure 8A:
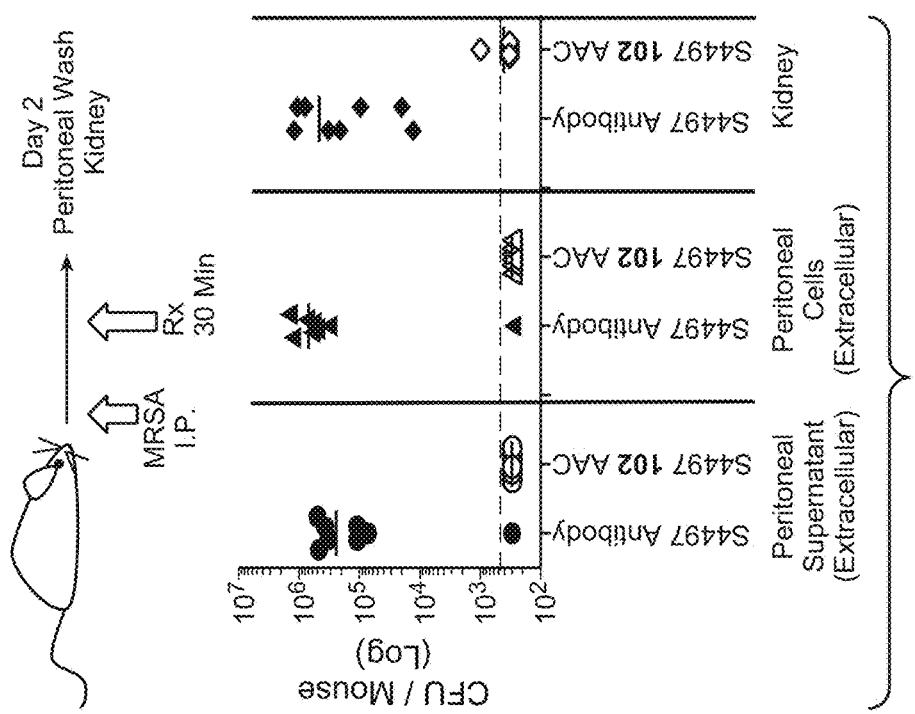
FIG. 8A shows in vivo efficacy of thio-S4497-HC-A118C-MC-vc-PAB-pipBOR 102 AAC in an intraperitoneal infection model in A/J mice. Mice were infected with MRSA by intraperitoneal injection and treated with 50 mg/Kg of S4497 antibody alone or with 50 mg/Kg of 102 AAC (HC-A114C Kabat=HC-A118C EU) by intraperitoneal injection. Mice were sacrificed 2 days post infection and the total bacterial load was assessed in the peritoneal supernatant (Extracellular bacteria), peritoneal cells (Intracellular bacteria) or in the kidney.

FIG. 8A shows in vivo efficacy of the S4497-pipBOR AAC 102. Intraperitoneal infection model in A/J mice. Mice were infected with $5 \times 10^7$ CFU of MRSA by intraperitoneal injection and treated with 50 mg/Kg of S4497 antibody alone or with 50 mg/Kg of the S4497-pipBOR AAC 102 by intraperitoneal injection (protocol 11-2032A). Mice were sacrificed 2 days post infection and the total bacterial load was assessed in the peritoneal supernatant (Extracellular bacteria), peritoneal cells (Intracellular bacteria) or in the kidney.

A/J mice were infected with USA300 and administered 50 mg/Kg of either S4497 antibody or S4497-pipBOR AAC 102 thirty minutes after infection. After 2 days, the mice were sacrificed and bacterial loads were monitored in the peritoneal wash and the kidney. To distinguish between extracellular and intracellular bacteria, the peritoneal wash was centrifuged gently to separate the supernatant, containing extracellular bacteria, and the peritoneal cells. Peritoneal cells were treated with lysostaphin to kill any contaminating extracellular bacteria and lysed to enumerate the total number of intracellular bacteria at the time of harvest. Although mice treated with antibody alone harbored between $10^5$ and $10^6$ CFU of both intracellular and extracellular bacteria in the peritoneal wash and between $10^4$ and $10^6$ bacteria in the kidney, the mice treated with the S4497-pipBOR AAC cleared the infection to below the limit of detection. These data revealed that although the AAC is designed to release active antibiotic inside the phagolysosome, excellent clearance of both the intracellular and extracellular pools of MRSA was observed. Since extracellular bacteria are not killed directly by the AAC, the fact that these bacteria were also cleared by AAC treatment suggests that either a significant fraction of the extracellular bacteria is taken up by cells at some time during the infection, or that the AAC is able to enhance uptake of extracellular bacteria thereby increasing the relative proportion of bacteria that are intracellular where they are effectively killed by the AAC.

Efficacy of the AAC in an intravenous infection model was also examined. In this model, *S. aureus* is taken up by circulating neutrophils shortly after infection such that the majority of bacteria found in blood are associated with host cells within minutes after infection (Rogers, et al (1956) J. Exp. Med. 103:713-742). A/J Mice were infected with $2 \times 10^6$ CFU of MRSA by intravenous injection, and then treated with 50 mg/Kg of AACs by intravenous injection 30 minutes post infection. In this model, the primary site of infection is the kidney, and mice develop large abscesses that are detectable by two days post infection and fail to be cleared for up to 30 days in the absence of treatment. Treatment with 50 mg/Kg of the S4497-pipBOR AAC 102 cleared the infection in all of the mice tested (FIG. 8B).

FIG. 8B shows intravenous infection model in A/J mice. Mice were infected with $2 \times 10^6$ CFU by intravenous injection and treated with 50 mg/Kg of S4497 antibody, 50 mg/Kg of S4497-pipBOR AAC 102 or a simple mixture of 50 mg/Kg of S4497 antibody+0.5 mg/Kg of free rifamycin. Treatments were delivered by IV injection 30 minutes post infection and kidneys were harvested 4 days post infection. The grey dashed line indicates the limit of detection for each organ. Control groups treated with 50 mg/Kg of S4497 antibody alone, or with a simple mixture of 50 mg/Kg of S4497 antibody plus 0.5 mg/kg free rifamycin (the equivalent dose of antibiotic present in 50 mg/Kg of AAC) were not efficacious.

Figure 9A:
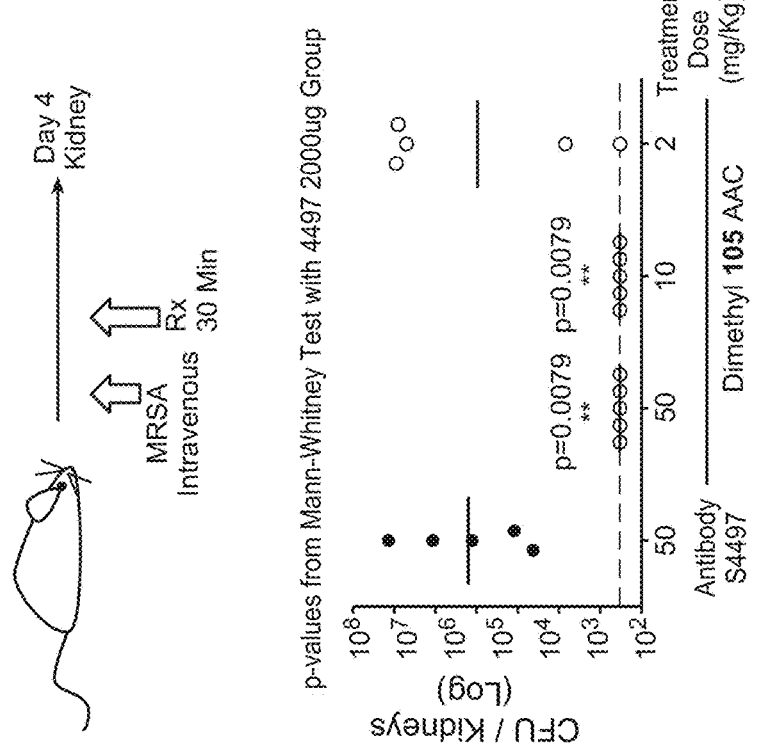
FIG. 9A shows efficacy of thio-S4497-HC-A118C-MC-vc-PAB-pipBOR 102 AAC in an intravenous infection model by titration of the S4497-pipBOR AAC.
Figure 9B:
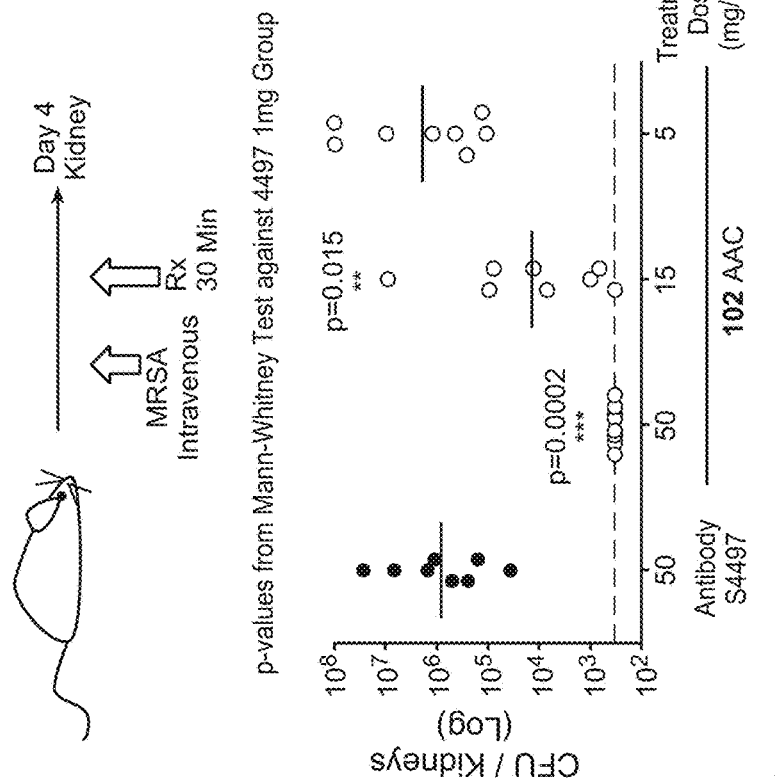
FIG. 9B shows thio-S4497-HC-A118C-MC-vc-PAB-dimethylpipBOR 105 AAC is more efficacious than thio-S4497-HC-A118C-MC-vc-PAB-pipBOR 102 AAC in an intravenous infection model by titration. Treatments with S4497 Antibody, 102 AAC or thio-S4497-HC-A118C-MC-vc-PAB-dimethyl-pipBOR 112 AAC were administered at the indicated doses 30 minutes after infection. Mice were sacrificed 4 days after infection and the total number of surviving bacteria per mouse (2 kidneys pooled) was determined by plating.

Efficacy of AAC made with pipBOR and dimethyl-pipBOR antibiotic moieties was compared in vivo in the intravenous infection model in A/J mice. The S4497-pipBOR AAC 102 (FIG. 9A) or the S4497-dimethyl-pipBOR AAC 105 (FIG. 9B) were administered at various doses ranging from 50 mg/Kg to 2 m/Kg 30 minutes after infection and kidneys were examined 4 days after infection to determine the total bacterial load. FIG. 9A shows efficacy of pipBOR AAC 102 in an intravenous infection model by titration of the S4497-pipBOR AAC 102. Seven week old female A/J Mice were infected with $2 \times 10^6$ CFU of MRSA (USA300 strain) by intravenous injection into the tail vein. FIG. 9B shows efficacy of diMethyl-pipBOR AAC 105 in the intravenous infection model by titration of the S4497-dimethyl-pipBOR AAC 105. Treatments with S4497 antibody, AAC 102 or AAC 105 were administered at the indicated doses 30 minutes after infection. Mice were sacrificed 4 days after infection and the total number of surviving bacteria per mouse (2 kidneys pooled) was determined by plating.

Both AAC were effective at the highest dose of 50 mg/Kg, however the S4497-pipBOR AAC 102 was only partially efficacious at lower doses. The S4497-dimethyl-pipBOR AAC 105 yielded complete bacterial clearance at doses above 10 mg/Kg. Subsequent experiments indicated that doses above 15 mg/Kg were required for consistent bacterial clearance. FIGS. 9A and 9B show thio-S4497-HC-A118C-MC-vc-PAB-dimethylpipBOR 105 AAC is more efficacious than thio-S4497-HC-A118C-MC-vc-PAB-pipBOR 102 AAC in an intravenous infection model indicating an effect of the carbamate (51) and dimethylpiperidyl (54) structural distinction between 102 and 105, respectively.

Mice were treated with the AAC 30 minutes after infection. To better replicate conditions likely to occur in MRSA patients seeking treatment, it was determined whether the AAC is effective at clearing an established infection and that linking of the antibiotic to an anti-S. aureus antibody provides a definite advantage over treatment with antibiotic alone. To this end, the efficacy of AAC with an equivalent dose of the antibiotic dimethyl-pipBOR was compared.

Figure 9C:
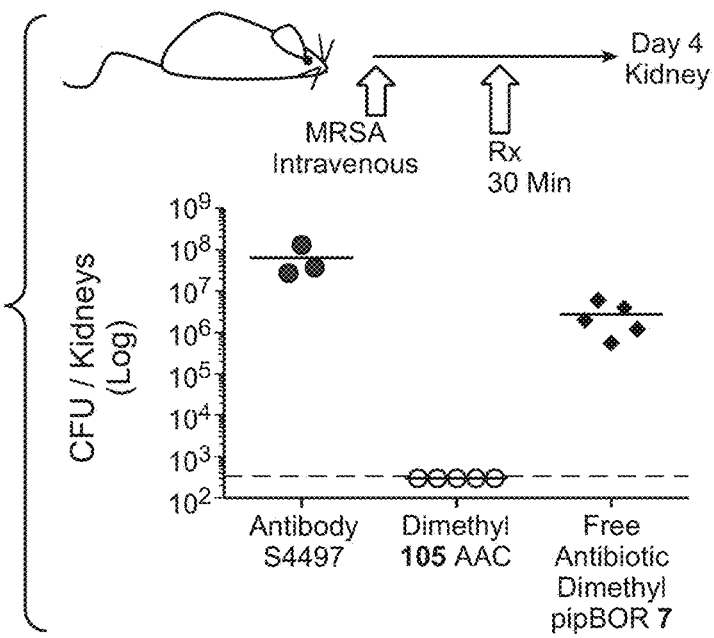
FIG. 9C shows that thio-S4497-HC-A118C-MC-vc-PAB-dimethylpipBOR 105 AAC is more efficacious than S4497 Antibody or dimethylpipBOR 7 antibiotic alone in an intravenous infection model. CB 17.SCID mice infected with $2 \times 10^7$ CFU of MRSA by intravenous injection. One day after infection, the mice were treated with 50 mg/Kg of S4497 antibody, 50 mg/Kg of AAC 105 or with 0.5 mg/Kg of dimethyl-pipBOR 7, the equivalent dose of antibiotic that is contained in 50 mg/Kg of AAC). Mice were sacrificed 4 days after infection and the total number of surviving bacteria per mouse (2 kidneys pooled) was determined by plating.

FIG. 9C shows CB17.SCID mice infected with $2 \times 10^7$ CFU of MRSA by intravenous injection (protocol 12-2418). One day after infection, the mice were treated with 50 mg/Kg of S4497 antibody, 50 mg/Kg of S4497 dimethyl-pipBOR AAC 105 or with 0.5 mg/Kg of dimethyl-pipBOR antibiotic 7, the equivalent dose of antibiotic that is contained in 50 mg/Kg of AAC). Mice were sacrificed 4 days after infection and the total number of surviving bacteria per mouse (2 kidneys pooled) was determined by plating. Treatment with 50 mg/Kg of S4497-dimethyl-pipBOR AAC was clearly efficacious when given 1 day post infection, whereas treatment with the equivalent dose of dimethyl-pipBOR alone failed to clear the infection.

Figure 10A:
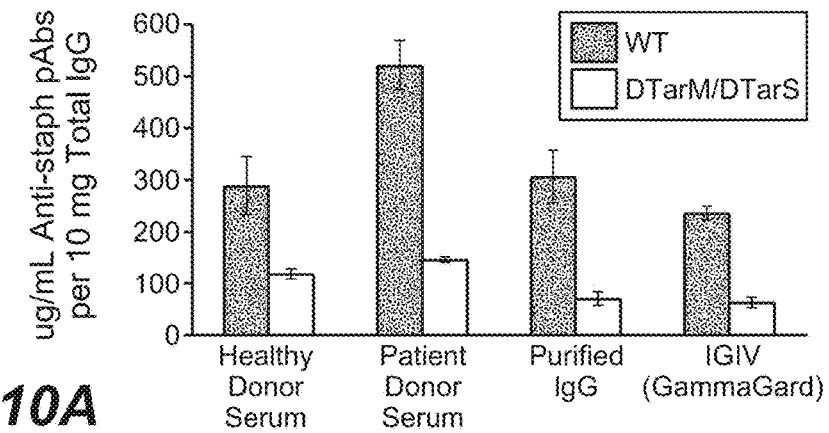
FIG. 10A shows the prevalence of anti-*S. aureus* antibodies in human serum. *S. aureus* infected patients or normal controls contain high amounts of WTA specific serum antibody with same specificity as anti-WTA S4497. Binding of various wild-type (WT) serum samples to MRSA that expressed the S4497 antigen was examined versus binding to a MRSA strain TarM/TarS DKO (double knockout) mutant which lacks the sugar modifications that are recognized by the S4497 antibody.

Treatment with an AAC is Efficacious in the Presence of Human Antibodies and Superior to Treatment with the Current Standard of Care (SOC) Vancomycin The S4497 antibody was cloned from B cells derived from S. aureus infected patients. This raised the concern that normal human serum, or serum present in MRSA infected patients may contain anti-MRSA antibodies that would compete for binding with our AAC. To address this, human serum derived from normal healthy donors and a panel of MRSA patients was tested to estimate the overall level of anti-MRSA antibodies that recognize the same antigen as the AAC. An ELISA based assay using cell wall preparations from MRSA was developed. To limit non-antigen specific binding to the cell wall preparations in these assays, a strain of MRSA that is deficient in the gene for protein A was utilized. Protein A binds to the Fc region of IgG antibodies. Binding of various wild-type (WT) serum samples to MRSA that expressed the S4497 antigen (FIG. 10A, WT) was examined versus binding to a MRSA strain TarM/TarS DKO (double knockout) mutant which lacks the sugar modifications that are recognized by the S4497 antibody. FIG. 10A shows prevalence of anti-S. aureus antibodies in human serum. S. aureus infected patients or normal controls contain high amounts of WTA specific serum antibody with same specificity as anti-WTA S4497.

A standard curve was generated using a monoclonal antibody that binds well to the same antigen that is recognized by S4497. By comparing the level of binding in serum samples to the signal obtained from the antibody used to generate the standard curve, the level of anti-MRSA antibodies present in serum samples derived from normal healthy donors or MRSA patients, or in total IgG preparations isolated from normal serum was estimated (FIG. 10A). Normal human serum contains 10-15 mg/mL of total IgG (Manz et al. (2005) Annu Rev. Immunol. 23:367). Analysis of anti-MRSA reactivity in the different serum samples revealed that up to 300 µg/mL of these antibodies are potentially reactive with the same antigen recognized by S4497 and are therefore likely to compete for binding with the AAC.

The S4497 antibody was used to generate AAC for properties including very high binding on MRSA (estimated 50,000 binding sites per bacterium). Sufficient numbers of AAC may be able to bind to MRSA even in the presence of the competing antibodies found in human serum. To test this directly, the S4497-dimethyl-pipBOR AAC in buffer supplemented with 10 mg/mL of human IgG (FIG. 10B, +IGIV) was titrated and the level of intracellular killing was measured in the macrophage intracellular killing assay.

Figure 10B:
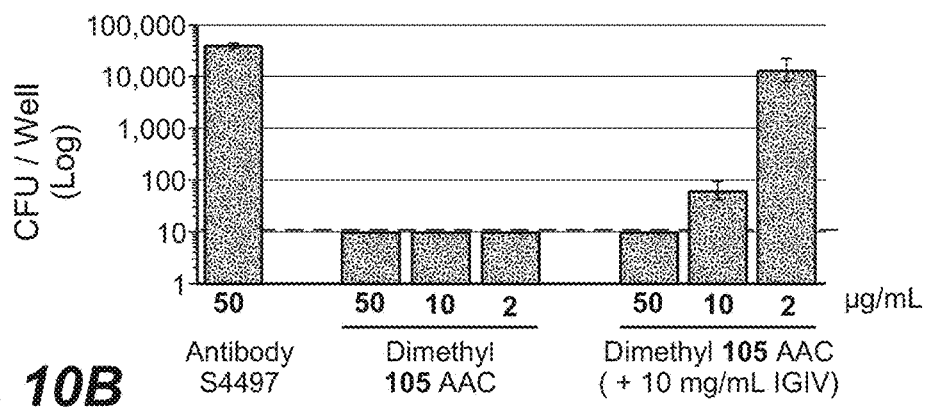
FIG. 10B shows an AAC is efficacious in the presence of physiological levels of human IgG (10 mg/mL) in an in vitro macrophage assay with the USA300 strain of MRSA. The thio-S4497-HC-A118C-MC-vc-PAB-dimethylpipBOR 105 is efficacious in the presence of 10 mg/mL of human IgG. The USA300 strain of MRSA was opsonized with AAC alone, or with AAC diluted in 10 mg/mL of human IgG. The total number of surviving intracellular bacteria was assessed 2 days post infection.

FIG. 10B shows an in vivo infection model demonstrating that AAC is efficacious in the presence of physiological levels of human IgG. In vitro macrophage assay with the USA300 strain of MRSA shows that S4497-dimethyl-pipBOR AAC 105 is efficacious in the presence of 10 mg/mL of human IgG. The USA300 strain of MRSA was opsonized with AAC alone, or with AAC diluted in 10 mg/mL of human IgG for 1 hour at 37° C. with shaking. The opsonized bacteria were added directly to murine peritoneal macrophages and incubated for 2 hours to permit phagocytosis. After infection, the macrophage cultures were maintained in complete media supplemented with gentamycin and the total number of surviving intracellular bacteria was assessed 2 days post infection. These data revealed that although the human IgG did inhibit AAC killing at the lower doses, excellent killing was achieved using doses above 10 µg/mL, an antibody concentration that is readily achievable in vivo. Normal serum IgG can diminish the functional effect of 105 AAC. Since maximal macrophage intracellular killing activity of an AAC may require both high antigen binding and efficient interaction with FcRs (for opsonophagocytosis), preexisting serum antibodies may both compete for binding to WTA and the corresponding formed immune complexes compete for binding to FcRs on macrophages.

To confirm that the AAC would be effective in the presence of competing human antibodies in vivo, the in vivo infection model was modified to generate mice that express normal levels of human IgG in the serum. CB17:SCID mice, that lack both T cells and B cells and therefore do not have antibodies in the serum (Bosna & Carroll, (1991) Ann Rev Immunol. 9:323, were reconstituted with 10 mg/mL of human IgG by daily dosing of highly concentrated human IgG (IGIV). Preliminary studies confirmed that these mice, termed SCID:hulgG, indeed had sustained levels of at least 10 mg/mL of human IgG in the serum and that these mice were equally susceptible to infection with MRSA compared to untreated controls. SCID:hulgG mice were infected with MRSA and treated with either S4497 antibody or with the S4497-dimethyl-pipBOR AAC (50 mg/Kg) 1 day after infection. Four days after infection the bacterial load in the kidneys (FIG. 10C) was assessed.

FIG. 10C shows the combined data from 3 independent experiments using 2 separate preparations of the thio-S4497-HC-A 118C-MC-vc-PAB-dimethyl-pipBOR AAC 105 or 112. CB17.SCID mice were reconstituted with human IgG using a dosing regimen optimized to yield constant levels of at least 10 mg/mL of human IgG in serum. Mice were treated with S4497 antibody (50 mg/Kg), or S4497-dimethyl-pipBOR AAC (50 mg/Kg). Mice treated with the AAC had a greater than 4-log reduction in bacterial loads (Students t-test p=0.0005). Bacterial loads were on average over 10,000 fold lower in the mice treated with the S4497-dimethyl-pipBOR AAC compared to mice treated with S4497 antibody control, indicating that the AAC was clearly effective even in the presence of high levels of competing human anti-MRSA antibodies.

Efficacy of the AAC was compared with that of treatment with vancomycin, the current standard of care treatment for MRSA infections. FIG. 11A shows in vivo infection model demonstrating that AAC is more efficacious than the current standard of care (SOC) antibiotic vancomycin in mice that are reconstituted with normal levels of human IgG. CB17.SCID mice were reconstituted with human IgG using a dosing regimen optimized to yield constant levels of at least 10 mg/mL of human IgG in serum. Mice were treated with S4497 antibody (50 mg/Kg), vancomycin (100 mg/Kg), S4497-dimethyl-pipBOR AAC (50 mg/Kg, 112 or an AAC made with an isotype control antibody that does not recognize MRSA, thio-hu-anti gD 5B5-HC-A118C-MC-vc-PAB-dimethylpipBOR AAC 110 (50 mg/Kg). Mice receiving AACs were given a single dose of AAC on day 1 post infection by intravenous injection. Mice receiving vancomycin treatments were given twice daily injections of the antibiotic by intraperitoneal injection. All mice were sacrificed on day 4 post infection, and the total number of surviving bacteria per mouse (2 kidneys pooled) was determined by plating.

Treatment with vancomycin is effective at treating MRSA infection in our murine intravenous infection model if the treatment is initiated 30 minutes after infection. Twice-daily dosing with 100 mg/Kg of vancomycin failed to clear the infection, and was only able to reduce bacterial loads by about 50 fold, when treatment was initiated more than 1 day post infection (FIG. 11A). Strikingly, treatment with a single dose of the S4497-dimethyl-pipBOR AAC 1 day after infection was able to clear the infection in the majority of mice. Surprisingly, treatment with control AAC made with a human IgG antibody that does not recognize *S. aureus* (gD-AAC) had some efficacy in this model. The gD antibody does not recognize *S. aureus* through its antigen binding site, however the antibody is able to bind to protein A found on *S. aureus*.

Figure 11B:
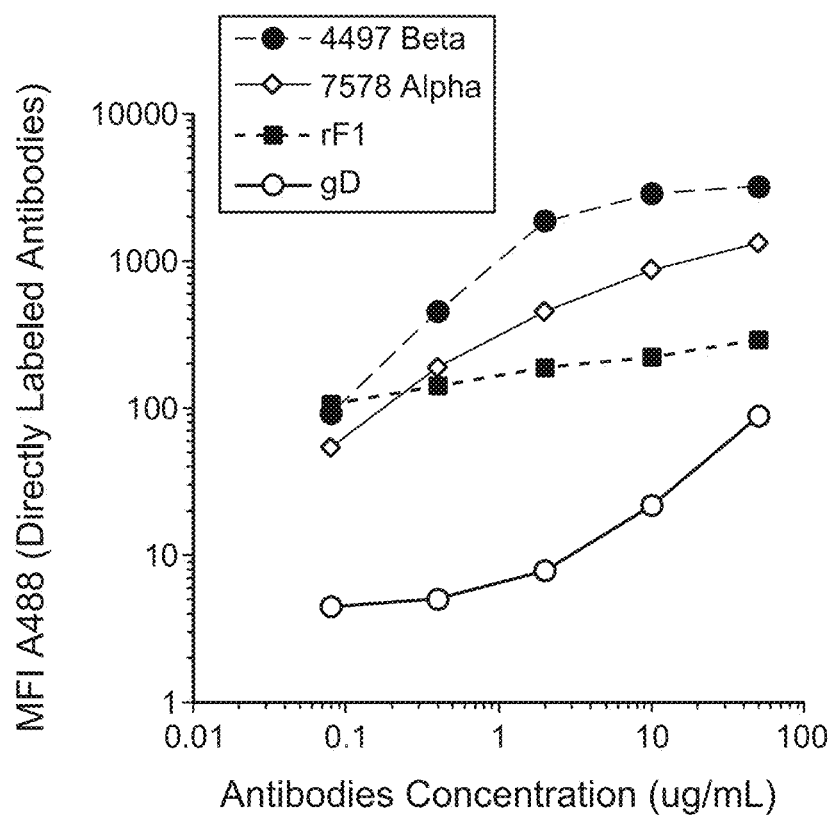
FIG. 11B shows the relative binding of anti-*Staph. aureus* antibodies to USA300 strain isolated from kidneys in an in vivo infection model, as determined by FACS. The S4497 antibody recognizes an N-acetylglucosamine modification that is linked to wall teichoic acid (WTA) via a beta-anomeric bond on the cell wall of *S. aureus*. The S7578 antibody binds to a similar N-acetylglucosamine modification that is joined to WTA via an alpha-anomeric bond. The rF1 antibody is a positive control anti-MRSA antibody that recognizes sugar modifications found on a family of SDR-repeat containing cell wall anchored proteins. The gD antibody is a negative control human IgG$_1$ that does not recognize *S. aureus*.
Figure 11C:
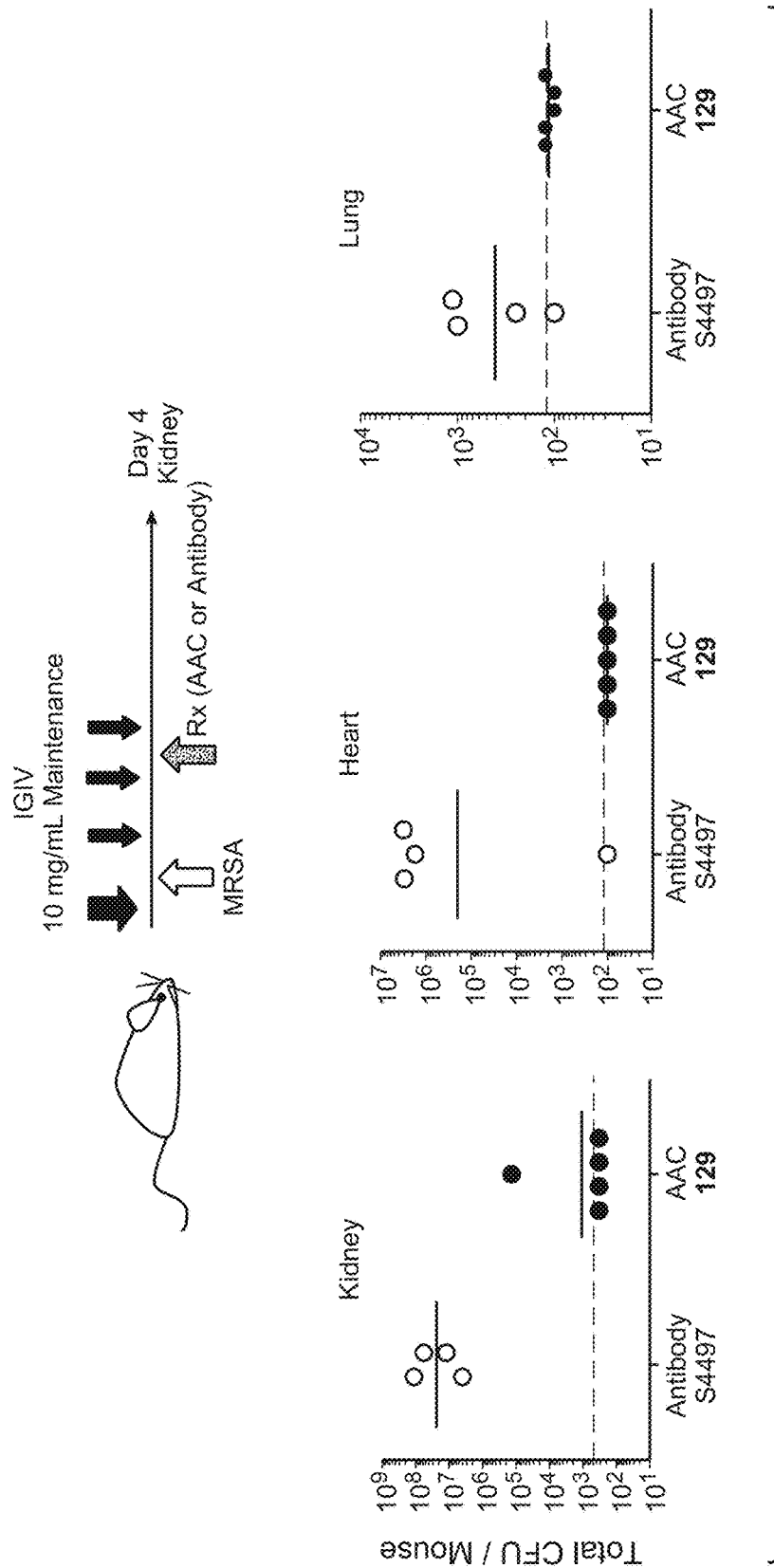
FIG. 11C shows in vivo infection model demonstrating that AAC, thio-S6078-HC A114C-LCWT-MC-vc-PAB-dimethylpipBOR 129 is more efficacious than naked anti-WTA antibody S4497, according to the same regimen as FIG. 11A, in mice that are reconstituted with normal levels of human IgG. Mice were treated with S4497 antibody (50 mg/Kg), or thio-S6078-HC A114C-LCWT-MC-vc-PAB-dimethylpipBOR 129 AAC (50 mg/Kg).

FIG. 11C shows in vivo infection model demonstrating that AAC, thio-S6078-HC A114C-LCWT-MC-vc-PAB-dimethylpipBOR 129 is more efficacious than naked anti-WTA antibody S4497, according to the same regimen as FIG. 11A, in mice that are reconstituted with normal levels of human IgG. CB17.SCID mice were reconstituted with human IgG using a dosing regimen optimized to yield constant levels of at least 10 mg/mL of human IgG in serum. Mice were treated with S4497 antibody (50 mg/Kg), or thio-S6078-HC A1114C-LCWT-MC-vc-PAB-dimethylpipBOR 129 AAC (50 mg/Kg).

FACS analysis showed that staining with high concentrations of the gD antibody on bacteria isolated from an in vivo infection yields low level binding to *S. aureus* relative to binding of anti-MRSA antibodies to MRSA isolated from infected kidneys (FIG. 11B). Mice were infected with MRSA by intravenous injection and infected kidneys were removed 3 days post infection and homogenized. Anti-MRSA or control antibodies were labeled with Alexa-488 and tested at a range of concentrations between 0.08 µg/mL and 50 µg/mL. The S4497 antibody recognizes an N-acetylglucosamine modification that is linked to wall teichoic acid (WTA) via a beta-anomeric bond on the cell wall of *S. aureus*. The S7578 antibody binds to a similar N-acetylglucosamine modification that is joined to WTA via an alpha-anomeric bond. The rF1 antibody is a positive control anti-MRSA antibody that recognizes sugar modifications found on a family of SDR-repeat containing cell wall anchored proteins. The gD antibody is a negative control human IgG$_1$ that does not recognize *S. aureus*. Although the overall level of binding with the gD antibody is significantly lower than that obtained with the S4497 antibody (estimated to be at least 30 fold lower by FACS analysis, FIG. 11B), the limited efficacy seen with the gD-AAC indicates that even low level binding of an AAC on MRSA in vivo is sufficient to yield efficacy that appeared equivalent to the reduction in CFUs obtained with vancomycin.

The above data clearly demonstrate that AAC are able to kill intracellular MRSA and that the S4497-pipBOR, and S4497 dimethyl-pipBOR AAC are effective at limiting infection with MRSA both in vitro and in vivo. AAC of the invention act by killing bacteria inside mammalian cells and thereby provide a unique therapeutic that is more effective at killing populations of bacteria that are resistant to treatment with vancomycin.

Figure 20:
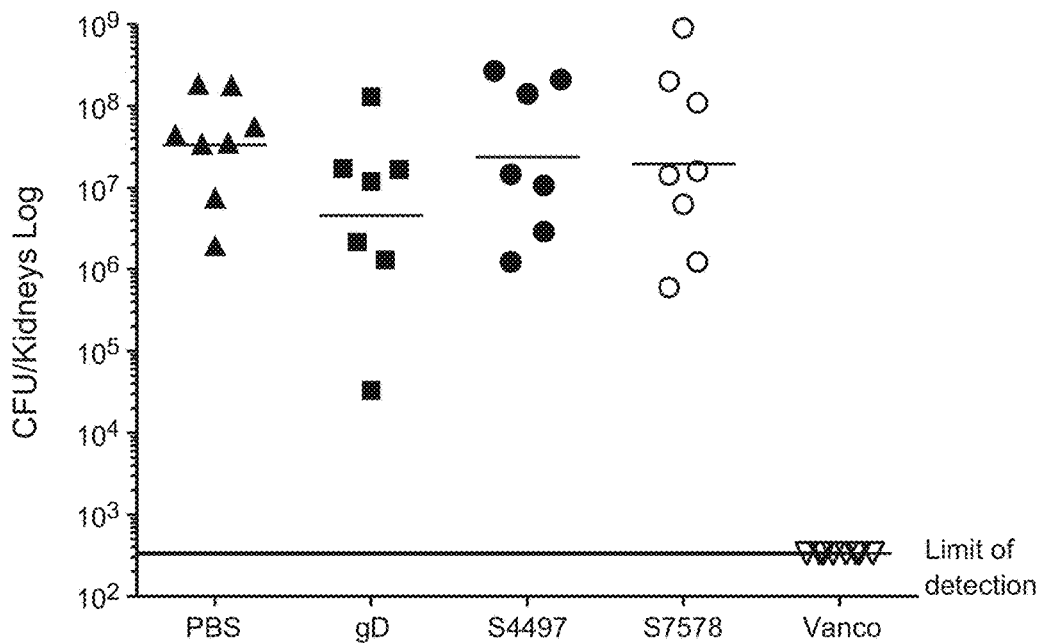
FIG. 20 shows that pre-treatment with 50 mg/kg of free antibodies is not efficacious in an intravenous infection model. Balb/c mice were given a single dose of vehicle control (PBS) or 50 mg/Kg of antibodies by intravenous injection 30 minutes prior to infection with $2 \times 10^7$ CFU of USA300. Treatment groups included an isotype control antibody that does not bind to *S. aureus* (gD), an antibody directed against the beta modification of wall teichoic acid (4497) or an antibody directed against the alpha modification of wall teichoic acid (7578). Control mice were given twice daily treatments with 110 mg/Kg of vancomycin by intraperitoneal injection (Vanco).

FIG. 20 shows that pre-treatment with 50 mg/kg of free antibodies is not efficacious in an intravenous infection model. Balb/c mice were given a single dose of vehicle control (PBS) or 50 mg/Kg of antibodies by intravenous injection 30 minutes prior to infection with 2×10$^7$ CFU of USA300. Treatment groups included an isotype control antibody that does not bind to *S. aureus* (gD), an antibody directed against the beta modification of wall teichoic acid (4497) or an antibody directed against the alpha modification of wall teichoic acid (7578). Control mice were given twice daily treatments with 110 mg/Kg of vancomycin by intraperitoneal injection (Vanco). All mice were sacrificed on day 4 post-infection, and the total number of surviving bacteria in kidneys (2 kidneys pooled) was determined by plating. Although pre-treatment with vancomycin cleared the infection in all of the mice tested, pre-treatment with antibodies directed against the cell wall of *S. aureus* had no effect on bacterial loads.

Figure 21:
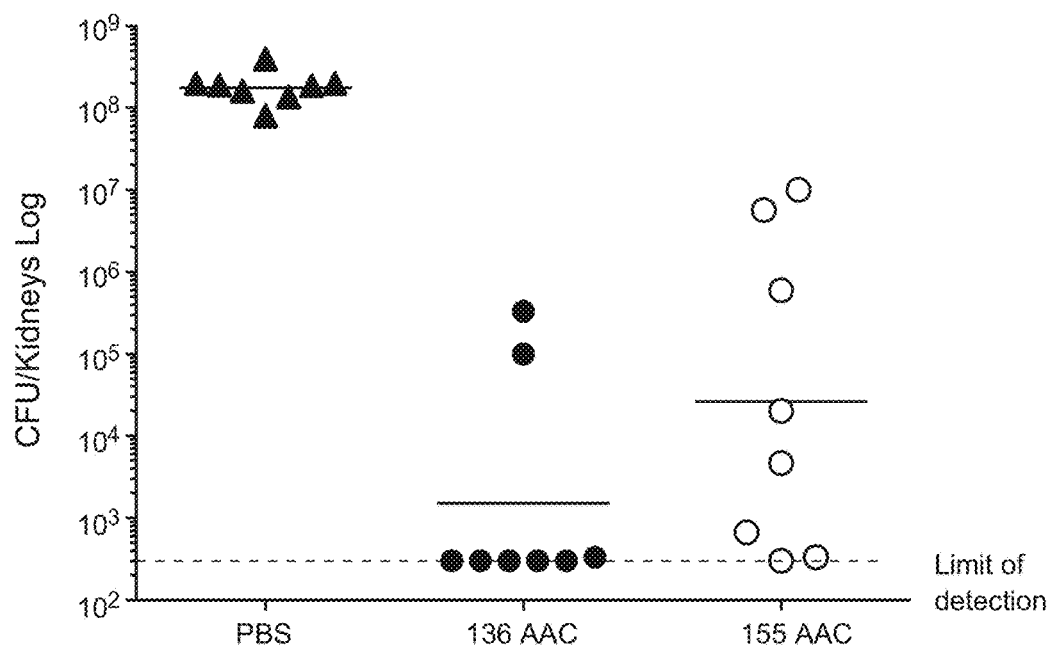
FIG. 21 and FIG. 22 show that AACs directed against either the beta modification of wall teichoic acid or the alpha modification of wall teichoic acid are efficacious in an intravenous infection model using mice that are reconstituted with normal levels of human IgG. CB17.SCID mice were reconstituted with human IgG using a dosing regimen optimized to yield constant levels of at least 10 mg/mL of human IgG in serum and infected with $2\times10^7$ CFU of USA300 by intravenous injection. Treatment was initiated 1 day after infection with buffer only control (PBS), 60 mg/Kg of beta-WTA AAC (136 AAC) or 60 mg/Kg of alpha-WTA AAC (155 AAC).
Figure 22:
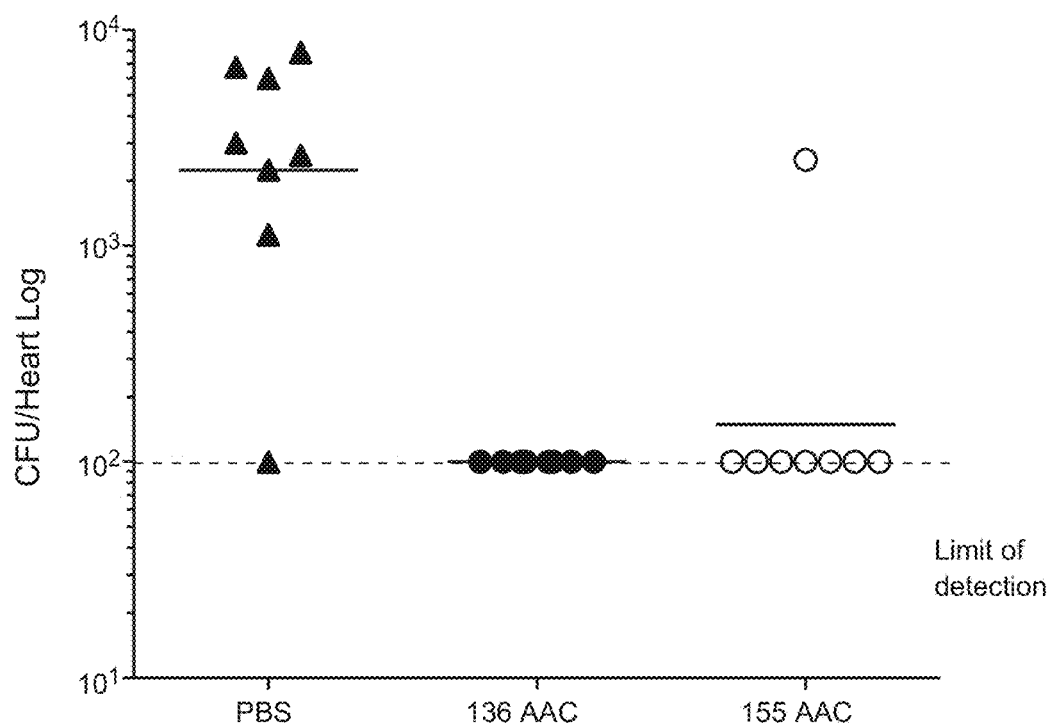

FIGS. 21 and 22 show that AACs directed against either the beta modification of wall teichoic acid or the alpha modification of wall teichoic acid are efficacious in an intravenous infection model using mice that are reconstituted with normal levels of human IgG. CB17.SCID mice were reconstituted with human IgG using a dosing regimen optimized to yield constant levels of at least 10 mg/mL of human IgG in serum and infected with 2×10$^7$ CFU of USA300 by intravenous injection. Treatment was initiated 1 day after infection with buffer only control (PBS), 60 mg/Kg of beta-WTA AAC (136 AAC) or 60 mg/Kg of alpha-WTA AAC (155 AAC). The mice were sacrificed on day 4 post infection, and the total number of surviving bacteria in kidneys (2 kidneys pooled, FIG. 21) and heart (FIG. 22) was determined by plating. Treatment with the beta-WTA AAC resulted in a 100,000 fold reduction in bacterial load in the kidney compared to mice treated with the vehicle control. Treatment with the alpha-WTA AAC resulted in an average 9,000 fold reduction in bacterial load in the kidney.

To date, it remains uncertain why the currently available antibiotics are often ineffective at killing intracellular stores of bacteria. Antibiotics could fail because they do not reach sufficient concentrations inside cells, either because they do not enter the phagolysosomal compartment where intracellular stores of bacteria reside, or because they may be subject to the activity of efflux pumps that remove the antibiotic from mammalian cells. Antibiotics may be damaged by harsh conditions found inside the phagolysosome including low pH, reducing agents and oxidizing agents that are released specifically to kill the phagocytosed bacterium. Alternatively, antibiotics may fail because the bacteria up regulate defense mechanisms or fail to divide inside the phagolysosome and are therefore rendered transiently insensitive to antibiotics. The relative importance of these mechanisms of antibiotic resistance will differ for different pathogens and for each antibiotic. The antibiotic component of our AAC, pipBOR and dimethyl-pipBOR are indeed more potent than rifampicin at killing intracellular MRSA when tested as free antibiotics. The linkage of these antibiotics to an antibody provides a real dose-dependent increase in efficacy that is apparent in vivo (FIG. 9C). In this case, improved efficacy of the AAC over antibiotic alone is likely due to a combination of its ability to opsonize bacteria and to improved pharmacokinetics of AAC. Most free antibiotics are rapidly cleared in vivo and require repeated dosing with high concentrations of antibiotic to maintain sufficient antibiotic concentrations in serum. In contrast, AAC have long half-lives in serum due to the antibody portion of the molecule. Since AAC release the antibiotic only after binding to S. aureus and being transported along with the bacterium into the confined space of the phagolysosome, they concentrate small doses of antibiotic specifically in a niche where most antibiotics fail. Therefore, in addition to targeting protected reservoirs of intracellular bacteria, AAC may facilitate the use of more potent antibiotics that may prove too toxic for use as a single agent by limiting the release of the antibiotic to where it is most needed.

Figure 35:
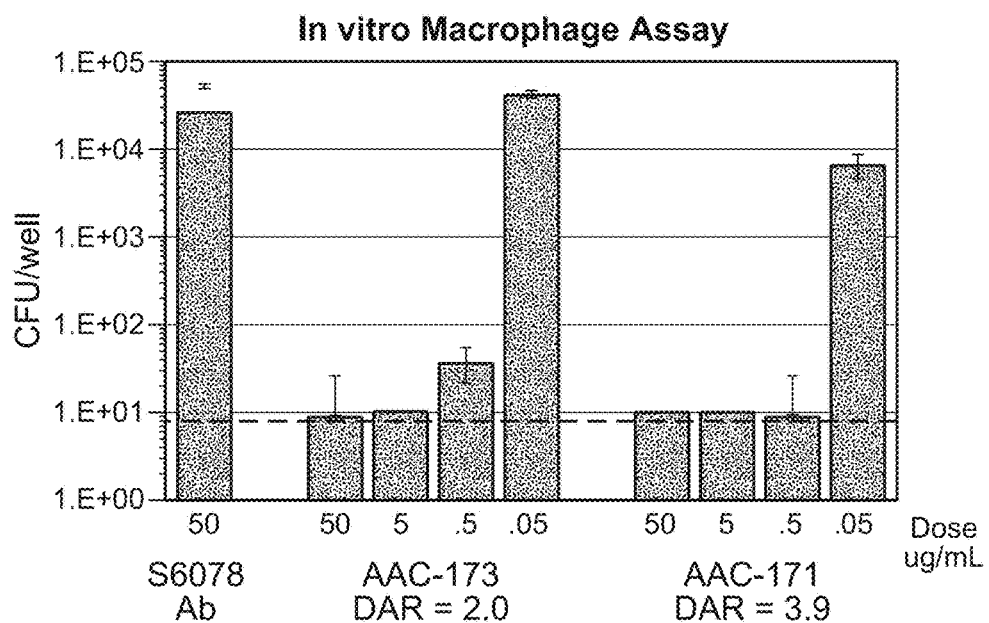
FIGS. 35 and 36 show results from the in vitro Macrophage Assay for thio-S6078 AAC.
Figure 36:
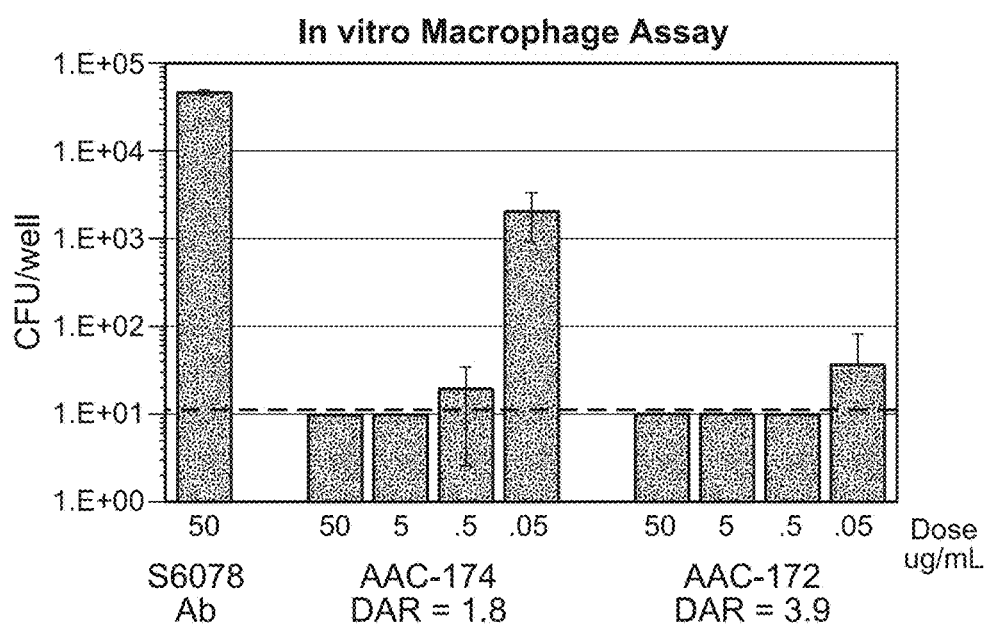

FIGS. 35 and 36 show results from the in vitro Macrophage Assay for thio-S6078 AAC. S. aureus (USA300 NRS384) was incubated with unconjugated S6078 antibody at 50 u/mL and AAC at 50 µg/mL, 5 µg/mL, 0.5 µg/mL or 0.05 µg/mL for 1 hour to permit binding of the antibody to the bacteria. The resulting opsonized bacteria were fed to murine macrophages and incubated at 37° C. to permit phagocytosis. After 2 hours, the infection mix was removed and replaced with normal growth media supplemented with 50 µg/mL of gentamycin to kill any remaining extracellular bacteria. The total number of surviving intracellular bacteria was determined 2 days later by plating serial dilutions of the macrophage lysates on Tryptic Soy Agar plates. In FIG. 35, thio-S6078.v4.HC-WT, LC-Cys-MC-vc-PAB-(dimethylpipBOR) AAC was effective at killing intracellular bacteria at doses at or above 0.5 µg/mL with an antibiotic loading of 2.0 (AAC-173) or 3.9 (AAC-171) dimethylpipBOR antibiotics (LA-54) per thio-S6078 antibody. In FIG. 36, thio-S6078.v4.HC-WT, LC-Cys-MC-vc-PAB-(piperazBOR) was effective at killing intracellular bacteria at doses at or above 0.5 µg/mL with an antibiotic loading of 1.8 (AAC-174) or 3.9 (AAC-172) piperazBOR antibiotics (LA-65) per thio-S6078 antibody.

Figure 37:
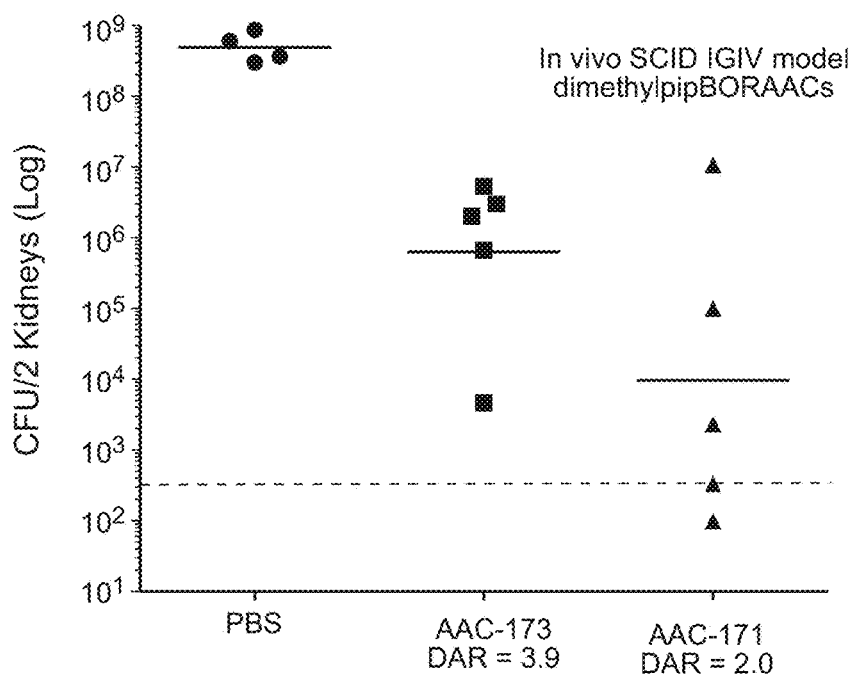
FIGS. 37 and 38 show results from in vivo efficacy of thio-S6078 AAC in a murine intravenous infection model. CB17.SCID mice were reconstituted with human IgG using a dosing regimen optimized to yield constant levels of at least 10 mg/mL of human IgG in serum. Mice were infected with USA300 and treated with vehicle control (PBS), thio-S6078.v4.HC-WT, LC-Cys-MC-vc-PAB-(dimethylpipBOR) AAC with an antibiotic loading of 2.0 (AAC-173) or 3.9 (AAC-171) dimethylpipBOR antibiotics (LA-54) per thio-S6078 antibody (FIG. 37) and thio-S6078.v4.HC-WT, LC-Cys-MC-vc-PAB-(piperazBOR) with an antibiotic loading of 1.8 (AAC-174) or 3.9 (AAC-172) piperazBOR antibiotics (LA-65) per thio-S6078 antibody (FIG. 38). Mice were given a single dose of AAC on day 1 post infection by intravenous injection and sacrificed on day 4 post infection. The total number of surviving bacteria in 2 kidneys was determined by plating. Treatment with AAC containing lower antibiotic loading reduced bacterial burdens by approximately 1,000-fold and treatment with the AAC containing higher antibiotic loading reduced bacterial burdens by more than 10,000-fold.
Figure 38:
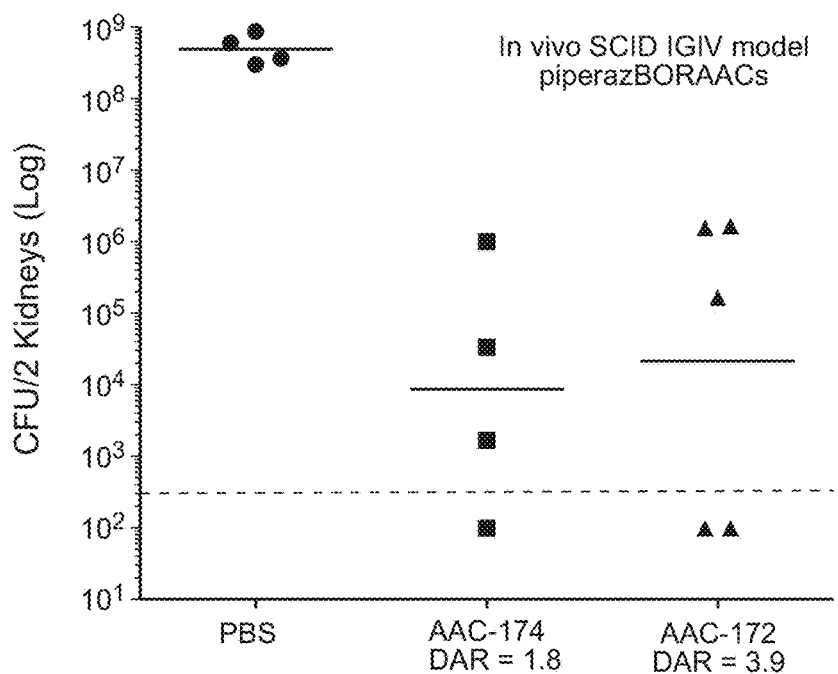

FIGS. 37 and 38 show results from in vivo efficacy of thio-S6078 AAC in a murine intravenous infection model. CB17.SCID mice were reconstituted with human IgG using a dosing regimen optimized to yield constant levels of at least 10 mg/mL of human IgG in serum. Mice were infected with USA300 and treated with vehicle control (PBS), thio-S6078.v4.HC-WT, LC-Cys-MC-vc-PAB-(dimethylpipBOR) AAC with an antibiotic loading of 2.0 (AAC-173) or 3.9 (AAC-171) dimethylpipBOR antibiotics (LA-54) per thio-S6078 antibody (FIG. 37) and thio-S6078.v4.HC-WT, LC-Cys-MC-vc-PAB-(piperazBOR) with an antibiotic loading of 1.8 (AAC-174) or 3.9 (AAC-172) piperazBOR antibiotics (LA-65) per thio-S6078 antibody (FIG. 38). Mice were given a single dose of AAC on day 1 post infection by intravenous injection and sacrificed on day 4 post infection. The total number of surviving bacteria in 2 kidneys was determined by plating. Treatment with AAC containing lower antibiotic loading reduced bacterial burdens by approximately 1,000-fold and treatment with the AAC containing higher antibiotic loading reduced bacterial burdens by more than 10,000-fold.

Staphopain B Cleavable Linkers for Antibody-Antibiotic Conjugates

A protease cleavable linker is described herein to be cleaved by staphopain B, a secreted S. aureus endopeptidase. To design a linker cleaved specifically by the Staphylococcus aureus bacterium, the protease activity of S. aureus culture supernatant was characterized using a FRET peptide library. From this screen, a unique substrate specificity was identified. Using this substrate, the enzyme responsible for activity was purified from culture supernatant and identified as staphopain B. Based on this identification, a staphopain B optimized linker was generated and linked to piperazino-rifamycin:

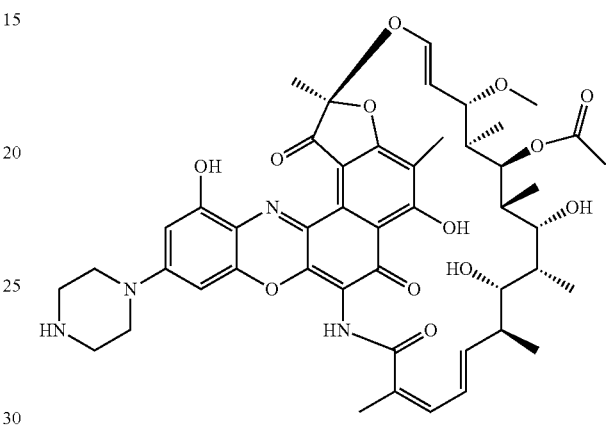

Piperazino-rifamycin is a potent rifalazil-like antibiotic. The resultant AAC has demonstrated efficacy in in vitro and in vivo models of MRSA infection, providing a novel mechanism by which to target MRSA infections. Staphopain B is a secreted cysteine protease from the papain family of endopeptidases (CAS Reg. No. 347841-89-8, Sigma-Aldrich #S3951, Filipek et al (2005) J. Biol. Chem. 280 (15): 14669-74) and has evolved to have a unique substrate specificity, preferring bulky aromatic side chains in the P2 position. Expression of staphopain B is controlled by the agr (or accessory gene regulator) quorum sensing system (Janzon, L. and S. Arvidson (1990) The EMBO journal 9(5): 1391-1399) as part of the staphylococcal proteolytic cascade (SCP). Agr modulates the expression of secreted proteases and other virulence factors of S. aureus including aureolysin, V8, and staphopain A (Shaw, L., E. Golonka, et al. (2004) Microbiology 150 (Pt 1): 217-228). Staphopain B has been implicated as a potent virulence factor due to its ability to degrade host connective tissue as well as augment several immune system proteins (Imamura, T., S. Tanase, et al. (2005) Journal of experimental medicine 201 (10): 1669-1676; Potempa, J., A. Dubin, et al. (1988) Journal of biological chemistry 263 (6): 2664-2667; Ohbayashi, T., A. Irie, et al. (2011) Microbiology 157 (Pt 3): 786-792; Smagur, J., K. Guzik, et al. (2009); Biological chemistry 390 (4): 361-371; Smagur, J., K. Guzik, et al. (2009); Journal of innate immunity 1 (2): 98-108; Kulig, P., B. A. Zabel, et al. (2007); Journal of immunology 178 (6): 3713-3720). Staphopain B's role as an important virulence factor makes it an attractive target for protease mediated antibiotic release.

Identifying Substrates Cleaved by *Staphylococcus aureus* Proteases:

To identify substrates readily cleaved by S. aureus endopeptidases, supernatant from an overnight culture of Wood46 strain S. aureus was incubated with a commercially available FRET peptide library. The Wood46 strain has a constitutively active agr locus, thus the Wood46 strain exhibits increased protease expression compared to wild type. The FRET peptide library, Rapid Endopeptidase Profiling Library or PepSets™ REPLi (Mimotopes, Victoria, Australia), consists of 512 wells with 8 internally quenched fluorogenic peptides per well in a 96-well plate format. The peptides fluoresce upon cleavage allowing for proteolytic activity to be monitored in real-time. Each peptide has a tripeptide variable core flanked by a series of glycine residues on either side and an additional two lysine residues at the C-terminus for solubility. Supernatant from the Wood46 culture was added to the library and plates were incubated overnight at 37° C. Wells showing greater than a 15-fold increase in fluorescence (12 out of 512 wells total) were analyzed by LC-MS (Agilent Q-TOF) to determine the cleavage products. Cleavage sites were ranked based on frequency (Table 4). Among the top hits, a pattern in substrate specificity was observed, specifically a preference for bulky hydrophobic side chains of Phe and Tyr in the P2 position.

TABLE 4

Amino acid preferences of REPLi sequences cleaved by Wood46 secreted proteases. Abundance at each position (%)

| Residues | P4 | P3 | P2 | P1 | P1' | P2' |
|---|---|---|---|---|---|---|
| G | 71.4 | 50.0 | 0.0 | 28.6 | 35.7 | 100.0 |
| I/L | 21.4 | 7.1 | 0.0 | 0.0 | 7.1 | 0.0 |
| A/V | 0.0 | 14.3 | 0.0 | 50.0 | 28.6 | 0.0 |
| N/Q | 7.1 | 7.1 | 0.0 | 0.0 | 7.1 | 0.0 |
| S/T | 0.0 | 14.3 | 0.0 | 14.3 | 0.0 | 0.0 |
| F/Y | 0.0 | 0.0 | 100.0 | 0.0 | 21.4 | 0.0 |
| K/R | 0.0 | 7.1 | 0.0 | 7.1 | 0.0 | 0.0 |

Abundance at each position of amino acid residues present in the FRET peptides of wells that showed the greatest increase in fluorescence. REPLi peptides contain the sequence MCA-Gly-Gly-Gly-Xaa-Yaa-Zaa-Gly-Gly-DPA-Lys-Lys (SEQ ID NO: 132), where Xaa, Yaa, and Zaa vary. Glycine residues present in the table represent the Gly residues that flank the variable core. While Gly residues are the most abundant in several positions, they give little insight to substrate specificity. When designing linkers, preference was given to amino acids from the variable core. Amino acids that were not in any of the top hits were omitted from the table.

Design and Conjugation of a FRET Substrate Cleaved by a MRSA Protease In Vitro:

A peptide was designed and synthesized using the most frequent residues in the cleaved peptides from the REPLi screen using specificity information for P1, P2, and P3. The peptide had the sequence GGAFAGGG (SEQ ID NO: 126), with cleavage expected between GGAFA (SEQ ID NO: 131) and GGG. The peptide was synthesized using solid phase synthesis incorporating fluorescent dyes, tetramethylrhodamine (TAMRA) and fluorescein as a FRET pair (FIG. 26) with maleimido-propionic-acid added to the N-terminus to allow for conjugation to antibody cysteine residues. The resultant mal-FRET-peptide, maleimido-propionic (MP)-Lys(TAMRA)-Gly-Gly-Ala-Phe-Ala-Gly-Gly-Gly-Lys (fluorescein) ("core peptide" disclosed as SEQ ID NO: 125), was conjugated to the cysteine-engineered thioMab antibody, thio-S4497. The mal-FRET-peptide was also conjugated to cysteine-engineered anti-Her2 thioMab trastuzumab, a nonbinding control.

Figure 28:
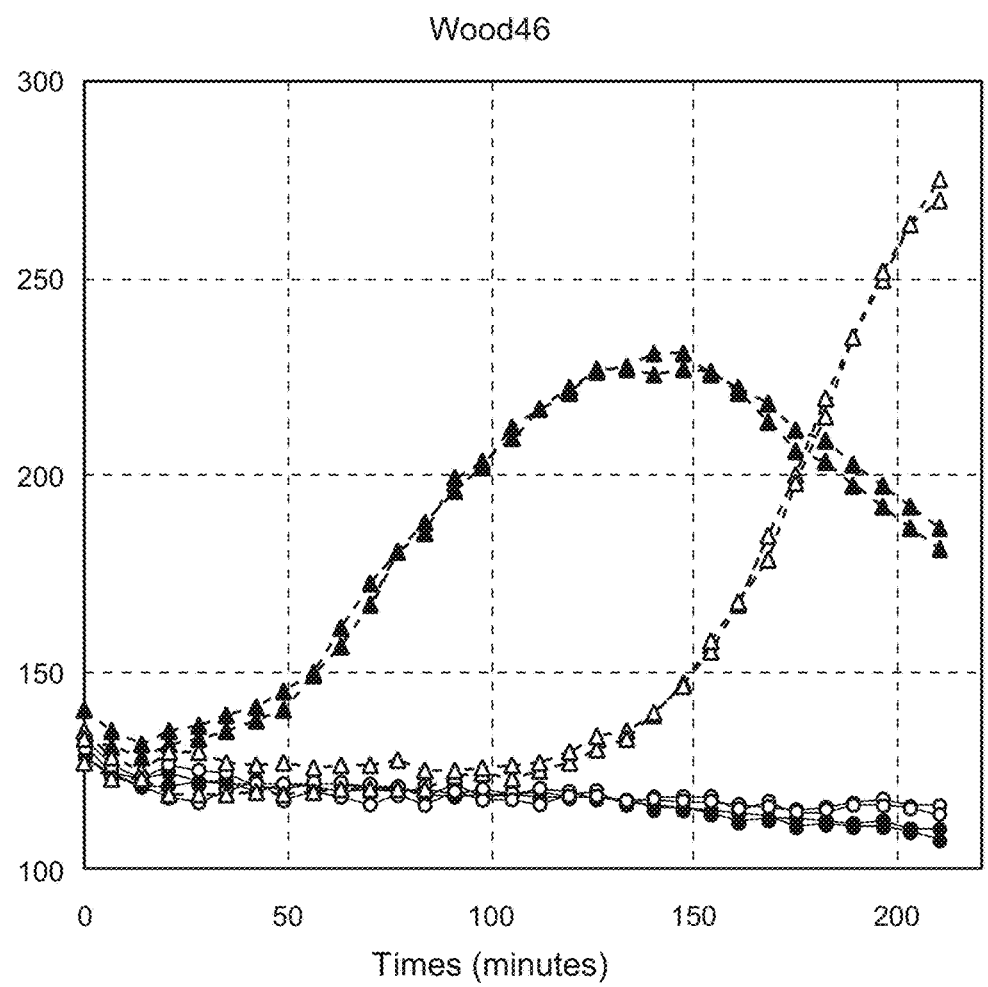
FIG. 28 and FIG. 29 show Mal-K(tamra)GGAFAGGGK (fluorescein) (SEQ ID NO: 125) AAC are cleaved in both Wood46 (FIG. 28) and USA300 (FIG. 29) when conjugated to an antibody that binds *S. aureus* (thio-54497) and not when conjugated to an antibody that does not bind to *S. aureus* (thio-trastuzumab). Fluorescence intensity measured over time of thioMAB 4497 mal-K(tamra)GGAFAGGGK (fluorescein) (SEQ ID NO: 125) incubated with log phase cultures of Wood46 and USA300 MRSA. The thioMAB 4497 FRET peptide conjugates made from mal-K(TAMRA) GGAFAGGGK(fluorescein) (SEQ ID NO: 125) of FIG. 26 show an increase in fluorescence in both strains, indicating that the experimental linker is cleaved by a *S. aureus* protease and that the protease is present in the clinically relevant strain of MRSA, USA300 (FIG. 29). Cell density affects the rate of cleavage, with cleavage occurring earlier in cultures of the higher cell density ($10^8$ cells/ml). The isotope control conjugate (thio-trastuzumab) did not show an increase in fluorescence in any condition.
Figure 29:
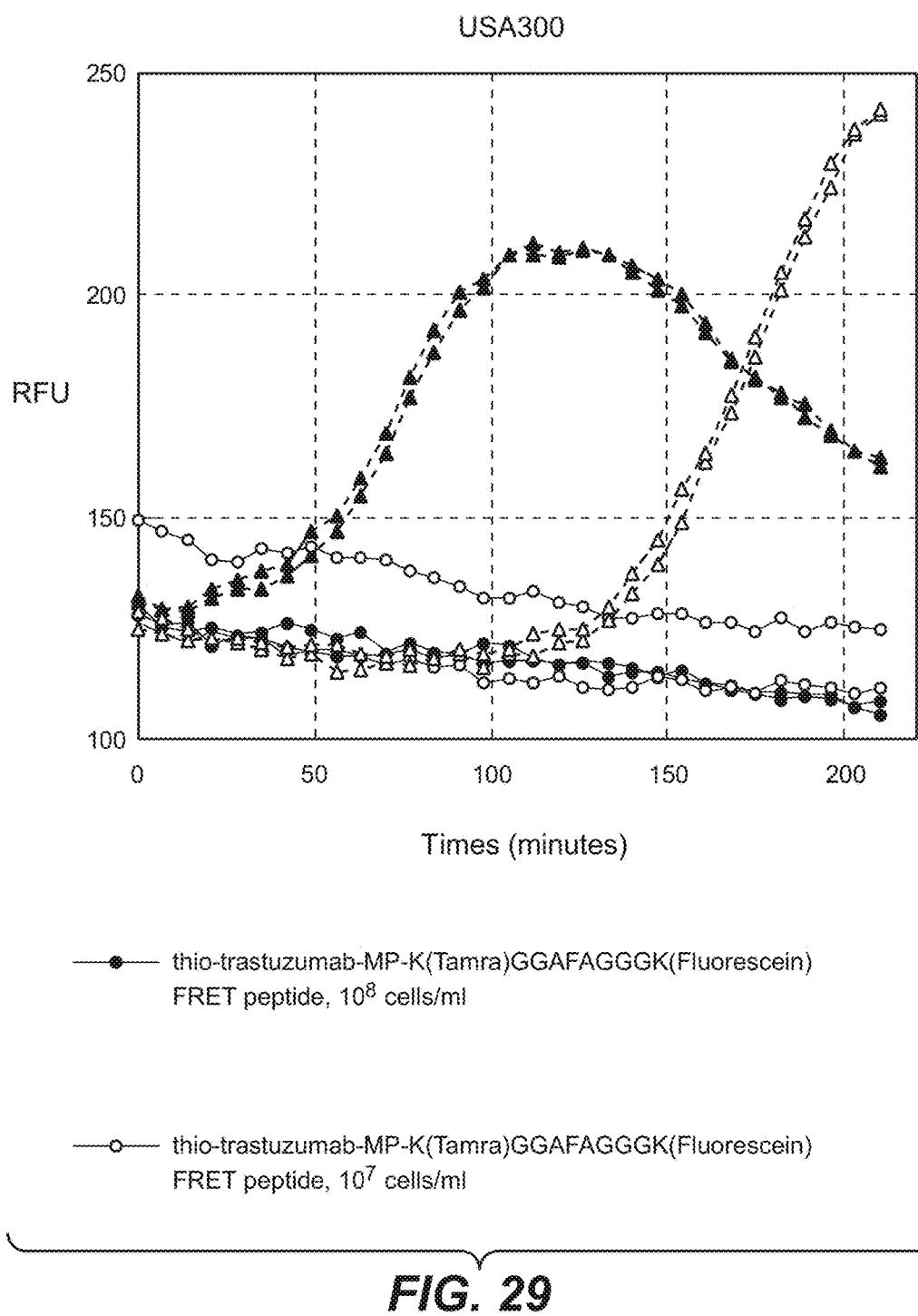

The thio-S4497-MP-K(Tamra)GGAFAGGGK(Fluorescein) ("core peptide" disclosed as SEQ ID NO: 125) FRET conjugate and non-binding control FRET conjugate, thio-trastuzumab-MP-K(Tamra)GGAFAGGGK(Fluorescein) ("core peptide" disclosed as SEQ ID NO: 125), were incubated with log phase cultures of Wood46 (FIG. 28) and the wild type, USA300 (FIG. 29), at cell densities of $10^8$ cells/ml and $10^7$ cells/ml in tryptic soy broth (TSB). The final concentration of MP-Lys(TAMRA)-Gly-Gly-Ala-Phe-Ala-Gly-Gly-Gly-Lys(fluorescein) ("core peptide" disclosed as SEQ ID NO: 125) for all wells was 2 µM. Fluorescence was monitored over time at 37° C., excitation $\lambda$495 nm/emission $\lambda$518 nm. An increase in fluorescence was observed with the 4497-mal-FRET-peptide conjugate in both Wood46 and USA300, indicating that the FRET peptide is cleaved by a S. aureus protease and that the protease is present in both strains. The linker unit MP-K(Tamra)GGAFAGGGK(Fluorescein) ("core peptide" disclosed as SEQ ID NO: 125) is cleaved in both Wood46 and USA300 when conjugated to an antibody that binds S. aureus. Validating the cleavage of this model linker in USA300 was critical due to its relevance to the clinical strain of MRSA that a potential therapeutic antibody-antibiotic conjugate (AAC) would target. The thio-S4497-MP-K(Tamra)GGAF-AGGGK(Fluorescein) ("core peptide" disclosed as SEQ ID NO: 125) FRET conjugate shows an increase in fluorescence in both strains, indicating that the linker is cleaved by a S. aureus protease and that the protease is present in the clinically relevant strain of MRSA, USA300. Cell density affects the rate of cleavage, with cleavage occurring earlier in cultures of the higher cell density. The non-binding control thio-trastuzumab-MP-K(Tamra)GGAFAGGGK (Fluorescein) ("core peptide" disclosed as SEQ ID NO: 125) conjugate did not show an increase in fluorescence in any condition tested.

Figure 27:
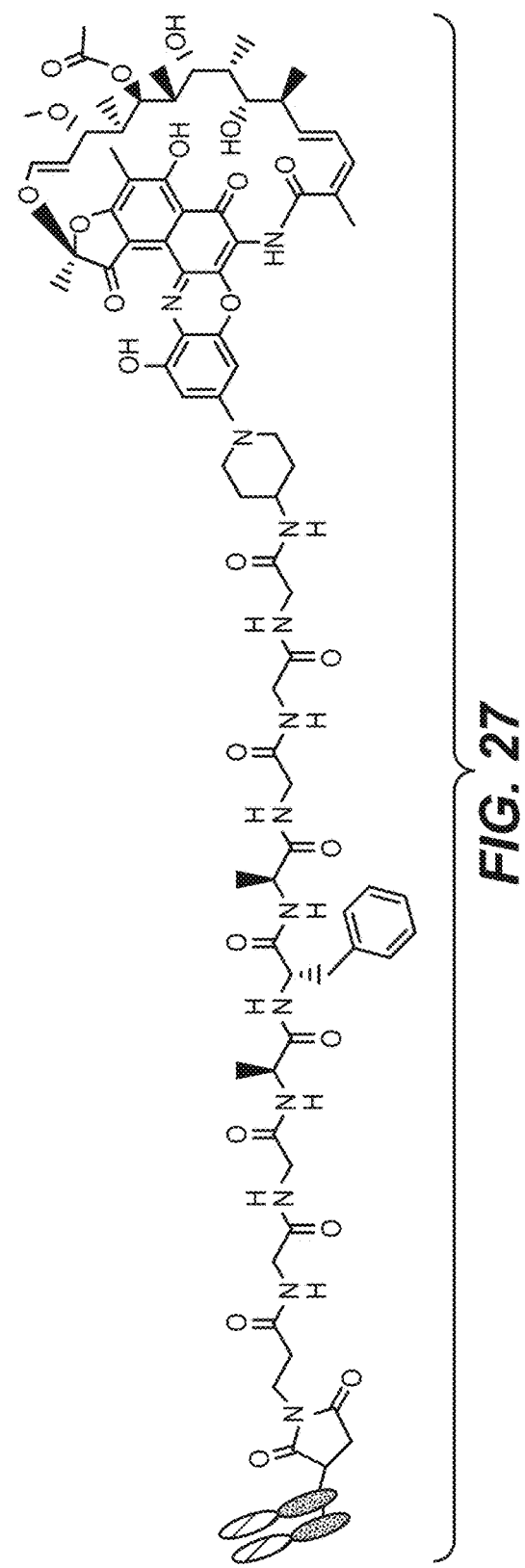
FIG. 27 shows the structure of thioFAB S4497-MC-GGAFAGGG-(pipBOR) ("core peptide" disclosed as SEQ ID NO: 126), a tool compound used for identifying active fractions containing the protease of interest. Mal-GGAF-AGGG-DNA31 ("core peptide" disclosed as SEQ ID NO: 126) was conjugated to THIOFAB 4497. THIOFABs contain one reactive cysteine. The *S. aureus* protease cleaved the linker C-terminal to Ala, releasing Gly-Gly-Gly-(pipBOR).

Based on the cleaved substrate from the cell based assays, linker-antibiotic intermediate LA-59 (Table 2) was prepared and conjugated to antibodies to form anti-MRSA heavy chain, cysteine engineered thio-S4497 (AAC-113) and thio-S4462 (AAC-114), and anti-HER2 light chain thio-trastuzumab (AAC-115) of Table 3. The GGAFAGGG (SEQ ID NO: 126) linked AAC demonstrated better rates of cleavage than the FRET-peptide when incubated with concentrated supernatant from a Wood46 overnight culture, indicating that the linker-antibiotic is a better substrate for the unknown protease of interest. Cleavage occurred at the expected site between alanine and glycine in the GGAFAGGG-linked ("core peptide" disclosed as SEQ ID NO: 126) AAC (AAC-113, AAC-114, AAC-115). This linker-antibiotic (LA-59) is not an optimized delivery system for the antibiotic because upon cleavage, GGG-rifamycin as opposed to free rifamycin is released. While the therapeutic potential of this linker-antibiotic may be uncertain, its ability to be efficiently cleaved by protease make it a useful tool compound to identify fractions containing the active protease of interest. Linker-antibiotic intermediate LA-59 was conjugated to the Fab portion of the thio-S4497 antibody (Scheer, J. M., W. Sandoval, et al. (2012). PloS one 7 (12): e51817). Cysteine-engineered Fab antibodies, "thioFABs", have one reactive cysteine that enables the site-specific conjugation of one thiol reactive compound. thioFAB S-4497 was reacted with a 3 fold molar excess of LA-59 over thioFAB for 1 hr in 50 mM TRIS pH 7.5, 150 mM NaCl at room temperature. Excess LA-59 was separated from AAC by diafiltration in PBS. The resultant conjugate, thioFAB S4497-MC-GGAF-AGGG-(pipBOR) ("core peptide" disclosed as SEQ ID NO: 126) (FIG. 27), was used as a tool compound to identify active fractions, with cleavage of the linker detected by LC-MS analysis.

Figure 30:
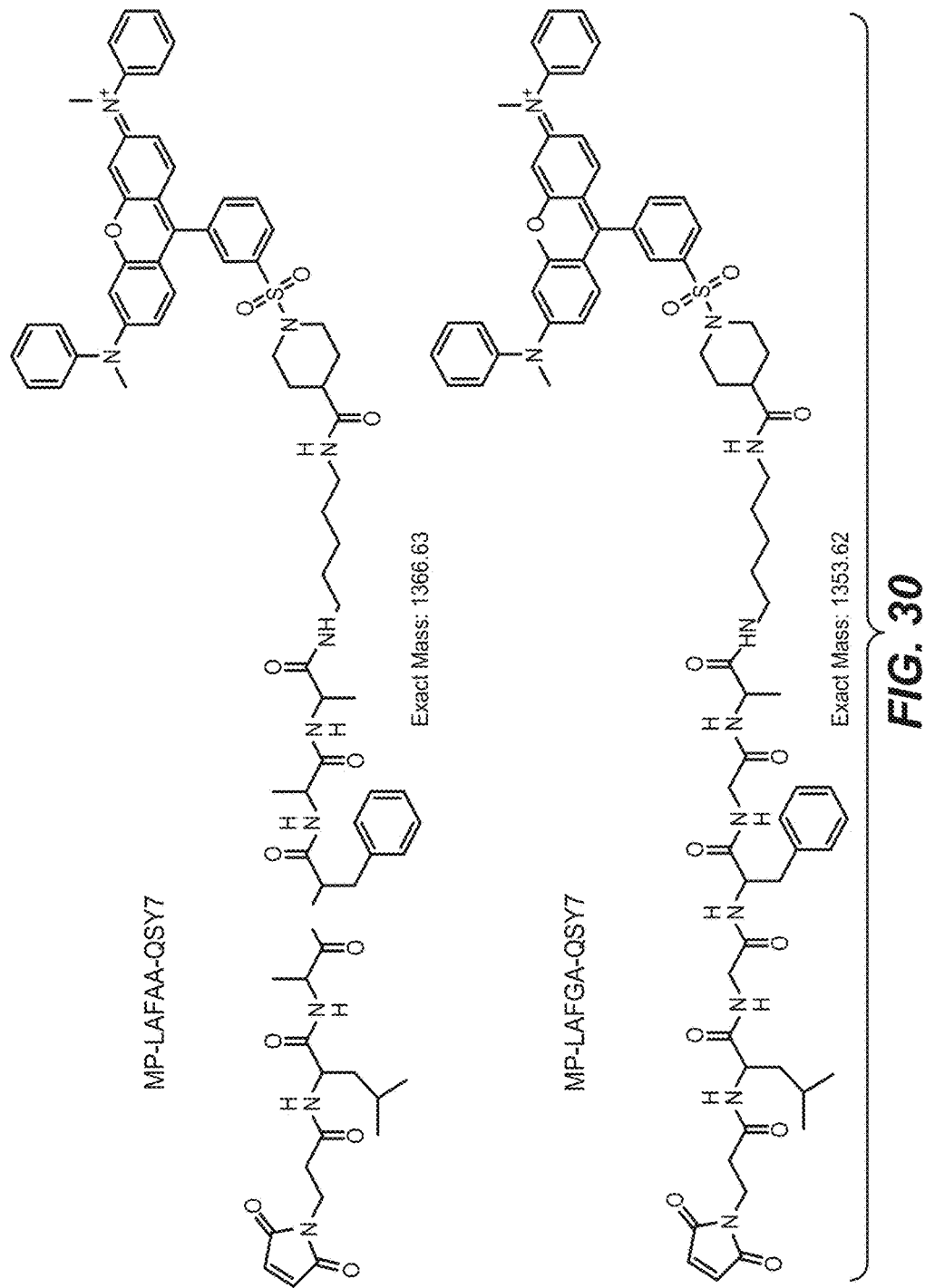
FIG. 30 show two optimized linkers for staphopain B cleavage in AAC. Linkers optimized for cleavage by staphopain B, including residue preferences for P4 and P1'. Linkers were designed using data from the REPLi screen. QSY7 was added to the C-terminus of each linker to act as an antibiotic surrogate.

Optimizing Linkers for Efficient Cleavage by Staphopain B:

The linker-antibiotic intermediate LA-59, MC-GGAF-AGGG-(pipBOR) ("core peptide" disclosed as SEQ ID NO: 126), has substrate residues optimized for the P1, P2, and P3 positions. Using the results from the REPLi screen, two new linkers were designed and synthesized incorporating a residue preference for P4 (FIG. 30). Maleimido-propionic-Leu-Ala-Phe-Ala-Ala ("core peptide" disclosed as SEQ ID NO: 136) and maleimido-propionic-Leu-Ala-Phe-Gly-Ala ("core peptide" disclosed as SEQ ID NO: 135) were synthesized using solid phase synthesis. Isoleucine and Leucine were the most frequent residues in P4 in the REPLi screen (disregarding Glycine). Only one residue, Leucine, was chosen to limit the number of linkers synthesized. Ala and Gly were alternated in the P1 position to examine the effect on cleavability. A residue in P1', Ala, was also included. QSY®7 (xanthylium, 9-[2-[[4-[[(2,5-dioxo-1-pyrrolidinyl) oxy]carbonyl]-1-piperidinyl]sulfonyl]phenyl]-3,6-bis(methylphenylamino)-NHS ester, chloride, CAS Reg. No. 304014-12-8, Life Technologies) was added to the C-terminus of both linkers to act as an antibiotic surrogate (FIG. 30). Incorporating QSY®7 allowed for the cleavability of these linkers to be evaluated without consuming costly and labor-intensive antibiotics.

The experimental mal-peptide-QSY7 linkers were conjugated to THIOFAB S4497 to evaluate the cleavability of these linkers. Conjugations were performed as previously described. The resultant THIOFAB S4497 linker-QSY7 conjugates were assessed for cleavability by staphopain B, staphopain A, and human cathepsin B at pH 7.2 (Table 5). Like staphopain B, staphopain A is a secreted cysteine protease of *S. aureus* from the papain family of proteases. It is structurally similar to staphopain B, but has a broader substrate specificity (Filipek, R., M. Rzychon, et al. (2003). The Journal of biological chemistry 278 (42): 40959-40966). Cathepsin B, a mammalian cysteine lysosomal protease, is also a member of the papain family of endopeptidases. It is thought to cleave the valine-citruline linkers used in other AAC linkers described in this patent.

TABLE 5

Cleavage of optimized linkers by staphopains and human cathepsin B

| | | Staphopain A | Staphopain B | Cathepsin B |
|---|---|---|---|---|
| MP-LAFGA-QSY7 ("core peptide" disclosed as SEQ ID NO: 135) (FIG. 30) | Percent cleavage pH 7.2 | 38 | 100 | 100 |
| | Cleavage product | A-QSY7 | A-QSY7 | A-QSY7 |
| MP-LAFAA-QSY7 ("core peptide" disclosed as SEQ ID NO: 136) (FIG. 30) | Percent cleavage pH 7.2 | 23 | 100 | 100 |
| | Cleavage product | A-QSY7 | A-QSY7 | A-QSY7, QSY7 |
| MP-LAFG-PABC-(piperazinoBOR) ("core peptide" disclosed as SEQ ID NO: 128) LA-104 | Percent cleavage pH 5 | 100 | 100 | 100 |
| | Percent cleavage pH 7.2 | 46 | 100 | 64 |
| | Cleavage product | piperazino-rifamycin | piperazino-rifamycin | |

Table 5 shows data from cleavage of optimized linkers conjugated to thioFAB by staphopain A, staphopain B, and Cathepsin B. The final linker-antibiotic, MP-LAFG-piperazino-rifamycin ("core peptide" disclosed as SEQ ID NO: 128) is efficiently cleaved by all three proteases. Cleavage by the staphopains results in the release free rifamycin. Cleavage by cathepsin B releases Phe-Gly-piperazino-rifamycin (Example 26).

Design and Conjugation of a Staphopain B Cleavable Linker that Releases Free Antibiotic:

From the cleavage assays of the experimental linkers tested, mal-LAFGA ("core peptide" disclosed as SEQ ID NO: 135) was selected for antibiotic attachment. Further optimization of this linker was required to achieve free antibiotic release upon proteolytic cleavage. To accomplish this, Ala in P1' was replaced by p-aminobenzyl (PAB) or p-aminobenzyloxycarbonyl (PABC). piperazino-rifamycin was added to the C-terminus of this linker to complete the linker-antibiotic intermediates LA-88 MC-LAFG-PAB-(dimethylamino-3-pyrroloBOR) ("core peptide" disclosed as SEQ ID NO: 128) and LA-104, MP-LAFG-PABC-(piperazinoBOR) ("core peptide" disclosed as SEQ ID NO: 128). Upon cleavage after Gly in the P1 position, the PAB and PABC groups are designed to self-immolate, releasing free antibiotic. LA-88 was conjugated to form thio-S4497-v8-LCV205C-MC-LAFG-PAB-(dimethylamino-3-pyrroloBOR) AAC-163 ("core peptide" disclosed as SEQ ID NO: 128) (Table 3). LA-104 was conjugated to form AAC-193, AAC-215, and AAC-222. Cleavage assays of AAC 193 with staphopain A, staphopain B, and cathepsin B were performed at pH 7.2 and pH 5. These pH values were selected to either mimic plasma (pH 7.2) or the environment of the phagolysosome (pH 5). Staphopain B achieved 100% cleavage at both pH 5 and 7.2. Staphopain A showed 100% cleavage at pH5 and 64% cleavage at pH 7.2.

The substitution of PABC for Ala in the P1' group changed the location at which cathepsin B cleaves the linker. Upon cleavage by cathepsin B, Phe-Gly-PABC-(piperazino-BOR) was released. As a therapeutic, potential cleavage of this linker by cathepsin B would most likely occur in the lysosomal compartment of macrophages. Under these circumstances, other proteases, including staphopain B, may further process FG-PABC-piperazino-rifamycin to liberate free antibiotic.

Linker-antibiotic intermediate, MP-LAFG-PABC-(piperazinoBOR) ("core peptide" disclosed as SEQ ID NO: 128) LA-104 was conjugated to thioMAB S4497 to evaluate the in vitro and in vivo efficacy of the resultant AACs AAC-193, AAC-215, AAC-222. Two control conjugates were also made by conjugating LA-104 to thioMAB anti-Her2 and thioMAB anti-gD, both isotype controls. The light chain linked, thioMAB 4497 MP-LAFG-PABC-piperazino-rifamycin conjugate ("core peptide" disclosed as SEQ ID NO: 128) AAC-215 had a drug to antibody ratio (DAR) of 1.6, as did the thioMAB anti-gD control conjugate. The thioMAB anti-Her2 mal-LAFG-PABC-piperazino-rifamycin ("core peptide" disclosed as SEQ ID NO: 128) conjugate had a DAR of 1.5.

*S. aureus* culture supernatant was screened using a FRET peptide library to identify substrates readily cleaved by secreted proteases. The results of this screen showed the overwhelming majority of measured protease activity may be attributed to one secreted cysteine protease of *S. aureus*, staphopain B. Peptide linkers designed for cleavage by staphopain B were optimized and an efficiently cleaved substrate was identified that released free antibiotic. The resultant linker is also cleaved by *S. aureus* protease staphopain A and human protease cathepsin B, both also cysteine proteases.

When conjugated to an antibody that binds *S. aureus*, the resultant AAC show efficacy both in vitro and in vivo. The endogenous endopeptidases of MRSA provide a mechanism to target MRSA infections and release payload in a disease specific manner. The ability of this linker to be cleaved by secreted proteases of *S. aureus* allows for targeting of MRSA present in both human neutrophils as well as extra-cellularly in host plasma/tissue. This dual targeting may enable the release of a high concentration of antibiotic at both intra- and extra-cellular sites of infection.

Staphopain A and B expression are up-regulated in human neutrophils and are thought to be important virulence factors (Burlak, C., et al. (2007) Cellular microbiology 9 (5):1172-1190), making them attractive targets for protease mediated release of antibiotic. Human cathepsin B also cleaves the linker, presenting an alternate pathway of release. The observed efficacy of the AAC is likely to be the result of multiple proteases, both from *S. aureus* and the host, involved in the release of antibiotic or antibiotic moieties. A serum-stable linker that is cleaved by an assortment of proteases provides a release mechanism that may outmaneuver resistance mutations of the bacterium.

Methods of Treating and Preventing Infections with Antibody-Antibiotic Conjugates The AAC of the invention are useful as antimicrobial agents effective against a number of human and veterinary Gram positive bacteria, including the Staphylococci, for example *S. aureus, S. saprophyticus* and *S. simulans; Listeria*, for example *Listeria monocytogenes*; Enterococci, for example *E. faecalis*; Streptococci, for example *S. pneumoniae; Clostridium*, for example *C. difficile*.

Persistent bacteremia can result from internalization into host cells. While not entirely understood, internalized pathogens are able to escape immune recognition by surviving inside host cells. Such organisms include *S. aureus, Salmonella* (e.g., *S. typi, S. choreraesuis* and *S. enteritidis*), *Legionella* (e.g., *L. pneumophila*), *Listeria* (e.g., *L. monocytogenes*), *Brucella* (e.g., *B. abortus, B. melitensis, B. suis*), *Chlamydia* (*C. pneumoniea, C. trachomati*), *Rickettsia* spp., *Shigella* (e.g., *S. flexneri*), and mycobacteria.

Following entry into the bloodstream, *S. aureus* can cause metastatic infection in almost any organ. Secondary infections occur in about one-third of cases before the start of therapy (Fowler et al., (2003) Arch. Intern. Med. 163:2066-2072), and even in 10% of patients after the start of therapy (Khatib et al., (2006) Scand. J. Infect. Dis., 38:7-14). Hallmarks of infections are large reservoirs of pus, tissue destruction, and the formation of abcesses (all of which contain large quantities of neutrophils). While only about 5% of patients develop complications if the bacteremia is extinguished within 48 hours, the levels rises to 40%, if bacteraemia persists beyond three days.

While *S. aureus* is generally considered to be an extracellular pathogen that secretes toxins, evidence exists that it can survive inside endothelial cells, keratinocytes, fibroblasts, and osteoclasts (Alexander et al, (2001) Appl. Microbiol. Biotechnol. 56:361-366; Garzoni et al, (2009) Trends Microbiol. 17:59-65). Neutrophils and macrophages are key components of the host innate immune response to bacterial infection. These cells internalize *S. aureus* by phagocytosis, which may be enhanced by antibody, complement, or host lectins such as mannose binding protein, which can bind simultaneously to pathogen and neutrophils, macrophages, and other professional phagocytes. As previously mentioned, *S. aureus* not only survives in the lysosomal environment, but may actually exploit it as a mechanism for developing persistence in the host.

The antibody-antibiotic conjugates (AAC) of the invention have significant therapeutic advantages for treating intracellular pathogens, including those residing in phagolysosomes. In one embodiment, the pathogen is internalized into leukocyte cells, and the intracellular component is a phagolysosome. In an intact AAC, the antibody variable region binds to a cell surface antigen on the bacteria (opsonization). Not to be limited by any one theory, in one mechanism, by the antibody component of the AAC binding to the bacterial cell surface, phagocytes are attracted to the bacterium. The Fc portion of the antibody binds to an Fc receptor on the phagocyte, facilitating phagocytosis. After the AAC-bacteria complex is phagocytosed, upon fusing to lysosome, the AAC linker is cleaved by exposure to phagolysosomal enzymes, releasing an active antibiotic. Due to the confined space and relatively high local Abx concentration (about $10^4$ per bacterium), the result is that the phagolysosome no longer supports the survival of the intracellular pathogen (FIG. 5). Because the AAC is essentially an inactive prodrug, the therapeutic index of the antibiotic can be extended relative to the free (unconjugated) form. The antibody provides pathogen specific targeting, while the cleavable linker is cleaved under conditions specific to the intracellular location of the pathogen. The effect can be both directly on the opsonized pathogen as well as other pathogens that are co-localized in the phagolysosome. In a specific aspect, the pathogen is *S. aureus*.

Antibiotic tolerance is the ability of a disease-causing pathogen to resist killing by antibiotics and other antimicrobials and is mechanistically distinct from multidrug resistance (Lewis K (2007). "Persister cells, dormancy and infectious disease". Nature Reviews Microbiology 5 (1): 48-56. doi:10.1038/nrmicro1557). Rather, this form of tolerance is caused by a small sub-population of microbial cells called persisters (Bigger J W (14 Oct. 1944). "Treatment of staphylococcal infections with penicillin by intermittent sterilization". Lancet 244 (6320): 497-500). These cells are not multidrug resistant in the classical sense, but rather are dormant cells that are tolerant to antibiotic treatment that can kill their genetically identical siblings. This antibiotic tolerance is induced by a non- or extremely slow dividing physiological state. When antimicrobial treatment fails to eradicate these persister cells, they become a reservoir for recurring chronic infections. The antibody-antibiotic conjugates of the invention possess a unique property to kill these persister cells and suppress the emergence of multidrug tolerant bacterial populations.

In another embodiment, the AAC of the invention may be used to treat infection regardless of the intracellular compartment in which the pathogen survives.

In another embodiment, AACs could also be used to target bacteria in planktonic or biofilm form (example: *S. aureus, K. pneumonia, E. coli, A. baumannii, P. aeruginosa* and Enterobacteriaceae) by antibody-mediated opsonization, leading to internalization by professional phagocytes. When the phagosome fuses with a lysosome, sufficiently high concentrations of free antibiotic will be released from the AAC in the acidic or proteolytic environment of the phagolysosome to kill the phagocytosed pathogen.

Methods of treating infection with antibody-antibiotic conjugates (AAC) of the invention include treating bacterial lung infections, such as *S. aureus* pneumonia or tuberculosis infections, bacterial ocular infections, such as trachoma and conjunctivitis, heart, brain or skin infections, infections of the gastrointestinal tract, such as travelers' diarrhea, osteomyelitis, ulcerative colitis, irritable bowel syndrome (IBS), Crohn's disease, and IBD (inflammatory bowel disease) in general, bacterial meningitis, and abscesses in any organ, such as muscle, liver, meninges, or lung. The bacterial infectious can be in other parts of the body like the urinary tract, the bloodstream, a wound or a catheter insertion site. The AACs of the invention are useful for difficult-to-treat infections that involve biofilms, implants or sanctuary sites (e.g., osteomyelitis and prosthetic joint infections), and high mortality infections such as hospital acquired pneumonia and bacteremia. Vulnerable patient groups that can be treated to prevent Staphylococcal aureus infection include hemodialysis patients, immune-compromised patients, patients in intensive care units, and certain surgical patients. In another aspect, the invention provides a method of killing, treating, or preventing a microbial infection in an animal, preferably a mammal, and most preferably a human, that includes administering to the animal an AAC or pharmaceutical formulation of an AAC of the invention. The invention further features treating or preventing diseases associated with or which opportunistically result from such microbial infections. Such methods of treatment or prevention may include the oral, topical, intravenous, intramuscular, or subcutaneous administration of a composition of the invention. For example, prior to surgery or insertion of an IV catheter, in ICU care, in transplant medicine, with or post cancer chemotherapy, or other activities that bear a high risk of infection, the AAC of the invention may be administered to prevent the onset or spread of infection.

The bacterial infection may be caused by a bacteria with an active and inactive form, and the AAC is administered in an amount and for a duration sufficient to treat both the active and the inactive, latent form of the bacterial infection, which duration is longer than is needed to treat the active form of the bacterial infection.

Analysis of various Gram+ bacteria found WTA beta expressed on all *S. aureus*, including MRSA and MSSA strains, as well as non-aureus *Staph* strains such as *S. saprophyticus* and *S. simulans*. WTA alpha (Alpha-GLcNAc ribitol WTA) is present on most, but not all *S. aureus*, and also present on *Listeria monocytogenes*. WTA is not present on Gram-bacteria. Therefore one aspect of the invention is a method of treating a patient infected with *S. aureus* or *S. saprophyticus* or *S. simulans* by administering a therapeutically effective amount of an anti-WTA beta-AAC of the invention. Another aspect of the invention is a method of treating a patient infected with *S. aureus* or *Listeria monocytogenes* by administering a therapeutically effective amount of an anti-WTA alpha-AAC of the invention. The invention also contemplates a method of preventing infections by *S. aureus* or *S. saprophyticus* or *S. simulans* by administering a therapeutically effective amount of an anti-WTA beta-AAC of the invention in hospital settings such as surgery, burn patient, and organ transplantation.

The patient needing treatment for a bacterial infection as determined by a physician of skill in the art may have already been, but does not need to be diagnosed with the kind of bacteria that he/she is infected with. Since a patient with a bacterial infection can take a turn for the worse very quickly, in a matter of hours, the patient upon admission into the hospital can be administered the anti-WTA-AACs of the invention along with one or more standard of care Abx such as vancomycin. When the diagnostic results become available and indicate the presence of, e.g., *S. aureus* in the infection, the patient can continue with treatment with the anti-WTA AAC. Therefore, in one embodiment of the method of treating a bacterial infection or specifically a *S. aureus* infection, the patient is administered a therapeutically effective amount of an anti-WTA beta AAC. In the methods of treatment or prevention of the present invention, an AAC of the invention can be administered as the sole therapeutic agent or in conjunction with other agents such as those described below. The AACs of the invention show superiority to vancomycin in the treatment of MRSA in pre-clinical models. Comparison of AACs to SOC can be measured, e.g., by a reduction in mortality rate. The patient being treated would be assessed for responsiveness to the AAC treatment by a variety of measurable factors. Examples of signs and symptoms that clinicians might use to assess improvement in their patients includes the following: normalization of the white blood cell count if elevated at diagnosis, normalization of body temperature if elevated (fever) at the time of diagnosis, clearance of blood cultures, visual improvement in wound including less erythema and drainage of pus, reduction in ventilator requirements such as requiring less oxygen or reduced rate of ventilation in a patient who is ventilated, coming off of the ventilator entirely if the patient is ventilated at the time of diagnosis, use of less medications to support a stable blood pressure if these medications were required at the time of diagnosis, normalization of lab abnormalities that suggest end-organ failure such as elevated creatinine or liver function tests if they were abnormal at the time of diagnosis, and improvement in radiologic imaging (e.g. chest x-ray that previously suggested pneumonia showing resolution). In a patient in the ICU, these factors might be measured at least daily. Fever is monitored closely as is white blood cell count including absolute neutrophil counts as well as evidence that a "left shift" (appearance of blasts indicating increased neutrophil production in response to an active infection) has resolved.

In the context of the present methods of treatment of the invention, a patient with a bacterial infection is considered to be treated if there is significant measurable improvement as assessed by the physician of skill in the art, in at least two or more of the preceding factors compared to the values, signs or symptoms before or at the start of treatment or at the time of diagnosis. In some embodiments, there is measurable improvement in 3, 4, 5, 6 or more of the aforementioned factors. If some embodiments, the improvement in the measured factors is by at least 50%, 60%, 70%, 80%, 90%, 95% or 100% compared to the values before treatment. Typically, a patient can be considered completely treated of the bacterial infection (e.g., *S. aureus* infection) if the patient's measurable improvements include the following: i) repeat blood or tissue cultures (typically several) that do not grow out the bacteria that was originally identified; ii) fever is normalized; iii) WBC is normalized; and iv) evidence that end-organ failure (lungs, liver, kidneys, vascular collapse) has resolved either fully or partially given the pre-existent co-morbidities that the patient had.

Dosing

In any of the foregoing aspects, in treating an infected patient, the dosage of an AAC is normally about 0.001 to 1000 mg/kg/day. In one embodiment the patient with a bacterial infection is treated at an AAC dose in the range of about 1 mg/kg to about 100 mg/kg, typically about 5 mg/kg to about 90 mg/kg, more specifically 10 mg/kg to 50 mg/kg. The AAC may be given daily (e.g., a single dose of 5 to 50 mg/kg/day) or less frequently (e.g., a single dose of 5, 12.5, or 25 mg/kg/week). One dose may be split over 2 days, for example, 25 mg/kg on one day and 25 mg/kg the next day. The patient can be administered a dose once every 3 days (q3D), once a week to every other week (qOW), for a duration of 1-8 weeks. In one embodiment, the patient is administered an AAC of the invention via IV once a week for 2-6 weeks with standard of care (SOC) to treat the bacterial infection such as a *staph* A infection. Treatment length would be dictated by the condition of the patient or the extent of the infection, e.g. a duration of 2 weeks for uncomplicated bacteremia, or 6 weeks for bacteremia with endocarditis.

In one embodiment, an AAC administered at an initial dose of 2.5 to 100 mg/kg for one to seven consecutive days, followed by a maintenance dose of 0.005 to 10 mg/kg once every one to seven days for one month.

Route of Administration

For treating the bacterial infections, the AACs of the invention can be administered at any of the preceding dosages intravenously (i.v.) or subcutaneously. In one embodiment, the WTA-AAC is administered intravenously. In a specific embodiment, the WTA-AAC administered via i.v. is a WTA-beta AAC, more specifically, wherein the WTA-beta antibody is one selected from the group of Abs with amino acid sequences as disclosed in FIG. 14, FIG. 15A, FIG. 15B, FIG. 16A, and FIG. 16B.

Combination Therapy

An AAC may be administered in conjunction with one or more additional, e.g. second, therapeutic or prophylactic agents as appropriate as determined by the physician treating the patient.

In one embodiment, the second antibiotic administered in combination with the antibody-antibiotic conjugate compound of the invention is selected from the structural classes: (i) aminoglycosides; (ii) beta-lactams; (iii) macrolides/cyclic peptides; (iv) tetracyclines; (v) fluoroquinolines/fluoroquinolones; (vi) and oxazolidinones. See: Shaw, K. and Barbachyn, M. (2011) Ann. N.Y. Acad. Sci. 1241:48-70; Sutcliffe, J. (2011) Ann. N.Y. Acad. Sci. 1241: 122-152.

In one embodiment, the second antibiotic administered in combination with the antibody-antibiotic conjugate compound of the invention is selected from clindamycin, novobiocin, retapamulin, daptomycin, GSK-2140944, CG-400549, sitafloxacin, teicoplanin, triclosan, napthyridone, radezolid, doxorubicin, ampicillin, vancomycin, imipenem, doripenem, gemcitabine, dalbavancin, and azithromycin.

Additional examples of these additional therapeutic or prophylactic agents are anti-inflammatory agents (e.g., non-steroidal anti-inflammatory drugs (NSAIDs; e.g., detoprofen, diclofenac, diflunisal, etodolac, fenoprofen, flurbiprofen, ibuprofen, indomethacin, ketoprofen, meclofenameate, mefenamic acid, meloxicam, nabumeone, naproxen sodium, oxaprozin, piroxicam, sulindac, tolmetin, celecoxib, rofecoxib, aspirin, choline salicylate, salsalte, and sodium and magnesium salicylate) and steroids (e.g., cortisone, dexamethasone, hydrocortisone, methylprednisolone, prednisolone, prednisone, triamcinolone)), antibacterial agents (e.g., azithromycin, clarithromycin, erythromycin, gatifloxacin, levofloxacin, amoxicillin, metronidazole, penicillin G, penicillin V, methicillin, oxacillin, cloxacillin, dicloxacillin, nafcillin, ampicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmatozole, cefotaxime, ceftizoxime, ceftriaxone, cefoperazone, ceftazidime, cefixime, cefpodoxime, ceftibuten, cefdinir, cefpirome, cefepime, BAL5788, BAL9141, imipenem, ertapenem, meropenem, astreonam, clavulanate, sulbactam, tazobactam, streptomycin, neomycin, kanamycin, paromycin, gentamicin, tobramycin, amikacin, netilmicin, spectinomycin, sisomicin, dibekalin, isepamicin, tetracycline, chlortetracycline, demeclocycline, minocycline, oxytetracycline, methacycline, doxycycline, telithromycin, ABT-773, lincomycin, clindamycin, vancomycin, oritavancin, dalbavancin, teicoplanin, quinupristin and dalfopristin, sulphanilamide, para-aminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, moxifloxacin, gemifloxacin, sitafloxacin, daptomycin, garenoxacin, ramoplanin, faropenem, polymyxin, tigecycline, AZD2563, or trimethoprim), antibacterial antibodies including antibodies to the same or different antigen from the AAC targeted Ag, platelet aggregation inhibitors (e.g., abciximab, aspirin, cilostazol, clopidogrel, dipyridamole, eptifibatide, ticlopidine, or tirofiban), anticoagulants (e.g., dalteparin, danaparoid, enoxaparin, heparin, tinzaparin, or warfarin), antipyretics (e.g., acetaminophen), or lipid lowering agents (e.g., cholestyramine, colestipol, nicotinic acid, gemfibrozil, probucol, ezetimibe, or statins such as atorvastatin, rosuvastatin, lovastatin simvastatin, pravastatin, cerivastatin, and fluvastatin). In one embodiment the AAC of the invention is administered in combination with standard of care (SOC) for *S. aureus* (including methicillin-resistant and methicillin-sensitive strains). MSSA is usually typically treated with nafcillin or oxacillin and MRSA is typically treated with vancomycin or cefazolin.

These additional agents may be administered within 14 days, 7 days, 1 day, 12 hours, or 1 hour of administration of an AAC, or simultaneously therewith. The additional therapeutic agents may be present in the same or different pharmaceutical compositions as an AAC. When present in different pharmaceutical compositions, different routes of administration may be used. For example, an AAC may be administered intravenous or subcutaneously, while a second agent may be administered orally.

Pharmaceutical Formulations

The present invention also provides pharmaceutical compositions containing the AAC, and to methods of treating a bacterial infection using the pharmaceutical compositions containing AAC. Such compositions may further comprise suitable excipients, such as pharmaceutically acceptable excipients (carriers) including buffers, acids, bases, sugars, diluents, glidants, preservatives and the like, which are well known in the art and are described herein. The present methods and compositions may be used alone or in combinations with other conventions methods and/or agents for treating infectious diseases. In one aspect, the invention further provides pharmaceutical formulations comprising at least one antibody of the invention and/or at least one antibody-antibiotic conjugate (AAC) thereof. In some embodiments, a pharmaceutical formulation comprises 1) an antibody of the invention and/or an AAC thereof, and 2) a pharmaceutically acceptable carrier. In some embodiments, a pharmaceutical formulation comprises 1) an antibody of the invention and/or an AAC thereof, and optionally, 2) at least one additional therapeutic agent.

Pharmaceutical formulations comprising an antibody or AAC of the invention are prepared for storage by mixing the antibody or AAC having the desired degree of purity with optional physiologically acceptable carriers, excipients or stabilizers (*Remington's Pharmaceutical Sciences* 16th edition, Osol, A. Ed. (1980)) in the form of aqueous solutions or lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride); phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutical formulations to be used for in vivo administration are generally sterile, readily accomplished by filtration through sterile filtration membranes.

Active ingredients may also be entrapped in microcapsule prepared, for example, by co-acervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or AAC of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies or AAC remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

An antibody may be formulated in any suitable form for delivery to a target cell/tissue. For example, antibodies may be formulated as liposomes, a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., (1985) *Proc. Natl. Acad. Sci. USA* 82:3688; Hwang et al., (1980) *Proc. Natl. Acad. Sci. USA* 77:4030; U.S. Pat. No. 4,485,045; U.S. Pat. No. 4,544,545; WO 97/38731; U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., (1982) *J. Biol. Chem.* 257:286-288 via a disulfide interchange reaction. A chemotherapeutic agent is optionally contained within the liposome (Gabizon et al., (1989) *J. National Cancer Inst.* 81 (19): 1484).

Methods and Compositions for Diagnostics and Detection

In certain embodiments, any of the antibodies provided herein is useful for detecting the presence of MRSA in a biological sample. The term "detecting" as used herein encompasses quantitative or qualitative detection. A "biological sample" comprises, e.g., blood, serum, plasma, tissue, sputum, aspirate, swab, etc.

In one embodiment, an anti-WTA antibody for use in a method of diagnosis or detection is provided. In a further aspect, a method of detecting the presence of WTA in a biological sample is provided. In certain embodiments, the method comprises contacting the biological sample with an anti-WTA antibody as described herein under conditions permissive for binding of the anti-WTA antibody to WTA, and detecting whether a complex is formed between the anti-WTA antibody and WTA in the biological sample. Such method may be an in vitro or in vivo method. In one embodiment, an anti-MRSA antibody is used to select subjects eligible for therapy with an anti-MRSA antibody, e.g. where MRSA is a biomarker for selection of patients.

In one exemplary embodiment, an anti-WTA antibody is used in vivo to detect, e.g., by in vivo imaging, an MRSA-positive infection in a subject, e.g., for the purposes of diagnosing, prognosing, or staging treatment of an infection, determining the appropriate course of therapy, or monitoring response of the infection to therapy. One method known in the art for in vivo detection is immuno-positron emission tomography (immuno-PET), as described, e.g., in van Dongen et al., (2007) The Oncologist 12:1379-1389 and Verel et al., (2003) J. Nucl. Med. 44:1271-1281. In such embodiments, a method is provided for detecting an *Staph*-positive infection in a subject, the method comprising administering a labeled anti-Staph antibody to a subject having or suspected of having an *Staph*-positive infection, and detecting the labeled anti-Staph antibody in the subject, wherein detection of the labeled anti-Staph antibody indicates a *Staph*-positive infection in the subject. In certain of such embodiments, the labeled anti-Staph antibody comprises an anti-Staph antibody conjugated to a positron emitter, such as $^{68}$Ga, $^{18}$F, $^{64}$Cu, $^{86}$Y, $^{76}$Br, $^{89}$Zr, and $^{124}$I. In a particular embodiment, the positron emitter is $^{89}$Zr.

In further embodiments, a method of diagnosis or detection comprises contacting a first anti-Staph antibody immobilized to a substrate with a biological sample to be tested for the presence of *Staph*, exposing the substrate to a second anti-Staph antibody, and detecting whether the second anti-Staph antibody is bound to a complex between the first anti-Staph antibody and *Staph* in the biological sample. A substrate may be any supportive medium, e.g., glass, metal, ceramic, polymeric beads, slides, chips, and other substrates. In certain embodiments, a biological sample comprises a cell or tissue (e.g., biopsy material, including cancerous or potentially cancerous colorectal, endometrial, pancreatic or ovarian tissue). In certain embodiments, the first or second anti-Staph antibody is any of the antibodies described herein. In such embodiments, the second anti-WTA antibody may be anti-WTA antibodies S4497, S4462, S6978, S4487, or antibodies derived from them as described herein.

Exemplary disorders that may be diagnosed or detected according to any of the above embodiments include MRSA-positive infection, using test such as immunohistochemistry (IHC) or in situ hybridization (ISH). In some embodiments, a *Staph*-positive infection is an infection that expresses *Staph* according to a reverse-transcriptase PCR (RT-PCR) assay that detects *Staph* mRNA. In some embodiments, the RT-PCR is quantitative RT-PCR (Francois P and Schrenzel J (2008). "Rapid Diagnosis and Typing of *Staphylococcus aureus*". *Staphylococcus: Molecular Genetics*. Caister Academic Press; Mackay 1M, ed. (2007)), and real time PCR ("*Real-Time PCR in Microbiology: From Diagnosis to Characterization*. Caister Academic Press).

In certain embodiments, labeled anti-wall teichoic acid (WTA) antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

Clinically, the symptoms of infections with MRSA are similar to those of methicillin-sensitive *Staphylococcus aureus* (MSSA), and include abscesses and cellulitis. Often, the abscesses are accompanied by an areas of central necrosis. Furuncles (boils) are also common, particularly in the context of a MRSA outbreak. Lesions may also be misreported as a spider bite due the general redness which progresses to a necrotic center. Additionally, infections can appear as impetigo, folliculitis, deep-seated abscesses, pyomyositis, osteomyelitis, necrotizing fasciitis, staphylococcal toxic-shock syndrome, pneumonia and sepsis. Serious systemic infections are more common among persons with a history of injection drug use, diabetes or other immunocompromising conditions.

Standard treatment options for MRSA infections include conservative, mechanical options such as: (i) warm soaks and compresses, (ii) incision and drainage, and (iii) remove of foreign device (e.g., catheter) causing the infection. For more serious infections, especially those displaying cellulitis, antibiotics (Abx) are prescribed. For mild to moderate infections, antibiotics include trimethoprim-sulfamethoxazole (TMP-SMX), clindamycin, doxycycline, minocycline, tetracycline, rifampin, vancomycin, linezolid. Typically, a treatment regimen occurs for 5-10 with periotic reexamination and evaluation both during and after the treatment period.

Additional treatment options include decolonization, especially in the setting where a patient experiences recurring infection or where they are in an environment where a MRSA outbreak is ongoing. Decolonization is a procedure where the flora inhibiting the nares of the patient is removed. This is done through topical application of 2% mupirocin ointment applied generously within both nostrils for 5-10 days and topical cleansing with chlorhexidine gluconate 4% for 5 days.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice. Moreover, the article of manufacture may comprise (a) a first container with a composition contained therein, wherein the composition comprises an antibody or immunoconjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

EXAMPLES

The following are examples of methods and compositions of the invention. It is understood that various other embodiments may be practiced, given the general description provided above.

Example 1 MC-vc-PAB-pipBOR 51

2-Nitrobenzene-1,3-diol 1 was hydrogenated under hydrogen gas with palladium/carbon catalyst in ethanol solvent to give 2-aminobenzene-1,3-diol 2, isolated as the hydrochloride salt (FIGS. 23A and 23B). Mono-protection of 2 with tert-butyldimethylsilyl chloride and triethylamine in dichloromethane/tetrahydrofuran gave 2-amino-3-(tert-butyldimethylsilyloxy)phenol 3. Rifamycin S (ChemShuttle Inc., Fremont, Calif., U.S. Pat. No. 7,342,011; U.S. Pat. No. 7,271,165; U.S. Pat. No. 7,547,692) was reacted with 3 by oxidative condensation with manganese oxide or oxygen gas in toluene at room temperature to give TBS-protected benzoxazino rifamycin 4. Reaction of 4 with piperidin-4-amine and manganese oxide gave piperidyl benzoxazino rifamycin (pipBOR) 5.

Piperidyl benzoxazino rifamycin (pipBOR) 5 (0.02 mmol) and 4-((S)-2-((S)-2-(6-(2,5-dioxo-2,5-dihydro-1H-pyrrol-1-yl)hexanamido)-3-methylbutanamido)-5-ureidopentanamido)benzyl 4-nitrophenyl carbonate 6 (0.02 mmol) were mixed in DMF (0.4 ml) at room temperature (RT). To this was added 2.5 equivalents of N,N'-diisopropylethylamine. The solution was stirred from one to about 12 hours and was monitored by LC/MS. Upon completion, the solution was diluted with DMF and injected onto HPLC and purified under acidic conditions to give MC-vc-PAB-pipBOR 51. M/Z=1498.9. Yield 40%

Example 2 MC-fk-PAB-pipBOR 52

Following the procedure of Example 1, 6-(2,5-dioxo-2,5-dihydro-1H-pyrrol-1-yl)-N—((S)-1-((S)-5-guanidino-1-(4-(hydroxymethyl)phenylamino)-1-oxopentan-2-ylamino)-1-oxo-3-phenylpropan-2-yl)hexanamide 12 was converted to 4-((S)-2-((S)-2-(6-(2,5-dioxo-2,5-dihydro-1H-pyrrol-1-yl)hexanamido)-3-phenylpropanamido)-5-guanidinopentanamido)benzyl 4-nitrophenyl carbonate 13.

Piperidyl benzoxazino rifamycin (pipBOR) 5 (0.02 mmol) and 13 (0.02 mmol) were mixed in DMF (0.4 ml) at room temperature (RT). To this was added 2.5 equivalents of N,N'-diisopropylethylamine. The solution was stirred from one to about 12 hours and was monitored by LC/MS. Upon completion, the solution was diluted with DMF and injected onto HPLC and purified under acidic conditions to give MC-fk-PAB-pipBOR 52. M/Z=1545.8. Yield 32%

Example 3 MP-vc-PAB-pipBOR 53

Following the procedure of Example 1,6-(2-(2-(2-(2,5-dioxo-2,5-dihydro-1H-pyrrol-1-yl)ethoxy)ethoxy)acetamido)-N—((S)-1-((S)-1-(4-(hydroxymethyl)phenylamino)-1-oxo-5-ureidopentan-2-ylamino)-3-methyl-1-oxobutan-2-yl)hexanamide 14 was converted to 4-((17S,20S)-1-(2,5-dioxo-2,5-dihydro-1H-pyrrol-1-yl)-17-isopropyl-8,15,18-trioxo-20-(3-ureidopropyl)-3,6-dioxa-9,16,19-triazahenicosanamido)benzyl 4-nitrophenyl carbonate 15.

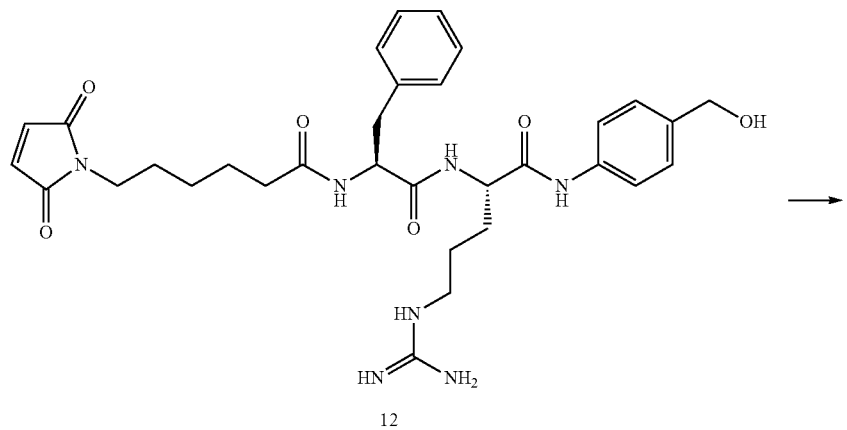

12

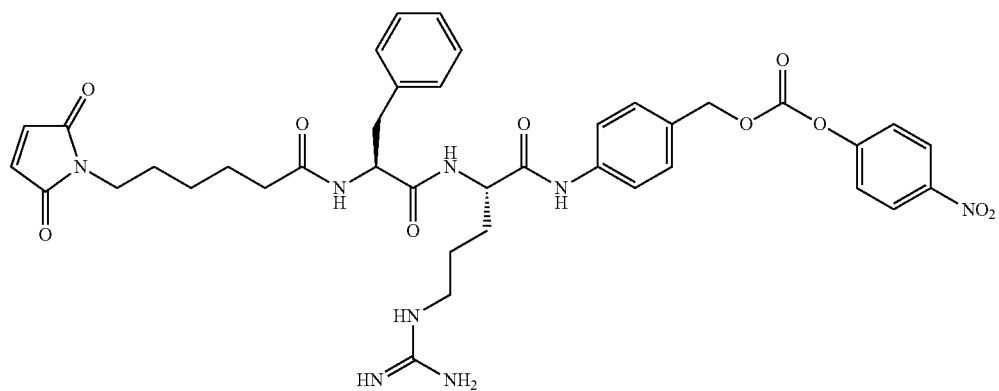

13

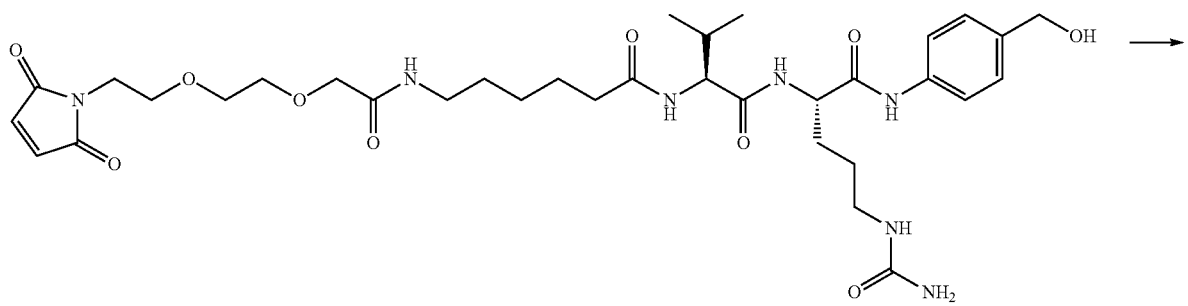

14

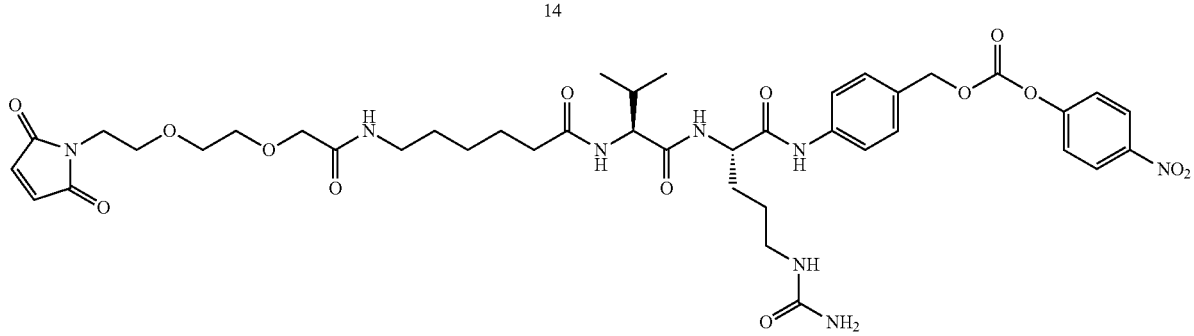

15

Piperidyl benzoxazino rifamycin (pipBOR) 5 (0.02 mmol) and 15 (0.02 mmol) were mixed in DMF (0.4 ml) at room temperature (RT). To this was added 2.5 equivalents of N,N'-diisopropylethylamine. The solution was stirred from one to about 12 hours and was monitored by LC/MS. Upon completion, the solution was diluted with DMF and injected onto HPLC and purified under acidic conditions to give MP-vc-PAB-pipBOR 53. M/Z=1644.8. Yield 57%

Example 4 MC-vc-PAB-dimethylpipBOR 54

Reaction of N,N-dimethylpiperidin-4-amine with TBS-protected benzoxazino rifamycin 4 gave dimethylpiperidyl benzoxazino rifamycin (dimethyl pipBOR) 7 (FIG. 24).

Figure 25B:
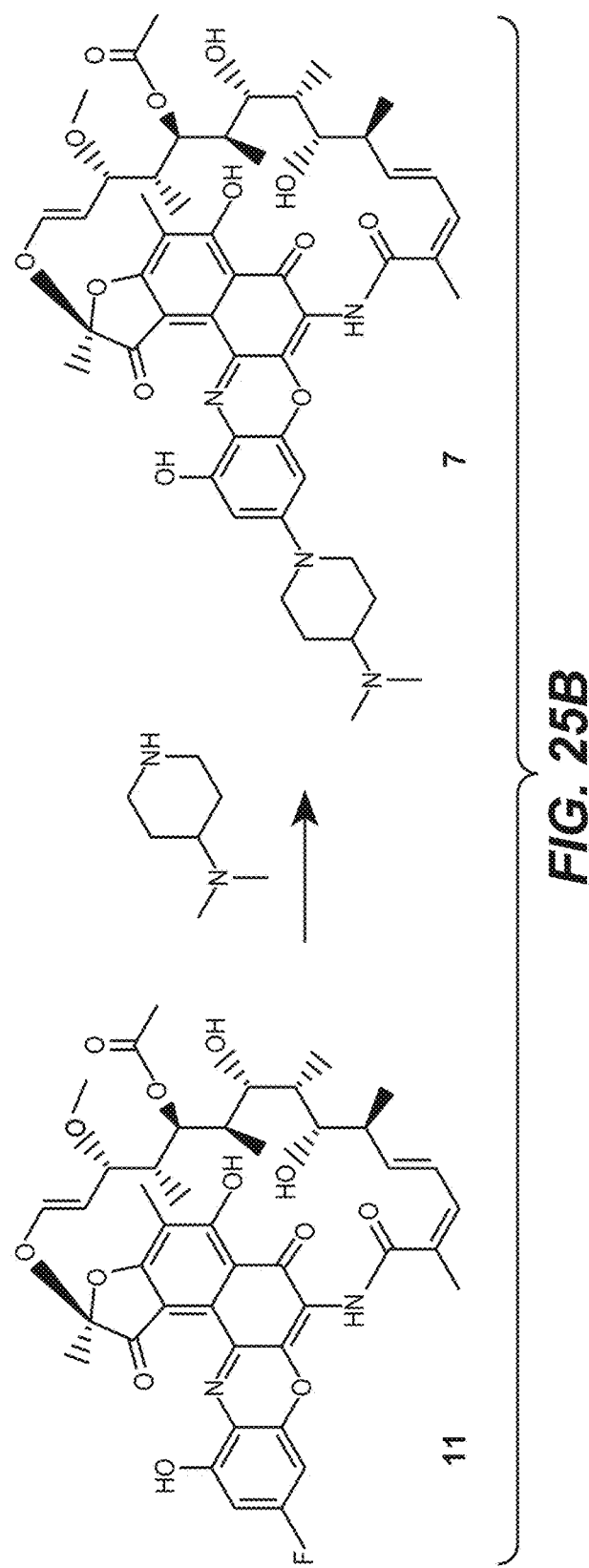

Alternatively, (5-fluoro-2-nitro-1,3-phenylene)bis(oxy)bis(methylene)dibenzene 9 was hydrogenated under hydrogen gas with palladium/carbon catalyst in tetrahydrofuran/methanol solvent to remove the benzyl groups to give 2-amino-5-fluorobenzene-1,3-diol 10. Commercially available Rifamycin S or Rifamycin SV sodium salt (Chem-Shuttle Inc., Fremont, Calif.) was reacted with 2-amino-5-fluorobenzene-1,3-diol 10 by oxidative condensation in air or potassium ferric cyanide in ethylacetate at 60° C. to give fluoro benzoxazino rifamycin 11. Displacement of fluoro with N,N-dimethylpiperidin-4-amine gave dimethyl pipBOR 7 (FIGS. 25A and 25B).

6-(2,5-Dioxo-2,5-dihydro-1H-pyrrol-1-yl)-N—((S)-1-((S)-1-(4-(hydroxymethyl)phenylamino)-1-oxo-5-ureidopentan-2-ylamino)-3-methyl-1-oxobutan-2-yl)hexanamide 8, prepared according to procedures in WO 2012113847; U.S. Pat. No. 7,659,241; U.S. Pat. No. 7,498,298; US 20090111756; US 20090018086; U.S. Pat. No. 6,214,345; Dubowchik et al (2002) Bioconjugate Chem. 13 (4):855-869 (1.009 g, 1.762 mmol, 1.000, 1009 mg) was taken up in N,N-dimethylformamide (6 mL, 77 mmol, 44, 5700 mg). To this was added a solution of thionyl chloride (1.1 equiv., 1.938 mmol, 1.100, 231 mg) in dichloromethane (DCM) (1 mL, 15.44 mmol, 8.765, 1325 mg) in portions dropwise (½ was added over 1 hour, stirred one hour at room temperature (RT) then added the other half over another hour). The solution remained a yellow color. Another 0.6 eq of thionyl chloride was added as a solution in 0.5 mL DCM dropwise, carefully. The reaction remained yellow and was stirred sealed overnight at RT. The reaction was monitored by LC/MS to 88% product benzyl chloride 9. Another 0.22 eq of thionyl chloride was added dropwise as a solution in 0.3 mL DCM. When the reaction approached 92% benzyl chloride 9, the reaction was bubbled with $N_2$. The concentration was reduced from 0.3 M to 0.6 M. The product N—((S)-1-((S)-1-(4-(chloromethyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide 9 was stored in the refrigerator as a 0.6 M solution and used as is. M/Z 591.3, 92% yield.

In a flask, N—((S)-1-((S)-1-(4-(chloromethyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide 9, (0.9 mmol) was cooled to 0° C. and dimethylpiperidyl benzoxazino rifamycin (dimethyl pipBOR) 7 (0.75 g, 0.81 mmol, 0.46, 750 mg) was added. The mixture was diluted with another 1.5 mL of DMF to reach 0.3 M. Stirred open to air for 30 minutes. N,N-diisopropylethylamine (3.5 mmol, 3.5 mmol, 2.0, 460 mg) was added and the reaction stirred overnight open to air. Over the course of 4 days, 4 additions of 0.2 eq N,N-diisopropylethylamine base was added while the reaction stirred open to air, until the reaction appeared to stop progressing. The reaction was diluted with DMF and purified on HPLC (20-60% ACN/FA.H2O) in several batches to give MC-vc-PAB-dimethylpipBOR 54.

M/Z=1482.8 yield: 32%

Example 5 MC-vc-PAB-monomethylpip, desacetylBOR 55

Following the procedures of Example 1, N-methylpiperidin-4-amine and TBS-protected desacetyl, benzoxazino rifamycin were reacted with manganese oxide to give monomethylpiperidyl benzoxazino rifamycin (pipBOR) 16.

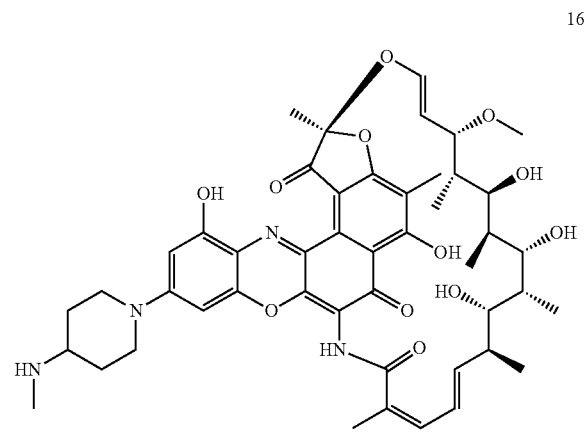

16

4-((S)-2-((S)-2-(6-(2,5-Dioxo-2,5-dihydro-1H-pyrrol-1-yl)hexanamido)-3-methylbutanamido)-5-ureidopentanamido)benzyl 4-nitrophenyl carbonate 6 and 16 were reacted to give MC-vc-PAB-monomethylpip, desacetylBOR 55 in 26% yield (M/Z=1456.5).

Example 6 MC-vc-PAB-monomethylpipBOR 56

Following the procedures of Example 1, N-methylpiperidin-4-amine and TBS-protected, benzoxazino rifamycin 4 were reacted with manganese oxide to give monomethylpiperidyl benzoxazino rifamycin (pipBOR) 17.

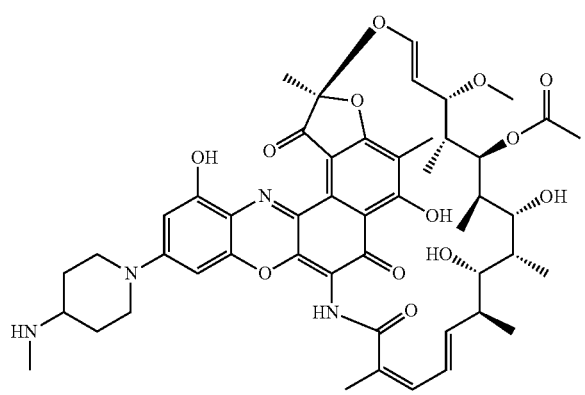

17

4-((S)-2-((S)-2-(6-(2,5-Dioxo-2,5-dihydro-1H-pyrrol-1-yl)hexanamido)-3-methylbutanamido)-5-ureidopentanamido)benzyl 4-nitrophenyl carbonate 6 and 17 were reacted to give MC-vc-PAB-monomethylpipBOR 56 in 25% yield (M/Z=1471.0).

Example 7 MC-vc-PAB-pip, desacetylBOR 57

Following the procedures of Example 1, piperidin-4-amine and TBS-protected desacetyl, benzoxazino rifamycin 18 were reacted with manganese oxide to give piperidyl, des-acetyl benzoxazino rifamycin (pip desacetyl BOR) 19.

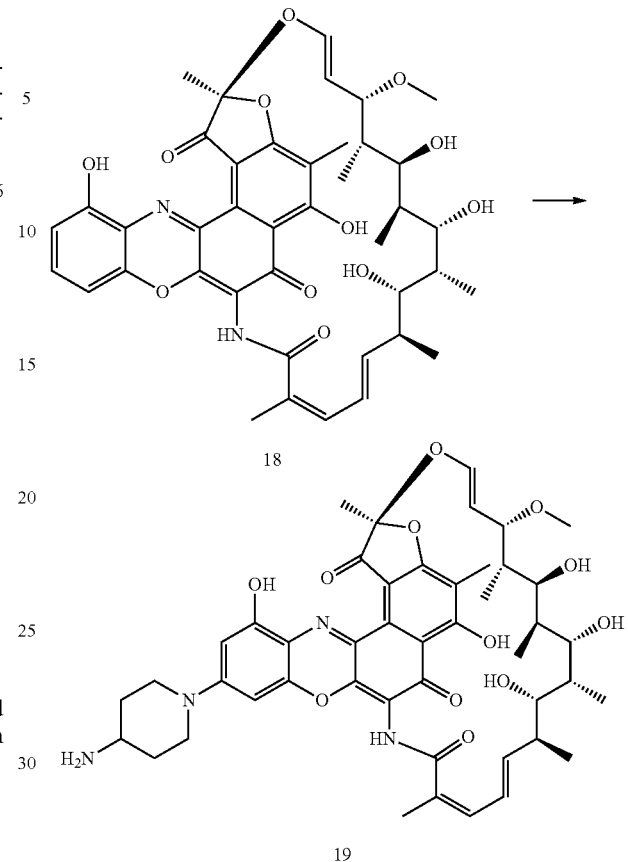

Piperidyl, des-acetyl benzoxazino rifamycin 19 (0.02 mmol) and 4-((S)-2-((S)-2-(6-(2,5-dioxo-2,5-dihydro-1H-pyrrol-1-yl)hexanamido)-3-methylbutanamido)-5-ureidopentanamido)benzyl 4-nitrophenyl carbonate 6 (0.02 mmol) were reacted to give MC-vc-PAB-pip, desacetylBOR 57. M/Z=1456.6. Yield 13%

Example 8 MC-vc-PAB-rifabutin 58

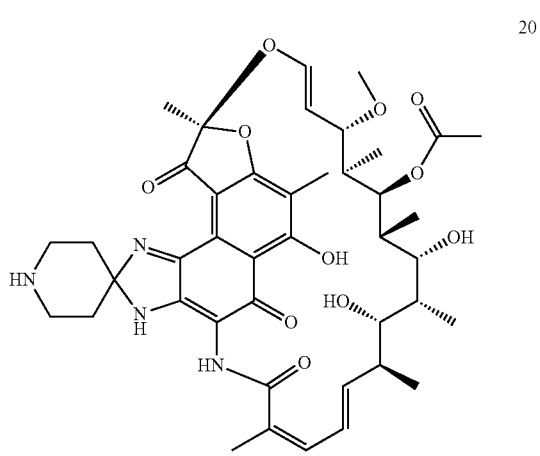 [SMILES: CO[C@H]1/C=C/O[C@@]2(C)Oc3c(C)c(O)c4c(c3C2=O)C2=NC3(CCNCC3)NC2=C(NC(=O)/C(C)=C\C=C\[C@H](C)[C@H](O)[C@@H](C)[C@@H](O)[C@@H](C)[C@H](OC(C)=O)[C@@H]1C)C4=O]

20

Following the procedures of Example 1, des-isobutyl rifabutin 20 (0.02 mmol) and 4-((S)-2-((S)-2-(6-(2,5-dioxo-2,5-dihydro-1H-pyrrol-1-yl)hexanamido)-3-methylbutanamido)-5-ureidopentanamido)benzyl 4-nitrophenyl carbonate 6 (0.02 mmol) were reacted to give MC-vc-PAB-rifabutin 58. M/Z=1389.6. Yield 21%

Example 9 MC-GGAFAGGG-pipBOR ("core peptide" disclosed as SEQ ID NO: 126) 59

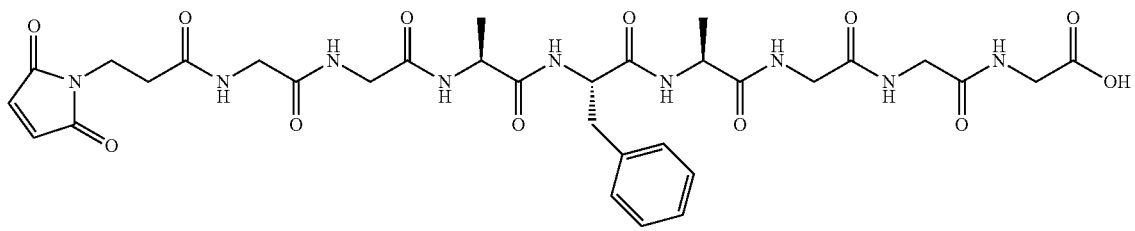

21

Following the procedures of Example 1, maleimide peptide 21 was coupled with piperidyl benzoxazino rifamycin (pipBOR) 5 under standard amide bond forming conditions to give MC-GGAFAGGG-pipBOR ("core peptide" disclosed as SEQ ID NO: 126) 59.

M/Z=1626.0. Yield 13%

Example 10 MC-vc-PAB-rif 60

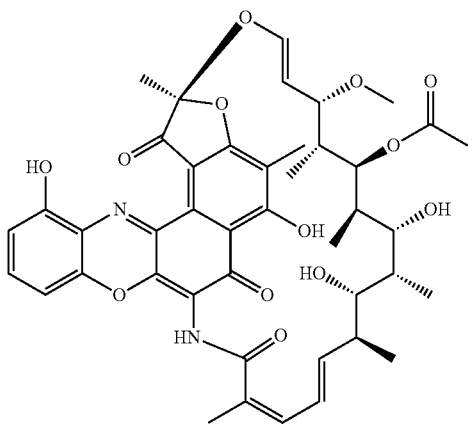

22

In a small vial, 0.05 mL of a 0.6 M solution of N—((S)-1-((S)-1-(4-(chloromethyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide 9, prepared by the procedure of Example 4 was cooled to 0° C. and 1 equiv. of benzoxazino rifamycin 22 was added and the mixture was stirred for 5 minutes. To this 0° C. solution was added K₂CO₃ (15 eq) and the sides of the vial were washed with 0.05 mL of DMF. The reaction was stirred open to air to room temperature for 1-4 hours. When all 9 was consumed, the solids were filtered off, and the collected filtrate was diluted with DMF. Purification by HPLC gave MC-vc-PAB-rif 60 in 11% yield (M/Z=1356.9).

Example 11 MC-vc-PAB-dimethylpip, desacetylBOR 61

23

Following the procedures of Example 4, N—((S)-1-((S)-1-(4-(chloromethyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide 9 was reacted with dimethylpiperidyl, desacetyl benzoxazino rifamycin (dimethyl, desacetyl pipBOR) 23 to give MC-vc-PAB-dimethylpip, desacetylBOR 61. M/Z=1440.66

Example 12 MC-vc-PAB-piperazBTR 62

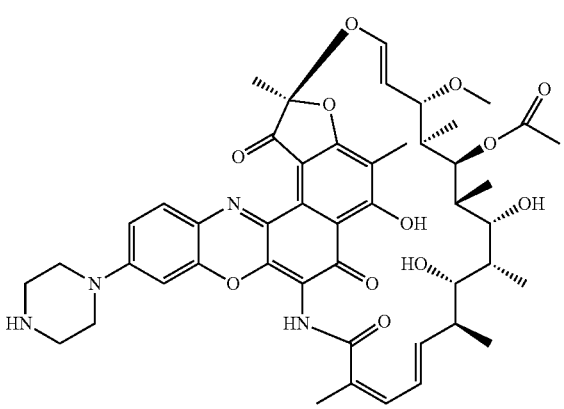

24

Following the procedures of Example 1,4-((S)-2-((S)-2-(6-(2,5-dioxo-2,5-dihydro-1H-pyrrol-1-yl)hexanamido)-3-methylbutanamido)-5-ureidopentanamido)benzyl 4-nitrophenyl carbonate 6 was reacted with piperazino benzthiazino rifamycin (piperazBTR) 24 to give MC-vc-PAB-piperazBTR 62. M/Z=1483.7

Example 13 MC-vc-PAB-piperaz, desacetylBTR 63

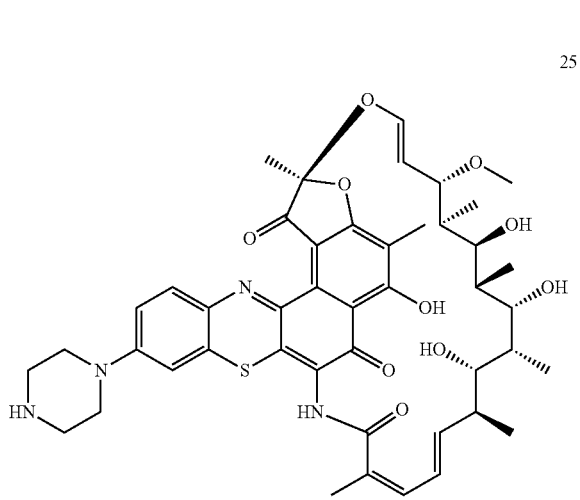 [SMILES: CO[C@H]1/C=C/O[C@@]2(C)Oc3c(C)c(O)c4c(=O)c(c5sc6cc(N7CCNCC7)ccc6nc-5c4c3C2=O)NC(=O)/C(C)=C\C=C\[C@H](C)[C@H](O)[C@@H](C)[C@@H](O)[C@@H](C)[C@H](O)[C@@H]1C]

Following the procedures of Example 1,4-((S)-2-((S)-2-(6-(2,5-dioxo-2,5-dihydro-1H-pyrrol-1-yl)hexanamido)-3-methylbutanamido)-5-ureidopentanamido)benzyl 4-nitrophenyl carbonate 6 was reacted with piperazino, desacetyl benzthiazino rifamycin (pipBTR) 25 to give MC-vc-PAB-piperaz, desacetylBTR 63. M/Z=1441.6

Example 14 MC-vc-PAB-piperaz, desacetylBOR 64

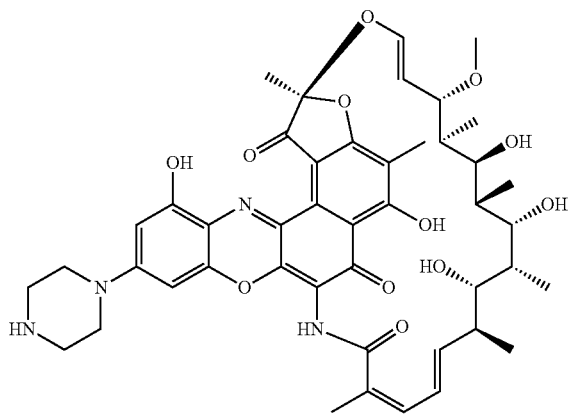

Following the procedures of Example 1,4-((S)-2-((S)-2-(6-(2,5-dioxo-2,5-dihydro-1H-pyrrol-1-yl)hexanamido)-3-methylbutanamido)-5-ureidopentanamido)benzyl 4-nitrophenyl carbonate 6 was reacted with piperazyl, desacetyl benzoxazino rifamycin (desacetyl pipBOR) 26 to give MC-vc-PAB-piperaz, desacetylBOR 64. M/Z=1441.6

Example 15 MC-vc-PAB-piperazBOR 65

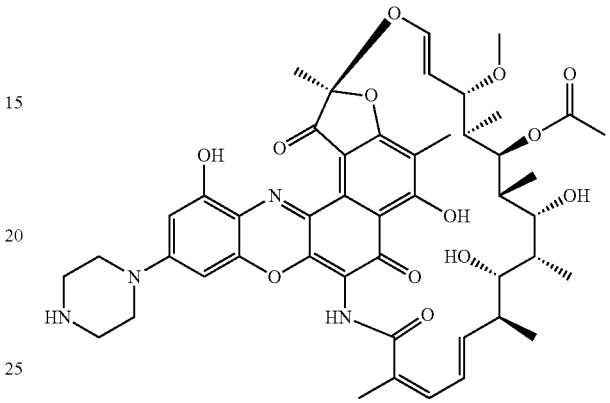

Following the procedures of Example 1,4-((S)-2-((S)-2-(6-(2,5-dioxo-2,5-dihydro-1H-pyrrol-1-yl)hexanamido)-3-methylbutanamido)-5-ureidopentanamido)benzyl 4-nitrophenyl carbonate 6 was reacted with piperazyl benzoxazino rifamycin (piperazylBOR) 27 to give MC-vc-PAB-piperazBOR 65. M/Z=1482.7

Example 16 MC-vc-bisPAB-dimethylpipBOR 66

In a vial, 4-((S)-2-((S)-2-(6-(2,5-dioxo-2,5-dihydro-1H-pyrrol-1-yl)hexanamido)-3-methylbutanamido)-5-ureidopentanamido)benzyl 4-nitrophenyl carbonate 6 (1.56 g, 2.11 mmol, 100 mass %) was taken up in DMF (55 equiv., 116 mmol, 55.0, 8.5 g) and stirred at RT. To this cloudy yellow mixture was added (4-aminophenyl)methanol (PAB, 1.1 equiv., 2.33 mmol, 1.10, 286 mg) and 1-hydroxybenzotriazole (0.37 equiv., 0.782 mmol, 0.370, 106 mg) followed by N,N'-diisopropylethylamine (1 equiv., 2.11 mmol, 1.00, 276 mg). The reaction was stirred for 2 hours and monitored by LC/MS. An additional 1 equivalent of N,N'-diisopropylethylamine (Hunigs Base) and 100 mg of (4-aminophenyl)methanol were added. The reaction was stirred overnight at RT sealed. About 0.5 L of diethyl ether was added dropwise to precipitate out product. The ether was decanted, the solid was redissolved in DMF, and purified directly onto HPLC in several batches to give 4-((S)-2-((S)-2-(6-(2,5-dioxo-2,5-dihydro-1H-pyrrol-1-yl)hexanamido)-3-methylbutanamido)-5-ureidopentanamido)benzyl 4-(hydroxymethyl)phenylcarbamate 28 (0.435 g) in 28% overall isolated yield (M/Z: 722.5), having the structure:

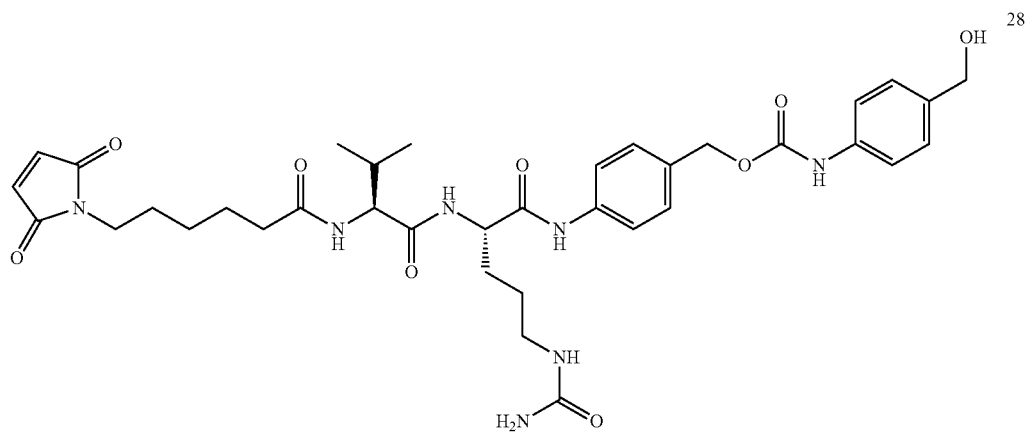 [SMILES: CC(C)[C@H](NC(=O)CCCCCN1C(=O)C=CC1=O)C(=O)N[C@@H](CCCNC(N)=O)C(=O)Nc1ccc(COC(=O)Nc2ccc(CO)cc2)cc1]

Following the procedure of Example 4,4-((S)-2-((S)-2-(6-(2,5-dioxo-2,5-dihydro-1H-pyrrol-1-yl)hexanamido)-3-methylbutanamido)-5-ureidopentanamido)benzyl 4-(hydroxymethyl)phenylcarbamate 28 was reacted with thionyl chloride to give 4-((S)-2-((S)-2-(6-(2,5-dioxo-2,5-dihydro-1H-pyrrol-1-yl)hexanamido)-3-methylbutanamido)-5-ureidopentanamido)benzyl 4-(chloromethyl)phenylcarbamate 29 in 47% isolated yield (M/Z: 740.4), having the structure:

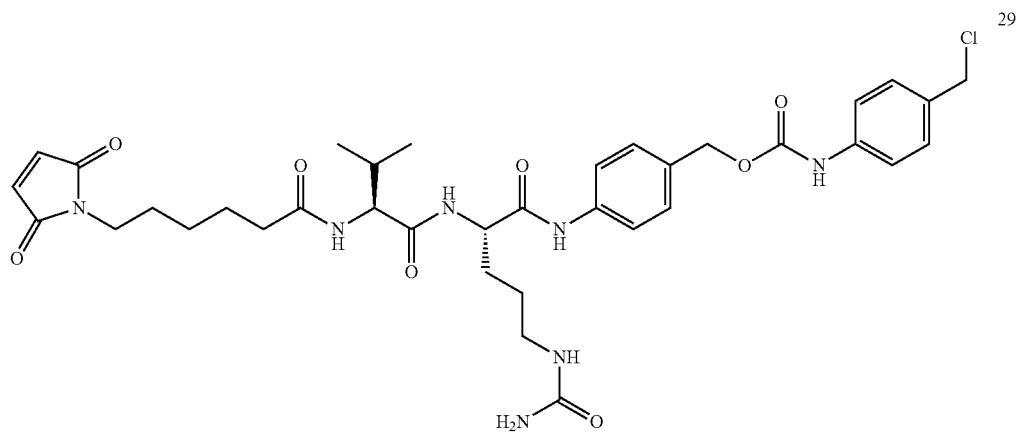 [SMILES: CC(C)[C@H](NC(=O)CCCCCN1C(=O)C=CC1=O)C(=O)N[C@@H](CCCNC(N)=O)C(=O)Nc1ccc(COC(=O)Nc2ccc(CCl)cc2)cc1]

Following the procedure of Example 4,4-((S)-2-((S)-2-(6-(2,5-dioxo-2,5-dihydro-1H-pyrrol-1-yl)hexanamido)-3-methylbutanamido)-5-ureidopentanamido)benzyl 4-(chloromethyl)phenylcarbamate 29 was reacted with dimethylpiperidyl benzoxazino rifamycin (dimethyl pipBOR) 7 to give MC-vc-bisPAB-dimethylpipBOR 66 in 5% yield (M/Z: 1632.1)

Example 17 MC-vc-PAB-methylpiperaz BOR 67

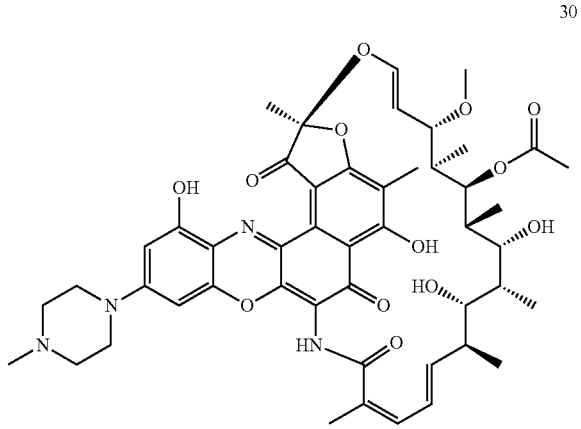 [SMILES: CO[C@H]1/C=C/O[C@@]2(C)Oc3c(C)c(O)c4c(=O)c(c5oc6cc(N7CCN(C)CC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

Following the procedure of Example 4, N—((S)-1-((S)-1-(4-(chloromethyl)phenylamino)-1-oxo-5-ureidopentan-2-ylamino)-3-methyl-1-oxobutan-2-yl)-6-(2,5-dioxo-2,5-dihydro-1H-pyrrol-1-yl)hexanamide 9 was reacted with methylpiperazino benzoxazino rifamycin (methyl piperaz-BOR) 30 to give MC-vc-PAB-methylpiperaz BOR 67. M/Z=1454.68

Example 18 Intracellular MRSA are Protected from Antibiotics

This example provides evidence that MRSA can survive intracellularly in vivo. In an infection, intracellular MRSA are protected from and able to survive antibiotic treatment (such as SOC Vancomycin), enabling transfer of infection from one cell to another.

MIC Determinations for Extracellular Bacteria:

The MIC for extracellular bacteria was determined by preparing serial 2-fold dilutions of the antibiotic in Tryptic Soy Broth. Dilutions of the antibiotic were made in quadruplicate in 96 well culture dishes. MRSA (NRS384 strain of USA300) was taken from an exponentially growing culture and diluted to $1 \times 10^4$ CFU/mL. Bacteria was cultured in the presence of antibiotic for 18-24 hours with shaking at 37° C. and bacterial growth was determined by reading the Optical Density (OD) at 630 nM. The MIC was determined to be the dose of antibiotic that inhibited bacterial growth by >90%.

MIC Determinations for Intracellular Bacteria:

Intracellular MIC was determined on bacteria that were sequestered inside mouse peritoneal macrophages. Macrophages were plated in 24 well culture dishes at a density of $4 \times 10^5$ cells/mL and infected with MRSA (NRS384 strain of USA300) at a ratio of 10-20 bacteria per macrophage. Macrophage cultures were maintained in growth media supplemented with 50 µg/mL of gentamycin to inhibit the growth of extracellular bacteria and test antibiotics were added to the growth media 1 day after infection. The survival of intracellular bacteria was assessed 24 hours after addition of the antibiotics. Macrophages were lysed with Hanks Buffered Saline Solution supplemented with 0.1% Bovine Serum Albumin and 0.1% Triton-X, and serial dilutions of the lysate were made in Phosphate Buffered Saline solution containing 0.05% Tween-20. The number of surviving intracellular bacteria was determined by plating on Tryptic Soy Agar plates with 5% defibrinated sheep blood.

Isolation of Peritoneal Macrophages:

Peritoneal macrophages were isolated from the peritoneum of 6-8 week old Balb/c mice (Charles River Laboratories, Hollister, Calif.). To increase the yield of macrophages, mice were pre-treated by intraperitoneal injection with 1 mL of thioglycolate media (Becton Dickinson). The thioglycolate media was prepared at a concentration of 4% in water, sterilized by autoclaving, and aged for 20 days to 6 months prior to use. Peritoneal macrophages were harvested 4 days post treatment with thioglycolate by washing the peritoneal cavity with cold phosphate buffered saline. Macrophages were plated in Dulbecco's Modified Eagle Medium (DMEM) supplemented with 10% Fetal Calf Serum, and 10 mM HEPES, without antibiotics, at a density of $4 \times 10^5$ cells/well in 24 well culture dishes. Macrophages were cultured over night to permit adherence to the plate. This assay was also utilized to test intracellular killing in non-phagocytic cell types. MG63 (CRL-1427) and A549 (CCL185) cell lines were obtained from ATCC and maintained in RPMI 1640 tissue culture media supplemented with 10 mM Hepes and 10% Fetal Calf Serum (RPMI-10). HUVEC cells were obtained from Lonza and maintained in EGM Endothelial Cell Complete Media (Lonza, Walkersville, Md.).

Infection of Macrophages with Opsonized MRSA:

The USA300 strain of MRSA (NRS384) was obtained from the NARSA repository (Chantilly, Va.). Some experiments utilized the Newman strain of S. aureus (ATCC25904). In all experiments bacteria were cultured in Tryptic Soy Broth. To assess intracellular killing with AAC, USA300 was taken from an exponentially growing culture and washed in HB (Hanks Balanced Salt Solution supplemented with 10 mM HEPES and 0.1% Bovine Serum Albumin). AAC or antibodies were diluted in HB and incubated with the bacteria for 1 hour to permit antibody binding to the bacteria (opsonization), and the opsonized bacteria were used to infect macrophages at a ratio of 10-20 bacteria per macrophage ($4 \times 10^6$ bacteria in 250 µL of HB per well. Macrophages were pre-washed with serum free DMEM media immediately before infection, and infected by incubation at 37° C. in a humidified tissue culture incubator with 5% $CO_2$ to permit phagocytosis of the bacteria. After 2 hours, the infection mix was removed and replaced with normal growth media (DMEM supplemented with 10% Fetal Calf Serum, 10 mM HEPES and gentamycin was added at 50 µg/ml to prevent growth of extracellular bacteria. At the end of the incubation period, the macrophages were washed with serum free media, and the cells were lysed in HB supplemented with 0.1% triton-X (lyses the macrophages without damaging the intracellular bacteria). In some experiments viability of the macrophages was assessed at the end of the culture period by detecting release of cytoplasmic lactate dehydrogenase (LDH) into the culture supernatant using an LDH Cytotoxicity Detection Kit (Product 11644793001, Roche Diagnostics Corp, Indianapolis, Ind.). Supernatants were collected and analyzed immediately according to the manufacturer's instructions. Serial dilutions of the lysate were made in phosphate buffered saline solution supplemented with 0.05% Tween-20 (to disrupt aggregates of bacteria) and the total number of surviving intracellular bacteria was determined by plating on Tryptic Soy Agar with 5% defibrinated sheep blood.

Generation of MRSA Infected Peritoneal Cells.

6-8 week old female A/J mice (JAX™ Mice, Jackson Laboratories) were infected with $1 \times 10^8$ CFU of the NRS384 strain of USA300 by peritoneal injection. The peritoneal wash was harvested 1 day post infection, and the infected peritoneal cells were treated with 50 µg/mL of lysostaphin diluted in Hepes Buffer supplemented with 0.1% BSA (HB buffer) for 30 minutes at 37° C. Peritoneal cells were then washed 2× in ice cold HB buffer. The peritoneal cells were diluted to 1×10$^6$ cells/mL in RPMI 1640 tissue culture media supplemented with 10 mM Hepes and 10% Fetal Calf Serum, and 5 µg/mL vancomycin. Free MRSA from the primary infection was stored overnight at 4° C. in Phosphate Buffered Saline Solution as a control for extracellular bacteria that were not subject to neutrophil killing.

Transfer of Infection from Peritoneal Cells to Osteoblasts:

MG63 osteoblast cell line was obtained from ATCC (CRL-1427) and maintained in RPMI 1640 tissue culture media supplemented with 10 mM Hepes and 10% Fetal Calf Serum (RPMI-10). Osteoblasts were plated in 24 well tissue culture plates and cultured to obtain a confluent layer. On the day of the experiment, the osteoblasts were washed once in RPMI (without supplements). MRSA or infected peritoneal cells were diluted in complete RPMI-10 and vancomycin was added at 5 µg/mL immediately prior to infection. Peritoneal cells were added to the osteoblasts at 1×10$^6$ peritoneal cells/mL. A sample of the cells was lysed with 0.1% triton-x to determine the actual concentration of live intracellular bacteria at the time of infection. The actual titer for all infections was determined by plating serial dilutions of the bacteria on Tryptic Soy Agar with 5% defibrinated sheep blood.

MG63 osteoblasts were plated in 4 well glass chamber slides and cultured in RPMI 1640 tissue culture media supplemented with 10 mM Hepes and 10% Fetal Calf Serum (RPMI-10) until they formed confluent layers. On the day of infection, the wells were washed with serum free media and infected with a suspension of infected peritoneal cells, or with the USA300 strain of MRSA diluted in complete RPMI-10 supplemented with 5 µg/mL of vancomycin. One day after infection, the cells were washed with phosphate buffered saline (PBS) and fixed for 30 minutes at room temperature in PBS with 2% paraformaldehyde. Wells were washed 3× in PBS and permeabilized with PBS with 0.1% saponin for 30 minutes at room temperature.

Immunofluorescence:

MRSA was identified by staining with 20 µg/mL of rabbit anti-Staph 20920, (abcam, Cambridge, Mass.) followed by anti-rabbit Rhodamine (Jackson ImmunoResearch, 711-026-152). The cell membranes of peritoneal cells were stained with Cholera-Toxin-Beta subunit-biotin (Invitrogen, Carlsbad, Calif.) followed by streptavidin Cy5 (BD Biosciences San Jose, Calif.). Binding of the cholera-toxin to peritoneal cells was confirmed by co-staining with anti-CD11b Alexa 488 clone M1/70 (BD biosciences). Slides were mounted with Prolong Gold with DAPI (Invitrogen, Carlsbad Calif.). Slides were viewed using a Leica SPE confocal microscope. Images were collected as a series of Z-stacks and compiled to generate the maximum projection images shown.

Survival of *S. aureus* inside mammalian cells provides a viable niche that permits persistent infection in the presence of antibiotic therapy. *S. aureus* is able to infect and survive inside a number of mammalian cell types including neutrophils, macrophages, osteoblasts and epithelial cells (Garzoni, C. and W. L. Kelley (2009) *Trends Microbiol* 17(2): 59-65). To test directly whether intracellular MRSA is protected from antibiotics, a number of clinically approved antibiotics were compared for their ability to kill extracellular MRSA cultured in standard bacterial growth media, with their ability to kill intracellular MRSA that is sequestered inside murine macrophages (Table 1). Murine peritoneal macrophages were selected for this analysis because these cells represent a genetically normal primary cell type that is a natural component of the innate immune response to *S. aureus*. Analysis confirmed that these cells are easily infected and cultured in vitro. MRSA is able to survive intracellularly for up to six days after infection of the macrophages (Kubica, M., K. Guzik, et al. (2008) *PLoS One* 3 (1): e1409). To test the intracellular effect of antibiotics, macrophages were infected with MRSA, and cultured in the presence of gentamycin, an antibiotic that is known to be inactive inside the phagolysosome due to poor cellular uptake of the antibiotic (Vaudaux, P. and F. A. Waldvogel (1979) *Antimicrob Agents Chemother* 16 (6): 743-749). Test antibiotics were added to the culture media (in addition to gentamycin) one day after infection at a range of doses chosen to include the clinically achievable serum levels (shown as serum Cmax in Table 1). This analysis revealed that although extracellular MRSA is highly susceptible to growth inhibition by low doses of vancomycin, daptomycin, linezolid or rifampicin in liquid culture, all four antibiotics failed to kill the same strain of intracellular MRSA that was sequestered inside macrophages. Remarkably, even rifampicin, which is reported to be one of the best antibiotics for treating intracellular infections such at tuberculosis yielded minimal killing of intracellular MRSA over the time and dose range of the experiment.

TABLE 1

Minimum inhibitory concentrations (MIC) of several antibiotics

| Antibiotics (Abx) | Extracellular MRSA MIC (µg/mL) | Intracellular MRSA MIC (µg/mL) | Serum Cmax (µg/mL) |
| --- | --- | --- | --- |
| Vancomycin | 1 | >100 | 10-40 |
| Daptomycin | 4 | >100 | 80 |
| Linezolid | 0.3 | >20 | 10 |
| Rifampicin | 0.004 | >20 | 20 |

The above data confirmed that intracellular bacteria are protected from antibiotics during the time that they are sequestered inside cells. However, MRSA is not thought to be a true intracellular pathogen in that it is not able to infect neighboring cells by direct cell to cell transfer, and the majority of infected cells will eventually lyse releasing the intracellular bacteria. Therefore, it remained possible that the intracellular pool, once released, would inevitably be exposed to extracellular antibiotics at least transiently, even if the bacteria were immediately taken up by neighboring cells. Uptake of free MRSA by macrophages requires between 15 and 90 minutes (data not shown), suggesting that if the bacteria were able to resist a brief exposure to antibiotic, it could remain protected in the intracellular niche by moving sequentially from a dying cell to a new host. To determine whether a brief exposure to antibiotics was sufficient to kill MRSA, vancomycin, the current standard of care treatment for MRSA infections, and rifampin were tested. MRSA was taken from an actively growing culture and diluted to 1×10$^6$ bacteria/mL in normal growth media. Antibiotics were added at two doses representing between 2× and 10× the expected minimum inhibitory concentration (MIC). Samples were removed at various times between 30 minutes and 5 hours, and the antibiotic was removed by centrifugation and dilution. The total number of surviving bacteria in the culture was determined by plating on agar plates.

FIG. 1 shows comparison of the time of kill for vancomycin (vanco) and rifampicin (Rifa) on actively dividing MRSA. MRSA was cultured for 5 hours in TSB media in the presence of antibiotics. At the indicated times, a sample of the culture was taken and the antibiotic was removed by centrifugation. The total number of surviving bacteria was determined at each time point by plating. Vancomycin was tested at 2 μg/mL (open square) and 20 μg/mL (closed square). Rifampin was tested at 0.02 μg/mL (open triangle) and 0.2 μg/mL (closed triangle). These data (FIG. 1) revealed that although both antibiotics were able to inhibit bacterial growth effectively, and by 5 hours a 100 fold loss in viable bacteria was observed, the bacteria were killed gradually over the 5 hour observation period and 90% of the bacteria remained viable during the first two hours of antibiotic treatment permitting ample time for potential uptake by host cells.

Intracellular stores of MRSA were assayed for transfer of infection to a permissive intracellular niche in the presence of vancomycin. S. aureus can survive inside osteoblasts, and intracellular stores of S. aureus have been observed in patients with osteomyelitis, a condition where chronic infection with S. aureus is known to be recalcitrant to antibiotic treatment (Thwaites and Gant, (2011) Nature Reviews Microbiology 9:215-222; Ellington et al., (2006) J. Orthopedic Research 24 (1): 87-93; Bosse et al., (2005) J. Bone and Joint Surgery, 87(6): 1343-1347). An in vitro assay was developed using an osteoblast cell line MG63 since this cell line was reported to be capable of harboring intracellular S. aureus (Garzoni and Kelly, (2008) Trends in Microbiology). This assay confirmed that MRSA is able to infect MG63 cells, and viable intracellular bacteria can be recovered from infected MG63 cells for up to 6 days in vitro. To generate a pool of intracellular S. aureus, peritoneal cells were harvested from mice that were infected by peritoneal injection of MRSA (FIG. 2).

FIG. 2 shows transfer of infection from infected peritoneal cells to osteoblasts in the presence of vancomycin. To generate a pool of intracellular S. aureus, A/J mice were infected with MRSA and infected peritoneal cells were taken 1 day post infection. Similarly generated cells have been reported to harbor viable intracellular bacteria that are capable of transferring infection in an in vivo infection model (Gresham et al J Immunol 2000; 164:3713-3722). The infected peritoneal cells consisted of a mixture of primarily neutrophils and macrophages and approximately 10% of the cells harbored intracellular bacteria. The cells were treated with lysostaphin to remove extracellular bacteria and suspended in growth media supplemented with 5 μg/mL of vancomycin. A sample of the peritoneal cells used for infection was lysed to determine the precise dose of viable intracellular MRSA at the time infection was initiated, and various doses of free extracellular MRSA were also diluted into media with vancomycin for comparison. The peritoneal cells (intracellular MRSA), or free bacteria (extracellular MRSA) were then added to monolayers of MG63 osteoblasts and cultured for 4 hours (open bars) or 1 day (closed bars). The total number of surviving intracellular bacteria in each well was determined by plating cell lysates on agar plates. Intracellular MRSA were protected from vancomycin compared to the extracellular MRSA controls. Wells infected with $3 \times 10^4$ intracellular bacteria yielded 8,750 intracellular bacteria (about 1 third of the infection dose) 1 day after infection, whereas the extracellular bacteria were efficiently killed as infection with a similar dose of free MRSA yielded only 375 intracellular bacteria 1 day post infection Immunofluorescence microscopy also demonstrated transfer of infection from peritoneal cells to MG63 osteoblasts. Peritoneal cells were collected from mice 1 day after infection with MRSA and treated with lysostaphin to kill any contaminating extracellular bacteria (Intracellular Infection). Free MRSA was taken from an actively growing culture and washed in PBS (Extracellular Infection). The total number of viable bacteria in the Intracellular and Extracellular infection samples was confirmed by plating on agar plates and both samples were suspended in media supplemented with 5 μg/mL of vancomycin immediately before addition to confluent layers of MG63 osteoblasts cultured in chamber slides. One day after infection, the MG63 cells were washed to remove extracellular bacteria, permeabilized and stained with an anti-S. aureus antibody to identify intracellular MRSA and cholera toxin which bound preferentially to the peritoneal cell membranes. All of the cell nuclei were co-stained with DAPI to confirm that the MG63 monolayer was intact. Slides were examined by confocal microscopy.

Wells infected with peritoneal cells contained a confluent monolayer of MG63 cells and peritoneal macrophages were clearly visible on top of the MG63 layer. Many of the macrophages were clearly infected with MRSA which is visible as clusters of red bacteria in the single color image or white particles in the overlay image. In addition to the infected macrophages, clear examples were observed of bacteria that were associated only with the MG63 cells. These infected MG63 cells were also visible in wells that were infected with the free MRSA. Infection with free MRSA required a much higher inoculum to achieve a similar level of infection in the MG63 cells.

The above results established that both free MRSA and intracellular MRSA are able to survive and infect MG63 cells in the presence of vancomycin. Bacteria from the intracellular infection were significantly better able to survive vancomycin treatment than the free bacteria under these conditions. Infection with $3 \times 10^4$ CFU of intracellular bacteria yielded $8.7 \times 10^3$ CFUs of intracellular bacteria 1 day post infection. Infection with a similar dose of free bacteria yielded only 375 intracellular bacteria 1 day post infection, indicating that the intracellular bacteria were up to 20 times better able to survive than the free bacteria. All infection doses recovered more intracellular bacteria (between 1.5 to 6 times) when wells were harvested 1 day vs. 4 hours after infection. Since vancomycin completely inhibits growth when added to free MRSA (FIG. 1), these data suggest that the MRSA must have replicated at some time despite constant exposure to vancomycin in the culture media. Although MRSA does not replicate significantly inside murine macrophages (our unpublished observations), there is considerable evidence that S. aureus is able to escape the phagolysosome and replicate within the cytoplasm of non-phagocytic cell types (Jarry, T. M., G. Memmi, et al. (2008) Cell Microbiol 10 (9): 1801-1814). Together the above observations suggest that even under constant exposure to vancomycin, free MRSA can infect cells and intracellular MRSA can transfer from one cell to another cell. These observations reveal a potential mechanism for maintenance and even spread of infection that could occur in the presence of constant antibiotic therapy.

Example 19 In Vivo Infection Models

Peritonitis Model.

7 week old female A/J mice (Jackson Laboratories) were infected by peritoneal injection with $5 \times 10^7$ CFU of USA300. Mice were sacrificed 2 days post infection and the peritoneum was flushed with 5 mL of cold phosphate buffered saline solution (PBS). Kidneys were homogenized in 5 mL of PBS as described below for the intravenous infection model. Peritoneal washes were centrifuged for 5 minutes at 1,000 rpm at 4° C. in a table top centrifuge. The supernatant was collected as the extracellular bacteria and the cell pellet containing peritoneal cells was collected as the intracellular fraction. The cells were treated with 50 μg/mL of lysostaphin for 20 minutes at 37° C. to kill contaminating extracellular bacteria. Peritoneal cells were washed 3× in ice cold PBS to remove the lysostaphin prior to analysis. To count the number of intracellular CFUs, peritoneal cells were lysed in HB (Hanks Balanced Salt Solution supplemented with 10 mM HEPES and 0.1% Bovine Serum Albumin) with 0.1% Triton-X, and serial dilutions of the lysate were made in PBS with 0.05% tween-20.

Intravenous Infection Model:

7 week old female mice were used for all in vivo experiments and infections were carried out by intravenous injection into the tail vein. A/J mice (Jackson Lab) were infected with a dose of $2\times10^6$ CFU. Balb/c mice (Charles River Laboratories, Hollister, Calif.) were infected with a dose of $2\times10^7$ CFU. For studies examining the role of competing human IgG (SCID IVIG model), CB17.SCID mice (Charles River Laboratories, Hollister, Calif.) were reconstituted with GammaGard S/D IGIV Immune Globulin (ASD Healthcare, Brooks Ky.) using a dosing regimen optimized to achieve constant serum levels of >10 mg/mL of human IgG. IGIV was administered with an initial intravenous dose of 30 mg per mouse followed by a second dose of 15 mg/mouse by intraperitoneal injection after 6 hours, and subsequent daily dosings of 15 mg per mouse by intraperitoneal injection for 3 consecutive days. Mice were infected 4 hours after the first dose of IGIV with $2\times10^7$ CFU of MRSA diluted in phosphate buffered saline by intravenous injection. Mice that received vancomycin were treated with twice daily intraperitoneal injections of 100 mg/Kg of vancomycin starting between 6 and 24 hours post infection for the duration of the study. Experimental therapeutics (AAC, anti-MRSA antibodies or free dimethyl-pipBOR antibiotic) were diluted in phosphate buffered saline and administered with a single intravenous injection 30 minutes to 24 hours after infection. All mice were sacrificed on day 4 after infection, and kidneys were harvested in 5 mL of phosphate buffered saline. The tissue samples were homogenized using a GentleMACS Dissociator™ (Miltenyi Biotec, Auburn, Calif.). The total number of bacteria recovered per mouse (2 kidneys) was determined by plating serial dilutions of the tissue homogenate in PBS 0.05% Tween on Tryptic Soy Agar with 5% defibrinated sheep blood.

Example 20 Cathepsin/Caspase Release Assay

To quantify the amount of active antibiotic released from AAC following treatment with cathepsin B, AAC were diluted to 200 μg/mL in cathepsin buffer (20 mM Sodium Acetate, 1 mM EDTA, 5 mM L-Cysteine). See: page 863 of Dubowchik et al (2002) Bioconj. Chem. 13:855-869, incorporated by reference for the purposes of this assay. Cathepsin B (from bovine spleen, SIGMA C7800) was added at 10 μg/mL and the samples were incubated for 1 hour at 37° C. As a control, AAC were incubated in buffer alone. The reaction was stopped by addition of 10 volumes of bacterial growth media, Tryptic Soy Broth pH 7.4 (TSB). To estimate the total release of active antibiotic, serial dilutions of the reaction mixture were made in quadruplicate in TSB in 96 well plates and the USA300 strain of S. aureus was added to each well at a final density of $2\times10^3$ CFU/mL. The cultures were incubated over night at 3° C. with shaking and bacterial growth was measured by reading absorbance at 630 nM using a plate reader.

Example 21 Production of Anti-WTA Antibodies

Antibody Generation, Screening and Selection

Abbreviations: MRSA (methicillin-resistant S. aureus); MSSA (methicillin-sensitive S. aureus); VISA (vancomycin intermediate-resistant S. aureus); LTA (lipoteichoic acid); TSB (tryptic soy broth); CWP (cell wall preparation).

Human IgG antibodies were cloned from peripheral B cells from patients post S. aureus infection using the Symplex™ technology (Symphogen, Lyngby, Denmark) which conserves the cognate pairing of antibody heavy and light chains, as described in U.S. Pat. No. 8,283,294: "Method for cloning cognate antibodies"; Meijer P J et al. Journal of Molecular Biology 358:764-772 (2006); and Lantto J et al. J. Virol. 85 (4):1820-33 (February 2011); Plasma and memory cells were used as genetic source for the recombinant full-length IgG repertoires. Individual antibody clones were expressed by transfection of mammalian cells as described in Meijer P J, et al. Methods in Molecular Biology 525: 261-277, xiv. (2009). Supernatants containing full length IgG1 antibodies were harvested after seven days and used to screen for antigen binding by indirect ELISA in the primary screening. A library of mAbs showing positive ELISA binding to cell wall preparations from USA300 or Wood46 strain S. aureus strains was generated. Antibodies were subsequently produced in 200-ml transient transfections and purified with Protein A chromatography (MabSelect SuRe, GE Life Sciences, Piscataway, N.J.) for further testing. For larger scale antibody production, antibodies were produced in CHO cells. Vectors coding for VL and VH were transfected into CHO cells and IgG was purified from cell culture media by protein A affinity chromatography.

TABLE 7

List of antigens used to isolate the Abs

| Ag | Description | Vendor/source | Coating |
|---|---|---|---|
| WTA | Wall Teichoic acid (WTA) from Staph A. Cat. No. R84500 (2 mg/vial), lot no. 5E14909. | Meridian Life Sciences | 2 μg/ml |
| PGN | Peptidoglycan from Staphylococcus aureus; Cat no. 77140, lot no. 1396845 | Sigma | 2 μg/ml |
| CW #1 | CW USA300, RPMI, iron deplet. Stationary Phase | Genentech, 100x | |
| CW #3 | CW USA300, TSB. Stationary Phase | Genentech, 500X | |
| CW #4 | CW Wood46, TSB. Stationary Phase | Genentech, 500X | |

CW#1 and CW#3 were always mixed together in making the ELISA coating:

FIG. 6 summarizes the primary screening of the antibodies by the ELISA. All (except 4569) were isolated when screened with the USA300 Cell wall prep mixture (iron depleted:TSB in a 96:4 ratio). All GlcNAc beta (except 6259), SDR, and PGN (4479) mAbs were also positive for PGN and WTA in primary screening. All GlcNAc alpha were found exclusively by screening for binding with the USA300 CW mix. The 4569 (LTA specific) was found by screening on Wood46 CWP.

Selection of Anti-WTA mAb from the Library Using Ex Vivo Flow Cytometry

Each mAb within this library was queried for three selection criteria: (1) relative intensity of mAb binding to the MRSA surface, as an indication of high expression of the corresponding cognate antigen which would favor high antibiotic delivery; (2) consistency of mAb binding to MRSA isolated from a diverse variety of infected tissues, as an indication of the stable expression of the cognate antigen at the MRSA surface in vivo during infections; and (3) mAb binding capacity to a panel of clinical *S. aureus* strains, as an indication of conservation of expression of the cognate surface antigen. To this end, flow cytometry was used to test all of these pre-selected culture supernatants of mAbs in the library for reactivity with *S. aureus* from a variety of infected tissues and from different *S. aureus* strains.

All mAbs in the library were analyzed for their capacity to bind MRSA from infected kidneys, spleens, livers, and lungs from mice which were infected with MRSA USA300; and within hearts or kidneys from rabbits which were infected with USA300 COL in a rabbit endocarditis model. The capacity of an antibody to recognize *S. aureus* from a variety of infected tissues raises the probability of the therapeutic antibody being active in a wide variety of different clinical infections with *S. aureus*. Bacteria were analyzed immediately upon harvest of the organs, i.e. without subculture, to prevent phenotypic changes caused by in vitro culture conditions. We had previously observed that several *S. aureus* surface antigens, while being expressed during in vitro culture, lost expression in infected tissues. Antibodies directed against such antigens would be unlikely to be useful to treat infections. During the analysis of this mAb library on a variety of infected tissues, this observation was confirmed for a significant number of antibodies, which showed significant binding to *S. aureus* bacteria from culture, but absence of binding to bacteria from all of the tested infected tissues. Some antibodies bound to bacteria from some but not all tested infected tissues. Therefore, in the present invention, we selected for antibodies that were able to recognize bacteria from all infection conditions tested. Parameters that were assessed were (1) relative fluorescence intensity, as a measure for antigen abundance; (2) number of organs that stained positive, as a measure for stability of antigen expression; and (3) mAb binding capacity to a panel of clinical *S. aureus* strains as an indication of conservation of expression of the cognate surface antigen. Fluorescence intensity of the test antibodies was determined as relative to an isotype control antibody that was directed against a non-relevant antigen, for example, IgG1 mAb anti-herpes virus gD:5237 (referenced below). mAbs against WTA-beta not only showed the highest antigen abundance, but also showed very consistent binding to MRSA from all infected tissues tested and specified above.

Additionally, we tested the capacity of these mAbs to bind to the following *S. aureus* strains, which were cultured in vitro in TSB: USA300 (MRSA), USA400 (MRSA), COL (MRSA), MRSA252 (MRSA), Wood46 (MSSA), Rosenbach (MSSA), Newman (MSSA), and Mu50 (VISA). Anti-WTA beta mAbs but not anti-WTA alpha mAbs were found to be reactive with all of these strains. The analysis of binding to different strains indicated that WTA beta is more conserved than WTA alpha and therefore more suitable for AAC.

Example 22 Characterization of Antibodies with Specificity Against Wall Teichoic Acids on *S. aureus* i) Confirming WTA Specificity of Abs

Cell wall preparations (CWP) from a *S. aureus* wild-type (WT) strain and a *S. aureus* mutant strain lacking WTA (ΔTagO; WTA-null strain) were generated by incubating 40 mg of pelleted *S. aureus* strains with 1 mL of 10 mM Tris-HCl (pH 7.4) supplemented with 30% raffinose, 100 μg/ml of lysostaphin (Cell Sciences, Canton, Mass.), and EDTA-free protease inhibitor cocktail (Roche, Pleasanton, Calif.), for 30 min at 37° C. The lysates were centrifuged at 11,600×g for 5 min, and the supernatants containing cell wall components were collected. For immunoblot analysis, proteins were separated on a 4-12% Tris-glycine gel, and transferred to a nitrocellulose membrane (Invitrogen, Carlsbad, Calif.), followed by blotting with indicated test antibodies against WTA, or with control antibodies against PGN and LTA.

Immunoblotting shows that the antibodies against WTA bind to WT cell wall preparations from WT *S. aureus* but not to cell wall preparations from the ΔTagO strain lacking WTA. The control antibodies against peptidoglycan (anti-PGN) and lipoteichoic acid (anti-LTA) bind well to both cell wall preparations. These data indicate the specificity of the test antibodies against WTA.

ii) Flow Cytometry to Determine Extent of mAb Binding to MRSA Surface

Surface antigen expression on whole bacteria from infected tissues was analyzed by flow cytometry using the following protocol. For antibody staining of bacteria from infected mouse tissues, 6-8 weeks old female C57B1/6 mice (Charles River, Wilmington, Mass.) were injected intravenously with $10^8$ CFU of log phase-grown USA300 in PBS. Mouse organs were harvested two days after infection. Rabbit infective endocarditis (IE) was established as previously described in Tattevin P. et al. Antimicrobial agents and chemotherapy 54: 610-613 (2010). Rabbits were injected intravenously with $5 \times 10^7$ CFU of stationary-phase grown MRSA strain COL, and heart vegetations were harvested eighteen hours later. Treatment with 30 mg/kg of vancomycin was given intravenously b.i.d. 18 h after infection with $7 \times 10^7$ CFU stationary-phase To lyse mouse or rabbit cells, tissues were homogenized in M tubes (Miltenyi, Auburn, Calif.) using a gentleMACS cell dissociator (Miltenyi), followed by incubation for 10 min at RT in PBS containing 0.1% Triton-X100 (Thermo), 10 μg/mL of DNAseI (Roche) and Complete Mini protease inhibitor cocktail (Roche). The suspensions were passed through a 40 micron filter (BD), and washed with HBSS without phenol red supplemented with 0.1% IgG free BSA (Sigma) and 10 mM Hepes, pH 7.4 (HB buffer). The bacterial suspensions were next incubated with 300 μg/mL of rabbit IgG (Sigma) in HB buffer for 1 h at room temperature (RT) to block nonspecific IgG binding. Bacteria were stained with 2 μg/mL of primary antibodies, including rF1 or isotype control IgG1 mAb anti-herpes virus gD:5237 (Nakamura G R et al., J Virol 67: 6179-6191 (1993)), and next with fluorescent anti-human IgG secondary antibodies (Jackson Immunoresearch, West Grove, Pa.). In order to enable differentiation of bacteria from mouse or rabbit organ debris, a double staining was performed using 20 g/mL mouse mAb 702 anti-*S. aureus* peptidoglycan (Abcam, Cambridge, Mass.) and a fluorochrome-labeled anti-mouse IgG secondary antibody (Jackson Immunoresearch). The bacteria were washed and analyzed by FACSCalibur (BD).

During flow cytometry analysis, bacteria were gated for positive staining with mAb 702 from double fluorescence plots.

iii) Measuring Binding Affinity to *S. aureus* and Antigen Density on MRSA

Table 8 shows equilibrium binding analysis of MRSA antibodies binding to Newman-ΔSPA strain, and the antigen density on the bacterium.

TABLE 8

| MRSA Antibody | Specificity | ave$K_D$, nM (n = 2) | Antigen Density, aveSites/Bacterium |
|---|---|---|---|
| 4497 | b-WTA | 2.5 | 50,000 |
| 4462 | b-WTA | 3.1 | 43,000 |
| 6263 | b-WTA | 1.4 | 22,000 |
| 6297 | b-WTA | 1.1 | 21,000 |
| 7578 | a-WTA | 0.4 | 16,000 |
| rF1 | SDR-glyco | 0.3 | 1600 |

The $K_D$ and antigen density were derived using a radioligand cell binding assay under the following assay conditions: DMEM+2.5% mouse serum binding buffer; solution binding for 2 hrs at room temperature (RT); and using 400,000 bacteria/well. Ab 6263 is 6078-like in that the sequences are very similar. Except for the second residue (R versus G) in CDR H3, all the other L and H chain CDR sequences are identical.

Example 23 Engineering WTA Antibody Mutants

In summary, the VH region of each of the anti-WTA beta Abs were cloned out and linked to human H chain gamma1 constant region and the VL linked to kappa constant region to express the Abs as IgG1. In some cases the wild type sequences were altered at certain positions to improve the antibody stability as described below. Cysteine engineered Abs (ThioMabs) were then generated.

i. Linking Variable Regions to Constant Regions

The VH regions of the WTA beta Abs identified from the human antibody library above were linked to human γ1 constant regions to make full length IgG1 Abs. The L chains were kappa L chains.

ii. Generating Stability Variants

The WTA Abs in FIG. 14, (see in particular, FIGS. 15A, 15B, 16A, 16B) were engineered to improve certain properties (such as to avoid deamidation, aspartic acid isomerization, oxidation or N-linked glycosylation) and tested for retention of antigen binding as well as chemical stability after amino acid replacements. Single stranded DNA of clones encoding the heavy or light chains was purified from M13KO7 phage particles grown in *E. coli* CJ236 cells using a QIAprep Spin M13 kit (Qiagen). 5' phosphorylated synthetic oligonucleotides with the sequences:

```
                                    (SEQ ID NO. 152)
5'-CCCAGACTGCACCAGCTGGATCTCTGAATGTACTCCAGTTGC-3'

(SEQ ID NO. 153)
5'-CCAGACTGCACCAGCTGCACCTCTGAATGTACTCCAGTTGC-3'

(SEQ ID NO. 154)
5'CCAGGGTTCCCTGGCCCCAWTMGTCAAGTCCASCWKCACCTCT
TGCACAGTAATAGACAGC-3'
and;
```

```
                                    (SEQ ID NO. 155)
5'-CCTGGCCCCAGTCGTCAAGTCCTCCTTCACCTCTTGCACA
GTAATAGACAGC-3'
(IUPAC codes)
``` were used to mutate the clones encoding the antibodies by oligonucleotide-directed site mutagenesis as described by site-specific mutagenesis following the methodology as described in Kunkel, T. A. (1985). Rapid and efficient site-specific mutagenesis without phenotypic selection. Proceedings of the National Academy of Sciences USA 82 (2): 488-492. Mutagenized DNA was used to transform *E. coli* XL1-Blue cells (Agilent Technologies) and plated on Luria Broth plates containing 50 µg/ml Carbenicillin. Colonies were individually picked and grown in liquid Luria Broth media containing 50 µg/ml Carbenicillin. Miniprep DNA was sequenced to confirm the presence of mutations.

For Ab 6078, the second amino acid in the VH, met (met-2), is prone to oxidation. Therefore met-2 was mutated to Ile or Val, to avoid oxidation of the residue. Since the alteration of met-2 may affect binding affinity, the mutants were tested for binding to Staph CWP by ELISA.

Figures 18A, 18B:
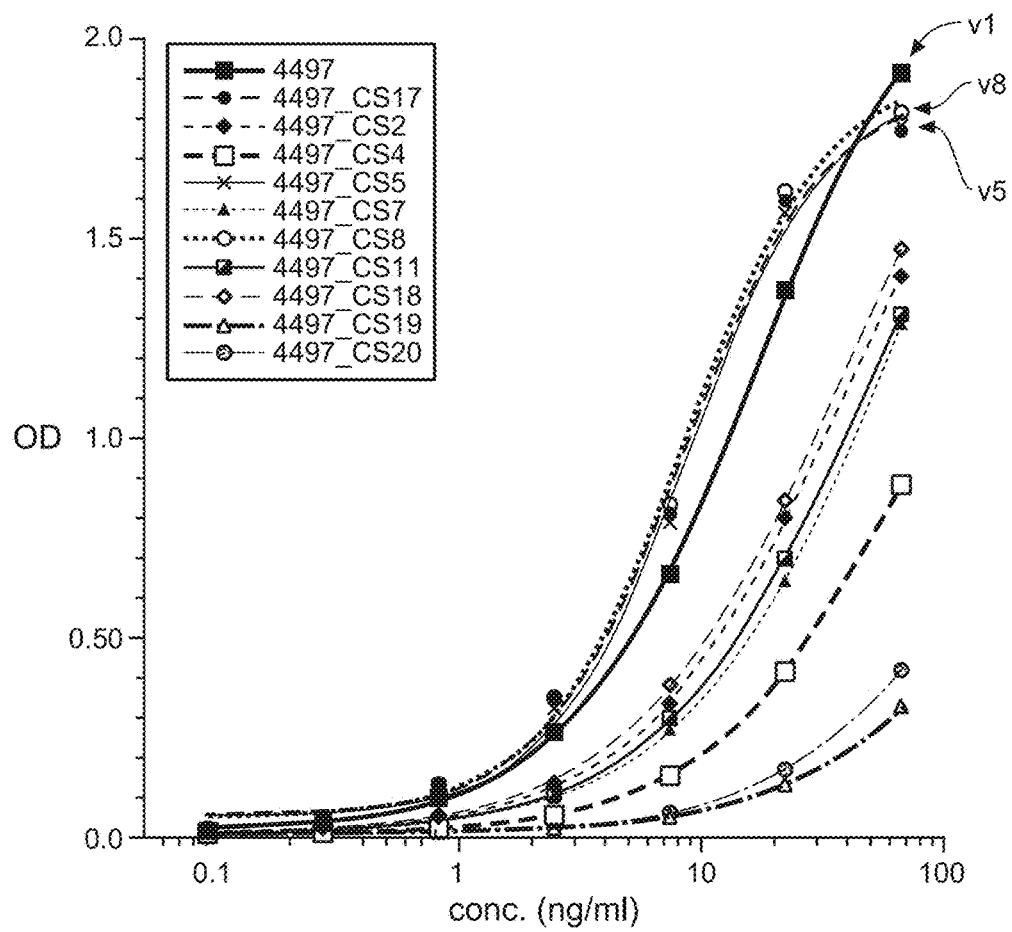
FIG. 18A shows binding of Ab 4497 mutants to *S. aureus* cell wall as analyzed by ELISA.
FIG. 18B shows a comparison of Ab 4497 and its mutants (SEQ ID NOS 177, 177, 177-178, 178-179, 179-180, 180 and 180, respectively, in order of appearance) in the highlighted amino acid positions and their relative antigen binding strength as tested by ELISA.

CDR H3 "DG" or "DD" motifs were found to be prone to transform to iso-aspartic acid. Ab 4497 contains DG in CDR H3 positions 96 and 97 (see FIG. 18B) and was altered for stability. CDR H3 is generally critical for antigen binding so several mutants were tested for antigen binding and chemical stability (see FIG. 18A). Mutant D96E (v8) retains binding to antigen, similar to wild-type Ab 4497 (FIG. 18A; FIG. 18B), and is stable and does not form iso-aspartic acid.

Staph CWP ELISA

For analysis of 6078 antibody mutants, a lysostaphin-treated USA300 ΔSPA *S. aureus* cell well preparation (WT) consisting of 1×10⁹ bugs/ml was diluted 1/100 in 0.05 Sodium Carbonate pH 9.6 and coated onto 384-well ELISA plates (Nunc; Neptune, N.J.) during an overnight incubation at 4° C. Plates were washed with PBS plus 0.05% Tween-20 and blocked during a 2-hour incubation with PBS plus 0.5% bovine serum albumin (BSA). This and all subsequent incubations were performed at room temperature with gentle agitation. Antibody samples were diluted in sample/standard dilution buffer (PBS, 0.5% BSA, 0.05% Tween 20, 0.25% CHAPS, 5 mM EDTA, 0.35M NaCl, 15 ppm Proclin, (pH 7.4)), added to washed plates, and incubated for 1.5-2 hours. Plate-bound anti-*S. aureus* antibodies were detected during a 1-hour incubation with a peroxidase-conjugated goat anti-human IgG(Fc™) F(ab')2 fragment (Jackson ImmunoResearch; West Grove, Pa.) diluted to 40 ng/mL in assay buffer (PBS, 0.5% BSA, 15 ppm Proclin, 0.05% Tween 20). After a final wash, tetramethyl benzidine (KPL, Gaithersburg, Md.) was added, color was developed for 5-10 minutes, and the reaction was stopped with 1 M phosphoric acid. The plates were read at 450 nm with a 620 nm reference using a microplate reader.

iii. Generating Cys Engineered Mutants (ThioMabs)

Full length ThioMabs were produced by introducing a Cysteine into the H chain (in CH1) or the L chain (CK) at a predetermined position as previously taught and described below to allow conjugation of the antibody to a linker-antibiotic intermediate. H and L chains are then cloned into separate plasmids and the H and L encoding plasmids co-transfected into 293 cells where they are expressed and assembled into intact Abs. Both H and L chains can also be cloned into the same expression plasmid. IgG1 are made having 2 engineered Cys, one in each of H chains, or 2 engineered Cys, one in each of the L chains, or a combination of 2 H and 2L chains each with engineered Cys (HCLCCys) were generated by expressing the desired combination of cys mutant chains and wild type chains.

Figure 19:
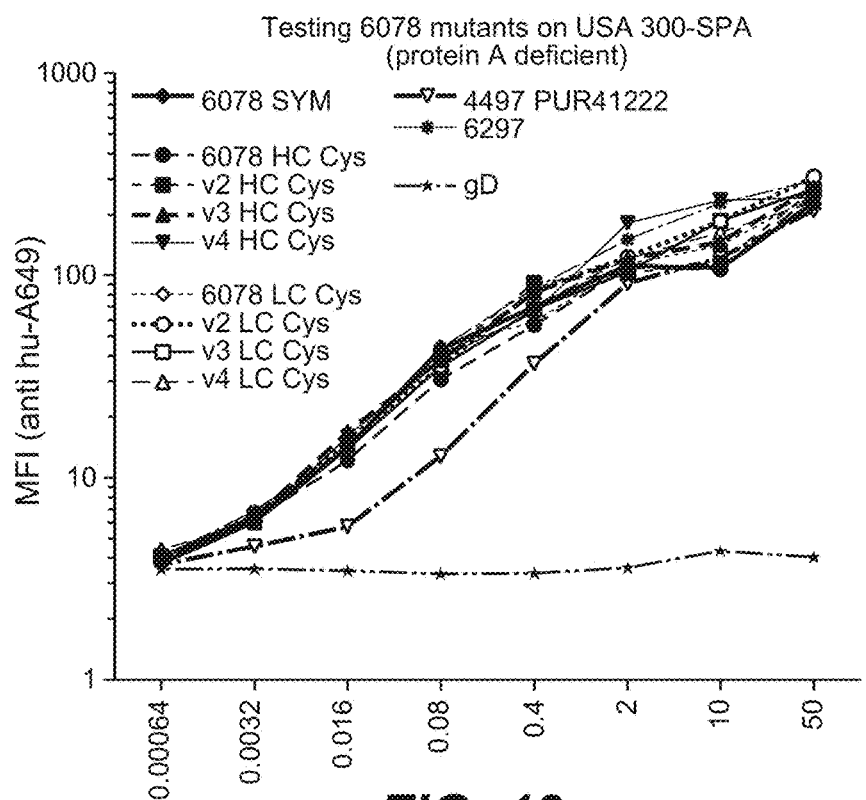
FIG. 19 shows the results of FACS analysis of Ab 6078 WT and mutants binding to protein A deficient strain of USA300 (USA300-SPA), as described in Example 23. The mutants showed unimpaired binding to *S. aureus*.

FIGS. 15A and 15B shows the 6078 WT and mutant Abs with the combination of HC Cys and LC Cys. The 6078 mutants were also tested for their ability to bind protein A deficient USA300 *Staph* A from overnight culture. From the results from the FACS analysis as shown in FIG. 19, the mutant Abs bound USA300 similarly to the 6078 WT (unaltered) antibody; the amino acid alterations in the mutants did not impair binding to Staph A. gD is a non-specific negative control antibody.

Example 24 Preparation of Anti-WTA Antibody-Antibiotic Conjugates

Anti-wall teichoic acid antibody-antibiotic conjugates (AAC) Table 3 were prepared by conjugating an anti-WTA antibody to a linker-antibiotic intermediate, including those from Table 2. Prior to conjugation, the anti-WTA antibodies were partially reduced with TCEP using standard methods in accordance with the methodology described in WO 2004/010957, the teachings of which are incorporated by reference for this purpose. The partially reduced antibodies were conjugated to the linker-antibiotic intermediate using standard methods in accordance with the methodology described, e.g., in Doronina et al. (2003) *Nat. Biotechnol.* 21:778-784 and US 2005/0238649 A1. Briefly, the partially reduced antibodies were combined with the linker-antibiotic intermediate to allow conjugation of the linker-antibiotic intermediate to reduced cysteine residues of the antibody. The conjugation reactions were quenched, and the AAC were purified. The antibiotic load (average number of antibiotic moieties per antibody) for each AAC was determined and was between about 1 to about 2 for the anti-wall teichoic acid antibodies engineered with a single cysteine mutant site.

Reduction/Oxidation of ThioMabs for Conjugation:

Full length, cysteine engineered monoclonal antibodies (ThioMabs—Junutula, et al., 2008b Nature Biotech., 26 (8):925-932; Doman et al (2009) Blood 114 (13):2721-2729; U.S. Pat. No. 7,521,541; U.S. Pat. No. 7,723,485; WO2009/052249, Shen et al (2012) Nature Biotech., 30 (2):184-191; Junutula et al (2008) Jour of Immun. Methods 332:41-52) expressed in CHO cells were reduced with about a 20-40 fold excess of TCEP (tris(2-carboxyethyl)phosphine hydrochloride or DTT (dithiothreitol) in 50 mM Tris pH 7.5 with 2 mM EDTA for 3 hrs at 37° C. or overnight at room temperature. (Getz et al (1999) Anal. Biochem. Vol 273:73-80; Soltec Ventures, Beverly, Mass.). The reduced ThioMab was diluted and loaded onto a HiTrap S column in 10 mM sodium acetate, pH 5, and eluted with PBS containing 0.3M sodium chloride. Alternatively, the antibody was acidified by addition of $\frac{1}{20}^{th}$ volume of 10% acetic acid, diluted with 10 mM succinate pH 5, loaded onto the column and then washed with 10 column volumes of succinate buffer. The column was eluted with 50 mM Tris pH7.5, 2 mM EDTA.

The eluted reduced ThioMab was treated with 15 fold molar excess of DHAA (dehydroascorbic acid) or 200 nM aqueous copper sulfate ($CuSO_4$). Oxidation of the interchain disulfide bonds was complete in about three hours or more. Ambient air oxidation was also effective. The re-oxidized antibody was dialyzed into 20 mM sodium succinate pH 5, 150 mM NaCl, 2 mM EDTA and stored frozen at −20° C.

Conjugation of Thio-Mabs with Linker-Antibiotic Intermediates:

The deblocked, reoxidized, thio-antibodies (ThioMab) were reacted with 6-8 fold molar excess of the linker-antibiotic intermediate of Table 2 (from a DMSO stock at a concentration of 20 mM) in 50 mM Tris, pH 8, until the reaction was complete (16-24 hours) as determined by LC-MS analysis of the reaction mixture.

The crude antibody-antibiotic conjugates (AAC) were then applied to a cation exchange column after dilution with 20 mM sodium succinate, pH 5. The column was washed with at least 10 column volumes of 20 mM sodium succinate, pH 5, and the antibody was eluted with PBS. The AAC were formulated into 20 mM His/acetate, pH 5, with 240 mM sucrose using gel filtration columns. AAC were characterized by UV spectroscopy to determine protein concentration, analytical SEC (size-exclusion chromatography) for aggregation analysis and LC-MS before and after treatment with Lysine C endopeptidase.

Size exclusion chromatography was performed using a Shodex KW802.5 column in 0.2M potassium phosphate pH 6.2 with 0.25 mM potassium chloride and 15% IPA at a flow rate of 0.75 ml/min. Aggregation state of AAC was determined by integration of eluted peak area absorbance at 280 nm.

LC-MS analysis was performed using an Agilent QTOF 6520 ESI instrument. As an example, an AAC generated using this chemistry was treated with 1:500 w/w Endoproteinase Lys C (Promega) in Tris, pH 7.5, for 30 min at 37° C. The resulting cleavage fragments were loaded onto a 1000 A, 8 um PLRP-S column heated to 80° C. and eluted with a gradient of 30% B to 40% B in 5 minutes. Mobile phase A: $H_2O$ with 0.05% TFA. Mobile phase B: acetonitrile with 0.04% TFA. Flow rate: 0.5 ml/min. Protein elution was monitored by UV absorbance detection at 280 nm prior to electrospray ionization and MS analysis. Chromatographic resolution of the unconjugated Fc fragment, residual unconjugated Fab and antibiotic-Fab was usually achieved. The obtained m/z spectra were deconvoluted using Mass Hunter™ software (Agilent Technologies) to calculate the mass of the antibody fragments.

Example 25 Identification and Purification of Staphopain B as the Protease Responsible for Cleavage Supernatant from a 3 liter overnight culture of Wood46 was concentrated and buffer exchanged using TFF (10 kDa) into 50 mM sodium phosphate pH 7. The sample was loaded on Q Sepaharose FF and proteins were separated chromatographically using a gradient of 0-300 mM NaCl in 50 mM sodium phosphate pH 7. Active fractions were identified by incubating with thioFAB S4497-MC-GGAFAGGG-(pip-BOR) ("core peptide" disclosed as SEQ ID NO: 126) of FIG. 27 and assessing for cleavage of the linker at the expected site by LC-MS analysis. Active fractions were pooled and supplemented with ammonium sulphate to a concentration of 2M. Proteins were further purified by hydrophobic interaction chromatography on Phenyl Sepharose using a gradient of 2-0M ammonium sulfate in 50 mM TRIS pH 7.5. Again, active fractions were identified using the tool compound. These fractions were pooled and further purified on Mono Q in 50 mM Sodium Acetate pH 5.5 using a salt gradient of 0-1M NaCl. Active fractions from this chromatography step were identified as before, pooled and applied to size exclusion chromatography in PBS. Active fractions were identified and determined to contain a single protein of interest by SDS-PAGE.

Enriched active fractions from the Q Sepharose purification were characterized to identify the class of protease responsible for activity. The protease was found to be inhibited by N-ethylmaleimide, indicating that the enzyme is likely a cysteine protease. After reviewing the known secreted cysteine proteases of *Staphylococcus aureus*, staphopain B was identified to have similar substrate specificity to the specificity observed in the REPLi screen (Kalinska, M., T. Kantyka, et al. (2012). Biochimie 94 (2): 318). Purified staphopain B was purchased (Sigma-Aldrich) and incubated with thioFAB S4497-MC-GGAFAGGG-(pip-BOR) ("core peptide" disclosed as SEQ ID NO: 126) from FIG. 27. Staphopain B was found to cleave the linker at the same site as the active protease purified from Wood46 supernatant. Staphopain B and the active protease purified from culture supernatant were incubated with Alexa Fluor® 488 $C_5$ maleimide (Invitrogen, Life Technologies, Thermo Fisher Scientific Inc.) to label the active-site cysteines. Samples were run on SDS-PAGE to identify the protease as staphopain B. SDS-PAGE gels of active fractions from SEC purification were run alongside purified staphopain B, with and without Alexa Fluor 488.

Enriched active fractions for the Q sepharose purification were also analyzed by proteomic mass spectrometry. Ten micrograms of active fractions B11, B12, and C02 and ten micrograms of an active fractions, 1, 2, 3, and ten micrograms of an inactive fraction were run on SDS-PAGE. Bands were excised and subjected to overnight digestions by trypsin. The digested samples were analyzed by LC-MS/MS and tandem mass spectral results were submitted for database searching using the Mascot search algorithm. Staphopain B was the top hit for cysteine proteases present in the active fractions. Autolysin, which is also a cysteine protease, also appears as a top hit, with the highest abundance of unique peptides occurring in the inactive fraction, the negative control, thus autolysin was omitted from consideration. Mass spectral proteomic analysis of active fractions from the Q Sepharose purifications show a high abundance of staphopain B. T restle data was filtered for *S. aureus* proteins and ranked by number of peptides in Active fraction 1.

The active protease was purified from Wood46 *S. aureus* culture supernatant. The cells were grown overnight at 37° C. in 3 liters of TSB. Cells were removed by centrifugation at 10,000×g for 10 min. The supernatant was collected and passed through two 0.22 um filters. Next, it was concentrated and buffer exchanged into 50 mM Sodium Phosphate pH 7 using TFF with a 10 kD membrane. The sample was concentrated ten-fold to a volume of 300 ml. The sample was loaded on Q Sepharose FF (GE Healthcare Biosciences AB) and proteins were separated chromatographically using a gradient of 0-300 mM NaCl in 50 mM sodium phosphate pH 7. Active fractions were pooled and supplemented with ammonium sulfate to a concentration of 2M. Proteins were further purified by hydrophobic interaction chromatography on Phenyl Sepharose (GE Healthcare Biosciences AB) using a gradient of 2-0M ammonium sulfate in 50 mM TRIS pH 7.5. Active fractions were pooled and further purified on Mono Q (GE Healthcare Biosciences AB) in 50 mM Sodium Acetate pH 5.5 using a salt gradient of 0-1M NaCl. Active fractions from this chromatography step were identified as before, pooled and applied to size exclusion chromatography (Zenix-150, Sepax Technologies) in PBS.

To identify fractions containing our active protease of interest, 100 ul from each fraction was transferred to a 96-well plate where it was incubated with 25 ug of THIO-FAB 4497 mal-GGAFAGGG-DNA31 ("core peptide" disclosed as SEQ ID NO: 126). Fractions from each chromatography step were analyzed for activity, and 100 ul was used regardless of protein concentration. Samples were incubated overnight at 37° C. and subsequently analyzed by LC-MS to identify fractions where protease cleavage of the linker-antibiotic had occurred. Pooled active fractions from the Q Sepharose FF chromatography were measured to have a total protein concentration of 14 mg/ml. 200 µg of the pool was diluted to 2 mg/ml in PBS and was incubated with and without N-ethylmaleimide (NEM, Sigma) at a concentration of 0.1 mM final. Samples were incubated at room temperature for 1 hour. 25 ug of THIOFAB 4497 mal-GGGAF-AGGG-DNA31 ("core peptide" disclosed as SEQ ID NO: 126) was added to both samples and incubated at 37° C. for 2 hours. At 2 hours, samples were analyzed by LC-MS to identify whether protease cleavage of the linker-antibiotic had occurred. About 50 ul of the active fractions from SEC were incubated with 0.1 mM Alexa Fluor 488 $C_5$ maleimide (Invitrogen) for 1 hour regardless of protein concentration for labeling. Cleavage assays with purified proteases were performed by incubating 5 uM of the thioFAB conjugate with 50 nM protease in a final volume of 100 ul. Assays were either performed in PBS pH 7.2, 4 mM L-Cys, 2.5 mM EDTA or 100 mM Sodium Citrate pH 5, 100 mM NaCl, 4 mM L-Cys, 2.5 mM EDTA. Samples were incubated for 2 hours at 37° C. At 2 hours, cleavage reactions were quenched by diluting 1:1 with 1% TFA. Samples were subsequently run on LC-MS to determine percent linker cleavage. Percent cleavage was determined by integrating the $A_{280}$ chromatograms of the cleaved and intact species. The antibiotic or chromophore moieties added on the C-terminus of the linkers add significant hydrophobicity, such that thioFAB with intact linkers and thioFAB with cleaved linkers are baseline resolved.

For proteomic analysis of enriched fractions, ten micrograms of enriched active fractions from the Q Sepahrose® (GE Healthcare Life Sciences) purification were loaded onto a 4-12% Bis-Tris gel (Life Technologies). Entire gel lanes were excised and divided from top to bottom into 11 bands. The gel bands were destained with 50% acetonitrile/50 mM ammonium bicarbonate, reduced with dithiothreitol (50 mM final concentration) for 30 minutes at 50° C., and alkylated with iodoacetamide (50 mM final concentration) at room temperature in the dark for 30 minutes. The samples were then digested at 37° C. overnight with 0.02 µg/µl trypsin (Promega) in 50 mM ammonium bicarbonate. The digested samples were injected onto a 100 µm inner diameter capillary column (NanoAcquity UPLC column, 100 µm×100 mm, 1.7 µm, BEH130 C18, Waters Corp) and separated by capillary reverse phase chromatography on a NanoAcquity UPLC system (Waters Corp). Samples were loaded in 0.1% trifluoroacetic acid in water and eluted with a gradient of 2-90% Buffer B (where Buffer A is 0.1% formic acid/2% acetonitrile/98% water and Buffer B is 0.1% formic acid/2% water/98% acetonitrile) at 1.00 µl/min with a total analysis time of 45 minutes. Peptides were eluted directly into an LTQ-Orbitrap XL (ThermoFisher) mass spectrometer and ionized using an ADVANCE source (Michrom-Bruker) with a spray voltage of 1.4 kV. Mass spectral data were acquired using a method comprising of one full MS scan (375-1600 m/z) in the Orbitrap at resolution of 60,000 M/ΔM at m/z 400 followed by collision-induced dissociation (CID) of the top 8 most abundant ions detected in the full MS scan in a cycle repeated throughout the LC gradient in the linear ion trap. Tandem mass spectral results were submitted for database searching using the Mascot® search algorithm version 2.3.02 (Matrix Sciences) against a concatenated target-decoy database, Uniprot ver 2010_12, comprising of *S. aureus* proteins and common laboratory contaminants. The data was searched with tryptic specificity, variable modifications of cysteine carbamidomethylation (+57.0215 Da) and methionine oxidation (+15.995 Da), allowing 2 miscleavages, 20 ppm precursor ion mass, and 0.5 Da fragment ion mass tolerance specified. Peptide spectral matches were filtered using a linear discriminant algorithm (LDA) to a false discovery rate (FDR) of 1%.

Example 26 Staphopain Cleavage of thioFab FRET Peptides and AAC

5 µM of thioFAB 4497 MP-LAFGA-QSY7("core peptide" disclosed as SEQ ID NO: 135) and thioFAB 4497 MP-LAFAA-QSY7 ("core peptide" disclosed as SEQ ID NO: 136) (FIG. 30) were incubated with 50 nM of protease in PBS pH 7.2, 4 mM L-Cys, 2.5 mM EDTA for 2 hours at 37° C. At 2 hours, cleavage reactions were quenched by diluting 1:1 with 1% TFA. Samples were subsequently run on LC-MS to determine percent linker cleavage. All the proteases tested cleaved the two linkers, although at varying degrees and locations (Table 4). Staphopain A and staphopain B cleave the linkers at the same sites: MP-LAFG-A-QSY7 ("core peptide" disclosed as SEQ ID NO: 135) and MP-LAFA↓A-QSY7 ("core peptide" disclosed as SEQ ID NO: 136). Staphopain B achieves 100% cleavage of both linkers at the concentration tested. Cathepsin B also achieved 100% cleavage for both linkers under these conditions, although the sites of cleavage were mixed. Cathepsin B cleaved mal-LAFGA-QSY7 ("core peptide" disclosed as SEQ ID NO: 135) exclusively at MP-LAFGA-QSY7 ("core peptide" disclosed as SEQ ID NO: 135), while it cleaved mal-LAFAA-QSY7 ("core peptide" disclosed as SEQ ID NO: 136) at both MP-LAFA↓A-QSY7 ("core peptide" disclosed as SEQ ID NO: 136) and MP-LAFAA↓-QSY7 ("core peptide" disclosed as SEQ ID NO: 136). MP-LAFAA-QSY7 ("core peptide" disclosed as SEQ ID NO: 136) cleavage by staphopain A was 23%, while cleavage of m MP-LAFGA-QSY7 ("core peptide" disclosed as SEQ ID NO: 135) was 38%.

5 µM of AAC-193 was incubated with 50 nM of protease in either PBS pH 7.2, 4 mM L-Cys, 2.5 mM EDTA or 100 mM Sodium Citrate pH 5, 100 mM NaCl, 4 mM L-Cys, 2.5 mM EDTA for 2 hours at 37° C. At 2 hours, cleavage reactions were quenched by diluting 1:1 with 1% TFA. Samples were subsequently run on LC-MS to determine percent linker cleavage. The optimized linker-antibiotic was efficiently cleaved by all proteases tested. Upon cleavage by staphopain A and staphopain B, free piperazino-rifamycin was released. Staphopain B achieved 100% cleavage at both pH 5 and 7.2. Staphopain A showed 100% cleavage at pH5 and 64% cleavage at pH 7.2.

Example 27 Antibody-Antibiotic Conjugate, Thio-54497 LC v8-MP-LAFG-PABC-(piperazinoBOR) ("Core Peptide" Disclosed as SEQ ID NO: 128) AAC-215, Inhibits *S. aureus* In Vitro 1×10⁸ stationary phase Wood46 bacteria were suspended in 10 µL of HB buffer (Hanks Balanced Salt Solution supplemented with 0.1% Bovine Serum Albumin) containing 100 µg/mL of thio-S4497 LC v8-MP-LAFG-PABC-(piperazinoBOR) ("core peptide" disclosed as SEQ ID NO: 128) AAC-215 or thio-S4497-HC-A118C-MC-vc-PABC-(piperazBOR) AAC-126. The latter uses a valine-citrulline (vc) cathepsin B cleavable linker to deliver the same antibiotic.

After 1 hour, samples were diluted 10-fold by addition of 90 µL of HB, or 90 uL of cathepsin B (10 µg/mL of Cathepsin B in 20 mM Sodium Acetate, 1 mM EDTA, 5 mM L-Cysteine pH 5) and incubated at 37° C. for an additional 3 hours. Release of active antibiotic was inferred by determining whether incubation of AACs with the bacteria was able to inhibit subsequent bacterial growth. Bacteria/AAC suspensions were spotted directly onto Tryptic Soy Agar plates and bacterial growth was visualized after overnight incubation at 37° C. Active drug is released from AAC conjugated with MC-LAFG-PAB-(piperazinoBOR) ("core peptide" disclosed as SEQ ID NO: 128) linker-antibiotic intermediate.

Bacteria that were incubated without AAC grew well and were not affected by cathepsin B treatment. Bacteria treated with AAC-126 containing the cathepsin B cleavable linker, valine-citrulline (vc) grew well after incubation in HB buffer alone, but failed to grow after treatment with AAC-126+ Cathepsin B, indicating that the enzyme treatment was required to release active antibiotic. In contrast, bacteria incubated with AAC-215 containing the staphopain cleavable linker LAFG (SEQ ID NO: 128) failed to grow after incubation with HB buffer alone, suggesting that the bacterial suspension contained enzymatic activity that was sufficient to release active antibiotic from the staphopain cleavable linker AAC.

Figure 31:
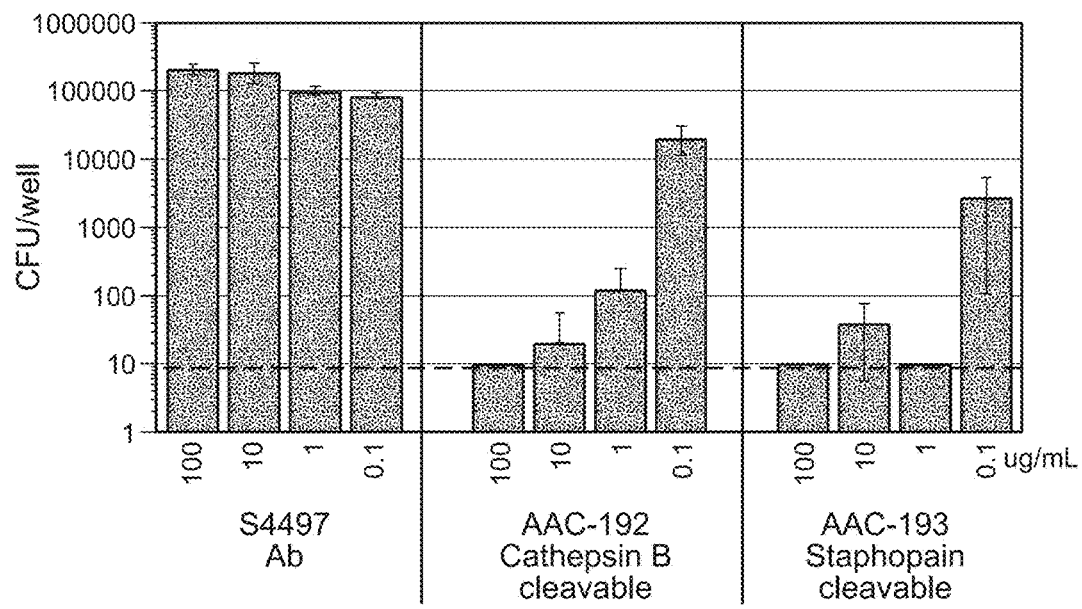
FIG. 31 shows results from the Macrophage Assay, demonstrating that staphopain cleavable AAC is able to kill intracellular bacteria. The USA300 strain of *S. aureus* was incubated with various doses (100 µg/mL, 10 µg/mL, 1 µg/mL or 0.1 ug/mL) of S4497 antibody alone, thio-S4497 HC WT (v8), LC V205C-MC-vc-PAB-(dimethylpipBOR) AAC-192 or thio-S4497 HC v1-MP-LAFG-PABC-(piperazinoBOR) ("core peptide" disclosed as SEQ ID NO: 128) AAC-193 to permit binding of the AACs to the bacteria (FIG. 31). After 1 hour incubation, the opsonized bacteria were fed to murine macrophages and incubated at 37° C. for 2 hours to permit phagocytosis. After phagocytosis was complete, the infection mix was replaced with normal growth media supplemented with 50 ug/mL of gentamycin to kill any remaining extracellular bacteria and the total number of surviving intracellular bacteria was determined 2 days later by plating serial dilutions of the macrophage lysates on Tryptic Soy Agar plates. The staphopain cleavable AAC was able to kill intracellular USA300 with similar potency compared to the cathepsin B cleavable AAC. Gray dashed line indicates the limit of detection for the assay (10 CFU/well).

Example 28 Antibody-Antibiotic Conjugate, Thio-S4497 HC v1-MP-LAFG-PABC-(piperazinoBOR) ("Core Peptide" Disclosed as SEQ ID NO: 128) AAC-193 Kills Intracellular MRSA in a Macrophage Assay The USA300 strain of *S. aureus* was incubated with various doses (100 µg/mL, 10 µg/mL, 1 µg/mL or 0.1 µg/mL) of S4497 antibody alone, thio-S4497 HC WT (v8) (SEQ ID NO: 137), LC V205C-MC-vc-PAB-(dimethylpipBOR) ("core peptide" disclosed as SEQ ID NO: 128) AAC-192, or thio-S4497 HC v1-MP-LAFG-PABC-(piperazinoBOR) AAC-193 to permit binding of the AAC to the bacteria (FIG. 31).

```
S4497 HC WT (v8) 446aa
                                    (SEQ ID NO: 137)
EVQ LVE SGG GLV QPG GSL RLS CSA SGF SFN SFW MHW

VRQ VPG KGL VWI SFT NNE GTT TAY ADS VRG RFI ISR

DNA KNT LYL EMN NLR GED TAV YYC ARG DGG LDD WGQ

GTL VTV SSA STK GPS VFP LAP SSK STS GGT AAL GCL

VKD YFP EPV TVS WNS GAL TSG VHT FPA VLQ SSG LYS

LSS VVT VPS SSL GTQ TYI CNV NHK PSN TKV DKK VEP

KSC DKT HTC PPC PAP ELL GGP SVF LFP PKP KDT LMI

SRT PEV TCV VVD VSH EDP EVK FNW YVD GVE VHN AKT

KPR EEQ YNS TYR VVS VLT VLH QDW LNG KEY KCK VSN

KAL PAP IEK TIS KAK GQP REP QVY TLP PSR EEM TKN

QVS LTC LVK GFY PSD IAV EWE SNG QPE NNY KTT PPV

LDS DGS FFL YSK LTV DKS RWQ QGN VFS CSV MHE ALH

NHY TQK SLS LSP GK
```

After 1 hour incubation, the opsonized bacteria were fed to murine macrophages and incubated at 37 C for 2 hours to permit phagocytosis. After phagocytosis was complete, the infection mix was replaced with normal growth media supplemented with 50 µg/mL of gentamycin to kill any remaining extracellular bacteria and the total number of surviving intracellular bacteria was determined 2 days later by plating serial dilutions of the macrophage lysates on Tryptic Soy Agar plates (FIG. 31). The staphopain cleavable AAC was able to kill intracellular USA300 with similar potency compared to the cathepsin B cleavable AAC. Gray dashed line indicates the limit of detection for the assay (10 CFU/well).

Figure 32:
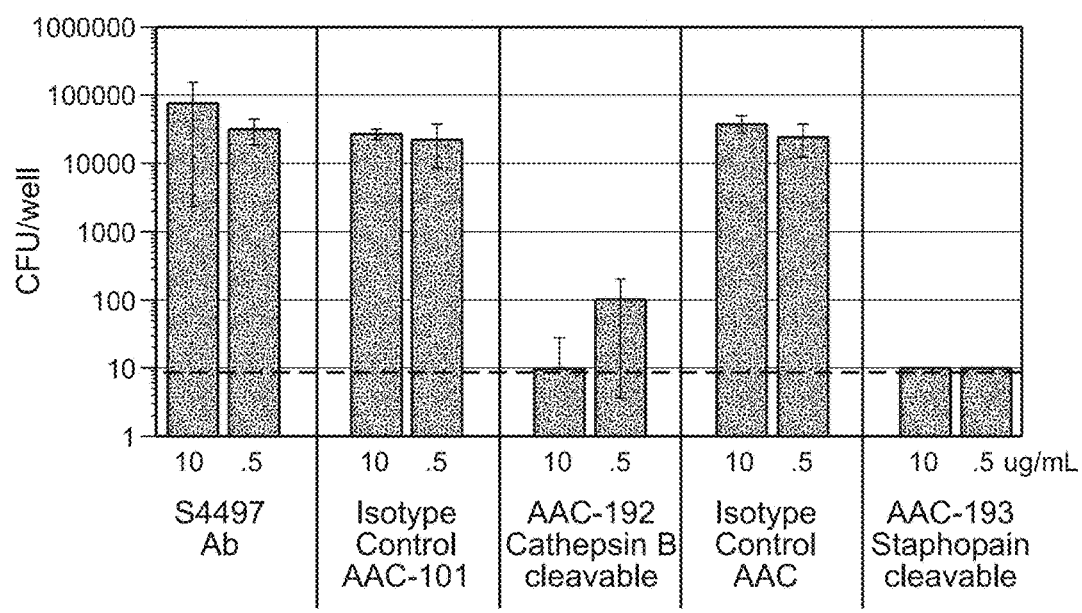
FIG. 32 shows results from the Macrophage Assay, demonstrating that staphopain cleavable AAC is able to kill intracellular bacteria. AACs target antibiotic killing to *S. aureus* via antigen specific binding of the antibody. The Wood46 strain of *S. aureus* was chosen for this experiment because it does not express protein A, a molecule that binds to the Fc region of IgG antibodies. The Wood46 strain of *S. aureus* was incubated with 10 µg/mL or 0.5 µg/mL of S4497 antibody, Isotype control-AAC containing a cathepsin B cleavable linker thio-trastuzumab HC A118C-MC-vc-PAB-(dimethyl-pipBOR) AAC-101, thio-54497 HC WT (v8), LC V205C-MC-vc-PAB-(dimethylpipBOR) AAC-192, Isotype control-AAC containing a staphopain cleavable linker thio-trastuzumab HC A1118C-MP-LAFG-PABC-(piperazino-BOR) ("core peptide" disclosed as SEQ ID NO: 128), or thio-54497 HC v1-MP-LAFG-PABC-(piperazinoBOR) ("core peptide" disclosed as SEQ ID NO: 128) AAC-193 for 1 hour to permit binding of the AACs to bacteria. To limit non-specific binding of the AACs, the opsonized bacteria were centrifuged, washed once and resuspended in buffer before being fed to murine macrophages. After phagocytosis was complete, the infection mix was replaced with normal growth media supplemented with 50 µg/mL of gentamycin to kill any remaining extracellular bacteria and the total number of surviving intracellular bacteria was determined 2 days later by plating serial dilutions of the macrophage lystes on Tryptic Soy Agar plates. The 4497-AAC containing a staphopain cleavable linker was able to kill all detectable intracellular bacteria, whereas the isotype control AAC showed no activity.
Figure 33:
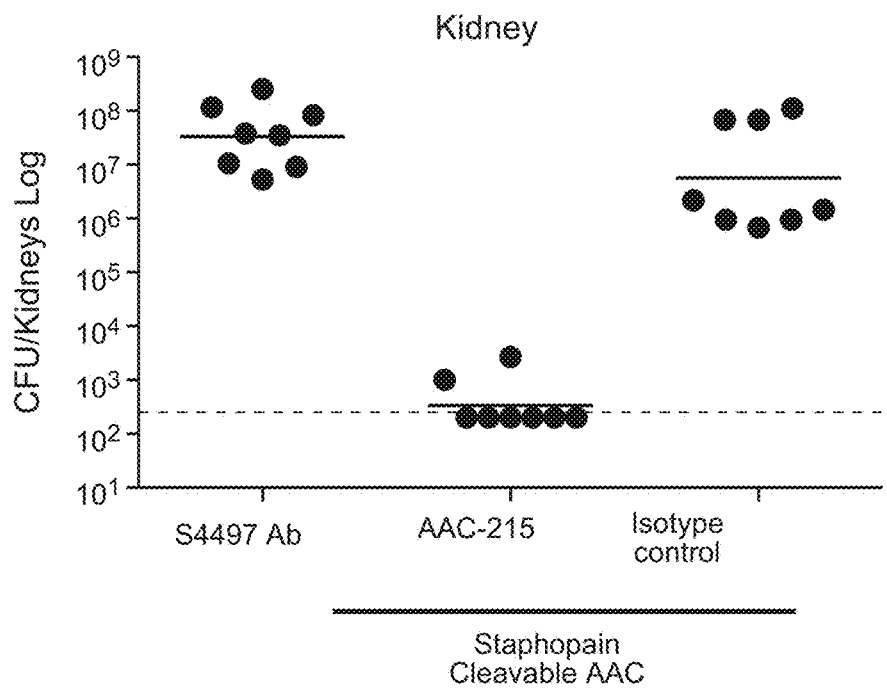
FIGS. 33 and 34 show Staphopain AAC is active in vivo in a murine intravenous infection model. CB17.SCID mice were reconstituted with human IgG using a dosing regimen optimized to yield constant levels of at least 10 mg/mL of human IgG in serum. Mice were treated with 4497 antibody (50 mg/kg), AAC-215 with staphopain cleavable linker (50 mg/kg,) or an isotype control, anti-gD AAC containing staphopain cleavable linker (50 mg/kg). Mice were given a single dose of AAC-215 on day 1 post infection by intravenous injection. Total number of surviving bacteria in 2 kidneys (FIG. 33) or in heart (FIG. 34) was determined by plating.
Figure 34:
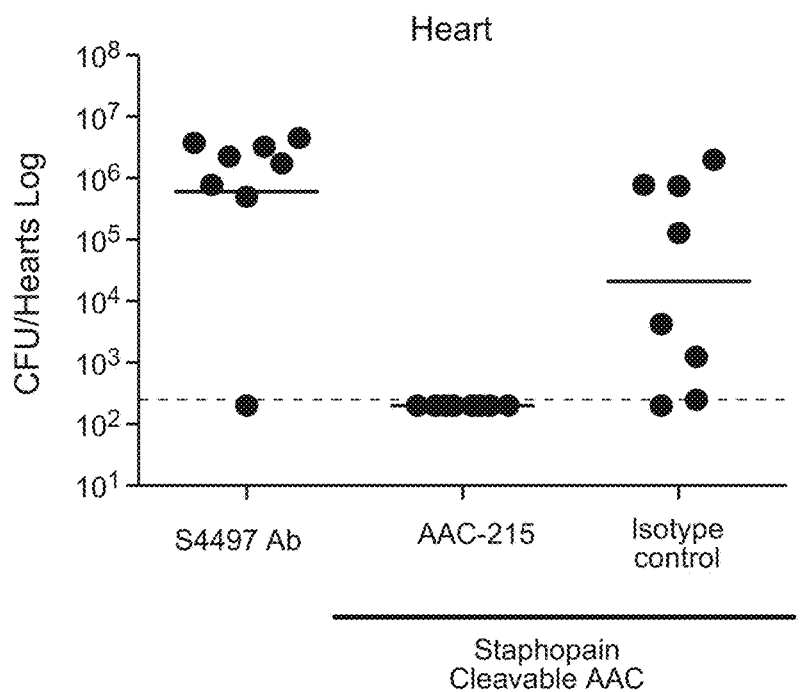

Example 29 AAC Target Antibiotic Killing to S. aureus Via Antigen Specific Binding of the Antibody The Wood46 strain of S. aureus was chosen because it does not express protein A, a molecule that binds to the Fc region of IgG antibodies. The Wood46 strain of S. aureus was incubated with 10 µg/mL or 0.5 µg/mL of S4497 antibody, Isotype control-AAC containing a cathepsin B cleavable linker, thio-trastuzumab HC A118C-MC-vc-PAB-(dimethyl-pipBOR) AAC-101, thio-S4497 HC WT (v8), LC V205C-MC-vc-PAB-(dimethylpipBOR) AAC-192, Isotype control-AAC containing a staphopain cleavable linker, thio-trastuzumab HC A1118C-MP-LAFG-PABC-(piperazino-BOR) ("core peptide" disclosed as SEQ ID NO: 128) or thio-S4497 HC v1-MP-LAFG-PABC-(piperazinoBOR) ("core peptide" disclosed as SEQ ID NO: 128) AAC-193 for 1 hour to permit binding of the AAC to bacteria (FIG. 32). To limit non-specific binding of the AAC, the opsonized bacteria were centrifuged, washed once and resuspended in buffer before being fed to murine macrophages. After phagocytosis was complete, the infection mix was replaced with normal growth media supplemented with 50 µg/mL of gentamycin to kill any remaining extracellular bacteria and the total number of surviving intracellular bacteria was determined 2 days later by plating serial dilutions of the macrophage lystes on Tryptic Soy Agar plates (FIG. 32). The AAC containing a staphopain cleavable linker, AAC-193, was able to kill all detectable intracellular bacteria, whereas the isotype control AAC showed no activity. The Macrophage Assay demonstrates that staphopain cleavable AAC are able to kill intracellular bacteria. Antibody-antibiotic conjugate, thio-54497 LC v8-MP-LAFG-PABC-(piperazinoBOR) ("core peptide" disclosed as SEQ ID NO: 128) AAC-215 is efficacious in vivo in a MRSA infection model: CB17.SCID mice were reconstituted with human IgG using a dosing regimen optimized to yield constant levels of at least 10 mg/mL of human IgG in serum. Mice were treated with 4497 antibody (50 mg/kg), AAC-215 with staphopain cleavable linker (50 mg/kg) or an isotype control, anti-gD AAC containing staphopain cleavable linker (50 mg/kg). Mice were given a single dose of AAC-215 on day 1 post infection by intravenous injection. All mice were sacrificed on day 4 post infection, and the total number of surviving bacteria in 2 kidneys (FIG. 33) or in heart (FIG. 34) was determined by plating. Treatment with AAC-215 containing a staphopain cleavable linker reduced bacterial loads to below the limit of detection in 6 out of the 8 mice tested, whereas the isotype control AAC showed limited activity. The dashed line indicates the limit of detection for the assay (333 CFU/mouse).

Example 30 Growth of S. aureus and Protease Activity Profiling

Staphylococcus aureus strain Wood46 (ATCC10832) was cultured overnight at 37° C. in tryptic soy broth (TSB) with shaking. Cultures were centrifuged at 10,000×g for 10 min. Supernatant was collected and passed through two 0.22 um filters.

S. aureus protease activity profiling: 150 ml of culture supernatant was concentrated and buffer exchanged into phosphate buffered saline (PBS) using TFF (Millipore Pellicon XL Cassette Biomax 10 kDa) to a final volume of 38 ml with a final total protein concentration of 1 mg/ml. Protease activity assay of Wood46 supernatant was performed using the Rapid Endopeptidase Profiling Library or REPLi (Mimotopes, Victoria, Australia). The library consists of 3375 internally quenched fluorogenic peptides in a 96-well format arranged in 512 groups. Library peptides contain the sequence MCA-Gly-Gly-Gly-Xaa-Yaa-Zaa-Gly-Gly-DPA-Lys-Lys (SEQ ID NO: 132) where MCA corresponds to 7-methoxycoumarin-4-acetic acid (fluorescent donor) and DPA corresponds to $N^b$-(2,4-dinitrophenyl)-L-2,3-diaminopropionic acid (fluorescence acceptor). Wells containing 5 nmol of the FRET peptides were solubilized in 5 ul of 50% acetonitrile (Sigma). 50 µl (microliters) of the concentrated Wood46 supernatant and 50 ul of PBS were added to each well. Plates were incubated at 37° C. and fluorescence measurements were taken at 0, 30, 60, 140, and 170 minutes. Fluorescence data were obtained on a Tecan Saphire$^2$, excitation λ320 nm/emission λ400 nm. Endpoint fluorescence intensity fold change was calculated as $F_{final}/F_{initial}$.

Substrate cleavage sites were determined by LC-MS performed with an Agilent Q-TOF using an ESI source. 10 ul from each well were injected and separated by reversed phase chromatography on a Waters Xbridge OST C18 2.5 um column (4.6×50 mm) using an Agilent 1260 HPLC system. Samples were eluted with a gradient of 2-90% Buffer B (where Buffer A is 0.05% trifluoroacetic acid/99.95% water and Buffer B is 0.04% % trifluoroacetic acid/99.96% acetonitrile) at 500 µl/min with a total analysis time of 20 minutes. Peptides were eluted directly into a Q-TOF mass spectrometer. Cleavage products were assigned based on comparing observed molecular weights with calculated masses corresponding to cleavage at each possible site.

Example 31 Synthesis of Maleimido FRET Peptide Linker

Figure 26:
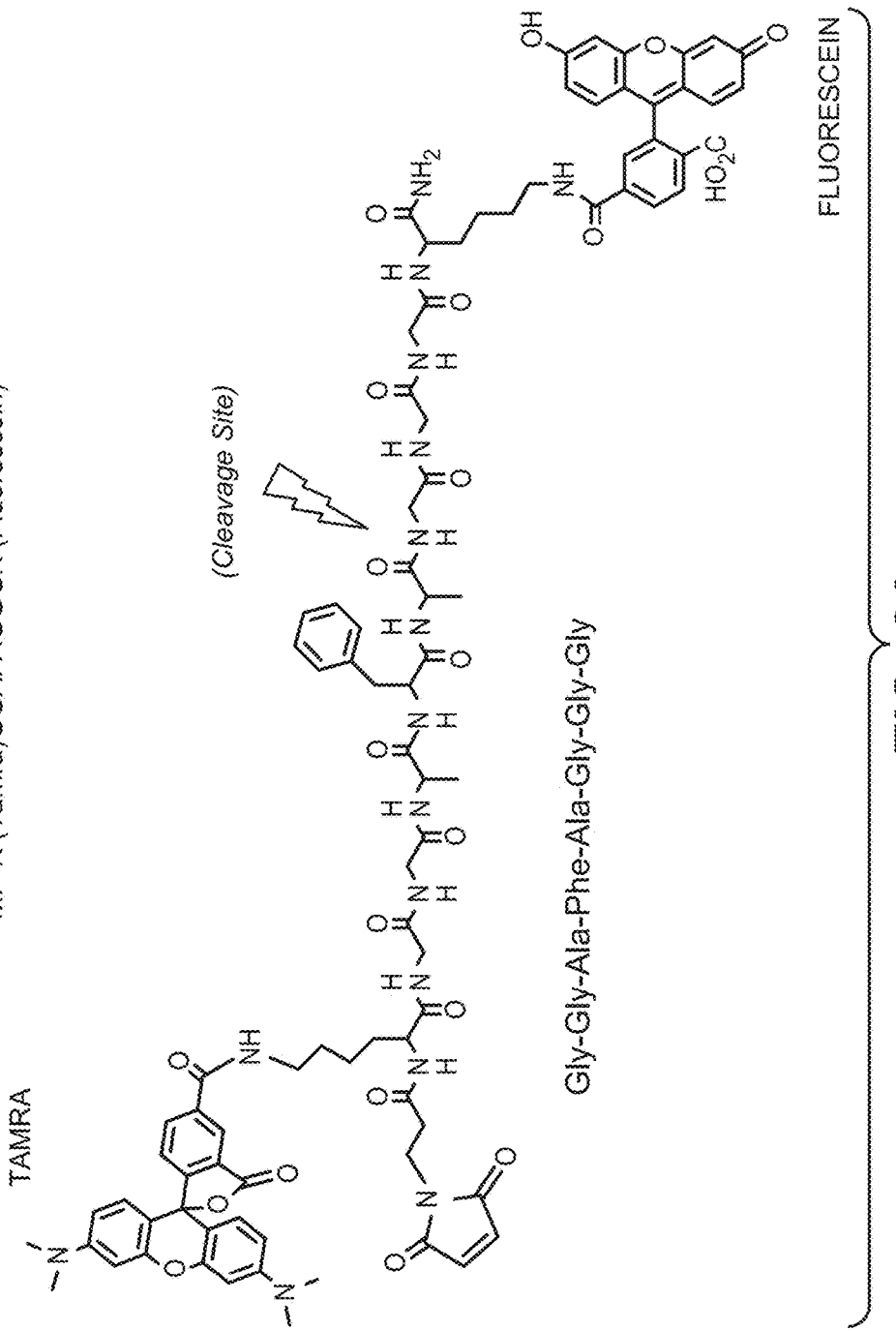
FIG. 26 shows the structure of a FRET peptide substrate for cleavage validation, mal-K(TAMRA)GGAFAGGGK (fluorescein) (SEQ ID NO: 125) containing the most abundant residues in P1, P2, and P3 from the REPLi protease activity screen. Flanking Gly residues from the REPLi FRET peptide structure were conserved. A thiol-reactive maleimide group on the N-terminus allowed for conjugation to antibodies with reactive cysteines. Upon cleavage of the FRET peptide, the quenching effect is lost and an increase in fluorescence is observed.

The maleimido FRET peptide, (MP-Lys(TAMRA)-Gly-Gly-Ala-Phe-Ala-Gly-Gly-Gly-Lys(fluorescein) ("core peptide" disclosed as SEQ ID NO: 125) of FIG. 26 was synthesized by standard Fmoc solid-phase chemistry using a PS3 peptide synthesizer (Protein Technologies, Inc.). 0.1 mmol of Fmoc-Lys(Boc)-Rink amide resin (Novabiochem) was used to generate a C-terminal carboxamide. Fmoc-Lys (Mtt)-OH (Novabiochem) was added at the first N-terminal residue to allow for additional side-chain chemistry after removal of the Mtt group. A fluorescence acceptor, 5(6)-carboxy tetramethylrhodamine, or TAMRA (Novabiochem), was attached to this side-chain amine on the resin after the Mtt group was removed by three consecutive 30 min washes of 1% TFA in dichloromethane with 3% triisopropylsilane (TIS). The reaction was allowed to proceed for 20 hours. After this step, the terminal Fmoc group is removed by 20% piperidine in DMF and coupled with maleimido-propionic acid (Bachem AG) by HBTU. The TAMRA-labeled intermediate peptides were cleaved off from the resin with 95:2.5:2.5 trifluoroacetic acid (TFA)/TIS/water (v/v/v) for 2 hours at room temperature with gentle shaking. The cleavage solution was filtered and evaporated under a stream of nitrogen to remove the TFA. The crude intermediates dissolved in a mixture of water and acetonitrile were subjected to further purification by reverse-phase HPLC with a Jupiter 5µ C4 column (5 µm, 10 mm×250 mm) from Phenomenex. After lyophilization, the purified intermediates were then reacted with 10 eq. NHS-fluorescein (Thermo Scientific) in 50/50 phosphate buffered saline (PBS)/dimethylformamide (DMF) (v/v) for 20 hours to label the free amine at the C-terminal lysine. The FRET peptide was then purified and lyophilized as described above. All reaction mixtures and final products were analyzed and confirmed by LC-MS.

Solid phase synthesis of linkers: All linkers described were synthesized using standard Fmoc solid-phase chemistry on a PS3 peptide synthesizer (Protein Technologies, Inc.). 0.1 mM of Fmoc-amino acid-Wang resin (Novabiochem) was used for all linkers to generate a C-terminal carboxyl. Linkers were purified as described above. QSY7 amine (Invitrogen) attachment was accomplished by reacting purified linkers with a 1.1 fold molar excess of QSY7 amine, a 1.1 fold molar excess of HATU, and a 2.2 fold molar excess of DIEA in DMF overnight at room temperature. Linker-QSY7 species were then purified as described above. All reaction mixtures and final products were analyzed and confirmed by LC-MS.

Example 32 Cell Based FRET Cleavage Assays

Cultures of Wood46 and USA300 were inoculated with a 1:200 dilution of overnight cultures (0.1 ml in 20 ml) in TSB and incubated at 37° C. with shaking. Strains were cultured to exponential phase of growth and plated at cell densities of $10^8$ cells/ml and 10' cells/ml in tryptic soy broth (TSB). thioMAB FRET peptide conjugates were added to wells at a final FRET peptide concentration of 2 µM. Plates were incubated at 37° C. and fluorescence was monitored over time, excitation λ495 nm/emission λ518 nm, for 210 minutes.

Cleavage of thioFAB FRET peptide and thioFAB mal-GGAFAGGG-DNA31 ("core peptide" disclosed as SEQ ID NO: 126) by concentrated active supernatant: thioFAB S4497 conjugated with either MP-Lys(TAMRA)-Gly-Gly-Ala-Phe-Ala-Gly-Gly-Gly-Lys(fluorescein) ("core peptide" disclosed as SEQ ID NO: 125) or MP-Gly-Gly-Ala-Phe-Ala-Gly-Gly-Gly-(pipBOR) LA-59 ("core peptide" disclosed as SEQ ID NO: 126) were incubated with concentrated Wood46 supernatant that had been processed as described above. thioFAB S4497 and supernatant were mixed 1:1 on a milligram basis (25 µg of thioFAB S4497 with 25 µg of proteinaceous supernatant) in PBS. Samples were incubated for 2 hours at 37° C. At 2 hours, the reaction was quenched by diluting 1:1 with 0.1% TFA. Samples were analyzed by LC-MS to determine amount of cleavage and cleavage products.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

We claim:

1. An antibody-antibiotic conjugate compound comprising an anti-wall teichoic acid (WTA) monoclonal antibody, wherein the anti-wall teichoic acid monoclonal antibody binds to *Staphylococcus aureus*, and covalently attached to a rifamycin-type antibiotic by a protease-cleavable, peptide linker, the antibody-antibiotic conjugate compound having Formula I:

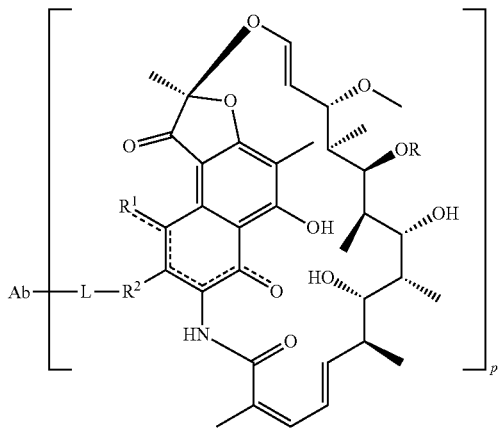

wherein:
the dashed lines indicate an optional bond;
R is H, $C_1$-$C_{12}$ alkyl, or C(O)$CH_3$;
$R^1$ is OH;
$R^2$ is CH=N-(heterocyclyl), wherein the heterocyclyl is optionally substituted with one or more groups independently selected from C(O)$CH_3$, $C_1$-$C_{12}$ alkyl, $C_1$-$C_{12}$ heteroaryl, $C_2$-$C_{20}$ heterocyclyl, $C_6$-$C_{20}$ aryl, and $C_3$-$C_{12}$ carbocyclyl;
or $R^1$ and $R^2$ form a five- or six-membered fused heteroaryl or heterocyclyl, and optionally forming a spiro or fused six-membered heteroaryl, heterocyclyl, aryl, or carbocyclyl ring, wherein the spiro or fused six-membered heteroaryl, heterocyclyl, aryl, or carbocyclyl ring is optionally substituted H, F, Cl, Br, I, $C_1$-$C_{12}$ alkyl, or OH;
L is the peptide linker attached to $R^2$ or the fused heteroaryl or heterocyclyl formed by $R^1$ and $R^2$;
Ab is the anti-wall teichoic acid monoclonal antibody; and
p is an integer from 1 to 8.

2. The antibody-antibiotic conjugate compound of claim 1, wherein the VL of the anti-WTA monoclonal antibody comprises-CDR L1 comprising the sequence of KSSQSIFRTSRNKNLLN (SEQ ID NO:99), CDR L2 comprising the sequence of WASTRKS (SEQ ID NO:100), and CDR L3 comprising the sequence of QQYFSPPYT (SEQ ID NO:101); and the VH of the anti-WTA monoclonal antibody comprises CDR H1 comprising the sequence of SFWMH (SEQ ID NO:102), CDR H2 comprising the sequence of FTNNEGTTTAYADSVRG (SEQ ID NO:103), and CDR H3 comprising the sequence of GEGGLDD (SEQ ID NO:118) or GDGGLDD (SEQ ID NO:104).

3. The antibody-antibiotic conjugate compound of claim 2, wherein the antibody comprises a VL comprising the amino acid sequence SEQ ID NO:119.

4. The antibody-antibiotic conjugate compound of claim 2, wherein the antibody comprises a VH comprising the amino acid sequence of SEQ ID NO:156.

5. The antibody-antibiotic conjugate compound of claim 2, wherein the antibody comprises a VL and a VH, wherein the VL comprises the sequence of SEQ ID NO:119 and the VH comprises the sequence SEQ ID NO:156.

6. The antibody-antibiotic conjugate compound of claim 2, wherein the antibody comprises a light chain and a heavy chain sequence of (a) SEQ ID NO:123 and SEQ ID NO:147, or (b) SEQ ID NO:145 and SEQ ID NO:147.

7. The antibody-antibiotic conjugate compound of claim 2, wherein the antibody comprises a VH comprising the amino acid sequence of SEQ ID NO:120.

8. The antibody-antibiotic conjugate compound of claim 2, wherein the antibody comprises a VL and a VH, wherein the VL comprises the sequence of SEQ ID NO:119 and the VH comprises the sequence SEQ ID NO:120.

9. The antibody-antibiotic conjugate compound of claim 2, wherein the antibody comprises a light chain (LC) wherein the LC comprises the amino acid sequence of SEQ ID NO:121, and a heavy chain (HC) wherein the HC comprises the amino acid sequence of SEQ ID NO:146.

10. The antibody-antibiotic conjugate compound of claim 1, wherein the rifamycin-type antibiotic comprises a quaternary amine attached to the peptide linker.

11. The antibody-antibiotic conjugate compound of claim 10, wherein the peptide linker is attached to a cysteine or an engineered cysteine of the anti-WTA antibody.

12. The antibody-antibiotic conjugate compound of claim 10, wherein the peptide linker is a *S. aureus* endopeptidase or cysteine protease cleavable linker.

13. The antibody-antibiotic conjugate compound of claim 12, wherein the peptide linker is a staphopain B or a staphopain A cleavable linker.

14. The antibody-antibiotic conjugate compound of claim 12, wherein the peptide linker is a human protease cathepsin B cleavable linker.

15. The antibody-antibiotic conjugate compound of claim 14, wherein the peptide linker is a val-cit dipeptide linker.

16. The antibody-antibiotic conjugate compound of claim 1, wherein:
L is the peptide linker having the formula:

-Str-Pep-Y- where Str is a stretcher unit; Pep is a peptide of two to twelve amino acid residues, and Y is a spacer unit.

17. The antibody-antibiotic conjugate compound of claim 16, wherein p is 2 to 4.

18. The antibody-antibiotic conjugate compound of claim 1 wherein the formula is selected from the group consisting of:

a)
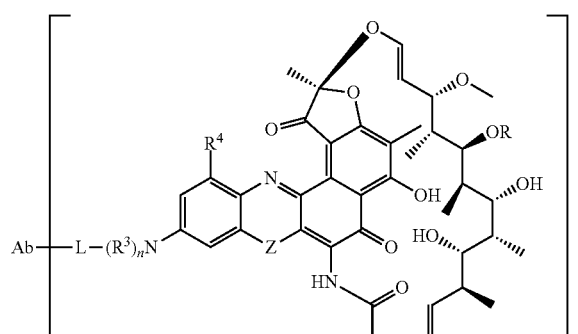
wherein
R³ is independently selected from H and C₁-C₁₂ alkyl;
n is 1 or 2;
R⁴ is selected from H, F, Cl, Br, I, C₁-C₁₂ alkyl, and OH; and
Z is selected from NH, N(C₁-C₁₂ alkyl), O and S;
b)
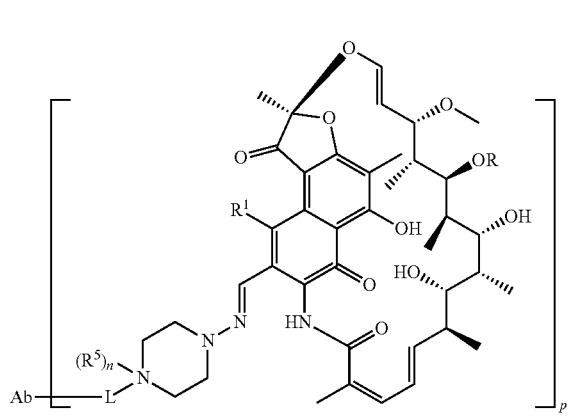
wherein
R⁵ is selected from H and C₁-C₁₂ alkyl; and
n is 0 or 1;
c)
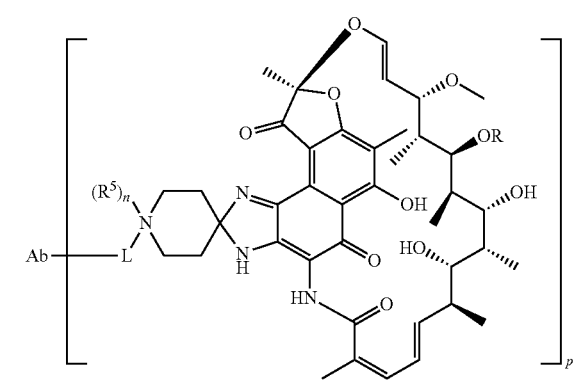
wherein
R⁵ is selected from H and C₁-C₁₂ alkyl; and
n is 0 or 1;
d)
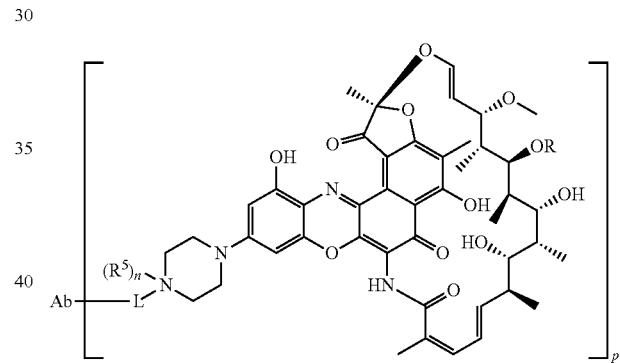
wherein
R⁵ is independently selected from H and C₁-C₁₂ alkyl; and
n is 0 or 1;
e)
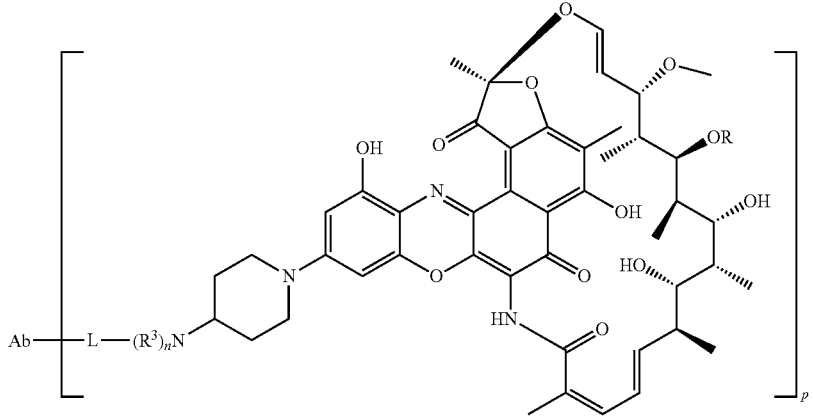

wherein
R³ is independently selected from H and C₁-C₁₂ alkyl; and
n is 1 or 2; and
f)

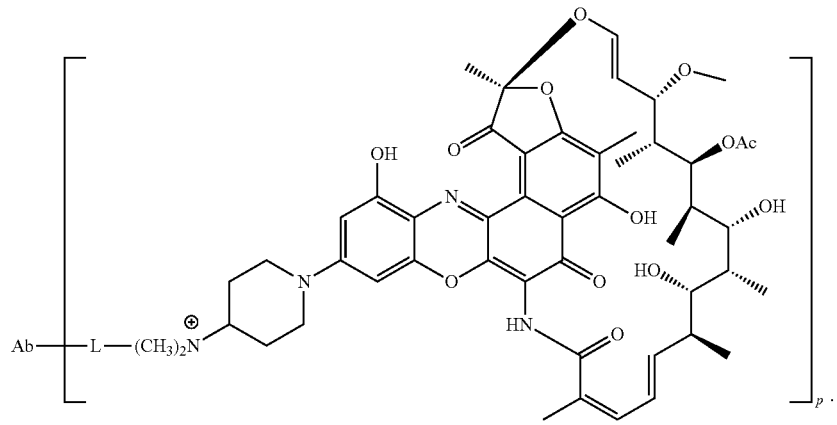

19. The antibody-antibiotic conjugate compound of claim 16, wherein Str has the formula:

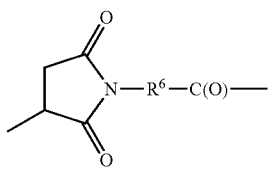

wherein R⁶ is selected from the group consisting of C₁-C₁₀ alkylene-, —C₃-C₈ carbocyclo, —O—(C₁-C₈ alkyl)-, -arylene-, —C₁-C₁₀ alkylene-arylene-, -arylene-C₁-C₁₀ alkylene-, —C₁-C₁₀ alkylene-(C₃-C₈ carbocyclo)-, —(C₃-C₈ carbocyclo)-C1-C10 alkylene-, —C₃-C₈ heterocyclo-, —C₁-C₁₀ alkylene-(C₃-C₈ heterocyclo)-, —(C₃-C₈ heterocyclo)-C₁-C₁₀ alkylene-, —(CH₂CH₂O)ᵣ—, and —(CH₂CH₂O)ᵣ—CH₂—; and r is an integer ranging from 1 to 10.

20. The antibody-antibiotic conjugate compound of claim 19, wherein R⁶ is —(CH₂)₅—.

21. The antibody-antibiotic conjugate compound of claim 16, wherein Pep comprises two to twelve amino acid residues independently selected from glycine, alanine, phenylalanine, lysine, arginine, valine, and citrulline.

22. The antibody-antibiotic conjugate compound of claim 21, wherein Pep is selected from valine-citrulline (val-cit, vc); phenylalanine-lysine (fk); and valine-citrulline-phenylalanine (val-cit-phe.

23. The antibody-antibiotic conjugate compound of claim 16, wherein Y comprises para-aminobenzyl or para-aminobenzyloxycarbonyl.

24. The antibody-antibiotic conjugate compound of claim 16 wherein L is the peptide linker having the formula:

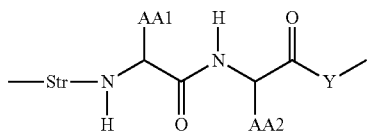

where AA1 and AA2 are independently selected from an amino acid side chain.

25. The antibody-antibiotic conjugate compound of claim 24, wherein the amino acid side chain is independently selected from H, —CH3, —CH₂(C₆H₅), —CH₂CH₂CH₂CH₂NH₂, —CH₂CH₂CH₂NHC(NH)NH₂, —CHCH(CH3)CH3, and —CH₂CH₂CH₂NHC(O)NH₂.

26. The antibody-antibiotic conjugate compound of claim 24 wherein L is the peptide linker having the formula:

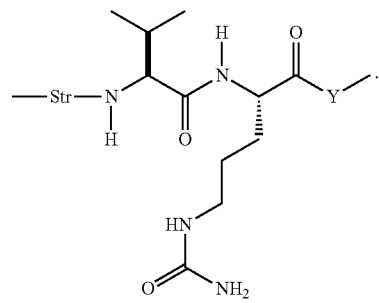

27. The antibody-antibiotic conjugate compound of claim 24 wherein L is the peptide linker having the formula:

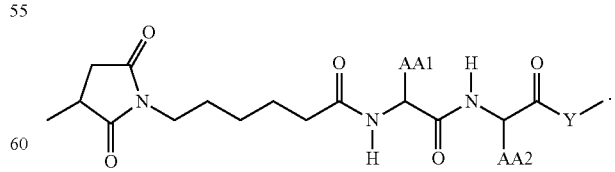

28. The antibody-antibiotic conjugate compound of claim 27 wherein L is the peptide linker having the formula:

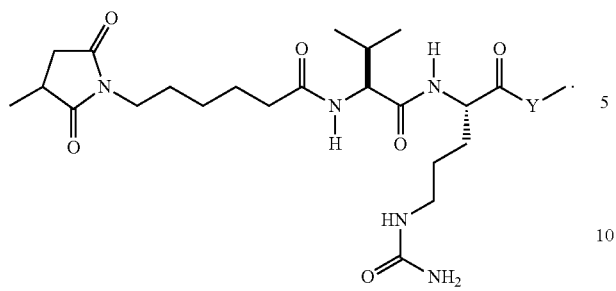

29. The antibody-antibiotic conjugate compound of claim 24 wherein L is the peptide linker having the formula:

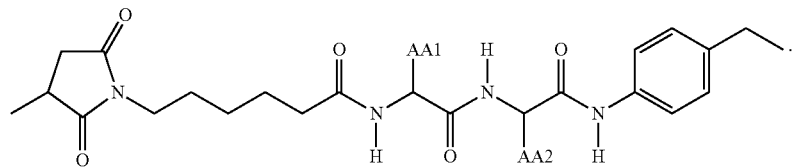

30. The antibody-antibiotic conjugate compound of claim 29 wherein L is the peptide linker having the formula:

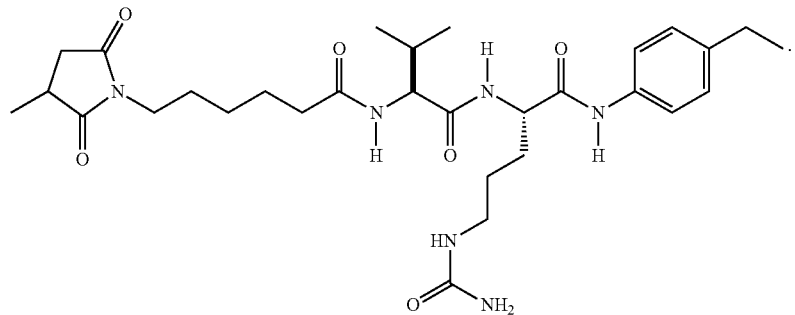 [SMILES: CCc1ccc(NC(=O)[C@H](CCCNC(N)=O)NC(=O)[C@@H](NC(=O)CCCCCN2C(=O)CC(C)C2=O)C(C)C)cc1]

31. The antibody-antibiotic conjugate compound of claim 24 wherein L is the peptide linker having the formula:

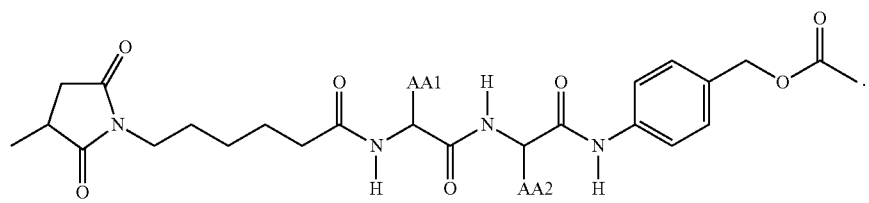

32. The antibody-antibiotic conjugate compound of claim 31 wherein L is the peptide linker having the formula:

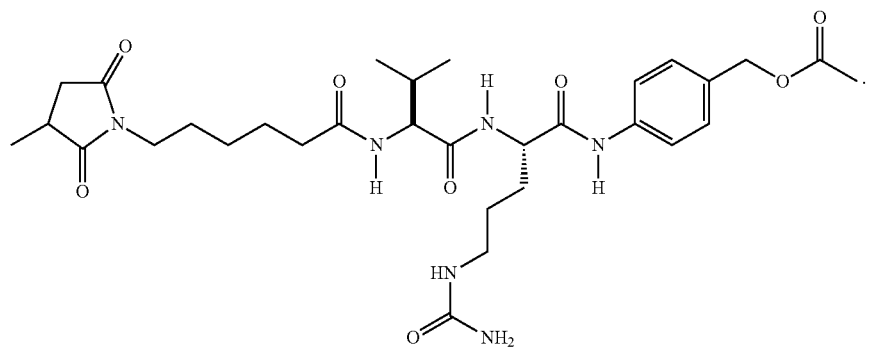 [SMILES: CC(=O)OCc1ccc(NC(=O)[C@H](CCCNC(N)=O)NC(=O)[C@@H](NC(=O)CCCCCN2C(=O)CC(C)C2=O)C(C)C)cc1]
33. The antibody-antibiotic conjugate compound of claim 24 wherein L is the peptide linker having the formula:
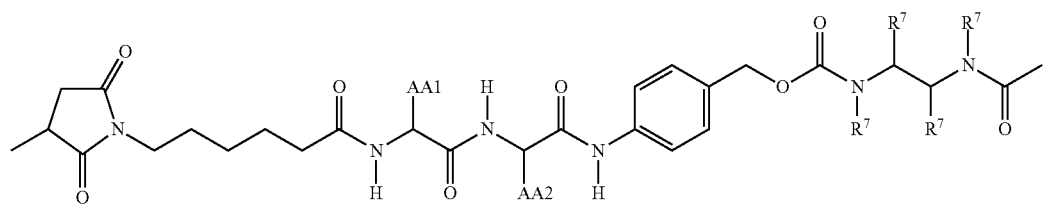
where $R^7$ is independently selected from H and $C_1$-$C_{12}$ alkyl.
34. The antibody-antibiotic conjugate compound of claim 24 having the formula:
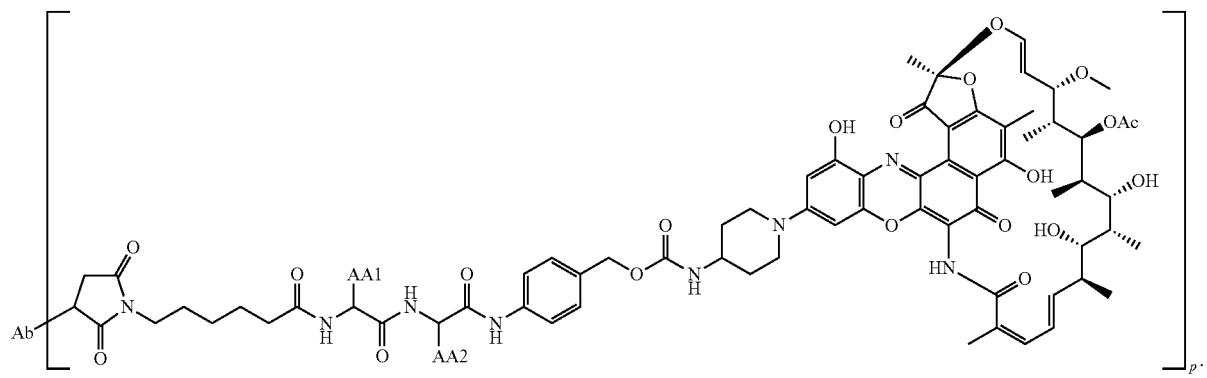
35. The antibody-antibiotic conjugate compound of claim 34 having the formula:

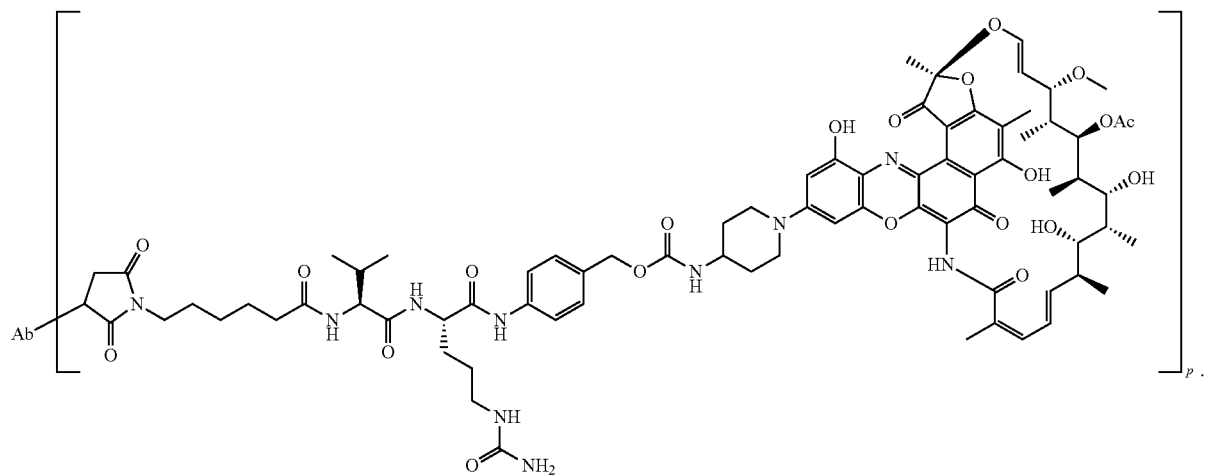
36. The antibody-antibiotic conjugate compound of claim 24 having the formula:
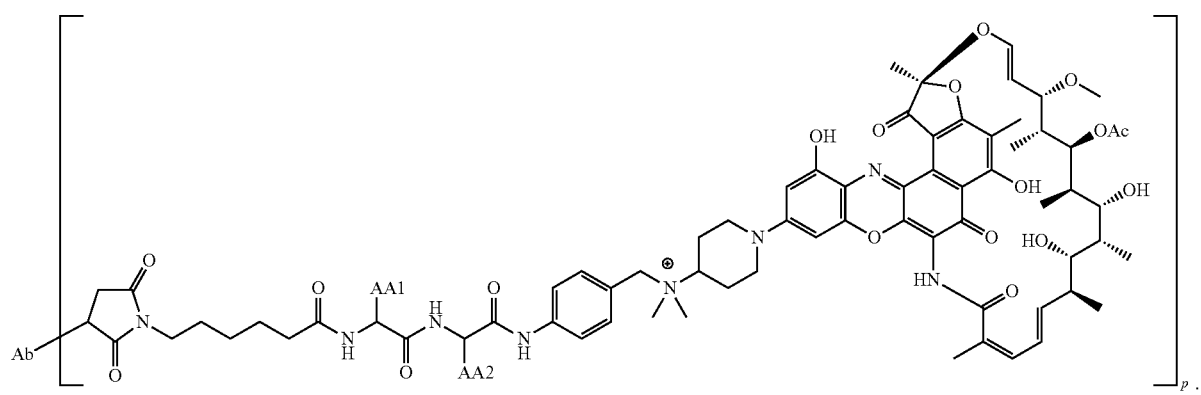
37. The antibody-antibiotic conjugate compound of claim 36 having the formula:
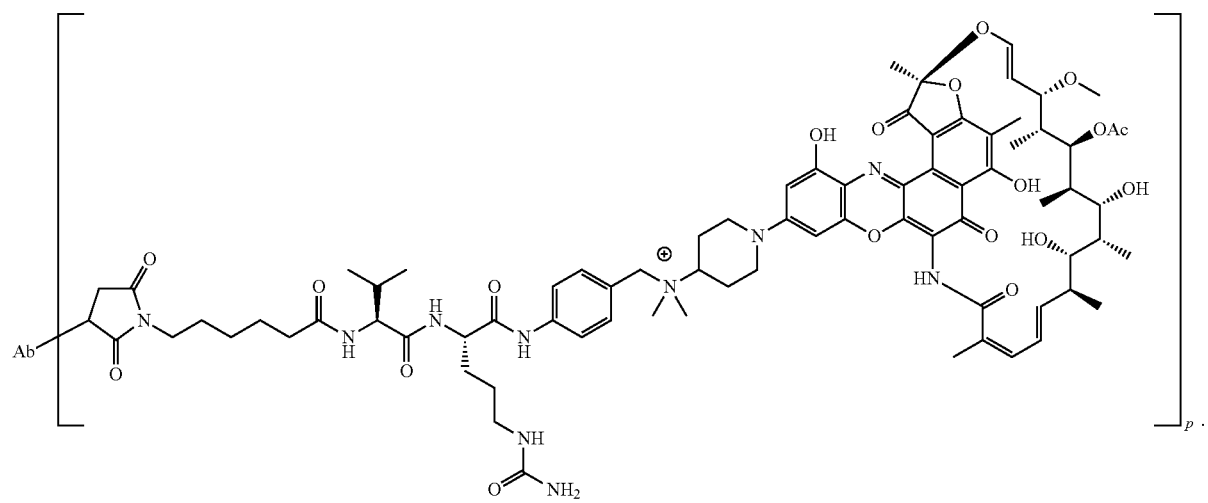

38. A pharmaceutical composition comprising the antibody-antibiotic conjugate compound of claim 1, and a pharmaceutically acceptable carrier, glidant, diluent, or excipient.

39. A process for making the antibody-antibiotic conjugate compound of claim 1, comprising the steps of:
a) preparing the anti-wall teichoic acid monoclonal antibody by reduction with DTT (dithiothreitol) or tricarbonylethylphosphine (TCEP); and
b) conjugating an antibiotic-linker intermediate having Formula II:

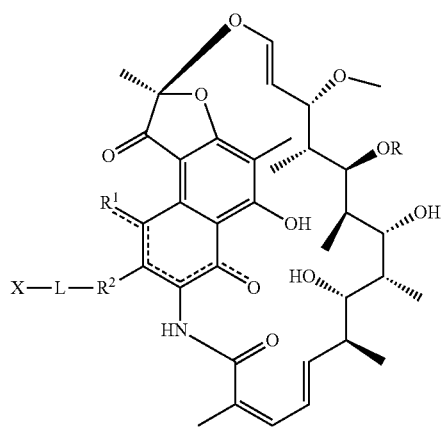

II wherein:
the dashed lines indicate an optional bond;
R is H, $C_1$-$C_{12}$ alkyl, or $C(O)CH_3$;
$R^1$ is OH;
$R^2$ is CH=N-(heterocyclyl), wherein the heterocyclyl is optionally substituted with one or more groups independently selected from $C(O)CH_3$, $C_1$-$C_{12}$ alkyl, $C_1$-$C_{12}$ heteroaryl, $C_2$-$C_{20}$ heterocyclyl, $C_6$-$C_{20}$ aryl, and $C_3$-$C_{12}$ carbocyclyl;
or $R^1$ and $R^2$ form a five- or six-membered fused heteroaryl or heterocyclyl, and optionally forming a spiro or fused six-membered heteroaryl, heterocyclyl, aryl, or carbocyclyl ring, wherein the spiro or fused six-membered heteroaryl, heterocyclyl, aryl, or carbocyclyl ring is optionally substituted H, F, Cl, Br, I, $C_1$-$C_{12}$ alkyl, or OH;
L is a peptide linker attached to $R^2$ or the fused heteroaryl or heterocyclyl formed by $R^1$ and $R^2$; and having the formula:

-Str-Pep-Y- where Str is a stretcher unit; Pep is a peptide of two to twelve amino acid residues, and Y is a spacer unit; and
X is a reactive functional group selected from maleimide, thiol, amino, bromide, bromoacetamido, iodoacetamido, p-toluenesulfonate, iodide, hydroxyl, carboxyl, pyridyl disulfide, and N-hydroxysuccinimide;
to the anti-wall teichoic acid monoclonal antibody
whereby the antibody-antibiotic conjugate compound is formed.

40. The process of claim 39, wherein the antibody-antibiotic conjugate compound has the formula:

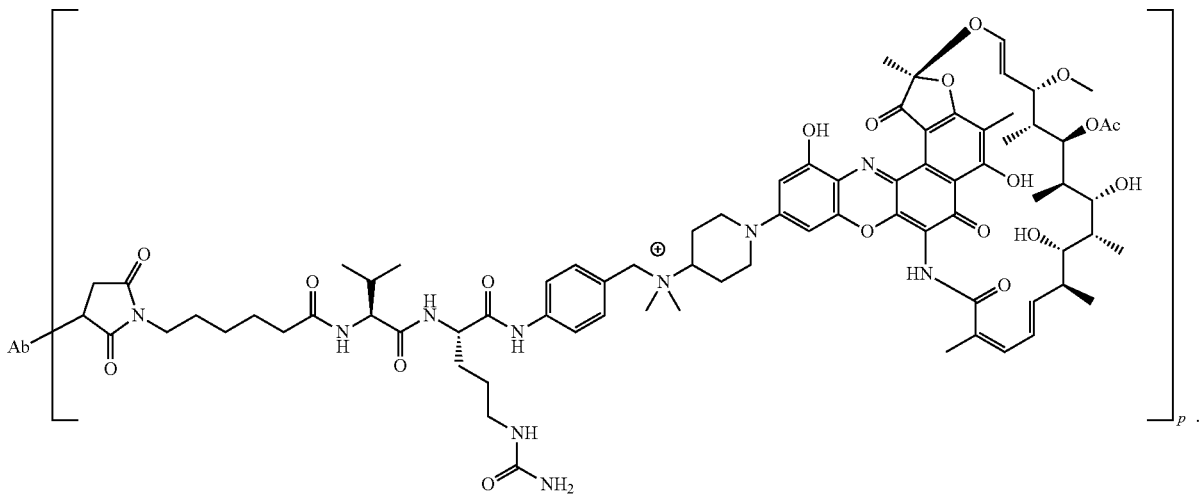

41. An antibody-antibiotic conjugate compound having the formula:

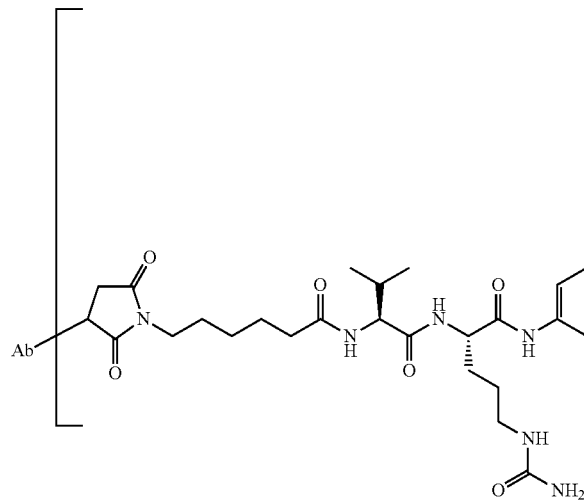

wherein Ab is an anti-wall teichoic acid (WTA) monoclonal antibody that binds to *Staphylococcus aureus*, and comprises a VL and a VH, wherein the VL comprises the sequence of SEQ ID NO:119 and the VH comprises the sequence SEQ ID NO:156; and p is an integer from 1 to 8.

42. The antibody-antibiotic conjugate compound of claim 41, wherein the antibody comprises a light chain (LC) wherein the LC comprises the amino acid sequence of SEQ ID NO:145, and a heavy chain (HC) wherein the HC comprises the amino acid sequence of SEQ ID NO:157.

43. An antibody-antibiotic conjugate compound having the formula:

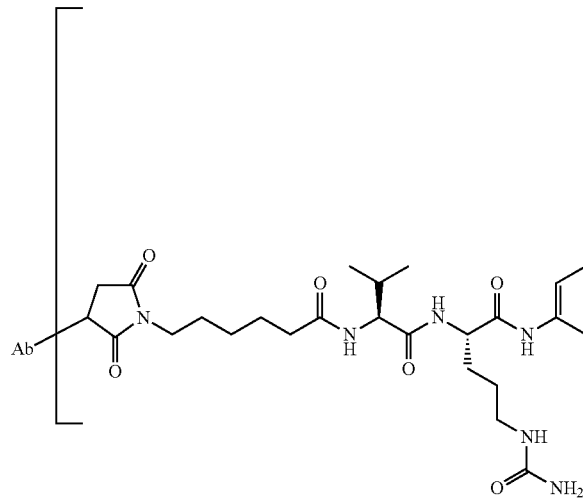

wherein Ab is anti-wall teichoic acid (WTA) monoclonal antibody that binds to *Staphylococcus aureus*, and comprises a VL and a VH, wherein the VL comprises the sequence of SEQ ID NO:119 and the VH comprises the sequence SEQ ID NO:156, and wherein p is an integer of 2.

44. The antibody-antibiotic conjugate compound of claim 43, wherein the antibody comprises a light chain (LC) wherein the LC comprises the amino acid sequence of SEQ ID NO:145, and a heavy chain (HC) wherein the HC comprises the amino acid sequence of SEQ ID NO:157.

45. A method of treating a bacterial infection comprising administering to a patient a therapeutically-effective amount of the antibody-antibiotic conjugate compound of claim 1, wherein the bacterial infection is a *Staphylococcus aureus* infection.

46. The method of claim 45, wherein the antibody-antibiotic conjugate compound comprises an antibody comprising a VL and a VH, wherein the VL comprises the sequence of SEQ ID NO:119 and the VH comprises the sequence SEQ ID NO:156.

47. The method of claim 45, wherein the antibody-antibiotic conjugate compound comprises an antibody comprising a LC and a HC, wherein the LC comprises the sequence of SEQ ID NO:145 and the HC comprises the sequence SEQ ID NO:157.

48. The method of claim 45, wherein bacterial load in the patient is reduced by the treatment.

49. A method of reducing the number of intracellular *Staphylococcus aureus* bacterial cells in the host cells of a *Staphylococcus aureus* infected patient without reducing the number of the host cells comprising administering to the patient the antibody-antibiotic conjugate compound of claim 1.

50. The method of claim 49, wherein the number of persistant persistent bacterial cells are reduced.

51. The method of claim 45, wherein the patient is a human.

52. The method of claim 45, further comprising administering a second therapeutic agent.

53. The method of claim 52, wherein the second therapeutic agent is an antibiotic.

54. The method of claim 53, wherein the antibiotic is selected from the structural class consisting of (i) aminoglycosides; (ii) beta-lactams; (iii) macrolides/cyclic peptides; (iv) tetracyclines; (v) fluoroquinolines/fluoroquinolones; and (vi) oxazolidinones.

55. The method of claim 53, wherein the antibiotic is selected from the group consisting of clindamycin, novobiocin, retapamulin, daptomycin, GSK-2140944 (gepotidacin) having the structure:

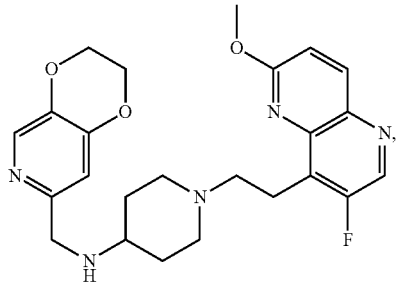

GSK-2140944

CG-400549 having the structure:

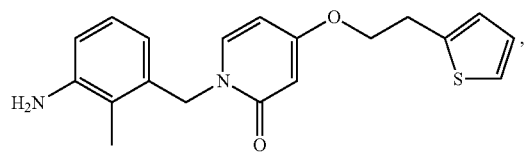

CG-400549 sitafloxacin, teicoplanin, triclosan, napthyridone, radezolid, doxorubicin, ampicillin, vancomycin, imipenem, doripenem, gemcitabine, dalbavancin, and azithromycin.

56. A kit for treating a bacterial infection, comprising:
 a) the pharmaceutical composition of claim 38; and
 b) instructions for use.

57. The antibody-antibiotic conjugate compound of claim 2, wherein the antibody comprises a light chain (LC) wherein the LC comprises the amino acid sequence of SEQ ID NO:145, and a heavy chain (HC) wherein the HC comprises the amino acid sequence of SEQ ID NO:157.

58. An antibody-antibiotic conjugate compound having the formula:

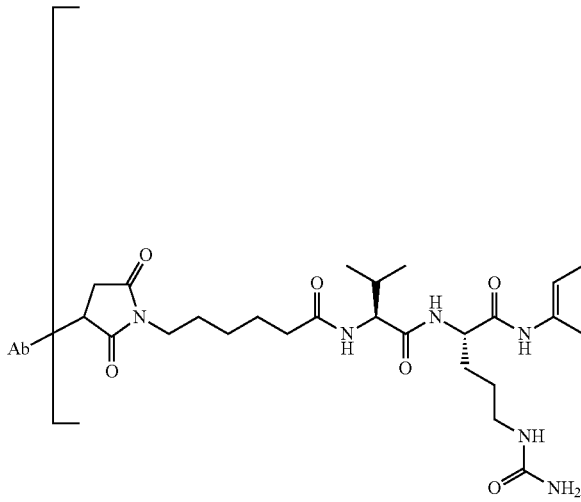
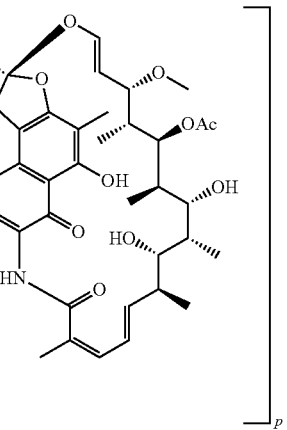

wherein Ab is an anti-wall teichoic acid (WTA)monoclonal antibody that binds to *Staphylococcus aureus*, wherein the VL of the anti-wall teichoic acid monoclonal antibody comprises CDR L1 comprising the sequence of KSSQSIFRTSRNKNLLN (SEQ ID NO:99), CDR L2 comprising the sequence of WASTRKS (SEQ ID NO:100), and CDR L3 comprising the sequence of QQYFSPPYT (SEQ ID NO:101); and the VH of the anti-WTA monoclonal antibody comprises CDR H1 comprising the sequence of SFWMH (SEQ ID NO:102), CDR H2 comprising the sequence of FTNNEGTTTAYADSVRG (SEQ ID NO:103), and CDR H3 comprising the sequence of GEGGLDD (SEQ ID NO:118); and
p is an integer from 1 to 8.

\* \* \* \* \*

UNITED STATES PATENT AND TRADEMARK OFFICE
CERTIFICATE OF CORRECTION

PATENT NO. : 9,803,002 B2
APPLICATION NO. : 14/292289
DATED : October 31, 2017
INVENTOR(S) : Eric J. Brown et al.

Page 1 of 1

It is certified that error appears in the above-identified patent and that said Letters Patent is hereby corrected as shown below:

On the Title Page

Item [73], delete "Genentench, Inc." and insert -- Genentech, Inc. --;

In the Claims

Column 385, Lines 32-45, Claim 18, delete the following structure:

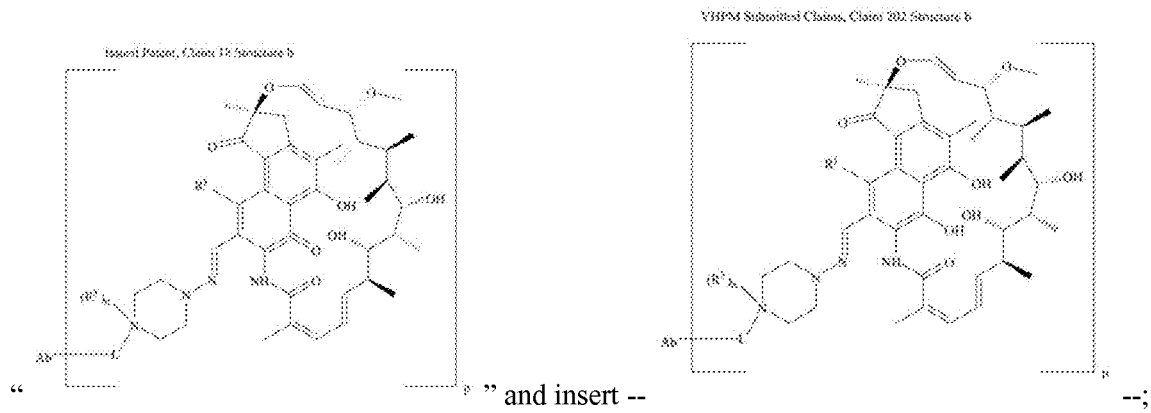

" and insert -- --;

Column 387, Line 40, Claim 19, delete "-C1-C10 alkylene-" and insert -- $-C_1-C_{10}$ alkylene- --;

Column 387, Line 54, Claim 21, delete "(val-cit-phe." and insert -- (val-cit-phe). --;

Column 399, Line 12, Claim 50, delete "persistant persistent" and insert -- persistent -- therefor.

Signed and Sealed this
First Day of May, 2018

Andrei Iancu
*Director of the United States Patent and Trademark Office*

SEQUENCE LISTING

```
<160> NUMBER OF SEQ ID NOS: 180

<210> SEQ ID NO 1
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Lys Ser Ser Gln Ser Val Leu Ser Arg Ala Asn Asn Asn Tyr Tyr Val
1               5                   10                  15

Ala

<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Trp Ala Ser Thr Arg Glu Phe
1               5

<210> SEQ ID NO 3
<211> LENGTH: 9
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 3

Gln Gln Tyr Tyr Thr Ser Arg Arg Thr
1               5

<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Asp Tyr Tyr Met His
1               5

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Trp Ile Asn Pro Lys Ser Gly Gly Thr Asn Tyr Ala Gln Arg Phe Gln
1               5                   10                  15

Gly

<210> SEQ ID NO 6
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Asp Cys Gly Ser Gly Gly Leu Arg Asp Phe
1               5                   10

<210> SEQ ID NO 7
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Arg Ser Asn Gln Asn Leu Leu Ser Ser Ser Asn Asn Tyr Leu Ala
1               5                   10                  15

<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 8

Trp Ala Ser Thr Arg Glu Ser
1               5

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gln Gln Tyr Tyr Ala Asn Pro Arg Thr
1               5

<210> SEQ ID NO 10
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Asp Tyr Tyr Ile His
1               5

<210> SEQ ID NO 11
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Trp Ile Asn Pro Asn Thr Gly Gly Thr Tyr Tyr Ala Gln Lys Phe Arg
1               5                   10                  15

Asp

<210> SEQ ID NO 12
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Asp Cys Gly Arg Gly Gly Leu Arg Asp Ile
1               5                   10

<210> SEQ ID NO 13
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13
```

```
Lys Ser Asn Gln Asn Val Leu Ala Ser Ser Asn Asp Lys Asn Tyr Leu
1               5                   10                  15
Ala
```

<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

```
Trp Ala Ser Ile Arg Glu Ser
1               5
```

<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

```
Gln Gln Tyr Tyr Thr Asn Pro Arg Thr
1               5
```

<210> SEQ ID NO 16
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

```
Asp Tyr Tyr Ile His
1               5
```

<210> SEQ ID NO 17
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

```
Trp Ile Asn Pro Asn Thr Gly Gly Thr Asn Tyr Ala Gln Lys Phe Gln
1               5                   10                  15
Gly
```

<210> SEQ ID NO 18
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

```
Asp Cys Gly Asn Ala Gly Leu Arg Asp Ile
1               5                   10

<210> SEQ ID NO 19
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Lys Ser Ser Gln Asn Val Leu Tyr Ser Ser Asn Asn Lys Asn Tyr Leu
1               5                   10                  15

Ala

<210> SEQ ID NO 20
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Trp Ala Ser Thr Arg Glu Ser
1               5

<210> SEQ ID NO 21
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gln Gln Tyr Tyr Thr Ser Pro Pro Tyr Thr
1               5                   10

<210> SEQ ID NO 22
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ser Tyr Trp Ile Gly
1               5

<210> SEQ ID NO 23
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Ile Ile His Pro Gly Asp Ser Lys Thr Arg Tyr Ser Pro Ser Phe Gln
```

```
1               5                   10                  15
Gly

<210> SEQ ID NO 24
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Leu Tyr Cys Ser Gly Gly Ser Cys Tyr Ser Asp Arg Ala Phe Ser Ser
1               5                   10                  15

Leu Gly Ala Gly Gly Tyr Tyr Tyr Tyr Gly Met Gly Val
            20                  25

<210> SEQ ID NO 25
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Ser Arg
            20                  25                  30

Ala Asn Asn Asn Tyr Tyr Val Ala Trp Tyr Gln His Lys Pro Gly Gln
        35                  40                  45

Pro Pro Lys Leu Leu Ile Tyr Trp Ala Ser Thr Arg Glu Phe Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Tyr Cys Gln Gln
                85                  90                  95

Tyr Tyr Thr Ser Arg Arg Thr Phe Gly Gln Gly Thr Lys Val Glu Ile
            100                 105                 110

Lys

<210> SEQ ID NO 26
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Gln Val Gln Leu Val Gln Ser Gly Ala Glu Val Arg Lys Pro Gly Ala
1               5                   10                  15

Ser Val Lys Val Ser Cys Lys Ala Ser Gly Tyr Ser Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Lys Ser Gly Gly Thr Asn Tyr Ala Gln Arg Phe
```

```
                    50                  55                  60
Gln Gly Arg Val Thr Met Thr Gly Asp Thr Ser Ile Ser Ala Ala Tyr
 65                  70                  75                  80

Met Asp Leu Ala Ser Leu Thr Ser Asp Thr Ala Val Tyr Tyr Cys
                     85                  90                  95

Val Lys Asp Cys Gly Ser Gly Gly Leu Arg Asp Phe Trp Gly Gln Gly
                100                 105                 110

Thr Thr Val Thr Val Ser Ser
            115

<210> SEQ ID NO 27
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Asp Ile Gln Met Thr Gln Ser Pro Asp Ser Leu Ser Val Ser Leu Gly
 1                5                  10                  15

Glu Arg Ala Thr Ile Asn Cys Arg Ser Asn Gln Asn Leu Leu Ser Ser
                 20                  25                  30

Ser Asn Asn Asn Tyr Leu Ala Trp Tyr Gln Gln Lys Pro Gly Gln Pro
             35                  40                  45

Leu Lys Leu Leu Ile Tyr Trp Ala Ser Thr Arg Glu Ser Gly Val Pro
         50                  55                  60

Asp Arg Phe Ser Gly Ser Gly Ser Gly Thr Asp Phe Thr Leu Thr Ile
 65                  70                  75                  80

Ser Ser Leu Gln Ala Glu Asp Val Ala Val Tyr Tyr Cys Gln Gln Tyr
                 85                  90                  95

Tyr Ala Asn Pro Arg Thr Phe Gly Gln Gly Thr Lys Val Glu Ile Lys
                100                 105                 110

<210> SEQ ID NO 28
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Gln Val Gln Leu Gln Gln Ser Arg Val Glu Val Lys Arg Pro Gly Thr
 1                5                  10                  15

Ser Val Lys Val Ser Cys Lys Thr Ser Gly Tyr Thr Phe Ser Asp Tyr
                 20                  25                  30

Tyr Ile His Trp Val Arg Leu Ala Pro Gly Gln Gly Leu Glu Leu Met
             35                  40                  45

Gly Trp Ile Asn Pro Asn Thr Gly Gly Thr Tyr Ala Gln Lys Phe
         50                  55                  60

Arg Asp Arg Val Thr Met Thr Arg Asp Thr Ser Ile Ala Thr Ala Tyr
 65                  70                  75                  80

Leu Glu Met Ser Ser Leu Thr Ser Asp Thr Ala Val Tyr Tyr Cys
                 85                  90                  95

Ala Lys Asp Cys Gly Arg Gly Gly Leu Arg Asp Ile Trp Gly Pro Gly
                100                 105                 110
```

Thr Met Val Thr Val Ser Ser
        115

<210> SEQ ID NO 29
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Glu Ile Val Leu Thr Gln Ser Pro Asp Ser Leu Ala Val Ser Leu Gly
1               5                   10                  15

Glu Arg Ala Thr Ile Asn Cys Lys Ser Asn Gln Asn Val Leu Ala Ser
            20                  25                  30

Ser Asn Asp Lys Asn Tyr Leu Ala Trp Phe Gln His Lys Pro Gly Gln
        35                  40                  45

Pro Leu Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Arg Ala Glu Asp Val Ala Val Tyr Tyr Cys Gln Gln
                85                  90                  95

Tyr Tyr Thr Asn Pro Arg Thr Phe Gly Gln Gly Thr Lys Val Glu Phe
            100                 105                 110

Asn

<210> SEQ ID NO 30
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Glu Val Gln Leu Val Gln Ser Gly Ala Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Tyr Ile His Trp Val Arg Leu Ala Pro Gly Gln Gly Leu Glu Leu Met
        35                  40                  45

Gly Trp Ile Asn Pro Asn Thr Gly Gly Thr Asn Tyr Ala Gln Lys Phe
    50                  55                  60

Gln Gly Arg Val Thr Met Thr Arg Asp Thr Ser Ile Ala Thr Ala Tyr
65                  70                  75                  80

Met Glu Leu Ser Ser Leu Thr Ser Asp Asp Thr Ala Val Tyr Tyr Cys
                85                  90                  95

Ala Lys Asp Cys Gly Asn Ala Gly Leu Arg Asp Ile Trp Gly Gln Gly
            100                 105                 110

Thr Thr Val Thr Val Ser Ser
        115

<210> SEQ ID NO 31
<211> LENGTH: 114
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 31

```
Asp Ile Gln Leu Thr Gln Ser Pro Asp Ser Leu Ala Val Ser Leu Gly
1               5                   10                  15
Glu Arg Ala Thr Ile Asn Cys Lys Ser Ser Gln Asn Val Leu Tyr Ser
            20                  25                  30
Ser Asn Asn Lys Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr Thr Ser Pro Pro Tyr Thr Phe Gly Gln Gly Thr Lys Leu Glu
            100                 105                 110
Ile Glu
```

<210> SEQ ID NO 32
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 32

```
Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Ser Tyr
            20                  25                  30
Trp Ile Gly Trp Val Arg Gln Met Pro Gly Lys Gly Leu Glu Trp Met
        35                  40                  45
Gly Ile Ile His Pro Gly Asp Ser Lys Thr Arg Tyr Ser Pro Ser Phe
    50                  55                  60
Gln Gly Gln Val Thr Ile Ser Ala Asp Lys Ser Ile Ser Thr Ala Tyr
65                  70                  75                  80
Leu Gln Trp Asn Ser Leu Lys Ala Ser Asp Thr Ala Met Tyr Tyr Cys
                85                  90                  95
Ala Arg Leu Tyr Cys Ser Gly Ser Cys Tyr Ser Asp Arg Ala Phe
            100                 105                 110
Ser Ser Leu Gly Ala Gly Gly Tyr Tyr Tyr Gly Met Gly Val Trp
        115                 120                 125
Gly Gln Gly Thr Thr Val Thr Val Ser Ser
    130                 135
```

<210> SEQ ID NO 33
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 33

Arg Ala Ser Gln Thr Ile Ser Gly Trp Leu Ala
1               5                   10

<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Lys Ala Ser Thr Leu Glu Ser
1               5

<210> SEQ ID NO 35
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Gln Gln Tyr Lys Ser Tyr Ser Phe Asn
1               5

<210> SEQ ID NO 36
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ser Tyr Asp Ile Asn
1               5

<210> SEQ ID NO 37
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Trp Met Asn Ala Asn Ser Gly Asn Thr Gly Tyr Ala Gln Lys Phe Gln
1               5                   10                  15

Gly

<210> SEQ ID NO 38
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38
```

```
Ser Ser Ile Leu Val Arg Gly Ala Leu Gly Arg Tyr Phe Asp Leu
1               5                   10                  15

<210> SEQ ID NO 39
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Arg Ala Ser Gln Thr Ile Ser Gly Trp Leu Ala
1               5                   10

<210> SEQ ID NO 40
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Lys Ala Ser Thr Leu Glu Ser
1               5

<210> SEQ ID NO 41
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gln Gln Tyr Lys Ser Tyr Ser Phe Asn
1               5

<210> SEQ ID NO 42
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ser Tyr Asp Ile Asn
1               5

<210> SEQ ID NO 43
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Trp Met Asn Ala Asn Ser Gly Asn Thr Gly Tyr Ala Gln Lys Phe Gln
1               5                   10                  15
```

-continued

Gly

<210> SEQ ID NO 44
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Ser Ser Ile Leu Val Arg Gly Ala Leu Gly Arg Tyr Phe Asp Leu
1               5                   10                  15

<210> SEQ ID NO 45
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Arg Ala Ser Gln Phe Val Ser Arg Thr Ser Leu Ala
1               5                   10

<210> SEQ ID NO 46
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Glu Thr Ser Ser Arg Ala Thr
1               5

<210> SEQ ID NO 47
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

His Lys Tyr Gly Ser Gly Pro Arg Thr
1               5

<210> SEQ ID NO 48
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Asn Tyr Asp Phe Ile
1               5

<210> SEQ ID NO 49

```
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Trp Met Asn Pro Asn Ser Tyr Asn Thr Gly Tyr Gly Gln Lys Phe Gln
1               5                   10                  15

Gly

<210> SEQ ID NO 50
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ala Val Arg Gly Gln Leu Leu Ser Glu Tyr
1               5                   10

<210> SEQ ID NO 51
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Arg Ala Ser Gln Ser Val Ser Ser Ser Tyr Leu Ala
1               5                   10

<210> SEQ ID NO 52
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Asp Ala Ser Ser Arg Ala Thr
1               5

<210> SEQ ID NO 53
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Gln Lys Tyr Gly Ser Thr Pro Arg Pro
1               5

<210> SEQ ID NO 54
<211> LENGTH: 5
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Ser Tyr Asp Ile Asn
1               5

<210> SEQ ID NO 55
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Trp Met Asn Pro Asn Ser Gly Asn Thr Asn Tyr Ala Gln Arg Phe Gln
1               5                   10                  15

Gly

<210> SEQ ID NO 56
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Glu Arg Trp Ser Lys Asp Thr Gly His Tyr Tyr Tyr Tyr Gly Met Asp
1               5                   10                  15

Val

<210> SEQ ID NO 57
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Arg Ala Ser Leu Asp Ile Thr Asn His Leu Ala
1               5                   10

<210> SEQ ID NO 58
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Glu Ala Ser Ile Leu Gln Ser
1               5

<210> SEQ ID NO 59
<211> LENGTH: 9
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Glu Lys Cys Asn Ser Thr Pro Arg Thr
1               5

<210> SEQ ID NO 60
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Asn Tyr Asp Ile Asn
1               5

<210> SEQ ID NO 61
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Trp Met Asn Pro Ser Ser Gly Arg Thr Gly Tyr Ala Pro Lys Phe Arg
1               5                   10                  15

Gly

<210> SEQ ID NO 62
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Gly Gly Gly Tyr Tyr Asp Ser Ser Gly Asn Tyr His Ile Ser Gly Leu
1               5                   10                  15

Asp Val

<210> SEQ ID NO 63
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Arg Ala Ser Gln Ser Val Gly Ala Ile Tyr Leu Ala
1               5                   10

<210> SEQ ID NO 64
<211> LENGTH: 7
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Gly Val Ser Asn Arg Ala Thr
1               5

<210> SEQ ID NO 65
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Gln Leu Tyr Thr Ser Ser Arg Ala Leu Thr
1               5                   10

<210> SEQ ID NO 66
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Ala Tyr Ala Met Asn
1               5

<210> SEQ ID NO 67
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Ser Ile Thr Lys Asn Ser Asp Ser Leu Tyr Tyr Ala Asp Ser Val Lys
1               5                   10                  15

Gly

<210> SEQ ID NO 68
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Leu Ala Ala Arg Ile Met Ala Thr Asp Tyr
1               5                   10

<210> SEQ ID NO 69
<211> LENGTH: 11
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 69

Arg Ala Ser Gln Gly Ile Arg Asn Gly Leu Gly
1               5                   10

<210> SEQ ID NO 70
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Pro Ala Ser Thr Leu Glu Ser
1               5

<210> SEQ ID NO 71
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Leu Gln Asp His Asn Tyr Pro Pro Thr
1               5

<210> SEQ ID NO 72
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Tyr Tyr Ser Met Ile
1               5

<210> SEQ ID NO 73
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Ser Ile Asp Ser Ser Ser Arg Tyr Leu Tyr Tyr Ala Asp Ser Val Lys
1               5                   10                  15

Gly

<210> SEQ ID NO 74
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 74

Asp Gly Asp Asp Ile Leu Ser Val Tyr Arg Gly Ser Gly Arg Pro Phe
1               5                   10                  15

Asp Tyr

<210> SEQ ID NO 75
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Arg Ala Ser Gln Gly Ile Arg Asn Gly Leu Gly
1               5                   10

<210> SEQ ID NO 76
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Pro Ala Ser Thr Leu Glu Ser
1               5

<210> SEQ ID NO 77
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Leu Gln Asp His Asn Tyr Pro Pro Ser
1               5

<210> SEQ ID NO 78
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Tyr Tyr Ser Met Ile
1               5

<210> SEQ ID NO 79
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 79

Ser Ile Asp Ser Ser Ser Arg Tyr Arg Tyr Tyr Thr Asp Ser Val Lys
1               5                   10                  15

Gly

<210> SEQ ID NO 80
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Asp Gly Asp Asp Ile Leu Ser Val Tyr Gln Gly Ser Gly Arg Pro Phe
1               5                   10                  15

Asp Tyr

<210> SEQ ID NO 81
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Arg Ala Ser Gln Ser Val Arg Thr Asn Val Ala
1               5                   10

<210> SEQ ID NO 82
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Gly Ala Ser Thr Arg Ala Ser
1               5

<210> SEQ ID NO 83
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Leu Gln Tyr Asn Thr Trp Pro Arg Thr
1               5

<210> SEQ ID NO 84
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 84

Thr Asn Asp Met Ser
1               5

<210> SEQ ID NO 85
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Thr Ile Ile Gly Ile Asp Asp Thr Thr His Tyr Ala Asp Ser Val Arg
1               5                   10                  15

Gly

<210> SEQ ID NO 86
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Asn Ser Gly Ile Tyr Ser Phe
1               5

<210> SEQ ID NO 87
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Arg Ala Ser Gln Asp Ile Gly Ser Ser Leu Ala
1               5                   10

<210> SEQ ID NO 88
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Ala Thr Ser Thr Leu Gln Ser
1               5

<210> SEQ ID NO 89
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89
```

```
Gln Gln Leu Asn Asn Tyr Val His Ser
1               5

<210> SEQ ID NO 90
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Asp Tyr Ala Met Gly
1               5

<210> SEQ ID NO 91
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Val Val Thr Gly His Ser Tyr Arg Thr His Tyr Ala Asp Ser Val Lys
1               5                   10                  15
Gly

<210> SEQ ID NO 92
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Arg Ile Trp Ser Tyr Gly Asp Asp Ser Phe Asp Val
1               5                   10

<210> SEQ ID NO 93
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Arg Ala Ser Gln Ser Ile Gly Asp Arg Leu Ala
1               5                   10

<210> SEQ ID NO 94
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Trp Ala Ser Asn Leu Glu Gly
1               5
```

```
<210> SEQ ID NO 95
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Gln Gln Tyr Lys Ser Gln Trp Ser
1               5

<210> SEQ ID NO 96
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Ser Tyr Ala Met Asn
1               5

<210> SEQ ID NO 97
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Tyr Ile Ser Ser Ile Glu Thr Ile Tyr Tyr Ala Asp Ser Val Lys Gly
1               5                   10                  15

<210> SEQ ID NO 98
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Asp Arg Leu Val Asp Val Pro Leu Ser Ser Pro Asn Ser
1               5                   10

<210> SEQ ID NO 99
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Lys Ser Ser Gln Ser Ile Phe Arg Thr Ser Arg Asn Lys Asn Leu Leu
1               5                   10                  15

Asn
```

```
<210> SEQ ID NO 100
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Trp Ala Ser Thr Arg Lys Ser
1               5

<210> SEQ ID NO 101
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Gln Gln Tyr Phe Ser Pro Pro Tyr Thr
1               5

<210> SEQ ID NO 102
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Ser Phe Trp Met His
1               5

<210> SEQ ID NO 103
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Phe Thr Asn Asn Glu Gly Thr Thr Thr Ala Tyr Ala Asp Ser Val Arg
1               5                   10                  15

Gly

<210> SEQ ID NO 104
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Gly Asp Gly Gly Leu Asp Asp
1               5

<210> SEQ ID NO 105
<211> LENGTH: 11
```

-continued

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Arg Ala Ser Gln Phe Thr Asn His Tyr Leu Asn
1               5                   10

<210> SEQ ID NO 106
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Val Ala Ser Asn Leu Gln Ser
1               5

<210> SEQ ID NO 107
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Gln Gln Ser Tyr Arg Thr Pro Tyr Thr
1               5

<210> SEQ ID NO 108
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Ser Gly Tyr Tyr Asn
1               5

<210> SEQ ID NO 109
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Tyr Ile Leu Ser Gly Ala His Thr Asp Ile Lys Ala Ser Leu Gly Ser
1               5                   10                  15

<210> SEQ ID NO 110
<211> LENGTH: 11
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 110

Ser Gly Val Tyr Ser Lys Tyr Ser Leu Asp Val
1               5                   10

<210> SEQ ID NO 111
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Asp Ile Val Met Thr Gln Ser Pro Ser Ile Leu Ser Ala Ser Val Gly
1               5                   10                  15

Asp Arg Val Thr Ile Thr Cys Arg Ala Ser Gln Thr Ile Ser Gly Trp
            20                  25                  30

Leu Ala Trp Tyr Gln Gln Lys Pro Ala Glu Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Gly Ile Tyr Tyr Cys Gln Gln Tyr Lys Ser Tyr Ser Phe
                85                  90                  95

Asn Phe Gly Gln Gly Thr Lys Val Glu Ile Lys
            100                 105

<210> SEQ ID NO 112
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: 1
<223> OTHER INFORMATION: Xaa = Gln or Glu
<220> FEATURE:
<221> NAME/KEY: VARIANT
<222> LOCATION: 2
<223> OTHER INFORMATION: Xaa = Met or Ile or Val

<400> SEQUENCE: 112

Xaa Xaa Gln Leu Val Gln Ser Gly Ala Glu Val Lys Lys Pro Gly Ala
1               5                   10                  15

Ser Val Lys Val Ser Cys Glu Ala Ser Gly Tyr Thr Leu Thr Ser Tyr
            20                  25                  30

Asp Ile Asn Trp Val Arg Gln Ala Thr Gly Gln Gly Pro Glu Trp Met
        35                  40                  45

Gly Trp Met Asn Ala Asn Ser Gly Asn Thr Gly Tyr Ala Gln Lys Phe
    50                  55                  60

Gln Gly Arg Val Thr Leu Thr Gly Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Ser Ser Ile Leu Val Arg Gly Ala Leu Gly Arg Tyr Phe Asp
            100                 105                 110

Leu Trp Gly Arg Gly Thr Leu Val Thr Val Ser Ser
        115                 120
```

<210> SEQ ID NO 113
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

```
Asp Ile Val Met Thr Gln Ser Pro Ser Ile Leu Ser Ala Ser Val Gly
1               5                   10                  15

Asp Arg Val Thr Ile Thr Cys Arg Ala Ser Gln Thr Ile Ser Gly Trp
            20                  25                  30

Leu Ala Trp Tyr Gln Gln Lys Pro Ala Glu Ala Pro Lys Leu Leu Ile
        35                  40                  45

Tyr Lys Ala Ser Thr Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Gly Ile Tyr Tyr Cys Gln Gln Tyr Lys Ser Tyr Ser Phe
                85                  90                  95

Asn Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 114
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

```
Gln Met Gln Leu Val Gln Ser Gly Ala Glu Val Lys Lys Pro Gly Ala
1               5                   10                  15

Ser Val Lys Val Ser Cys Glu Ala Ser Gly Tyr Thr Leu Thr Ser Tyr
            20                  25                  30

Asp Ile Asn Trp Val Arg Gln Ala Thr Gly Gln Gly Pro Glu Trp Met
```

```
            35                  40                  45
Gly Trp Met Asn Ala Asn Ser Gly Asn Thr Gly Tyr Ala Gln Lys Phe
 50                  55                  60

Gln Gly Arg Val Thr Leu Thr Gly Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ser Ile Leu Val Arg Gly Ala Leu Gly Arg Tyr Phe Asp
                100                 105                 110

Leu Trp Gly Arg Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
        210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly
        450
```

<210> SEQ ID NO 115
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 115

```
Asp Ile Val Met Thr Gln Ser Pro Ser Ile Leu Ser Ala Ser Val Gly
1               5                   10                  15

Asp Arg Val Thr Ile Thr Cys Arg Ala Ser Gln Thr Ile Ser Gly Trp
            20                  25                  30

Leu Ala Trp Tyr Gln Gln Lys Pro Ala Glu Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Gly Ile Tyr Tyr Cys Gln Gln Tyr Lys Ser Tyr Ser Phe
                85                  90                  95

Asn Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Cys Thr Lys Ser
        195                 200                 205

Phe Asn Arg Gly Glu Cys
    210
```

<210> SEQ ID NO 116
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: VARIANT
<222> LOCATION: 2
<223> OTHER INFORMATION: Xaa = Met or Ile or Val

<400> SEQUENCE: 116

```
Glu Xaa Gln Leu Val Gln Ser Gly Ala Glu Val Lys Lys Pro Gly Ala
1               5                   10                  15

Ser Val Lys Val Ser Cys Glu Ala Ser Gly Tyr Thr Leu Thr Ser Tyr
            20                  25                  30

Asp Ile Asn Trp Val Arg Gln Ala Thr Gly Gln Gly Pro Glu Trp Met
        35                  40                  45
```

```
Gly Trp Met Asn Ala Asn Ser Gly Asn Thr Gly Tyr Ala Gln Lys Phe
    50                  55                  60

Gln Gly Arg Val Thr Leu Thr Gly Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Ile Leu Val Arg Gly Ala Leu Gly Arg Tyr Phe Asp
                100                 105                 110

Leu Trp Gly Arg Gly Thr Leu Val Thr Val Ser Ser Ala Ser Thr Lys
                115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Leu Gly Thr Gln Thr Tyr Ile Cys Asn
                195                 200                 205

Val Asn His Lys Pro Ser Asn Thr Lys Val Asp Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
        435                 440                 445

Ser Leu Ser Pro Gly
    450
```

```
<210> SEQ ID NO 117
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: 2
<223> OTHER INFORMATION: Xaa = Met or Ile or Val

<400> SEQUENCE: 117

Glu Xaa Gln Leu Val Gln Ser Gly Ala Glu Val Lys Lys Pro Gly Ala
1               5                   10                  15

Ser Val Lys Val Ser Cys Glu Ala Ser Gly Tyr Thr Leu Thr Ser Tyr
            20                  25                  30

Asp Ile Asn Trp Val Arg Gln Ala Thr Gly Gln Gly Pro Glu Trp Met
        35                  40                  45

Gly Trp Met Asn Ala Asn Ser Gly Asn Thr Gly Tyr Ala Gln Lys Phe
    50                  55                  60

Gln Gly Arg Val Thr Leu Thr Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Ile Leu Val Arg Gly Ala Leu Gly Arg Tyr Phe Asp
            100                 105                 110

Leu Trp Gly Arg Gly Thr Leu Val Thr Val Ser Ser Cys Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335
```

```
Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 118
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Gly Glu Gly Gly Leu Asp Asp
1               5

<210> SEQ ID NO 119
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Ile Phe Arg Thr
            20                  25                  30

Ser Arg Asn Lys Asn Leu Leu Asn Trp Tyr Gln Gln Arg Pro Gly Gln
        35                  40                  45

Pro Pro Arg Leu Leu Ile His Trp Ala Ser Thr Arg Lys Ser Gly Val
    50                  55                  60

Pro Asp Arg Phe Ser Gly Ser Gly Phe Gly Thr Asp Phe Thr Leu Thr
65                  70                  75                  80

Ile Thr Ser Leu Gln Ala Glu Asp Val Ala Ile Tyr Tyr Cys Gln Gln
                85                  90                  95

Tyr Phe Ser Pro Pro Tyr Thr Phe Gly Gln Gly Thr Lys Leu Glu Ile
            100                 105                 110

Lys

<210> SEQ ID NO 120
<211> LENGTH: 116
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 120
```

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Asn Ser Phe
            20                  25                  30

Trp Met His Trp Val Arg Gln Val Pro Gly Lys Gly Leu Val Trp Ile
        35                  40                  45

Ser Phe Thr Asn Asn Glu Gly Thr Thr Thr Ala Tyr Ala Asp Ser Val
    50                  55                  60

Arg Gly Arg Phe Ile Ile Ser Arg Asp Asn Ala Lys Asn Thr Leu Tyr
65                  70                  75                  80

Leu Glu Met Asn Asn Leu Arg Gly Glu Asp Thr Ala Val Tyr Tyr Cys
                85                  90                  95

Ala Arg Gly Asp Gly Gly Leu Asp Asp Trp Gly Gln Gly Thr Leu Val
            100                 105                 110

Thr Val Ser Ser
        115

```
<210> SEQ ID NO 121
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121
```

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Ile Phe Arg Thr
            20                  25                  30

Ser Arg Asn Lys Asn Leu Leu Asn Trp Tyr Gln Gln Arg Pro Gly Gln
        35                  40                  45

Pro Pro Arg Leu Leu Ile His Trp Ala Ser Thr Arg Lys Ser Gly Val
    50                  55                  60

Pro Asp Arg Phe Ser Gly Ser Gly Phe Gly Thr Asp Phe Thr Leu Thr
65                  70                  75                  80

Ile Thr Ser Leu Gln Ala Glu Asp Val Ala Ile Tyr Tyr Cys Gln Gln
                85                  90                  95

Tyr Phe Ser Pro Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

-continued

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
    210                 215                 220

<210> SEQ ID NO 122
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Asn Ser Phe
            20                  25                  30

Trp Met His Trp Val Arg Gln Val Pro Gly Lys Gly Leu Val Trp Ile
        35                  40                  45

Ser Phe Thr Asn Asn Glu Gly Thr Thr Thr Ala Tyr Ala Asp Ser Val
    50                  55                  60

Arg Gly Arg Phe Ile Ile Ser Arg Asp Asn Ala Lys Asn Thr Leu Tyr
65                  70                  75                  80

Leu Glu Met Asn Asn Leu Arg Gly Glu Asp Thr Ala Val Tyr Tyr Cys
                85                  90                  95

Ala Arg Gly Glu Gly Gly Leu Asp Asp Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser

```
                    325                 330                 335
Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 123
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Ile Phe Arg Thr
            20                  25                  30

Ser Arg Asn Lys Asn Leu Leu Asn Trp Tyr Gln Gln Arg Pro Gly Gln
        35                  40                  45

Pro Pro Arg Leu Leu Ile His Trp Ala Ser Thr Arg Lys Ser Gly Val
    50                  55                  60

Pro Asp Arg Phe Ser Gly Ser Gly Phe Gly Asp Phe Thr Leu Thr
65                  70                  75                  80

Ile Thr Ser Leu Gln Ala Glu Asp Val Ala Ile Tyr Tyr Cys Gln Gln
                85                  90                  95

Tyr Phe Ser Pro Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 124
```

```
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Asn Ser Phe
            20                  25                  30

Trp Met His Trp Val Arg Gln Val Pro Gly Lys Gly Leu Val Trp Ile
        35                  40                  45

Ser Phe Thr Asn Asn Glu Gly Thr Thr Thr Ala Tyr Ala Asp Ser Val
    50                  55                  60

Arg Gly Arg Phe Ile Ile Ser Arg Asp Asn Ala Lys Asn Thr Leu Tyr
65                  70                  75                  80

Leu Glu Met Asn Asn Leu Arg Gly Glu Asp Thr Ala Val Tyr Tyr Cys
                85                  90                  95

Ala Arg Gly Glu Gly Gly Leu Asp Asp Trp Gly Gln Gly Thr Leu Val
            100                 105                 110

Thr Val Ser Ser Cys Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365
```

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 125
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Lys(TAMRA)
<220> FEATURE:
<221> NAME/KEY: MOD_RES
<222> LOCATION: (10)..(10)
<223> OTHER INFORMATION: Lys(fluorescein)

<400> SEQUENCE: 125

Lys Gly Gly Ala Phe Ala Gly Gly Gly Lys
1               5                   10

<210> SEQ ID NO 126
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Gly Gly Ala Phe Ala Gly Gly Gly
1               5

<210> SEQ ID NO 127
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Gln Met Gln Leu Gln Glu Ser Gly Pro Gly Leu Val Lys Pro Ser Glu
1               5                   10                  15

Thr Leu Ser Leu Ser Cys Ser Val Ser Gly Ala Ser Ala Ser Ser Gly
            20                  25                  30

Tyr Tyr Asn Trp Val Arg Gln Thr Pro Gly Gly Leu Glu Trp Ile
        35                  40                  45

Ala Tyr Ile Leu Ser Gly Ala His Thr Asp Ile Lys Ala Ser Leu Gly
    50                  55                  60

Ser Arg Val Ala Val Ser Val Asp Thr Ser Lys Asn Gln Val Thr Leu
65                  70                  75                  80

```
Arg Leu Ser Ser Val Thr Ala Ala Asp Thr Ala Thr Tyr Tyr Cys Ala
                85                  90                  95

Arg Ser Gly Val Tyr Ser Lys Tyr Ser Leu Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 128
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"
```

```
<400> SEQUENCE: 128

Leu Ala Phe Gly
1

<210> SEQ ID NO 129
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: Ile(me)

<400> SEQUENCE: 129

Gly Pro Ile Leu Phe Phe
1               5

<210> SEQ ID NO 130
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Gly Pro Ile Leu Phe Phe
1               5

<210> SEQ ID NO 131
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Gly Gly Ala Phe Ala
1               5

<210> SEQ ID NO 132
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(6)
<223> OTHER INFORMATION: Any amino acid
<220> FEATURE:
<221> NAME/KEY: MOD_RES
<222> LOCATION: (9)..(9)
<223> OTHER INFORMATION: DPA

<400> SEQUENCE: 132

Gly Gly Gly Xaa Xaa Xaa Gly Gly Xaa Lys Lys
1               5                   10
```

```
<210> SEQ ID NO 133
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133
```

Glu Val Gln Leu Val Gln Ser Gly Gly Asp Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Gly Trp Val Arg Gln Ala Pro Gly Lys Gly Leu Glu Trp Leu
        35                  40                  45

Ser Val Val Thr Gly His Ser Tyr Arg Thr His Tyr Ala Asp Ser Val
    50                  55                  60

Lys Gly Arg Phe Ile Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Arg Ile Trp Ser Tyr Gly Asp Asp Ser Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

```
Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 134
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Glu Val Gln Leu Val Gln Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Tyr Ile Ser Ser Ile Glu Thr Ile Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Asp Glu Asp Thr Ala Val Tyr Tyr Cys Ala
            85                  90                  95

Arg Asp Arg Leu Val Asp Val Pro Leu Ser Ser Pro Asn Ser Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255
```

```
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 135
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Leu Ala Phe Gly Ala
1               5

<210> SEQ ID NO 136
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Leu Ala Phe Ala Ala
1               5

<210> SEQ ID NO 137
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 137

```
Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Asn Ser Phe
            20                  25                  30

Trp Met His Trp Val Arg Gln Val Pro Gly Lys Gly Leu Val Trp Ile
        35                  40                  45

Ser Phe Thr Asn Asn Glu Gly Thr Thr Thr Ala Tyr Ala Asp Ser Val
    50                  55                  60

Arg Gly Arg Phe Ile Ile Ser Arg Asp Asn Ala Lys Asn Thr Leu Tyr
65                  70                  75                  80

Leu Glu Met Asn Asn Leu Arg Gly Glu Asp Thr Ala Val Tyr Tyr Cys
                85                  90                  95

Ala Arg Gly Asp Gly Gly Leu Asp Asp Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415
```

-continued

Gln Gln Gly Asn Val Phe Ser Cys Ser Val Met His Glu Ala Leu His
              420                 425                 430

Asn His Tyr Thr Gln Lys Ser Leu Ser Leu Ser Pro Gly Lys
              435                 440                 445

<210> SEQ ID NO 138
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Asn Ser Phe
            20                  25                  30

Trp Met His Trp Val Arg Gln Val Pro Gly Lys Gly Leu Val Trp Ile
        35                  40                  45

Ser Phe Thr Asn Asn Glu Gly Thr Thr Thr Ala Tyr Ala Asp Ser Val
    50                  55                  60

Arg Gly Arg Phe Ile Ile Ser Arg Asp Asn Ala Lys Asn Thr Leu Tyr
65                  70                  75                  80

Leu Glu Met Asn Asn Leu Arg Gly Glu Asp Thr Ala Val Tyr Tyr Cys
                85                  90                  95

Ala Arg Gly Asp Gly Gly Leu Asp Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

```
Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
                435                 440                 445

<210> SEQ ID NO 139
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 139

Glu Met Gln Leu Val Gln Ser Gly Ala Glu Val Lys Lys Pro Gly Ala
1               5                   10                  15

Ser Val Lys Val Ser Cys Glu Ala Ser Gly Tyr Thr Leu Thr Ser Tyr
            20                  25                  30

Asp Ile Asn Trp Val Arg Gln Ala Thr Gly Gln Gly Pro Glu Trp Met
        35                  40                  45

Gly Trp Met Asn Ala Asn Ser Gly Asn Thr Gly Tyr Ala Gln Lys Phe
    50                  55                  60

Gln Gly Arg Val Thr Leu Thr Gly Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Ile Leu Val Arg Gly Ala Leu Gly Arg Tyr Phe Asp
            100                 105                 110

Leu Trp Gly Arg Gly Thr Leu Val Thr Val Ser Ser Cys Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
```

```
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr Asn
                290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
                355                 360                 365

Gln Val Ser Leu Thr Cys Leu Val Lys Gly Phe Tyr Pro Ser Asp Ile
                370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly
        450

<210> SEQ ID NO 140
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140

Glu Met Gln Leu Val Gln Ser Gly Ala Glu Val Lys Lys Pro Gly Ala
1               5                   10                  15

Ser Val Lys Val Ser Cys Glu Ala Ser Gly Tyr Thr Leu Thr Ser Tyr
                20                  25                  30

Asp Ile Asn Trp Val Arg Gln Ala Thr Gly Gln Gly Pro Glu Trp Met
                35                  40                  45

Gly Trp Met Asn Ala Asn Ser Gly Asn Thr Gly Tyr Ala Gln Lys Phe
            50                  55                  60

Gln Gly Arg Val Thr Leu Thr Gly Asp Thr Ser Ile Ser Thr Ala Tyr
65              70                  75                  80

Met Glu Leu Ser Ser Leu Arg Ser Glu Asp Thr Ala Val Tyr Tyr Cys
                85                  90                  95

Ala Arg Ser Ser Ile Leu Val Arg Gly Ala Leu Gly Arg Tyr Phe Asp
                100                 105                 110

Leu Trp Gly Arg Gly Thr Leu Val Thr Val Ser Ser Ala Ser Thr Lys
                115                 120                 125
```

```
Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 141
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 141

Glu Ile Gln Leu Val Gln Ser Gly Ala Glu Val Lys Lys Pro Gly Ala
1               5                   10                  15
```

-continued

```
Ser Val Lys Val Ser Cys Glu Ala Ser Gly Tyr Thr Leu Thr Ser Tyr
                20                  25                  30

Asp Ile Asn Trp Val Arg Gln Ala Thr Gly Gln Gly Pro Glu Trp Met
            35                  40                  45

Gly Trp Met Asn Ala Asn Ser Gly Asn Thr Gly Tyr Ala Gln Lys Phe
    50                  55                  60

Gln Gly Arg Val Thr Leu Thr Gly Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Ile Leu Val Arg Gly Ala Leu Gly Tyr Phe Asp
            100                 105                 110

Leu Trp Gly Arg Gly Thr Leu Val Thr Val Ser Ser Cys Ser Thr Lys
    115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
    195                 200                 205

Val Asn His Lys Pro Ser Asn Thr Lys Val Asp Lys Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
    355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
```

Ser Leu Ser Pro Gly
    450

<210> SEQ ID NO 142
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 142

Glu Ile Gln Leu Val Gln Ser Gly Ala Glu Val Lys Lys Pro Gly Ala
1               5                   10                  15

Ser Val Lys Val Ser Cys Glu Ala Ser Gly Tyr Thr Leu Thr Ser Tyr
            20                  25                  30

Asp Ile Asn Trp Val Arg Gln Ala Thr Gly Gln Gly Pro Glu Trp Met
        35                  40                  45

Gly Trp Met Asn Ala Asn Ser Gly Asn Thr Gly Tyr Ala Gln Lys Phe
    50                  55                  60

Gln Gly Arg Val Thr Leu Thr Gly Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Ile Leu Val Arg Gly Ala Leu Gly Arg Tyr Phe Asp
            100                 105                 110

Leu Trp Gly Arg Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

```
Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly
    450

<210> SEQ ID NO 143
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 143

Glu Val Gln Leu Val Gln Ser Gly Ala Glu Val Lys Lys Pro Gly Ala
1               5                   10                  15

Ser Val Lys Val Ser Cys Glu Ala Ser Gly Tyr Thr Leu Thr Ser Tyr
            20                  25                  30

Asp Ile Asn Trp Val Arg Gln Ala Thr Gly Gln Gly Pro Glu Trp Met
        35                  40                  45

Gly Trp Met Asn Ala Asn Ser Gly Asn Thr Gly Tyr Ala Gln Lys Phe
    50                  55                  60

Gln Gly Arg Val Thr Leu Thr Gly Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Ile Leu Val Arg Gly Ala Leu Gly Arg Tyr Phe Asp
            100                 105                 110

Leu Trp Gly Arg Gly Thr Leu Val Thr Val Ser Ser Cys Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220
```

```
Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
        340                 345                 350

Pro Gln Val Tyr Thr Leu Pro Pro Ser Arg Glu Glu Met Thr Lys Asn
    355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
        420                 425                 430

Ser Val Met His Glu Ala Leu His Asn His Tyr Thr Gln Lys Ser Leu
    435                 440                 445

Ser Leu Ser Pro Gly
    450

<210> SEQ ID NO 144
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 144

Glu Val Gln Leu Val Gln Ser Gly Ala Glu Val Lys Lys Pro Gly Ala
1               5                   10                  15

Ser Val Lys Val Ser Cys Glu Ala Ser Gly Tyr Thr Leu Thr Ser Tyr
            20                  25                  30

Asp Ile Asn Trp Val Arg Gln Ala Thr Gly Gln Gly Pro Glu Trp Met
        35                  40                  45

Gly Trp Met Asn Ala Asn Ser Gly Asn Thr Gly Tyr Ala Gln Lys Phe
    50                  55                  60

Gln Gly Arg Val Thr Leu Thr Gly Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Ile Leu Val Arg Gly Ala Leu Gly Tyr Phe Asp
            100                 105                 110

Leu Trp Gly Arg Gly Thr Leu Val Thr Val Ser Ser Ala Ser Thr Lys
```

```
                115                 120                 125
Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
        450

<210> SEQ ID NO 145
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 145

Asp Ile Gln Leu Thr Gln Ser Pro Asp Ser Leu Ala Val Ser Leu Gly
1               5                   10                  15
```

```
Glu Arg Ala Thr Ile Asn Cys Lys Ser Ser Gln Ser Ile Phe Arg Thr
            20                  25                  30

Ser Arg Asn Lys Asn Leu Leu Asn Trp Tyr Gln Gln Arg Pro Gly Gln
        35                  40                  45

Pro Pro Arg Leu Leu Ile His Trp Ala Ser Thr Arg Lys Ser Gly Val
50                  55                  60

Pro Asp Arg Phe Ser Gly Ser Gly Phe Gly Thr Asp Phe Thr Leu Thr
65                  70                  75                  80

Ile Thr Ser Leu Gln Ala Glu Asp Val Ala Ile Tyr Tyr Cys Gln Gln
                85                  90                  95

Tyr Phe Ser Pro Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Cys Thr Lys Ser Phe Asn Arg Gly Glu Cys
210                 215                 220

<210> SEQ ID NO 146
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Asn Ser Phe
            20                  25                  30

Trp Met His Trp Val Arg Gln Val Pro Gly Lys Gly Leu Val Trp Ile
        35                  40                  45

Ser Phe Thr Asn Asn Glu Gly Thr Thr Thr Ala Tyr Ala Asp Ser Val
    50                  55                  60

Arg Gly Arg Phe Ile Ile Ser Arg Asp Asn Ala Lys Asn Thr Leu Tyr
65                  70                  75                  80

Leu Glu Met Asn Asn Leu Arg Gly Glu Asp Thr Ala Val Tyr Tyr Cys
                85                  90                  95

Ala Arg Gly Asp Gly Gly Leu Asp Asp Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140
```

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 147
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Asn Ser Phe
            20                  25                  30

Trp Met His Trp Val Arg Gln Val Pro Gly Lys Gly Leu Val Trp Ile
            35                  40                  45

Ser Phe Thr Asn Asn Glu Gly Thr Thr Thr Ala Tyr Ala Asp Ser Val

```
                50                  55                  60
Arg Gly Arg Phe Ile Ile Ser Arg Asp Asn Ala Lys Asn Thr Leu Tyr
 65                  70                  75                  80

Leu Glu Met Asn Asn Leu Arg Gly Glu Asp Thr Ala Val Tyr Tyr Cys
                 85                  90                  95

Ala Arg Gly Glu Gly Leu Asp Asp Trp Gly Gln Gly Thr Leu Val
                100                 105                 110

Thr Val Ser Ser Cys Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
                130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
                290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly
                435                 440                 445

<210> SEQ ID NO 148
<211> LENGTH: 330
<212> TYPE: PRT
<213> ORGANISM: Homo sapiens
```

<400> SEQUENCE: 148

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 149
<211> LENGTH: 330
<212> TYPE: PRT
<213> ORGANISM: Homo sapiens

<400> SEQUENCE: 149

```
Cys Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 150
<211> LENGTH: 107
<212> TYPE: PRT
<213> ORGANISM: Homo sapiens

<400> SEQUENCE: 150

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
```

```
                65                  70                  75                  80
Lys His Lys Val Tyr Ala Cys Glu Val Thr His Gln Gly Leu Ser Ser
                    85                  90                  95
Pro Val Thr Lys Ser Phe Asn Arg Gly Glu Cys
                100                 105

<210> SEQ ID NO 151
<211> LENGTH: 107
<212> TYPE: PRT
<213> ORGANISM: Homo sapiens

<400> SEQUENCE: 151

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
                20                  25                  30
Tyr Pro Arg Glu Ala Lys Val Gln Trp Lys Val Asp Asn Ala Leu Gln
            35                  40                  45
Ser Gly Asn Ser Gln Glu Ser Val Thr Glu Gln Asp Ser Lys Asp Ser
        50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                    85                  90                  95
Pro Cys Thr Lys Ser Phe Asn Arg Gly Glu Cys
                100                 105

<210> SEQ ID NO 152
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
cccagactgc accagctgga tctctgaatg tactccagtt gc                         42

<210> SEQ ID NO 153
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
ccagactgca ccagctgcac ctctgaatgt actccagttg c                          41

<210> SEQ ID NO 154
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
ccagggttcc ctggccccaw tmgtcaagtc cascwkcacc tcttgcacag taatagacag      60
```

-continued c                                                                61

<210> SEQ ID NO 155
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
cctggcccca gtcgtcaagt cctccttcac ctcttgcaca gtaatagaca gc            52

<210> SEQ ID NO 156
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 156

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Asn Ser Phe
            20                  25                  30

Trp Met His Trp Val Arg Gln Val Pro Gly Lys Gly Leu Val Trp Ile
        35                  40                  45

Ser Phe Thr Asn Asn Glu Gly Thr Thr Thr Ala Tyr Ala Asp Ser Val
    50                  55                  60

Arg Gly Arg Phe Ile Ile Ser Arg Asp Asn Ala Lys Asn Thr Leu Tyr
65                  70                  75                  80

Leu Glu Met Asn Asn Leu Arg Gly Glu Asp Thr Ala Val Tyr Tyr Cys
                85                  90                  95

Ala Arg Gly Glu Gly Gly Leu Asp Asp Trp Gly Gln Gly Thr Leu Val
            100                 105                 110

Thr Val Ser Ser
        115

<210> SEQ ID NO 157
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 157

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Asn Ser Phe
            20                  25                  30

Trp Met His Trp Val Arg Gln Val Pro Gly Lys Gly Leu Val Trp Ile
        35                  40                  45

Ser Phe Thr Asn Asn Glu Gly Thr Thr Thr Ala Tyr Ala Asp Ser Val
    50                  55                  60

Arg Gly Arg Phe Ile Ile Ser Arg Asp Asn Ala Lys Asn Thr Leu Tyr
65                  70                  75                  80

Leu Glu Met Asn Asn Leu Arg Gly Glu Asp Thr Ala Val Tyr Tyr Cys
            85                  90                  95

Ala Arg Gly Glu Gly Gly Leu Asp Asp Trp Gly Gln Gly Thr Leu Val
        100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly
    435                 440                 445

<210> SEQ ID NO 158
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 158

Asp Ile Gln Leu Thr Gln Ser Pro Ser Ile Leu Ser Ala Ser Val Gly
1               5                   10                  15

Asp Arg Val Thr Ile Thr Cys Arg Ala Ser Gln Thr Ile Ser Gly Trp
            20                  25                  30

Leu Ala Trp Tyr Gln Gln Lys Pro Ala Glu Ala Pro Lys Leu Leu Ile
        35                  40                  45

Tyr Lys Ala Ser Thr Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Gly Ile Tyr Tyr Cys Gln Gln Tyr Lys Ser Tyr Ser Phe
                85                  90                  95

Asn Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 159
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 159

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Phe Val Ser Arg Thr
            20                  25                  30

Ser Leu Ala Trp Phe Gln Gln Lys Pro Gly Gln Pro Arg Leu Leu Leu
        35                  40                  45

Ile Tyr Glu Thr Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Met Tyr Tyr Cys His Lys Tyr Gly Ser Gly Pro
                85                  90                  95

Arg Thr Phe Gly Gln Gly Thr Lys Val Glu Val Lys Arg Thr Val Ala
            100                 105                 110

Ala Pro Ser Val Phe Ile Phe Pro Pro Ser Asp Glu Gln Leu Lys Ser
        115                 120                 125
```

-continued

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 160
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 160

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Lys Val Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Lys Tyr Gly Ser Thr Pro
                85                  90                  95

Arg Pro Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 161
<211> LENGTH: 214
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 161

Asp Val Val Met Thr Gln Ser Ser Ser Leu Ser Ala Ser Val Gly
1               5                   10                  15

Asp Arg Val Thr Ile Thr Cys Arg Ala Ser Leu Asp Ile Thr Asn His
            20                  25                  30

Leu Ala Trp Tyr Gln Gln Lys Pro Gly Glu Leu Pro Lys Leu Leu Ile
        35                  40                  45

Tyr Glu Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Val Ala Thr Tyr Tyr Cys Gln Lys Cys Asn Ser Thr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 162
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 162

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ala Ile
            20                  25                  30

Tyr Leu Ala Trp Tyr Gln Gln Glu Pro Gly Arg Ala Pro Thr Leu Leu
        35                  40                  45

Phe Tyr Gly Val Ser Asn Arg Ala Thr Gly Ile Pro Asp Arg Phe Ser
    50                  55                  60

Cys Ser Gly Ser Gly Thr Asp Phe Thr Leu Thr Ile Ser Arg Leu Glu
65              70                  75                  80

Pro Glu Asp Phe Ala Val Tyr Tyr Cys Gln Leu Tyr Thr Ser Ser Arg
                85                  90                  95

Ala Leu Thr Phe Gly Gly Gly Thr Lys Val Glu Ile Lys Arg Thr Val
```

```
                  100                 105                 110
Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
            130                 135             140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys
            210                 215

<210> SEQ ID NO 163
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 163

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Gly
            20                  25                  30

Leu Gly Trp Tyr Gln Gln Thr Pro Gly Lys Ala Pro Lys Leu Leu Ile
        35                  40                  45

Tyr Pro Ala Ser Thr Leu Glu Ser Gly Val Pro Ser Arg Phe Ser Gly
    50                  55                  60

Ser Gly Ser Asp Arg Asp Phe Thr Leu Thr Ile Thr Ser Leu Gln Pro
65                  70                  75                  80

Glu Asp Phe Ala Thr Tyr Tyr Cys Leu Gln Asp His Asn Tyr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135             140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 164
```

```
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Gly
            20                  25                  30

Leu Gly Trp Tyr Gln Gln Ile Pro Gly Lys Ala Pro Lys Leu Leu Ile
        35                  40                  45

Tyr Pro Ala Ser Thr Leu Glu Ser Gly Val Pro Ser Arg Phe Ser Gly
    50                  55                  60

Ser Gly Ser Asp Arg Asp Phe Thr Leu Thr Ile Thr Ser Leu Gln Pro
65                  70                  75                  80

Glu Asp Phe Ala Thr Tyr Tyr Cys Leu Gln Asp His Asn Tyr Pro Pro
                85                  90                  95

Ser Phe Ser Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 165
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 165

Asp Ile Gln Met Thr Gln Ser Pro Ala Thr Leu Ser Val Ser Pro Gly
1               5                   10                  15

Glu Thr Val Thr Leu Ser Cys Arg Ala Ser Gln Ser Val Arg Thr Asn
            20                  25                  30

Val Ala Trp Tyr Arg His Lys Ala Gly Gln Ala Pro Met Ile Leu Val
        35                  40                  45

Ser Gly Ala Ser Thr Arg Ala Ser Gly Ala Pro Ala Arg Phe Ser Gly
    50                  55                  60

Ser Gly Tyr Gly Thr Glu Phe Thr Leu Thr Ile Thr Ser Leu Gln Ser
65                  70                  75                  80
```

Glu Asp Phe Ala Val Tyr Tyr Cys Leu Gln Tyr Asn Thr Trp Pro Arg
            85                  90                  95

Thr Phe Gly Gln Gly Thr Lys Val Glu Val Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 166
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 166

Asp Val Val Met Thr Gln Ser Pro Ser Phe Leu Ser Ala Ser Val Gly
1               5                   10                  15

Asp Arg Val Thr Leu Thr Cys Arg Ala Ser Gln Asp Ile Gly Ser Ser
            20                  25                  30

Leu Ala Trp Tyr Gln Gln Arg Pro Gly Lys Ala Pro Asn Leu Leu Ile
            35                  40                  45

Tyr Ala Thr Ser Thr Leu Gln Ser Gly Val Pro Ser Arg Phe Ser Gly
    50                  55                  60

Ser Gly Phe Gly Thr Glu Phe Thr Leu Thr Ile Ser Thr Leu Gln Pro
65                  70                  75                  80

Glu Asp Phe Ala Thr Tyr Tyr Cys Gln Gln Leu Asn Asn Tyr Val His
            85                  90                  95

Ser Phe Gly Pro Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys

```
<210> SEQ ID NO 167
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 167

Glu Thr Thr Leu Thr Gln Ser Pro Ser Thr Leu Ser Ala Ser Val Gly
1               5                   10                  15

Asp Arg Val Thr Ile Thr Cys Arg Ala Ser Gln Ser Ile Gly Asp Arg
            20                  25                  30

Leu Ala Trp Tyr Gln Gln Lys Pro Gly Lys Ala Pro Lys Val Leu Ile
        35                  40                  45

Tyr Trp Ala Ser Asn Leu Glu Gly Gly Val Pro Ser Arg Phe Ser Gly
50                  55                  60

Thr Gly Ser Gly Thr Glu Phe Ala Leu Thr Ile Ser Gly Leu Gln Pro
65                  70                  75                  80

Asp Asp Leu Ala Thr Tyr Tyr Cys Gln Gln Tyr Lys Ser Gln Trp Ser
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 168
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 168

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Phe Thr Asn His Tyr
            20                  25                  30

Leu Asn Trp Tyr Gln His Lys Pro Gly Arg Ala Pro Lys Leu Met Ile
        35                  40                  45

Ser Val Ala Ser Asn Leu Gln Ser Gly Val Pro Ser Arg Phe Thr Gly
50                  55                  60
```

Ser Glu Ser Gly Thr Asp Phe Thr Leu Thr Ile Ser Gly Leu Gln Pro
65                  70                  75                  80

Glu Asp Phe Ala Thr Tyr Tyr Cys Gln Gln Ser Tyr Arg Thr Pro Tyr
                85                  90                  95

Thr Phe Gly Gln Gly Ser Arg Leu Glu Met Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 169
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 169

Gln Val Gln Leu Gln Gln Ser Gly Ala Glu Val Lys Lys Pro Gly Ala
1               5                   10                  15

Ser Val Lys Val Ser Cys Glu Ala Ser Gly Tyr Thr Leu Thr Ser Tyr
                20                  25                  30

Asp Ile Asn Trp Val Arg Gln Ala Thr Gly Gln Gly Pro Glu Trp Met
            35                  40                  45

Gly Trp Met Asn Ala Asn Ser Gly Asn Thr Gly Tyr Ala Gln Lys Phe
        50                  55                  60

Gln Gly Arg Val Thr Leu Thr Gly Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Ser Ser Ile Leu Val Arg Gly Ala Leu Gly Tyr Phe Asp
            100                 105                 110

Leu Trp Gly Arg Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

```
Val Thr Val Pro Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
        450

<210> SEQ ID NO 170
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 170

Glu Val Gln Leu Val Gln Ser Gly Ala Glu Val Lys Pro Gly Ala
1               5                   10                  15

Ser Leu Lys Val Ser Cys Lys Ala Ser Gly Tyr Ile Ile Asn Tyr
            20                  25                  30

Asp Phe Ile Trp Val Arg Gln Ala Thr Gly Gln Gly Pro Glu Trp Met
            35                  40                  45

Gly Trp Met Asn Pro Asn Ser Tyr Asn Thr Gly Tyr Gly Gln Lys Phe
        50                  55                  60

Gln Gly Arg Val Thr Met Thr Trp Asp Ser Ser Met Ser Thr Ala Tyr
65                  70                  75                  80

Met Glu Leu Ser Ser Leu Thr Ser Ala Asp Thr Ala Val Tyr Tyr Cys
```

```
                85                  90                  95
Ala Arg Ala Val Arg Gly Gln Leu Leu Ser Glu Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 171
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 171

-continued

```
Gln Val Gln Leu Gln Gln Ser Gly Ala Glu Lys Lys Pro Gly Ala
1               5                   10                  15

Ser Val Lys Val Ser Cys Arg Ala Ser Gly Tyr Thr Phe Thr Ser Tyr
            20                  25                  30

Asp Ile Asn Trp Val Arg Gln Ala Pro Gly Gln Gly Leu Glu Trp Met
            35                  40                  45

Gly Trp Met Asn Pro Asn Ser Gly Asn Thr Tyr Ala Gln Arg Phe
50                  55                  60

Gln Gly Arg Leu Thr Met Thr Lys Asn Thr Ser Ile Asn Thr Ala Tyr
65                  70                  75                  80

Met Glu Leu Ser Ser Leu Arg Ser Glu Asp Thr Ala Val Tyr Tyr Cys
                85                  90                  95

Ala Thr Glu Arg Trp Ser Lys Asp Thr Gly His Tyr Tyr Tyr Gly
                100                 105                 110

Met Asp Val Trp Gly Gln Gly Thr Thr Val Thr Val Ser Ser Ala Ser
            115                 120                 125

Thr Lys Gly Pro Ser Val Phe Pro Leu Ala Pro Ser Ser Lys Ser Thr
            130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
            355                 360                 365

Lys Asn Gln Val Ser Leu Thr Cys Leu Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415
```

Ser Lys Leu Thr Val Asp Lys Ser Arg Trp Gln Gln Gly Asn Val Phe
        420                 425                 430

Ser Cys Ser Val Met His Glu Ala Leu His Asn His Tyr Thr Gln Lys
        435                 440                 445

Ser Leu Ser Leu Ser Pro Gly
    450                 455

<210> SEQ ID NO 172
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 172

Gln Val Gln Leu Gln Gln Ser Gly Ala Glu Val Lys Arg Pro Gly Ala
1               5                   10                  15

Ser Val Lys Val Ser Cys Glu Ala Ser Gly Tyr Thr Val Ser Asn Tyr
            20                  25                  30

Asp Ile Asn Trp Val Arg Gln Ala Thr Gly Gln Gly Leu Glu Trp Met
        35                  40                  45

Gly Trp Met Asn Pro Ser Ser Gly Arg Thr Gly Tyr Ala Pro Lys Phe
    50                  55                  60

Arg Gly Arg Val Thr Met Thr Arg Ser Thr Ser Ile Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Gly Gly Gly Tyr Tyr Asp Ser Ser Gly Asn Tyr His Ile Ser
            100                 105                 110

Gly Leu Asp Val Trp Gly Gln Gly Thr Thr Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His

-continued

```
305                 310                 315                 320
Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly
    450                 455

<210> SEQ ID NO 173
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 173

Gln Ile Thr Leu Lys Glu Ser Gly Gly Gly Leu Ile Lys Pro Gly Gly
1               5                   10                  15

Ser Leu Arg Leu Ser Cys Ala Thr Ser Gly Phe Pro Phe Ser Ala Tyr
            20                  25                  30

Ala Met Asn Trp Val Arg Gln Ala Pro Gly Arg Gly Leu Glu Trp Val
        35                  40                  45

Ser Ser Ile Thr Lys Asn Ser Asp Ser Leu Tyr Tyr Ala Asp Ser Val
    50                  55                  60

Lys Gly Arg Phe Thr Ile Ser Arg Asp Asn Ala Gly Asn Ser Leu Tyr
65                  70                  75                  80

Leu Gln Met Asn Ser Leu Arg Val Glu Asp Thr Ala Val Tyr Tyr Cys
                85                  90                  95

Ala Thr Leu Ala Ala Arg Ile Met Ala Thr Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

-continued

```
Ser Asn Thr Lys Val Asp Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 174
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 174

```
Glu Val Gln Leu Val Gln Ser Gly Gly Gly Leu Val Lys Pro Gly Glu
1               5                   10                  15

Ser Leu Arg Leu Ser Cys Ala Ala Ser Gly Phe Ser Phe Asp Tyr Tyr
            20                  25                  30

Ser Met Ile Trp Val Arg Gln Ala Pro Gly Lys Gly Leu Glu Trp Val
        35                  40                  45

Ser Ser Ile Asp Ser Ser Ser Arg Tyr Leu Tyr Tyr Ala Asp Ser Val
    50                  55                  60

Lys Gly Arg Phe Thr Ile Ser Arg Asp Asn Ala Gln Asn Ser Leu Tyr
65                  70                  75                  80

Leu Gln Met Ser Gly Leu Arg Val Glu Asp Thr Ala Val Tyr Tyr Cys
                85                  90                  95

Ala Arg Asp Gly Asp Asp Ile Leu Ser Val Tyr Arg Gly Ser Gly Arg
            100                 105                 110
```

```
Pro Phe Asp Tyr Trp Gly Gln Gly Thr Leu Val Thr Val Ser Ser Ala
            115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
275                 280                 285

Val Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
            355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
435                 440                 445

Lys Ser Leu Ser Leu Ser Pro Gly
450                 455

<210> SEQ ID NO 175
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 175

Gln Val Gln Leu Gln Gln Ser Gly Gly Gly Leu Val Asn Pro Gly Glu
```

-continued

```
1               5                   10                  15
Ser Leu Arg Leu Ser Cys Ala Ala Ser Gly Phe Ser Phe Asn Tyr Tyr
                20                  25                  30
Ser Met Ile Trp Val Arg Gln Ala Pro Gly Lys Gly Leu Glu Trp Val
                35                  40                  45
Ser Ser Ile Asp Ser Ser Ser Arg Tyr Arg Tyr Tyr Thr Asp Ser Val
                50                  55                  60
Lys Gly Arg Phe Thr Ile Ser Arg Asp Asn Ala Gln Asn Ser Leu Tyr
65                  70                  75                  80
Leu Gln Met Ser Ala Leu Arg Val Glu Asp Thr Ala Val Tyr Tyr Cys
                85                  90                  95
Ala Arg Asp Gly Asp Asp Ile Leu Ser Val Tyr Gln Gly Ser Gly Arg
                100                 105                 110
Pro Phe Asp Tyr Trp Gly Gln Gly Thr Leu Val Thr Val Ser Ser Ala
                115                 120                 125
Ser Thr Lys Gly Pro Ser Val Phe Pro Leu Ala Pro Ser Ser Lys Ser
                130                 135                 140
Thr Ser Gly Gly Thr Ala Ala Leu Gly Cys Leu Val Lys Asp Tyr Phe
145                 150                 155                 160
Pro Glu Pro Val Thr Val Ser Trp Asn Ser Gly Ala Leu Thr Ser Gly
                165                 170                 175
Val His Thr Phe Pro Ala Val Leu Gln Ser Ser Gly Leu Tyr Ser Leu
                180                 185                 190
Ser Ser Val Val Thr Val Pro Ser Ser Ser Leu Gly Thr Gln Thr Tyr
                195                 200                 205
Ile Cys Asn Val Asn His Lys Pro Ser Asn Thr Lys Val Asp Lys Lys
210                 215                 220
Val Glu Pro Lys Ser Cys Asp Lys Thr His Thr Cys Pro Pro Cys Pro
225                 230                 235                 240
Ala Pro Glu Leu Leu Gly Gly Pro Ser Val Phe Leu Phe Pro Pro Lys
                245                 250                 255
Pro Lys Asp Thr Leu Met Ile Ser Arg Thr Pro Glu Val Thr Cys Val
                260                 265                 270
Val Val Asp Val Ser His Glu Asp Pro Glu Val Lys Phe Asn Trp Tyr
                275                 280                 285
Val Asp Gly Val Glu Val His Asn Ala Lys Thr Lys Pro Arg Glu Glu
290                 295                 300
Gln Tyr Asn Ser Thr Tyr Arg Val Val Ser Val Leu Thr Val Leu His
305                 310                 315                 320
Gln Asp Trp Leu Asn Gly Lys Glu Tyr Lys Cys Lys Val Ser Asn Lys
                325                 330                 335
Ala Leu Pro Ala Pro Ile Glu Lys Thr Ile Ser Lys Ala Lys Gly Gln
                340                 345                 350
Pro Arg Glu Pro Gln Val Tyr Thr Leu Pro Pro Ser Arg Glu Glu Met
                355                 360                 365
Thr Lys Asn Gln Val Ser Leu Thr Cys Leu Val Lys Gly Phe Tyr Pro
370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
                405                 410                 415
Tyr Ser Lys Leu Thr Val Asp Lys Ser Arg Trp Gln Gln Gly Asn Val
                420                 425                 430
```

```
Phe Ser Cys Ser Val Met His Glu Ala Leu His Asn His Tyr Thr Gln
        435                 440                 445

Lys Ser Leu Ser Leu Ser Pro Gly
    450                 455

<210> SEQ ID NO 176
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 176

Gln Val Gln Leu Gln Gln Ser Gly Gly Gly Leu Glu Gln Pro Gly Gly
1               5                   10                  15

Ser Leu Arg Ile Ser Cys Ala Ala Ser Gly Phe Thr Phe Asn Thr Asn
            20                  25                  30

Asp Met Ser Trp Val Arg Gln Ala Pro Gly Lys Gly Leu Gln Trp Val
        35                  40                  45

Ser Thr Ile Ile Gly Ile Asp Asp Thr Thr His Tyr Ala Asp Ser Val
    50                  55                  60

Arg Gly Arg Phe Thr Val Ser Arg Asp Thr Ser Lys Asn Met Val Tyr
65                  70                  75                  80

Leu Gln Met Asn Ser Leu Arg Val Glu Asp Thr Ala Leu Tyr Tyr Cys
                85                  90                  95

Val Lys Asn Ser Gly Ile Tyr Ser Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 177
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Ala Arg Gly Asp Gly Gly Leu
1               5

<210> SEQ ID NO 178
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Ala Arg Gly Asp Ala Gly Leu
1               5

<210> SEQ ID NO 179
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179

Ala Arg Gly Glu Gly Gly Leu
1               5

<210> SEQ ID NO 180
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 180

Ala Arg Gly Ala Gly Gly Leu
1               5
```